US011453891B2

(12) United States Patent
Yeo et al.

(10) Patent No.: US 11,453,891 B2
(45) Date of Patent: Sep. 27, 2022

(54) DIRECTED EDITING OF CELLULAR RNA VIA NUCLEAR DELIVERY OF CRISPR/CAS9

(71) Applicant: The Regents of the University of California, Oakland, CA (US)

(72) Inventors: Eugene Yeo, La Jolla, CA (US); Kristopher Brannan, La Jolla, CA (US); Ryan Marina, La Jolla, CA (US); David Nelles, La Jolla, CA (US)

(73) Assignee: The Regents of the University of California, Oakland, CA (US)

(*) Notice: Subject to any disclaimer, the term of this patent is extended or adjusted under 35 U.S.C. 154(b) by 589 days.

(21) Appl. No.: 15/975,728

(22) Filed: May 9, 2018

(65) Prior Publication Data

US 2018/0334685 A1 Nov. 22, 2018

Related U.S. Application Data

(60) Provisional application No. 62/504,497, filed on May 10, 2017.

(51) Int. Cl.
```
C12N 15/00    (2006.01)
C12N 15/85    (2006.01)
C12N 15/11    (2006.01)
A61P 21/00    (2006.01)
C12N 9/22     (2006.01)
C12N 15/113   (2010.01)
A61K 48/00    (2006.01)
```

(52) U.S. Cl.
CPC .............. *C12N 15/85* (2013.01); *A61P 21/00* (2018.01); *C12N 9/22* (2013.01); *C12N 15/11* (2013.01); *C12N 15/113* (2013.01); *A61K 48/00* (2013.01); *C12N 2310/20* (2017.05); *C12N 2740/16043* (2013.01); *C12N 2750/14143* (2013.01)

(58) Field of Classification Search
CPC .......... C12N 15/85; C12N 9/22; C12N 15/11; C12N 15/113; C12N 2310/20; C12N 2740/16043; C12N 2750/14143; A61P 21/00; A61K 48/00
See application file for complete search history.

(56) References Cited

U.S. PATENT DOCUMENTS

| | | | |
|---|---|---|---|
| 3,687,808 A | 8/1972 | Merigan et al. |
| 5,034,506 A | 7/1991 | Summerton et al. |
| 5,166,315 A | 11/1992 | Summerton et al. |
| 5,185,444 A | 2/1993 | Summerton et al. |
| 5,214,134 A | 5/1993 | Weis et al. |
| 5,216,141 A | 6/1993 | Benner |
| 5,235,033 A | 8/1993 | Summerton et al. |
| 5,264,562 A | 11/1993 | Matteucci |
| 5,264,564 A | 11/1993 | Matteucci |
| 5,405,938 A | 4/1995 | Summerton et al. |
| 5,434,257 A | 7/1995 | Matteucci et al. |
| 5,466,677 A | 11/1995 | Baxter et al. |
| 5,470,967 A | 11/1995 | Huie et al. |
| 5,489,677 A | 2/1996 | Sanghvi et al. |
| 5,539,082 A | 7/1996 | Nielsen et al. |
| 5,541,307 A | 7/1996 | Cook et al. |
| 5,561,225 A | 10/1996 | Maddry et al. |
| 5,596,086 A | 1/1997 | Matteucci et al. |
| 5,602,240 A | 2/1997 | De Mesmaeket et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,633,360 A | 5/1997 | Bischofberger et al. |
| 5,663,312 A | 9/1997 | Chaturvedula |
| 5,677,437 A | 10/1997 | Teng et al. |
| 5,677,439 A | 10/1997 | Weis et al. |
| 5,714,331 A | 2/1998 | Buchardt et al. |
| 5,719,262 A | 2/1998 | Buchardt et al. |
| 6,013,639 A | 1/2000 | Peyman et al. |
| 6,461,864 B1 | 10/2002 | Soriano et al. |
| 6,471,996 B1 | 10/2002 | Sokoll et al. |
| 6,472,375 B1 | 10/2002 | Hoon et al. |
| 7,078,387 B1 | 7/2006 | Leiden et al. |
| 8,697,359 B1 | 4/2014 | Zhang |
| 9,074,199 B1 | 7/2015 | Chavez et al. |
| 2002/0068709 A1 | 6/2002 | Orum et al. |
| 2015/0056702 A1 | 2/2015 | Conway |
| 2015/0071899 A1 | 3/2015 | Liu et al. |

(Continued)

FOREIGN PATENT DOCUMENTS

| | | |
|---|---|---|
| CN | 108103090 | 6/2018 |
| CN | 110055284 | 7/2019 |

(Continued)

OTHER PUBLICATIONS

Cox et al (Science, published Nov. 24, 2017; vol. 358, pp. 1019-1027). (Year: 2017).*
Wang & Beal (NAR 2016, vol. 44, No. 20, published online Sep. 9, 2016, pp. 9872-9880). (Year: 2016).*
Doench et al., "Rational design of highly active sgRNAs for CRISPR-Cas9-mediated gene inactivation," Nature biotechnology, 2014, 32(12):1262-7.
Fukuda et al., "Construction of a guide-RNA for site-directed RNA mutagenesis utilizing intracellular A-to-I RNA editing," Sci Rep, 2017, 7:41478.
Graham et al., "Resources for the design of CRISPR gene editing experiments," Genome Biol., 2015, 16(1):260.

(Continued)

*Primary Examiner* — Catherine S Hibbert
(74) *Attorney, Agent, or Firm* — Fish & Richardson P.C.

(57) ABSTRACT

Disclosed herein is a technology to perform programmable RNA editing at single-nucleotide resolution using RNA-targeting CRISPR/Cas9. This approach, which Applicants have termed "Cas9-directed RNA editing" or "CREDIT," provides a means to reversibly alter genetic information in a temporal manner, unlike traditional CRISPR/Cas9 driven genomic engineering which relies on permanently altering DNA sequence.

20 Claims, 14 Drawing Sheets

Specification includes a Sequence Listing.

(56) References Cited

U.S. PATENT DOCUMENTS

| | | |
|---|---|---|
| 2015/0232844 A1 | 8/2015 | Ozsolak |
| 2015/0353905 A1 | 12/2015 | Weiss |
| 2016/0214276 A1 | 7/2016 | Liu |
| 2016/0238593 A1 | 8/2016 | Biyden et al. |
| 2016/0289659 A1* | 10/2016 | Doudna ............... C12N 15/113 |
| 2016/0304846 A1 | 10/2016 | Liu et al. |
| 2016/0362667 A1 | 12/2016 | Donohue et al. |
| 2018/0073012 A1* | 3/2018 | Liu ........................ A61P 43/00 |
| 2018/0208924 A1 | 7/2018 | Fukuda et al. |
| 2018/0273576 A1 | 9/2018 | Hogrefe et al. |
| 2019/0062724 A1 | 2/2019 | Hsu et al. |
| 2020/0239863 A1 | 7/2020 | Yeo |
| 2021/0079366 A1 | 3/2021 | Zhang et al. |
| 2021/0332344 A1 | 10/2021 | Yeo et al. |
| 2021/0340197 A1 | 11/2021 | Yeo et al. |
| 2022/0127621 A1 | 4/2022 | Yeo et al. |

FOREIGN PATENT DOCUMENTS

| | | | |
|---|---|---|---|
| JP | 2015-506669 | 3/2015 | |
| WO | WO 1998/39352 | 9/1998 | |
| WO | WO 1999/14226 | 3/1999 | |
| WO | WO 2000/066604 | 11/2000 | |
| WO | WO 2012/068627 | 5/2012 | |
| WO | WO 2013/058404 | 4/2013 | |
| WO | WO 2013/082548 | 6/2013 | |
| WO | WO 2013/130684 | 9/2013 | |
| WO | WO 2014/093622 | 6/2014 | |
| WO | WO 2014/093635 | 6/2014 | |
| WO | WO 2014/093661 | 6/2014 | |
| WO | WO 2014/113493 | 7/2014 | |
| WO | WO 2014/191521 | 12/2014 | |
| WO | WO 2015/006294 | 1/2015 | |
| WO | WO 2015/048690 | 4/2015 | |
| WO | WO 2015/089277 | 6/2015 | |
| WO | WO 2015/089351 | 6/2015 | |
| WO | WO 2016/19655 | 2/2016 | |
| WO | WO 2016/106236 | 6/2016 | |
| WO | WO-2016097212 A1 * | 6/2016 | ........... C12N 15/113 |
| WO | WO 2016/183402 | 11/2016 | |
| WO | WO 2016/191684 | 12/2016 | |
| WO | WO 2016/196655 | 12/2016 | |
| WO | WO 2016/196805 | 12/2016 | |
| WO | WO 2016/201138 | 12/2016 | |
| WO | WO-2016201138 A1 * | 12/2016 | ........... C12Q 1/6876 |
| WO | WO 2017/010556 | 1/2017 | |
| WO | WO 2017/053312 | 3/2017 | |
| WO | WO-2017053312 A1 * | 3/2017 | ............. C12N 11/14 |
| WO | WO 2017/091630 | 6/2017 | |
| WO | WO 2017/219027 | 12/2017 | |
| WO | WO 2018/002697 | 1/2018 | |
| WO | WO-2018/027078 A1 | 2/2018 | |
| WO | WO 2018/154387 | 8/2018 | |
| WO | WO 2018/183703 | 10/2018 | |
| WO | WO 2019/006471 | 1/2019 | |
| WO | WO 2019/040664 | 2/2019 | |
| WO | WO 2019/060746 | 3/2019 | |
| WO | WO 2019/204828 | 10/2019 | |

OTHER PUBLICATIONS

Halo et al "NanoFlares for the detection, isolation, and culture of live tumor cells from human blood" PNAS, 2014, 111(48):17104-17109.

Hanswillemenke et al., "Site-Directed RNA Editing in Vivo Can Be Triggered by the Light-Driven Assembly of an Artificial Riboprotein," J Am Chem Soc, 2015, 137(50):15875-81.

Hermonat & Muzyczka, "Use of adeno-associated virus as a mammalian DNA cloning vector: transduction of neomycin resistance into mammalian tissue culture cells," Proc. Natl. Acad. Sci. USA, 1984, 81:6466-6470.

Higuchi et al., "RNA editing of AMPA receptor subunit GluR-B: a base-paired intron-exon structure determines position and efficiency," Cell, 1993, 75(7):1361-70.

Hua et al "Peripheral SMN restoration is essential for long-term rescue of a severe spinal muscular atrophy mouse model." Nature, 2011, 478(7367):123-6.

International Preliminary Report on Patentability in International Appln. No. PCT/US2018/031913, dated Nov. 12, 2019, 9 pages.

Konermann et al., "Genome-scale transcriptional activation by an engineered CRISPR-Cas9 complex," Nature, 2015, 517(7356):583-588.

Kotterman et al., "Viral Vectors for Gene Therapy: Translational and Clinical Outlook," Annual Review of Biomedical Engineering, 2015, 17:63-89.

Kuttan & Bass, "Mechanistic insights into editing-site specificity of ADARs," PNAS, 2012, 109(48):E3295-E3304.

Lebkowski et al., "Adeno-associated virus: a vector system for efficient introduction and integration of DNA into a variety of mammalian cell types," Mol. Cell. Biol., 1988, 8:3988-3996.

McMahon et al., "TRIBE: Hijacking an RNA-Editing Enzyme to Identify Cell-Specific Targets of RNA-Binding Proteins," Cell, 2016, 165(3):742-53.

Montiel-Gonzalez et al "An efficient system for selectively altering genetic information within mRNAs." Nucleic Acids Res., 2016, 44:e157.

Montiel-Gonzalez et al., "Correction of mutations within the cystic fibrosis transmembrane conductance regulator by site-directed RNA editing," PNAS, 2013, 110(45):18285-90.

Nishikura, "A-to-I editing of coding and non-coding RNAs by ADARs," Nat Rev Mol Cell Biol, 2016, 17(2):83-96.

O'Connell et al., "Programmable RNA recognition and cleavage by CRISPR/Cas9," Nature., 2014, 516(7530):263-266.

O'Keefe et al., "Scaleable manufacture of HIV-1 entry inhibitor griffithsin and validation of its safety and efficacy as a topical microbicide component," Proc. Nat. Acad. Sci. USA, 2009, 106(15):6099-6104.

Phelps et al., "Recognition of duplex RNA by the deaminase domain of the RNA editing enzyme ADAR2," Nuc. Acid Res., 2015, 43(2):1123-1132.

Schellenberger et al., "A recombinant polypeptide extends the in vivo half-life of peptides and proteins in a tunable manner," Nat Biotechnol., 2009, 27(12):1186-1190.

Schlesinger & Dubensky, "Alphavirus vectors for gene expression and vaccines," Curr. Opin. Biotechnol., 1999, 10(5):434-439.

Schneider et al "Optimal guideRNAs for re-directing deaminase activity of hADAR1 and hADAR2 in trans." Nucleic Acids Res., 2014, 42:e87.

Wang et al "Engineering splicing factors with designed specificities," Nat Methods., 2009, 6(11):825-830.

Wold and Toth, "Adenovirus Vectors for Gene Therapy, Vaccination and Cancer Gene Therapy," Curr. Gene. Ther., 2013, 13(6):421-433.

Wright et al., "Biology and Applications of CRISPR Systems: Harnessing Nature's Toolbox for Genome Engineering," Cell, 2016, 164(1-2):29-44.

Ying et al., "Cancer therapy using a self-replicating RNA vaccine," Nat. Med., 1999, 5(7):823-827.

Bjerke, JN et al., "Recent Advances in CRISPR Base Editing: From A to RNA", Biochemistry, Jan. 26, 2018, vol. 57, pp. 886887; DOI: 10.1021/acs.biochem.7b01276.

International Search Report and Written Opinion dated Aug. 2, 2018, from application No. PCT/US2018/031913.

Matthews, MM et al., "Structures of human ADAR2 bound to dsRNA reveal base-flipping mechanism and basis for site selectivity", Nature Structural & Molecular Biology, May 2016, Epub Apr. 11, 2016, vol. 23, No. 5, pp. 426-433; abstract, p. 2, 3$^{rd}$ paragraph; DOI: 10.1038/nsmb.3203.

Wang, et al., "Unbiased detection of off-target cleavage by CRISPR-Cas9 and TALENs using integrase-defective lentviral vectors", Nature Biotechnology, Feb. 2015, Epub Jan. 19, 2015, vol. 33, No. 2, pp. 175-199; p. 177, 1$^{st}$ column, 1$^{st}$ paragraph; Figure 1C; DOI: 10.1038/nbt.3127.

Adamala et al., "Programmable RNA-binding protein composed of repeats of a single modular unit," Proceedings of the National Academy of Sciences, May 10, 2016, 113(19):E2579-E2588.

(56) References Cited

OTHER PUBLICATIONS

Akerstrom et al., "A physicochemical study of protein G, a molecule with unique immunoglobulin G-binding properties," J. Biol. Chem., 1986, 261: 10,240-10,247.
Bashor et al., "Using engineered scaffold interactions to reshape MAP kinase pathway signaling dynamics," Science, 2008, 319(5869):1539-1543.
Batra et al., "Elimination of Toxic Microsatellite Repeat Expansion RNA by RNA-Targeting Cas9," Cell, 2017, 170(5):889-912.e10, 34 Pages.
Batra et al., "Loss of MBNL Leads to Disruption of Developmentally Regulated Alternative Polyade in RNA-Mediated Disease," Mol. Cell, Oct. 2014, 56(2):311-322.
Bennett et al., "RNA targeting therapeutics: molecular mechanisms of antisense oligonucleotides as a therapeutic platform," Anmi Rev Pharmacol Toxicol, 2010, 50: 259-293.
Bertrand et al., "Localization of ASH1 mRNA particles in living yeast," Molecular cell, Oct. 1, 1998, 2(4):437-445.
Beuth et al., "Structure of a *Mycobacterium tuberculosis* NusA-RNA complex," The EMBO journal, Oct. 19, 2005, 24(20):3576-3587.
Bjorck et al., "Purification and some properties of streptococcal protein G, a novel IgG-binding reagent," J. Immunol., 1984, 133:969-974.
Braddock et al., "Structure and dynamics of KH domains from FBP bound to single-stranded DNA," Nature, Feb. 2002, 415(6875):1051-1056.
Buchan et al., "Eukaryotic stress granules: the ins and outs of translation," Molecular cell, Dec. 24, 2009, 36(6):932-941.
Buxbaum et al., "Single β-actin mRNA detection in neurons reveals a mechanism for regulating its translatability," Science, Jan. 24, 2014, 343(6169): 5 Pages.
Cao et al., "A universal strategy for regulating mRNA translation in prokaryotic and eukaryotic cells," Nucleic acids research, Apr. 30, 2015 43(8):4353-4362.
Cencic et al., "Protospacer adjacent motif (PAM)-distal sequences engage CRISPR Cas9 DNA target cleavage," PloS one, Oct. 2, 2014, 9(10):e109213, 13 Pages.
Chen et al., "Dynamic imaging of genomic loci in living human cells by an optimized CRISPR/Cas system," Cell, Dec. 19, 2013, 155(7):1479-1491.
Cheong et al., "Engineering RNA sequence specificity of Pumilio repeats," Proceedings of the National Academy of Sciences, Sep. 12, 2006, 103(37):13635-13639.
Cho et al., "Targeted genome engineering in human cells with the Cas9 RNA-guided endonuclease," Nature biotechnology, Mar. 2013, 31(3): 230-232.
Chou et al., "Picky: oligo microarray design for large genomes," Bioinformatics, 2004, 20(17):2893-28902.
Cong et al., "Multiplex genome engineering using CRISPR/Cas systems," Science, Feb. 15, 2013, 339(6121): 6 Pages.
Cooke et al., "Targeted translational regulation using the PUF protein family scaffold," Proceedings of the National Academy of Sciences, Sep. 20, 2011, 108(38):15870-15875.
DeJesus-Hernandez et al., "Expanded GGGGCC hexanucleotide repeat in noncoding region of C9ORF72 causes chromosome 9p-linked FTP and ALS," Neuron, Oct. 20, 2011, 72(2): 245-256.
Delebecque et al., "Organization of intracellular reactions with rationally designed RNA assemblies," Science, Jul. 22, 2011 333(6041): 7 Pages.
Dong et al., "Quantitative analysis of the packaging capacity of recombinant adeno-associated virus," Human gene therapy, Nov. 10, 1996, 7(17):2101-2112.
Donnelly et al., "Limited availability of ZBP1 restricts axonal mRNA localization and nerve regeneration capacity," The EMBO journal, Nov. 16, 2011, 30(22):4665-4677.
Dow et al., "Inducible in vivo genome editing with CRISPR-Cas9," Nature biotechnology, Apr. 2015, 33(4): 7 Pages.

Dueber et al., "Synthetic protein scaffolds provide modular control over metabolic flux," Nature biotechnology, Aug. 2009, 27(8): 9 Pages.
Durand et al., "The inside out of lentiviral vectors," Viruses, Feb. 2011, 3(2):132-159.
Eliasson et al., "Chimeric IgG-binding receptors engineered from staphylococcal protein A and streptococcal protein G," J. Biol. Chem., 1988, 263:4323-4327.
Encode Project ConsortiL.lm, The; "An integrated encyclopedia of ONA elements in the human genome," Nature, 2012, 489(7414): 57-74.
Esvelt et al., "Orthogonal Cas9 proteins for RNA-guided gene regulation and editing," Nature methods, Nov. 2013, 10(11): 8 Pages.
Filipovska et al., "A universal code for RNA recognition by PUF proteins," Nature chemical biology, Jul. 2011, 7(7): 4 Pages.
Fouts et al., "Functional recognition of fragmented operator sites by R17/MS2 coat protein, a translational repressor," Nucleic acids research, Nov. 1, 1997, 25(22):4464-4473.
Fu et al., "Improving CRISPR-Cas nuclease specificity using truncated guide RNAs," Nature biotechnology, Mar. 2014, 32(3): 8 Pages.
Fusco et al., Single mRNA molecules demonstrate probabilistic movement in living mammalian cells, Current Biology, Jan. 21, 2003, 13(2):161-167.
Garcia et al., "MS2 coat proteins bound to yeast mRNAs block 5' to 3' degradation and trap mRNA decay products: implications for the localization of mRNAs by MS2-MCP system," Rna, Aug. 1, 2015, 21(8): 4 Pages.
Geisler et al., "RNA in unexpected places: long non-coding RNA functions in diverse cellular contexts," Nature reviews Molecular cell biology, Nov. 2013, 14(11): 14 Pages.
Gentz et al., "Bioassay for trans-activation using purified human immunodeficiency virus tat-encoded protein: trans-activation requires mRNA synthesis," Proc. Natl. Acad. Sci., 1989, 86:821-824.
German-Retana et al., "Mutational analysis of plant cap-binding protein eIF4E reveals key amino acids involved in biochemical functions and potyvirus infection," Journal of virology, Aug. 1, 2008, 82(15):7601-7612.
Gerstberger et al., "Evolutionary conservation and expression of human RNA-binding proteins and their role in human genetic disease," InSystems biology of RNA binding proteins, 2014 pp. 1-55.
Gilbert et al., "CRISPR-mediated modular RNA-guided regulation of transcription in eukaryotes," Cell, Jul. 18, 2013, 154(2):442-451.
Graveley et al., "Arginine/serine-rich domains of SR proteins can function as activators of pre-mRNA splicing," Molecular cell, Apr. 1, 1998, 1(5):765-771.
Gritsenko et al., "Sequence features of viral and human Internal Ribosome Entry Sites predictive of their activity," PLoS computational biology, Sep. 18, 2017, 13(9):e1005734, 23 Pages.
Guss et al., "Structure of the IgG-binding regions of streptococcal protein G," EMBO J., 1986, 5: 1567-1575.
Hale et al., "RNA-guided RNA cleavage by a CRISPR RNA-Cas protein complex," Cell, Nov. 25, 2009, 139(5):945-956.
Hendel et al., "Chemically modified guide RNAs enhance CRISPR-Cas genome editing in human primary cells," Nature biotechnology, Jun. 29, 2015, 33(9):985-989.
Hjelm et al., "Immunologically active and structurally similar fragments of protein A from *Staphylococcus aureus*," Eur. J. Biochem., 1975, 57:395-403.
Ho et al., "Colocalization of muscleblind with RNA foci is separable from mis-regulation of alternative splicing in myotonic dystrophy," Journal of cell science, Jul. 1, 2005, 118(13):2923-2933.
Hsu et al., "Development and applications of CRISPR-Cas9 for genome engineering," Cell, 2014, 156(6):1262-1278.
Hua et al., "Antisense correction of SMN2 splicing in the CNS rescues necrosis in a type III SMA mouse model," Genes & development, Aug. 1, 2010, 24(15):1634-1644.
Hua et al., "Antisense masking of an hnRNP A1/A2 intronic splicing silencer corrects SMN2 splicing in transgenic mice," The American Journal of Human Genetics, Apr. 11, 2008, 82(4):834-848.

(56) References Cited

OTHER PUBLICATIONS

Hua et al., Peripheral SMN restoration is essential for long-term rescue of a severe spinal muscular atrophy mouse model, Nature, Oct. 2011, 478(7367):123-126.
Hwang et al., "Efficient in vivo genome editing using RNA-guided nucleases," Nature biotechnology, Mar. 2013, 31(3): 12 Pages.
International Search Report and Written Opinion in Application No. PCT/US19/28580, dated Aug. 27, 2019, 14 pages.
Jiang F, "Structures of a CRISPR-Cas9 R-loop complex primed for DNA cleavage," Science, 2016, 351(6275): 9 Pages.
Jinek et al., "A programmable dual RNA-guided DNA endonuclease in adaptive bacterial immunity," Science, 2012, 337(6096): 14 Pages.
Jinek et al., "RNA-programmed genome editing in human cells," elife, Jan. 29, 2013, 2:e00471, 9 Pages.
Kedersha et al., "Mammalian stress granules and processing bodies," Methods in enzymology, Jan. 1, 2007, 431:61-81.
Kelley et al., "Versatility of chemically synthesized guide RNAs for CRISPR-Cas9 genome editing," J. of Biotechnology, 2016, 233:25 Pages.
Kislauskis et al., "Sequences responsible for intracellular localization of beta-actin messenger RNA also affect cell phenotype," The Journal of cell biology, Oct. 15, 1994, 127(2):441-451.
Kodama et al., "An improved bimolecular fluorescence complementation assay with a high signal-to-noise ratio," Biotechniques, 2010, 49(5):793-805.
Konermann et al., "Transcriptome engineering with RNA-targeting type VI-D CRISPR effectors," Cell, Apr. 19, 2018, 173(3): 27 Pages.
Kuscu et al., "Genome-wide analysis reveals characteristics of off-target sites bound by the Cas9 endonuclease," Nature biotechnology, Jul. 2014, 32(7): 9 Pages.
Laird-Offringa et al., "Analysis of RNA-binding proteins by in vitro genetic selection: identification of an amino acid residue important for locking U1A onto its RNA target," Proceedings of the National Academy of Sciences, Dec. 5, 1995, 92(25):11859-11863.
Li et al., "Heritable gene targeting in the mouse and rat using a CRISPR-Cas system," Nature biotechnology, Aug. 2013, 31(8):681-683.
Li et al., "Stress granules as crucibles of ALS pathogenesis," Journal of cell biology, Apr. 29, 2013, 201(3):361-372.
Lionnet et al., "A transgenic mouse for in vivo detection of endogenous labeled mRNA," Nature methods, Feb. 2011, 8(2): 9 Pages.
Lovci et al., "Rbfox proteins regulate alternative mRNA splicing through evolutionarily conserved RNA bridges," Nature structural & molecular biology, Dec. 2013, 20(12): 11 Pages.
Lu et al., "MicroRNA expression profiles classify human cancers," nature, Jun. 2005, 435(7043):834-838.
MacKenzie et al., "Stromal expression of miR-21 identifies high-risk group in triple-negative breast cancer," The American journal of pathology, Dec. 1, 2014, 184(12):3217-3225.
Maddalo et al., "In vivo engineering of oncogenic chromosomal rearrangements with the CRISPR/Cas9 system," Nature, Dec. 2014, 516(7531): 15 Pages.
Mali et al., "CAS9 transcriptional activators for target specificity screening and paired nickases for cooperative genome engineering," Nature biotechnology, Sep. 2013, 31(9): 8 Pages.
Mali et al., "RNA-guided human genome engineering via Cas9," Science, Feb. 15, 2013, 339(6121): 5 Pages.
Manders et al., "Dynamics of three-dimensional replication patterns during the S-phase, analysed by double labelling of DNA and confocal microscopy," Journal of cell science, Nov. 1, 1992, 103(3):857-862.
Meng et al., "Towards a therapy for Angelman syndrome by targeting a long non-coding RNA," Nature, Feb. 2015, 518(7539): 16 Pages.
Mohr et al., "CRISPR guide RNA design for research applications," FEBS Journal, 2016, 283(17):3232-3238.

Muddashetty et al., "Reversible inhibition of PSD-95 mRNA translation by miR-125a, FMRP phosphorylation, and mGluR signaling," Molecular cell, Jun. 10, 2011, 42(5):673-688.
Nakayama et al., "Simple and efficient CRISPR/Cas9-mediated targeted mutagenesis in Xenopus tropicalis," genesis, Dec. 2013, 51(12):835-843.
Nelles et al., "Applications of Cas9 as an RNA-programmed RNA-binding protein," BioEssays, Jul. 2015, 37(7): 8 Pages.
Nelles et al., "Programmable RNA tracking in live cells with CRISPR/Cas9," Cell, Apr. 7, 2016, 165(2): 10 Pages.
Nissim-Rafinia et al., "Splicing regulation as a potential genetic modifier," TRENDS in Genetics, Mar. 1, 2002, 18(3):123-127.
Ozawa et al., "Imaging dynamics of endogenous mitochondrial RNA in single living cells," Nature methods, May 2007, 4(5):413-419.
Paige et al., "RNA mimics of green fluorescent protein," Science, Jul. 29, 2011, 333(6042): 35 Pages.
Park et al., "Visualization of dynamics of single endogenous mRNA labeled in live mouse," Science, Jan. 24, 2014, 343(6169):422-424.
Partial International Search Report dated Feb. 28, 2017 for corresponding Application No. PCT/US2016/063429.
Pasca et al. "Using iPSC-derived neurons to uncover cellular phenotypes associated with Timothy syndrome," Nat Med, 2011, 17(12):18 Pages.
Passini et al., "Antisense oligonucleotides delivered to the mouse CNS ameliorate symptoms of severe spinal muscular atrophy," Science translational medicine, Mar. 2, 2011, 3(72):72ra18, 11 Pages.
PCT International Preliminary Report on Patentability in International Appln. No. PCT/US2019/028580, dated Oct. 29, 2020, 9 pages.
PCT International Search Report and Written Opinion dated May 8, 2017 for corresponding Application PCT/US2016/063429, filed Nov. 22, 2016; 21 pages.
Price et al., "Cas9-mediated targeting of viral RNA in eukaryotic cells," Proceedings of the National Academy of Sciences, May 12, 2015, 112(19): 14 Pages.
Qi et al., "Repurposing CRISPR as an RNA-guided platform for sequence-specific control of gene expression," Cell, Feb. 28, 2013, 152(5):1173-1183.
Rackham et al., "Visualization of RNA-protein interactions in living cells: FMRP and IMP1 interact on mRNAs," The EMBO journal, Aug. 18, 2004, 23(16):3346-3355.
Rahdar et al., "Synthetic CRISPR RNA-Cas9-guided genome editing in human cells," Proceedings of the National Academy of Sciences, Dec. 22, 2015, 112(51):E7110-7117.
Rath et al., "Genetically encoded tools for RNA imaging in living cells," Current opinion in biotechnology, Feb. 1, 2015, 31:42-49.
Renton et al., "A hexanucleotide repeat expansion in C9ORF72 is the cause of chromosome 9p21-linked ALS-FTD," Neuron., Oct. 20, 2011, 72(2):257-268.
Sachdeva et al., "In vivo co-localization of enzymes on RNA scaffolds increases metabolic production in a geometrically dependent manner," Nucleic acids research, Aug. 18, 2014, 42(14):9493-9503.
Sampson et al., "A CRISPR/Cas system mediates bacterial innate immune evasion and virulence," Nature, May 2013, 497(7448): 5 Pages.
Sander et al., "CRISPR-Cas systems for editing, regulating and targeting genomes," Nature biotechnology, Apr. 2014, 32(4):347-355.
Schindelin et al., "Fiji: an open-source platform for biological-image analysis," Nature methods, Jul. 2012, 9(7):676-682.
Shestakova et al., "The physiological significance of β-actin mRNA localization in determining cell polarity and directional motility," Proceedings of the National Academy of Sciences, Jun. 19, 2001, 98(13):7045-7050.
Shin et al., "Live-cell imaging of Pol II promoter activity to monitor gene expression with RNA IMAGEtag reporters," Nucleic acids research, Jun. 17, 2014, 42(11):e90, 9 Pages.
Sikkema, "An Fc-binding protein," Amer. Biotech. Lab., 1989, 7:42.

(56) References Cited

OTHER PUBLICATIONS

Sjoquist et al., "Protein A isolated from *Staphylococcus aureus* after digestion with lysostaphin," Eur. J. Biochem., 1972, 29:572-578.
Staals et al., "RNA targeting by the type III-A CRISPR-Cas Csm complex of Thermus thermophilus," Molecular cell, Nov. 20, 2014, 56(4):518-530.
Stepto et al., "Modelling C9ORF72 hexanucleotide repeat expansion in amyotrophic lateral sclerosis and frontotemporal dementia," Acta Neuropathol., 2014, 127(3):377-89.
Sternberg et al., "DNA interrogation by the CRISPR RNA-guided endonuclease Cas9," Nature, Mar. 2014, 507(7490): 17 Pages.
Strack et al., "A superfolding Spinach2 reveals the dynamic nature of trinucleotide repeat-containing RNA," Nature methods, Dec. 2013, 10(12): 9 Pages.
Sunbul et al., "Contact-Mediated Quenching for RNA Imaging in Bacteria with a Fluorophore-Binding Aptamer," Angewandte Chemie International Edition, Dec. 9, 2013, 52(50), 13401-13404.
Swiech et al., "In vivo interrogation of gene function in the mammalian brain using CRISPR-Cas9," Nature biotechnology, Jan. 2015, 3(1): 9 Pages.
Tourriere et al., "The RasGAP-associated endoribonuclease G3BP assembles stress granules," The Journal of cell biology, Mar. 17, 2003, 160(6):823-831.
Tyagi et al., "Molecular beacons: probes that fluoresce upon hybridization," Nature biotechnology, Mar. 1996, 14(3):303-308.
Unsworth et al., "mRNA escape from stress granule sequestration is dictated by localization to the endoplasmic reticulum," The FASEB journal, Sep. 2010, 24(9):3370-3380.
Urnov et al., "Genome editing with engineered zinc finger nucleases," Nature Reviews Genetics, Sep. 2010, 11(9):636-646.
Wang et al., "Crystal structure of a Pumilio homology domain," Molecular cell, Apr. 1, 2001, 7(4):855-865.
Wang et al., "Modular recognition of RNA by a human pumilio-homology domain," Cell, Aug. 23, 2002, 110(4):501-512.
Wernersson et al., "Oligo Wiz 2.0—integrating sequence feature annotation into the design of microarray probes," Nucleic acids research, Jul. 1, 2005, 33(suppl_2):W611-615.
Weyn-Van Hentenryci et al., "HITS-CLIP and integrative modeling define the Rbfox splicing-regulatory network linked to brain development and autism," Cell Rep., Mar. 27, 2014, 6(6): 1139-1152.
Wiedenheft et al., "RNA-guided genetic silencing systems in bacteria and archaea," Nature, Feb. 2012, 482(7385):331-338.
Wilson et al., "The structure of an antigenic determinant in a protein," Cell, 1984, 37:767-778.
Wojciechowska et al., "Cellular toxicity of expanded RNA repeats: focus on RNA foci," Human Molecular Genetics, 2011, 20:3811-3821.
Wright et al., "Rational design of a split-Cas9 enzyme complex," Proceedings of the National Academy of Sciences, Mar. 10, 2015, 112(10):2984-2989.
Wu et al., "Target specificity of the CRISPRCas9 system," Quant Biol. 2014, 2(2):59-70.
Yan et al., "Cas13d is a compact RNA-targeting type VI CRISPR effector positively modulated by a WYL-domain-containing accessory protein," Molecular cell, Apr. 19, 2018 70(2):327-339.
Yang et al., "Effective gene targeting in rabbits using RNA-guided Cas9 nucleases," Journal of molecular cell biology, Feb. 1, 2014, 6(1):97-99.
Yeo. et al., "An RNA code for the FOX2 splicing regulator revealed by mapping RNA-protein interactions in stem cells," Nature structural & molecular biology, Feb. 2009, 16(2): 130-137.
Zambrowicz et al., "Disruption of overlapping transcripts in the ROSA beta geo 26 gene trap strain leads to widespread expression of beta-galactosidase in mouse embryos and hematopoietic cells," Proc. Natl. Acad. Sci., 1997, 94:3789-3794.
Zetche et al., "A split-Cas9 architecture for inducible genome editing and transcription modulation," Nat Biotechnol., 2015, 33(2): 6 Pages.

Zetsche et al., A split-Cas9 architecture for inducible genome editing and transcription modulation, Nature biotechnology, Feb. 2015, 33(2): 3 Pages.
Zhang et al., "Treatment of type 1 myotonic dystrophy by engineering site-specific RNA endonucleases that target (CUG)(n)," Molecular Therapy, Feb. 1, 2014, 22(2):312-320.
Zuris et al., "Efficient Delivery of Genome-Editing Proteins in vitro and in vivo," Nature Biotechnol., Jan. 2015, 33(1): 26 Pages.
Cox et al., "RNA editing with CRISPR_Cas13," Science, 2017, 358(6366):1019-1027.
Fernanda et al., "Current strategies for site-directed RNA editing using ADARs," Methods, 2018, 156:16-24.
Extended European Search Report in EP Appln. No. 18799398, dated May 15, 2020, 11 pages.
Supplementary Partial European Search Report in European Appln. No. 19788702.9, dated Jun. 11, 2021, 12 pages.
Anant et al., "Molecular mechanisms of apolipoprotein B mRNA editing," Current opinion in lipidology, Apr. 1, 2001, 12(2):159-165.
Blanc et al., "C-to-U RNA editing: mechanisms leading to genetic diversity," Journal of Biological Chemistry, Jan. 17, 2003, 278(3):1395-1398.
Cichowski et al., "NF1 tumor suppressor gene function: narrowing the GAP," Cell, Feb. 23, 2001, 104(4):593-604.
De Zoysa et al., "Posttranscriptional RNA pseudouridylation," The enzymes, Jan. 1, 2017, 41:151-167.
Du et al., "m 6 A RNA methylation controls neural development and is involved in human diseases," Molecular neurobiology, Mar. 2019, 56(3):1596-1606.
GenBank Accession No. NM_019852.4, "*Homo sapiens* methyltransferase like 3 (METTL3), mRNA," Oct. 21, 2018, 6 pages.
Guzzi et al., "Pseudouridylation of tRNA-derived fragments steers translational control in stem cells," Cell, May 17, 2018, 173(5): 40 pages.
Huang et al., "Inducing nonsense suppression by targeted pseudouridylation," nature protocols, Apr. 2012, 7(4):789-800.
Jia et al., "N 6-methyladenosine in nuclear RNA is a major substrate of the obesity-associated FTO," Nature chemical biology, Dec. 2011, 7(12):885-887.
Karijolich et al., "Converting nonsense codons into sense codons by targeted pseudouridylation," Nature, Jun. 2011, 474(7351):395-398.
Karijolich et al., "Transcriptome-wide dynamics of RNA pseudouridylation," Nature reviews Molecular cell biology, Oct. 2015, 16(10): 5 pages.
Li et al., "Targeted mRNA demethylation using an engineered dCas13b-ALKBH5 fusion protein," Nucleic acids research, Jun. 4, 2020, 48(10):5684-5694.
Maity et al., "N6-methyladenosine modification in mRNA: machinery, function and implications for health and diseases," The FEBS journal, May 2016, 283(9):1607-1630.
Mukhopadhyay et al., "C→ U editing of neurofibromatosis 1 mRNA occurs in tumors that express both the type II transcript and apobec-1, the catalytic subunit of the apolipoprotein B mRNA-editing enzyme," The American Journal of Human Genetics, Jan. 1, 2002, 70(1):38-50.
PCT International Preliminary Report on Patentability in International Appln. No. PCT/US2019/049182, dated Mar. 11, 2021, 7 pages.
PCT International Preliminary Report on Patentability in International Appln. No. PCT/US2019/049197, dated Mar. 11, 2021, 9 pages.
PCT International Search Report and Written Opinion in International Appln. No. PCT/US2019/049182, dated Dec. 6, 2019, 11 pages.
PCT International Search Report and Written Opinion in International Appln. No. PCT/US2019/049197, dated Dec. 12, 2019, 12 pages.
Shi et al., "YTHDF3 facilitates translation and decay of N 6-methyladenosine-modified RNA," Cell research, Mar. 2017, 27(3):315-328.
Skuse et al., "The neurofibromatosis type I messenger RNA undergoes base-modification RNA editing," Nucleic acids research, Feb. 1, 1996, 24(3):478-486.

(56) References Cited

OTHER PUBLICATIONS

Vu et al., "C-to-U editing and site-directed RNA editing for the correction of genetic mutations," Bioscience trends, Jun. 30, 2017, 11(3):243-253.

Warda et al., "Human METTL16 is a N6-methyladenosine (m6A) methyltransferase that targets pre-mRNAs and various non-coding RNAs," EMBO reports, Nov. 2017, 18(11):2004-2014.

Xiao et al., "Functionality and substrate specificity of human box H/ACA guide RNAs," Rna, Jan. 1, 2009, 15(1):176-186.

Xiao et al., "Nuclear m6A reader YTHDC1 regulates mRNA splicing," Molecular cell, Feb. 18, 2016, 61(4):507-519.

Yamanaka et al., "A novel translational repressor mRNA is edited extensively in livers containing tumors caused by the transgene expression of the apoB mRNA-editing enzyme," Genes & development, Feb. 1, 1997, 11(3):321-333.

Zaganelli et al., "The pseudouridine synthase RPUSD4 is an essential component of mitochondrial RNA granules," Journal of Biological Chemistry, Mar. 17, 2017, 292(11):4519-4532.

Allocca et al., "Novel adeno-associated virus serotypes efficiently transduce murine photoreceptors," Journal of virology, Oct. 15, 2007, 81(20):11372-11380.

Asokan et al., "The AAV vector toolkit: poised at the clinical crossroads," Molecular Therapy, Apr. 1, 2012, 20(4):699-708.

Basolo et al., "RET protein expression has no prognostic impact on the long-term outcome of papillary thyroid carcinoma," European journal of endocrinology, Nov. 1, 2001, 145(5):599-604.

Borghardt et al., "Inhaled Therapy in Respiratory Disease: The Complex Interplay of Pulmonary Kinetic Processes," Canadian Respiratory Journal, 2018, 1-11.

Braasch et al., "Novel antisense and peptide nucleic acid strategies for controlling gene expression," Biochemistry, Apr. 9, 2002,41(14):4503-4510.

Brezgin et al., "Dead Cas systems: types, principles, and applications," International journal of molecular sciences, Jan. 2019, 20(23):6041, 26 pages.

Cai et al., "Quantitative assessment of mRNA cap analogues as inhibitors of in vitro translation," Biochemistry, Jun. 29, 1999, 38(26):8538-8547.

Chen et al., "Structure-guided design, synthesis, and evaluation of guanine-derived inhibitors of the eIF4E mRNA-cap interaction," Journal of medicinal chemistiy, Apr. 26, 2012, 55(8):3837-3851.

Cokol et al., "Finding nuclear localization signals," EMBO reports, Nov. 1, 2000, 1(5):411-415.

De Mesmaeker et al., "Antisense oligonucleotides," Accounts of Chemical Research, Sep. 1, 1995, 28(9):366-374.

Deer et al., "High-level expression of proteins in mammalian cells using transcription regulatory sequences from the Chinese hamster EF-1α gene," Biotechnology progress, 2004, 20(3):880-889.

Deyle et al., "Adeno-associated virus vector integration," Current opinion in molecular therapeutics, Aug. 2009, 11(4):442-447.

Durocher et al., "High-level and high-throughput recombinant protein production by transient transfection of suspension-growing human 293-EBNA1 cells," Nucleic Acids Research, 2002, 30(2), 9 pages.

Englisch et al., "Chemically modified oligonucleotides as probes and inhibitors," Angewandte Chemie International Edition in English, Jun. 1991, 30(6):613-629.

Esakova et al., "Of proteins and RNA: the RNase P/MRP family," Rna, Sep. 1, 2010, 16(9):1725-1747.

Extended European Search Report in EP Appln. No. 19788702.9, dated Oct. 13, 2021, 11 pages.

Freitas et al., "Mechanisms and signals for the nuclear import of proteins," Current genomics, Dec. 2009, 10(8):550-557.

Gebeyehu et al., "Novel biotinylated nucleotide-analogs for labeling and colorimetric detection of DNA," Nucleic acids research, Jun. 11, 1987, 15(11):4513-4534.

GenBank Accession No. FJ209302, "*Homo sapiens* MALAT1-associated small cytoplasmic RNA, complete sequence," Dec. 2, 2008.

Hamajima et al., "Intranasal administration of HIV-DNA vaccine formulated with a polymer, carboxymethylcellulose, augments mucosal antibody production and cell-mediated immune response," Clinical immunology and immunopathology, Aug. 1, 1998, 88(2):205-210.

Heasman, "Morpholino oligos: making sense of antisense?" Developmental biology, Mar. 15, 2002, 243(2):209-214.

Hinnebusch, "Molecular Mechanism of Scanning and Start Codon Selection in Eukaryotes," Microbiology and Molecular Biology Reviews, Sep. 2011, 75(3):434-467.

International Preliminary Report on Patentability in International Appln. No. PCT/US2016/063429, dated May 29, 2018, 12 pages.

International Preliminary Report on Patentability in International Appln. PCT /US2020/028501, dated Oct. 28, 2021, 10 pages.

International Preliminary Report on Patentability in International Appln. PCT/US2020/028546, dated Oct. 28, 2021, 11 pages.

International Search Report and Written Opinion in International Appln. No. PCT/US2020/028501, dated Sep. 25, 2020, 12 pages.

International Search Report and Written Opinion in International Appln. No. PCT/US2020/028546, dated Jul. 14, 2020, 13 pages.

Kadokura et al., "Solid-phase synthesis of a 5'-terminal TMG-capped trinucleotide block of UI snRNA," Tetrahedron Letters, Dec. 10, 2001, 42(50):8853-8856.

Khani et al., "AAV-mediated expression targeting of rod and cone photoreceptors with a human rhodopsin kinase promoter," Investigative ophthalmology & visual science, Sep. 1, 2007, 48(9):3954-3961.

Kirsebom, "RNase P RNA mediated cleavage: substrate recognition and catalysis," Biochimie, Oct. 1, 2007, 89(10):1183-1194.

Kormann et al., "Expression of therapeutic proteins after delivery of chemically modified mRNA in mice," Nature biotechnology, Feb. 2011, 29(2):154-157.

Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron, Apr. 2, 1998, 54(14):3607-3630.

Lacerra et al., "Restoration of hemoglobin A synthesis in erythroid cells from peripheral blood of thalassemic patients," Proceedings of the National Academy of Sciences, Aug. 15, 2000, 97(17):9591-9596.

Lai et al., "Unexpected diversity of RNase P, an ancient tRNA processing enzyme: challenges and prospects," FEBS letters, Jan. 21, 2010, 584(2):287-296.

Martin, "Ein neuer Zugang zu 2'-O-Alkylribonucleosiden und Eigenschaften deren Oligonucleotide," Helvetica Chimica Acta, Mar. 22, 1995, 78(2):486-504.

Massie et al., "Inducible overexpression of a toxic protein by an adenovirus vector with a tetracycline-regulatable expression cassette," Journal of Virology, Mar. 1, 1998, 72(3):2289-2296.

Mingozzi et al., "Therapeutic in vivo gene transfer for genetic disease using AAV: progress and challenges," Nature reviews genetics, May 2011, 12(5):341-355.

Muzyczka, "Use of adeno-associated virus as a general transduction vector for mammalian cells," Viral expression vectors, 1992, 97-129.

Nasevicius et al., "Effective targeted gene 'knockdown' in zebrafish," Nature genetics, Oct. 2000, 26(2):216-220.

Nielsen "Sequence-selective recognition of DNA by strand displacement with a thymine-substituted polyamide," Science, Dec. 6, 1991, 254(5037):1497-1500.

Ohkubo et al., "Efficient solid-phase synthesis of oligodeoxynucleotides having a 5'-terminal 2, 2,7-trimethylguanosine pyrophosphate linkage," Bioorganic & medicinal chemistry, Jul. 1, 2009, 17(13):4819-4824.

Pang et al., "Comparative analysis of in vivo and in vitro AAV vector transduction in the neonatal mouse retina: effects of serotype and site of administration," Vision research, Feb. 1, 2008, 48(3):377-385.

Singh et al., "LNA (locked nucleic acids): synthesis and high-affinity nucleic acid recognition," Chemical communications, 1998, (4):455-456.

Soukarieh et al., "Design of nucleotide-mimetic and non-nucleotide inhibitors of the translation initiation factor eIF4E: Synthesis,

(56) References Cited

OTHER PUBLICATIONS structural and functional characterisation," European journal of medicinal chemistry, Nov. 29, 2016, 124:200-217.

Strenkowska et al., "Cap analogs modified with 1, 2-dithiodiphosphate moiety protect mRNA from decapping and enhance its translational potential. Nucleic acids research," Nov. 16, 2016, 44(20):9578-9590.

Wahlestedt et al., "Potent and nontoxic antisense oligonucleotides containing locked nucleic acids," Proceedings of the National Academy of Sciences, May 9, 2000, 97(10):5633-5638.

Walczak et al., "A novel route for preparing 5' cap mimics and capped RNAs: phosphate-modified cap analogues obtained via click chemistry," Chemical science, 2017, 8(1):260-267.

Wang et al., "Cyclohexene nucleic acids (CeNA): serum stable oligonucleotides that activate RNase H and increase duplex stability with complementary RNA," Journal of the American Chemical Society, Sep. 13, 2000, 122(36):8595-8602.

Wang et al., "Probing RNA recognition by human ADAR2 using a high-throughput mutagenesis method," Nucleic acids research, Nov. 2016, 44(20):9872-9880.

Warren et al., "Highly efficient reprogramming to pluripotency and directed differentiation of human cells with synthetic modified mRNA," Cell stem cell, Nov. 5, 2010, 7(5):618-630.

Xu et al., "A CRISPR-dCas toolbox for genetic engineering and synthetic biology," Journal of molecular biology, Jan. 4, 2019, 431(1):34-47.

\* cited by examiner

Sp-CREDITv1

Sa-CREDITv1

SEQUENCE LISTING

<160> NUMBER OF SEQ ID NOS: 55

<210> SEQ ID NO 1
<211> LENGTH: 1368
<212> TYPE: PRT
<213> ORGANISM: Streptococcus pyogenes

<400> SEQUENCE: 1

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365
```

```
Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
```

-continued

```
            785                 790                 795                 800
Val Glu Asn Thr Gln Leu Gln Asn Glu Lys Leu Tyr Leu Tyr Tyr Leu
                    805                 810                 815
Gln Asn Gly Arg Asp Met Tyr Val Asp Gln Glu Leu Asp Ile Asn Arg
                    820                 825                 830
Leu Ser Asp Tyr Asp Val Asp His Ile Val Pro Gln Ser Phe Leu Lys
                    835                 840                 845
Asp Asp Ser Ile Asp Asn Lys Val Leu Thr Arg Ser Asp Lys Asn Arg
    850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                    885                 890                 895
Phe Asp Asn Leu Thr Lys Ala Glu Arg Gly Gly Leu Ser Glu Leu Asp
                    900                 905                 910
Lys Ala Gly Phe Ile Lys Arg Gln Leu Val Glu Thr Arg Gln Ile Thr
                    915                 920                 925
Lys His Val Ala Gln Ile Leu Asp Ser Arg Met Asn Thr Lys Tyr Asp
                    930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                    965                 970                 975
Glu Ile Asn Asn Tyr His His Ala His Asp Ala Tyr Leu Asn Ala Val
                    980                 985                 990
Val Gly Thr Ala Leu Ile Lys Lys Tyr Pro Lys Leu Glu Ser Glu Phe
                    995                 1000                1005
Val Tyr Gly Asp Tyr Lys Val Tyr Asp Val Arg Lys Met Ile Ala
                    1010                1015                1020
Lys Ser Glu Gln Glu Ile Gly Lys Ala Thr Ala Lys Tyr Phe Phe
                    1025                1030                1035
Tyr Ser Asn Ile Met Asn Phe Phe Lys Thr Glu Ile Thr Leu Ala
                    1040                1045                1050
Asn Gly Glu Ile Arg Lys Arg Pro Leu Ile Glu Thr Asn Gly Glu
                    1055                1060                1065
Thr Gly Glu Ile Val Trp Asp Lys Gly Arg Asp Phe Ala Thr Val
                    1070                1075                1080
Arg Lys Val Leu Ser Met Pro Gln Val Asn Ile Val Lys Lys Thr
                    1085                1090                1095
Glu Val Gln Thr Gly Gly Phe Ser Lys Glu Ser Ile Leu Pro Lys
                    1100                1105                1110
Arg Asn Ser Asp Lys Leu Ile Ala Arg Lys Lys Asp Trp Asp Pro
                    1115                1120                1125
Lys Lys Tyr Gly Gly Phe Asp Ser Pro Thr Val Ala Tyr Ser Val
                    1130                1135                1140
Leu Val Val Ala Lys Val Glu Lys Gly Lys Ser Lys Lys Leu Lys
                    1145                1150                1155
Ser Val Lys Glu Leu Leu Gly Ile Thr Ile Met Glu Arg Ser Ser
                    1160                1165                1170
Phe Glu Lys Asn Pro Ile Asp Phe Leu Glu Ala Lys Gly Tyr Lys
                    1175                1180                1185
Glu Val Lys Lys Asp Leu Ile Ile Lys Leu Pro Lys Tyr Ser Leu
                    1190                1195                1200
```

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 2
<211> LENGTH: 1053
<212> TYPE: PRT
<213> ORGANISM: Staphylococcus aureus

<400> SEQUENCE: 2

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg His Arg Ile
        50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg

-continued

```
            195                 200                 205
Arg Thr Tyr Tyr Glu Gly Pro Gly Glu Gly Ser Pro Phe Gly Trp Lys
210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
            245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
            275                 280                 285

Lys Gln Lys Lys Lys Pro Thr Leu Lys Gln Ile Ala Lys Glu Ile Leu
290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
            325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
            355                 360                 365

Thr Asn Leu Asn Ser Glu Leu Thr Gln Glu Glu Ile Glu Gln Ile Ser
370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
            405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
            435                 440                 445

Val Val Lys Arg Ser Phe Ile Gln Ser Ile Lys Val Ile Asn Ala Ile
450                 455                 460

Ile Lys Lys Tyr Gly Leu Pro Asn Asp Ile Ile Glu Leu Ala Arg
465                 470                 475                 480

Glu Lys Asn Ser Lys Asp Ala Gln Lys Met Ile Asn Glu Met Gln Lys
            485                 490                 495

Arg Asn Arg Gln Thr Asn Glu Arg Ile Glu Glu Ile Ile Arg Thr Thr
            500                 505                 510

Gly Lys Glu Asn Ala Lys Tyr Leu Ile Glu Lys Ile Lys Leu His Asp
            515                 520                 525

Met Gln Glu Gly Lys Cys Leu Tyr Ser Leu Glu Ala Ile Pro Leu Glu
530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
            565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
            595                 600                 605

Leu Asn Leu Ala Lys Gly Lys Gly Arg Ile Ser Lys Thr Lys Lys Glu
            610                 615                 620
```

```
Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
            645                 650                 655

Met Asn Leu Leu Arg Ser Tyr Phe Arg Val Asn Asn Leu Asp Val Lys
        660                 665                 670

Val Lys Ser Ile Asn Gly Gly Phe Thr Ser Phe Leu Arg Arg Lys Trp
    675                 680                 685

Lys Phe Lys Lys Glu Arg Asn Lys Gly Tyr Lys His His Ala Glu Asp
690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
        755                 760                 765

Tyr Lys Tyr Ser His Arg Val Asp Lys Lys Pro Asn Arg Glu Leu Ile
770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Glu Glu Thr Gly Asn Tyr
850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
        915                 920                 925

Lys Asn Leu Asp Val Ile Lys Lys Glu Asn Tyr Tyr Glu Val Asn Ser
        930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
            965                 970                 975

Glu Leu Tyr Arg Val Ile Gly Val Asn Asn Asp Leu Leu Asn Arg Ile
        980                 985                 990

Glu Val Asn Met Ile Asp Ile Thr Tyr Arg Glu Tyr Leu Glu Asn Met
        995                 1000                1005

Asn Asp Lys Arg Pro Pro Arg Ile Ile Lys Thr Ile Ala Ser Lys
    1010                1015                1020

Thr Gln Ser Ile Lys Lys Tyr Ser Thr Asp Ile Leu Gly Asn Leu
    1025                1030                1035
```

```
Tyr Glu  Val Lys Ser Lys Lys  His Pro Gln Ile Ile  Lys Lys Gly
    1040             1045                 1050
```

<210> SEQ ID NO 3
<211> LENGTH: 1121
<212> TYPE: PRT
<213> ORGANISM: Streptococcus thermophilus

<400> SEQUENCE: 3

```
Met Ser Asp Leu Val Leu Gly Leu Asp Ile Gly Ile Gly Ser Val Gly
1               5                   10                  15

Val Gly Ile Leu Asn Lys Val Thr Gly Glu Ile Ile His Lys Asn Ser
            20                  25                  30

Arg Ile Phe Pro Ala Ala Gln Ala Glu Asn Asn Leu Val Arg Arg Thr
        35                  40                  45

Asn Arg Gln Gly Arg Arg Leu Ala Arg Arg Lys Lys His Arg Arg Val
    50                  55                  60

Arg Leu Asn Arg Leu Phe Glu Glu Ser Gly Leu Ile Thr Asp Phe Thr
65                  70                  75                  80

Lys Ile Ser Ile Asn Leu Asn Pro Tyr Gln Leu Arg Val Lys Gly Leu
                85                  90                  95

Thr Asp Glu Leu Ser Asn Glu Glu Leu Phe Ile Ala Leu Lys Asn Met
            100                 105                 110

Val Lys His Arg Gly Ile Ser Tyr Leu Asp Asp Ala Ser Asp Asp Gly
        115                 120                 125

Asn Ser Ser Val Gly Asp Tyr Ala Gln Ile Val Lys Glu Asn Ser Lys
    130                 135                 140

Gln Leu Glu Thr Lys Thr Pro Gly Gln Ile Gln Leu Glu Arg Tyr Gln
145                 150                 155                 160

Thr Tyr Gly Gln Leu Arg Gly Asp Phe Thr Val Glu Lys Asp Gly Lys
                165                 170                 175

Lys His Arg Leu Ile Asn Val Phe Pro Thr Ser Ala Tyr Arg Ser Glu
            180                 185                 190

Ala Leu Arg Ile Leu Gln Thr Gln Gln Glu Phe Asn Pro Gln Ile Thr
        195                 200                 205

Asp Glu Phe Ile Asn Arg Tyr Leu Glu Ile Leu Thr Gly Lys Arg Lys
    210                 215                 220

Tyr Tyr His Gly Pro Gly Asn Glu Lys Ser Arg Thr Asp Tyr Gly Arg
225                 230                 235                 240

Tyr Arg Thr Ser Gly Glu Thr Leu Asp Asn Ile Phe Gly Ile Leu Ile
                245                 250                 255

Gly Lys Cys Thr Phe Tyr Pro Asp Glu Phe Arg Ala Ala Lys Ala Ser
            260                 265                 270

Tyr Thr Ala Gln Glu Phe Asn Leu Leu Asn Asp Leu Asn Asn Leu Thr
        275                 280                 285

Val Pro Thr Glu Thr Lys Lys Leu Ser Lys Glu Gln Lys Asn Gln Ile
    290                 295                 300

Ile Asn Tyr Val Lys Asn Glu Lys Ala Met Gly Pro Ala Lys Leu Phe
305                 310                 315                 320

Lys Tyr Ile Ala Lys Leu Leu Ser Cys Asp Val Ala Asp Ile Lys Gly
                325                 330                 335

Tyr Arg Ile Asp Lys Ser Gly Lys Ala Glu Ile His Thr Phe Glu Ala
            340                 345                 350

Tyr Arg Lys Met Lys Thr Leu Glu Thr Leu Asp Ile Glu Gln Met Asp
        355                 360                 365
```

```
Arg Glu Thr Leu Asp Lys Leu Ala Tyr Val Leu Thr Leu Asn Thr Glu
    370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
            405                 410                 415

Ser Ser Ile Phe Gly Lys Gly Trp His Asn Phe Ser Val Lys Leu Met
            420                 425                 430

Met Glu Leu Ile Pro Glu Leu Tyr Glu Thr Ser Glu Glu Gln Met Thr
        435                 440                 445

Ile Leu Thr Arg Leu Gly Lys Gln Lys Thr Thr Ser Ser Ser Asn Lys
    450                 455                 460

Thr Lys Tyr Ile Asp Glu Lys Leu Leu Thr Glu Glu Ile Tyr Asn Pro
465                 470                 475                 480

Val Val Ala Lys Ser Val Arg Gln Ala Ile Lys Ile Val Asn Ala Ala
            485                 490                 495

Ile Lys Glu Tyr Gly Asp Phe Asp Asn Ile Val Ile Glu Met Ala Arg
            500                 505                 510

Glu Thr Asn Glu Asp Asp Glu Lys Lys Ala Ile Gln Lys Ile Gln Lys
    515                 520                 525

Ala Asn Lys Asp Glu Lys Asp Ala Ala Met Leu Lys Ala Ala Asn Gln
    530                 535                 540

Tyr Asn Gly Lys Ala Glu Leu Pro His Ser Val Phe His Gly His Lys
545                 550                 555                 560

Gln Leu Ala Thr Lys Ile Arg Leu Trp His Gln Gln Gly Glu Arg Cys
            565                 570                 575

Leu Tyr Thr Gly Lys Thr Ile Ser Ile His Asp Leu Ile Asn Asn Ser
            580                 585                 590

Asn Gln Phe Glu Val Asp His Ile Leu Pro Leu Ser Ile Thr Phe Asp
    595                 600                 605

Asp Ser Leu Ala Asn Lys Val Leu Val Tyr Ala Thr Ala Asn Gln Glu
    610                 615                 620

Lys Gly Gln Arg Thr Pro Tyr Gln Ala Leu Asp Ser Met Asp Asp Ala
625                 630                 635                 640

Trp Ser Phe Arg Glu Leu Lys Ala Phe Val Arg Glu Ser Lys Thr Leu
            645                 650                 655

Ser Asn Lys Lys Lys Glu Tyr Leu Leu Thr Glu Glu Asp Ile Ser Lys
            660                 665                 670

Phe Asp Val Arg Lys Lys Phe Ile Glu Arg Asn Leu Val Asp Thr Arg
        675                 680                 685

Tyr Ala Ser Arg Val Val Leu Asn Ala Leu Gln Glu His Phe Arg Ala
    690                 695                 700

His Lys Ile Asp Thr Lys Val Ser Val Val Arg Gly Gln Phe Thr Ser
705                 710                 715                 720

Gln Leu Arg Arg His Trp Gly Ile Glu Lys Thr Arg Asp Thr Tyr His
            725                 730                 735

His His Ala Val Asp Ala Leu Ile Ile Ala Ala Ser Ser Gln Leu Asn
            740                 745                 750

Leu Trp Lys Lys Gln Lys Asn Thr Leu Val Ser Tyr Ser Glu Asp Gln
        755                 760                 765

Leu Leu Asp Ile Glu Thr Gly Glu Leu Ile Ser Asp Asp Glu Tyr Lys
    770                 775                 780
```

-continued

```
Glu Ser Val Phe Lys Ala Pro Tyr Gln His Phe Val Asp Thr Leu Lys
785                 790                 795                 800

Ser Lys Glu Phe Glu Asp Ser Ile Leu Phe Ser Tyr Gln Val Asp Ser
            805                 810                 815

Lys Phe Asn Arg Lys Ile Ser Asp Ala Thr Ile Tyr Ala Thr Arg Gln
        820                 825                 830

Ala Lys Val Gly Lys Asp Lys Ala Asp Glu Thr Tyr Val Leu Gly Lys
    835                 840                 845

Ile Lys Asp Ile Tyr Thr Gln Asp Gly Tyr Asp Ala Phe Met Lys Ile
850                 855                 860

Tyr Lys Lys Asp Lys Ser Lys Phe Leu Met Tyr Arg His Asp Pro Gln
865                 870                 875                 880

Thr Phe Glu Lys Val Ile Glu Pro Ile Leu Glu Asn Tyr Pro Asn Lys
            885                 890                 895

Gln Ile Asn Asp Lys Gly Lys Glu Val Pro Cys Asn Pro Phe Leu Lys
        900                 905                 910

Tyr Lys Glu Glu His Gly Tyr Ile Arg Lys Tyr Ser Lys Lys Gly Asn
    915                 920                 925

Gly Pro Glu Ile Lys Ser Leu Lys Tyr Tyr Asp Ser Lys Leu Gly Asn
930                 935                 940

His Ile Asp Ile Thr Pro Lys Asp Ser Asn Asn Lys Val Val Leu Gln
945                 950                 955                 960

Ser Val Ser Pro Trp Arg Ala Asp Val Tyr Phe Asn Lys Thr Thr Gly
            965                 970                 975

Lys Tyr Glu Ile Leu Gly Leu Lys Tyr Ala Asp Leu Gln Phe Asp Lys
        980                 985                 990

Gly Thr Gly Thr Tyr Lys Ile Ser Gln Glu Lys Tyr Asn Asp Ile Lys
    995                 1000                1005

Lys Lys Glu Gly Val Asp Ser Asp Ser Glu Phe Lys Phe Thr Leu
    1010                1015                1020

Tyr Lys Asn Asp Leu Leu Val Lys Asp Thr Glu Thr Lys Glu
    1025                1030                1035

Gln Gln Leu Phe Arg Phe Leu Ser Arg Thr Met Pro Lys Gln Lys
    1040                1045                1050

His Tyr Val Glu Leu Lys Pro Tyr Asp Lys Gln Lys Phe Glu Gly
    1055                1060                1065

Gly Glu Ala Leu Ile Lys Val Leu Gly Asn Val Ala Asn Ser Gly
    1070                1075                1080

Gln Cys Lys Lys Gly Leu Gly Lys Ser Asn Ile Ser Ile Tyr Lys
    1085                1090                1095

Val Arg Thr Asp Val Leu Gly Asn Gln His Ile Ile Lys Asn Glu
    1100                1105                1110

Gly Asp Lys Pro Lys Leu Asp Phe
    1115                1120

<210> SEQ ID NO 4
<211> LENGTH: 1082
<212> TYPE: PRT
<213> ORGANISM: Neisseria meningitidis

<400> SEQUENCE: 4

Met Ala Ala Phe Lys Pro Asn Pro Ile Asn Tyr Ile Leu Gly Leu Asp
1               5                   10                  15

Ile Gly Ile Ala Ser Val Gly Trp Ala Met Val Glu Ile Asp Glu Asp
            20                  25                  30
```

```
Glu Asn Pro Ile Cys Leu Ile Asp Leu Gly Val Arg Val Phe Glu Arg
            35                  40                  45

Ala Glu Val Pro Lys Thr Gly Asp Ser Leu Ala Met Ala Arg Arg Leu
 50                  55                  60

Ala Arg Ser Val Arg Arg Leu Thr Arg Arg Ala His Arg Leu Leu
 65                  70                  75                  80

Arg Ala Arg Arg Leu Leu Lys Arg Glu Gly Val Leu Gln Ala Ala Asp
                    85                  90                  95

Phe Asp Glu Asn Gly Leu Ile Lys Ser Leu Pro Asn Thr Pro Trp Gln
                100                 105                 110

Leu Arg Ala Ala Ala Leu Asp Arg Lys Leu Thr Pro Leu Glu Trp Ser
                115                 120                 125

Ala Val Leu Leu His Leu Ile Lys His Arg Gly Tyr Leu Ser Gln Arg
                130                 135                 140

Lys Asn Glu Gly Glu Thr Ala Asp Lys Glu Leu Gly Ala Leu Leu Lys
145                 150                 155                 160

Gly Val Ala Asp Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
                180                 185                 190

Arg Asn Gln Arg Gly Asp Tyr Ser His Thr Phe Ser Arg Lys Asp Leu
                195                 200                 205

Gln Ala Glu Leu Ile Leu Leu Phe Glu Lys Gln Lys Glu Phe Gly Asn
                210                 215                 220

Pro His Val Ser Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
                260                 265                 270

Thr Ala Glu Arg Phe Ile Trp Leu Thr Lys Leu Asn Asn Leu Arg Ile
                275                 280                 285

Leu Glu Gln Gly Ser Glu Arg Pro Leu Thr Asp Thr Glu Arg Ala Thr
                290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
                340                 345                 350

Tyr His Ala Ile Ser Arg Ala Leu Glu Lys Glu Gly Leu Lys Asp Lys
                355                 360                 365

Lys Ser Pro Leu Asn Leu Ser Pro Glu Leu Gln Asp Glu Ile Gly Thr
                370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
                420                 425                 430

Pro Leu Met Glu Gln Gly Lys Arg Tyr Asp Glu Ala Cys Ala Glu Ile
                435                 440                 445
```

```
Tyr Gly Asp His Tyr Gly Lys Lys Asn Thr Glu Glu Lys Ile Tyr Leu
    450             455                 460
Pro Pro Ile Pro Ala Asp Glu Ile Arg Asn Pro Val Val Leu Arg Ala
465             470                 475                 480
Leu Ser Gln Ala Arg Lys Val Ile Asn Gly Val Val Arg Arg Tyr Gly
                485                 490                 495
Ser Pro Ala Arg Ile His Ile Glu Thr Ala Arg Glu Val Gly Lys Ser
            500                 505                 510
Phe Lys Asp Arg Lys Glu Ile Glu Lys Arg Gln Glu Glu Asn Arg Lys
        515                 520                 525
Asp Arg Glu Lys Ala Ala Ala Lys Phe Arg Glu Tyr Phe Pro Asn Phe
    530                 535                 540
Val Gly Glu Pro Lys Ser Lys Asp Ile Leu Lys Leu Arg Leu Tyr Glu
545                 550                 555                 560
Gln Gln His Gly Lys Cys Leu Tyr Ser Gly Lys Glu Ile Asn Leu Gly
                565                 570                 575
Arg Leu Asn Glu Lys Gly Tyr Val Glu Ile Asp His Ala Leu Pro Phe
            580                 585                 590
Ser Arg Thr Trp Asp Asp Ser Phe Asn Asn Lys Val Leu Val Leu Gly
        595                 600                 605
Ser Glu Asn Gln Asn Lys Gly Asn Gln Thr Pro Tyr Glu Tyr Phe Asn
    610                 615                 620
Gly Lys Asp Asn Ser Arg Glu Trp Gln Glu Phe Lys Ala Arg Val Glu
625                 630                 635                 640
Thr Ser Arg Phe Pro Arg Ser Lys Lys Gln Arg Ile Leu Leu Gln Lys
                645                 650                 655
Phe Asp Glu Asp Gly Phe Lys Glu Arg Asn Leu Asn Asp Thr Arg Tyr
            660                 665                 670
Val Asn Arg Phe Leu Cys Gln Phe Val Ala Asp Arg Met Arg Leu Thr
        675                 680                 685
Gly Lys Gly Lys Lys Arg Val Phe Ala Ser Asn Gly Gln Ile Thr Asn
    690                 695                 700
Leu Leu Arg Gly Phe Trp Gly Leu Arg Lys Val Arg Ala Glu Asn Asp
705             710                 715                 720
Arg His His Ala Leu Asp Ala Val Val Val Ala Cys Ser Thr Val Ala
                725                 730                 735
Met Gln Gln Lys Ile Thr Arg Phe Val Arg Tyr Lys Glu Met Asn Ala
            740                 745                 750
Phe Asp Gly Lys Thr Ile Asp Lys Glu Thr Gly Glu Val Leu His Gln
        755                 760                 765
Lys Thr His Phe Pro Gln Pro Trp Glu Phe Phe Ala Gln Glu Val Met
    770                 775                 780
Ile Arg Val Phe Gly Lys Pro Asp Gly Lys Pro Glu Phe Glu Glu Ala
785             790                 795                 800
Asp Thr Pro Glu Lys Leu Arg Thr Leu Leu Ala Glu Lys Leu Ser Ser
                805                 810                 815
Arg Pro Glu Ala Val His Glu Tyr Val Thr Pro Leu Phe Val Ser Arg
            820                 825                 830
Ala Pro Asn Arg Lys Met Ser Gly Gln Gly His Met Glu Thr Val Lys
        835                 840                 845
Ser Ala Lys Arg Leu Asp Glu Gly Val Ser Val Leu Arg Val Pro Leu
    850                 855                 860
Thr Gln Leu Lys Leu Lys Asp Leu Glu Lys Met Val Asn Arg Glu Arg
```

```
                    865                 870                 875                 880
Glu Pro Lys Leu Tyr Glu Ala Leu Lys Ala Arg Leu Glu Ala His Lys
                    885                 890                 895

Asp Asp Pro Ala Lys Ala Phe Ala Glu Pro Phe Tyr Lys Tyr Asp Lys
                    900                 905                 910

Ala Gly Asn Arg Thr Gln Gln Val Lys Ala Val Arg Val Glu Gln Val
                    915                 920                 925

Gln Lys Thr Gly Val Trp Val Arg Asn His Asn Gly Ile Ala Asp Asn
                    930                 935                 940

Ala Thr Met Val Arg Val Asp Val Phe Glu Lys Gly Asp Lys Tyr Tyr
945                 950                 955                 960

Leu Val Pro Ile Tyr Ser Trp Gln Val Ala Lys Gly Ile Leu Pro Asp
                    965                 970                 975

Arg Ala Val Val Gln Gly Lys Asp Glu Glu Asp Trp Gln Leu Ile Asp
                    980                 985                 990

Asp Ser Phe Asn Phe Lys Phe Ser Leu His Pro Asn Asp Leu Val Glu
                    995                 1000                1005

Val Ile Thr Lys Lys Ala Arg Met Phe Gly Tyr Phe Ala Ser Cys
            1010                1015                1020

His Arg Gly Thr Gly Asn Ile Asn Ile Arg Ile His Asp Leu Asp
            1025                1030                1035

His Lys Ile Gly Lys Asn Gly Ile Leu Glu Gly Ile Gly Val Lys
            1040                1045                1050

Thr Ala Leu Ser Phe Gln Lys Tyr Gln Ile Asp Glu Leu Gly Lys
            1055                1060                1065

Glu Ile Arg Pro Cys Arg Leu Lys Lys Arg Pro Pro Val Arg
            1070                1075                1080

<210> SEQ ID NO 5
<211> LENGTH: 1037
<212> TYPE: PRT
<213> ORGANISM: Parvibaculum lavamentivorans

<400> SEQUENCE: 5

Met Glu Arg Ile Phe Gly Phe Asp Ile Gly Thr Thr Ser Ile Gly Phe
1               5                   10                  15

Ser Val Ile Asp Tyr Ser Ser Thr Gln Ser Ala Gly Asn Ile Gln Arg
                20                  25                  30

Leu Gly Val Arg Ile Phe Pro Glu Ala Arg Asp Pro Asp Gly Thr Pro
            35                  40                  45

Leu Asn Gln Gln Arg Arg Gln Lys Arg Met Met Arg Gln Leu Arg
        50                  55                  60

Arg Arg Arg Ile Arg Arg Lys Ala Leu Asn Glu Thr Leu His Glu Ala
65                  70                  75                  80

Gly Phe Leu Pro Ala Tyr Gly Ser Ala Asp Trp Pro Val Val Met Ala
                85                  90                  95

Asp Glu Pro Tyr Glu Leu Arg Arg Gly Leu Glu Glu Gly Leu Ser
                100                 105                 110

Ala Tyr Glu Phe Gly Arg Ala Ile Tyr His Leu Ala Gln His Arg His
            115                 120                 125

Phe Lys Gly Arg Glu Leu Glu Glu Ser Asp Thr Pro Asp Pro Asp Val
        130                 135                 140

Asp Asp Glu Lys Glu Ala Ala Asn Glu Arg Ala Ala Thr Leu Lys Ala
145                 150                 155                 160
```

-continued

Leu Lys Asn Glu Gln Thr Thr Leu Gly Ala Trp Leu Ala Arg Arg Pro
            165                 170                 175

Pro Ser Asp Arg Lys Arg Gly Ile His Ala His Arg Asn Val Val Ala
            180                 185                 190

Glu Glu Phe Glu Arg Leu Trp Glu Val Gln Ser Lys Phe His Pro Ala
            195                 200                 205

Leu Lys Ser Glu Glu Met Arg Ala Arg Ile Ser Asp Thr Ile Phe Ala
            210                 215                 220

Gln Arg Pro Val Phe Trp Arg Lys Asn Thr Leu Gly Glu Cys Arg Phe
225                 230                 235                 240

Met Pro Gly Glu Pro Leu Cys Pro Lys Gly Ser Trp Leu Ser Gln Gln
            245                 250                 255

Arg Arg Met Leu Glu Lys Leu Asn Asn Leu Ala Ile Ala Gly Gly Asn
            260                 265                 270

Ala Arg Pro Leu Asp Ala Glu Arg Asp Ala Ile Leu Ser Lys Leu
            275                 280                 285

Gln Gln Gln Ala Ser Met Ser Trp Pro Gly Val Arg Ser Ala Leu Lys
            290                 295                 300

Ala Leu Tyr Lys Gln Arg Gly Glu Pro Gly Ala Glu Lys Ser Leu Lys
305                 310                 315                 320

Phe Asn Leu Glu Leu Gly Gly Glu Ser Lys Leu Leu Gly Asn Ala Leu
            325                 330                 335

Glu Ala Lys Leu Ala Asp Met Phe Gly Pro Asp Trp Pro Ala His Pro
            340                 345                 350

Arg Lys Gln Glu Ile Arg His Ala Val His Glu Arg Leu Trp Ala Ala
            355                 360                 365

Asp Tyr Gly Glu Thr Pro Asp Lys Lys Arg Val Ile Ile Leu Ser Glu
            370                 375                 380

Lys Asp Arg Lys Ala His Arg Glu Ala Ala Ala Asn Ser Phe Val Ala
385                 390                 395                 400

Asp Phe Gly Ile Thr Gly Glu Gln Ala Ala Gln Leu Gln Ala Leu Lys
            405                 410                 415

Leu Pro Thr Gly Trp Glu Pro Tyr Ser Ile Pro Ala Leu Asn Leu Phe
            420                 425                 430

Leu Ala Glu Leu Glu Lys Gly Glu Arg Phe Gly Ala Leu Val Asn Gly
            435                 440                 445

Pro Asp Trp Glu Gly Trp Arg Arg Thr Asn Phe Pro His Arg Asn Gln
450                 455                 460

Pro Thr Gly Glu Ile Leu Asp Lys Leu Pro Ser Pro Ala Ser Lys Glu
465                 470                 475                 480

Glu Arg Glu Arg Ile Ser Gln Leu Arg Asn Pro Thr Val Val Arg Thr
            485                 490                 495

Gln Asn Glu Leu Arg Lys Val Val Asn Asn Leu Ile Gly Leu Tyr Gly
            500                 505                 510

Lys Pro Asp Arg Ile Arg Ile Glu Val Gly Arg Asp Val Gly Lys Ser
            515                 520                 525

Lys Arg Glu Arg Glu Glu Ile Gln Ser Gly Ile Arg Arg Asn Glu Lys
            530                 535                 540

Gln Arg Lys Lys Ala Thr Glu Asp Leu Ile Lys Asn Gly Ile Ala Asn
545                 550                 555                 560

Pro Ser Arg Asp Asp Val Glu Lys Trp Ile Leu Trp Lys Glu Gly Gln
            565                 570                 575

Glu Arg Cys Pro Tyr Thr Gly Asp Gln Ile Gly Phe Asn Ala Leu Phe

```
              580                 585                 590
Arg Glu Gly Arg Tyr Glu Val Glu His Ile Trp Pro Arg Ser Arg Ser
            595                 600                 605

Phe Asp Asn Ser Pro Arg Asn Lys Thr Leu Cys Arg Lys Asp Val Asn
            610                 615                 620

Ile Glu Lys Gly Asn Arg Met Pro Phe Glu Ala Phe Gly His Asp Glu
625                 630                 635                 640

Asp Arg Trp Ser Ala Ile Gln Ile Arg Leu Gln Gly Met Val Ser Ala
                645                 650                 655

Lys Gly Gly Thr Gly Met Ser Pro Gly Lys Val Lys Arg Phe Leu Ala
                660                 665                 670

Lys Thr Met Pro Glu Asp Phe Ala Ala Arg Gln Leu Asn Asp Thr Arg
            675                 680                 685

Tyr Ala Ala Lys Gln Ile Leu Ala Gln Leu Lys Arg Leu Trp Pro Asp
            690                 695                 700

Met Gly Pro Glu Ala Pro Val Lys Val Glu Ala Val Thr Gly Gln Val
705                 710                 715                 720

Thr Ala Gln Leu Arg Lys Leu Trp Thr Leu Asn Asn Ile Leu Ala Asp
                725                 730                 735

Asp Gly Glu Lys Thr Arg Ala Asp His Arg His Ala Ile Asp Ala
                740                 745                 750

Leu Thr Val Ala Cys Thr His Pro Gly Met Thr Asn Lys Leu Ser Arg
                755                 760                 765

Tyr Trp Gln Leu Arg Asp Asp Pro Arg Ala Glu Lys Pro Ala Leu Thr
            770                 775                 780

Pro Pro Trp Asp Thr Ile Arg Ala Asp Ala Glu Lys Ala Val Ser Glu
785                 790                 795                 800

Ile Val Val Ser His Arg Val Arg Lys Val Ser Gly Pro Leu His
                805                 810                 815

Lys Glu Thr Thr Tyr Gly Asp Thr Gly Thr Asp Ile Lys Thr Lys Ser
                820                 825                 830

Gly Thr Tyr Arg Gln Phe Val Thr Arg Lys Lys Ile Glu Ser Leu Ser
                835                 840                 845

Lys Gly Glu Leu Asp Glu Ile Arg Asp Pro Arg Ile Lys Glu Ile Val
            850                 855                 860

Ala Ala His Val Ala Gly Arg Gly Asp Pro Lys Lys Ala Phe Pro
865                 870                 875                 880

Pro Tyr Pro Cys Val Ser Pro Gly Gly Pro Glu Ile Arg Lys Val Arg
                885                 890                 895

Leu Thr Ser Lys Gln Gln Leu Asn Leu Met Ala Gln Thr Gly Asn Gly
            900                 905                 910

Tyr Ala Asp Leu Gly Ser Asn His His Ile Ala Ile Tyr Arg Leu Pro
            915                 920                 925

Asp Gly Lys Ala Asp Phe Glu Ile Val Ser Leu Phe Asp Ala Ser Arg
930                 935                 940

Arg Leu Ala Gln Arg Asn Pro Ile Val Gln Arg Thr Arg Ala Asp Gly
945                 950                 955                 960

Ala Ser Phe Val Met Ser Leu Ala Ala Gly Glu Ala Ile Met Ile Pro
                965                 970                 975

Glu Gly Ser Lys Lys Gly Ile Trp Ile Val Gln Gly Val Trp Ala Ser
                980                 985                 990

Gly Gln Val Val Leu Glu Arg Asp  Thr Asp Ala Asp His  Ser Thr Thr
            995                 1000                1005
```

```
Thr Arg Pro Met Pro Asn Pro Ile Leu Lys Asp Asp Ala Lys Lys
    1010            1015                1020

Val Ser Ile Asp Pro Ile Gly Arg Val Arg Pro Ser Asn Asp
    1025            1030                1035

<210> SEQ ID NO 6
<211> LENGTH: 1084
<212> TYPE: PRT
<213> ORGANISM: Corynebacter diphtheria

<400> SEQUENCE: 6

Met Lys Tyr His Val Gly Ile Asp Val Gly Thr Phe Ser Val Gly Leu
1               5                   10                  15

Ala Ala Ile Glu Val Asp Asp Ala Gly Met Pro Ile Lys Thr Leu Ser
                20                  25                  30

Leu Val Ser His Ile His Asp Ser Gly Leu Asp Pro Asp Glu Ile Lys
            35                  40                  45

Ser Ala Val Thr Arg Leu Ala Ser Ser Gly Ile Ala Arg Arg Thr Arg
        50                  55                  60

Arg Leu Tyr Arg Arg Lys Arg Arg Leu Gln Gln Leu Asp Lys Phe
65                  70                  75                  80

Ile Gln Arg Gln Gly Trp Pro Val Ile Glu Leu Glu Asp Tyr Ser Asp
                85                  90                  95

Pro Leu Tyr Pro Trp Lys Val Arg Ala Glu Leu Ala Ala Ser Tyr Ile
                100                 105                 110

Ala Asp Glu Lys Glu Arg Gly Glu Lys Leu Ser Val Ala Leu Arg His
            115                 120                 125

Ile Ala Arg His Arg Gly Trp Arg Asn Pro Tyr Ala Lys Val Ser Ser
        130                 135                 140

Leu Tyr Leu Pro Asp Gly Pro Ser Asp Ala Phe Lys Ala Ile Arg Glu
145                 150                 155                 160

Glu Ile Lys Arg Ala Ser Gly Gln Pro Val Pro Glu Thr Ala Thr Val
                165                 170                 175

Gly Gln Met Val Thr Leu Cys Glu Leu Gly Thr Leu Lys Leu Arg Gly
                180                 185                 190

Glu Gly Gly Val Leu Ser Ala Arg Leu Gln Gln Ser Asp Tyr Ala Arg
            195                 200                 205

Glu Ile Gln Glu Ile Cys Arg Met Gln Glu Ile Gly Gln Glu Leu Tyr
        210                 215                 220

Arg Lys Ile Ile Asp Val Val Phe Ala Ala Glu Ser Pro Lys Gly Ser
225                 230                 235                 240

Ala Ser Ser Arg Val Gly Lys Asp Pro Leu Gln Pro Gly Lys Asn Arg
                245                 250                 255

Ala Leu Lys Ala Ser Asp Ala Phe Gln Arg Tyr Arg Ile Ala Ala Leu
            260                 265                 270

Ile Gly Asn Leu Arg Val Arg Val Asp Gly Glu Lys Arg Ile Leu Ser
        275                 280                 285

Val Glu Glu Lys Asn Leu Val Phe Asp His Leu Val Asn Leu Thr Pro
290                 295                 300

Lys Lys Glu Pro Glu Trp Val Thr Ile Ala Glu Ile Leu Gly Ile Asp
305                 310                 315                 320

Arg Gly Gln Leu Ile Gly Thr Ala Thr Met Thr Asp Asp Gly Glu Arg
                325                 330                 335

Ala Gly Ala Arg Pro Pro Thr His Asp Thr Asn Arg Ser Ile Val Asn
```

```
                340             345             350
Ser Arg Ile Ala Pro Leu Val Asp Trp Trp Lys Thr Ala Ser Ala Leu
            355                 360                 365
Glu Gln His Ala Met Val Lys Ala Leu Ser Asn Ala Glu Val Asp Asp
            370                 375                 380
Phe Asp Ser Pro Glu Gly Ala Lys Val Gln Ala Phe Phe Ala Asp Leu
385                 390                 395                 400
Asp Asp Asp Val His Ala Lys Leu Asp Ser Leu His Leu Pro Val Gly
                405                 410                 415
Arg Ala Ala Tyr Ser Glu Asp Thr Leu Val Arg Leu Thr Arg Arg Met
            420                 425                 430
Leu Ser Asp Gly Val Asp Leu Tyr Thr Ala Arg Leu Gln Glu Phe Gly
            435                 440                 445
Ile Glu Pro Ser Trp Thr Pro Pro Thr Pro Arg Ile Gly Glu Pro Val
            450                 455                 460
Gly Asn Pro Ala Val Asp Arg Val Leu Lys Thr Val Ser Arg Trp Leu
465                 470                 475                 480
Glu Ser Ala Thr Lys Thr Trp Gly Ala Pro Glu Arg Val Ile Ile Glu
                485                 490                 495
His Val Arg Glu Gly Phe Val Thr Glu Lys Arg Ala Arg Glu Met Asp
                500                 505                 510
Gly Asp Met Arg Arg Arg Ala Ala Arg Asn Ala Lys Leu Phe Gln Glu
            515                 520                 525
Met Gln Glu Lys Leu Asn Val Gln Gly Lys Pro Ser Arg Ala Asp Leu
            530                 535                 540
Trp Arg Tyr Gln Ser Val Gln Arg Gln Asn Cys Gln Cys Ala Tyr Cys
545                 550                 555                 560
Gly Ser Pro Ile Thr Phe Ser Asn Ser Glu Met Asp His Ile Val Pro
                565                 570                 575
Arg Ala Gly Gln Gly Ser Thr Asn Thr Arg Glu Asn Leu Val Ala Val
            580                 585                 590
Cys His Arg Cys Asn Gln Ser Lys Gly Asn Thr Pro Phe Ala Ile Trp
            595                 600                 605
Ala Lys Asn Thr Ser Ile Glu Gly Val Ser Val Lys Glu Ala Val Glu
            610                 615                 620
Arg Thr Arg His Trp Val Thr Asp Thr Gly Met Arg Ser Thr Asp Phe
625                 630                 635                 640
Lys Lys Phe Thr Lys Ala Val Val Glu Arg Phe Gln Arg Ala Thr Met
                645                 650                 655
Asp Glu Glu Ile Asp Ala Arg Ser Met Glu Ser Val Ala Trp Met Ala
                660                 665                 670
Asn Glu Leu Arg Ser Arg Val Ala Gln His Phe Ala Ser His Gly Thr
            675                 680                 685
Thr Val Arg Val Tyr Arg Gly Ser Leu Thr Ala Glu Ala Arg Arg Ala
            690                 695                 700
Ser Gly Ile Ser Gly Lys Leu Lys Phe Phe Asp Gly Val Gly Lys Ser
705                 710                 715                 720
Arg Leu Asp Arg Arg His His Ala Ile Asp Ala Ala Val Ile Ala Phe
                725                 730                 735
Thr Ser Asp Tyr Val Ala Glu Thr Leu Ala Val Arg Ser Asn Leu Lys
            740                 745                 750
Gln Ser Gln Ala His Arg Gln Glu Ala Pro Gln Trp Arg Glu Phe Thr
            755                 760                 765
```

Gly Lys Asp Ala Glu His Arg Ala Ala Trp Arg Val Trp Cys Gln Lys
        770                 775                 780

Met Glu Lys Leu Ser Ala Leu Leu Thr Glu Asp Leu Arg Asp Asp Arg
785                 790                 795                 800

Val Val Val Met Ser Asn Val Arg Leu Arg Leu Gly Asn Gly Ser Ala
                805                 810                 815

His Lys Glu Thr Ile Gly Lys Leu Ser Lys Val Lys Leu Ser Ser Gln
            820                 825                 830

Leu Ser Val Ser Asp Ile Asp Lys Ala Ser Ser Glu Ala Leu Trp Cys
        835                 840                 845

Ala Leu Thr Arg Glu Pro Gly Phe Asp Pro Lys Glu Gly Leu Pro Ala
    850                 855                 860

Asn Pro Glu Arg His Ile Arg Val Asn Gly Thr His Val Tyr Ala Gly
865                 870                 875                 880

Asp Asn Ile Gly Leu Phe Pro Val Ser Ala Gly Ser Ile Ala Leu Arg
                885                 890                 895

Gly Gly Tyr Ala Glu Leu Gly Ser Ser Phe His His Ala Arg Val Tyr
            900                 905                 910

Lys Ile Thr Ser Gly Lys Lys Pro Ala Phe Ala Met Leu Arg Val Tyr
        915                 920                 925

Thr Ile Asp Leu Leu Pro Tyr Arg Asn Gln Asp Leu Phe Ser Val Glu
    930                 935                 940

Leu Lys Pro Gln Thr Met Ser Met Arg Gln Ala Glu Lys Lys Leu Arg
945                 950                 955                 960

Asp Ala Leu Ala Thr Gly Asn Ala Glu Tyr Leu Gly Trp Leu Val Val
                965                 970                 975

Asp Asp Glu Leu Val Val Asp Thr Ser Lys Ile Ala Thr Asp Gln Val
            980                 985                 990

Lys Ala Val Glu Ala Glu Leu Gly Thr Ile Arg Arg Trp Arg Val Asp
        995                 1000                1005

Gly Phe Phe Ser Pro Ser Lys Leu Arg Leu Arg Pro Leu Gln Met
        1010                1015                1020

Ser Lys Glu Gly Ile Lys Lys Glu Ser Ala Pro Glu Leu Ser Lys
        1025                1030                1035

Ile Ile Asp Arg Pro Gly Trp Leu Pro Ala Val Asn Lys Leu Phe
        1040                1045                1050

Ser Asp Gly Asn Val Thr Val Val Arg Arg Asp Ser Leu Gly Arg
        1055                1060                1065

Val Arg Leu Glu Ser Thr Ala His Leu Pro Val Thr Trp Lys Val
        1070                1075                1080

Gln

<210> SEQ ID NO 7
<211> LENGTH: 1130
<212> TYPE: PRT
<213> ORGANISM: Streptococcus pasteurianus

<400> SEQUENCE: 7

Met Thr Asn Gly Lys Ile Leu Gly Leu Asp Ile Gly Ile Ala Ser Val
1               5                   10                  15

Gly Val Gly Ile Ile Glu Ala Lys Thr Gly Lys Val Val His Ala Asn
            20                  25                  30

Ser Arg Leu Phe Ser Ala Ala Asn Ala Glu Asn Ala Glu Arg Arg
        35                  40                  45

```
Gly Phe Arg Gly Ser Arg Arg Leu Asn Arg Arg Lys His Arg Val
 50                  55                  60
Lys Arg Val Arg Asp Leu Phe Glu Lys Tyr Gly Ile Val Thr Asp Phe
 65                  70                  75                  80
Arg Asn Leu Asn Leu Asn Pro Tyr Glu Leu Arg Val Lys Gly Leu Thr
                 85                  90                  95
Glu Gln Leu Lys Asn Glu Glu Leu Phe Ala Ala Leu Arg Thr Ile Ser
            100                 105                 110
Lys Arg Arg Gly Ile Ser Tyr Leu Asp Asp Ala Glu Asp Asp Ser Thr
        115                 120                 125
Gly Ser Thr Asp Tyr Ala Lys Ser Ile Asp Glu Asn Arg Arg Leu Leu
    130                 135                 140
Lys Asn Lys Thr Pro Gly Gln Ile Gln Leu Glu Arg Leu Glu Lys Tyr
145                 150                 155                 160
Gly Gln Leu Arg Gly Asn Phe Thr Val Tyr Asp Glu Asn Gly Glu Ala
                165                 170                 175
His Arg Leu Ile Asn Val Phe Ser Thr Ser Asp Tyr Glu Lys Glu Ala
            180                 185                 190
Arg Lys Ile Leu Glu Thr Gln Ala Asp Tyr Asn Lys Lys Ile Thr Ala
        195                 200                 205
Glu Phe Ile Asp Asp Tyr Val Glu Ile Leu Thr Gln Lys Arg Lys Tyr
    210                 215                 220
Tyr His Gly Pro Gly Asn Glu Lys Ser Arg Thr Asp Tyr Gly Arg Phe
225                 230                 235                 240
Arg Thr Asp Gly Thr Thr Leu Glu Asn Ile Phe Gly Ile Leu Ile Gly
                245                 250                 255
Lys Cys Asn Phe Tyr Pro Asp Glu Tyr Arg Ala Ser Lys Ala Ser Tyr
            260                 265                 270
Thr Ala Gln Glu Tyr Asn Phe Leu Asn Asp Leu Asn Asn Leu Lys Val
        275                 280                 285
Ser Thr Glu Thr Gly Lys Leu Ser Thr Glu Gln Lys Glu Ser Leu Val
    290                 295                 300
Glu Phe Ala Lys Asn Thr Ala Thr Leu Gly Pro Ala Lys Leu Leu Lys
305                 310                 315                 320
Glu Ile Ala Lys Ile Leu Asp Cys Lys Val Asp Glu Ile Lys Gly Tyr
                325                 330                 335
Arg Glu Asp Asp Lys Gly Lys Pro Asp Leu His Thr Phe Glu Pro Tyr
            340                 345                 350
Arg Lys Leu Lys Phe Asn Leu Glu Ser Ile Asn Ile Asp Asp Leu Ser
        355                 360                 365
Arg Glu Val Ile Asp Lys Leu Ala Asp Ile Leu Thr Leu Asn Thr Glu
    370                 375                 380
Arg Glu Gly Ile Glu Asp Ala Ile Lys Arg Asn Leu Pro Asn Gln Phe
385                 390                 395                 400
Thr Glu Glu Gln Ile Ser Glu Ile Ile Lys Val Arg Lys Ser Gln Ser
                405                 410                 415
Thr Ala Phe Asn Lys Gly Trp His Ser Phe Ser Ala Lys Leu Met Asn
            420                 425                 430
Glu Leu Ile Pro Glu Leu Tyr Ala Thr Ser Asp Glu Gln Met Thr Ile
        435                 440                 445
Leu Thr Arg Leu Glu Lys Phe Lys Val Asn Lys Lys Ser Ser Lys Asn
    450                 455                 460
```

```
Thr Lys Thr Ile Asp Glu Lys Glu Val Thr Asp Glu Ile Tyr Asn Pro
465                 470                 475                 480

Val Val Ala Lys Ser Val Arg Gln Thr Ile Lys Ile Ile Asn Ala Ala
                485                 490                 495

Val Lys Lys Tyr Gly Asp Phe Asp Lys Ile Val Ile Glu Met Pro Arg
                500                 505                 510

Asp Lys Asn Ala Asp Asp Glu Lys Lys Phe Ile Asp Lys Arg Asn Lys
                515                 520                 525

Glu Asn Lys Lys Glu Lys Asp Asp Ala Leu Lys Arg Ala Ala Tyr Leu
                530                 535                 540

Tyr Asn Ser Ser Asp Lys Leu Pro Asp Glu Val Phe His Gly Asn Lys
545                 550                 555                 560

Gln Leu Glu Thr Lys Ile Arg Leu Trp Tyr Gln Gln Gly Glu Arg Cys
                565                 570                 575

Leu Tyr Ser Gly Lys Pro Ile Ser Ile Gln Glu Leu Val His Asn Ser
                580                 585                 590

Asn Asn Phe Glu Ile Asp His Ile Leu Pro Leu Ser Leu Ser Phe Asp
                595                 600                 605

Asp Ser Leu Ala Asn Lys Val Leu Val Tyr Ala Trp Thr Asn Gln Glu
                610                 615                 620

Lys Gly Gln Lys Thr Pro Tyr Gln Val Ile Asp Ser Met Asp Ala Ala
625                 630                 635                 640

Trp Ser Phe Arg Glu Met Lys Asp Tyr Val Leu Lys Gln Lys Gly Leu
                645                 650                 655

Gly Lys Lys Lys Arg Asp Tyr Leu Leu Thr Thr Glu Asn Ile Asp Lys
                660                 665                 670

Ile Glu Val Lys Lys Lys Phe Ile Glu Arg Asn Leu Val Asp Thr Arg
                675                 680                 685

Tyr Ala Ser Arg Val Val Leu Asn Ser Leu Gln Ser Ala Leu Arg Glu
                690                 695                 700

Leu Gly Lys Asp Thr Lys Val Ser Val Val Arg Gly Gln Phe Thr Ser
705                 710                 715                 720

Gln Leu Arg Arg Lys Trp Lys Ile Asp Lys Ser Arg Glu Thr Tyr His
                725                 730                 735

His His Ala Val Asp Ala Leu Ile Ile Ala Ala Ser Ser Gln Leu Lys
                740                 745                 750

Leu Trp Glu Lys Gln Asp Asn Pro Met Phe Val Asp Tyr Gly Lys Asn
                755                 760                 765

Gln Val Val Asp Lys Gln Thr Gly Glu Ile Leu Ser Val Ser Asp Asp
                770                 775                 780

Glu Tyr Lys Glu Leu Val Phe Gln Pro Pro Tyr Gln Gly Phe Val Asn
785                 790                 795                 800

Thr Ile Ser Ser Lys Gly Phe Glu Asp Glu Ile Leu Phe Ser Tyr Gln
                805                 810                 815

Val Asp Ser Lys Tyr Asn Arg Lys Val Ser Asp Ala Thr Ile Tyr Ser
                820                 825                 830

Thr Arg Lys Ala Lys Ile Gly Lys Asp Lys Lys Glu Glu Thr Tyr Val
                835                 840                 845

Leu Gly Lys Ile Lys Asp Ile Tyr Ser Gln Asn Gly Phe Asp Thr Phe
                850                 855                 860

Ile Lys Lys Tyr Asn Lys Asp Lys Thr Gln Phe Leu Met Tyr Gln Lys
865                 870                 875                 880

Asp Ser Leu Thr Trp Glu Asn Val Ile Glu Val Ile Leu Arg Asp Tyr
```

885                 890                 895

Pro Thr Thr Lys Lys Ser Glu Asp Gly Lys Asn Asp Val Lys Cys Asn
                900                 905                 910

Pro Phe Glu Glu Tyr Arg Arg Glu Asn Gly Leu Ile Cys Lys Tyr Ser
                915                 920                 925

Lys Lys Gly Lys Gly Thr Pro Ile Lys Ser Leu Lys Tyr Tyr Asp Lys
                930                 935                 940

Lys Leu Gly Asn Cys Ile Asp Ile Thr Pro Glu Glu Ser Arg Asn Lys
945                 950                 955                 960

Val Ile Leu Gln Ser Ile Asn Pro Trp Arg Ala Asp Val Tyr Phe Asn
                965                 970                 975

Pro Glu Thr Leu Lys Tyr Glu Leu Met Gly Leu Lys Tyr Ser Asp Leu
                980                 985                 990

Ser Phe Glu Lys Gly Thr Gly Asn Tyr His Ile Ser Gln Glu Lys Tyr
                995                 1000                1005

Asp Ala Ile Lys Glu Lys Glu Gly Ile Gly Lys Lys Ser Glu Phe
        1010                1015                1020

Lys Phe Thr Leu Tyr Arg Asn Asp Leu Ile Leu Ile Lys Asp Ile
        1025                1030                1035

Ala Ser Gly Glu Gln Glu Ile Tyr Arg Phe Leu Ser Arg Thr Met
        1040                1045                1050

Pro Asn Val Asn His Tyr Val Glu Leu Lys Pro Tyr Asp Lys Glu
        1055                1060                1065

Lys Phe Asp Asn Val Gln Glu Leu Val Glu Ala Leu Gly Glu Ala
        1070                1075                1080

Asp Lys Val Gly Arg Cys Ile Lys Gly Leu Asn Lys Pro Asn Ile
        1085                1090                1095

Ser Ile Tyr Lys Val Arg Thr Asp Val Leu Gly Asn Lys Tyr Phe
        1100                1105                1110

Val Lys Lys Lys Gly Asp Lys Pro Lys Leu Asp Phe Lys Asn Asn
        1115                1120                1125

Lys Lys
        1130

<210> SEQ ID NO 8
<211> LENGTH: 1082
<212> TYPE: PRT
<213> ORGANISM: Neisseria cinerea

<400> SEQUENCE: 8

Met Ala Ala Phe Lys Pro Asn Pro Met Asn Tyr Ile Leu Gly Leu Asp
1               5                   10                  15

Ile Gly Ile Ala Ser Val Gly Trp Ala Ile Val Glu Ile Asp Glu Glu
                20                  25                  30

Glu Asn Pro Ile Arg Leu Ile Asp Leu Gly Val Arg Val Phe Glu Arg
            35                  40                  45

Ala Glu Val Pro Lys Thr Gly Asp Ser Leu Ala Ala Ala Arg Arg Leu
        50                  55                  60

Ala Arg Ser Val Arg Arg Leu Thr Arg Arg Arg Ala His Arg Leu Leu
65                  70                  75                  80

Arg Ala Arg Arg Leu Leu Lys Arg Glu Gly Val Leu Gln Ala Ala Asp
                85                  90                  95

Phe Asp Glu Asn Gly Leu Ile Lys Ser Leu Pro Asn Thr Pro Trp Gln
            100                 105                 110

```
Leu Arg Ala Ala Ala Leu Asp Arg Lys Leu Thr Pro Leu Glu Trp Ser
            115                 120                 125

Ala Val Leu Leu His Leu Ile Lys His Arg Gly Tyr Leu Ser Gln Arg
        130                 135                 140

Lys Asn Glu Gly Glu Thr Ala Asp Lys Glu Leu Gly Ala Leu Leu Lys
145                 150                 155                 160

Gly Val Ala Asp Asn Thr His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Gln Arg Gly Asp Tyr Ser His Thr Phe Asn Arg Lys Asp Leu
        195                 200                 205

Gln Ala Glu Leu Asn Leu Leu Phe Glu Lys Gln Lys Glu Phe Gly Asn
    210                 215                 220

Pro His Val Ser Asp Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Thr Glu Pro Lys Ala Ala Lys Asn Thr Tyr
            260                 265                 270

Thr Ala Glu Arg Phe Val Trp Leu Thr Lys Leu Asn Asn Leu Arg Ile
        275                 280                 285

Leu Glu Gln Gly Ser Glu Arg Pro Leu Thr Asp Thr Glu Arg Ala Thr
    290                 295                 300

Leu Met Asp Glu Pro Tyr Arg Lys Ser Lys Leu Thr Tyr Ala Gln Ala
305                 310                 315                 320

Arg Lys Leu Leu Asp Leu Asp Thr Ala Phe Phe Lys Gly Leu Arg
                325                 330                 335

Tyr Gly Lys Asp Asn Ala Glu Ala Ser Thr Leu Met Glu Met Lys Ala
            340                 345                 350

Tyr His Ala Ile Ser Arg Ala Leu Glu Lys Gly Leu Lys Asp Lys
        355                 360                 365

Lys Ser Pro Leu Asn Leu Ser Pro Glu Leu Gln Asp Glu Ile Gly Thr
370                 375                 380

Ala Phe Ser Leu Phe Lys Thr Asp Glu Asp Ile Thr Gly Arg Leu Lys
385                 390                 395                 400

Asp Arg Val Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
            420                 425                 430

Pro Leu Met Glu Gln Gly Asn Arg Tyr Asp Glu Ala Cys Thr Glu Ile
        435                 440                 445

Tyr Gly Asp His Tyr Gly Lys Lys Asn Thr Glu Glu Lys Ile Tyr Leu
    450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Gly Val Val Arg Arg Tyr Gly
                485                 490                 495

Ser Pro Ala Arg Ile His Ile Glu Thr Ala Arg Glu Val Gly Lys Ser
            500                 505                 510

Phe Lys Asp Arg Lys Glu Ile Glu Lys Arg Gln Glu Glu Asn Arg Lys
        515                 520                 525

Asp Arg Glu Lys Ser Ala Ala Lys Phe Arg Glu Tyr Phe Pro Asn Phe
```

-continued

```
                530             535             540
Val Gly Glu Pro Lys Ser Lys Asp Ile Leu Lys Leu Arg Leu Tyr Glu
545                 550             555                 560

Gln Gln His Gly Lys Cys Leu Tyr Ser Gly Lys Glu Ile Asn Leu Gly
                565             570             575

Arg Leu Asn Glu Lys Gly Tyr Val Glu Ile Asp His Ala Leu Pro Phe
            580             585             590

Ser Arg Thr Trp Asp Asp Ser Phe Asn Asn Lys Val Leu Ala Leu Gly
        595             600             605

Ser Glu Asn Gln Asn Lys Gly Asn Gln Thr Pro Tyr Glu Tyr Phe Asn
    610             615             620

Gly Lys Asp Asn Ser Arg Glu Trp Gln Glu Phe Lys Ala Arg Val Glu
625             630             635             640

Thr Ser Arg Phe Pro Arg Ser Lys Lys Gln Arg Ile Leu Leu Gln Lys
                645             650             655

Phe Asp Glu Asp Gly Phe Lys Glu Arg Asn Leu Asn Asp Thr Arg Tyr
            660             665             670

Ile Asn Arg Phe Leu Cys Gln Phe Val Ala Asp His Met Leu Leu Thr
        675             680             685

Gly Lys Gly Lys Arg Arg Val Phe Ala Ser Asn Gly Gln Ile Thr Asn
690             695             700

Leu Leu Arg Gly Phe Trp Gly Leu Arg Lys Val Arg Ala Glu Asn Asp
705             710             715             720

Arg His His Ala Leu Asp Ala Val Val Ala Cys Ser Thr Ile Ala
                725             730             735

Met Gln Gln Lys Ile Thr Arg Phe Val Arg Tyr Lys Glu Met Asn Ala
                740             745             750

Phe Asp Gly Lys Thr Ile Asp Lys Glu Thr Gly Glu Val Leu His Gln
            755             760             765

Lys Ala His Phe Pro Gln Pro Trp Glu Phe Phe Ala Gln Glu Val Met
770             775             780

Ile Arg Val Phe Gly Lys Pro Asp Gly Lys Pro Glu Phe Glu Glu Ala
785             790             795             800

Asp Thr Pro Glu Lys Leu Arg Thr Leu Leu Ala Glu Lys Leu Ser Ser
                805             810             815

Arg Pro Glu Ala Val His Lys Tyr Val Thr Pro Leu Phe Ile Ser Arg
            820             825             830

Ala Pro Asn Arg Lys Met Ser Gly Gln Gly His Met Glu Thr Val Lys
        835             840             845

Ser Ala Lys Arg Leu Asp Glu Gly Ile Ser Val Leu Arg Val Pro Leu
850             855             860

Thr Gln Leu Lys Leu Lys Asp Leu Glu Lys Met Val Asn Arg Glu Arg
865             870             875             880

Glu Pro Lys Leu Tyr Glu Ala Leu Lys Ala Arg Leu Glu Ala His Lys
                885             890             895

Asp Asp Pro Ala Lys Ala Phe Ala Glu Pro Phe Tyr Lys Tyr Asp Lys
            900             905             910

Ala Gly Asn Arg Thr Gln Gln Val Lys Ala Val Arg Val Glu Gln Val
        915             920             925

Gln Lys Thr Gly Val Trp Val His Asn His Asn Gly Ile Ala Asp Asn
930             935             940

Ala Thr Ile Val Arg Val Asp Val Phe Glu Lys Gly Gly Lys Tyr Tyr
945             950             955             960
```

```
Leu Val Pro Ile Tyr Ser Trp Gln Val Ala Lys Gly Ile Leu Pro Asp
                965                 970                 975

Arg Ala Val Val Gln Gly Lys Asp Glu Asp Trp Thr Val Met Asp
            980                 985                 990

Asp Ser Phe Glu Phe Lys Phe Val Leu Tyr Ala Asn Asp Leu Ile Lys
            995                 1000                1005

Leu Thr Ala Lys Lys Asn Glu Phe Leu Gly Tyr Phe Val Ser Leu
        1010                1015                1020

Asn Arg Ala Thr Gly Ala Ile Asp Ile Arg Thr His Asp Thr Asp
        1025                1030                1035

Ser Thr Lys Gly Lys Asn Gly Ile Phe Gln Ser Val Gly Val Lys
        1040                1045                1050

Thr Ala Leu Ser Phe Gln Lys Tyr Gln Ile Asp Glu Leu Gly Lys
        1055                1060                1065

Glu Ile Arg Pro Cys Arg Leu Lys Lys Arg Pro Pro Val Arg
        1070                1075                1080

<210> SEQ ID NO 9
<211> LENGTH: 1003
<212> TYPE: PRT
<213> ORGANISM: Campylobacter lari

<400> SEQUENCE: 9

Met Arg Ile Leu Gly Phe Asp Ile Gly Ile Asn Ser Ile Gly Trp Ala
1               5                   10                  15

Phe Val Glu Asn Asp Glu Leu Lys Asp Cys Gly Val Arg Ile Phe Thr
            20                  25                  30

Lys Ala Glu Asn Pro Lys Asn Lys Glu Ser Leu Ala Leu Pro Arg Arg
        35                  40                  45

Asn Ala Arg Ser Ser Arg Arg Leu Lys Arg Arg Lys Ala Arg Leu
    50                  55                  60

Ile Ala Ile Lys Arg Ile Leu Ala Lys Glu Leu Lys Leu Asn Tyr Lys
65                  70                  75                  80

Asp Tyr Val Ala Ala Asp Gly Glu Leu Pro Lys Ala Tyr Glu Gly Ser
                85                  90                  95

Leu Ala Ser Val Tyr Glu Leu Arg Tyr Lys Ala Leu Thr Gln Asn Leu
            100                 105                 110

Glu Thr Lys Asp Leu Ala Arg Val Ile Leu His Ile Ala Lys His Arg
        115                 120                 125

Gly Tyr Met Asn Lys Asn Glu Lys Ser Asn Asp Ala Lys Lys Gly
    130                 135                 140

Lys Ile Leu Ser Ala Leu Lys Asn Asn Ala Leu Lys Leu Glu Asn Tyr
145                 150                 155                 160

Gln Ser Val Gly Glu Tyr Phe Tyr Lys Glu Phe Gln Lys Tyr Lys
                165                 170                 175

Lys Asn Thr Lys Asn Phe Ile Lys Ile Arg Asn Thr Lys Asp Asn Tyr
            180                 185                 190

Asn Asn Cys Val Leu Ser Ser Asp Leu Glu Lys Glu Leu Lys Leu Ile
        195                 200                 205

Leu Glu Lys Gln Lys Glu Phe Gly Tyr Asn Tyr Ser Glu Asp Phe Ile
    210                 215                 220

Asn Glu Ile Leu Lys Val Ala Phe Phe Gln Arg Pro Leu Lys Asp Phe
225                 230                 235                 240

Ser His Leu Val Gly Ala Cys Thr Phe Phe Glu Glu Glu Lys Arg Ala
```

```
            245                 250                 255
Cys Lys Asn Ser Tyr Ser Ala Trp Glu Phe Val Ala Leu Thr Lys Ile
            260                 265                 270
Ile Asn Glu Ile Lys Ser Leu Glu Lys Ile Ser Gly Glu Ile Val Pro
            275                 280                 285
Thr Gln Thr Ile Asn Glu Val Leu Asn Leu Ile Leu Asp Lys Gly Ser
            290                 295                 300
Ile Thr Tyr Lys Lys Phe Arg Ser Cys Ile Asn Leu His Glu Ser Ile
305                 310                 315                 320
Ser Phe Lys Ser Leu Lys Tyr Asp Lys Glu Asn Ala Glu Asn Ala Lys
            325                 330                 335
Leu Ile Asp Phe Arg Lys Leu Val Glu Phe Lys Lys Ala Leu Gly Val
            340                 345                 350
His Ser Leu Ser Arg Gln Glu Leu Asp Gln Ile Ser Thr His Ile Thr
            355                 360                 365
Leu Ile Lys Asp Asn Val Lys Leu Lys Thr Val Leu Glu Lys Tyr Asn
            370                 375                 380
Leu Ser Asn Glu Gln Ile Asn Asn Leu Leu Glu Ile Glu Phe Asn Asp
385                 390                 395                 400
Tyr Ile Asn Leu Ser Phe Lys Ala Leu Gly Met Ile Leu Pro Leu Met
            405                 410                 415
Arg Glu Gly Lys Arg Tyr Asp Glu Ala Cys Glu Ile Ala Asn Leu Lys
            420                 425                 430
Pro Lys Thr Val Asp Glu Lys Lys Asp Phe Leu Pro Ala Phe Cys Asp
            435                 440                 445
Ser Ile Phe Ala His Glu Leu Ser Asn Pro Val Val Asn Arg Ala Ile
            450                 455                 460
Ser Glu Tyr Arg Lys Val Leu Asn Ala Leu Leu Lys Lys Tyr Gly Lys
465                 470                 475                 480
Val His Lys Ile His Leu Glu Leu Ala Arg Asp Val Gly Leu Ser Lys
            485                 490                 495
Lys Ala Arg Glu Lys Ile Glu Lys Gln Lys Glu Asn Gln Ala Val
            500                 505                 510
Asn Ala Trp Ala Leu Lys Glu Cys Glu Asn Ile Gly Leu Lys Ala Ser
            515                 520                 525
Ala Lys Asn Ile Leu Lys Leu Lys Leu Trp Lys Glu Gln Lys Glu Ile
            530                 535                 540
Cys Ile Tyr Ser Gly Asn Lys Ile Ser Ile Glu His Leu Lys Asp Glu
545                 550                 555                 560
Lys Ala Leu Glu Val Asp His Ile Tyr Pro Tyr Ser Arg Ser Phe Asp
            565                 570                 575
Asp Ser Phe Ile Asn Lys Val Leu Val Phe Thr Lys Glu Asn Gln Glu
            580                 585                 590
Lys Leu Asn Lys Thr Pro Phe Glu Ala Phe Gly Lys Asn Ile Glu Lys
            595                 600                 605
Trp Ser Lys Ile Gln Thr Leu Ala Gln Asn Leu Pro Tyr Lys Lys Lys
            610                 615                 620
Asn Lys Ile Leu Asp Glu Asn Phe Lys Asp Lys Gln Gln Glu Asp Phe
625                 630                 635                 640
Ile Ser Arg Asn Leu Asn Asp Thr Arg Tyr Ile Ala Thr Leu Ile Ala
            645                 650                 655
Lys Tyr Thr Lys Glu Tyr Leu Asn Phe Leu Leu Leu Ser Glu Asn Glu
            660                 665                 670
```

```
Asn Ala Asn Leu Lys Ser Gly Glu Lys Gly Ser Lys Ile His Val Gln
            675                 680                 685

Thr Ile Ser Gly Met Leu Thr Ser Val Leu Arg His Thr Trp Gly Phe
        690                 695                 700

Asp Lys Lys Asp Arg Asn Asn His Leu His His Ala Leu Asp Ala Ile
705                 710                 715                 720

Ile Val Ala Tyr Ser Thr Asn Ser Ile Ile Lys Ala Phe Ser Asp Phe
                725                 730                 735

Arg Lys Asn Gln Glu Leu Leu Lys Ala Arg Phe Tyr Ala Lys Glu Leu
            740                 745                 750

Thr Ser Asp Asn Tyr Lys His Gln Val Lys Phe Glu Pro Phe Lys
            755                 760                 765

Ser Phe Arg Glu Lys Ile Leu Ser Lys Ile Asp Glu Ile Phe Val Ser
    770                 775                 780

Lys Pro Pro Arg Lys Arg Ala Arg Arg Ala Leu His Lys Asp Thr Phe
785                 790                 795                 800

His Ser Glu Asn Lys Ile Ile Asp Lys Cys Ser Tyr Asn Ser Lys Glu
                805                 810                 815

Gly Leu Gln Ile Ala Leu Ser Cys Gly Arg Val Arg Lys Ile Gly Thr
            820                 825                 830

Lys Tyr Val Glu Asn Asp Thr Ile Val Arg Val Asp Ile Phe Lys Lys
            835                 840                 845

Gln Asn Lys Phe Tyr Ala Ile Pro Ile Tyr Ala Met Asp Phe Ala Leu
    850                 855                 860

Gly Ile Leu Pro Asn Lys Ile Val Ile Thr Gly Lys Asp Lys Asn Asn
865                 870                 875                 880

Asn Pro Lys Gln Trp Gln Thr Ile Asp Glu Ser Tyr Glu Phe Cys Phe
                885                 890                 895

Ser Leu Tyr Lys Asn Asp Leu Ile Leu Leu Gln Lys Lys Asn Met Gln
            900                 905                 910

Glu Pro Glu Phe Ala Tyr Tyr Asn Asp Phe Ser Ile Ser Thr Ser Ser
        915                 920                 925

Ile Cys Val Glu Lys His Asp Asn Lys Phe Glu Asn Leu Thr Ser Asn
    930                 935                 940

Gln Lys Leu Leu Phe Ser Asn Ala Lys Glu Gly Ser Val Lys Val Glu
945                 950                 955                 960

Ser Leu Gly Ile Gln Asn Leu Lys Val Phe Glu Lys Tyr Ile Ile Thr
                965                 970                 975

Pro Leu Gly Asp Lys Ile Lys Ala Asp Phe Gln Pro Arg Glu Asn Ile
            980                 985                 990

Ser Leu Lys Thr Ser Lys Lys Tyr Gly Leu Arg
            995                 1000

<210> SEQ ID NO 10
<211> LENGTH: 1395
<212> TYPE: PRT
<213> ORGANISM: Treponema denticola

<400> SEQUENCE: 10

Met Lys Lys Glu Ile Lys Asp Tyr Phe Leu Gly Leu Asp Val Gly Thr
1               5                   10                  15

Gly Ser Val Gly Trp Ala Val Thr Asp Thr Asp Tyr Lys Leu Leu Lys
            20                  25                  30

Ala Asn Arg Lys Asp Leu Trp Gly Met Arg Cys Phe Glu Thr Ala Glu
```

```
                 35                  40                  45
Thr Ala Glu Val Arg Arg Leu His Arg Gly Ala Arg Arg Ile Glu
 50                  55                  60
Arg Arg Lys Lys Arg Ile Lys Leu Leu Gln Glu Leu Phe Ser Gln Glu
 65                  70                  75                  80
Ile Ala Lys Thr Asp Glu Gly Phe Phe Gln Arg Met Lys Glu Ser Pro
                     85                  90                  95
Phe Tyr Ala Glu Asp Lys Thr Ile Leu Gln Glu Asn Thr Leu Phe Asn
                    100                 105                 110
Asp Lys Asp Phe Ala Asp Lys Thr Tyr His Lys Ala Tyr Pro Thr Ile
                    115                 120                 125
Asn His Leu Ile Lys Ala Trp Ile Glu Asn Lys Val Lys Pro Asp Pro
                    130                 135                 140
Arg Leu Leu Tyr Leu Ala Cys His Asn Ile Ile Lys Lys Arg Gly His
145                 150                 155                 160
Phe Leu Phe Glu Gly Asp Phe Asp Ser Glu Asn Gln Phe Asp Thr Ser
                    165                 170                 175
Ile Gln Ala Leu Phe Glu Tyr Leu Arg Glu Asp Met Glu Val Asp Ile
                    180                 185                 190
Asp Ala Asp Ser Gln Lys Val Lys Glu Ile Leu Lys Asp Ser Ser Leu
                    195                 200                 205
Lys Asn Ser Glu Lys Gln Ser Arg Leu Asn Lys Ile Leu Gly Leu Lys
210                 215                 220
Pro Ser Asp Lys Gln Lys Lys Ala Ile Thr Asn Leu Ile Ser Gly Asn
225                 230                 235                 240
Lys Ile Asn Phe Ala Asp Leu Tyr Asp Asn Pro Asp Leu Lys Asp Ala
                    245                 250                 255
Glu Lys Asn Ser Ile Ser Phe Ser Lys Asp Asp Phe Asp Ala Leu Ser
                    260                 265                 270
Asp Asp Leu Ala Ser Ile Leu Gly Asp Ser Phe Glu Leu Leu Leu Lys
                    275                 280                 285
Ala Lys Ala Val Tyr Asn Cys Ser Val Leu Ser Lys Val Ile Gly Asp
                    290                 295                 300
Glu Gln Tyr Leu Ser Phe Ala Lys Val Lys Ile Tyr Glu Lys His Lys
305                 310                 315                 320
Thr Asp Leu Thr Lys Leu Lys Asn Val Ile Lys Lys His Phe Pro Lys
                    325                 330                 335
Asp Tyr Lys Lys Val Phe Gly Tyr Asn Lys Asn Glu Lys Asn Asn Asn
                    340                 345                 350
Asn Tyr Ser Gly Tyr Val Gly Val Cys Lys Thr Lys Ser Lys Lys Leu
                    355                 360                 365
Ile Ile Asn Asn Ser Val Asn Gln Glu Asp Phe Tyr Lys Phe Leu Lys
                    370                 375                 380
Thr Ile Leu Ser Ala Lys Ser Glu Ile Lys Glu Val Asn Asp Ile Leu
385                 390                 395                 400
Thr Glu Ile Glu Thr Gly Thr Phe Leu Pro Lys Gln Ile Ser Lys Ser
                    405                 410                 415
Asn Ala Glu Ile Pro Tyr Gln Leu Arg Lys Met Glu Leu Glu Lys Ile
                    420                 425                 430
Leu Ser Asn Ala Glu Lys His Phe Ser Phe Leu Lys Gln Lys Asp Glu
                    435                 440                 445
Lys Gly Leu Ser His Ser Glu Lys Ile Ile Met Leu Leu Thr Phe Lys
450                 455                 460
```

```
Ile Pro Tyr Tyr Ile Gly Pro Ile Asn Asp Asn His Lys Lys Phe Phe
465                 470                 475                 480

Pro Asp Arg Cys Trp Val Val Lys Lys Glu Lys Ser Pro Ser Gly Lys
                485                 490                 495

Thr Thr Pro Trp Asn Phe Phe Asp His Ile Asp Lys Glu Lys Thr Ala
            500                 505                 510

Glu Ala Phe Ile Thr Ser Arg Thr Asn Phe Cys Thr Tyr Leu Val Gly
        515                 520                 525

Glu Ser Val Leu Pro Lys Ser Ser Leu Leu Tyr Ser Glu Tyr Thr Val
    530                 535                 540

Leu Asn Glu Ile Asn Asn Leu Gln Ile Ile Asp Gly Lys Asn Ile
545                 550                 555                 560

Cys Asp Ile Lys Leu Lys Gln Lys Ile Tyr Glu Asp Leu Phe Lys Lys
                565                 570                 575

Tyr Lys Lys Ile Thr Gln Lys Gln Ile Ser Thr Phe Ile Lys His Glu
            580                 585                 590

Gly Ile Cys Asn Lys Thr Asp Glu Val Ile Ile Leu Gly Ile Asp Lys
        595                 600                 605

Glu Cys Thr Ser Ser Leu Lys Ser Tyr Ile Glu Leu Lys Asn Ile Phe
    610                 615                 620

Gly Lys Gln Val Asp Glu Ile Ser Thr Lys Asn Met Leu Glu Glu Ile
625                 630                 635                 640

Ile Arg Trp Ala Thr Ile Tyr Asp Glu Gly Glu Gly Lys Thr Ile Leu
                645                 650                 655

Lys Thr Lys Ile Lys Ala Glu Tyr Gly Lys Tyr Cys Ser Asp Glu Gln
            660                 665                 670

Ile Lys Lys Ile Leu Asn Leu Lys Phe Ser Gly Trp Gly Arg Leu Ser
        675                 680                 685

Arg Lys Phe Leu Glu Thr Val Thr Ser Glu Met Pro Gly Phe Ser Glu
    690                 695                 700

Pro Val Asn Ile Ile Thr Ala Met Arg Glu Thr Gln Asn Asn Leu Met
705                 710                 715                 720

Glu Leu Leu Ser Ser Glu Phe Thr Phe Thr Glu Asn Ile Lys Lys Ile
                725                 730                 735

Asn Ser Gly Phe Glu Asp Ala Glu Lys Gln Phe Ser Tyr Asp Gly Leu
            740                 745                 750

Val Lys Pro Leu Phe Leu Ser Pro Ser Val Lys Lys Met Leu Trp Gln
        755                 760                 765

Thr Leu Lys Leu Val Lys Glu Ile Ser His Ile Thr Gln Ala Pro Pro
    770                 775                 780

Lys Lys Ile Phe Ile Glu Met Ala Lys Gly Ala Glu Leu Glu Pro Ala
785                 790                 795                 800

Arg Thr Lys Thr Arg Leu Lys Ile Leu Gln Asp Leu Tyr Asn Asn Cys
                805                 810                 815

Lys Asn Asp Ala Asp Ala Phe Ser Ser Glu Ile Lys Asp Leu Ser Gly
            820                 825                 830

Lys Ile Glu Asn Glu Asp Asn Leu Arg Leu Arg Ser Asp Lys Leu Tyr
        835                 840                 845

Leu Tyr Tyr Thr Gln Leu Gly Lys Cys Met Tyr Cys Gly Lys Pro Ile
    850                 855                 860

Glu Ile Gly His Val Phe Asp Thr Ser Asn Tyr Asp Ile Asp His Ile
865                 870                 875                 880
```

```
Tyr Pro Gln Ser Lys Ile Lys Asp Asp Ser Ile Ser Asn Arg Val Leu
                885                 890                 895
Val Cys Ser Ser Cys Asn Lys Asn Lys Glu Asp Lys Tyr Pro Leu Lys
            900                 905                 910
Ser Glu Ile Gln Ser Lys Gln Arg Gly Phe Trp Asn Phe Leu Gln Arg
            915                 920                 925
Asn Asn Phe Ile Ser Leu Glu Lys Leu Asn Arg Leu Thr Arg Ala Thr
930                 935                 940
Pro Ile Ser Asp Asp Glu Thr Ala Lys Phe Ile Ala Arg Gln Leu Val
945                 950                 955                 960
Glu Thr Arg Gln Ala Thr Lys Val Ala Ala Lys Val Leu Glu Lys Met
            965                 970                 975
Phe Pro Glu Thr Lys Ile Val Tyr Ser Lys Ala Glu Thr Val Ser Met
            980                 985                 990
Phe Arg Asn Lys Phe Asp Ile Val Lys Cys Arg Glu Ile Asn Asp Phe
            995                 1000                1005
His His Ala His Asp Ala Tyr Leu Asn Ile Val Val Gly Asn Val
        1010                1015                1020
Tyr Asn Thr Lys Phe Thr Asn Asn Pro Trp Asn Phe Ile Lys Glu
        1025                1030                1035
Lys Arg Asp Asn Pro Lys Ile Ala Asp Thr Tyr Asn Tyr Tyr Lys
        1040                1045                1050
Val Phe Asp Tyr Asp Val Lys Arg Asn Asn Ile Thr Ala Trp Glu
        1055                1060                1065
Lys Gly Lys Thr Ile Ile Thr Val Lys Asp Met Leu Lys Arg Asn
        1070                1075                1080
Thr Pro Ile Tyr Thr Arg Gln Ala Ala Cys Lys Lys Gly Glu Leu
        1085                1090                1095
Phe Asn Gln Thr Ile Met Lys Lys Gly Leu Gly Gln His Pro Leu
        1100                1105                1110
Lys Lys Glu Gly Pro Phe Ser Asn Ile Ser Lys Tyr Gly Gly Tyr
        1115                1120                1125
Asn Lys Val Ser Ala Ala Tyr Tyr Thr Leu Ile Glu Tyr Glu Glu
        1130                1135                1140
Lys Gly Asn Lys Ile Arg Ser Leu Glu Thr Ile Pro Leu Tyr Leu
        1145                1150                1155
Val Lys Asp Ile Gln Lys Asp Gln Asp Val Leu Lys Ser Tyr Leu
        1160                1165                1170
Thr Asp Leu Leu Gly Lys Lys Glu Phe Lys Ile Leu Val Pro Lys
        1175                1180                1185
Ile Lys Ile Asn Ser Leu Leu Lys Ile Asn Gly Phe Pro Cys His
        1190                1195                1200
Ile Thr Gly Lys Thr Asn Asp Ser Phe Leu Leu Arg Pro Ala Val
        1205                1210                1215
Gln Phe Cys Cys Ser Asn Asn Glu Val Leu Tyr Phe Lys Lys Ile
        1220                1225                1230
Ile Arg Phe Ser Glu Ile Arg Ser Gln Arg Glu Lys Ile Gly Lys
        1235                1240                1245
Thr Ile Ser Pro Tyr Glu Asp Leu Ser Phe Arg Ser Tyr Ile Lys
        1250                1255                1260
Glu Asn Leu Trp Lys Lys Thr Lys Asn Asp Glu Ile Gly Glu Lys
        1265                1270                1275
Glu Phe Tyr Asp Leu Leu Gln Lys Lys Asn Leu Glu Ile Tyr Asp
```

```
                    1280                1285                1290

Met Leu Leu Thr Lys His Lys Asp Thr Ile Tyr Lys Lys Arg Pro
            1295                1300                1305

Asn Ser Ala Thr Ile Asp Ile Leu Val Lys Gly Lys Glu Lys Phe
        1310                1315                1320

Lys Ser Leu Ile Ile Glu Asn Gln Phe Glu Val Ile Leu Glu Ile
    1325                1330                1335

Leu Lys Leu Phe Ser Ala Thr Arg Asn Val Ser Asp Leu Gln His
1340                1345                1350

Ile Gly Gly Ser Lys Tyr Ser Gly Val Ala Lys Ile Gly Asn Lys
        1355                1360                1365

Ile Ser Ser Leu Asp Asn Cys Ile Leu Ile Tyr Gln Ser Ile Thr
    1370                1375                1380

Gly Ile Phe Glu Lys Arg Ile Asp Leu Leu Lys Val
1385                1390                1395

<210> SEQ ID NO 11
<211> LENGTH: 1345
<212> TYPE: PRT
<213> ORGANISM: Streptococcus mutans

<400> SEQUENCE: 11

Met Lys Lys Pro Tyr Ser Ile Gly Leu Asp Ile Gly Thr Asn Ser Val
1               5                   10                  15

Gly Trp Ala Val Val Thr Asp Asp Tyr Lys Val Pro Ala Lys Lys Met
            20                  25                  30

Lys Val Leu Gly Asn Thr Asp Lys Ser His Ile Glu Lys Asn Leu Leu
        35                  40                  45

Gly Ala Leu Leu Phe Asp Ser Gly Asn Thr Ala Glu Asp Arg Arg Leu
    50                  55                  60

Lys Arg Thr Ala Arg Arg Tyr Thr Arg Arg Arg Asn Arg Ile Leu
65                  70                  75                  80

Tyr Leu Gln Glu Ile Phe Ser Glu Glu Met Gly Lys Val Asp Asp Ser
                85                  90                  95

Phe Phe His Arg Leu Glu Asp Ser Phe Leu Val Thr Glu Asp Lys Arg
            100                 105                 110

Gly Glu Arg His Pro Ile Phe Gly Asn Leu Glu Glu Val Lys Tyr
        115                 120                 125

His Glu Asn Phe Pro Thr Ile Tyr His Leu Arg Gln Tyr Leu Ala Asp
    130                 135                 140

Asn Pro Glu Lys Val Asp Leu Arg Leu Val Tyr Leu Ala Leu Ala His
145                 150                 155                 160

Ile Ile Lys Phe Arg Gly His Phe Leu Ile Glu Gly Lys Phe Asp Thr
                165                 170                 175

Arg Asn Asn Asp Val Gln Arg Leu Phe Gln Glu Phe Leu Ala Val Tyr
            180                 185                 190

Asp Asn Thr Phe Glu Asn Ser Ser Leu Gln Glu Gln Asn Val Gln Val
        195                 200                 205

Glu Glu Ile Leu Thr Asp Lys Ile Ser Lys Ser Ala Lys Lys Asp Arg
    210                 215                 220

Val Leu Lys Leu Phe Pro Asn Glu Lys Ser Asn Gly Arg Phe Ala Glu
225                 230                 235                 240

Phe Leu Lys Leu Ile Val Gly Asn Gln Ala Asp Phe Lys Lys His Phe
                245                 250                 255
```

```
Glu Leu Glu Glu Lys Ala Pro Leu Gln Phe Ser Lys Asp Thr Tyr Glu
            260                 265                 270

Glu Glu Leu Glu Val Leu Leu Ala Gln Ile Gly Asp Asn Tyr Ala Glu
        275                 280                 285

Leu Phe Leu Ser Ala Lys Lys Leu Tyr Asp Ser Ile Leu Leu Ser Gly
    290                 295                 300

Ile Leu Thr Val Thr Asp Val Gly Thr Lys Ala Pro Leu Ser Ala Ser
305                 310                 315                 320

Met Ile Gln Arg Tyr Asn Glu His Gln Met Asp Leu Ala Gln Leu Lys
            325                 330                 335

Gln Phe Ile Arg Gln Lys Leu Ser Asp Lys Tyr Asn Glu Val Phe Ser
        340                 345                 350

Asp Val Ser Lys Asp Gly Tyr Ala Gly Tyr Ile Asp Gly Lys Thr Asn
    355                 360                 365

Gln Glu Ala Phe Tyr Lys Tyr Leu Lys Gly Leu Leu Asn Lys Ile Glu
370                 375                 380

Gly Ser Gly Tyr Phe Leu Asp Lys Ile Glu Arg Glu Asp Phe Leu Arg
385                 390                 395                 400

Lys Gln Arg Thr Phe Asp Asn Gly Ser Ile Pro His Gln Ile His Leu
            405                 410                 415

Gln Glu Met Arg Ala Ile Ile Arg Arg Gln Ala Glu Phe Tyr Pro Phe
        420                 425                 430

Leu Ala Asp Asn Gln Asp Arg Ile Glu Lys Leu Leu Thr Phe Arg Ile
    435                 440                 445

Pro Tyr Tyr Val Gly Pro Leu Ala Arg Gly Lys Ser Asp Phe Ala Trp
450                 455                 460

Leu Ser Arg Lys Ser Ala Asp Lys Ile Thr Pro Trp Asn Phe Asp Glu
465                 470                 475                 480

Ile Val Asp Lys Glu Ser Ser Ala Glu Ala Phe Ile Asn Arg Met Thr
            485                 490                 495

Asn Tyr Asp Leu Tyr Leu Pro Asn Gln Lys Val Leu Pro Lys His Ser
        500                 505                 510

Leu Leu Tyr Glu Lys Phe Thr Val Tyr Asn Glu Leu Thr Lys Val Lys
    515                 520                 525

Tyr Lys Thr Glu Gln Gly Lys Thr Ala Phe Phe Asp Ala Asn Met Lys
530                 535                 540

Gln Glu Ile Phe Asp Gly Val Phe Lys Val Tyr Arg Lys Val Thr Lys
545                 550                 555                 560

Asp Lys Leu Met Asp Phe Leu Glu Lys Glu Phe Asp Glu Phe Arg Ile
            565                 570                 575

Val Asp Leu Thr Gly Leu Asp Lys Glu Asn Lys Val Phe Asn Ala Ser
        580                 585                 590

Tyr Gly Thr Tyr His Asp Leu Cys Lys Ile Leu Asp Lys Asp Phe Leu
    595                 600                 605

Asp Asn Ser Lys Asn Glu Lys Ile Leu Glu Asp Ile Val Leu Thr Leu
610                 615                 620

Thr Leu Phe Glu Asp Arg Glu Met Ile Arg Lys Arg Leu Glu Asn Tyr
625                 630                 635                 640

Ser Asp Leu Leu Thr Lys Glu Gln Val Lys Lys Leu Glu Arg Arg His
            645                 650                 655

Tyr Thr Gly Trp Gly Arg Leu Ser Ala Glu Leu Ile His Gly Ile Arg
        660                 665                 670

Asn Lys Glu Ser Arg Lys Thr Ile Leu Asp Tyr Leu Ile Asp Asp Gly
```

```
                675                 680                 685
Asn Ser Asn Arg Asn Phe Met Gln Leu Ile Asn Asp Asp Ala Leu Ser
690                 695                 700
Phe Lys Glu Glu Ile Ala Lys Ala Gln Val Ile Gly Glu Thr Asp Asn
705                 710                 715                 720
Leu Asn Gln Val Val Ser Asp Ile Ala Gly Ser Pro Ala Ile Lys Lys
                725                 730                 735
Gly Ile Leu Gln Ser Leu Lys Ile Val Asp Glu Leu Val Lys Ile Met
                740                 745                 750
Gly His Gln Pro Glu Asn Ile Val Val Glu Met Ala Arg Glu Asn Gln
                755                 760                 765
Phe Thr Asn Gln Gly Arg Arg Asn Ser Gln Arg Leu Lys Gly Leu
770                 775                 780
Thr Asp Ser Ile Lys Glu Phe Gly Ser Gln Ile Leu Lys Glu His Pro
785                 790                 795                 800
Val Glu Asn Ser Gln Leu Gln Asn Asp Arg Leu Phe Leu Tyr Tyr Leu
                805                 810                 815
Gln Asn Gly Arg Asp Met Tyr Thr Gly Glu Glu Leu Asp Ile Asp Tyr
                820                 825                 830
Leu Ser Gln Tyr Asp Ile Asp His Ile Ile Pro Gln Ala Phe Ile Lys
                835                 840                 845
Asp Asn Ser Ile Asp Asn Arg Val Leu Thr Ser Ser Lys Glu Asn Arg
850                 855                 860
Gly Lys Ser Asp Asp Val Pro Ser Lys Asp Val Val Arg Lys Met Lys
865                 870                 875                 880
Ser Tyr Trp Ser Lys Leu Leu Ser Ala Lys Leu Ile Thr Gln Arg Lys
                885                 890                 895
Phe Asp Asn Leu Thr Lys Ala Glu Arg Gly Gly Leu Thr Asp Asp Asp
                900                 905                 910
Lys Ala Gly Phe Ile Lys Arg Gln Leu Val Glu Thr Arg Gln Ile Thr
                915                 920                 925
Lys His Val Ala Arg Ile Leu Asp Glu Arg Phe Asn Thr Glu Thr Asp
                930                 935                 940
Glu Asn Asn Lys Lys Ile Arg Gln Val Lys Ile Val Thr Leu Lys Ser
945                 950                 955                 960
Asn Leu Val Ser Asn Phe Arg Lys Glu Phe Glu Leu Tyr Lys Val Arg
                965                 970                 975
Glu Ile Asn Asp Tyr His His Ala His Asp Ala Tyr Leu Asn Ala Val
                980                 985                 990
Ile Gly Lys Ala Leu Leu Gly Val Tyr Pro Gln Leu Glu Pro Glu Phe
                995                 1000                1005
Val Tyr Gly Asp Tyr Pro His Phe His Gly His Lys Glu Asn Lys
    1010                1015                1020
Ala Thr Ala Lys Lys Phe Phe Tyr Ser Asn Ile Met Asn Phe Phe
    1025                1030                1035
Lys Lys Asp Asp Val Arg Thr Asp Lys Asn Gly Glu Ile Ile Trp
    1040                1045                1050
Lys Lys Asp Glu His Ile Ser Asn Ile Lys Val Leu Ser Tyr
    1055                1060                1065
Pro Gln Val Asn Ile Val Lys Val Glu Glu Gln Thr Gly Gly
    1070                1075                1080
Phe Ser Lys Glu Ser Ile Leu Pro Lys Gly Asn Ser Asp Lys Leu
    1085                1090                1095
```

-continued

Ile Pro Arg Lys Thr Lys Lys Phe Tyr Trp Asp Thr Lys Lys Tyr
1100                1105                1110

Gly Gly Phe Asp Ser Pro Ile Val Ala Tyr Ser Ile Leu Val Ile
1115                1120                1125

Ala Asp Ile Glu Lys Gly Lys Ser Lys Lys Leu Lys Thr Val Lys
1130                1135                1140

Ala Leu Val Gly Val Thr Ile Met Glu Lys Met Thr Phe Glu Arg
1145                1150                1155

Asp Pro Val Ala Phe Leu Glu Arg Lys Gly Tyr Arg Asn Val Gln
1160                1165                1170

Glu Glu Asn Ile Ile Lys Leu Pro Lys Tyr Ser Leu Phe Lys Leu
1175                1180                1185

Glu Asn Gly Arg Lys Arg Leu Leu Ala Ser Ala Arg Glu Leu Gln
1190                1195                1200

Lys Gly Asn Glu Ile Val Leu Pro Asn His Leu Gly Thr Leu Leu
1205                1210                1215

Tyr His Ala Lys Asn Ile His Lys Val Asp Glu Pro Lys His Leu
1220                1225                1230

Asp Tyr Val Asp Lys His Lys Asp Glu Phe Lys Glu Leu Leu Asp
1235                1240                1245

Val Val Ser Asn Phe Ser Lys Lys Tyr Thr Leu Ala Glu Gly Asn
1250                1255                1260

Leu Glu Lys Ile Lys Glu Leu Tyr Ala Gln Asn Asn Gly Glu Asp
1265                1270                1275

Leu Lys Glu Leu Ala Ser Ser Phe Ile Asn Leu Leu Thr Phe Thr
1280                1285                1290

Ala Ile Gly Ala Pro Ala Thr Phe Lys Phe Phe Asp Lys Asn Ile
1295                1300                1305

Asp Arg Lys Arg Tyr Thr Ser Thr Thr Glu Ile Leu Asn Ala Thr
1310                1315                1320

Leu Ile His Gln Ser Ile Thr Gly Leu Tyr Glu Thr Arg Ile Asp
1325                1330                1335

Leu Asn Lys Leu Gly Gly Asp
1340                1345

<210> SEQ ID NO 12
<211> LENGTH: 1388
<212> TYPE: PRT
<213> ORGANISM: Streptococcus thermophilus

<400> SEQUENCE: 12

Met Thr Lys Pro Tyr Ser Ile Gly Leu Asp Ile Gly Thr Asn Ser Val
1               5                   10                  15

Gly Trp Ala Val Thr Thr Asp Asn Tyr Lys Val Pro Ser Lys Lys Met
                20                  25                  30

Lys Val Leu Gly Asn Thr Ser Lys Lys Tyr Ile Lys Lys Asn Leu Leu
            35                  40                  45

Gly Val Leu Leu Phe Asp Ser Gly Ile Thr Ala Glu Gly Arg Arg Leu
        50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Thr Glu Met Ala Thr Leu Asp Asp Ala
                85                  90                  95

Phe Phe Gln Arg Leu Asp Asp Ser Phe Leu Val Pro Asp Asp Lys Arg

```
            100                 105                 110
Asp Ser Lys Tyr Pro Ile Phe Gly Asn Leu Val Glu Glu Lys Ala Tyr
        115                 120                 125

His Asp Glu Phe Pro Thr Ile Tyr His Leu Arg Lys Tyr Leu Ala Asp
        130                 135                 140

Ser Thr Lys Lys Ala Asp Leu Arg Leu Val Tyr Leu Ala Leu Ala His
145                 150                 155                 160

Met Ile Lys Tyr Arg Gly His Phe Leu Ile Glu Gly Glu Phe Asn Ser
                165                 170                 175

Lys Asn Asn Asp Ile Gln Lys Asn Phe Gln Asp Phe Leu Asp Thr Tyr
            180                 185                 190

Asn Ala Ile Phe Glu Ser Asp Leu Ser Leu Glu Asn Ser Lys Gln Leu
            195                 200                 205

Glu Glu Ile Val Lys Asp Lys Ile Ser Lys Leu Glu Lys Lys Asp Arg
        210                 215                 220

Ile Leu Lys Leu Phe Pro Gly Glu Lys Asn Ser Gly Ile Phe Ser Glu
225                 230                 235                 240

Phe Leu Lys Leu Ile Val Gly Asn Gln Ala Asp Phe Arg Lys Cys Phe
                245                 250                 255

Asn Leu Asp Glu Lys Ala Ser Leu His Phe Ser Lys Glu Ser Tyr Asp
            260                 265                 270

Glu Asp Leu Glu Thr Leu Leu Gly Tyr Ile Gly Asp Asp Tyr Ser Asp
            275                 280                 285

Val Phe Leu Lys Ala Lys Lys Leu Tyr Asp Ala Ile Leu Leu Ser Gly
        290                 295                 300

Phe Leu Thr Val Thr Asp Asn Glu Thr Glu Ala Pro Leu Ser Ser Ala
305                 310                 315                 320

Met Ile Lys Arg Tyr Asn Glu His Lys Glu Asp Leu Ala Leu Leu Lys
                325                 330                 335

Glu Tyr Ile Arg Asn Ile Ser Leu Lys Thr Tyr Asn Glu Val Phe Lys
            340                 345                 350

Asp Asp Thr Lys Asn Gly Tyr Ala Gly Tyr Ile Asp Gly Lys Thr Asn
            355                 360                 365

Gln Glu Asp Phe Tyr Val Tyr Leu Lys Lys Leu Leu Ala Glu Phe Glu
        370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
                405                 410                 415

Gln Glu Met Arg Ala Ile Leu Asp Lys Gln Ala Lys Phe Tyr Pro Phe
            420                 425                 430

Leu Ala Lys Asn Lys Glu Arg Ile Glu Lys Ile Leu Thr Phe Arg Ile
            435                 440                 445

Pro Tyr Tyr Val Gly Pro Leu Ala Arg Gly Asn Ser Asp Phe Ala Trp
        450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
                485                 490                 495

Ser Phe Asp Leu Tyr Leu Pro Glu Glu Lys Val Leu Pro Lys His Ser
            500                 505                 510

Leu Leu Tyr Glu Thr Phe Asn Val Tyr Asn Glu Leu Thr Lys Val Arg
            515                 520                 525
```

```
Phe Ile Ala Glu Ser Met Arg Asp Tyr Gln Phe Leu Asp Ser Lys Gln
            530                 535                 540

Lys Lys Asp Ile Val Arg Leu Tyr Phe Lys Asp Lys Arg Lys Val Thr
545                 550                 555                 560

Asp Lys Asp Ile Ile Glu Tyr Leu His Ala Ile Tyr Gly Tyr Asp Gly
                    565                 570                 575

Ile Glu Leu Lys Gly Ile Glu Lys Gln Phe Asn Ser Ser Leu Ser Thr
                580                 585                 590

Tyr His Asp Leu Leu Asn Ile Ile Asn Asp Lys Glu Phe Leu Asp Asp
            595                 600                 605

Ser Ser Asn Glu Ala Ile Ile Glu Glu Ile Ile His Thr Leu Thr Ile
            610                 615                 620

Phe Glu Asp Arg Glu Met Ile Lys Gln Arg Leu Ser Lys Phe Glu Asn
625                 630                 635                 640

Ile Phe Asp Lys Ser Val Leu Lys Lys Leu Ser Arg Arg His Tyr Thr
                645                 650                 655

Gly Trp Gly Lys Leu Ser Ala Lys Leu Ile Asn Gly Ile Arg Asp Glu
                660                 665                 670

Lys Ser Gly Asn Thr Ile Leu Asp Tyr Leu Ile Asp Asp Gly Ile Ser
            675                 680                 685

Asn Arg Asn Phe Met Gln Leu Ile His Asp Asp Ala Leu Ser Phe Lys
            690                 695                 700

Lys Lys Ile Gln Lys Ala Gln Ile Ile Gly Asp Glu Asp Lys Gly Asn
705                 710                 715                 720

Ile Lys Glu Val Val Lys Ser Leu Pro Gly Ser Pro Ala Ile Lys Lys
                725                 730                 735

Gly Ile Leu Gln Ser Ile Lys Ile Val Asp Glu Leu Val Lys Val Met
                740                 745                 750

Gly Gly Arg Lys Pro Glu Ser Ile Val Val Glu Met Ala Arg Glu Asn
            755                 760                 765

Gln Tyr Thr Asn Gln Gly Lys Ser Asn Ser Gln Gln Arg Leu Lys Arg
            770                 775                 780

Leu Glu Lys Ser Leu Lys Glu Leu Gly Ser Lys Ile Leu Lys Glu Asn
785                 790                 795                 800

Ile Pro Ala Lys Leu Ser Lys Ile Asp Asn Asn Ala Leu Gln Asn Asp
                805                 810                 815

Arg Leu Tyr Leu Tyr Leu Gln Asn Gly Lys Asp Met Tyr Thr Gly
                820                 825                 830

Asp Asp Leu Asp Ile Asp Arg Leu Ser Asn Tyr Asp Ile Asp His Ile
            835                 840                 845

Ile Pro Gln Ala Phe Leu Lys Asp Asn Ser Ile Asp Asn Lys Val Leu
            850                 855                 860

Val Ser Ser Ala Ser Asn Arg Gly Lys Ser Asp Asp Val Pro Ser Leu
865                 870                 875                 880

Glu Val Val Lys Lys Arg Lys Thr Phe Trp Tyr Gln Leu Leu Lys Ser
                885                 890                 895

Lys Leu Ile Ser Gln Arg Lys Phe Asp Asn Leu Thr Lys Ala Glu Arg
                900                 905                 910

Gly Gly Leu Ser Pro Glu Asp Lys Ala Gly Phe Ile Gln Arg Gln Leu
            915                 920                 925

Val Glu Thr Arg Gln Ile Thr Lys His Val Ala Arg Leu Leu Asp Glu
            930                 935                 940
```

-continued

```
Lys Phe Asn Asn Lys Lys Asp Glu Asn Asn Arg Ala Val Arg Thr Val
945                 950                 955                 960

Lys Ile Ile Thr Leu Lys Ser Thr Leu Val Ser Gln Phe Arg Lys Asp
            965                 970                 975

Phe Glu Leu Tyr Lys Val Arg Glu Ile Asn Asp Phe His His Ala His
            980                 985                 990

Asp Ala Tyr Leu Asn Ala Val Val Ala Ser Ala Leu Leu Lys Lys Tyr
        995                1000                1005

Pro Lys Leu Glu Pro Glu Phe Val Tyr Gly Asp Tyr Pro Lys Tyr
    1010                1015                1020

Asn Ser Phe Arg Glu Arg Lys Ser Ala Thr Glu Lys Val Tyr Phe
    1025                1030                1035

Tyr Ser Asn Ile Met Asn Ile Phe Lys Lys Ser Ile Ser Leu Ala
    1040                1045                1050

Asp Gly Arg Val Ile Glu Arg Pro Leu Ile Glu Val Asn Glu Glu
    1055                1060                1065

Thr Gly Glu Ser Val Trp Asn Lys Glu Ser Asp Leu Ala Thr Val
    1070                1075                1080

Arg Arg Val Leu Ser Tyr Pro Gln Val Asn Val Val Lys Lys Val
    1085                1090                1095

Glu Glu Gln Asn His Gly Leu Asp Arg Gly Lys Pro Lys Gly Leu
    1100                1105                1110

Phe Asn Ala Asn Leu Ser Ser Lys Pro Lys Pro Asn Ser Asn Glu
    1115                1120                1125

Asn Leu Val Gly Ala Lys Glu Tyr Leu Asp Pro Lys Lys Tyr Gly
    1130                1135                1140

Gly Tyr Ala Gly Ile Ser Asn Ser Phe Thr Val Leu Val Lys Gly
    1145                1150                1155

Thr Ile Glu Lys Gly Ala Lys Lys Lys Ile Thr Asn Val Leu Glu
    1160                1165                1170

Phe Gln Gly Ile Ser Ile Leu Asp Arg Ile Asn Tyr Arg Lys Asp
    1175                1180                1185

Lys Leu Asn Phe Leu Leu Glu Lys Gly Tyr Lys Asp Ile Glu Leu
    1190                1195                1200

Ile Ile Glu Leu Pro Lys Tyr Ser Leu Phe Glu Leu Ser Asp Gly
    1205                1210                1215

Ser Arg Arg Met Leu Ala Ser Ile Leu Ser Thr Asn Asn Lys Arg
    1220                1225                1230

Gly Glu Ile His Lys Gly Asn Gln Ile Phe Leu Ser Gln Lys Phe
    1235                1240                1245

Val Lys Leu Leu Tyr His Ala Lys Arg Ile Ser Asn Thr Ile Asn
    1250                1255                1260

Glu Asn His Arg Lys Tyr Val Glu Asn His Lys Lys Glu Phe Glu
    1265                1270                1275

Glu Leu Phe Tyr Tyr Ile Leu Glu Phe Asn Glu Asn Tyr Val Gly
    1280                1285                1290

Ala Lys Lys Asn Gly Lys Leu Leu Asn Ser Ala Phe Gln Ser Trp
    1295                1300                1305

Gln Asn His Ser Ile Asp Glu Leu Cys Ser Ser Phe Ile Gly Pro
    1310                1315                1320

Thr Gly Ser Glu Arg Lys Gly Leu Phe Glu Leu Thr Ser Arg Gly
    1325                1330                1335

Ser Ala Ala Asp Phe Glu Phe Leu Gly Val Lys Ile Pro Arg Tyr
```

```
                    1340              1345              1350

Arg  Asp  Tyr  Thr  Pro  Ser  Ser  Leu  Leu  Lys  Asp  Ala  Thr  Leu  Ile
     1355                    1360                    1365

His  Gln  Ser  Val  Thr  Gly  Leu  Tyr  Glu  Thr  Arg  Ile  Asp  Leu  Ala
          1370                    1375                    1380

Lys  Leu  Gly  Glu  Gly
          1385

<210> SEQ ID NO 13
<211> LENGTH: 984
<212> TYPE: PRT
<213> ORGANISM: Campylobacter jejuni

<400> SEQUENCE: 13

Met  Ala  Arg  Ile  Leu  Ala  Phe  Asp  Ile  Gly  Ile  Ser  Ser  Ile  Gly  Trp
1                   5                       10                      15

Ala  Phe  Ser  Glu  Asn  Asp  Glu  Leu  Lys  Asp  Cys  Gly  Val  Arg  Ile  Phe
               20                      25                      30

Thr  Lys  Val  Glu  Asn  Pro  Lys  Thr  Gly  Glu  Ser  Leu  Ala  Leu  Pro  Arg
          35                      40                      45

Arg  Leu  Ala  Arg  Ser  Ala  Arg  Lys  Arg  Leu  Ala  Arg  Lys  Ala  Arg
     50                      55                      60

Leu  Asn  His  Leu  Lys  His  Leu  Ile  Ala  Asn  Glu  Phe  Lys  Leu  Asn  Tyr
65                  70                      75                      80

Glu  Asp  Tyr  Gln  Ser  Phe  Asp  Glu  Ser  Leu  Ala  Lys  Ala  Tyr  Lys  Gly
               85                      90                      95

Ser  Leu  Ile  Ser  Pro  Tyr  Glu  Leu  Arg  Phe  Arg  Ala  Leu  Asn  Glu  Leu
               100                     105                     110

Leu  Ser  Lys  Gln  Asp  Phe  Ala  Arg  Val  Ile  Leu  His  Ile  Ala  Lys  Arg
          115                     120                     125

Arg  Gly  Tyr  Asp  Asp  Ile  Lys  Asn  Ser  Asp  Asp  Lys  Glu  Lys  Gly  Ala
     130                     135                     140

Ile  Leu  Lys  Ala  Ile  Lys  Gln  Asn  Glu  Glu  Lys  Leu  Ala  Asn  Tyr  Gln
145                 150                     155                     160

Ser  Val  Gly  Glu  Tyr  Leu  Tyr  Lys  Glu  Tyr  Phe  Gln  Lys  Phe  Lys  Glu
               165                     170                     175

Asn  Ser  Lys  Glu  Phe  Thr  Asn  Val  Arg  Asn  Lys  Lys  Glu  Ser  Tyr  Glu
               180                     185                     190

Arg  Cys  Ile  Ala  Gln  Ser  Phe  Leu  Lys  Asp  Glu  Leu  Lys  Leu  Ile  Phe
          195                     200                     205

Lys  Lys  Gln  Arg  Glu  Phe  Gly  Phe  Ser  Phe  Ser  Lys  Lys  Phe  Glu  Glu
     210                     215                     220

Glu  Val  Leu  Ser  Val  Ala  Phe  Tyr  Lys  Arg  Ala  Leu  Lys  Asp  Phe  Ser
225                 230                     235                     240

His  Leu  Val  Gly  Asn  Cys  Ser  Phe  Phe  Thr  Asp  Glu  Lys  Arg  Ala  Pro
               245                     250                     255

Lys  Asn  Ser  Pro  Leu  Ala  Phe  Met  Phe  Val  Ala  Leu  Thr  Arg  Ile  Ile
               260                     265                     270

Asn  Leu  Leu  Asn  Asn  Leu  Lys  Asn  Thr  Glu  Gly  Ile  Leu  Tyr  Thr  Lys
          275                     280                     285

Asp  Asp  Leu  Asn  Ala  Leu  Leu  Asn  Glu  Val  Leu  Lys  Asn  Gly  Thr  Leu
     290                     295                     300

Thr  Tyr  Lys  Gln  Thr  Lys  Lys  Leu  Leu  Gly  Leu  Ser  Asp  Asp  Tyr  Glu
305                 310                     315                     320
```

-continued

Phe Lys Gly Glu Lys Gly Thr Tyr Phe Ile Glu Phe Lys Lys Tyr Lys
                    325                 330                 335

Glu Phe Ile Lys Ala Leu Gly Glu His Asn Leu Ser Gln Asp Asp Leu
            340                 345                 350

Asn Glu Ile Ala Lys Asp Ile Thr Leu Ile Lys Asp Glu Ile Lys Leu
            355                 360                 365

Lys Lys Ala Leu Ala Lys Tyr Asp Leu Asn Gln Asn Gln Ile Asp Ser
370                 375                 380

Leu Ser Lys Leu Glu Phe Lys Asp His Leu Asn Ile Ser Phe Lys Ala
385                 390                 395                 400

Leu Lys Leu Val Thr Pro Leu Met Leu Glu Gly Lys Lys Tyr Asp Glu
                405                 410                 415

Ala Cys Asn Glu Leu Asn Leu Lys Val Ala Ile Asn Glu Asp Lys Lys
            420                 425                 430

Asp Phe Leu Pro Ala Phe Asn Glu Thr Tyr Lys Asp Glu Val Thr
            435                 440                 445

Asn Pro Val Val Leu Arg Ala Ile Lys Glu Tyr Arg Lys Val Leu Asn
            450                 455                 460

Ala Leu Leu Lys Lys Tyr Gly Lys Val His Lys Ile Asn Ile Glu Leu
465                 470                 475                 480

Ala Arg Glu Val Gly Lys Asn His Ser Gln Arg Ala Lys Ile Glu Lys
                485                 490                 495

Glu Gln Asn Glu Asn Tyr Lys Ala Lys Asp Ala Glu Leu Glu Cys
            500                 505                 510

Glu Lys Leu Gly Leu Lys Ile Asn Ser Lys Asn Ile Leu Lys Leu Arg
            515                 520                 525

Leu Phe Lys Glu Gln Lys Glu Phe Cys Ala Tyr Ser Gly Glu Lys Ile
530                 535                 540

Lys Ile Ser Asp Leu Gln Asp Glu Lys Met Leu Glu Ile Asp His Ile
545                 550                 555                 560

Tyr Pro Tyr Ser Arg Ser Phe Asp Asp Ser Tyr Met Asn Lys Val Leu
                565                 570                 575

Val Phe Thr Lys Gln Asn Gln Glu Lys Leu Asn Gln Thr Pro Phe Glu
            580                 585                 590

Ala Phe Gly Asn Asp Ser Ala Lys Trp Gln Lys Ile Glu Val Leu Ala
            595                 600                 605

Lys Asn Leu Pro Thr Lys Lys Gln Lys Arg Ile Leu Asp Lys Asn Tyr
            610                 615                 620

Lys Asp Lys Glu Gln Lys Asn Phe Lys Asp Arg Asn Leu Asn Asp Thr
625                 630                 635                 640

Arg Tyr Ile Ala Arg Leu Val Leu Asn Tyr Thr Lys Asp Tyr Leu Asp
                645                 650                 655

Phe Leu Pro Leu Ser Asp Asp Glu Asn Thr Lys Leu Asn Asp Thr Gln
            660                 665                 670

Lys Gly Ser Lys Val His Val Glu Ala Lys Ser Gly Met Leu Thr Ser
            675                 680                 685

Ala Leu Arg His Thr Trp Gly Phe Ser Ala Lys Asp Arg Asn Asn His
            690                 695                 700

Leu His His Ala Ile Asp Ala Val Ile Ile Ala Tyr Ala Asn Asn Ser
705                 710                 715                 720

Ile Val Lys Ala Phe Ser Asp Phe Lys Lys Glu Gln Glu Ser Asn Ser
                725                 730                 735

Ala Glu Leu Tyr Ala Lys Lys Ile Ser Glu Leu Asp Tyr Lys Asn Lys

```
            740                 745                 750
Arg Lys Phe Phe Glu Pro Phe Ser Gly Phe Arg Gln Lys Val Leu Asp
        755                 760                 765

Lys Ile Asp Glu Ile Phe Val Ser Lys Pro Glu Arg Lys Lys Pro Ser
    770                 775                 780

Gly Ala Leu His Glu Thr Phe Arg Lys Glu Glu Phe Tyr Gln
785                 790                 795                 800

Ser Tyr Gly Gly Lys Glu Gly Val Leu Lys Ala Leu Glu Leu Gly Lys
                    805                 810                 815

Ile Arg Lys Val Asn Gly Lys Ile Val Lys Asn Gly Asp Met Phe Arg
                820                 825                 830

Val Asp Ile Phe Lys His Lys Lys Thr Asn Lys Phe Tyr Ala Val Pro
            835                 840                 845

Ile Tyr Thr Met Asp Phe Ala Leu Lys Val Leu Pro Asn Lys Ala Val
        850                 855                 860

Ala Arg Ser Lys Lys Gly Glu Ile Lys Asp Trp Ile Leu Met Asp Glu
865                 870                 875                 880

Asn Tyr Glu Phe Cys Phe Ser Leu Tyr Lys Asp Ser Leu Ile Leu Ile
                    885                 890                 895

Gln Thr Lys Asp Met Gln Glu Pro Glu Phe Val Tyr Tyr Asn Ala Phe
                900                 905                 910

Thr Ser Thr Val Ser Leu Ile Val Ser Lys His Asp Asn Lys Phe
            915                 920                 925

Glu Thr Leu Ser Lys Asn Gln Lys Ile Leu Phe Lys Asn Ala Asn Glu
        930                 935                 940

Lys Glu Val Ile Ala Lys Ser Ile Gly Ile Gln Asn Leu Lys Val Phe
945                 950                 955                 960

Glu Lys Tyr Ile Val Ser Ala Leu Gly Glu Val Thr Lys Ala Glu Phe
                    965                 970                 975

Arg Gln Arg Glu Asp Phe Lys Lys
            980

<210> SEQ ID NO 14
<211> LENGTH: 1056
<212> TYPE: PRT
<213> ORGANISM: Pasteurella multocida

<400> SEQUENCE: 14

Met Gln Thr Thr Asn Leu Ser Tyr Ile Leu Gly Leu Asp Leu Gly Ile
1               5                   10                  15

Ala Ser Val Gly Trp Ala Val Val Glu Ile Asn Glu Asn Glu Asp Pro
            20                  25                  30

Ile Gly Leu Ile Asp Val Gly Val Arg Ile Phe Glu Arg Ala Glu Val
        35                  40                  45

Pro Lys Thr Gly Glu Ser Leu Ala Leu Ser Arg Arg Leu Ala Arg Ser
    50                  55                  60

Thr Arg Arg Leu Ile Arg Arg Ala His Arg Leu Leu Ala Lys
65                  70                  75                  80

Arg Phe Leu Lys Arg Glu Gly Ile Leu Ser Thr Ile Asp Leu Glu Lys
                    85                  90                  95

Gly Leu Pro Asn Gln Ala Trp Glu Leu Arg Val Ala Gly Leu Glu Arg
                100                 105                 110

Arg Leu Ser Ala Ile Glu Trp Gly Ala Val Leu Leu His Leu Ile Lys
            115                 120                 125
```

-continued

```
His Arg Gly Tyr Leu Ser Lys Arg Lys Asn Glu Ser Gln Thr Asn Asn
    130                 135                 140

Lys Glu Leu Gly Ala Leu Leu Ser Gly Val Ala Gln Asn His Gln Leu
145                 150                 155                 160

Leu Gln Ser Asp Asp Tyr Arg Thr Pro Ala Glu Leu Ala Leu Lys Lys
                165                 170                 175

Phe Ala Lys Glu Glu Gly His Ile Arg Asn Gln Arg Gly Ala Tyr Thr
            180                 185                 190

His Thr Phe Asn Arg Leu Asp Leu Leu Ala Glu Leu Asn Leu Leu Phe
        195                 200                 205

Ala Gln Gln His Gln Phe Gly Asn Pro His Cys Lys Glu His Ile Gln
    210                 215                 220

Gln Tyr Met Thr Glu Leu Leu Met Trp Gln Lys Pro Ala Leu Ser Gly
225                 230                 235                 240

Glu Ala Ile Leu Lys Met Leu Gly Lys Cys Thr His Glu Lys Asn Glu
                245                 250                 255

Phe Lys Ala Ala Lys His Thr Tyr Ser Ala Glu Arg Phe Val Trp Leu
            260                 265                 270

Thr Lys Leu Asn Asn Leu Arg Ile Leu Glu Asp Gly Ala Glu Arg Ala
        275                 280                 285

Leu Asn Glu Glu Glu Arg Gln Leu Leu Ile Asn His Pro Tyr Glu Lys
    290                 295                 300

Ser Lys Leu Thr Tyr Ala Gln Val Arg Lys Leu Leu Gly Leu Ser Glu
305                 310                 315                 320

Gln Ala Ile Phe Lys His Leu Arg Tyr Ser Lys Glu Asn Ala Glu Ser
                325                 330                 335

Ala Thr Phe Met Glu Leu Lys Ala Trp His Ala Ile Arg Lys Ala Leu
            340                 345                 350

Glu Asn Gln Gly Leu Lys Asp Thr Trp Gln Asp Leu Ala Lys Lys Pro
        355                 360                 365

Asp Leu Leu Asp Glu Ile Gly Thr Ala Phe Ser Leu Tyr Lys Thr Asp
    370                 375                 380

Glu Asp Ile Gln Gln Tyr Leu Thr Asn Lys Val Pro Asn Ser Val Ile
385                 390                 395                 400

Asn Ala Leu Leu Val Ser Leu Asn Phe Asp Lys Phe Ile Glu Leu Ser
                405                 410                 415

Leu Lys Ser Leu Arg Lys Ile Leu Pro Leu Met Glu Gln Gly Lys Arg
            420                 425                 430

Tyr Asp Gln Ala Cys Arg Glu Ile Tyr Gly His His Tyr Gly Glu Ala
        435                 440                 445

Asn Gln Lys Thr Ser Gln Leu Leu Pro Ala Ile Pro Ala Gln Glu Ile
    450                 455                 460

Arg Asn Pro Val Val Leu Arg Thr Leu Ser Gln Ala Arg Lys Val Ile
465                 470                 475                 480

Asn Ala Ile Ile Arg Gln Tyr Gly Ser Pro Ala Arg Val His Ile Glu
                485                 490                 495

Thr Gly Arg Glu Leu Gly Lys Ser Phe Lys Glu Arg Glu Ile Gln
            500                 505                 510

Lys Gln Gln Glu Asp Asn Arg Thr Lys Arg Glu Ser Ala Val Gln Lys
        515                 520                 525

Phe Lys Glu Leu Phe Ser Asp Phe Ser Ser Glu Pro Lys Ser Lys Asp
    530                 535                 540

Ile Leu Lys Phe Arg Leu Tyr Glu Gln Gln His Gly Lys Cys Leu Tyr
```

```
              545                 550                 555                 560
        Ser Gly Lys Glu Ile Asn Ile His Arg Leu Asn Glu Lys Gly Tyr Val
                            565                 570                 575

Glu Ile Asp His Ala Leu Pro Phe Ser Arg Thr Trp Asp Asp Ser Phe
                            580                 585                 590

Asn Asn Lys Val Leu Val Leu Ala Ser Glu Asn Gln Asn Lys Gly Asn
                            595                 600                 605

Gln Thr Pro Tyr Glu Trp Leu Gln Gly Lys Ile Asn Ser Glu Arg Trp
                            610                 615                 620

Lys Asn Phe Val Ala Leu Val Leu Gly Ser Gln Cys Ser Ala Ala Lys
        625                 630                 635                 640

Lys Gln Arg Leu Leu Thr Gln Val Ile Asp Asp Asn Lys Phe Ile Asp
                            645                 650                 655

Arg Asn Leu Asn Asp Thr Arg Tyr Ile Ala Arg Phe Leu Ser Asn Tyr
                            660                 665                 670

Ile Gln Glu Asn Leu Leu Val Gly Lys Asn Lys Lys Asn Val Phe
                            675                 680                 685

Thr Pro Asn Gly Gln Ile Thr Ala Leu Leu Arg Ser Arg Trp Gly Leu
                            690                 695                 700

Ile Lys Ala Arg Glu Asn Asn Asn Arg His His Ala Leu Asp Ala Ile
        705                 710                 715                 720

Val Val Ala Cys Ala Thr Pro Ser Met Gln Gln Lys Ile Thr Arg Phe
                            725                 730                 735

Ile Arg Phe Lys Glu Val His Pro Tyr Lys Ile Glu Asn Arg Tyr Glu
                            740                 745                 750

Met Val Asp Gln Glu Ser Gly Glu Ile Ile Ser Pro His Phe Pro Glu
                            755                 760                 765

Pro Trp Ala Tyr Phe Arg Gln Glu Val Asn Ile Arg Val Phe Asp Asn
                            770                 775                 780

His Pro Asp Thr Val Leu Lys Glu Met Leu Pro Asp Arg Pro Gln Ala
        785                 790                 795                 800

Asn His Gln Phe Val Gln Pro Leu Phe Val Ser Arg Ala Pro Thr Arg
                            805                 810                 815

Lys Met Ser Gly Gln Gly His Met Glu Thr Ile Lys Ser Ala Lys Arg
                            820                 825                 830

Leu Ala Glu Gly Ile Ser Val Leu Arg Ile Pro Leu Thr Gln Leu Lys
                            835                 840                 845

Pro Asn Leu Leu Glu Asn Met Val Asn Lys Glu Arg Glu Pro Ala Leu
        850                 855                 860

Tyr Ala Gly Leu Lys Ala Arg Leu Ala Glu Phe Asn Gln Asp Pro Ala
        865                 870                 875                 880

Lys Ala Phe Ala Thr Pro Phe Tyr Lys Gln Gly Gly Gln Gln Val Lys
                            885                 890                 895

Ala Ile Arg Val Glu Gln Val Gln Lys Ser Gly Val Leu Val Arg Glu
                            900                 905                 910

Asn Asn Gly Val Ala Asp Asn Ala Ser Ile Val Arg Thr Asp Val Phe
                            915                 920                 925

Ile Lys Asn Asn Lys Phe Phe Leu Val Pro Ile Tyr Thr Trp Gln Val
                            930                 935                 940

Ala Lys Gly Ile Leu Pro Asn Lys Ala Ile Val Ala His Lys Asn Glu
        945                 950                 955                 960

Asp Glu Trp Glu Glu Met Asp Glu Gly Ala Lys Phe Lys Phe Ser Leu
                            965                 970                 975
```

```
Phe Pro Asn Asp Leu Val Glu Leu Lys Thr Lys Lys Glu Tyr Phe Phe
            980                 985                 990

Gly Tyr Tyr Ile Gly Leu Asp Arg  Ala Thr Gly Asn Ile  Ser Leu Lys
        995                 1000                1005

Glu His Asp Gly Glu Ile Ser  Lys Gly Lys Asp Gly  Val Tyr Arg
    1010                1015                1020

Val Gly Val Lys Leu Ala Leu  Ser Phe Glu Lys Tyr  Gln Val Asp
    1025                1030                1035

Glu Leu Gly Lys Asn Arg Gln  Ile Cys Arg Pro Gln  Gln Arg Gln
    1040                1045                1050

Pro Val Arg
    1055

<210> SEQ ID NO 15
<211> LENGTH: 1629
<212> TYPE: PRT
<213> ORGANISM: Francisella novicida

<400> SEQUENCE: 15

Met Asn Phe Lys Ile Leu Pro Ile Ala Ile Asp Leu Gly Val Lys Asn
1               5                   10                  15

Thr Gly Val Phe Ser Ala Phe Tyr Gln Lys Gly Thr Ser Leu Glu Arg
            20                  25                  30

Leu Asp Asn Lys Asn Gly Lys Val Tyr Glu Leu Ser Lys Asp Ser Tyr
        35                  40                  45

Thr Leu Leu Met Asn Asn Arg Thr Ala Arg Arg His Gln Arg Arg Gly
    50                  55                  60

Ile Asp Arg Lys Gln Leu Val Lys Arg Leu Phe Lys Leu Ile Trp Thr
65                  70                  75                  80

Glu Gln Leu Asn Leu Glu Trp Asp Lys Asp Thr Gln Gln Ala Ile Ser
                85                  90                  95

Phe Leu Phe Asn Arg Arg Gly Phe Ser Phe Ile Thr Asp Gly Tyr Ser
            100                 105                 110

Pro Glu Tyr Leu Asn Ile Val Pro Glu Gln Val Lys Ala Ile Leu Met
        115                 120                 125

Asp Ile Phe Asp Asp Tyr Asn Gly Glu Asp Asp Leu Asp Ser Tyr Leu
    130                 135                 140

Lys Leu Ala Thr Glu Gln Glu Ser Lys Ile Ser Glu Ile Tyr Asn Lys
145                 150                 155                 160

Leu Met Gln Lys Ile Leu Glu Phe Lys Leu Met Lys Leu Cys Thr Asp
                165                 170                 175

Ile Lys Asp Asp Lys Val Ser Thr Lys Thr Leu Lys Glu Ile Thr Ser
            180                 185                 190

Tyr Glu Phe Glu Leu Leu Ala Asp Tyr Leu Ala Asn Tyr Ser Glu Ser
        195                 200                 205

Leu Lys Thr Gln Lys Phe Ser Tyr Thr Asp Lys Gln Gly Asn Leu Lys
    210                 215                 220

Glu Leu Ser Tyr Tyr His His Asp Lys Tyr Asn Ile Gln Glu Phe Leu
225                 230                 235                 240

Lys Arg His Ala Thr Ile Asn Asp Arg Ile Leu Asp Thr Leu Leu Thr
                245                 250                 255

Asp Asp Leu Asp Ile Trp Asn Phe Asn Phe Glu Lys Phe Asp Phe Asp
            260                 265                 270

Lys Asn Glu Glu Lys Leu Gln Asn Gln Glu Asp Lys Asp His Ile Gln
```

```
                275                 280                 285
Ala His Leu His His Phe Val Phe Ala Val Asn Lys Ile Lys Ser Glu
290                 295                 300
Met Ala Ser Gly Gly Arg His Arg Ser Gln Tyr Phe Gln Glu Ile Thr
305                 310                 315                 320
Asn Val Leu Asp Glu Asn Asn His Gln Glu Gly Tyr Leu Lys Asn Phe
                325                 330                 335
Cys Glu Asn Leu His Asn Lys Lys Tyr Ser Asn Leu Ser Val Lys Asn
                340                 345                 350
Leu Val Asn Leu Ile Gly Asn Leu Ser Asn Leu Glu Leu Lys Pro Leu
                355                 360                 365
Arg Lys Tyr Phe Asn Asp Lys Ile His Ala Lys Ala Asp His Trp Asp
                370                 375                 380
Glu Gln Lys Phe Thr Glu Thr Tyr Cys His Trp Ile Leu Gly Glu Trp
385                 390                 395                 400
Arg Val Gly Val Lys Asp Gln Asp Lys Lys Asp Gly Ala Lys Tyr Ser
                405                 410                 415
Tyr Lys Asp Leu Cys Asn Glu Leu Lys Gln Lys Val Thr Lys Ala Gly
                420                 425                 430
Leu Val Asp Phe Leu Leu Glu Leu Asp Pro Cys Arg Thr Ile Pro Pro
                435                 440                 445
Tyr Leu Asp Asn Asn Arg Lys Pro Pro Lys Cys Gln Ser Leu Ile
450                 455                 460
Leu Asn Pro Lys Phe Leu Asp Asn Gln Tyr Pro Asn Trp Gln Gln Tyr
465                 470                 475                 480
Leu Gln Glu Leu Lys Lys Leu Gln Ser Ile Gln Asn Tyr Leu Asp Ser
                485                 490                 495
Phe Glu Thr Asp Leu Lys Val Leu Lys Ser Ser Lys Asp Gln Pro Tyr
                500                 505                 510
Phe Val Glu Tyr Lys Ser Ser Asn Gln Gln Ile Ala Ser Gly Gln Arg
                515                 520                 525
Asp Tyr Lys Asp Leu Asp Ala Arg Ile Leu Gln Phe Ile Phe Asp Arg
                530                 535                 540
Val Lys Ala Ser Asp Glu Leu Leu Leu Asn Glu Ile Tyr Phe Gln Ala
545                 550                 555                 560
Lys Lys Leu Lys Gln Lys Ala Ser Ser Glu Leu Glu Lys Leu Glu Ser
                565                 570                 575
Ser Lys Lys Leu Asp Glu Val Ile Ala Asn Ser Gln Leu Ser Gln Ile
                580                 585                 590
Leu Lys Ser Gln His Thr Asn Gly Ile Phe Glu Gln Gly Thr Phe Leu
                595                 600                 605
His Leu Val Cys Lys Tyr Tyr Lys Gln Arg Gln Arg Ala Arg Asp Ser
                610                 615                 620
Arg Leu Tyr Ile Met Pro Glu Tyr Arg Tyr Asp Lys Lys Leu His Lys
625                 630                 635                 640
Tyr Asn Asn Thr Gly Arg Phe Asp Asp Asn Gln Leu Leu Thr Tyr
                645                 650                 655
Cys Asn His Lys Pro Arg Gln Lys Arg Tyr Gln Leu Leu Asn Asp Leu
                660                 665                 670
Ala Gly Val Leu Gln Val Ser Pro Asn Phe Leu Lys Asp Lys Ile Gly
                675                 680                 685
Ser Asp Asp Leu Phe Ile Ser Lys Trp Leu Val Glu His Ile Arg
690                 695                 700
```

```
Gly Phe Lys Lys Ala Cys Glu Asp Ser Leu Lys Ile Gln Lys Asp Asn
705                 710                 715                 720

Arg Gly Leu Leu Asn His Lys Ile Asn Ile Ala Arg Asn Thr Lys Gly
            725                 730                 735

Lys Cys Glu Lys Glu Ile Phe Asn Leu Ile Cys Lys Ile Glu Gly Ser
        740                 745                 750

Glu Asp Lys Lys Gly Asn Tyr Lys His Gly Leu Ala Tyr Glu Leu Gly
            755                 760                 765

Val Leu Leu Phe Gly Glu Pro Asn Glu Ala Ser Lys Pro Glu Phe Asp
770                 775                 780

Arg Lys Ile Lys Lys Phe Asn Ser Ile Tyr Ser Phe Ala Gln Ile Gln
785                 790                 795                 800

Gln Ile Ala Phe Ala Glu Arg Lys Gly Asn Ala Asn Thr Cys Ala Val
                805                 810                 815

Cys Ser Ala Asp Asn Ala His Arg Met Gln Gln Ile Lys Ile Thr Glu
            820                 825                 830

Pro Val Glu Asp Asn Lys Asp Lys Ile Ile Leu Ser Ala Lys Ala Gln
        835                 840                 845

Arg Leu Pro Ala Ile Pro Thr Arg Ile Val Asp Gly Ala Val Lys Lys
    850                 855                 860

Met Ala Thr Ile Leu Ala Lys Asn Ile Val Asp Asp Asn Trp Gln Asn
865                 870                 875                 880

Ile Lys Gln Val Leu Ser Ala Lys His Gln Leu His Ile Pro Ile Ile
                885                 890                 895

Thr Glu Ser Asn Ala Phe Glu Phe Glu Pro Ala Leu Ala Asp Val Lys
            900                 905                 910

Gly Lys Ser Leu Lys Asp Arg Arg Lys Lys Ala Leu Glu Arg Ile Ser
        915                 920                 925

Pro Glu Asn Ile Phe Lys Asp Lys Asn Asn Arg Ile Lys Glu Phe Ala
    930                 935                 940

Lys Gly Ile Ser Ala Tyr Ser Gly Ala Asn Leu Thr Asp Gly Asp Phe
945                 950                 955                 960

Asp Gly Ala Lys Glu Glu Leu Asp His Ile Ile Pro Arg Ser His Lys
                965                 970                 975

Lys Tyr Gly Thr Leu Asn Asp Glu Ala Asn Leu Ile Cys Val Thr Arg
            980                 985                 990

Gly Asp Asn Lys Asn Lys Gly Asn Arg Ile Phe Cys Leu Arg Asp Leu
        995                 1000                1005

Ala Asp Asn Tyr Lys Leu Lys Gln Phe Glu Thr Thr Asp Asp Leu
    1010                1015                1020

Glu Ile Glu Lys Lys Ile Ala Asp Thr Ile Trp Asp Ala Asn Lys
    1025                1030                1035

Lys Asp Phe Lys Phe Gly Asn Tyr Arg Ser Phe Ile Asn Leu Thr
    1040                1045                1050

Pro Gln Glu Gln Lys Ala Phe Arg His Ala Leu Phe Leu Ala Asp
    1055                1060                1065

Glu Asn Pro Ile Lys Gln Ala Val Ile Arg Ala Ile Asn Asn Arg
    1070                1075                1080

Asn Arg Thr Phe Val Asn Gly Thr Gln Arg Tyr Phe Ala Glu Val
    1085                1090                1095

Leu Ala Asn Asn Ile Tyr Leu Arg Ala Lys Lys Glu Asn Leu Asn
    1100                1105                1110
```

```
Thr Asp Lys Ile Ser Phe Asp Tyr Phe Gly Ile Pro Thr Ile Gly
    1115                1120                1125

Asn Gly Arg Gly Ile Ala Glu Ile Arg Gln Leu Tyr Glu Lys Val
    1130                1135                1140

Asp Ser Asp Ile Gln Ala Tyr Ala Lys Gly Asp Lys Pro Gln Ala
    1145                1150                1155

Ser Tyr Ser His Leu Ile Asp Ala Met Leu Ala Phe Cys Ile Ala
    1160                1165                1170

Ala Asp Glu His Arg Asn Asp Gly Ser Ile Gly Leu Glu Ile Asp
    1175                1180                1185

Lys Asn Tyr Ser Leu Tyr Pro Leu Asp Lys Asn Thr Gly Glu Val
    1190                1195                1200

Phe Thr Lys Asp Ile Phe Ser Gln Ile Lys Ile Thr Asp Asn Glu
    1205                1210                1215

Phe Ser Asp Lys Lys Leu Val Arg Lys Lys Ala Ile Glu Gly Phe
    1220                1225                1230

Asn Thr His Arg Gln Met Thr Arg Asp Gly Ile Tyr Ala Glu Asn
    1235                1240                1245

Tyr Leu Pro Ile Leu Ile His Lys Glu Leu Asn Glu Val Arg Lys
    1250                1255                1260

Gly Tyr Thr Trp Lys Asn Ser Glu Glu Ile Lys Ile Phe Lys Gly
    1265                1270                1275

Lys Lys Tyr Asp Ile Gln Gln Leu Asn Asn Leu Val Tyr Cys Leu
    1280                1285                1290

Lys Phe Val Asp Lys Pro Ile Ser Ile Asp Ile Gln Ile Ser Thr
    1295                1300                1305

Leu Glu Glu Leu Arg Asn Ile Leu Thr Thr Asn Asn Ile Ala Ala
    1310                1315                1320

Thr Ala Glu Tyr Tyr Tyr Ile Asn Leu Lys Thr Gln Lys Leu His
    1325                1330                1335

Glu Tyr Tyr Ile Glu Asn Tyr Asn Thr Ala Leu Gly Tyr Lys Lys
    1340                1345                1350

Tyr Ser Lys Glu Met Glu Phe Leu Arg Ser Leu Ala Tyr Arg Ser
    1355                1360                1365

Glu Arg Val Lys Ile Lys Ser Ile Asp Asp Val Lys Gln Val Leu
    1370                1375                1380

Asp Lys Asp Ser Asn Phe Ile Ile Gly Lys Ile Thr Leu Pro Phe
    1385                1390                1395

Lys Lys Glu Trp Gln Arg Leu Tyr Arg Glu Trp Gln Asn Thr Thr
    1400                1405                1410

Ile Lys Asp Asp Tyr Glu Phe Leu Lys Ser Phe Phe Asn Val Lys
    1415                1420                1425

Ser Ile Thr Lys Leu His Lys Lys Val Arg Lys Asp Phe Ser Leu
    1430                1435                1440

Pro Ile Ser Thr Asn Glu Gly Lys Phe Leu Val Lys Arg Lys Thr
    1445                1450                1455

Trp Asp Asn Asn Phe Ile Tyr Gln Ile Leu Asn Asp Ser Asp Ser
    1460                1465                1470

Arg Ala Asp Gly Thr Lys Pro Phe Ile Pro Ala Phe Asp Ile Ser
    1475                1480                1485

Lys Asn Glu Ile Val Glu Ala Ile Ile Asp Ser Phe Thr Ser Lys
    1490                1495                1500

Asn Ile Phe Trp Leu Pro Lys Asn Ile Glu Leu Gln Lys Val Asp
```

```
            1505                1510                1515

Asn Lys Asn Ile Phe Ala Ile Asp Thr Ser Lys Trp Phe Glu Val
    1520                1525                1530

Glu Thr Pro Ser Asp Leu Arg Asp Ile Gly Ile Ala Thr Ile Gln
    1535                1540                1545

Tyr Lys Ile Asp Asn Asn Ser Arg Pro Lys Val Arg Val Lys Leu
    1550                1555                1560

Asp Tyr Val Ile Asp Asp Ser Lys Ile Asn Tyr Phe Met Asn
    1565                1570                1575

His Ser Leu Leu Lys Ser Arg Tyr Pro Asp Lys Val Leu Glu Ile
    1580                1585                1590

Leu Lys Gln Ser Thr Ile Ile Glu Phe Glu Ser Ser Gly Phe Asn
    1595                1600                1605

Lys Thr Ile Lys Glu Met Leu Gly Met Lys Leu Ala Gly Ile Tyr
    1610                1615                1620

Asn Glu Thr Ser Asn Asn
    1625

<210> SEQ ID NO 16
<211> LENGTH: 1371
<212> TYPE: PRT
<213> ORGANISM: Lactobacillus buchneri

<400> SEQUENCE: 16

Met Lys Val Asn Asn Tyr His Ile Gly Leu Asp Ile Gly Thr Ser Ser
1               5                   10                  15

Ile Gly Trp Val Ala Ile Gly Lys Asp Gly Lys Pro Leu Arg Val Lys
                20                  25                  30

Gly Lys Thr Ala Ile Gly Ala Arg Leu Phe Gln Glu Gly Asn Pro Ala
            35                  40                  45

Ala Asp Arg Arg Met Phe Arg Thr Thr Arg Arg Leu Ser Arg Arg
        50                  55                  60

Lys Trp Arg Leu Lys Leu Leu Glu Glu Ile Phe Asp Pro Tyr Ile Thr
65                  70                  75                  80

Pro Val Asp Ser Thr Phe Phe Ala Arg Leu Lys Gln Ser Asn Leu Ser
                85                  90                  95

Pro Lys Asp Ser Arg Lys Glu Phe Lys Gly Ser Met Leu Phe Pro Asp
            100                 105                 110

Leu Thr Asp Met Gln Tyr His Lys Asn Tyr Pro Thr Ile Tyr His Leu
        115                 120                 125

Arg His Ala Leu Met Thr Gln Asp Lys Lys Phe Asp Ile Arg Met Val
    130                 135                 140

Tyr Leu Ala Ile His His Ile Val Lys Tyr Arg Gly Asn Phe Leu Asn
145                 150                 155                 160

Ser Thr Pro Val Asp Ser Phe Lys Ala Ser Lys Val Asp Phe Val Asp
                165                 170                 175

Gln Phe Lys Lys Leu Asn Glu Leu Tyr Ala Ala Ile Asn Pro Glu Glu
            180                 185                 190

Ser Phe Lys Ile Asn Leu Ala Asn Ser Glu Asp Ile Gly His Gln Phe
        195                 200                 205

Leu Asp Pro Ser Ile Arg Lys Phe Asp Lys Lys Gln Ile Pro Lys
    210                 215                 220

Ile Val Pro Val Met Met Asn Asp Lys Val Thr Asp Arg Leu Asn Gly
225                 230                 235                 240
```

```
Lys Ile Ala Ser Glu Ile Ile His Ala Ile Leu Gly Tyr Lys Ala Lys
                245                 250                 255

Leu Asp Val Val Leu Gln Cys Thr Pro Val Asp Ser Lys Pro Trp Ala
            260                 265                 270

Leu Lys Phe Asp Asp Glu Asp Ile Asp Ala Lys Leu Glu Lys Ile Leu
        275                 280                 285

Pro Glu Met Asp Glu Asn Gln Gln Ser Ile Val Ala Ile Leu Gln Asn
    290                 295                 300

Leu Tyr Ser Gln Val Thr Leu Asn Gln Ile Val Pro Asn Gly Met Ser
305                 310                 315                 320

Leu Ser Glu Ser Met Ile Glu Lys Tyr Asn Asp His His Asp His Leu
                325                 330                 335

Lys Leu Tyr Lys Lys Leu Ile Asp Gln Leu Ala Asp Pro Lys Lys Lys
            340                 345                 350

Ala Val Leu Lys Lys Ala Tyr Ser Gln Tyr Val Gly Asp Asp Gly Lys
        355                 360                 365

Val Ile Glu Gln Ala Glu Phe Trp Ser Val Lys Lys Asn Leu Asp
    370                 375                 380

Asp Ser Glu Leu Ser Lys Gln Ile Met Asp Leu Ile Asp Ala Glu Lys
385                 390                 395                 400

Phe Met Pro Lys Gln Arg Thr Ser Gln Asn Gly Val Ile Pro His Gln
                405                 410                 415

Leu His Gln Arg Glu Leu Asp Glu Ile Glu His Gln Ser Lys Tyr
            420                 425                 430

Tyr Pro Trp Leu Val Glu Ile Asn Pro Asn Lys His Asp Leu His Leu
        435                 440                 445

Ala Lys Tyr Lys Ile Glu Gln Leu Val Ala Phe Arg Val Pro Tyr Tyr
    450                 455                 460

Val Gly Pro Met Ile Thr Pro Lys Asp Gln Ala Glu Ser Ala Glu Thr
465                 470                 475                 480

Val Phe Ser Trp Met Glu Arg Lys Gly Thr Glu Thr Gly Gln Ile Thr
                485                 490                 495

Pro Trp Asn Phe Asp Glu Lys Val Asp Arg Lys Ala Ser Ala Asn Arg
            500                 505                 510

Phe Ile Lys Arg Met Thr Thr Lys Asp Thr Tyr Leu Ile Gly Glu Asp
        515                 520                 525

Val Leu Pro Asp Glu Ser Leu Leu Tyr Glu Lys Phe Lys Val Leu Asn
    530                 535                 540

Glu Leu Asn Met Val Arg Val Asn Gly Lys Leu Leu Val Ala Asp
545                 550                 555                 560

Lys Gln Ala Ile Phe Gln Asp Leu Phe Glu Asn Tyr Lys His Val Ser
                565                 570                 575

Val Lys Lys Leu Gln Asn Tyr Ile Lys Ala Lys Thr Gly Leu Pro Ser
            580                 585                 590

Asp Pro Glu Ile Ser Gly Leu Ser Asp Pro His Phe Asn Asn Ser
        595                 600                 605

Leu Gly Thr Tyr Asn Asp Phe Lys Lys Leu Phe Gly Ser Lys Val Asp
    610                 615                 620

Glu Pro Asp Leu Gln Asp Asp Phe Glu Lys Ile Val Glu Trp Ser Thr
625                 630                 635                 640

Val Phe Glu Asp Lys Lys Ile Leu Arg Glu Lys Leu Asn Glu Ile Thr
                645                 650                 655

Trp Leu Ser Asp Gln Gln Lys Asp Val Leu Glu Ser Ser Arg Tyr Gln
```

```
                660             665             670
Gly Trp Gly Arg Leu Ser Lys Lys Leu Leu Thr Gly Ile Val Asn Asp
            675             680             685

Gln Gly Glu Arg Ile Ile Asp Lys Leu Trp Asn Thr Asn Lys Asn Phe
        690             695             700

Met Gln Ile Gln Ser Asp Asp Phe Ala Lys Arg Ile His Glu Ala
705             710             715             720

Asn Ala Asp Gln Met Gln Ala Val Asp Val Glu Asp Val Leu Ala Asp
                725             730             735

Ala Tyr Thr Ser Pro Gln Asn Lys Lys Ala Ile Arg Gln Val Val Lys
            740             745             750

Val Val Asp Asp Ile Gln Lys Ala Met Gly Gly Val Ala Pro Lys Tyr
        755             760             765

Ile Ser Ile Glu Phe Thr Arg Ser Glu Asp Arg Asn Pro Arg Arg Thr
    770             775             780

Ile Ser Arg Gln Arg Gln Leu Glu Asn Thr Leu Lys Asp Thr Ala Lys
785             790             795             800

Ser Leu Ala Lys Ser Ile Asn Pro Glu Leu Leu Ser Glu Leu Asp Asn
                805             810             815

Ala Ala Lys Ser Lys Lys Gly Leu Thr Asp Arg Leu Tyr Leu Tyr Phe
            820             825             830

Thr Gln Leu Gly Lys Asp Ile Tyr Thr Gly Glu Pro Ile Asn Ile Asp
        835             840             845

Glu Leu Asn Lys Tyr Asp Ile Asp His Ile Leu Pro Gln Ala Phe Ile
    850             855             860

Lys Asp Asn Ser Leu Asp Asn Arg Val Leu Val Leu Thr Ala Val Asn
865             870             875             880

Asn Gly Lys Ser Asp Asn Val Pro Leu Arg Met Phe Gly Ala Lys Met
                885             890             895

Gly His Phe Trp Lys Gln Leu Ala Glu Ala Gly Leu Ile Ser Lys Arg
            900             905             910

Lys Leu Lys Asn Leu Gln Thr Asp Pro Asp Thr Ile Ser Lys Tyr Ala
        915             920             925

Met His Gly Phe Ile Arg Arg Gln Leu Val Glu Thr Ser Gln Val Ile
    930             935             940

Lys Leu Val Ala Asn Ile Leu Gly Asp Lys Tyr Arg Asn Asp Asp Thr
945             950             955             960

Lys Ile Ile Glu Ile Thr Ala Arg Met Asn His Gln Met Arg Asp Glu
                965             970             975

Phe Gly Phe Ile Lys Asn Arg Glu Ile Asn Asp Tyr His His Ala Phe
            980             985             990

Asp Ala Tyr Leu Thr Ala Phe Leu Gly Arg Tyr Leu Tyr His Arg Tyr
        995             1000            1005

Ile Lys Leu Arg Pro Tyr Phe Val Tyr Gly Asp Phe Lys Lys Phe
    1010            1015            1020

Arg Glu Asp Lys Val Thr Met Arg Asn Phe Asn Phe Leu His Asp
    1025            1030            1035

Leu Thr Asp Asp Thr Gln Glu Lys Ile Ala Asp Ala Glu Thr Gly
    1040            1045            1050

Glu Val Ile Trp Asp Arg Glu Asn Ser Ile Gln Gln Leu Lys Asp
    1055            1060            1065

Val Tyr His Tyr Lys Phe Met Leu Ile Ser His Glu Val Tyr Thr
    1070            1075            1080
```

Leu Arg Gly Ala Met Phe Asn Gln Thr Val Tyr Pro Ala Ser Asp
1085                1090                1095

Ala Gly Lys Arg Lys Leu Ile Pro Val Lys Ala Asp Arg Pro Val
    1100                1105                1110

Asn Val Tyr Gly Gly Tyr Gly Ser Ala Asp Ala Tyr Met Ala
    1115                1120                1125

Ile Val Arg Ile His Asn Lys Lys Gly Asp Lys Tyr Arg Val Val
    1130                1135                1140

Gly Val Pro Met Arg Ala Leu Asp Arg Leu Asp Ala Ala Lys Asn
    1145                1150                1155

Val Ser Asp Ala Asp Phe Asp Arg Ala Leu Lys Asp Val Leu Ala
    1160                1165                1170

Pro Gln Leu Thr Lys Thr Lys Ser Arg Lys Thr Gly Glu Ile
1175                1180                1185

Thr Gln Val Ile Glu Asp Phe Glu Ile Val Leu Gly Lys Val Met
    1190                1195                1200

Tyr Arg Gln Leu Met Ile Asp Gly Asp Lys Lys Phe Met Leu Gly
    1205                1210                1215

Ser Ser Thr Tyr Gln Tyr Asn Ala Lys Gln Leu Val Leu Ser Asp
    1220                1225                1230

Gln Ser Val Lys Thr Leu Ala Ser Lys Gly Arg Leu Asp Pro Leu
    1235                1240                1245

Gln Glu Ser Met Asp Tyr Asn Asn Val Tyr Thr Glu Ile Leu Asp
    1250                1255                1260

Lys Val Asn Gln Tyr Phe Ser Leu Tyr Asp Met Asn Lys Phe Arg
1265                1270                1275

His Lys Leu Asn Leu Gly Phe Ser Lys Phe Ile Ser Phe Pro Asn
    1280                1285                1290

His Asn Val Leu Asp Gly Asn Thr Lys Val Ser Ser Gly Lys Arg
    1295                1300                1305

Glu Ile Leu Gln Glu Ile Leu Asn Gly Leu His Ala Asn Pro Thr
    1310                1315                1320

Phe Gly Asn Leu Lys Asp Val Gly Ile Thr Thr Pro Phe Gly Gln
1325                1330                1335

Leu Gln Gln Pro Asn Gly Ile Leu Leu Ser Asp Glu Thr Lys Ile
    1340                1345                1350

Arg Tyr Gln Ser Pro Thr Gly Leu Phe Glu Arg Thr Val Ser Leu
    1355                1360                1365

Lys Asp Leu
    1370

<210> SEQ ID NO 17
<211> LENGTH: 1334
<212> TYPE: PRT
<213> ORGANISM: Listeria innocua

<400> SEQUENCE: 17

Met Lys Lys Pro Tyr Thr Ile Gly Leu Asp Ile Gly Thr Asn Ser Val
1               5                   10                  15

Gly Trp Ala Val Leu Thr Asp Gln Tyr Asp Leu Val Lys Arg Lys Met
            20                  25                  30

Lys Ile Ala Gly Asp Ser Glu Lys Lys Gln Ile Lys Lys Asn Phe Trp
        35                  40                  45

Gly Val Arg Leu Phe Asp Glu Gly Gln Thr Ala Ala Asp Arg Arg Met

```
                50                  55                  60
Ala Arg Thr Ala Arg Arg Ile Glu Arg Arg Asn Arg Ile Ser
 65                  70                  75                  80

Tyr Leu Gln Gly Ile Phe Ala Glu Glu Met Ser Lys Thr Asp Ala Asn
                     85                  90                  95

Phe Phe Cys Arg Leu Ser Asp Ser Phe Tyr Val Asp Asn Glu Lys Arg
                100                 105                 110

Asn Ser Arg His Pro Phe Phe Ala Thr Ile Glu Glu Val Glu Tyr
                115                 120                 125

His Lys Asn Tyr Pro Thr Ile Tyr His Leu Arg Glu Glu Leu Val Asn
                130                 135                 140

Ser Ser Glu Lys Ala Asp Leu Arg Leu Val Tyr Leu Ala Leu Ala His
145                 150                 155                 160

Ile Ile Lys Tyr Arg Gly Asn Phe Leu Ile Glu Gly Ala Leu Asp Thr
                165                 170                 175

Gln Asn Thr Ser Val Asp Gly Ile Tyr Lys Gln Phe Ile Gln Thr Tyr
                180                 185                 190

Asn Gln Val Phe Ala Ser Gly Ile Glu Asp Gly Ser Leu Lys Lys Leu
                195                 200                 205

Glu Asp Asn Lys Asp Val Ala Lys Ile Leu Val Glu Lys Val Thr Arg
210                 215                 220

Lys Glu Lys Leu Glu Arg Ile Leu Lys Leu Tyr Pro Gly Glu Lys Ser
225                 230                 235                 240

Ala Gly Met Phe Ala Gln Phe Ile Ser Leu Ile Val Gly Ser Lys Gly
                245                 250                 255

Asn Phe Gln Lys Pro Phe Asp Leu Ile Glu Lys Ser Asp Ile Glu Cys
                260                 265                 270

Ala Lys Asp Ser Tyr Glu Glu Asp Leu Glu Ser Leu Leu Ala Leu Ile
                275                 280                 285

Gly Asp Glu Tyr Ala Glu Leu Phe Val Ala Ala Lys Asn Ala Tyr Ser
                290                 295                 300

Ala Val Val Leu Ser Ser Ile Ile Thr Val Ala Glu Thr Glu Thr Asn
305                 310                 315                 320

Ala Lys Leu Ser Ala Ser Met Ile Glu Arg Phe Asp Thr His Glu Glu
                325                 330                 335

Asp Leu Gly Glu Leu Lys Ala Phe Ile Lys Leu His Leu Pro Lys His
                340                 345                 350

Tyr Glu Glu Ile Phe Ser Asn Thr Glu Lys His Gly Tyr Ala Gly Tyr
                355                 360                 365

Ile Asp Gly Lys Thr Lys Gln Ala Asp Phe Tyr Lys Tyr Met Lys Met
                370                 375                 380

Thr Leu Glu Asn Ile Glu Gly Ala Asp Tyr Phe Ile Ala Lys Ile Glu
385                 390                 395                 400

Lys Glu Asn Phe Leu Arg Lys Gln Arg Thr Phe Asp Asn Gly Ala Ile
                405                 410                 415

Pro His Gln Leu His Leu Glu Glu Leu Glu Ala Ile Leu His Gln Gln
                420                 425                 430

Ala Lys Tyr Tyr Pro Phe Leu Lys Glu Asn Tyr Asp Lys Ile Lys Ser
                435                 440                 445

Leu Val Thr Phe Arg Ile Pro Tyr Phe Val Gly Pro Leu Ala Asn Gly
                450                 455                 460

Gln Ser Glu Phe Ala Trp Leu Thr Arg Lys Ala Asp Gly Glu Ile Arg
465                 470                 475                 480
```

```
Pro Trp Asn Ile Glu Glu Lys Val Asp Phe Gly Lys Ser Ala Val Asp
                485                 490                 495

Phe Ile Glu Lys Met Thr Asn Lys Asp Thr Tyr Leu Pro Lys Glu Asn
            500                 505                 510

Val Leu Pro Lys His Ser Leu Cys Tyr Gln Lys Tyr Leu Val Tyr Asn
            515                 520                 525

Glu Leu Thr Lys Val Arg Tyr Ile Asn Asp Gln Gly Lys Thr Ser Tyr
            530                 535                 540

Phe Ser Gly Gln Glu Lys Glu Gln Ile Phe Asn Asp Leu Phe Lys Gln
545                 550                 555                 560

Lys Arg Lys Val Lys Lys Asp Leu Glu Leu Phe Leu Arg Asn Met
                565                 570                 575

Ser His Val Glu Ser Pro Thr Ile Glu Gly Leu Glu Asp Ser Phe Asn
            580                 585                 590

Ser Ser Tyr Ser Thr Tyr His Asp Leu Leu Lys Val Gly Ile Lys Gln
            595                 600                 605

Glu Ile Leu Asp Asn Pro Val Asn Thr Glu Met Leu Glu Asn Ile Val
            610                 615                 620

Lys Ile Leu Thr Val Phe Glu Asp Lys Arg Met Ile Lys Glu Gln Leu
625                 630                 635                 640

Gln Gln Phe Ser Asp Val Leu Asp Gly Val Val Leu Lys Lys Leu Glu
                645                 650                 655

Arg Arg His Tyr Thr Gly Trp Gly Arg Leu Ser Ala Lys Leu Leu Met
                660                 665                 670

Gly Ile Arg Asp Lys Gln Ser His Leu Thr Ile Leu Asp Tyr Leu Met
                675                 680                 685

Asn Asp Asp Gly Leu Asn Arg Asn Leu Met Gln Leu Ile Asn Asp Ser
            690                 695                 700

Asn Leu Ser Phe Lys Ser Ile Ile Glu Lys Glu Gln Val Thr Thr Ala
705                 710                 715                 720

Asp Lys Asp Ile Gln Ser Ile Val Ala Asp Leu Ala Gly Ser Pro Ala
                725                 730                 735

Ile Lys Lys Gly Ile Leu Gln Ser Leu Lys Ile Val Asp Glu Leu Val
                740                 745                 750

Ser Val Met Gly Tyr Pro Pro Gln Thr Ile Val Val Glu Met Ala Arg
                755                 760                 765

Glu Asn Gln Thr Thr Gly Lys Gly Lys Asn Asn Ser Arg Pro Arg Tyr
            770                 775                 780

Lys Ser Leu Glu Lys Ala Ile Lys Glu Phe Gly Ser Gln Ile Leu Lys
785                 790                 795                 800

Glu His Pro Thr Asp Asn Gln Glu Leu Arg Asn Asn Arg Leu Tyr Leu
            805                 810                 815

Tyr Tyr Leu Gln Asn Gly Lys Asp Met Tyr Thr Gly Gln Asp Leu Asp
                820                 825                 830

Ile His Asn Leu Ser Asn Tyr Asp Ile Asp His Ile Val Pro Gln Ser
            835                 840                 845

Phe Ile Thr Asp Asn Ser Ile Asp Asn Leu Val Leu Thr Ser Ser Ala
850                 855                 860

Gly Asn Arg Glu Lys Gly Asp Asp Val Pro Pro Leu Glu Ile Val Arg
865                 870                 875                 880

Lys Arg Lys Val Phe Trp Glu Leu Tyr Gln Gly Asn Leu Met Ser
                885                 890                 895
```

```
Lys Arg Lys Phe Asp Tyr Leu Thr Lys Ala Glu Arg Gly Gly Leu Thr
            900                 905                 910

Glu Ala Asp Lys Ala Arg Phe Ile His Arg Gln Leu Val Glu Thr Arg
        915                 920                 925

Gln Ile Thr Lys Asn Val Ala Asn Ile Leu His Gln Arg Phe Asn Tyr
    930                 935                 940

Glu Lys Asp Asp His Gly Asn Thr Met Lys Gln Val Arg Ile Val Thr
945                 950                 955                 960

Leu Lys Ser Ala Leu Val Ser Gln Phe Arg Lys Gln Phe Gln Leu Tyr
            965                 970                 975

Lys Val Arg Asp Val Asn Asp Tyr His His Ala His Asp Ala Tyr Leu
        980                 985                 990

Asn Gly Val Val Ala Asn Thr Leu Leu Lys Val Tyr Pro Gln Leu Glu
    995                 1000                1005

Pro Glu Phe Val Tyr Gly Asp Tyr His Gln Phe Asp Trp Phe Lys
    1010                1015                1020

Ala Asn Lys Ala Thr Ala Lys Lys Gln Phe Tyr Thr Asn Ile Met
    1025                1030                1035

Leu Phe Phe Ala Gln Lys Asp Arg Ile Ile Asp Glu Asn Gly Glu
    1040                1045                1050

Ile Leu Trp Asp Lys Lys Tyr Leu Asp Thr Val Lys Lys Val Met
    1055                1060                1065

Ser Tyr Arg Gln Met Asn Ile Val Lys Lys Thr Glu Ile Gln Lys
    1070                1075                1080

Gly Glu Phe Ser Lys Ala Thr Ile Lys Pro Lys Gly Asn Ser Ser
    1085                1090                1095

Lys Leu Ile Pro Arg Lys Thr Asn Trp Asp Pro Met Lys Tyr Gly
    1100                1105                1110

Gly Leu Asp Ser Pro Asn Met Ala Tyr Ala Val Val Ile Glu Tyr
    1115                1120                1125

Ala Lys Gly Lys Asn Lys Leu Val Phe Glu Lys Lys Ile Ile Arg
    1130                1135                1140

Val Thr Ile Met Glu Arg Lys Ala Phe Glu Lys Asp Glu Lys Ala
    1145                1150                1155

Phe Leu Glu Glu Gln Gly Tyr Arg Gln Pro Lys Val Leu Ala Lys
    1160                1165                1170

Leu Pro Lys Tyr Thr Leu Tyr Glu Cys Glu Glu Gly Arg Arg Arg
    1175                1180                1185

Met Leu Ala Ser Ala Asn Glu Ala Gln Lys Gly Asn Gln Gln Val
    1190                1195                1200

Leu Pro Asn His Leu Val Thr Leu Leu His His Ala Ala Asn Cys
    1205                1210                1215

Glu Val Ser Asp Gly Lys Ser Leu Asp Tyr Ile Glu Ser Asn Arg
    1220                1225                1230

Glu Met Phe Ala Glu Leu Leu Ala His Val Ser Glu Phe Ala Lys
    1235                1240                1245

Arg Tyr Thr Leu Ala Glu Ala Asn Leu Asn Lys Ile Asn Gln Leu
    1250                1255                1260

Phe Glu Gln Asn Lys Glu Gly Asp Ile Lys Ala Ile Ala Gln Ser
    1265                1270                1275

Phe Val Asp Leu Met Ala Phe Asn Ala Met Gly Ala Pro Ala Ser
    1280                1285                1290

Phe Lys Phe Phe Glu Thr Thr Ile Glu Arg Lys Arg Tyr Asn Asn
```

```
                1295                1300                1305
Leu Lys  Glu Leu Leu Asn Ser  Thr Ile Ile Tyr Gln  Ser Ile Thr
        1310                1315                1320

Gly Leu  Tyr Glu Ser Arg Lys  Arg Leu Asp Asp
        1325                1330

<210> SEQ ID NO 18
<211> LENGTH: 1372
<212> TYPE: PRT
<213> ORGANISM: Legionella pneumophila

<400> SEQUENCE: 18

Met Glu Ser Ser Gln Ile Leu Ser Pro Ile Gly Ile Asp Leu Gly Gly
1               5                   10                  15

Lys Phe Thr Gly Val Cys Leu Ser His Leu Glu Ala Phe Ala Glu Leu
            20                  25                  30

Pro Asn His Ala Asn Thr Lys Tyr Ser Val Ile Leu Ile Asp His Asn
        35                  40                  45

Asn Phe Gln Leu Ser Gln Ala Gln Arg Arg Ala Thr Arg His Arg Val
    50                  55                  60

Arg Asn Lys Lys Arg Asn Gln Phe Val Lys Arg Val Ala Leu Gln Leu
65                  70                  75                  80

Phe Gln His Ile Leu Ser Arg Asp Leu Asn Ala Lys Glu Glu Thr Ala
                85                  90                  95

Leu Cys His Tyr Leu Asn Asn Arg Gly Tyr Thr Tyr Val Asp Thr Asp
            100                 105                 110

Leu Asp Glu Tyr Ile Lys Asp Glu Thr Thr Ile Asn Leu Leu Lys Glu
        115                 120                 125

Leu Leu Pro Ser Glu Ser Glu His Asn Phe Ile Asp Trp Phe Leu Gln
    130                 135                 140

Lys Met Gln Ser Ser Glu Phe Arg Lys Ile Leu Val Ser Lys Val Glu
145                 150                 155                 160

Glu Lys Lys Asp Asp Lys Glu Leu Lys Asn Ala Val Lys Asn Ile Lys
                165                 170                 175

Asn Phe Ile Thr Gly Phe Glu Lys Asn Ser Val Glu Gly His Arg His
            180                 185                 190

Arg Lys Val Tyr Phe Glu Asn Ile Lys Ser Asp Ile Thr Lys Asp Asn
        195                 200                 205

Gln Leu Asp Ser Ile Lys Lys Lys Ile Pro Ser Val Cys Leu Ser Asn
    210                 215                 220

Leu Leu Gly His Leu Ser Asn Leu Gln Trp Lys Asn Leu His Arg Tyr
225                 230                 235                 240

Leu Ala Lys Asn Pro Lys Gln Phe Asp Glu Gln Thr Phe Gly Asn Glu
                245                 250                 255

Phe Leu Arg Met Leu Lys Asn Phe Arg His Leu Lys Gly Ser Gln Glu
            260                 265                 270

Ser Leu Ala Val Arg Asn Leu Ile Gln Gln Leu Glu Gln Ser Gln Asp
        275                 280                 285

Tyr Ile Ser Ile Leu Glu Lys Thr Pro Pro Glu Ile Thr Ile Pro Pro
    290                 295                 300

Tyr Glu Ala Arg Thr Asn Thr Gly Met Glu Lys Asp Gln Ser Leu Leu
305                 310                 315                 320

Leu Asn Pro Glu Lys Leu Asn Asn Leu Tyr Pro Asn Trp Arg Asn Leu
                325                 330                 335
```

-continued

```
Ile Pro Gly Ile Ile Asp Ala His Pro Phe Leu Glu Lys Asp Leu Glu
            340                 345                 350

His Thr Lys Leu Arg Asp Arg Lys Arg Ile Ile Ser Pro Ser Lys Gln
        355                 360                 365

Asp Glu Lys Arg Asp Ser Tyr Ile Leu Gln Arg Tyr Leu Asp Leu Asn
    370                 375                 380

Lys Lys Ile Asp Lys Phe Lys Ile Lys Lys Gln Leu Ser Phe Leu Gly
385                 390                 395                 400

Gln Gly Lys Gln Leu Pro Ala Asn Leu Ile Glu Thr Gln Lys Glu Met
                405                 410                 415

Glu Thr His Phe Asn Ser Ser Leu Val Ser Val Leu Ile Gln Ile Ala
            420                 425                 430

Ser Ala Tyr Asn Lys Glu Arg Glu Asp Ala Ala Gln Gly Ile Trp Phe
        435                 440                 445

Asp Asn Ala Phe Ser Leu Cys Glu Leu Ser Asn Ile Asn Pro Pro Arg
    450                 455                 460

Lys Gln Lys Ile Leu Pro Leu Leu Val Gly Ala Ile Leu Ser Glu Asp
465                 470                 475                 480

Phe Ile Asn Asn Lys Asp Lys Trp Ala Lys Phe Lys Ile Phe Trp Asn
                485                 490                 495

Thr His Lys Ile Gly Arg Thr Ser Leu Lys Ser Lys Cys Lys Glu Ile
            500                 505                 510

Glu Glu Ala Arg Lys Asn Ser Gly Asn Ala Phe Lys Ile Asp Tyr Glu
        515                 520                 525

Glu Ala Leu Asn His Pro Glu His Ser Asn Asn Lys Ala Leu Ile Lys
    530                 535                 540

Ile Ile Gln Thr Ile Pro Asp Ile Ile Gln Ala Ile Gln Ser His Leu
545                 550                 555                 560

Gly His Asn Asp Ser Gln Ala Leu Ile Tyr His Asn Pro Phe Ser Leu
                565                 570                 575

Ser Gln Leu Tyr Thr Ile Leu Glu Thr Lys Arg Asp Gly Phe His Lys
            580                 585                 590

Asn Cys Val Ala Val Thr Cys Glu Asn Tyr Trp Arg Ser Gln Lys Thr
        595                 600                 605

Glu Ile Asp Pro Glu Ile Ser Tyr Ala Ser Arg Leu Pro Ala Asp Ser
    610                 615                 620

Val Arg Pro Phe Asp Gly Val Leu Ala Arg Met Met Gln Arg Leu Ala
625                 630                 635                 640

Tyr Glu Ile Ala Met Ala Lys Trp Glu Gln Ile Lys His Ile Pro Asp
                645                 650                 655

Asn Ser Ser Leu Leu Ile Pro Ile Tyr Leu Glu Gln Asn Arg Phe Glu
            660                 665                 670

Phe Glu Glu Ser Phe Lys Lys Ile Lys Gly Ser Ser Asp Lys Thr
        675                 680                 685

Leu Glu Gln Ala Ile Glu Lys Gln Asn Ile Gln Trp Glu Glu Lys Phe
    690                 695                 700

Gln Arg Ile Ile Asn Ala Ser Met Asn Ile Cys Pro Tyr Lys Gly Ala
705                 710                 715                 720

Ser Ile Gly Gly Gln Gly Glu Ile Asp His Ile Tyr Pro Arg Ser Leu
                725                 730                 735

Ser Lys Lys His Phe Gly Val Ile Phe Asn Ser Glu Val Asn Leu Ile
            740                 745                 750

Tyr Cys Ser Ser Gln Gly Asn Arg Glu Lys Lys Glu Glu His Tyr Leu
```

-continued

```
           755                 760                 765
Leu Glu His Leu Ser Pro Leu Tyr Leu Lys His Gln Phe Gly Thr Asp
           770                 775                 780
Asn Val Ser Asp Ile Lys Asn Phe Ile Ser Gln Asn Val Ala Asn Ile
785                            790                 795             800
Lys Lys Tyr Ile Ser Phe His Leu Leu Thr Pro Glu Gln Gln Lys Ala
                   805                 810                 815
Ala Arg His Ala Leu Phe Leu Asp Tyr Asp Asp Glu Ala Phe Lys Thr
               820                 825                 830
Ile Thr Lys Phe Leu Met Ser Gln Gln Lys Ala Arg Val Asn Gly Thr
           835                 840                 845
Gln Lys Phe Leu Gly Lys Gln Ile Met Glu Phe Leu Ser Thr Leu Ala
850                            855                 860
Asp Ser Lys Gln Leu Gln Leu Glu Phe Ser Ile Lys Gln Ile Thr Ala
865                            870                 875             880
Glu Glu Val His Asp His Arg Glu Leu Leu Ser Lys Gln Glu Pro Lys
                   885                 890                 895
Leu Val Lys Ser Arg Gln Gln Ser Phe Pro Ser His Ala Ile Asp Ala
               900                 905                 910
Thr Leu Thr Met Ser Ile Gly Leu Lys Glu Phe Pro Gln Phe Ser Gln
           915                 920                 925
Glu Leu Asp Asn Ser Trp Phe Ile Asn His Leu Met Pro Asp Glu Val
           930                 935                 940
His Leu Asn Pro Val Arg Ser Lys Glu Lys Tyr Asn Lys Pro Asn Ile
945                            950                 955             960
Ser Ser Thr Pro Leu Phe Lys Asp Ser Leu Tyr Ala Glu Arg Phe Ile
                   965                 970                 975
Pro Val Trp Val Lys Gly Glu Thr Phe Ala Ile Gly Phe Ser Glu Lys
               980                 985                 990
Asp Leu Phe Glu Ile Lys Pro Ser Asn Lys Glu Lys Leu Phe Thr Leu
           995                 1000                1005
Leu Lys Thr Tyr Ser Thr Lys Asn Pro Gly Glu Ser Leu Gln Glu
           1010                1015                1020
Leu Gln Ala Lys Ser Lys Ala Lys Trp Leu Tyr Phe Pro Ile Asn
           1025                1030                1035
Lys Thr Leu Ala Leu Glu Phe Leu His His Tyr Phe His Lys Glu
           1040                1045                1050
Ile Val Thr Pro Asp Asp Thr Val Cys His Phe Ile Asn Ser
           1055                1060                1065
Leu Arg Tyr Tyr Thr Lys Lys Glu Ser Ile Thr Val Lys Ile Leu
           1070                1075                1080
Lys Glu Pro Met Pro Val Leu Ser Val Lys Phe Glu Ser Ser Lys
           1085                1090                1095
Lys Asn Val Leu Gly Ser Phe Lys His Thr Ile Ala Leu Pro Ala
           1100                1105                1110
Thr Lys Asp Trp Glu Arg Leu Phe Asn His Pro Asn Phe Leu Ala
           1115                1120                1125
Leu Lys Ala Asn Pro Ala Pro Asn Pro Lys Glu Phe Asn Glu Phe
           1130                1135                1140
Ile Arg Lys Tyr Phe Leu Ser Asp Asn Asn Pro Asn Ser Asp Ile
           1145                1150                1155
Pro Asn Asn Gly His Asn Ile Lys Pro Gln Lys His Lys Ala Val
           1160                1165                1170
```

```
Arg Lys Val Phe Ser Leu Pro Val Ile Pro Gly Asn Ala Gly Thr
    1175            1180            1185

Met Met Arg Ile Arg Lys Asp Asn Lys Gly Gln Pro Leu Tyr
    1190            1195            1200

Gln Leu Gln Thr Ile Asp Asp Thr Pro Ser Met Gly Ile Gln Ile
    1205            1210            1215

Asn Glu Asp Arg Leu Val Lys Gln Glu Val Leu Met Asp Ala Tyr
    1220            1225            1230

Lys Thr Arg Asn Leu Ser Thr Ile Asp Gly Ile Asn Asn Ser Glu
    1235            1240            1245

Gly Gln Ala Tyr Ala Thr Phe Asp Asn Trp Leu Thr Leu Pro Val
    1250            1255            1260

Ser Thr Phe Lys Pro Glu Ile Ile Lys Leu Glu Met Lys Pro His
    1265            1270            1275

Ser Lys Thr Arg Arg Tyr Ile Arg Ile Thr Gln Ser Leu Ala Asp
    1280            1285            1290

Phe Ile Lys Thr Ile Asp Glu Ala Leu Met Ile Lys Pro Ser Asp
    1295            1300            1305

Ser Ile Asp Asp Pro Leu Asn Met Pro Asn Glu Ile Val Cys Lys
    1310            1315            1320

Asn Lys Leu Phe Gly Asn Glu Leu Lys Pro Arg Asp Gly Lys Met
    1325            1330            1335

Lys Ile Val Ser Thr Gly Lys Ile Val Thr Tyr Glu Phe Glu Ser
    1340            1345            1350

Asp Ser Thr Pro Gln Trp Ile Gln Thr Leu Tyr Val Thr Gln Leu
    1355            1360            1365

Lys Lys Gln Pro
    1370

<210> SEQ ID NO 19
<211> LENGTH: 1082
<212> TYPE: PRT
<213> ORGANISM: Neisseria lactamica

<400> SEQUENCE: 19

Met Ala Ala Phe Lys Pro Asn Pro Met Asn Tyr Ile Leu Gly Leu Asp
1               5                   10                  15

Ile Gly Ile Ala Ser Val Gly Trp Ala Met Val Glu Val Asp Glu Glu
                20                  25                  30

Glu Asn Pro Ile Arg Leu Ile Asp Leu Gly Val Arg Val Phe Glu Arg
            35                  40                  45

Ala Glu Val Pro Lys Thr Gly Asp Ser Leu Ala Met Ala Arg Arg Leu
        50                  55                  60

Ala Arg Ser Val Arg Arg Leu Thr Arg Arg Arg Ala His Arg Leu Leu
65                  70                  75                  80

Arg Ala Arg Arg Leu Leu Lys Arg Glu Gly Val Leu Gln Asp Ala Asp
                85                  90                  95

Phe Asp Glu Asn Gly Leu Val Lys Ser Leu Pro Asn Thr Pro Trp Gln
            100                 105                 110

Leu Arg Ala Ala Ala Leu Asp Arg Lys Leu Thr Cys Leu Glu Trp Ser
        115                 120                 125

Ala Val Leu Leu His Leu Val Lys His Arg Gly Tyr Leu Ser Gln Arg
    130                 135                 140

Lys Asn Glu Gly Glu Thr Ala Asp Lys Glu Leu Gly Ala Leu Leu Lys
```

-continued

```
            145                 150                 155                 160
        Gly Val Ala Asp Asn Ala His Ala Leu Gln Thr Gly Asp Phe Arg Thr
                        165                 170                 175
        Pro Ala Glu Leu Ala Leu Asn Lys Phe Glu Lys Glu Ser Gly His Ile
                        180                 185                 190
        Arg Asn Gln Arg Gly Asp Tyr Ser His Thr Phe Ser Arg Lys Asp Leu
                        195                 200                 205
        Gln Ala Glu Leu Asn Leu Leu Phe Glu Lys Gln Lys Glu Phe Gly Asn
                210                 215                 220
        Pro His Val Ser Asp Gly Leu Lys Glu Asp Ile Glu Thr Leu Leu Met
        225                 230                 235                 240
        Ala Gln Arg Pro Ala Leu Ser Gly Asp Ala Val Gln Lys Met Leu Gly
                        245                 250                 255
        His Cys Thr Phe Glu Pro Ala Glu Pro Lys Ala Ala Lys Asn Thr Tyr
                        260                 265                 270
        Thr Ala Glu Arg Phe Ile Trp Leu Thr Lys Leu Asn Asn Leu Arg Ile
                        275                 280                 285
        Leu Glu Gln Gly Ser Glu Arg Pro Leu Thr Asp Thr Glu Arg Ala Thr
                290                 295                 300
        Leu Met Asp Glu Pro Tyr Arg Lys Ser Lys Leu Thr Tyr Ala Gln Ala
        305                 310                 315                 320
        Arg Lys Leu Leu Gly Leu Glu Asp Thr Ala Phe Phe Lys Gly Leu Arg
                        325                 330                 335
        Tyr Gly Lys Asp Asn Ala Glu Ala Ser Thr Leu Met Glu Met Lys Ala
                        340                 345                 350
        Tyr His Ala Ile Ser Arg Ala Leu Glu Lys Glu Gly Leu Lys Asp Lys
                        355                 360                 365
        Lys Ser Pro Leu Asn Leu Ser Thr Glu Leu Gln Asp Glu Ile Gly Thr
                370                 375                 380
        Ala Phe Ser Leu Phe Lys Thr Asp Lys Asp Ile Thr Gly Arg Leu Lys
        385                 390                 395                 400
        Asp Arg Val Gln Pro Glu Ile Leu Glu Ala Leu Leu Lys His Ile Ser
                        405                 410                 415
        Phe Asp Lys Phe Val Gln Ile Ser Leu Lys Ala Leu Arg Arg Ile Val
                        420                 425                 430
        Pro Leu Met Glu Gln Gly Lys Arg Tyr Asp Glu Ala Cys Ala Glu Ile
                435                 440                 445
        Tyr Gly Asp His Tyr Cys Lys Lys Asn Ala Glu Glu Lys Ile Tyr Leu
        450                 455                 460
        Pro Pro Ile Pro Ala Asp Glu Ile Arg Asn Pro Val Val Leu Arg Ala
        465                 470                 475                 480
        Leu Ser Gln Ala Arg Lys Val Ile Asn Cys Val Val Arg Arg Tyr Gly
                        485                 490                 495
        Ser Pro Ala Arg Ile His Ile Glu Thr Ala Arg Glu Val Gly Lys Ser
                        500                 505                 510
        Phe Lys Asp Arg Lys Glu Ile Glu Lys Arg Gln Glu Glu Asn Arg Lys
                        515                 520                 525
        Asp Arg Glu Lys Ala Ala Ala Lys Phe Arg Glu Tyr Phe Pro Asn Phe
                530                 535                 540
        Val Gly Glu Pro Lys Ser Lys Asp Ile Leu Lys Leu Arg Leu Tyr Glu
        545                 550                 555                 560
        Gln Gln His Gly Lys Cys Leu Tyr Ser Gly Lys Glu Ile Asn Leu Val
                        565                 570                 575
```

```
Arg Leu Asn Glu Lys Gly Tyr Val Glu Ile Asp His Ala Leu Pro Phe
            580                 585                 590

Ser Arg Thr Trp Asp Asp Ser Phe Asn Asn Lys Val Leu Val Leu Gly
            595                 600                 605

Ser Glu Asn Gln Asn Lys Gly Asn Gln Thr Pro Tyr Glu Tyr Phe Asn
    610                 615                 620

Gly Lys Asp Asn Ser Arg Glu Trp Gln Glu Phe Lys Ala Arg Val Glu
625                 630                 635                 640

Thr Ser Arg Phe Pro Arg Ser Lys Gln Arg Ile Leu Leu Gln Lys
                645                 650                 655

Phe Asp Glu Glu Gly Phe Lys Glu Arg Asn Leu Asn Asp Thr Arg Tyr
            660                 665                 670

Val Asn Arg Phe Leu Cys Gln Phe Val Ala Asp His Ile Leu Leu Thr
            675                 680                 685

Gly Lys Gly Lys Arg Arg Val Phe Ala Ser Asn Gly Gln Ile Thr Asn
            690                 695                 700

Leu Leu Arg Gly Phe Trp Gly Leu Arg Lys Val Arg Thr Glu Asn Asp
705                 710                 715                 720

Arg His His Ala Leu Asp Ala Val Val Ala Cys Ser Thr Val Ala
                725                 730                 735

Met Gln Gln Lys Ile Thr Arg Phe Val Arg Tyr Lys Glu Met Asn Ala
            740                 745                 750

Phe Asp Gly Lys Thr Ile Asp Lys Glu Thr Gly Glu Val Leu His Gln
            755                 760                 765

Lys Ala His Phe Pro Gln Pro Trp Glu Phe Phe Ala Gln Glu Val Met
            770                 775                 780

Ile Arg Val Phe Gly Lys Pro Asp Gly Lys Pro Glu Phe Glu Glu Ala
785                 790                 795                 800

Asp Thr Pro Glu Lys Leu Arg Thr Leu Leu Ala Glu Lys Leu Ser Ser
                805                 810                 815

Arg Pro Glu Ala Val His Glu Tyr Val Thr Pro Leu Phe Val Ser Arg
            820                 825                 830

Ala Pro Asn Arg Lys Met Ser Gly Gln Gly His Met Glu Thr Val Lys
            835                 840                 845

Ser Ala Lys Arg Leu Asp Glu Gly Ile Ser Val Leu Arg Val Pro Leu
            850                 855                 860

Thr Gln Leu Lys Leu Lys Gly Leu Glu Lys Met Val Asn Arg Glu Arg
865                 870                 875                 880

Glu Pro Lys Leu Tyr Asp Ala Leu Lys Ala Gln Leu Glu Thr His Lys
                885                 890                 895

Asp Asp Pro Ala Lys Ala Phe Ala Glu Pro Phe Tyr Lys Tyr Asp Lys
            900                 905                 910

Ala Gly Ser Arg Thr Gln Gln Val Lys Ala Val Arg Ile Glu Gln Val
            915                 920                 925

Gln Lys Thr Gly Val Trp Val Arg Asn His Asn Gly Ile Ala Asp Asn
            930                 935                 940

Ala Thr Met Val Arg Val Asp Val Phe Glu Lys Gly Lys Tyr Tyr
945                 950                 955                 960

Leu Val Pro Ile Tyr Ser Trp Gln Val Ala Lys Gly Ile Leu Pro Asp
                965                 970                 975

Arg Ala Val Val Ala Phe Lys Asp Glu Glu Asp Trp Thr Val Met Asp
            980                 985                 990
```

-continued

Asp Ser Phe Glu Phe Arg Phe Val Leu Tyr Ala Asn Asp Leu Ile Lys
            995                 1000                1005

Leu Thr Ala Lys Lys Asn Glu Phe Leu Gly Tyr Phe Val Ser Leu
    1010                1015                1020

Asn Arg Ala Thr Gly Ala Ile Asp Ile Arg Thr His Asp Thr Asp
    1025                1030                1035

Ser Thr Lys Gly Lys Asn Gly Ile Phe Gln Ser Val Gly Val Lys
    1040                1045                1050

Thr Ala Leu Ser Phe Gln Lys Asn Gln Ile Asp Glu Leu Gly Lys
    1055                1060                1065

Glu Ile Arg Pro Cys Arg Leu Lys Lys Arg Pro Pro Val Arg
    1070                1075                1080

<210> SEQ ID NO 20
<211> LENGTH: 1082
<212> TYPE: PRT
<213> ORGANISM: Neisseria meningitidis

<400> SEQUENCE: 20

Met Ala Ala Phe Lys Pro Asn Pro Ile Asn Tyr Ile Leu Gly Leu Asp
1               5                   10                  15

Ile Gly Ile Ala Ser Val Gly Trp Ala Met Val Glu Ile Asp Glu Asp
            20                  25                  30

Glu Asn Pro Ile Cys Leu Ile Asp Leu Gly Val Arg Val Phe Glu Arg
        35                  40                  45

Ala Glu Val Pro Lys Thr Gly Asp Ser Leu Ala Met Ala Arg Arg Leu
    50                  55                  60

Ala Arg Ser Val Arg Arg Leu Thr Arg Arg Arg Ala His Arg Leu Leu
65                  70                  75                  80

Arg Ala Arg Arg Leu Leu Lys Arg Glu Gly Val Leu Gln Ala Ala Asp
                85                  90                  95

Phe Asp Glu Asn Gly Leu Ile Lys Ser Leu Pro Asn Thr Pro Trp Gln
            100                 105                 110

Leu Arg Ala Ala Ala Leu Asp Arg Lys Leu Thr Pro Leu Glu Trp Ser
        115                 120                 125

Ala Val Leu Leu His Leu Ile Lys His Arg Gly Tyr Leu Ser Gln Arg
    130                 135                 140

Lys Asn Glu Gly Glu Thr Ala Asp Lys Glu Leu Gly Ala Leu Leu Lys
145                 150                 155                 160

Gly Val Ala Asp Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Gln Arg Gly Asp Tyr Ser His Thr Phe Ser Arg Lys Asp Leu
        195                 200                 205

Gln Ala Glu Leu Ile Leu Leu Phe Glu Lys Gln Lys Glu Phe Gly Asn
    210                 215                 220

Pro His Val Ser Gly Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
            260                 265                 270

Thr Ala Glu Arg Phe Ile Trp Leu Thr Lys Leu Asn Asn Leu Arg Ile
        275                 280                 285

```
Leu Glu Gln Gly Ser Glu Arg Pro Leu Thr Asp Thr Glu Arg Ala Thr
    290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
                340                 345                 350

Tyr His Ala Ile Ser Arg Ala Leu Glu Lys Glu Gly Leu Lys Asp Lys
                355                 360                 365

Lys Ser Pro Leu Asn Leu Ser Pro Glu Leu Gln Asp Glu Ile Gly Thr
370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
                420                 425                 430

Pro Leu Met Glu Gln Gly Lys Arg Tyr Asp Glu Ala Cys Ala Glu Ile
                435                 440                 445

Tyr Gly Asp His Tyr Gly Lys Lys Asn Thr Glu Glu Lys Ile Tyr Leu
450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Gly Val Val Arg Arg Tyr Gly
                485                 490                 495

Ser Pro Ala Arg Ile His Ile Glu Thr Ala Arg Glu Val Gly Lys Ser
                500                 505                 510

Phe Lys Asp Arg Lys Glu Ile Glu Lys Arg Gln Glu Glu Asn Arg Lys
                515                 520                 525

Asp Arg Glu Lys Ala Ala Ala Lys Phe Arg Glu Tyr Phe Pro Asn Phe
                530                 535                 540

Val Gly Glu Pro Lys Ser Lys Asp Ile Leu Lys Leu Arg Leu Tyr Glu
545                 550                 555                 560

Gln Gln His Gly Lys Cys Leu Tyr Ser Gly Lys Glu Ile Asn Leu Gly
                565                 570                 575

Arg Leu Asn Glu Lys Gly Tyr Val Glu Ile Asp His Ala Leu Pro Phe
                580                 585                 590

Ser Arg Thr Trp Asp Asp Ser Phe Asn Asn Lys Val Leu Val Leu Gly
                595                 600                 605

Ser Glu Asn Gln Asn Lys Gly Asn Gln Thr Pro Tyr Glu Tyr Phe Asn
                610                 615                 620

Gly Lys Asp Asn Ser Arg Glu Trp Gln Glu Phe Lys Ala Arg Val Glu
625                 630                 635                 640

Thr Ser Arg Phe Pro Arg Ser Lys Lys Gln Arg Ile Leu Leu Gln Lys
                645                 650                 655

Phe Asp Glu Asp Gly Phe Lys Glu Arg Asn Leu Asn Asp Thr Arg Tyr
                660                 665                 670

Val Asn Arg Phe Leu Cys Gln Phe Val Ala Asp Arg Met Arg Leu Thr
                675                 680                 685

Gly Lys Gly Lys Lys Arg Val Phe Ala Ser Asn Gly Gln Ile Thr Asn
                690                 695                 700
```

```
Leu Leu Arg Gly Phe Trp Gly Leu Arg Lys Val Ala Glu Asn Asp
705                 710                 715                 720

Arg His His Ala Leu Asp Ala Val Val Ala Cys Ser Thr Val Ala
        725                 730                 735

Met Gln Gln Lys Ile Thr Arg Phe Val Arg Tyr Lys Glu Met Asn Ala
            740                 745                 750

Phe Asp Gly Lys Thr Ile Asp Lys Glu Thr Gly Glu Val Leu His Gln
        755                 760                 765

Lys Thr His Phe Pro Gln Pro Trp Glu Phe Phe Ala Gln Glu Val Met
    770                 775                 780

Ile Arg Val Phe Gly Lys Pro Asp Gly Lys Pro Glu Phe Glu Glu Ala
785                 790                 795                 800

Asp Thr Pro Glu Lys Leu Arg Thr Leu Leu Ala Glu Lys Leu Ser Ser
                805                 810                 815

Arg Pro Glu Ala Val His Glu Tyr Val Thr Pro Leu Phe Val Ser Arg
                820                 825                 830

Ala Pro Asn Arg Lys Met Ser Gly Gln Gly His Met Glu Thr Val Lys
            835                 840                 845

Ser Ala Lys Arg Leu Asp Glu Gly Val Ser Val Leu Arg Val Pro Leu
850                 855                 860

Thr Gln Leu Lys Leu Lys Asp Leu Glu Lys Met Val Asn Arg Glu Arg
865                 870                 875                 880

Glu Pro Lys Leu Tyr Glu Ala Leu Lys Ala Arg Leu Glu Ala His Lys
                885                 890                 895

Asp Asp Pro Ala Lys Ala Phe Glu Pro Phe Tyr Lys Tyr Asp Lys
            900                 905                 910

Ala Gly Asn Arg Thr Gln Gln Val Lys Ala Val Arg Val Glu Gln Val
            915                 920                 925

Gln Lys Thr Gly Val Trp Val Arg Asn His Asn Gly Ile Ala Asp Asn
930                 935                 940

Ala Thr Met Val Arg Val Asp Val Phe Glu Lys Gly Asp Lys Tyr Tyr
945                 950                 955                 960

Leu Val Pro Ile Tyr Ser Trp Gln Val Ala Lys Gly Ile Leu Pro Asp
                965                 970                 975

Arg Ala Val Val Gln Gly Lys Asp Glu Glu Asp Trp Gln Leu Ile Asp
            980                 985                 990

Asp Ser Phe Asn Phe Lys Phe Ser Leu His Pro Asn Asp Leu Val Glu
            995                 1000                1005

Val Ile Thr Lys Lys Ala Arg Met Phe Gly Tyr Phe Ala Ser Cys
    1010                1015                1020

His Arg Gly Thr Gly Asn Ile Asn Ile Arg Ile His Asp Leu Asp
    1025                1030                1035

His Lys Ile Gly Lys Asn Gly Ile Leu Glu Gly Ile Gly Val Lys
    1040                1045                1050

Thr Ala Leu Ser Phe Gln Lys Tyr Gln Ile Asp Glu Leu Gly Lys
    1055                1060                1065

Glu Ile Arg Pro Cys Arg Leu Lys Lys Arg Pro Val Arg
    1070                1075                1080

<210> SEQ ID NO 21
<211> LENGTH: 1187
<212> TYPE: PRT
<213> ORGANISM: Bifidobacterium longum

<400> SEQUENCE: 21
```

```
Met Leu Ser Arg Gln Leu Leu Gly Ala Ser His Leu Ala Arg Pro Val
1               5                   10                  15

Ser Tyr Ser Tyr Asn Val Gln Asp Asn Asp Val His Cys Ser Tyr Gly
            20                  25                  30

Glu Arg Cys Phe Met Arg Gly Lys Arg Tyr Arg Ile Gly Ile Asp Val
        35                  40                  45

Gly Leu Asn Ser Val Gly Leu Ala Ala Val Glu Val Ser Asp Glu Asn
    50                  55                  60

Ser Pro Val Arg Leu Leu Asn Ala Gln Ser Val Ile His Asp Gly Gly
65                  70                  75                  80

Val Asp Pro Gln Lys Asn Lys Glu Ala Ile Thr Arg Lys Asn Met Ser
                85                  90                  95

Gly Val Ala Arg Arg Thr Arg Arg Met Arg Arg Lys Arg Glu Arg
            100                 105                 110

Leu His Lys Leu Asp Met Leu Leu Gly Lys Phe Gly Tyr Pro Val Ile
            115                 120                 125

Glu Pro Glu Ser Leu Asp Lys Pro Phe Glu Glu Trp His Val Arg Ala
        130                 135                 140

Glu Leu Ala Thr Arg Tyr Ile Glu Asp Glu Leu Arg Arg Glu Ser
145                 150                 155                 160

Ile Ser Ile Ala Leu Arg His Met Ala Arg His Arg Gly Trp Arg Asn
            165                 170                 175

Pro Tyr Arg Gln Val Asp Ser Leu Ile Ser Asp Asn Pro Tyr Ser Lys
        180                 185                 190

Gln Tyr Gly Glu Leu Lys Glu Lys Ala Lys Ala Tyr Asn Asp Asp Ala
    195                 200                 205

Thr Ala Ala Glu Glu Glu Ser Thr Pro Ala Gln Leu Val Val Ala Met
210                 215                 220

Leu Asp Ala Gly Tyr Ala Glu Ala Pro Arg Leu Arg Trp Arg Thr Gly
225                 230                 235                 240

Ser Lys Lys Pro Asp Ala Glu Gly Tyr Leu Pro Val Arg Leu Met Gln
            245                 250                 255

Glu Asp Asn Ala Asn Glu Leu Lys Gln Ile Phe Arg Val Gln Arg Val
            260                 265                 270

Pro Ala Asp Glu Trp Lys Pro Leu Phe Arg Ser Val Phe Tyr Ala Val
        275                 280                 285

Ser Pro Lys Gly Ser Ala Glu Gln Arg Val Gly Gln Asp Pro Leu Ala
    290                 295                 300

Pro Glu Gln Ala Arg Ala Leu Lys Ala Ser Leu Ala Phe Gln Glu Tyr
305                 310                 315                 320

Arg Ile Ala Asn Val Ile Thr Asn Leu Arg Ile Lys Asp Ala Ser Ala
            325                 330                 335

Glu Leu Arg Lys Leu Thr Val Asp Glu Lys Gln Ser Ile Tyr Asp Gln
            340                 345                 350

Leu Val Ser Pro Ser Ser Glu Asp Ile Thr Trp Ser Asp Leu Cys Asp
        355                 360                 365

Phe Leu Gly Phe Lys Arg Ser Gln Leu Lys Gly Val Gly Ser Leu Thr
370                 375                 380

Glu Asp Gly Glu Glu Arg Ile Ser Ser Arg Pro Arg Leu Thr Ser
385                 390                 395                 400

Val Gln Arg Ile Tyr Glu Ser Asp Asn Lys Ile Arg Lys Pro Leu Val
            405                 410                 415
```

```
Ala Trp Trp Lys Ser Ala Ser Asp Asn Glu His Glu Ala Met Ile Arg
                420                 425                 430

Leu Leu Ser Asn Thr Val Asp Ile Asp Lys Val Arg Glu Asp Val Ala
            435                 440                 445

Tyr Ala Ser Ala Ile Glu Phe Ile Asp Gly Leu Asp Asp Asp Ala Leu
        450                 455                 460

Thr Lys Leu Asp Ser Val Asp Leu Pro Ser Gly Arg Ala Ala Tyr Ser
465                 470                 475                 480

Val Glu Thr Leu Gln Lys Leu Thr Arg Gln Met Leu Thr Asp Asp
                485                 490                 495

Asp Leu His Glu Ala Arg Lys Thr Leu Phe Asn Val Thr Asp Ser Trp
            500                 505                 510

Arg Pro Pro Ala Asp Pro Ile Gly Glu Pro Leu Gly Asn Pro Ser Val
        515                 520                 525

Asp Arg Val Leu Lys Asn Val Asn Arg Tyr Leu Met Asn Cys Gln Gln
        530                 535                 540

Arg Trp Gly Asn Pro Val Ser Val Asn Ile Glu His Val Arg Ser Ser
545                 550                 555                 560

Phe Ser Ser Val Ala Phe Ala Arg Lys Asp Lys Arg Glu Tyr Glu Lys
                565                 570                 575

Asn Asn Glu Lys Arg Ser Ile Phe Arg Ser Ser Leu Ser Glu Gln Leu
            580                 585                 590

Arg Ala Asp Glu Gln Met Glu Lys Val Arg Glu Ser Asp Leu Arg Arg
        595                 600                 605

Leu Glu Ala Ile Gln Arg Gln Asn Gly Gln Cys Leu Tyr Cys Gly Arg
610                 615                 620

Thr Ile Thr Phe Arg Thr Cys Glu Met Asp His Ile Val Pro Arg Lys
625                 630                 635                 640

Gly Val Gly Ser Thr Asn Thr Arg Thr Asn Phe Ala Ala Val Cys Ala
                645                 650                 655

Glu Cys Asn Arg Met Lys Ser Asn Thr Pro Phe Ala Ile Trp Ala Arg
            660                 665                 670

Ser Glu Asp Ala Gln Thr Arg Gly Val Ser Leu Ala Glu Ala Lys Lys
        675                 680                 685

Arg Val Thr Met Phe Thr Phe Asn Pro Lys Ser Tyr Ala Pro Arg Glu
        690                 695                 700

Val Lys Ala Phe Lys Gln Ala Val Ile Ala Arg Leu Gln Gln Thr Glu
705                 710                 715                 720

Asp Asp Ala Ala Ile Asp Asn Arg Ser Ile Glu Ser Val Ala Trp Met
                725                 730                 735

Ala Asp Glu Leu His Arg Arg Ile Asp Trp Tyr Phe Asn Ala Lys Gln
            740                 745                 750

Tyr Val Asn Ser Ala Ser Ile Asp Asp Ala Glu Ala Glu Thr Met Lys
        755                 760                 765

Thr Thr Val Ser Val Phe Gln Gly Arg Val Thr Ala Ser Ala Arg Arg
        770                 775                 780

Ala Ala Gly Ile Glu Gly Lys Ile His Phe Ile Gly Gln Gln Ser Lys
785                 790                 795                 800

Thr Arg Leu Asp Arg Arg His His Ala Val Asp Ala Ser Val Ile Ala
                805                 810                 815

Met Met Asn Thr Ala Ala Ala Gln Thr Leu Met Glu Arg Glu Ser Leu
            820                 825                 830

Arg Glu Ser Gln Arg Leu Ile Gly Leu Met Pro Gly Glu Arg Ser Trp
```

835                 840                 845
Lys Glu Tyr Pro Tyr Glu Gly Thr Ser Arg Tyr Glu Ser Phe His Leu
    850                 855                 860

Trp Leu Asp Asn Met Asp Val Leu Glu Leu Leu Asn Asp Ala Leu
865                 870                 875                 880

Asp Asn Asp Arg Ile Ala Val Met Gln Ser Gln Arg Tyr Val Leu Gly
                885                 890                 895

Asn Ser Ile Ala His Asp Ala Thr Ile His Pro Leu Glu Lys Val Pro
                900                 905                 910

Leu Gly Ser Ala Met Ser Ala Asp Leu Ile Arg Arg Ala Ser Thr Pro
                915                 920                 925

Ala Leu Trp Cys Ala Leu Thr Arg Leu Pro Asp Tyr Asp Glu Lys Glu
    930                 935                 940

Gly Leu Pro Glu Asp Ser His Arg Glu Ile Arg Val His Asp Thr Arg
945                 950                 955                 960

Tyr Ser Ala Asp Asp Glu Met Gly Phe Phe Ala Ser Gln Ala Ala Gln
                965                 970                 975

Ile Ala Val Gln Glu Gly Ser Ala Asp Ile Gly Ser Ala Ile His His
                980                 985                 990

Ala Arg Val Tyr Arg Cys Trp Lys Thr Asn Ala Lys Gly Val Arg Lys
    995                 1000                1005

Tyr Phe Tyr Gly Met Ile Arg Val Phe Gln Thr Asp Leu Leu Arg
    1010                1015                1020

Ala Cys His Asp Asp Leu Phe Thr Val Pro Leu Pro Pro Gln Ser
    1025                1030                1035

Ile Ser Met Arg Tyr Gly Glu Pro Arg Val Val Gln Ala Leu Gln
    1040                1045                1050

Ser Gly Asn Ala Gln Tyr Leu Gly Ser Leu Val Val Gly Asp Glu
    1055                1060                1065

Ile Glu Met Asp Phe Ser Ser Leu Asp Val Asp Gly Gln Ile Gly
    1070                1075                1080

Glu Tyr Leu Gln Phe Phe Ser Gln Phe Ser Gly Gly Asn Leu Ala
    1085                1090                1095

Trp Lys His Trp Val Val Asp Gly Phe Asn Gln Thr Gln Leu
    1100                1105                1110

Arg Ile Arg Pro Arg Tyr Leu Ala Ala Glu Gly Leu Ala Lys Ala
    1115                1120                1125

Phe Ser Asp Asp Val Val Pro Asp Gly Val Gln Lys Ile Val Thr
    1130                1135                1140

Lys Gln Gly Trp Leu Pro Pro Val Asn Thr Ala Ser Lys Thr Ala
    1145                1150                1155

Val Arg Ile Val Arg Arg Asn Ala Phe Gly Glu Pro Arg Leu Ser
    1160                1165                1170

Ser Ala His His Met Pro Cys Ser Trp Gln Trp Arg His Glu
    1175                1180                1185

<210> SEQ ID NO 22
<211> LENGTH: 1101
<212> TYPE: PRT
<213> ORGANISM: Akkermansia muciniphila

<400> SEQUENCE: 22

Met Ser Arg Ser Leu Thr Phe Ser Phe Asp Ile Gly Tyr Ala Ser Ile
1               5                   10                  15

```
Gly Trp Ala Val Ile Ala Ser Ala Ser His Asp Asp Ala Asp Pro Ser
             20                  25                  30

Val Cys Gly Cys Gly Thr Val Leu Phe Pro Lys Asp Asp Cys Gln Ala
         35                  40                  45

Phe Lys Arg Arg Glu Tyr Arg Arg Leu Arg Arg Asn Ile Arg Ser Arg
     50                  55                  60

Arg Val Arg Ile Glu Arg Ile Gly Arg Leu Leu Val Gln Ala Gln Ile
 65                  70                  75                  80

Ile Thr Pro Glu Met Lys Glu Thr Ser Gly His Pro Ala Pro Phe Tyr
                 85                  90                  95

Leu Ala Ser Glu Ala Leu Lys Gly His Arg Thr Leu Ala Pro Ile Glu
            100                 105                 110

Leu Trp His Val Leu Arg Trp Tyr Ala His Asn Arg Gly Tyr Asp Asn
            115                 120                 125

Asn Ala Ser Trp Ser Asn Ser Leu Ser Glu Asp Gly Gly Asn Gly Glu
        130                 135                 140

Asp Thr Glu Arg Val Lys His Ala Gln Asp Leu Met Asp Lys His Gly
145                 150                 155                 160

Thr Ala Thr Met Ala Glu Thr Ile Cys Arg Glu Leu Lys Leu Glu Glu
                165                 170                 175

Gly Lys Ala Asp Ala Pro Met Glu Val Ser Thr Pro Ala Tyr Lys Asn
            180                 185                 190

Leu Asn Thr Ala Phe Pro Arg Leu Ile Val Glu Lys Glu Val Arg Arg
        195                 200                 205

Ile Leu Glu Leu Ser Ala Pro Leu Ile Pro Gly Leu Thr Ala Glu Ile
210                 215                 220

Ile Glu Leu Ile Ala Gln His His Pro Leu Thr Thr Glu Gln Arg Gly
225                 230                 235                 240

Val Leu Leu Gln His Gly Ile Lys Leu Ala Arg Arg Tyr Arg Gly Ser
                245                 250                 255

Leu Leu Phe Gly Gln Leu Ile Pro Arg Phe Asp Asn Arg Ile Ile Ser
            260                 265                 270

Arg Cys Pro Val Thr Trp Ala Gln Val Tyr Glu Ala Glu Leu Lys Lys
        275                 280                 285

Gly Asn Ser Glu Gln Ser Ala Arg Glu Arg Ala Glu Lys Leu Ser Lys
    290                 295                 300

Val Pro Thr Ala Asn Cys Pro Glu Phe Tyr Glu Tyr Arg Met Ala Arg
305                 310                 315                 320

Ile Leu Cys Asn Ile Arg Ala Asp Gly Glu Pro Leu Ser Ala Glu Ile
                325                 330                 335

Arg Arg Glu Leu Met Asn Gln Ala Arg Gln Glu Gly Lys Leu Thr Lys
            340                 345                 350

Ala Ser Leu Glu Lys Ala Ile Ser Ser Arg Leu Gly Lys Glu Thr Glu
        355                 360                 365

Thr Asn Val Ser Asn Tyr Phe Thr Leu His Pro Asp Ser Glu Glu Ala
    370                 375                 380

Leu Tyr Leu Asn Pro Ala Val Glu Val Leu Gln Arg Ser Gly Ile Gly
385                 390                 395                 400

Gln Ile Leu Ser Pro Ser Val Tyr Arg Ile Ala Ala Asn Arg Leu Arg
                405                 410                 415

Arg Gly Lys Ser Val Thr Pro Asn Tyr Leu Leu Asn Leu Leu Lys Ser
            420                 425                 430

Arg Gly Glu Ser Gly Glu Ala Leu Glu Lys Lys Ile Glu Lys Glu Ser
```

```
                    435                 440                 445
Lys Lys Lys Glu Ala Asp Tyr Ala Asp Thr Pro Leu Lys Pro Lys Tyr
450                 455                 460

Ala Thr Gly Arg Ala Pro Tyr Ala Arg Thr Val Leu Lys Lys Val Val
465                 470                 475                 480

Glu Glu Ile Leu Asp Gly Glu Asp Pro Thr Arg Pro Ala Arg Gly Glu
                485                 490                 495

Ala His Pro Asp Gly Glu Leu Lys Ala His Asp Gly Cys Leu Tyr Cys
                500                 505                 510

Leu Leu Asp Thr Asp Ser Ser Val Asn Gln His Gln Lys Glu Arg Arg
                515                 520                 525

Leu Asp Thr Met Thr Asn Asn His Leu Val Arg His Arg Met Leu Ile
                530                 535                 540

Leu Asp Arg Leu Leu Lys Asp Leu Ile Gln Asp Phe Ala Asp Gly Gln
545                 550                 555                 560

Lys Asp Arg Ile Ser Arg Val Cys Val Glu Val Gly Lys Glu Leu Thr
                565                 570                 575

Thr Phe Ser Ala Met Asp Ser Lys Lys Ile Gln Arg Glu Leu Thr Leu
                580                 585                 590

Arg Gln Lys Ser His Thr Asp Ala Val Asn Arg Leu Lys Arg Lys Leu
                595                 600                 605

Pro Gly Lys Ala Leu Ser Ala Asn Leu Ile Arg Lys Cys Arg Ile Ala
610                 615                 620

Met Asp Met Asn Trp Thr Cys Pro Phe Thr Gly Ala Thr Tyr Gly Asp
625                 630                 635                 640

His Glu Leu Glu Asn Leu Glu Leu Glu His Ile Val Pro His Ser Phe
                645                 650                 655

Arg Gln Ser Asn Ala Leu Ser Ser Leu Val Leu Thr Trp Pro Gly Val
                660                 665                 670

Asn Arg Met Lys Gly Gln Arg Thr Gly Tyr Asp Phe Val Glu Gln Glu
                675                 680                 685

Gln Glu Asn Pro Val Pro Asp Lys Pro Asn Leu His Ile Cys Ser Leu
690                 695                 700

Asn Asn Tyr Arg Glu Leu Val Glu Lys Leu Asp Asp Lys Lys Gly His
705                 710                 715                 720

Glu Asp Asp Arg Arg Lys Lys Arg Lys Ala Leu Leu Met Val
                725                 730                 735

Arg Gly Leu Ser His Lys His Gln Ser Gln Asn His Glu Ala Met Lys
                740                 745                 750

Glu Ile Gly Met Thr Glu Gly Met Met Thr Gln Ser Ser His Leu Met
                755                 760                 765

Lys Leu Ala Cys Lys Ser Ile Lys Thr Ser Leu Pro Asp Ala His Ile
                770                 775                 780

Asp Met Ile Pro Gly Ala Val Thr Ala Glu Val Arg Lys Ala Trp Asp
785                 790                 795                 800

Val Phe Gly Val Phe Lys Glu Leu Cys Pro Glu Ala Ala Asp Pro Asp
                805                 810                 815

Ser Gly Lys Ile Leu Lys Glu Asn Leu Arg Ser Leu Thr His Leu His
                820                 825                 830

His Ala Leu Asp Ala Cys Val Leu Gly Leu Ile Pro Tyr Ile Ile Pro
                835                 840                 845

Ala His His Asn Gly Leu Leu Arg Arg Val Leu Ala Met Arg Arg Ile
850                 855                 860
```

```
Pro Glu Lys Leu Ile Pro Gln Val Arg Pro Val Ala Asn Gln Arg His
865                 870                 875                 880

Tyr Val Leu Asn Asp Asp Gly Arg Met Met Leu Arg Asp Leu Ser Ala
                885                 890                 895

Ser Leu Lys Glu Asn Ile Arg Glu Gln Leu Met Glu Gln Arg Val Ile
            900                 905                 910

Gln His Val Pro Ala Asp Met Gly Gly Ala Leu Leu Lys Glu Thr Met
        915                 920                 925

Gln Arg Val Leu Ser Val Asp Gly Ser Gly Glu Asp Ala Met Val Ser
    930                 935                 940

Leu Ser Lys Lys Lys Asp Gly Lys Lys Glu Lys Asn Gln Val Lys Ala
945                 950                 955                 960

Ser Lys Leu Val Gly Val Phe Pro Glu Gly Pro Ser Lys Leu Lys Ala
                965                 970                 975

Leu Lys Ala Ala Ile Glu Ile Asp Gly Asn Tyr Gly Val Ala Leu Asp
            980                 985                 990

Pro Lys Pro Val Val Ile Arg His Ile Lys Val Phe Lys Arg Ile Met
        995                 1000                1005

Ala Leu Lys Glu Gln Asn Gly Gly Lys Pro Val Arg Ile Leu Lys
    1010                1015                1020

Lys Gly Met Leu Ile His Leu Thr Ser Ser Lys Asp Pro Lys His
    1025                1030                1035

Ala Gly Val Trp Arg Ile Glu Ser Ile Gln Asp Ser Lys Gly Gly
    1040                1045                1050

Val Lys Leu Asp Leu Gln Arg Ala His Cys Ala Val Pro Lys Asn
    1055                1060                1065

Lys Thr His Glu Cys Asn Trp Arg Glu Val Asp Leu Ile Ser Leu
    1070                1075                1080

Leu Lys Lys Tyr Gln Met Lys Arg Tyr Pro Thr Ser Tyr Thr Gly
    1085                1090                1095

Thr Pro Arg
    1100

<210> SEQ ID NO 23
<211> LENGTH: 1498
<212> TYPE: PRT
<213> ORGANISM: Odoribacter laneus

<400> SEQUENCE: 23

Met Glu Thr Thr Leu Gly Ile Asp Leu Gly Thr Asn Ser Ile Gly Leu
1               5                   10                  15

Ala Leu Val Asp Gln Glu Glu His Gln Ile Leu Tyr Ser Gly Val Arg
                20                  25                  30

Ile Phe Pro Glu Gly Ile Asn Lys Asp Thr Ile Gly Leu Gly Glu Lys
            35                  40                  45

Glu Glu Ser Arg Asn Ala Thr Arg Arg Ala Lys Arg Gln Met Arg Arg
        50                  55                  60

Gln Tyr Phe Arg Lys Lys Leu Arg Lys Ala Lys Leu Leu Glu Leu Leu
65                  70                  75                  80

Ile Ala Tyr Asp Met Cys Pro Leu Lys Pro Glu Asp Val Arg Arg Trp
                85                  90                  95

Lys Asn Trp Asp Lys Gln Gln Lys Ser Thr Val Arg Gln Phe Pro Asp
            100                 105                 110

Thr Pro Ala Phe Arg Glu Trp Leu Lys Gln Asn Pro Tyr Glu Leu Arg
```

```
            115                 120                 125
Lys Gln Ala Val Thr Glu Asp Val Thr Arg Pro Glu Leu Gly Arg Ile
    130                 135                 140
Leu Tyr Gln Met Ile Gln Arg Arg Gly Phe Leu Ser Ser Arg Lys Gly
145                 150                 155                 160
Lys Glu Glu Gly Lys Ile Phe Thr Gly Lys Asp Arg Met Val Gly Ile
                165                 170                 175
Asp Glu Thr Arg Lys Asn Leu Gln Lys Gln Thr Leu Gly Ala Tyr Leu
            180                 185                 190
Tyr Asp Ile Ala Pro Lys Asn Gly Glu Lys Tyr Arg Phe Arg Thr Glu
        195                 200                 205
Arg Val Arg Ala Arg Tyr Thr Leu Arg Asp Met Tyr Ile Arg Glu Phe
    210                 215                 220
Glu Ile Ile Trp Gln Arg Gln Ala Gly His Leu Gly Leu Ala His Glu
225                 230                 235                 240
Gln Ala Thr Arg Lys Lys Asn Ile Phe Leu Glu Gly Ser Ala Thr Asn
                245                 250                 255
Val Arg Asn Ser Lys Leu Ile Thr His Leu Gln Ala Lys Tyr Gly Arg
            260                 265                 270
Gly His Val Leu Ile Glu Asp Thr Arg Ile Thr Val Thr Phe Gln Leu
        275                 280                 285
Pro Leu Lys Glu Val Leu Gly Gly Lys Ile Glu Ile Glu Glu Glu Gln
    290                 295                 300
Leu Lys Phe Lys Ser Asn Glu Ser Val Leu Phe Trp Gln Arg Pro Leu
305                 310                 315                 320
Arg Ser Gln Lys Ser Leu Leu Ser Lys Cys Val Phe Glu Gly Arg Asn
                325                 330                 335
Phe Tyr Asp Pro Val His Gln Lys Trp Ile Ile Ala Gly Pro Thr Pro
            340                 345                 350
Ala Pro Leu Ser His Pro Glu Phe Glu Glu Phe Arg Ala Tyr Gln Phe
        355                 360                 365
Ile Asn Asn Ile Ile Tyr Gly Lys Asn Glu His Leu Thr Ala Ile Gln
    370                 375                 380
Arg Glu Ala Val Phe Glu Leu Met Cys Thr Glu Ser Lys Asp Phe Asn
385                 390                 395                 400
Phe Glu Lys Ile Pro Lys His Leu Lys Leu Phe Glu Lys Phe Asn Phe
                405                 410                 415
Asp Asp Thr Thr Lys Val Pro Ala Cys Thr Thr Ile Ser Gln Leu Arg
            420                 425                 430
Lys Leu Phe Pro His Pro Val Trp Glu Glu Lys Arg Glu Glu Ile Trp
        435                 440                 445
His Cys Phe Tyr Phe Tyr Asp Asp Asn Thr Leu Leu Phe Glu Lys Leu
    450                 455                 460
Gln Lys Asp Tyr Ala Leu Gln Thr Asn Asp Leu Glu Lys Ile Lys Lys
465                 470                 475                 480
Ile Arg Leu Ser Glu Ser Tyr Gly Asn Val Ser Leu Lys Ala Ile Arg
                485                 490                 495
Arg Ile Asn Pro Tyr Leu Lys Lys Gly Tyr Ala Tyr Ser Thr Ala Val
            500                 505                 510
Leu Leu Gly Gly Ile Arg Asn Ser Phe Gly Lys Arg Phe Glu Tyr Phe
        515                 520                 525
Lys Glu Tyr Glu Pro Glu Ile Glu Lys Ala Val Cys Arg Ile Leu Lys
    530                 535                 540
```

-continued

```
Glu Lys Asn Ala Glu Gly Glu Val Ile Arg Lys Ile Lys Asp Tyr Leu
545                 550                 555                 560

Val His Asn Arg Phe Gly Phe Ala Lys Asn Asp Arg Ala Phe Gln Lys
                565                 570                 575

Leu Tyr His His Ser Gln Ala Ile Thr Thr Gln Ala Gln Lys Glu Arg
                580                 585                 590

Leu Pro Glu Thr Gly Asn Leu Arg Asn Pro Ile Val Gln Gln Gly Leu
                595                 600                 605

Asn Glu Leu Arg Arg Thr Val Asn Lys Leu Leu Ala Thr Cys Arg Glu
                610                 615                 620

Lys Tyr Gly Pro Ser Phe Lys Phe Asp His Ile His Val Glu Met Gly
625                 630                 635                 640

Arg Glu Leu Arg Ser Ser Lys Thr Glu Arg Glu Lys Gln Ser Arg Gln
                645                 650                 655

Ile Arg Glu Asn Glu Lys Lys Asn Glu Ala Ala Lys Val Lys Leu Ala
                660                 665                 670

Glu Tyr Gly Leu Lys Ala Tyr Arg Asp Asn Ile Gln Lys Tyr Leu Leu
                675                 680                 685

Tyr Lys Glu Ile Glu Glu Lys Gly Gly Thr Val Cys Cys Pro Tyr Thr
690                 695                 700

Gly Lys Thr Leu Asn Ile Ser His Thr Leu Gly Ser Asp Asn Ser Val
705                 710                 715                 720

Gln Ile Glu His Ile Ile Pro Tyr Ser Ile Ser Leu Asp Asp Ser Leu
                725                 730                 735

Ala Asn Lys Thr Leu Cys Asp Ala Thr Phe Asn Arg Glu Lys Gly Glu
                740                 745                 750

Leu Thr Pro Tyr Asp Phe Tyr Gln Lys Asp Pro Ser Pro Glu Lys Trp
                755                 760                 765

Gly Ala Ser Ser Trp Glu Glu Ile Glu Asp Arg Ala Phe Arg Leu Leu
                770                 775                 780

Pro Tyr Ala Lys Ala Gln Arg Phe Ile Arg Arg Lys Pro Gln Glu Ser
785                 790                 795                 800

Asn Glu Phe Ile Ser Arg Gln Leu Asn Asp Thr Arg Tyr Ile Ser Lys
                805                 810                 815

Lys Ala Val Glu Tyr Leu Ser Ala Ile Cys Ser Asp Val Lys Ala Phe
                820                 825                 830

Pro Gly Gln Leu Thr Ala Glu Leu Arg His Leu Trp Gly Leu Asn Asn
                835                 840                 845

Ile Leu Gln Ser Ala Pro Asp Ile Thr Phe Pro Leu Pro Val Ser Ala
                850                 855                 860

Thr Glu Asn His Arg Glu Tyr Tyr Val Ile Thr Asn Glu Gln Asn Glu
865                 870                 875                 880

Val Ile Arg Leu Phe Pro Lys Gln Gly Glu Thr Pro Arg Thr Glu Lys
                885                 890                 895

Gly Glu Leu Leu Leu Thr Gly Glu Val Glu Arg Lys Val Phe Arg Cys
                900                 905                 910

Lys Gly Met Gln Glu Phe Gln Thr Asp Val Ser Asp Gly Lys Tyr Trp
                915                 920                 925

Arg Arg Ile Lys Leu Ser Ser Ser Val Thr Trp Ser Pro Leu Phe Ala
                930                 935                 940

Pro Lys Pro Ile Ser Ala Asp Gly Gln Ile Val Leu Lys Gly Arg Ile
945                 950                 955                 960
```

```
Glu Lys Gly Val Phe Val Cys Asn Gln Leu Lys Gln Lys Leu Lys Thr
            965                 970                 975

Gly Leu Pro Asp Gly Ser Tyr Trp Ile Ser Leu Pro Val Ile Ser Gln
            980                 985                 990

Thr Phe Lys Glu Gly Glu Ser Val Asn Asn Ser Lys Leu Thr Ser Gln
            995                 1000                1005

Gln Val Gln Leu Phe Gly Arg Val Arg Glu Gly Ile Phe Arg Cys
        1010                1015                1020

His Asn Tyr Gln Cys Pro Ala Ser Gly Ala Asp Gly Asn Phe Trp
        1025                1030                1035

Cys Thr Leu Asp Thr Asp Thr Ala Gln Pro Ala Phe Thr Pro Ile
        1040                1045                1050

Lys Asn Ala Pro Pro Gly Val Gly Gly Gly Gln Ile Ile Leu Thr
        1055                1060                1065

Gly Asp Val Asp Asp Lys Gly Ile Phe His Ala Asp Asp Asp Leu
        1070                1075                1080

His Tyr Glu Leu Pro Ala Ser Leu Pro Lys Gly Lys Tyr Tyr Gly
        1085                1090                1095

Ile Phe Thr Val Glu Ser Cys Asp Pro Thr Leu Ile Pro Ile Glu
        1100                1105                1110

Leu Ser Ala Pro Lys Thr Ser Lys Gly Glu Asn Leu Ile Glu Gly
        1115                1120                1125

Asn Ile Trp Val Asp Glu His Thr Gly Glu Val Arg Phe Asp Pro
        1130                1135                1140

Lys Lys Asn Arg Glu Asp Gln Arg His His Ala Ile Asp Ala Ile
        1145                1150                1155

Val Ile Ala Leu Ser Ser Gln Ser Leu Phe Gln Arg Leu Ser Thr
        1160                1165                1170

Tyr Asn Ala Arg Arg Glu Asn Lys Lys Arg Gly Leu Asp Ser Thr
        1175                1180                1185

Glu His Phe Pro Ser Pro Trp Pro Gly Phe Ala Gln Asp Val Arg
        1190                1195                1200

Gln Ser Val Val Pro Leu Leu Val Ser Tyr Lys Gln Asn Pro Lys
        1205                1210                1215

Thr Leu Cys Lys Ile Ser Lys Thr Leu Tyr Lys Asp Gly Lys Lys
        1220                1225                1230

Ile His Ser Cys Gly Asn Ala Val Arg Gly Gln Leu His Lys Glu
        1235                1240                1245

Thr Val Tyr Gly Gln Arg Thr Ala Pro Gly Ala Thr Glu Lys Ser
        1250                1255                1260

Tyr His Ile Arg Lys Asp Ile Arg Glu Leu Lys Thr Ser Lys His
        1265                1270                1275

Ile Gly Lys Val Val Asp Ile Thr Ile Arg Gln Met Leu Leu Lys
        1280                1285                1290

His Leu Gln Glu Asn Tyr His Ile Asp Ile Thr Gln Glu Phe Asn
        1295                1300                1305

Ile Pro Ser Asn Ala Phe Phe Lys Glu Gly Val Tyr Arg Ile Phe
        1310                1315                1320

Leu Pro Asn Lys His Gly Glu Pro Val Pro Ile Lys Lys Ile Arg
        1325                1330                1335

Met Lys Glu Glu Leu Gly Asn Ala Glu Arg Leu Lys Asp Asn Ile
        1340                1345                1350

Asn Gln Tyr Val Asn Pro Arg Asn Asn His His Val Met Ile Tyr
```

```
                    1355                1360                1365

Gln Asp  Ala Asp Gly Asn Leu  Lys Glu Glu Ile  Val Ser Phe Trp
    1370             1375             1380

Ser Val  Ile Glu Arg Gln Asn  Gln Gly Gln Pro  Ile Tyr Gln Leu
    1385             1390             1395

Pro Arg  Glu Gly Arg Asn Ile  Val Ser Ile Leu  Gln Ile Asn Asp
    1400             1405             1410

Thr Phe  Leu Ile Gly Leu Lys  Glu Glu Glu Pro  Glu Val Tyr Arg
    1415             1420             1425

Asn Asp  Leu Ser Thr Leu Ser  Lys His Leu Tyr  Arg Val Gln Lys
    1430             1435             1440

Leu Ser  Gly Met Tyr Tyr Thr  Phe Arg His His  Leu Ala Ser Thr
    1445             1450             1455

Leu Asn  Asn Glu Arg Glu Glu  Phe Arg Ile Gln  Ser Leu Glu Ala
    1460             1465             1470

Trp Lys  Arg Ala Asn Pro Val  Lys Val Gln Ile  Asp Glu Ile Gly
    1475             1480             1485

Arg Ile  Thr Phe Leu Asn Gly  Pro Leu Cys
    1490             1495

<210> SEQ ID NO 24
<211> LENGTH: 931
<212> TYPE: PRT
<213> ORGANISM: Homo sapiens

<400> SEQUENCE: 24

Met Ala Glu Ile Lys Glu Lys Ile Cys Asp Tyr Leu Phe Asn Val Ser
1               5                   10                  15

Asp Ser Ser Ala Leu Asn Leu Ala Lys Asn Ile Gly Leu Thr Lys Ala
            20                  25                  30

Arg Asp Ile Asn Ala Val Leu Ile Asp Met Glu Arg Gln Gly Asp Val
        35                  40                  45

Tyr Arg Gln Gly Thr Thr Pro Pro Ile Trp His Leu Thr Asp Lys Lys
    50                  55                  60

Arg Glu Arg Met Gln Ile Lys Arg Asn Thr Asn Ser Val Pro Glu Thr
65                  70                  75                  80

Ala Pro Ala Ala Ile Pro Glu Thr Lys Arg Asn Ala Glu Phe Leu Thr
                85                  90                  95

Cys Asn Ile Pro Thr Ser Asn Ala Ser Asn Asn Met Val Thr Thr Glu
            100                 105                 110

Lys Val Glu Asn Gly Gln Glu Pro Val Ile Lys Leu Glu Asn Arg Gln
        115                 120                 125

Glu Ala Arg Pro Glu Pro Ala Arg Leu Lys Pro Val His Tyr Asn
    130                 135                 140

Gly Pro Ser Lys Ala Gly Tyr Val Asp Phe Glu Asn Gly Gln Trp Ala
145                 150                 155                 160

Thr Asp Asp Ile Pro Asp Asp Leu Asn Ser Ile Arg Ala Ala Pro Gly
                165                 170                 175

Glu Phe Arg Ala Ile Met Glu Met Pro Ser Phe Tyr Ser His Gly Leu
            180                 185                 190

Pro Arg Cys Ser Pro Tyr Lys Lys Leu Thr Glu Cys Gln Leu Lys Asn
        195                 200                 205

Pro Ile Ser Gly Leu Leu Glu Tyr Ala Gln Phe Ala Ser Gln Thr Cys
    210                 215                 220
```

```
Glu Phe Asn Met Ile Glu Gln Ser Gly Pro Pro His Glu Pro Arg Phe
225                 230                 235                 240

Lys Phe Gln Val Val Ile Asn Gly Arg Glu Phe Pro Pro Ala Glu Ala
            245                 250                 255

Gly Ser Lys Lys Val Ala Lys Gln Asp Ala Ala Met Lys Ala Met Thr
        260                 265                 270

Ile Leu Leu Glu Glu Ala Lys Ala Lys Asp Ser Gly Lys Ser Glu Glu
    275                 280                 285

Ser Ser His Tyr Ser Thr Glu Lys Ser Glu Lys Thr Ala Glu Ser
290                 295                 300

Gln Thr Pro Thr Pro Ser Ala Thr Ser Phe Phe Ser Gly Lys Ser Pro
305                 310                 315                 320

Val Thr Thr Leu Leu Glu Cys Met His Lys Leu Gly Asn Ser Cys Glu
            325                 330                 335

Phe Arg Leu Leu Ser Lys Glu Gly Pro Ala His Glu Pro Lys Phe Gln
            340                 345                 350

Tyr Cys Val Ala Val Gly Ala Gln Thr Phe Pro Ser Val Ser Ala Pro
        355                 360                 365

Ser Lys Lys Val Ala Lys Gln Met Ala Ala Glu Glu Ala Met Lys Ala
    370                 375                 380

Leu His Gly Glu Ala Thr Asn Ser Met Ala Ser Asp Asn Gln Pro Glu
385                 390                 395                 400

Gly Met Ile Ser Glu Ser Leu Asp Asn Leu Glu Ser Met Met Pro Asn
                405                 410                 415

Lys Val Arg Lys Ile Gly Glu Leu Val Arg Tyr Leu Asn Thr Asn Pro
            420                 425                 430

Val Gly Gly Leu Leu Glu Tyr Ala Arg Ser His Gly Phe Ala Ala Glu
        435                 440                 445

Phe Lys Leu Val Asp Gln Ser Gly Pro Pro His Glu Pro Lys Phe Val
    450                 455                 460

Tyr Gln Ala Lys Val Gly Gly Arg Trp Phe Pro Ala Val Cys Ala His
465                 470                 475                 480

Ser Lys Lys Gln Gly Lys Gln Glu Ala Ala Asp Ala Ala Leu Arg Val
                485                 490                 495

Leu Ile Gly Glu Asn Glu Lys Ala Glu Arg Met Gly Phe Thr Glu Val
            500                 505                 510

Thr Pro Val Thr Gly Ala Ser Leu Arg Arg Thr Met Leu Leu Leu Ser
        515                 520                 525

Arg Ser Pro Glu Ala Gln Pro Lys Thr Leu Pro Leu Thr Gly Ser Thr
530                 535                 540

Phe His Asp Gln Ile Ala Met Leu Ser His Arg Cys Phe Asn Thr Leu
545                 550                 555                 560

Thr Asn Ser Phe Gln Pro Ser Leu Leu Gly Arg Lys Ile Leu Ala Ala
                565                 570                 575

Ile Ile Met Lys Lys Asp Ser Glu Asp Met Gly Val Val Val Ser Leu
            580                 585                 590

Gly Thr Gly Asn Arg Cys Val Lys Gly Asp Ser Leu Ser Leu Lys Gly
        595                 600                 605

Glu Thr Val Asn Asp Cys His Ala Glu Ile Ile Ser Arg Arg Gly Phe
    610                 615                 620

Ile Arg Phe Leu Tyr Ser Glu Leu Met Lys Tyr Asn Ser Gln Thr Ala
625                 630                 635                 640

Lys Asp Ser Ile Phe Glu Pro Ala Lys Gly Gly Glu Lys Leu Gln Ile
```

```
                    645                 650                 655
Lys Lys Thr Val Ser Phe His Leu Tyr Ile Ser Thr Ala Pro Cys Gly
                660                 665                 670

Asp Gly Ala Leu Phe Asp Lys Ser Cys Ser Asp Arg Ala Met Glu Ser
            675                 680                 685

Thr Glu Ser Arg His Tyr Pro Val Phe Glu Asn Pro Lys Gln Gly Lys
        690                 695                 700

Leu Arg Thr Lys Val Glu Asn Gly Glu Gly Thr Ile Pro Val Glu Ser
705                 710                 715                 720

Ser Asp Ile Val Pro Thr Trp Asp Gly Ile Arg Leu Gly Glu Arg Leu
                725                 730                 735

Arg Thr Met Ser Cys Ser Asp Lys Ile Leu Arg Trp Asn Val Leu Gly
                740                 745                 750

Leu Gln Gly Ala Leu Leu Thr His Phe Leu Gln Pro Ile Tyr Leu Lys
                755                 760                 765

Ser Val Thr Leu Gly Tyr Leu Phe Ser Gln Gly His Leu Thr Arg Ala
            770                 775                 780

Ile Cys Cys Arg Val Thr Arg Asp Gly Ser Ala Phe Glu Asp Gly Leu
785                 790                 795                 800

Arg His Pro Phe Ile Val Asn His Pro Lys Val Gly Arg Val Ser Ile
                805                 810                 815

Tyr Asp Ser Lys Arg Gln Ser Gly Lys Thr Lys Glu Thr Ser Val Asn
            820                 825                 830

Trp Cys Leu Ala Asp Gly Tyr Asp Leu Glu Ile Leu Asp Gly Thr Arg
        835                 840                 845

Gly Thr Val Asp Gly Pro Arg Asn Glu Leu Ser Arg Val Ser Lys Lys
    850                 855                 860

Asn Ile Phe Leu Leu Phe Lys Lys Leu Cys Ser Phe Arg Tyr Arg Arg
865                 870                 875                 880

Asp Leu Leu Arg Leu Ser Tyr Gly Glu Ala Lys Lys Ala Ala Arg Asp
                885                 890                 895

Tyr Glu Thr Ala Lys Asn Tyr Phe Lys Lys Gly Leu Lys Asp Met Gly
            900                 905                 910

Tyr Gly Asn Trp Ile Ser Lys Pro Gln Glu Glu Lys Asn Phe Tyr Leu
        915                 920                 925

Cys Pro Val
    930

<210> SEQ ID NO 25
<211> LENGTH: 701
<212> TYPE: PRT
<213> ORGANISM: Homo sapiens

<400> SEQUENCE: 25

Met Asp Ile Glu Asp Glu Glu Asn Met Ser Ser Ser Ser Thr Asp Val
1               5                   10                  15

Lys Glu Asn Arg Asn Leu Asp Asn Val Ser Pro Lys Asp Gly Ser Thr
                20                  25                  30

Pro Gly Pro Gly Glu Gly Ser Gln Leu Ser Asn Gly Gly Gly Gly Gly
            35                  40                  45

Pro Gly Arg Lys Arg Pro Leu Glu Glu Gly Ser Asn Gly His Ser Lys
        50                  55                  60

Tyr Arg Leu Lys Lys Arg Arg Lys Thr Pro Gly Pro Val Leu Pro Lys
65                  70                  75                  80
```

```
Asn Ala Leu Met Gln Leu Asn Glu Ile Lys Pro Gly Leu Gln Tyr Thr
                85                  90                  95

Leu Leu Ser Gln Thr Gly Pro Val His Ala Pro Leu Phe Val Met Ser
            100                 105                 110

Val Glu Val Asn Gly Gln Val Phe Glu Gly Ser Gly Pro Thr Lys Lys
        115                 120                 125

Lys Ala Lys Leu His Ala Ala Glu Lys Ala Leu Arg Ser Phe Val Gln
    130                 135                 140

Phe Pro Asn Ala Ser Glu Ala His Leu Ala Met Gly Arg Thr Leu Ser
145                 150                 155                 160

Val Asn Thr Asp Phe Thr Ser Asp Gln Ala Asp Phe Pro Asp Thr Leu
                165                 170                 175

Phe Asn Gly Phe Glu Thr Pro Asp Lys Ala Glu Pro Pro Phe Tyr Val
            180                 185                 190

Gly Ser Asn Gly Asp Asp Ser Phe Ser Ser Gly Asp Leu Ser Leu
        195                 200                 205

Ser Ala Ser Pro Val Pro Ala Ser Leu Ala Gln Pro Leu Pro Val
    210                 215                 220

Leu Pro Pro Phe Pro Pro Ser Gly Lys Asn Pro Val Met Ile Leu
225                 230                 235                 240

Asn Glu Leu Arg Pro Gly Leu Lys Tyr Asp Phe Leu Ser Glu Ser Gly
                245                 250                 255

Glu Ser His Ala Lys Ser Phe Val Met Ser Val Val Asp Gly Gln
            260                 265                 270

Phe Phe Glu Gly Ser Gly Arg Asn Lys Lys Leu Ala Lys Ala Arg Ala
        275                 280                 285

Ala Gln Ser Ala Leu Ala Ala Ile Phe Asn Leu His Leu Asp Gln Thr
    290                 295                 300

Pro Ser Arg Gln Pro Ile Pro Ser Glu Gly Leu Gln Leu His Leu Pro
305                 310                 315                 320

Gln Val Leu Ala Asp Ala Val Ser Arg Leu Val Leu Gly Lys Phe Gly
                325                 330                 335

Asp Leu Thr Asp Asn Phe Ser Ser Pro His Ala Arg Arg Lys Val Leu
            340                 345                 350

Ala Gly Val Val Met Thr Thr Gly Thr Asp Val Lys Asp Ala Lys Val
        355                 360                 365

Ile Ser Val Ser Thr Gly Thr Lys Cys Ile Asn Gly Glu Tyr Met Ser
    370                 375                 380

Asp Arg Gly Leu Ala Leu Asn Asp Cys His Ala Glu Ile Ile Ser Arg
385                 390                 395                 400

Arg Ser Leu Leu Arg Phe Leu Tyr Thr Gln Leu Glu Leu Tyr Leu Asn
                405                 410                 415

Asn Lys Asp Asp Gln Lys Arg Ser Ile Phe Gln Lys Ser Glu Arg Gly
            420                 425                 430

Gly Phe Arg Leu Lys Glu Asn Val Gln Phe His Leu Tyr Ile Ser Thr
        435                 440                 445

Ser Pro Cys Gly Asp Ala Arg Ile Phe Ser Pro His Glu Pro Ile Leu
    450                 455                 460

Glu Glu Pro Ala Asp Arg His Pro Asn Arg Lys Ala Arg Gly Gln Leu
465                 470                 475                 480

Arg Thr Lys Ile Glu Ser Gly Glu Gly Thr Ile Pro Val Arg Ser Asn
                485                 490                 495

Ala Ser Ile Gln Thr Trp Asp Gly Val Leu Gln Gly Glu Arg Leu Leu
```

-continued

```
                500                 505                 510
Thr Met Ser Cys Ser Asp Lys Ile Ala Arg Trp Asn Val Val Gly Ile
            515                 520                 525

Gln Gly Ser Leu Leu Ser Ile Phe Val Glu Pro Ile Tyr Phe Ser Ser
        530                 535                 540

Ile Ile Leu Gly Ser Leu Tyr His Gly Asp His Leu Ser Arg Ala Met
545                 550                 555                 560

Tyr Gln Arg Ile Ser Asn Ile Glu Asp Leu Pro Pro Leu Tyr Thr Leu
                565                 570                 575

Asn Lys Pro Leu Leu Ser Gly Ile Ser Asn Ala Glu Ala Arg Gln Pro
            580                 585                 590

Gly Lys Ala Pro Asn Phe Ser Val Asn Trp Thr Val Gly Asp Ser Ala
        595                 600                 605

Ile Glu Val Ile Asn Ala Thr Thr Gly Lys Asp Glu Leu Gly Arg Ala
610                 615                 620

Ser Arg Leu Cys Lys His Ala Leu Tyr Cys Arg Trp Met Arg Val His
625                 630                 635                 640

Gly Lys Val Pro Ser His Leu Leu Arg Ser Lys Ile Thr Lys Pro Asn
                645                 650                 655

Val Tyr His Glu Ser Lys Leu Ala Ala Lys Glu Tyr Gln Ala Ala Lys
            660                 665                 670

Ala Arg Leu Phe Thr Ala Phe Ile Lys Ala Gly Leu Gly Ala Trp Val
        675                 680                 685

Glu Lys Pro Thr Glu Gln Asp Gln Phe Ser Leu Thr Pro
690                 695                 700

<210> SEQ ID NO 26
<211> LENGTH: 739
<212> TYPE: PRT
<213> ORGANISM: Homo sapiens

<400> SEQUENCE: 26

Met Ala Ser Val Leu Gly Ser Gly Arg Gly Ser Gly Leu Ser Ser
1               5                   10                  15

Gln Leu Lys Cys Lys Ser Lys Arg Arg Arg Arg Arg Ser Lys Arg
            20                  25                  30

Lys Asp Lys Val Ser Ile Leu Ser Thr Phe Leu Ala Pro Phe Lys His
        35                  40                  45

Leu Ser Pro Gly Ile Thr Asn Thr Glu Asp Asp Thr Leu Ser Thr
    50                  55                  60

Ser Ser Ala Glu Val Lys Glu Asn Arg Asn Val Gly Asn Leu Ala Ala
65                  70                  75                  80

Arg Pro Pro Pro Ser Gly Asp Arg Ala Arg Gly Gly Ala Pro Gly Ala
                85                  90                  95

Lys Arg Lys Arg Pro Leu Glu Glu Gly Asn Gly Gly His Leu Cys Lys
            100                 105                 110

Leu Gln Leu Val Trp Lys Lys Leu Ser Trp Ser Val Ala Pro Lys Asn
        115                 120                 125

Ala Leu Val Gln Leu His Glu Leu Arg Pro Gly Leu Gln Tyr Arg Thr
    130                 135                 140

Val Ser Gln Thr Gly Pro Val His Ala Pro Val Phe Ala Val Ala Val
145                 150                 155                 160

Glu Val Asn Gly Leu Thr Phe Glu Gly Thr Gly Pro Thr Lys Lys Lys
                165                 170                 175
```

-continued

```
Ala Lys Met Arg Ala Ala Glu Leu Ala Leu Arg Ser Phe Val Gln Phe
            180                 185                 190
Pro Asn Ala Cys Gln Ala His Leu Ala Met Gly Gly Pro Gly Pro
        195                 200                 205
Gly Thr Asp Phe Thr Ser Asp Gln Ala Asp Phe Pro Asp Thr Leu Phe
    210                 215                 220
Gln Glu Phe Glu Pro Pro Ala Pro Arg Pro Gly Leu Ala Gly Gly Arg
225                 230                 235                 240
Pro Gly Asp Ala Ala Leu Leu Ser Ala Ala Tyr Gly Arg Arg Arg Leu
                245                 250                 255
Leu Cys Arg Ala Leu Asp Leu Val Gly Pro Thr Pro Ala Thr Pro Ala
            260                 265                 270
Ala Pro Gly Glu Arg Asn Pro Val Val Leu Leu Asn Arg Leu Arg Ala
        275                 280                 285
Gly Leu Arg Tyr Val Cys Leu Ala Glu Pro Ala Glu Arg Arg Ala Arg
    290                 295                 300
Ser Phe Val Met Ala Val Ser Val Asp Gly Arg Thr Phe Glu Gly Ser
305                 310                 315                 320
Gly Arg Ser Lys Lys Leu Ala Arg Gly Gln Ala Ala Gln Ala Ala Leu
                325                 330                 335
Gln Glu Leu Phe Asp Ile Gln Met Pro Gly His Ala Pro Gly Arg Ala
            340                 345                 350
Arg Arg Thr Pro Met Pro Gln Glu Phe Ala Asp Ser Ile Ser Gln Leu
        355                 360                 365
Val Thr Gln Lys Phe Arg Glu Val Thr Thr Asp Leu Thr Pro Met His
    370                 375                 380
Ala Arg His Lys Ala Leu Ala Gly Ile Val Met Thr Lys Gly Leu Asp
385                 390                 395                 400
Ala Arg Gln Ala Gln Val Val Ala Leu Ser Ser Gly Thr Lys Cys Ile
                405                 410                 415
Ser Gly Glu His Leu Ser Asp Gln Gly Leu Val Val Asn Asp Cys His
            420                 425                 430
Ala Glu Val Val Ala Arg Arg Ala Phe Leu His Phe Leu Tyr Thr Gln
        435                 440                 445
Leu Glu Leu His Leu Ser Lys Arg Arg Glu Asp Ser Glu Arg Ser Ile
    450                 455                 460
Phe Val Arg Leu Lys Glu Gly Gly Tyr Arg Leu Arg Glu Asn Ile Leu
465                 470                 475                 480
Phe His Leu Tyr Val Ser Thr Ser Pro Cys Gly Asp Ala Arg Leu His
                485                 490                 495
Ser Pro Tyr Glu Ile Thr Thr Asp Leu His Ser Ser Lys His Leu Val
            500                 505                 510
Arg Lys Phe Arg Gly His Leu Arg Thr Lys Ile Glu Ser Gly Glu Gly
        515                 520                 525
Thr Val Pro Val Arg Gly Pro Ser Ala Val Gln Thr Trp Asp Gly Val
    530                 535                 540
Leu Leu Gly Glu Gln Leu Ile Thr Met Ser Cys Thr Asp Lys Ile Ala
545                 550                 555                 560
Arg Trp Asn Val Leu Gly Leu Gln Gly Ala Leu Leu Ser His Phe Val
                565                 570                 575
Glu Pro Val Tyr Leu Gln Ser Ile Val Val Gly Ser Leu His His Thr
            580                 585                 590
Gly His Leu Ala Arg Val Met Ser His Arg Met Glu Gly Val Gly Gln
```

| | | 595 | | | 600 | | | 605 | | | |
|---|---|---|---|---|---|---|---|---|---|---|---|

Leu Pro Ala Ser Tyr Arg His Asn Arg Pro Leu Leu Ser Gly Val Ser
610                     615                 620

Asp Ala Glu Ala Arg Gln Pro Gly Lys Ser Pro Pro Phe Ser Met Asn
625                 630                 635                 640

Trp Val Val Gly Ser Ala Asp Leu Glu Ile Ile Asn Ala Thr Thr Gly
                    645                 650                 655

Arg Arg Ser Cys Gly Gly Pro Ser Arg Leu Cys Lys His Val Leu Ser
                660                 665                 670

Ala Arg Trp Ala Arg Leu Tyr Gly Arg Leu Ser Thr Arg Thr Pro Ser
            675                 680                 685

Pro Gly Asp Thr Pro Ser Met Tyr Cys Glu Ala Lys Leu Gly Ala His
690                 695                 700

Thr Tyr Gln Ser Val Lys Gln Gln Leu Phe Lys Ala Phe Gln Lys Ala
705                 710                 715                 720

Gly Leu Gly Thr Trp Val Arg Lys Pro Pro Glu Gln Gln Gln Phe Leu
                725                 730                 735

Leu Thr Leu

<210> SEQ ID NO 27
<211> LENGTH: 10826
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

| | | | | | |
|---|---|---|---|---|---|
| gacggatcgg | gagatctccc | gatcccctat | ggtgcactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggag | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggctagc | 900 |
| gtttaaacgg | gccctctaga | ctcgagcggc | cgccactgtg | ctggatatct | gcagagaacc | 960 |
| atgttagctg | acgctgtctc | acgcctggtc | ctgggtaagt | tggtgacct | gaccgacaac | 1020 |
| ttctcctccc | ctcacgctcg | cagaaaagtg | ctggctggag | tcgtcatgac | aacaggcaca | 1080 |
| gatgttaaag | atgccaaggt | gataagtgtt | tctacaggaa | caaatgtat | taatggtgaa | 1140 |
| tacatgagtg | atcgtggcct | tgcattaaat | gactgccatg | cagaaataat | atctcggaga | 1200 |

```
tccttgctca gatttctttta tacacaactt gagctttact taaataacaa agatgatcaa    1260
aaaagatcca tctttcagaa atcagagcga ggggggttta ggctgaagga gaatgtccag    1320
tttcatctgt acatcagcac ctctccctgt ggagatgcca gaatcttctc accacatgag    1380
ccaatcctgg aagaaccagc agatagacac ccaaatcgta aagcaagagg acagctacgg    1440
accaaaatag agtctggtga ggggacgatt ccagtgcgct ccaatgcgag catccaaacg    1500
tgggacgggg tgctgcaagg ggagcggctg ctcaccatgt cctgcagtga caagattgca    1560
cgctggaacg tggtgggcat ccagggatcc ctgctcagca ttttcgtgga gcccatttac    1620
ttctcgagca tcatcctggg cagcctttac cacggggacc accttccag ggccatgtac    1680 cagcggatct ccaacataga ggacctgcca cctctctaca ccctcaacaa gcctttgctc    1740
agtggcatca gcaatgcaga agcacggcag ccagggaagg cccccaactt cagtgtcaac    1800
tggacggtag gcgactccgc tattgaggtc atcaacgcca cgactgggaa ggatgagctg    1860
ggccgcgcgt cccgcctgtg taagcacgcg ttgtactgtc gctggatgcg tgtgcacggc    1920
aaggttccct cccacttact acgctccaag attaccaagc caacgtgta ccatgagtcc    1980 aagctggcgg caaaggagta ccaggccgcc aaggcgcgtc tgttcacagc cttcatcaag    2040
gcggggctgg gggcctgggt ggagaagccc accgagcagg accagttctc actcacgccc    2100
agtggaagtg agacaccggg aacctcagag agcgccacgc cagaaagcat ggacaagaag    2160
tacagcatcg gcctggccat cggcaccaac tctgtgggct gggccgtgat caccgacgag    2220
tacaaggtgc ccagcaagaa attcaaggtg ctgggcaaca ccgaccggca cagcatcaag    2280
aagaacctga tcggcgccct gctgttcgac agcggagaaa cagccgaggc cacccggctg    2340
aagagaaccg ccagaagaag atacaccaga cggaagaacc ggatctgcta tctgcaagag    2400
atcttcagca acgagatggc caaggtggac gacagcttct ccacagact ggaagagtcc    2460 ttcctggtgg aagaggataa gaagcacgag cggcacccca tcttcggcaa catcgtggac    2520
gaggtggcct accacgagaa gtaccccacc atctaccacc tgagaaagaa actggtggac    2580
agcaccgaca aggccgacct gcggctgatc tatctggccc tggcccacat gatcaagttc    2640
cggggccact tcctgatcga gggcgacctg aaccccgaca cagcgacgt ggacaagctg    2700 ttcatccagc tggtgcagac ctacaaccag ctgttcgagg aaaaccccat caacgccagc    2760
ggcgtggacg ccaaggccat cctgtctgcc agactgagca gagcagacg gctggaaaat    2820 ctgatcgccc agctgcccgg cgagaagaag aatggcctgt cggcaacct gattgccctg    2880 agcctgggcc tgaccccaa cttcaagagc aacttcgacc tggccgagga tgccaaactg    2940
cagctgagca aggacaccta cgacgacgac ctggacaacc tgctggccca gatcggcgac    3000
cagtacgccg acctgtttct ggccgccaag aacctgtccg acgccatcct gctgagcgac    3060
atcctgagag tgaacaccga gatcaccaag gccccctga gcgcctctat gatcaagaga    3120
tacgacgagc accaccagga cctgaccctg ctgaaagctc tcgtgcggca gcagctgcct    3180
gagaagtaca agagatttt cttcgaccag agcaagaacg gctacgccgg ctacatcgat    3240
ggcggagcca gccaggaaga gttctacaag ttcatcaagc ccatcctgga aaagatggac    3300
ggcaccgagg aactgctcgt gaagctgaac agagaggacc tgctgcggaa gcagcggacc    3360
ttcgacaacg gcagcatccc ccaccagatc cacctgggag agctgcacgc cattctgcgg    3420
cggcaggaag atttttaccc attcctgaag gacaaccggg aaaagatcga gaagatcctg    3480
accttccgca tcccctacta cgtgggccct ctggccaggg gaaacagcag attcgcctgg    3540
atgaccagaa agagcgagga aaccatcacc ccctggaact tcgaggaagt ggtggacaag    3600
```

```
ggcgccagcg cccagagctt catcgagcgg atgaccaact tcgataagaa cctgcccaac   3660
gagaaggtgc tgcccaagca cagcctgctg tacgagtact tcaccgtgta caacgagctg   3720
accaaagtga atacgtgac cgagggaatg agaaagcccg ccttcctgag cggcgagcag   3780
aaaaaagcca tcgtggacct gctgttcaag accaaccgga agtgaccgt gaagcagctg   3840 aaagaggact acttcaagaa aatcgagtgc ttcgactccg tggaaatctc cggcgtggaa   3900
gatcggttca acgcctccct gggcacatac cacgatctgc tgaaaattat caaggacaag   3960
gacttcctgg acaatgagga aaacgaggac attctggaag atatcgtgct gaccctgaca   4020
ctgtttgagg acagagagat gatcgaggaa cggctgaaaa cctatgccca cctgttcgac   4080
gacaaagtga tgaagcagct gaagcggcgg agatacaccg gctggggcag gctgagccgg   4140
aagctgatca acggcatccg ggacaagcag tccggcaaga caatcctgga tttcctgaag   4200
tccgacggct tcgccaacag aaacttcatg cagctgatcc acgacgacag cctgaccttt   4260
aaagaggaca tccagaaagc ccaggtgtcc ggcagggcg atagcctgca cgagcacatt   4320
gccaatctgg ccggcagccc cgccattaag aagggcatcc tgcagacagt gaaggtggtg   4380
gacgagctcg tgaaagtgat gggccggcac aagcccgaga acatcgtgat cgaaatggcc   4440
agagagaacc agaccaccca aagggacag aagaacagcc gcgagagaat gaagcggatc   4500
gaagagggca tcaaagagct gggcagccag atcctgaaag aacacccgt ggaaaacacc   4560 cagctgcaga acgagaagct gtacctgtac tacctgcaga atgggcggga tatgtacgtg   4620
gaccaggaac tggacatcaa ccggctgtcc gactacgatg tggacgctat cgtgcctcag   4680
agctttctga aggacgactc catcgataac aaagtgctga ctcggagcga caagaaccgg   4740
ggcaagagcg acaacgtgcc ctccgaagag gtcgtgaaga agatgaagaa ctactggcgc   4800
cagctgctga atgccaagct gattacccag aggaagttcg acaatctgac caaggccgag   4860
agaggcggcc tgagcgaact ggataaggcc ggcttcatca agagacagct ggtggaaacc   4920
cggcagatca caaagcacgt ggcacagatc ctggactccc ggatgaacac taagtacgac   4980
gagaacgaca aactgatccg ggaagtgaaa gtgatcaccc tgaagtccaa gctggtgtcc   5040
gatttccgga aggatttcca gttttacaaa gtgcgcgaga tcaacaacta ccaccacgcc   5100
cacgacgcct acctgaacgc cgtcgtggga accgccctga tcaaaaagta ccctaagctg   5160
gaaagcgagt tcgtgtacgg cgactacaag gtgtacgacg tgcggaagat gatcgccaag   5220
agcgagcagg aaatcggcaa ggctaccgcc aagtacttct tctacagcaa catcatgaac   5280 ttttcaaga ccgagattac cctggccaac ggcgagatcc ggaagcggcc tctgatcgag   5340
acaaacggcg aaacaggcga gatcgtgtgg gataagggcc gggactttgc caccgtgcgg   5400
aaagtgctgt ctatgcccca agtgaatatc gtgaaaaaga ccgaggtgca gacaggcggc   5460
ttcagcaaag agtctatcct gcccaagagg aacagcgaca agctgatcgc cagaaagaag   5520
gactgggacc ctaagaagta cggcggcttc gacagcccca ccgtggccta ttctgtgctg   5580
gtggtggcca agtggaaaa gggcaagtcc aagaaactga agagtgtgaa agagctgctg   5640
gggatcacca tcatggaaag aagcagcttc gagaagaatc ccatcgactt tctggaagcc   5700
aagggctaca aagaagtgaa aaaggacctg atcatcaagc tgcctaagta ctccctgttc   5760
gagctggaaa acggccggaa gagaatgctg gcctctgccg gcgaactgca aaagggaaac   5820
gaactggccc tgcctccaa atatgtgaac ttcctgtacc tggccagcca ctatgagaag   5880
ctgaagggct ccccccgagga taatgagcag aaacagctgt ttgtggaaca gcacaaacac   5940
```

```
tacctggacg agatcatcga gcagatcagc gagttctcca agagagtgat cctggccgac    6000
gctaatctgg acaaggtgct gagcgcctac aacaagcaca gagacaagcc tatcagagag    6060
caggccgaga atatcatcca cctgtttacc ctgaccaatc tgggagcccc tgccgccttc    6120
aagtactttg acaccaccat cgaccggaag aggtacacca gcaccaaaga ggtgctggac    6180
gccaccctga tccaccagag catcaccggc ctgtacgaga cacggatcga cctgtctcag    6240
ctggaggcg acgcctatcc ctatgacgtg cccgattatg ccagcctggg cagcggctcc     6300
cccaagaaaa aacgcaaggt ggaagatcct aagaaaaagc ggaaagtgga cgtgtaacca    6360
ccacactgga ctagtggatc cgagctcggt accaagctta gtttaaaccc gctgatcagc    6420
ctcgactgtg ccttctagtt gccagccatc tgttgtttgc ccctcccccg tgccttcctt    6480
gacccctggaa ggtgccactc ccactgtcct ttcctaataa aatgaggaaa ttgcatcgca   6540
ttgtctgagt aggtgtcatt ctattctggg gggtggggtg gggcaggaca gcaagggga    6600
ggattgggaa gacaatagca ggcatgctgg ggatgcggtg ggctctatgg cttctgaggc    6660
ggaaagaacc agctggggct ctaggggta tccccacgcg ccctgtagcg cgcattaag     6720
cgcggcgggt gtggtggtta cgcgcagcgt gaccgctaca cttgccagcg ccctagcgcc    6780
cgctcctttc gctttcttcc cttcctttct cgccacgttc gccggctttc cccgtcaagc    6840
tctaaatcgg gggctccctt tagggttccg atttagtgct ttacggcacc tcgaccccaa    6900
aaaacttgat tagggtgatg gttcacgtag tgggccatcg ccctgataga cggttttcg    6960
ccctttgacg ttggagtcca cgttctttaa tagtggactc ttgttccaaa ctggaacaac    7020
actcaaccct atctcggtct attcttttga tttataaggg attttgccga tttcggccta    7080
ttggttaaaa aatgagctga tttaacaaaa atttaacgcg aattaattct gtggaatgtg    7140
tgtcagttag ggtgtggaaa gtccccaggc tccccagcag gcagaagtat gcaaagcatg    7200
catctcaatt agtcagcaac caggtgtgga aagtccccag gctccccagc aggcagaagt    7260
atgcaaagca tgcatctcaa ttagtcagca accatagtcc cgcccctaac tccgcccatc    7320
ccgcccctaa ctccgcccag ttccgcccat tctccgcccc atggctgact aattttttt     7380
atttatgcag aggccgaggc cgcctctgcc tctgagctat tccagaagta gtgaggaggc    7440
tttttttggag gcctaggctt ttgcaaaaag ctcccgggag cttgtatatc cattttcgga    7500
tctgatcaag agacaggatg aggatcgttt cgcatgattg aacaagatgg attgcacgca    7560
ggttctccgg ccgcttgggt ggagaggcta ttcggctatg actgggcaca acagacaatc    7620
ggctgctctg atgccgccgt gttccggctg tcagcgcagg ggcgcccggt tctttttgtc    7680
aagaccgacc tgtccggtgc cctgaatgaa ctgcaggacg aggcagcgcg gctatcgtgg    7740
ctggccacga cgggcgttcc ttgcgcagct gtgctcgacg ttgtcactga agcgggaagg    7800
gactggctgc tattgggcga agtgccgggg caggatctcc tgtcatctca ccttgctcct    7860
gccgagaaag tatccatcat ggctgatgca atgcggcggc tgcatacgct tgatccggct    7920
acctgcccat tcgaccacca agcgaaacat cgcatcgagc gagcacgtac tcggatggaa    7980
gccggtcttg tcgatcagga tgatctggac gaagagcatc aggggctcgc gccagccgaa    8040
ctgttcgcca ggctcaaggc gcgcatgccc gacggcgagg atctcgtcgt gacccatggc    8100
gatgcctgct tgccgaatat catggtggaa aatggccgct tttctggatt catcgactgt    8160
ggccggctgg gtgtggcgga ccgctatcag gacatagcgt tggctacccg tgatattgct    8220
gaagagcttg gcggcgaatg ggctgaccgc ttcctcgtgc tttacggtat cgccgctccc    8280
gattcgcagc gcatcgcctt ctatcgcctt cttgacgagt tcttctgagc gggactctgg    8340
```

-continued

```
ggttcgaaat gaccgaccaa gcgacgccca acctgccatc acgagatttc gattccaccg   8400
ccgccttcta tgaaaggttg ggcttcggaa tcgttttccg ggacgccggc tggatgatcc   8460
tccagcgcgg ggatctcatg ctggagttct tcgcccaccc caacttgttt attgcagctt   8520
ataatggtta caaataaagc aatagcatca caaatttcac aaataaagca ttttttttcac  8580
tgcattctag ttgtggtttg tccaaactca tcaatgtatc ttatcatgtc tgtataccgt   8640
cgacctctag ctagagcttg gcgtaatcat ggtcatagct gtttcctgtg tgaaattgtt   8700
atccgctcac aattccacac aacatacgag ccggaagcat aaagtgtaaa gcctggggtg   8760
cctaatgagt gagctaactc acattaattg cgttgcgctc actgcccgct ttccagtcgg   8820
gaaacctgtc gtgccagctg cattaatgaa tcggccaacg cgcggggaga ggcggtttgc   8880
gtattgggcg ctcttccgct tcctcgctca ctgactcgct gcgctcggtc gttcggctgc   8940
ggcgagcggt atcagctcac tcaaaggcgg taatacggtt atccacagaa tcagggggata  9000
acgcaggaaa gaacatgtga gcaaaaggcc agcaaaaggc caggaaccgt aaaaaggccg   9060
cgttgctggc gtttttccat aggctccgcc cccctgacga gcatcacaaa aatcgacgct   9120
caagtcagag gtggcgaaac ccgacaggac tataaagata ccaggcgttt ccccctggaa   9180
gctccctcgt gcgctctcct gttccgaccc tgccgcttac cggatacctg tccgcctttc   9240
tcccttcggg aagcgtggcg ctttctcata gctcacgctg taggtatctc agttcggtgt   9300
aggtcgttcg ctccaagctg ggctgtgtgc acgaaccccc cgttcagccc gaccgctgcg   9360
ccttatccgg taactatcgt cttgagtcca acccggtaag acacgactta tcgccactgg   9420
cagcagccac tggtaacagg attagcagag cgaggtatgt aggcggtgct acagagttct   9480
tgaagtggtg gcctaactac ggctacacta gaagaacagt atttggtatc tgcgctctgc   9540
tgaagccagt taccttcgga aaaagagttg gtagctcttg atccggcaaa caaaccaccg   9600
ctggtagcgg tggttttttt gttgcaagca gcagattacg cgcagaaaaa aaggatctcaag  9660
aagatccttt gatcttttct acggggtctg acgctcagtg gaacgaaaac tcacgttaag   9720
ggattttggt catgagatta tcaaaaagga tcttcaccta gatccttttta aattaaaaat   9780
gaagttttaa atcaatctaa agtatatatg agtaaacttg gtctgacagt taccaatgct   9840
taatcagtga ggcacctatc tcagcgatct gtctatttcg ttcatccata gttgcctgac   9900
tccccgtcgt gtagataact acgatacggg agggcttacc atctggcccc agtgctgcaa   9960
tgataccgcg agacccacgc tcaccggctc cagatttatc agcaataaac cagccagccg  10020
gaagggccga gcgcagaagt ggtcctgcaa ctttatccgc ctccatccag tctattaatt  10080
gttgccggga agctagagta agtagttcgc cagttaatag tttgcgcaac gttgttgcca  10140
ttgctacagg catcgtggtg tcacgctcgt cgtttggtat ggcttcattc agctccggtt  10200
cccaacgatc aaggcgagtt acatgatccc ccatgttgtg caaaaaagcg gttagctcct  10260
tcggtcctcc gatcgttgtc agaagtaagt tggccgcagt gttatcactc atggttatgg  10320
cagcactgca taattctctt actgtcatgc catccgtaag atgcttttct gtgactggtg  10380
agtactcaac caagtcattc tgagaatagt gtatgcggcg accgagttgc tcttgcccgg  10440
cgtcaatacg ggataatacc gcgccacata gcagaacttt aaaagtgctc atcattggaa  10500
aacgttcttc ggggcgaaaa ctctcaagga tcttaccgct gttgagatcc agttcgatgt  10560
aacccactcg tgcacccaac tgatcttcag catcttttac tttcaccagc gtttctgggt  10620
gagcaaaaac aggaaggcaa aatgccgcaa aaaagggaat aagggcgaca cggaaatgtt  10680
```

```
gaatactcat actcttcctt tttcaatatt attgaagcat ttatcagggt tattgtctca    10740
tgagcggata catatttgaa tgtatttaga aaaataaaca aatagggtt ccgcgcacat    10800 ttccccgaaa agtgccacct gacgtc                                        10826
```

<210> SEQ ID NO 28
<211> LENGTH: 6722
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaacgg gccctctaga ctcgagcggc cgccactgtg ctggatatct gcagagaacc    960
atgttagctg acgctgtctc acgcctggtc ctgggtaagt ttggtgacct gaccgacaac   1020
ttctcctccc ctcacgctcg cagaaaagtg ctggctggag tcgtcatgac aacaggcaca   1080
gatgttaaag atgccaaggt gataagtgtt tctacaggaa caaatgtat taatggtgaa   1140 tacatgagtg atcgtggcct tgcattaaat gactgccatg cagaaataat atctcggaga   1200
tccttgctca gatttcttta tacacaactt gagctttact taaataacaa agatgatcaa   1260
aaaagatcca tctttcagaa atcagagcga ggggggttta ggctgaagga gaatgtccag   1320
tttcatctgt acatcagcac ctctcccctgt ggagatgcca gaatcttctc accacatgag   1380
ccaatcctgg aagaaccagc agatagacac ccaaatcgta aagcaagagg acagctacgg   1440
accaaaatag agtctggtga ggggacgatt ccagtgcgct ccaatgcgag catccaaacg   1500
tgggacgggg tgctgcaagg ggagcggctg ctcaccatgt cctgcagtga caagattgca   1560
cgctggaacg tggtgggcat ccagggatcc ctgctcagca ttttcgtgga gcccatttac   1620
ttctcgagca tcatcctggg cagcctttac acggggacc acctttccag ggccatgtac   1680
cagcggatct ccaacataga ggacctgcca cctctctaca ccctcaacaa gcctttgctc   1740
agtggcatca gcaatgcaga agcacggcag ccagggaagg cccccaactt cagtgtcaac   1800
tggacggtag gcgactccgc tattgaggtc atcaacgcca cgactgggaa ggatgagctg   1860
```

```
ggccgcgcgt cccgcctgtg taagcacgcg ttgtactgtc gctggatgcg tgtgcacggc    1920
aaggttccct cccacttact acgctccaag attaccaagc ccaacgtgta ccatgagtcc    1980
aagctggcgg caaaggagta ccaggccgcc aaggcgcgtc tgttcacagc cttcatcaag    2040
gcggggctgg gggcctgggt ggagaagccc accgagcagg accagttctc actcacgccc    2100
agtggaagtg agacaccggg aacctcagag agcgccacgc cagaaagcgc ctatccctat    2160
gacgtgcccg attatgccag cctgggcagc ggctccccca agaaaaaacg caaggtggaa    2220
gatcctaaga aaaagcggaa agtggacgtg taaccaccac actggactag tggatccgag    2280
ctcggtacca agcttaagtt taaaccgctg atcagcctcg actgtgcctt ctagttgcca    2340
gccatctgtt gtttgcccct cccccgtgcc ttccttgacc ctggaaggtg ccactcccac    2400
tgtcctttcc taataaaatg aggaaattgc atcgcattgt ctgagtaggt gtcattctat    2460
tctggggggt ggggtggggc aggacagcaa ggggaggat tggaagaca atagcaggca     2520
tgctggggat gcggtgggct ctatggcttc tgaggcggaa agaaccagct ggggctctag    2580
ggggtatccc cacgcgccct gtagcggcgc attaagcgcg gcgggtgtgg tggttacgcg    2640
cagcgtgacc gctacacttg ccagcgccct agcgcccgct cctttcgctt tcttcccttc    2700
ctttctcgcc acgttcgccg gctttccccg tcaagctcta aatcggggc tccctttagg     2760
gttccgattt agtgctttac ggcacctcga ccccaaaaaa cttgattagg gtgatggttc    2820
acgtagtggg ccatcgccct gatagacggt ttttcgccct tgacgttgg agtccacgtt     2880
ctttaatagt ggactcttgt tccaaactgg aacaacactc aaccctatct cggtctattc    2940
ttttgattta taggattt tgccgatttc ggcctattgg ttaaaaatg agctgattta       3000
acaaaattt aacgcgaatt aattctgtgg aatgtgtgtc agttagggtg tggaaagtcc     3060
ccaggctccc cagcaggcag aagtatgcaa agcatgcatc tcaattagtc agcaaccagg    3120
tgtggaaagt ccccaggctc cccagcaggc agaagtatgc aaagcatgca tctcaattag    3180
tcagcaacca tagtcccgcc cctaactccg cccatcccgc ccctaactcc gcccagttcc    3240
gcccattctc cgccccatgg ctgactaatt ttttttattt atgcagaggc cgaggccgcc    3300
tctgcctctg agctattcca gaagtagtga ggaggctttt ttggaggcct aggcttttgc    3360
aaaaagctcc cgggagcttg tatatccatt ttcggatctg atcaagagac aggatgagga    3420
tcgtttcgca tgattgaaca agatggattg cacgcaggtt ctccggccgc ttgggtggag    3480
aggctattcg gctatgactg ggcacaacag acaatcggct gctctgatgc cgccgtgttc    3540
cggctgtcag cgcaggggcg cccggttctt tttgtcaaga ccgacctgtc cggtgccctg    3600
aatgaactgc aggacgaggc agcgcggcta tcgtggctgg ccacgacggg cgttccttgc    3660
gcagctgtgc tcgacgttgt cactgaagcg ggaagggact ggctgctatt gggcgaagtg    3720
ccggggcagg atctcctgtc atctcacctt gctcctgccg agaaagtatc catcatggct    3780
gatgcaatgc ggcggctgca tacgcttgat ccggctacct gcccattcga ccaccaagcg    3840
aaacatcgca tcgagcgagc acgtactcgg atggaagccg gtcttgtcga tcaggatgat    3900
ctggacgaag agcatcaggg gctcgcgcca gccgaactgt tcgccaggct caaggcgcgc    3960
atgcccgacg gcgaggatct cgtcgtgacc catggcgatg cctgcttgcc gaatatcatg    4020
gtggaaaatg gccgcttttc tggattcatc gactgtggcc ggctgggtgt ggcggaccgc    4080
tatcaggaca tagcgttggc taccgtgat attgctgaag agcttggcgg cgaatgggct    4140
gaccgcttcc tcgtgcttta cggtatcgcc gctcccgatt cgcagcgcat cgccttctat    4200
cgccttcttg acgagttctt ctgagcggga ctctggggtt cgaaatgacc gaccaagcga    4260
```

-continued

```
cgcccaacct gccatcacga gatttcgatt ccaccgccgc cttctatgaa aggttgggct    4320
tcggaatcgt tttccgggac gccggctgga tgatcctcca gcgcgggat ctcatgctgg     4380 agttcttcgc ccaccccaac ttgtttattg cagcttataa tggttacaaa taaagcaata    4440
gcatcacaaa tttcacaaat aaagcatttt tttcactgca ttctagttgt ggtttgtcca    4500
aactcatcaa tgtatcttat catgtctgta taccgtcgac ctctagctag agcttggcgt    4560
aatcatggtc atagctgttt cctgtgtgaa attgttatcc gctcacaatt ccacacaaca    4620
tacgagccgg aagcataaag tgtaaagcct ggggtgccta atgagtgagc taactcacat    4680
taattgcgtt gcgctcactg cccgctttcc agtcggaaaa cctgtcgtgc cagctgcatt    4740
aatgaatcgg ccaacgcgcg gggagaggcg gtttgcgtat tgggcgctct tccgcttcct    4800
cgctcactga ctcgctgcgc tcggtcgttc ggctgcggcg agcggtatca gctcactcaa    4860
aggcggtaat acggttatcc acagaatcag gggataacgc aggaaagaac atgtgagcaa    4920
aaggccagca aaaggccagg aaccgtaaaa aggccgcgtt gctggcgttt ttccataggc    4980
tccgcccccc tgacgagcat cacaaaaatc gacgctcaag tcagaggtgg cgaaacccga    5040
caggactata aagataccag gcgtttcccc ctggaagctc cctcgtgcgc tctcctgttc    5100
cgaccctgcc gcttaccgga tacctgtccg cctttctccc ttcgggaagc gtggcgcttt    5160
ctcatagctc acgctgtagg tatctcagtt cggtgtaggt cgttcgctcc aagctgggct    5220
gtgtgcacga accccccgtt cagcccgacc gctgcgcctt atccggtaac tatcgtcttg    5280
agtccaaccc ggtaagacac gacttatcgc cactggcagc agccactggt aacaggatta    5340
gcagagcgag gtatgtaggc ggtgctacag agttcttgaa gtggtggcct aactacggct    5400
acactagaag aacagtattt ggtatctgcg ctctgctgaa gccagttacc ttcggaaaaa    5460
gagttggtag ctcttgatcc ggcaaacaaa ccaccgctgg tagcggtttt tttgtttgca    5520
agcagcagat tacgcgcaga aaaaaaggat ctcaagaaga tcctttgatc ttttctacgg    5580
ggtctgacgc tcagtggaac gaaaactcac gttaagggat tttggtcatg agattatcaa    5640
aaaggatctt cacctagatc cttttaaatt aaaaatgaag ttttaaatca atctaaagta    5700
tatatgagta aacttggtct gacagttacc aatgcttaat cagtgaggca cctatctcag    5760
cgatctgtct atttcgttca tccatagttg cctgactccc cgtcgtgtag ataactacga    5820
tacgggaggg cttaccatct ggccccagtg ctgcaatgat accgcgagac ccacgctcac    5880
cggctccaga tttatcagca ataaaccagc cagccggaag ggccgagcgc agaagtggtc    5940
ctgcaacttt atccgcctcc atccagtcta ttaattgttg ccgggaagct agagtaagta    6000
gttcgccagt taatagtttg cgcaacgttg ttgccattgc tacaggcatc gtggtgtcac    6060
gctcgtcgtt tggtatggct tcattcagct ccggttccca acgatcaagg cgagttacat    6120 gatccccat gttgtgcaaa aaagcggtta gctccttcgg tcctccgatc gttgtcagaa    6180
gtaagttggc cgcagtgtta tcactcatgg ttatggcagc actgcataat tctcttactg    6240
tcatgccatc cgtaagatgc ttttctgtga ctggtgagta ctcaaccaag tcattctgag    6300
aatagtgtat gcggcgaccg agttgctctt gcccggcgtc aatacgggat aataccgcgc    6360
cacatagcag aactttaaaa gtgctcatca ttggaaaacg ttcttcgggg cgaaaactct    6420
caaggatctt accgctgttg agatccagtt cgatgtaacc cactcgtgca cccaactgat    6480
cttcagcatc ttttactttc accagcgttt ctgggtgagc aaaaacagga aggcaaaatg    6540
ccgcaaaaaa gggaataagg gcgacacgga aatgttgaat actcatactc ttcctttttc    6600
```

```
aatattattg aagcatttat cagggttatt gtctcatgag cggatacata tttgaatgta    6660
tttagaaaaa taaacaaata ggggttccgc gcacatttcc ccgaaaagtg ccacctgacg    6720
tc                                                                   6722
```

<210> SEQ ID NO 29
<211> LENGTH: 10826
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaacgg gccctctaga ctcgagcggc cgccactgtg ctggatatct gcagagaacc    960
atgttagctg acgctgtctc acgcctggtc ctgggtaagt ttggtgacct gaccgacaac   1020
ttctcctccc ctcacgctcg cagaaaagtg ctggctggag tcgtcatgac aacaggcaca   1080
gatgttaaag atgccaaggt gataagtgtt tctacaggaa caaatgtat taatggtgaa   1140 tacatgagtg atcgtggcct tgcattaaat gactgccatg cagaaataat atctcggaga   1200
tccttgctca gatttctta tacacaactt gagcttact taaataacaa agatgatcaa   1260
aaaagatcca tctttcagaa atcagagcga gggggttta ggctgaagga gaatgtccag   1320
tttcatctgt acatcagcac ctctccctgt ggagatgcca gaatcttctc accacatgag   1380
ccaatcctgg aagaaccagc agatagacac ccaaatcgta aagcaagagg acagctacgg   1440
accaaaatag agtctggtca ggggacgatt ccagtgcgct ccaatgcgag catccaaacg   1500
tgggacgggg tgctgcaagg ggagcggctg ctcaccatgt cctgcagtga caagattgca   1560
cgctggaacg tggtgggcat ccagggatcc ctgctcagca tttttcgtgga gcccatttac   1620 ttctcgagca tcatcctggg cagcctttac cacgggacc accttccag ggccatgtac   1680 cagcggatct ccaacataga ggacctgcca cctctctaca ccctcaacaa gcctttgctc   1740
agtggcatca gcaatgcaga agcacggcag ccagggaagg ccccaacttc agtgtcaac   1800 tggacggtag gcgactccgc tattgaggtc atcaacgcca cgactgggaa ggatgagctg   1860
```

```
ggccgcgcgt cccgcctgtg taagcacgcg ttgtactgtc gctggatgcg tgtgcacggc      1920
aaggttccct cccacttact acgctccaag attaccaagc ccaacgtgta ccatgagtcc      1980
aagctggcgg caaaggagta ccaggccgcc aaggcgcgtc tgttcacagc cttcatcaag      2040
gcggggctgg gggcctgggt ggagaagccc accgagcagg accagttctc actcacgccc      2100
agtggaagtg agacaccggg aacctcagag agcgccacgc cagaaagcat ggacaagaag      2160
tacagcatcg gcctggccat cggcaccaac tctgtgggct gggccgtgat caccgacgag      2220
tacaaggtgc ccagcaagaa attcaaggtg ctgggcaaca ccgaccggca cagcatcaag      2280
aagaacctga tcggcgccct gctgttcgac agcggagaaa cagccgaggc cacccggctg      2340
aagagaaccg ccagaagaag atacaccaga cggaagaacc ggatctgcta tctgcaagag      2400
atcttcagca acgagatggc caaggtggac gacagcttct ccacagact ggaagagtcc      2460 ttcctggtgg aagaggataa gaagcacgag cggcacccca tcttcggcaa catcgtggac      2520
gaggtggcct accacgagaa gtaccccacc atctaccacc tgagaaagaa actggtggac      2580
agcaccgaca aggccgacct gcggctgatc tatctggccc tggcccacat gatcaagttc      2640
cggggccact tcctgatcga gggcgacctg aaccccgaca acagcgacgt ggacaagctg      2700
ttcatccagc tggtgcagac ctacaaccag ctgttcgagg aaaacccat caacgccagc      2760 ggcgtggacg ccaaggccat cctgtctgcc agactgagca agagcagacg gctggaaaat      2820
ctgatcgccc agctgcccgg cgagaagaag aatggcctgt cggcaacct gattgccctg      2880 agcctgggcc tgacccccaa cttcaagagc aacttcgacc tggccgagga tgccaaactg      2940
cagctgagca aggacaccta cgacgacgac ctggacaacc tgctggccca gatcggcgac      3000
cagtacgccg acctgtttct ggccgccaag aacctgtccg acgccatcct gctgagcgac      3060
atcctgagag tgaacaccga gatcaccaag gccccctga cgcctctat gatcaagaga      3120 tacgacgagc accaccagga cctgaccctg ctgaaagctc tcgtgcggca gcagctgcct      3180
gagaagtaca aagagatttt cttcgaccag agcaagaacg gctacgccgg ctacatcgat      3240
ggcggagcca gccaggaaga gttctacaag ttcatcaagc ccatcctgga aaagatggac      3300
ggcaccgagg aactgctcgt gaagctgaac agagaggacc tgctgcggaa gcagcggacc      3360
ttcgacaacg gcagcatccc ccaccagatc cacctgggag agctgcacgc cattctgcgg      3420
cggcaggaag attttttaccc cattcctgaag gacaaccggg aaaagatcga aagatcctg      3480 accttccgca tcccctacta cgtgggccct ctggccaggg gaaacagcag attcgcctgg      3540
atgaccagaa agagcgagga aaccatcacc ccctggaact tcgaggaagt ggtggacaag      3600
ggcgccagcg cccagagctt catcgagcgg atgaccaact tcgataagaa cctgcccaac      3660
gagaaggtgc tgcccaagca cagcctgctg tacgagtact tcaccgtgta caacgagctg      3720
accaaagtga aatacgtgac cgagggaatg agaaagcccg ccttcctgag cggcgagcag      3780
aaaaaagcca tcgtggacct gctgttcaag accaaccgga aagtgaccgt gaagcagctg      3840
aaagaggact acttcaagaa aatcgagtgc ttcgactccg tggaaatctc cggcgtggaa      3900
gatcggttca acgcctccct gggcacatac cacgatctgc tgaaaattat caaggacaag      3960
gacttcctgg acaatgagga aaacgaggac attctggaag atatcgtgct gacccctgaca      4020 ctgtttgagg acagagagat gatcgaggaa cggctgaaaa cctatgccca cctgttcgac      4080
gacaaagtga tgaagcagct gaagcggcgg agatacaccg gctggggcag gctgagccgg      4140
aagctgatca acggcatccg ggacaagcag tccggcaaga caatcctgga tttcctgaag      4200
tccgacggct tcgccaacag aaacttcatg cagctgatcc acgacgacag cctgacctttt      4260
```

```
aaagaggaca tccagaaagc ccaggtgtcc ggccagggcg atagcctgca cgagcacatt      4320
gccaatctgg ccggcagccc cgccattaag aagggcatcc tgcagacagt gaaggtggtg      4380
gacgagctcg tgaaagtgat gggccggcac aagcccgaga acatcgtgat cgaaatggcc      4440
agagagaacc agaccaccca gaagggacag aagaacagcc gcgagagaat gaagcggatc      4500
gaagagggca tcaaagagct gggcagccag atcctgaaag aacaccccgt ggaaaacacc      4560
cagctgcaga acgagaagct gtacctgtac tacctgcaga tgggcgggga tatgtacgtg      4620
gaccaggaac tggacatcaa ccggctgtcc gactacgatg tggacgctat cgtgcctcag      4680
agctttctga aggacgactc catcgataac aaagtgctga ctcggagcga caagaaccgg      4740
ggcaagagcg acaacgtgcc ctccgaagag gtcgtgaaga agatgaagaa ctactggcgc      4800
cagctgctga atgccaagct gattacccag aggaagttcg acaatctgac caaggccgag      4860
agaggcggcc tgagcgaact ggataaggcc ggcttcatca agagacagct ggtggaaacc      4920
cggcagatca caaagcacgt ggcacagatc ctggactccc ggatgaacac taagtacgac      4980
gagaacgaca aactgatccg ggaagtgaaa gtgatcaccc tgaagtccaa gctggtgtcc      5040
gatttccgga aggatttcca gttttacaaa gtgcgcgaga tcaacaacta ccaccacgcc      5100
cacgacgcct acctgaacgc cgtcgtggga accgccctga tcaaaaagta ccctaagctg      5160
gaaagcgagt tcgtgtacgg cgactacaag gtgtacgacg tgcggaagat gatcgccaag      5220
agcgagcagg aaatcggcaa ggctaccgcc aagtacttct tctacagcaa catcatgaac      5280
tttttcaaga ccgagattac cctggccaac ggcgagatcc ggaagcggcc tctgatcgag      5340
acaaacggcg aaacaggcga gatcgtgtgg gataagggcc gggactttgc caccgtgcgg      5400
aaagtgctgt ctatgcccca agtgaatatc gtgaaaaaga ccgaggtgca gacaggcggc      5460
ttcagcaaag agtctatcct gcccaagagg aacagcgaca gctgatcgc cagaaagaag      5520 gactgggacc ctaagaagta cggcggcttc gacagcccca ccgtggccta ttctgtgctg      5580
gtggtggcca agtggaaaa gggcaagtcc aagaaactga gagtgtgaa agagctgctg      5640 gggatcacca tcatggaaag aagcagcttc gagaagaatc ccatcgactt tctggaagcc      5700
aagggctaca aagaagtgaa aaaggacctg atcatcaagc tgcctaagta ctccctgttc      5760
gagctggaaa acggccggaa gagaatgctg gcctctgccg gcgaactgca gaagggaaac      5820
gaactggccc tgcccctcaa atatgtgaac ttcctgtacc tggccagcca ctatgagaag      5880
ctgaagggct cccccgagga taatgagcag aaacagctgt tgtggaaca gcacaaacac      5940 tacctggacg agatcatcga gcagatcagc gagttctcca agagagtgat cctggccgac      6000
gctaatctgg acaaggtgct gagcgcctac aacaagcaca gagacaagcc tatcagagag      6060
caggccgaga atatcatcca cctgtttacc ctgaccaatc tgggagcccc tgccgccttc      6120
aagtactttg acaccaccat cgaccggaag aggtacacca gcaccaaaga ggtgctggac      6180
gccaccctga tccaccagag catcaccggc ctgtacgaga cacggatcga cctgtctcag      6240
ctgggaggcg acgcctatcc ctatgacgtg cccgattatg ccagcctggg cagcggctcc      6300
cccaagaaaa aacgcaaggt ggaagatcct aagaaaaagc ggaaagtgga cgtgtaacca      6360
ccacactgga ctagtggatc cgagctcggt accaagctta gtttaaaccc gctgatcagc      6420
ctcgactgtg ccttctagtt gccagccatc tgttgtttgc ccctcccccg tgccttcctt      6480
gaccctggaa ggtgccactc ccactgtcct ttcctaataa aatgaggaaa ttgcatcgca      6540
ttgtctgagt aggtgtcatt ctattctggg gggtggggtg gggcaggaca gcaagggga      6600
```

```
ggattgggaa gacaatagca ggcatgctgg ggatgcggtg ggctctatgg cttctgaggc    6660
ggaaagaacc agctggggct ctaggggta tccccacgcg ccctgtagcg gcgcattaag     6720
cgcggcgggt gtggtggtta cgcgcagcgt gaccgctaca cttgccagcg ccctagcgcc    6780
cgctcctttc gctttcttcc cttcctttct cgccacgttc gccggctttc ccgtcaagc     6840
tctaaatcgg gggctcccctt taggggttccg atttagtgct ttacggcacc tcgacccaa    6900
aaaacttgat tagggtgatg gttcacgtag tgggccatcg ccctgataga cggttttcg     6960
ccctttgacg ttggagtcca cgttctttaa tagtggactc ttgttccaaa ctggaacaac    7020
actcaaccct atctcggtct attcttttga ttataaggg attttgccga tttcggccta     7080
ttggttaaaa aatgagctga tttaacaaaa atttaacgcg aattaattct gtggaatgtg    7140
tgtcagttag ggtgtggaaa gtccccaggc tccccagcag gcagaagtat gcaaagcatg    7200
catctcaatt agtcagcaac caggtgtgga aagtccccag gctccccagc aggcagaagt    7260
atgcaaagca tgcatctcaa ttagtcagca accatagtcc cgcccctaac tccgcccatc    7320
ccgcccctaa ctccgcccag ttccgcccat tctccgcccc atggctgact aattttttt     7380
atttatgcag aggccgaggc cgcctctgcc tctgagctat tccagaagta gtgaggaggc    7440
ttttttggag gcctaggctt ttgcaaaaag ctcccgggag cttgtatatc cattttcgga    7500
tctgatcaag agacaggatg aggatcgttt cgcatgattg aacaagatgg attgcacgca    7560
ggttctccgg ccgcttgggt ggagaggcta ttcggctatg actgggcaca acagacaatc    7620
ggctgctctg atgccgccgt gttccggctg tcagcgcagg ggcgcccggt tctttttgtc    7680
aagaccgacc tgtccggtgc cctgaatgaa ctgcaggacg aggcagcgcg gctatcgtgg    7740
ctggccacga cgggcgttcc ttgcgcagct gtgctcgacg ttgtcactga agcgggaagg    7800
gactggctgc tattgggcga agtgccgggg caggatctcc tgtcatctca ccttgctcct    7860
gccgagaaag tatccatcat ggctgatgca atgcggcggc tgcatacgct tgatccggct    7920
acctgcccat tcgaccacca agcgaaacat cgcatcgagc gagcacgtac tcggatggaa    7980
gccggtcttg tcgatcagga tgatctggac gaagagcatc aggggctcgc gccagccgaa    8040
ctgttcgcca ggctcaaggc gcgcatgccc gacggcgagg atctcgtcgt gacccatggc    8100
gatgcctgct tgccgaatat catggtggaa aatggccgct tttctggatt catcgactgt    8160
ggccggctgg gtgtggcgga ccgctatcag gacatagcgt tggctacccg tgatattgct    8220
gaagagcttg gcggcgaatg ggctgaccgc ttcctcgtgc tttacggtat cgccgctccc    8280
gattcgcagc gcatcgcctt ctatcgcctt cttgacgagt tcttctgagc gggactctgg    8340
ggttcgaaat gaccgaccaa gcgacgccca acctgccatc acgagatttc gattccaccg    8400
ccgccttcta tgaaaggttg gcttcggaa tcgtttttccg ggacgccggc tggatgatcc    8460
tccagcgcgg ggatctcatg ctggagttct tcgcccaccc caacttgttt attgcagctt    8520
ataatggtta caaataaagc aatagcatca caaatttcac aaataaagca ttttttttcac    8580
tgcattctag ttgtggtttg tccaaactca tcaatgtatc ttatcatgtc tgtataccgt    8640
cgacctctag ctagagcttg gcgtaatcat ggtcatagct gtttcctgtg tgaaattgtt    8700
atccgctcac aattccacac aacatacgag ccggaagcat aaagtgtaaa gcctggggtg    8760
cctaatgagt gagctaactc acattaattg cgttgcgctc actgcccgct ttccagtcgg    8820
gaaacctgtc gtgccagctg cattaatgaa tcggccaacg cgcggggaga ggcggtttgc    8880
gtattgggcg ctcttccgct tcctcgctca ctgactcgct gcgctcggtc gttcggctgc    8940
ggcgagcggt atcagctcac tcaaaggcgg taatacggtt atccacagaa tcaggggata    9000
```

| | | |
|---|---|---|
| acgcaggaaa gaacatgtga gcaaaaggcc agcaaaaggc caggaaccgt aaaaaggccg | 9060 |
| cgttgctggc gttttttccat aggctccgcc ccctgacga gcatcacaaa aatcgacgct | 9120 |
| caagtcagag gtggcgaaac ccgacaggac tataaagata ccaggcgttt ccccctggaa | 9180 |
| gctccctcgt gcgctctcct gttccgaccc tgccgcttac cggatacctg tccgcctttc | 9240 |
| tcccttcggg aagcgtggcg ctttctcata gctcacgctg taggtatctc agttcggtgt | 9300 |
| aggtcgttcg ctccaagctg gctgtgtgc acgaaccccc cgttcagccc gaccgctgcg | 9360 |
| ccttatccgg taactatcgt cttgagtcca acccggtaag acacgactta tcgccactgg | 9420 |
| cagcagccac tggtaacagg attagcagag cgaggtatgt aggcggtgct acagagttct | 9480 |
| tgaagtggtg gcctaactac ggctacacta agaacagt atttggtatc tgcgctctgc | 9540 |
| tgaagccagt taccttcgga aaagagttg gtagctcttg atccggcaaa caaaccaccg | 9600 |
| ctggtagcgg tttttttgtt tgcaagcagc agattacgcg cagaaaaaaa ggatctcaag | 9660 |
| aagatccttt gatcttttct acggggtctg acgctcagtg gaacgaaaac tcacgttaag | 9720 |
| ggattttggt catgagatta tcaaaaagga tcttcaccta gatccttta aattaaaaat | 9780 |
| gaagttttaa atcaatctaa agtatatatg agtaaacttg gtctgacagt taccaatgct | 9840 |
| taatcagtga ggcacctatc tcagcgatct gtctatttcg ttcatccata gttgcctgac | 9900 |
| tccccgtcgt gtagataact acgatacggg agggcttacc atctggcccc agtgctgcaa | 9960 |
| tgataccgcg agacccacgc tcaccggctc cagatttatc agcaataaac cagccagccg | 10020 |
| gaagggccga gcgcagaagt ggtcctgcaa ctttatccgc ctccatccag tctattaatt | 10080 |
| gttgccggga agctagagta agtagttcgc cagttaatag tttgcgcaac gttgttgcca | 10140 |
| ttgctacagg catcgtggtg tcacgctcgt cgtttggtat ggcttcattc agctccggtt | 10200 |
| cccaacgatc aaggcgagtt acatgatccc ccatgttgtg caaaaaagcg gttagctcct | 10260 |
| tcggtcctcc gatcgttgtc agaagtaagt tggccgcagt gttatcactc atggttatgg | 10320 |
| cagcactgca taattctctt actgtcatgc catccgtaag atgcttttct gtgactggtg | 10380 |
| agtactcaac caagtcattc tgagaatagt gtatgcggcg accgagttgc tcttgcccgg | 10440 |
| cgtcaatacg ggataatacc gcgccacata gcagaacttt aaaagtgctc atcattggaa | 10500 |
| aacgttcttc ggggcgaaaa ctctcaagga tcttaccgct gttgagatcc agttcgatgt | 10560 |
| aacccactcg tgcacccaac tgatcttcag catcttttac tttcaccagc gtttctgggt | 10620 |
| gagcaaaaac aggaaggcaa aatgccgcaa aaaagggaat aagggcgaca cggaaatgtt | 10680 |
| gaatactcat actcttcctt tttcaatatt attgaagcat ttatcagggt tattgtctca | 10740 |
| tgagcggata catatttgaa tgtatttaga aaataaaca aatagggggtt ccgcgcacat | 10800 |
| ttccccgaaa agtgccacct gacgtc | 10826 |

<210> SEQ ID NO 30
<211> LENGTH: 6722
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

| | | |
|---|---|---|
| gacggatcgg gagatctccc gatccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |

```
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaacgg gccctctaga ctcgagcggc cgccactgtg ctggatatct gcagagaacc    960
atgttagctg acgctgtctc acgcctggtc ctgggtaagt tggtgaccct gaccgacaac   1020
ttctcctccc ctcacgctcg cagaaaagtg ctggctggag tcgtcatgac aacaggcaca   1080
gatgttaaag atgccaaggt gataagtgtt tctacaggaa caaatgtat taatggtgaa    1140 tacatgagtg atcgtggcct tgcattaaat gactgccatg cagaaataat atctcggaga   1200
tccttgctca gatttcttta tacacaactt gagctttact aaataacaa agatgatcaa    1260 aaaagatcca tctttcagaa atcagagcga ggggggttta ggctgaagga gaatgtccag   1320
tttcatctgt acatcagcac ctctcccctgt ggagatgcca gaatcttctc accacatgag   1380
ccaatcctgg aagaaccagc agatagacac ccaaatcgta agcaagagg acagctacgg    1440 accaaaatag agtctggtca ggggacgatt ccagtgcgct ccaatgcgag catccaaacg   1500
tgggacgggg tgctgcaagg ggagcggctg ctcaccatgt cctgcagtga caagattgca   1560
cgctggaacg tggtgggcat ccagggatcc ctgctcagca ttttcgtgga gcccatttac   1620
ttctcgagca tcatcctggg cagcctttac acggggacc accttccag ggccatgtac    1680 cagcggatct ccaacataga ggacctgcca cctctctaca ccctcaacaa gcctttgctc   1740
agtggcatca gcaatgcaga agcacggcag ccagggaagg cccccaactt cagtgtcaac   1800
tggacggtag cgactccgc tattgaggtc atcaacgcca cgactgggaa ggatgagctg   1860
ggccgcgcgt cccgcctgtg taagcacgcg ttgtactgtc gctggatgcg tgtgcacggc   1920
aaggttccct cccacttact acgctccaag attaccaagc caacgtgta ccatgagtcc    1980 aagctggcg caaaggagta ccaggccgcc aaggcgcgtc tgttcacagc cttcatcaag   2040
gcggggctgg gggcctgggt ggagaagccc accgagcagg accagttctc actcacgccc   2100
agtggaagtg agacaccggg aacctcagag agcgccacgc cagaaagcgc ctatccctat   2160
gacgtgcccg attatgccag cctgggcagc ggctccccca agaaaaaacg caaggtggaa   2220
gatcctaaga aaaagcggaa agtggacgtg taaccaccac actggactag tggatccgag   2280
ctcggtacca agcttaagtt taaaccgctg atcagcctcg actgtgcctt ctagttgcca   2340
gccatctgtt gtttgcccct cccccgtgcc ttccttgacc ctggaaggtg ccactcccac   2400
tgtcctttcc taataaaatg aggaaattgc atcgcattgt ctgagtaggt gtcattctat   2460 tctgggggt ggggtggggc aggacagcaa ggggaggat tggaagaca atagcaggca     2520
```

```
tgctggggat gcggtgggct ctatggcttc tgaggcggaa agaaccagct ggggctctag    2580
ggggtatccc cacgcgccct gtagcggcgc attaagcgcg gcgggtgtgg tggttacgcg    2640
cagcgtgacc gctacacttg ccagcgccct agcgcccgct cctttcgctt tcttcccttc    2700
ctttctcgcc acgttcgccg gctttccccg tcaagctcta aatcggggc tcccttagg     2760
gttccgattt agtgctttac ggcacctcga ccccaaaaaa cttgattagg gtgatggttc    2820
acgtagtggg ccatcgccct gatagacggt ttttcgccct ttgacgttgg agtccacgtt    2880
ctttaatagt ggactcttgt tccaaactgg aacaacactc aaccctatct cggtctattc    2940
ttttgattta aagggatttt tgccgatttc ggcctattgg ttaaaaaatg agctgattta    3000
acaaaaattt aacgcgaatt aattctgtgg aatgtgtgtc agttagggtg tggaaagtcc    3060
ccaggctccc cagcaggcag aagtatgcaa agcatgcatc tcaattagtc agcaaccagg    3120
tgtggaaagt ccccaggctc cccagcaggc agaagtatgc aaagcatgca tctcaattag    3180
tcagcaacca tagtcccgcc cctaactccg cccatcccgc cctaactccg cccagttcc     3240
gcccattctc cgccccatgg ctgactaatt ttttttattt atgcagaggc cgaggccgcc    3300
tctgcctctg agctattcca gaagtagtga ggaggctttt ttggaggcct aggcttttgc    3360
aaaaagctcc cgggagcttg tatatccatt ttcggatctg atcaagagac aggatgagga    3420
tcgtttcgca tgattgaaca agatggattg cacgcaggtt ctccggccgc ttgggtggag    3480
aggctattcg gctatgactg ggcacaacag acaatcggct gctctgatgc cgccgtgttc    3540
cggctgtcag cgcaggggcg cccggttctt tttgtcaaga ccgacctgtc cggtgccctg    3600
aatgaactgc aggacgaggc agcgcggcta tcgtggctgg ccacgacggg cgttccttgc    3660
gcagctgtgc tcgacgttgt cactgaagcg ggaagggact ggctgctatt gggcgaagtg    3720
ccggggcagg atctcctgtc atctcacctt gctcctgccg agaaagtatc catcatggct    3780
gatgcaatgc ggcggctgca tacgcttgat ccggctacct gcccattcga ccaccaagcg    3840
aaacatcgca tcgagcgagc acgtactcgg atggaagccg gtcttgtcga tcaggatgat    3900
ctggacgaag agcatcaggg gctcgcgcca gccgaactgt tcgccaggct caaggcgcgc    3960
atgcccgacg cgaggatct cgtcgtgacc catggcgatg cctgcttgcc gaatatcatg    4020
gtggaaaatg gccgcttttc tggattcatc gactgtggcc ggctgggtgt ggcggaccgc    4080
tatcaggaca tagcgttggc tacccgtgat attgctgaag agcttggcgg cgaatgggct    4140
gaccgcttcc tcgtgcttta cggtatcgcc gctcccgatt cgcagcgcat cgccttctat    4200
cgccttcttg acgagttctt ctgagcggga ctctggggtt cgaaatgacc gaccaagcga    4260
cgcccaacct gccatcacga gatttcgatt ccaccgccgc cttctatgaa aggttgggct    4320
tcggaatcgt tttccgggac gccggctgga tgatcctcca gcgcgggat ctcatgctgg    4380
agttcttcgc ccaccccaac ttgtttattg cagcttataa tggttacaaa taaagcaata    4440
gcatcacaaa tttcacaaat aaagcatttt tttcactgca ttctagttgt ggtttgtcca    4500
aactcatcaa tgtatcttat catgtctgta taccgtcgac ctctagctag agcttggcgt    4560
aatcatggtc atagctgttt cctgtgtgaa attgttatcc gctcacaatt ccacacaaca    4620
tacgagccgg aagcataaag tgtaaagcct ggggtgccta atgagtgagc taactcacat    4680
taattgcgtt gcgctcactg cccgctttcc agtcgggaaa cctgtcgtgc cagctgcatt    4740
aatgaatcgg ccaacgcgcg gggagaggcg gtttgcgtat tgggcgctct tccgcttcct    4800
cgctcactga ctcgctgcgc tcggtcgttc ggctgcggcg agcggtatca gctcactcaa    4860
aggcggtaat acggttatcc acagaatcag gggataacgc aggaaagaac atgtgagcaa    4920
```

```
aaggccagca aaaggccagg aaccgtaaaa aggccgcgtt gctggcgttt ttccataggc    4980 tccgccccc  tgacgagcat cacaaaaatc gacgctcaag tcagaggtgg cgaaacccga    5040
caggactata aagataccag gcgtttcccc ctggaagctc cctcgtgcgc tctcctgttc    5100
cgaccctgcc gcttaccgga tacctgtccg ccttcctccc ttcgggaagc gtggcgcttt    5160
ctcatagctc acgctgtagg tatctcagtt cggtgtaggt cgttcgctcc aagctgggct    5220
gtgtgcacga accccccgtt cagcccgacc gctgcgcctt atccggtaac tatcgtcttg    5280
agtccaaccc ggtaagacac gacttatcgc cactggcagc agccactggt aacaggatta    5340
gcagagcgag gtatgtaggc ggtgctacag agttcttgaa gtggtggcct aactacggct    5400
acactagaag aacagtattt ggtatctgcg ctctgctgaa gccagttacc ttcggaaaaa    5460
gagttggtag ctcttgatcc ggcaaacaaa ccaccgctgg tagcggtttt ttgtttgca    5520 agcagcagat tacgcgcaga aaaaaggat  ctcaagaaga tcctttgatc ttttctacgg    5580
ggtctgacgc tcagtggaac gaaaactcac gttaagggat tttggtcatg agattatcaa    5640
aaaggatctt cacctagatc cttttaaatt aaaaatgaag ttttaaatca atctaaagta    5700
tatatgagta aacttggtct gacagttacc aatgcttaat cagtgaggca cctatctcag    5760
cgatctgtct atttcgttca tccatagttg cctgactccc cgtcgtgtag ataactacga    5820
tacgggaggg cttaccatct ggccccagtg ctgcaatgat accgcgagac ccacgctcac    5880
cggctccaga tttatcagca ataaaccagc cagccggaag ggccgagcgc agaagtggtc    5940
ctgcaacttt atccgcctcc atccagtcta ttaattgttg ccgggaagct agagtaagta    6000
gttcgccagt taatagtttg cgcaacgttg ttgccattgc tacaggcatc gtggtgtcac    6060
gctcgtcgtt tggtatggct tcattcagct ccggttccca acgatcaagg cgagttacat    6120 gatccccat  gttgtgcaaa aaagcggtta gctccttcgg tcctccgatc gttgtcagaa    6180
gtaagttggc cgcagtgtta tcactcatgg ttatggcagc actgcataat tctcttactg    6240
tcatgccatc cgtaagatgc ttttctgtga ctggtgagta ctcaaccaag tcattctgag    6300
aatagtgtat gcggcgaccg agttgctctt gcccggcgtc aatacgggat aataccgcgc    6360
cacatagcag aactttaaaa gtgctcatca ttggaaaacg ttcttcgggg cgaaaactct    6420
caaggatctt accgctgttg agatccagtt cgatgtaacc cactcgtgca cccaactgat    6480
cttcagcatc ttttactttc accagcgttt ctgggtgagc aaaaacagga aggcaaaatg    6540
ccgcaaaaaa gggaataagg gcgacacgga aatgttgaat actcatactc ttcctttttc    6600
aatattattg aagcatttat cagggttatt gtctcatgag cggatacata tttgaatgta    6660
tttagaaaaa taaacaaata ggggttccgc gcacatttcc ccgaaaagtg ccacctgacg    6720
tc                                                                  6722
```

<210> SEQ ID NO 31
<211> LENGTH: 4951
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
ttttttcct  gcagcccggg aaggatctgc gatcgctccg gtgcccgtca gtgggcagag     60
cgcacatcgc ccacagtccc cgagaagttg ggggagggg  tcggcaattg aacgggtgcc    120
tagagaaggt ggcgcggggt aaactgggaa agtgatgtcg tgtactggct ccgcctttt    180
```

```
cccgagggtg ggggagaacc gtatataagt gcagtagtcg ccgtgaacgt tcttttttcgc    240 aacgggtttg ccgccagaac acagctgaag cttcgagggg ctcgcatctc tccttcacgc    300
gcccgccgcc ctacctgagg ccgccatcca cgccggttga gtcgcgttct gccgcctccc    360
gcctgtggtg cctcctgaac tgcgtccgcc gtctaggtaa gtttaaagct caggtcgaga    420
ccgggccttt gtccggcgct cccttggagc ctacctagac tcagccggct ctccacgctt    480
tgcctgaccc tgcttgctca actctacgtc tttgtttcgt tttctgttct gcgccgttac    540
agatccaagc tgtgaccggc gcctacgcta gatggtgagc aagggcgagg aggataacat    600
ggccatcatc aaggagttca tgcgcttcaa ggtgcacatg gagggctccg tgaacggcca    660
cgagttcgag atcgagggcg agggcgaggg ccgcccctac gagggcaccc agaccgccaa    720
gctgaaggtg accaagggtg gccccctgcc cttcgcctgg gacatcctgt cccctcagtt    780
catgtacggc tccaaggcct acgtgaagca ccccgccgac atccccgact acttgaagct    840
gtccttcccc gagggcttca gtgggagcg cgtgatgaac ttcgaggacg gcggcgtggt    900
gaccgtgacc caggactcct ccctgcagga cggcgagttc atctacaagg tgaagctgcg    960
cggcaccaac ttcccctccg acggccccgt aatgcagaag aagaccatgg gctgggaggc   1020
ctcctccgag cggatgtacc ccgaggacgg cgccctgaag ggcgagatca gcagaggct   1080 gaagctgaag gacggcggcc actacgacgc tgaggtcaag accacctaca aggccaagaa   1140
gcccgtgcag ctgcccggcg cctacaacgt caacatcaag ttggacatca cctcccacaa   1200
cgaggactac accatcgtgg aacagtacga acgcgccgag ggcgccact ccaccggcgg   1260 catggacgag ctgtacaagt aatccgagct cggtaccaag cttaagttta aaccgctgat   1320
cagcctcgac tgtgccttct agttgccagc catctgttgt ttgcccctcc cccgtgcctt   1380
ccttgaccct ggaaggtgcc actcccactg tcctttccta taaaatgag gaaattgcat   1440 cgcattgtct gagtaggtgt cattctattc tggggggtgg ggtggggcag gacagcaagg   1500
gggaggattg ggaagacaat agcaggcatg ctggggatgc ggtgggctct atgggggatc   1560
cactagttct agagcggccg ccaccgcggt ggagctccag cttttgttcc ctttagtgag   1620
ggttaattgc gcgcttggcg taatcatggt catagctgtt tcctgtgtga aattgttatc   1680
cgctcacaat tccacacaac atacgagccg gaagcataaa gtgtaaagcc tggggtgcct   1740
aatgagtgag ctaactcaca ttaattgcgt tgcgctcact gcccgctttc cagtcgggaa   1800
acctgtcgtg ccagctgcat taatgaatcg gccaacgcgc ggggagaggc ggtttgcgta   1860
ttgggcgctc ttccgcttcc tcgctcactg actcgctgcg ctcggtcgtt cggctgcggc   1920
gagcggtatc agctcactca aaggcggtaa tacggttatc cacagaatca ggggataacg   1980
caggaaagaa catgtgagca aaaggccagc aaaaggccag gaaccgtaaa aaggccgcgt   2040
tgctggcgtt tttccatagg ctccgccccc ctgacgagca tcacaaaaat cgacgctcaa   2100
gtcagaggtg gcgaaacccg acaggactat aaagatacca ggcgtttccc cctggaagct   2160
ccctcgtgcg ctctcctgtt ccgaccctgc cgcttaccgg atacctgtcc gcctttctcc   2220
cttcgggaag cgtggcgctt tctcatagct cacgctgtag gtatctcagt tcggtgtagg   2280
tcgttcgctc caagctgggc tgtgtgcacg aacccccgt tcagcccgac cgctgcgcct   2340
tatccggtaa ctatcgtctt gagtccaacc cggtaagaca cgacttatcg ccactggcag   2400
cagccactgg taacaggatt agcagagcga ggtatgtagg cggtgctaca gagttcttga   2460
agtggtggcc taactacggc tacactagaa ggacagtatt tggtatctgc gctctgctga   2520
```

```
agccagttac cttcggaaaa agagttggta gctcttgatc cggcaaacaa accaccgctg    2580
gtagcggtgg ttttttttgtt tgcaagcagc agattacgcg cagaaaaaaa ggatctcaag    2640
aagatccttt gatcttttct acggggtctg acgctcagtg aacgaaaac tcacgttaag    2700 ggattttggt catgagatta tcaaaaagga tcttcaccta gatcctttta aattaaaaat    2760
gaagttttaa atcaatctaa agtatatatg agtaaacttg gtctgacagt taccaatgct    2820
taatcagtga ggcacctatc tcagcgatct gtctatttcg ttcatccata gttgcctgac    2880
tccccgtcgt gtagataact acgatacggg agggcttacc atctggcccc agtgctgcaa    2940
tgataccgcg agacccacgc tcaccggctc cagatttatc agcaataaac cagccagccg    3000
gaagggccga gcgcagaagt ggtcctgcaa ctttatccgc ctccatccag tctattaatt    3060
gttgccggga agctagagta agtagttcgc cagttaatag tttgcgcaac gttgttgcca    3120
ttgctacagg catcgtggtg tcacgctcgt cgtttggtat ggcttcattc agctccggtt    3180
cccaacgatc aaggcgagtt acatgatccc ccatgttgtg caaaaaagcg gttagctcct    3240
tcggtcctcc gatcgttgtc agaagtaagt tggccgcagt gttatcactc atggttatgg    3300
cagcactgca taattctctt actgtcatgc catccgtaag atgcttttct gtgactggtg    3360
agtactcaac caagtcattc tgagaatagt gtatgcggcg accgagttgc tcttgcccgg    3420
cgtcaatacg ggataatacc gcgccacata gcagaacttt aaaagtgctc atcattggaa    3480
aacgttcttc ggggcgaaaa ctctcaagga tcttaccgct gttgagatcc agttcgatgt    3540
aacccactcg tgcacccaac tgatcttcag catcttttac tttcaccagc gtttctgggt    3600
gagcaaaaac aggaaggcaa aatgccgcaa aaaagggaat aagggcgaca cggaaatgtt    3660
gaatactcat actcttcctt tttcaatatt attgaagcat ttatcagggt tattgtctca    3720
tgagcggata catatttgaa tgtatttaga aaaataaaca aataggggtt ccgcgcacat    3780
ttccccgaaa agtgccacct aaattgtaag cgttaatatt ttgttaaaat tcgcgttaaa    3840
tttttgttaa atcagctcat tttttaacca ataggccgaa atcggcaaaa tcccttataa    3900
atcaaaagaa tagaccgaga tagggttgag tgttgttcca gtttggaaca agagtccact    3960
attaaagaac gtggactcca acgtcaaagg gcgaaaaacc gtctatcagg gcgatggccc    4020
actacgtgaa ccatcaccct aatcaagttt tttggggtcg aggtgccgta agcactaaa    4080 tcggaaccct aaagggagcc ccgatttag agcttgacgg ggaaagccgg cgaacgtggc    4140
gagaaaggaa gggaagaaag cgaaaggagc gggcgctagg gcgctggcaa gtgtagcggt    4200
cacgctgcgc gtaaccacca cacccgccgc gcttaatgcg ccgctacagg gcgcgtccca    4260
ttcgccattc aggctgcgca actgttggga agggcgatcg gtgcgggcct cttcgctatt    4320
acgccagctg gcgaaagggg gatgtgctgc aaggcgatta agttgggtaa cgccagggtt    4380
ttcccagtca cgacgttgta aaacgacggc cagtgagcgc gcgtaatacg actcactata    4440
gggcgaattg ggtaccgggc cccccctcga ggtcgacggt atcgataagc ttgatatcgt    4500
gtacaaaaaa gcaggcttta aaggaaccaa ttcagtcgac tggatccggt accaaggtcg    4560
ggcaggaaga gggcctattt cccatgattc cttcatattt gcatatacga tacaaggctg    4620
ttagagagat aattagaatt aatttgactg taaacacaaa gatattagta caaaatacgt    4680
gacgtagaaa gtaataattt cttgggtagt ttgcagtttt aaaattatgt tttaaaatgg    4740
actatcatat gcttaccgta acttgaaagt atttcgattt cttggcttta tatatcttgt    4800
ggaaaggacg aaacaccgaa gtcatgccgt ttcatgtggt ttaagagcta tgctggaaac    4860
agcatagcaa gtttaaataa ggctagtccg ttatcaactt gaaaaagtgg caccgagtcg    4920
```

```
gtgcttcatt gtgtcggcca cggaacaggc a                            4951
```

<210> SEQ ID NO 32
<211> LENGTH: 4930
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
ctaaattgta agcgttaata ttttgttaaa attcgcgtta aatttttgtt aaatcagctc    60
attttttaac caataggccg aaatcggcaa aatcccttat aaatcaaaag aatagaccga   120
gatagggttg agtgttgttc cagtttggaa caagagtcca ctattaaaga acgtggactc   180
caacgtcaaa gggcgaaaaa ccgtctatca gggcgatggc ccactacgtg aaccatcacc   240
ctaatcaagt tttttggggt cgaggtgccg taaagcacta aatcggaacc ctaaagggag   300
cccccgattt agagcttgac ggggaaagcc ggcgaacgtg gcgagaaagg aagggaagaa   360
agcgaaagga gcgggcgcta gggcgctggc aagtgtagcg gtcacgctgc gcgtaaccac   420
cacacccgcc gcgcttaatg cgccgctaca gggcgcgtcc cattcgccat tcaggctgcg   480
caactgttgg gaagggcgat cggtgcgggc ctcttcgcta ttacgccagc tggcgaaagg   540
gggatgtgct gcaaggcgat taagttgggt aacgccaggg ttttcccagt cacgacgttg   600
taaaacgacg gccagtgagc gcgcgtaata cgactcacta tagggcgaat gggtaccgg    660
gccccccctc gaggtcgacg gtatcgataa gcttgatatc gtgtacaaaa aagcaggctt   720
taaggaacc aattcagtcg actggatccg gtaccaaggt cgggcaggaa gagggcctat    780
ttcccatgat tccttcatat ttgcatatac gatacaaggc tgttagagag ataattagaa   840
ttaatttgac tgtaaacaca aagatattag tacaaaatac gtgacgtaga aagtaataat   900
ttcttgggta gtttgcagtt ttaaaattat gttttaaaat ggactatcat atgcttaccg   960
taacttgaaa gtatttcgat ttcttggctt tatatatctt gtggaaagga cgaaacaccg  1020
tttaagagct atgctggaaa cagcatagca agtttaaata aggctagtcc gttatcaact  1080
tgaaaaagtg gcaccgagtc ggtgcttcat tgtgtcggcc acggaacagg cattttttc   1140
ctgcagcccg ggaaggatct gcgatcgctc cggtgcccgt cagtgggcag agcgcacatc  1200
gcccacagtc cccgagaagt tggggggagg ggtcggcaat tgaacgggtg cctagagaag  1260
gtggcgcggg gtaaactggg aaagtgatgt cgtgtactgg ctccgccttt ttcccgaggg  1320
tgggggagaa ccgtatataa gtgcagtagt cgccgtgaac gttctttttc gcaacgggtt  1380
tgccgccaga acacagctga agcttcgagg ggctcgcatc tctccttcac gcgcccgccg  1440
ccctacctga ggccgccatc cacgccggtt gagtcgcgtt ctgccgcctc ccgcctgtgg  1500
tgcctcctga actgcgtccg ccgtctaggt aagtttaaag ctcaggtcga ccgggcct    1560
ttgtccggcg ctcccttgga gcctacctag actcagccgg ctctccacgc tttgcctgac  1620
cctgcttgct caactctacg tctttgtttc gttttctgtt ctgcgccgtt acagatccaa  1680
gctgtgaccg gcgcctacgc tagatggtga gcaaggcga ggaggataac atggccatca   1740
tcaaggagtt catgcgcttc aaggtgcaca tggagggctc cgtgaacggc cacgagttcg  1800
agatcgaggg cgaggcgag ggccgccct acgagggcac ccagaccgcc aagctgaagg    1860
tgaccaaggg tggcccctg ccctcgcct gggacatcct gtcccctcag ttcatgtacg    1920
gctccaaggc ctacgtgaag caccccgccg acatccccga ctacttgaag ctgtccttcc  1980
```

```
ccgagggctt caagtgggag cgcgtgatga acttcgagga cggcggcgtg gtgaccgtga    2040
cccaggactc ctccctgcag gacggcgagt tcatctacaa ggtgaagctg cgcggcacca    2100
acttcccctc cgacggcccc gtaatgcaga agaagaccat gggctgggag gcctcctccg    2160
agcggatgta ccccgaggac ggcgccctga agggcgagat caagcagagg ctgaagctga    2220
aggacggcgg ccactacgac gctgaggtca agaccaccta caaggccaag aagcccgtgc    2280 agctgccegg cgcctacaac gtcaacatca gttggacat cacctcccac aacgaggact    2340
acaccatcgt ggaacagtac gaacgcgccg agggccgcca ctccaccggc ggcatggacg    2400
agctgtacaa gtaatccgag ctcggtacca agcttaagtt taaaccgctg atcagcctcg    2460
actgtgcctt ctagttgcca gccatctgtt gtttgcccct cccccgtgcc ttccttgacc    2520
ctggaaggtg ccactcccac tgtcctttcc taataaaatg aggaaattgc atcgcattgt    2580
ctgagtaggt gtcattctat tctggggggt ggggtggggc aggacagcaa gggggaggat    2640
tgggaagaca atagcaggca tgctggggat gcggtgggct ctatggggga tccactagtt    2700
ctagagcggc cgccaccgcg gtggagctcc agcttttgtt ccctttagtg agggttaatt    2760
gcgcgcttgg cgtaatcatg gtcatagctg tttcctgtgt gaaattgtta tccgctcaca    2820
attccacaca acatacgagc cggaagcata aagtgtaaag cctggggtgc ctaatgagtg    2880
agctaactca cattaattgc gttgcgctca ctgcccgctt tccagtcggg aaacctgtcg    2940
tgccagctgc attaatgaat cggccaacgc gcggggagag cggtttgcg tattgggcgc    3000 tcttccgctt cctcgctcac tgactcgctg cgctcggtcg ttcggctgcg gcgagcggta    3060
tcagctcact caaaggcggt aatacggtta tccacagaat caggggataa cgcaggaaag    3120
aacatgtgag caaaaggcca gcaaaaggcc aggaaccgta aaaaggccgc gttgctggcg    3180
tttttccata ggctccgccc ccctgacgag catcacaaaa atcgacgctc aagtcagagg    3240
tggcgaaacc cgacaggact ataaagatac caggcgtttc cccctggaag ctccctcgtg    3300
cgctctcctg ttccgaccct gccgcttacc ggatacctgt ccgcctttct cccttcggga    3360
agcgtggcgc tttctcatag ctcacgctgt aggtatctca gttcggtgta ggtcgttcgc    3420
tccaagctgg gctgtgtgca cgaaccccccc gttcagcccg accgctgcgc cttatccggt    3480
aactatcgtc ttgagtccaa cccggtaaga cacgacttat cgccactggc agcagccact    3540
ggtaacagga ttagcagagc gaggtatgta ggcggtgcta cagagttctt gaagtggtgg    3600
cctaactacg gctacactag aaggacagta tttggtatct gcgctctgct gaagccagtt    3660
accttcggaa aaagagttgg tagctcttga tccggcaaac aaaccaccgc tggtagcggt    3720
ggtttttttg tttgcaagca gcagattacg cgcagaaaaa aaggatctca agaagatcct    3780
ttgatctttt ctacggggtc tgacgctcag tggaacgaaa actcacgtta agggattttg    3840
gtcatgagat tatcaaaaag gatcttcacc tagatccttt taaattaaaa atgaagtttt    3900
aaatcaatct aaagtatata tgagtaaact tggtctgaca gttaccaatg cttaatcagt    3960
gaggcaccta tctcagcgat ctgtctattt cgttcatcca tagttgcctg actccccgtc    4020
gtgtagataa ctacgatacg ggagggctta ccatctggcc ccagtgctgc aatgataccg    4080
cgagacccac gctcaccggc tccagattta tcagcaataa accagccagc cggaagggcc    4140
gagcgcagaa gtggtcctgc aactttatcc gcctccatcc agtctattaa ttgttgccgg    4200
gaagctagag taagtagttc gccagttaat agtttcgcca acgttgttgc cattgctaca    4260
ggcatcgtgg tgtcacgctc gtcgtttggt atggcttcat tcagctccgg ttcccaacga    4320
```

-continued

| | |
|---|---|
| tcaaggcgag ttacatgatc ccccatgttg tgcaaaaaag cggttagctc cttcggtcct | 4380 |
| ccgatcgttg tcagaagtaa gttggccgca gtgttatcac tcatggttat ggcagcactg | 4440 |
| cataattctc ttactgtcat gccatccgta agatgctttt ctgtgactgg tgagtactca | 4500 |
| accaagtcat tctgagaata gtgtatgcgg cgaccgagtt gctcttgccc ggcgtcaata | 4560 |
| cgggataata ccgcgccaca tagcagaact ttaaaagtgc tcatcattgg aaaacgttct | 4620 |
| tcggggcgaa aactctcaag gatcttaccg ctgttgagat ccagttcgat gtaacccact | 4680 |
| cgtgcaccca actgatcttc agcatctttt actttcacca gcgtttctgg gtgagcaaaa | 4740 |
| acaggaaggc aaaatgccgc aaaaaaggga taaggggcga cacggaaatg ttgaatactc | 4800 |
| atactcttcc ttttcaata ttattgaagc atttatcagg gttattgtct catgagcgga | 4860 |
| tacatatttg aatgtattta gaaaaataaa caaataggggg ttccgcgcac atttccccga | 4920 |
| aaagtgccac | 4930 |

<210> SEQ ID NO 33
<211> LENGTH: 4930
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

| | |
|---|---|
| tttttttcct gcagcccggg aaggatctgc gatcgctccg gtgcccgtca gtgggcagag | 60 |
| cgcacatcgc ccacagtccc cgagaagttg ggggagggg tcggcaattg aacgggtgcc | 120 |
| tagagaaggt ggcgcggggt aaactgggaa agtgatgtcg tgtactggct ccgcctttttt | 180 |
| cccgagggtg ggggagaacc gtatataagt gcagtagtcg ccgtgaacgt tcttttttcgc | 240 |
| aacgggtttg ccgccagaac acagctgaag cttcgagggg ctcgcatctc tccttcacgc | 300 |
| gcccgccgcc ctacctgagg ccgccatcca cgccggttga gtcgcgttct gccgcctccc | 360 |
| gcctgtggtg cctcctgaac tgcgtccgcc gtctaggtaa gtttaaagct caggtcgaga | 420 |
| ccgggccttt gtccggcgct cccttggagc ctacctagac tcagccggct ctccacgctt | 480 |
| tgcctgaccc tgcttgctca actctacgtc tttgtttcgt tttctgttct gcgccgttac | 540 |
| agatccaagc tgtgaccggc gcctacgcta gatggtgagc aagggcgagg aggataacat | 600 |
| ggccatcatc aaggagttca tgcgcttcaa ggtgcacatg gagggctccg tgaacggcca | 660 |
| cgagttcgag atcgagggcg agggcgaggg ccgcccctac gagggcaccc agaccgccaa | 720 |
| gctgaaggtg accaagggtg gccccctgcc cttcgcctgg gacatcctgt cccctcagtt | 780 |
| catgtacggc tccaaggcct acgtgaagca ccccgccgac atccccgact acttgaagct | 840 |
| gtccttcccc gagggcttca gtgggacgcg tgatgaac ttcgaggacg gcggcgtggt | 900 |
| gaccgtgacc caggactcct ccctgcagga cggcgagttc atctacaagg tgaagctgcg | 960 |
| cggcaccaac ttcccctccg acggcccgt aatgcagaag aagaccatgg gctgggaggc | 1020 |
| ctcctccgag cggatgtacc ccgaggacgg cgccctgaag ggcgagatca gcagaggct | 1080 |
| gaagctgaag gacggcggcc actacgacgc tgaggtcaag accacctaca aggccaagaa | 1140 |
| gcccgtgcag ctgcccggcg cctacaacgt caacatcaag ttggacatca cctcccacaa | 1200 |
| cgaggactac accatcgtgg aacagtacga acgcgccgag ggccgccact ccaccggcgg | 1260 |
| catggacgag ctgtacaagt aatccgagct cggtaccaag cttaagttta aaccgctgat | 1320 |
| cagcctcgac tgtgccttct agttgccagc catctgttgt ttgcccctcc cccgtgcctt | 1380 |

```
ccttgaccct ggaaggtgcc actcccactg tcctttccta ataaaatgag gaaattgcat    1440
cgcattgtct gagtaggtgt cattctattc tgggggtgg ggtggggcag gacagcaagg    1500
gggaggattg ggaagacaat agcaggcatg ctggggatgc ggtgggctct atggggatc    1560
cactagttct agagcggccg ccaccgcggt ggagctccag cttttgttcc ctttagtgag    1620
ggttaattgc gcgcttggcg taatcatggt catagctgtt tcctgtgtga aattgttatc    1680
cgctcacaat tccacacaac atacgagccg aagcataaa gtgtaaagcc tggggtgcct    1740
aatgagtgag ctaactcaca ttaattgcgt tgcgctcact gcccgctttc cagtcgggaa    1800
acctgtcgtg ccagctgcat taatgaatcg gccaacgcgc ggggagaggc ggtttgcgta    1860
ttgggcgctc ttccgcttcc tcgctcactg actcgctgcg ctcggtcgtt cggctgcggc    1920
gagcggtatc agctcactca aaggcggtaa tacggttatc cacagaatca ggggataacg    1980
caggaaagaa catgtgagca aaaggccagc aaaaggccag gaaccgtaaa aaggccgcgt    2040
tgctggcgtt tttccatagg ctccgccccc ctgacgagca tcacaaaaat cgacgctcaa    2100
gtcagaggtg gcgaaacccg acaggactat aaagatacca ggcgtttccc cctggaagct    2160
ccctcgtgcg ctctcctgtt ccgaccctgc cgcttaccgg atacctgtcc gcctttctcc    2220
cttcgggaag cgtggcgctt tctcatagct cacgctgtag gtatctcagt tcggtgtagg    2280
tcgttcgctc caagctgggc tgtgtgcacg aaccccccgt tcagcccgac cgctgcgcct    2340
tatccggtaa ctatcgtctt gagtccaacc cggtaagaca cgacttatcg ccactggcag    2400
cagccactgg taacaggatt agcagagcga ggtatgtagg cggtgctaca gagttcttga    2460
agtggtggcc taactacggc tacactagaa ggacagtatt tggtatctgc gctctgctga    2520
agccagttac cttcggaaaa agagttggta gctcttgatc cggcaaacaa accaccgctg    2580
gtagcggtgg ttttttttgtt tgcaagcagc agattacgcg cagaaaaaaa ggatctcaag    2640
aagatccttt gatcttttct acggggtctg acgctcagtg gaacgaaaac tcacgttaag    2700
ggattttggt catgagatta tcaaaaagga tcttcaccta gatcctttta aattaaaaat    2760
gaagttttaa atcaatctaa agtatatatg agtaaacttg gtctgacagt taccaatgct    2820
taatcagtga ggcacctatc tcagcgatct gtctatttcg ttcatccata gttgcctgac    2880
tccccgtcgt gtagataact acgatacggg agggcttacc atctggcccc agtgctgcaa    2940
tgataccgcg agacccacgc tcaccggctc cagatttatc agcaataaac cagccagccg    3000
gaagggccga gcgcagaagt ggtcctgcaa ctttatccgc ctccatccag tctattaatt    3060
gttgccggga agctagagta agtagttcgc cagttaatag tttgcgcaac gttgttgcca    3120
ttgctacagg catcgtggtg tcacgctcgt cgtttggtat ggcttcattc agctccggtt    3180
cccaacgatc aaggcgagtt acatgatccc ccatgttgtg caaaaaagcg gttagctcct    3240
tcggtcctcc gatcgttgtc agaagtaagt tggccgcagt gttatcactc atggttatgg    3300
cagcactgca taattctctt actgtcatgc catccgtaag atgcttttct gtgactggtg    3360
agtactcaac caagtcattc tgagaatagt gtatgcggcg accgagttgc tcttgcccgg    3420
cgtcaatacg ggataatacc gcgccacata gcagaacttt aaaagtgctc atcattggaa    3480
aacgttcttc ggggcgaaaa ctctcaagga tcttaccgct gttgagatcc agttcgatgt    3540
aacccactcg tgcacccaac tgatcttcag catcttttac tttcaccagc gtttctgggt    3600
gagcaaaaac aggaaggcaa aatgccgcaa aaaagggaat aagggcgaca cggaaatgtt    3660
gaatactcat actcttcctt tttcaatatt attgaagcat ttatcagggt tattgtctca    3720
tgagcggata catatttgaa tgtatttaga aaataaaca aataggggtt ccgcgcacat    3780
```

```
ttccccgaaa agtgccacct aaattgtaag cgttaatatt ttgttaaaat tcgcgttaaa     3840 ttttttgttaa atcagctcat tttttaacca ataggccgaa atcggcaaaa tcccttataa    3900
atcaaaagaa tagaccgaga tagggttgag tgttgttcca gtttggaaca agagtccact    3960
attaaagaac gtggactcca acgtcaaagg gcgaaaaacc gtctatcagg gcgatggccc    4020
actacgtgaa ccatcaccct aatcaagttt ttgggggtcg aggtgccgta aagcactaaa    4080
tcggaaccct aaagggagcc cccgatttag agcttgacgg ggaaagccgg cgaacgtggc    4140
gagaaaggaa gggaagaaag cgaaaggagc gggcgctagg gcgctggcaa gtgtagcggt    4200
cacgctgcgc gtaaccacca cccgccgc gcttaatgcg ccgctacagg gcgcgtccca     4260
ttcgccattc aggctgcgca actgttggga agggcgatcg gtgcgggcct cttcgctatt    4320
acgccagctg gcgaaagggg gatgtgctgc aaggcgatta agttgggtaa cgccagggtt    4380
ttcccagtca cgacgttgta aaacgacggc cagtgagcgc gcgtaatacg actcactata    4440
gggcgaattg ggtaccgggc ccccctcga ggtcgacggt atcgataagc ttgatatcgt      4500
gtacaaaaaa gcaggcttta aggaaccaa ttcagtcgac tggatccggt accaaggtcg      4560
ggcaggaaga gggcctattt cccatgattc cttcatattt gcatatacga tacaaggctg    4620
ttagagagat aattagaatt aatttgactg taaacacaaa gatattagta caaaatacgt    4680
gacgtagaaa gtaataattt cttgggtagt ttgcagttttt aaaattatgt tttaaaatgg   4740
actatcatat gcttaccgta acttgaaagt atttcgattt cttggcttta tatatcttgt   4800
ggaaaggacg aaacaccgtt taagagctat gctggaaaca gcatagcaag tttaaataag   4860
gctagtccgt tatcaacttg aaaaagtggc accgagtcgg tgcttcattt gcctgttccg   4920
tggccgacac                                                           4930
```

<210> SEQ ID NO 34
<211> LENGTH: 3388
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
ctaaattgta agcgttaata tttttgttaaa attcgcgtta aatttttgtt aaatcagctc     60
attttttaac caataggccg aaatcggcaa aatcccttat aaatcaaaag aatagaccga    120 gataggggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt ttttggggt cgaggtgccg taaagcacta aatcggaacc ctaaagggag      300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tgggtaccgg    660
gccccccctc gaggtcgacg gtatcgataa gcttgatatc gtgtacaaaa aagcaggctt    720
taaaggaacc aattcagtcg actggatccg gtaccaaggt cgggcaggaa gagggcctat    780
ttcccatgat tccttcatat ttgcatatac gatacaaggc tgttagagag ataattagaa    840
```

```
ttaatttgac tgtaaacaca aagatattag tacaaaatac gtgacgtaga aagtaataat    900
ttcttgggta gtttgcagtt ttaaaattat gttttaaaat ggactatcat atgcttaccg    960
taacttgaaa gtatttcgat ttcttggctt tatatatctt gtggaaagga cgaaacaccg   1020
tgataagtgg aatgccatgg tttaagagct atgctggaaa cagcatagca agtttaaata   1080
aggctagtcc gttatcaact tgaaaaagtg gcaccgagtc ggtgcttttt ttcctgcagc   1140
ccgggggatc cactagttct agagcggccg ccaccgcggt ggagctccag cttttgttcc   1200
ctttagtgag ggttaattgc gcgcttggcg taatcatggt catagctgtt tcctgtgtga   1260
aattgttatc cgctcacaat tccacacaac atacgagccg gaagcataaa gtgtaaagcc   1320
tggggtgcct aatgagtgag ctaactcaca ttaattgcgt tgcgctcact gcccgctttc   1380
cagtcgggaa acctgtcgtg ccagctgcat taatgaatcg gccaacgcgc ggggagaggc   1440
ggtttgcgta ttgggcgctc ttccgcttcc tcgctcactg actcgctgcg ctcggtcgtt   1500
cggctgcggc gagcggtatc agctcactca aaggcggtaa tacggttatc cacagaatca   1560
ggggataacg caggaaagaa catgtgagca aaaggccagc aaaaggccag gaaccgtaaa   1620
aaggccgcgt tgctggcgtt tttccatagg ctccgccccc ctgacgagca tcacaaaaat   1680
cgacgctcaa gtcagaggtg gcgaaacccg acaggactat aaagatacca ggcgtttccc   1740
cctggaagct ccctcgtgcg ctctcctgtt ccgaccctgc cgcttaccgg atacctgtcc   1800
gcctttctcc cttcgggaag cgtggcgctt tctcatagct cacgctgtag gtatctcagt   1860
tcggtgtagg tcgttcgctc caagctgggc tgtgtgcacg aacccccgt tcagcccgac   1920
cgctgcgcct tatccggtaa ctatcgtctt gagtccaacc cggtaagaca cgacttatcg   1980
ccactggcag cagccactgg taacaggatt agcagagcga ggtatgtagg cggtgctaca   2040
gagttcttga agtggtggcc taactacggc tacactagaa ggacagtatt tggtatctgc   2100
gctctgctga agccagttac cttcggaaaa agagttggta gctcttgatc cggcaaacaa   2160
accaccgctg gtagcggtgg tttttttgtt tgcaagcagc agattacgcg cagaaaaaaa   2220
ggatctcaag aagatccttt gatcttttct acggggtctg acgctcagtg gaacgaaaac   2280
tcacgttaag ggattttggt catgagatta tcaaaaagga tcttcaccta gatccttta   2340
aattaaaaat gaagttttaa atcaatctaa agtatatatg agtaaacttg gtctgacagt   2400
taccaatgct taatcagtga ggcacctatc tcagcgatct gtctatttcg ttcatccata   2460
gttgcctgac tccccgtcgt gtagataact acgatacggg agggcttacc atctggcccc   2520
agtgctgcaa tgataccgcg agacccacgc tcaccggctc cagatttatc agcaataaac   2580
cagccagccg gaagggccga gcgcagaagt ggtcctgcaa ctttatccgc ctccatccag   2640
tctattaatt gttgccggga agctagagta agtagttcgc cagttaatag tttgcgcaac   2700
gttgttgcca ttgctacagg catcgtggtg tcacgctcgt cgtttggtat ggcttcattc   2760
agctccggtt cccaacgatc aaggcgagtt acatgatccc ccatgttgtg caaaaaagcg   2820
gttagctcct tcggtcctcc gatcgttgtc agaagtaagt tggccgcagt gttatcactc   2880
atggttatgg cagcactgca taattctctt actgtcatgc catccgtaag atgcttttct   2940
gtgactggtg agtactcaac caagtcattc tgagaatagt gtatgcggcg accgagttgc   3000
tcttgcccgg cgtcaatacg ggataatacc gcgccacata gcagaacttt aaaagtgctc   3060
atcattggaa aacgttcttc ggggcgaaaa ctctcaagga tcttaccgct gttgagatcc   3120
agttcgatgt aacccactcg tgcacccaac tgatcttcag catctttta  tttcaccagc   3180
```

```
gtttctgggt gagcaaaaac aggaaggcaa aatgccgcaa aaagggaat aagggcgaca   3240 cggaaatgtt gaatactcat actcttcctt tttcaatatt attgaagcat ttatcagggt   3300
tattgtctca tgagcggata catatttgaa tgtatttaga aaaataaaca aatagggggtt   3360 ccgcgcacat ttccccgaaa agtgccac                                      3388
```

<210> SEQ ID NO 35  
<211> LENGTH: 14250  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 35

```
acaaagaagg ctggacaggc taagaagaag aaagattaca aagacgatga cgataaggga     60
tccggcgcaa caaacttctc tctgctgaaa caagccggag atgtcgaaga gaatcctgga    120
ccgaccgagt acaagcccac ggtgcgcctc gccaccccgcg acgacgtccc cagggccgta   180
cgcaccctcg ccgccgcgtt cgccgactac cccgccacgc gccacaccgt cgatccggac    240
cgccacatcg agcgggtcac cgagctgcaa gaactcttcc tcacgcgcgt cgggctcgac    300
atcggcaagg tgtgggtcgc ggacgacggc gccgcggtgg cggtctggac cacgccggag    360
agcgtcgaag cgggggcggt gttcgccgag atcggcccgc gcatggccga gttgagcggt    420
tcccggctgg ccgcgcagca acagatggaa ggcctcctgg cgccgcaccg gcccaaggag    480
cccgcgtggt tcctggccac cgtcggagtc tcgcccgacc accagggcaa gggtctgggc    540
agcgccgtcg tgctccccgg agtggaggcg gccgagcgcg ccggggtgcc cgccttcctg    600
gagacctccg cgccccgcaa cctcccccttc tacgagcggc tcggcttcac cgtcaccgcc    660
gacgtcgagg tgcccgaagg accgcgcacc tggtgcatga cccgcaagcc cggtgcctga    720
acgcgttaag tcgacaatca acctctggat tacaaaattt gtgaaagatt gactggtatt    780
cttaactatg ttgctccttt tacgctatgt ggatacgctg ctttaatgcc tttgtatcat    840
gctattgctt cccgtatggc tttcattttc tcctccttgt ataaatcctg gttgctgtct    900
ctttatgagg agttgtggcc cgttgtcagg caacgtggcg tggtgtgcac tgtgtttgct    960
gacgcaaccc ccactggttg gggcattgcc accacctgtc agctccttc cgggactttc   1020 gctttccccc tccctattgc cacggcggaa ctcatcgccg cctgccttgc ccgctgctgg   1080
acaggggctc ggctgttggg cactgacaat tccgtggtgt tgtcggggaa atcatcgtcc   1140
tttccttggc tgctcgcctg tgttgccacc tggattctgc gcgggacgtc cttctgctac   1200
gtcccttcgg ccctcaatcc agcggacctt ccttcccgcg gcctgctgcc ggctctgcgg   1260
cctcttccgc gtcttcgcct tcgccctcag acgagtcgga tctcccttgg ccgcctcc    1320 ccgcgtcgac tttaagacca atgacttaca aggcagctgt agatcttagc cacttttaa    1380 aagaaaaggg gggactggaa gggctaattc actcccaacg aagacaagat ctgctttttg   1440
cttgtactgg gtctctctgg ttagaccaga tctgagcctg ggagctctct ggctaactag   1500
ggaacccact gcttaagcct caataaagct tgccttgagt gcttcaagta gtgtgtgccc   1560
gtctgttgtg tgactctggt aactagagat ccctcagacc cttttagtca gtgtggaaaa   1620
tctctagcag ggcccgttta aacccgctga tcagcctcga ctgtgccttc tagttgccag   1680
ccatctgttg tttgccccct ccccgtgcct tccttgaccc tggaaggtgc cactcccact   1740 gtccttttcct aataaaatga ggaaattgca tcgcattgtc tgagtaggtg tcattctatt   1800
```

```
ctgggggtg   gggtggggca   ggacagcaag   ggggaggatt   gggaagacaa   tagcaggcat   1860
gctggggatg   cggtgggctc   tatggcttct   gaggcggaaa   gaaccagctg   ggctctagg    1920
gggtatcccc   acgcgccctg   tagcggcgca   ttaagcgcgg   cgggtgtggt   ggttacgcgc   1980
agcgtgaccg   ctacacttgc   cagcgcccta   gcgcccgctc   ctttcgcttt   cttcccttcc   2040
tttctcgcca   cgttcgccgg   ctttccccgt   caagctctaa   atcgggggct   ccctttaggg   2100
ttccgattta   gtgctttacg   gcacctcgac   cccaaaaaac   ttgattaggg   tgatggttca   2160
cgtagtgggc   catcgccctg   atagacggtt   tttcgccctt   tgacgttgga   gtccacgttc   2220
tttaatagtg   gactcttgtt   ccaaactgga   acaacactca   accctatctc   ggtctattct   2280
tttgatttat   aagggatttt   gccgatttcg   gcctattggt   taaaaatga   gctgatttaa    2340
caaaaattta   acgcgaatta   attctgtgga   atgtgtgtca   gttagggtgt   ggaaagtccc   2400
caggctcccc   agcaggcaga   agtatgcaaa   gcatgcatct   caattagtca   gcaaccaggt   2460
gtggaaagtc   cccaggctcc   ccagcaggca   gaagtatgca   aagcatgcat   ctcaattagt   2520
cagcaaccat   agtcccgccc   ctaactccgc   ccatcccgcc   cctaactccg   cccagttccg   2580
cccattctcc   gccccatggc   tgactaattt   ttttatta    tgcagaggcc   gaggccgcct   2640
ctgcctctga   gctattccag   aagtagtgag   gaggcttttt   tggaggccta   ggcttttgca   2700
aaaagctccc   gggagcttgt   atatccattt   tcggatctga   tcagcacgtg   ttgacaatta   2760
atcatcggca   tagtatatcg   gcatagtata   atacgacaag   gtgaggaact   aaaccatggc   2820
caagttgacc   agtgccgttc   cggtgctcac   cgcgcgcgac   gtcgccggag   cggtcgagtt   2880
ctggaccgac   cggctcgggt   tctcccggga   cttcgtggag   gacgacttcg   ccggtgtggt   2940
ccgggacgac   gtgaccctgt   tcatcagcgc   ggtccaggac   caggtggtgc   cggacaacac   3000
cctggcctgg   gtgtgggtgc   gcggcctgga   cgagctgtac   gccgagtggt   cggaggtcgt   3060
gtccacgaac   ttccgggacg   cctccgggcc   ggccatgacc   gagatcggcg   agcagccgtg   3120
ggggcgggag   ttcgccctgc   gcgacccggc   cggcaactgc   gtgcacttcg   tggccgagga   3180
gcaggactga   cacgtgctac   gagatttcga   ttccaccgcc   gccttctatg   aaaggttggg   3240
cttcggaatc   gttttccggg   acgccggctg   gatgatcctc   cagcgcgggg   atctcatgct   3300
ggagttcttc   gcccaccccca   acttgtttat   tgcagcttat   aatggttaca   aataaagcaa   3360
tagcatcaca   aatttcacaa   ataaagcatt   tttttcactg   cattctagtt   gtggtttgtc   3420
caaactcatc   aatgtatctt   atcatgtctg   tataccgtcg   acctctagct   agagcttggc   3480
gtaatcatgg   tcatagctgt   ttcctgtgtg   aaattgttat   ccgctcacaa   ttccacacaa   3540
catacgagcc   ggaagcataa   agtgtaaagc   ctggggtgcc   taatgagtga   gctaactcac   3600
attaattgcg   ttgcgctcac   tgcccgcttt   ccagtcggga   aacctgtcgt   gccagctgca   3660
ttaatgaatc   ggccaacgcg   cggggagagg   cggtttgcgt   attgggcgct   cttccgcttc   3720
ctcgctcact   gactcgctgc   gctcggtcgt   tcggctgcgg   cgagcggtat   cagctcactc   3780
aaaggcggta   atacggttat   ccacagaatc   agggataac   gcaggaaaga   acatgtgagc    3840
aaaaggccag   caaaaggcca   ggaaccgtaa   aaaggccgcg   ttgctggcgt   ttttccatag   3900
gctccgcccc   cctgacgagc   atcacaaaaa   tcgacgctca   agtcagaggt   ggcgaaaccc   3960
gacaggacta   taaagatacc   aggcgtttcc   ccctggaagc   tccctcgtgc   gctctcctgt   4020
tccgaccctg   ccgcttaccg   gatacctgtc   cgcctttctc   ccttcgggaa   gcgtggcgct   4080
ttctcatagc   tcacgctgta   ggtatctcag   ttcggtgtag   tcgttcgct   ccaagctggg    4140
ctgtgtgcac   gaaccccccg   ttcagcccga   ccgctgcgcc   ttatccggta   actatcgtct   4200
```

| | |
|---|---|
| tgagtccaac ccggtaagac acgacttatc gccactggca gcagccactg gtaacaggat | 4260 |
| tagcagagcg aggtatgtag gcggtgctac agagttcttg aagtggtggc ctaactacgg | 4320 |
| ctacactaga agaacagtat ttggtatctg cgctctgctg aagccagtta ccttcggaaa | 4380 |
| aagagttggt agctcttgat ccggcaaaca aaccaccgct ggtagcggtg gttttttgt | 4440 |
| ttgcaagcag cagattacgc gcagaaaaaa aggatctcaa gaagatcctt tgatcttttc | 4500 |
| tacgggtct gacgctcagt ggaacgaaaa ctcacgttaa gggattttgg tcatgagatt | 4560 |
| atcaaaaagg atcttcacct agatcctttt aaattaaaaa tgaagtttta atcaatcta | 4620 |
| aagtatatat gagtaaactt ggtctgacag ttaccaatgc ttaatcagtg aggcaccta | 4680 |
| ctcagcgatc tgtctatttc gttcatccat agttgcctga ctccccgtcg tgtagataac | 4740 |
| tacgatacgg gagggcttac catctggccc cagtgctgca atgataccgc gagacccacg | 4800 |
| ctcaccggct ccagatttat cagcaataaa ccagccagcc ggaagggccg agcgcagaag | 4860 |
| tggtcctgca actttatccg cctccatcca gtctattaat tgttgccggg aagctagagt | 4920 |
| aagtagttcg ccagttaata gtttgcgcaa cgttgttgcc attgctacag gcatcgtggt | 4980 |
| gtcacgctcg tcgtttggta tggcttcatt cagctccggt tcccaacgat caaggcgagt | 5040 |
| tacatgatcc cccatgttgt gcaaaaaagc ggttagctcc ttcggtcctc cgatcgttgt | 5100 |
| cagaagtaag ttggccgcag tgttatcact catggttatg gcagcactgc ataattctct | 5160 |
| tactgtcatg ccatccgtaa gatgcttttc tgtgactggt gagtactcaa ccaagtcatt | 5220 |
| ctgagaatag tgtatgcggc gaccgagttg ctcttgcccg gcgtcaatac gggataatac | 5280 |
| cgcgccacat agcagaactt taaaagtgct catcattgga aaacgttctt cggggcgaaa | 5340 |
| actctcaagg atcttaccgc tgttgagatc cagttcgatg taacccactc gtgcacccaa | 5400 |
| ctgatcttca gcatctttta ctttcaccag cgtttctggg tgagcaaaaa caggaaggca | 5460 |
| aaatgccgca aaaaagggaa taagggcgac acggaaatgt tgaatactca tactcttcct | 5520 |
| ttttcaatat tattgaagca tttatcaggg ttattgtctc atgagcggat acatatttga | 5580 |
| atgtatttag aaaaataaac aaataggggt tccgcgcaca tttccccgaa aagtgccacc | 5640 |
| tgacgtcgac ggatcgggag atctcccgat cccctatggt gcactctcag tacaatctgc | 5700 |
| tctgatgccg catagttaag ccagtatctg ctccctgctt gtgtgttgga ggtcgctgag | 5760 |
| tagtgcgcga gcaaaattta agctacaaca aggcaaggct tgaccgacaa ttgcatgaag | 5820 |
| aatctgctta gggttaggcg ttttgcgctg cttcgcgatg tacgggccag atatacgcgt | 5880 |
| tgacattgat tattgactag ttattaatag taatcaatta cggggtcatt agttcatagc | 5940 |
| ccatatatgg agttccgcgt tacataactt acggtaaatg gcccgcctgg ctgaccgccc | 6000 |
| aacgaccccc gcccattgac gtcaataatg acgtatgttc ccatagtaac gccaataggg | 6060 |
| actttccatt gacgtcaatg ggtggagtat ttacggtaaa ctgcccactt ggcagtacat | 6120 |
| caagtgtatc atatgccaag tacgcccct attgacgtca atgacggtaa atggcccgcc | 6180 |
| tggcattatg cccagtacat gaccttatgg gactttccta cttggcagta catctacgta | 6240 |
| ttagtcatcg ctattaccat ggtgatgcgg ttttggcagt acatcaatgg gcgtggatag | 6300 |
| cggtttgact cacggggatt tccaagtctc cacccattg acgtcaatgg gagtttgttt | 6360 |
| tggcaccaaa atcaacggga ctttccaaaa tgtcgtaaca actccgcccc attgacgcaa | 6420 |
| atgggcggta ggcgtgtacg gtgggaggtc tatataagca gcgcgttttg cctgtactgg | 6480 |
| gtctctctgg ttagaccaga tctgagcctg ggagctctct ggctaactag ggaacccact | 6540 |

```
gcttaagcct caataaagct tgccttgagt gcttcaagta gtgtgtgccc gtctgttgtg    6600
tgactctggt aactagagat ccctcagacc ctttttagtca gtgtggaaaa tctctagcag    6660
tggcgcccga acagggactt gaaagcgaaa gggaaaccag aggagctctc tcgacgcagg    6720
actcggcttg ctgaagcgcg cacggcaaga ggcgaggggc ggcgactggt gagtacgcca    6780
aaaattttga ctagcggagg ctagaaggag agagatgggt gcgagagcgt cagtattaag    6840
cgggggagaa ttagatcgcg atgggaaaaa attcggttaa ggccagggggg aaagaaaaaa    6900 tataaattaa aacatatagt atgggcaagc agggagctag aacgattcgc agttaatcct    6960
ggcctgttag aaacatcaga aggctgtaga caaatactgg gacagctaca accatccctt    7020
cagacaggat cagaagaact tagatcatta tataatacag tagcaacccct ctattgtgtg    7080 catcaaagga tagagataaa agacaccaag gaagctttag acaagataga ggaagagcaa    7140
aacaaaagta agaccaccgc acagcaagcg gccgctgatc ttcagacctg gaggaggaga    7200
tatgagggac aattggagaa gtgaattata taaatataaa gtagtaaaaa ttgaaccatt    7260
aggagtagca cccaccaagg caaagagaag agtggtgcag agagaaaaaa gagcagtggg    7320
aataggagct ttgttccttg ggttcttggg agcagcagga agcactatgg gcgcagcgtc    7380
aatgacgctg acggtacagg ccagacaatt attgtctggt atagtgcagc agcagaacaa    7440
tttgctgagg gctattgagg cgcaacagca tctgttgcaa ctcacagtct ggggcatcaa    7500
gcagctccag gcaagaatcc tggctgtgga agataccta aaggatcaac agctcctggg    7560
gatttggggt tgctctggaa aactcatttg caccactgct gtgccttgga atgctagttg    7620
gagtaataaa tctctggaac agatttggaa tcacacgacc tggatggagt gggacagaga    7680
aattaacaat tacacaagct taatacactc cttaattgaa gaatcgcaaa accagcaaga    7740
aaagaatgaa caagaattat tggaattaga taaatgggca agtttgtgga attggtttaa    7800
cataacaaat tggctgtggt atataaaatt attcataatg atagtaggag gcttggtagg    7860
tttaagaata gttttttgctg tactttctat agtgaataga gttaggcagg gatattcacc    7920
attatcgttt cagacccacc tcccaacccc gaggggaccc gacaggcccg aaggaataga    7980
agaagaaggt ggagagagag acagagacag atccattcga ttagtgaacg gatcggcact    8040
gcgtgcgcca attctgcaga caaatggcag tattcatcca caattttaaa agaaaagggg    8100
ggattggggg gtacagtgca ggggaaagaa tagtagacat aatagcaaca gacatacaaa    8160
ctaaagaatt acaaaaacaa attacaaaaa ttcaaaattt tcgggtttat tacagggaca    8220
gcagagatcc agtttggtta attaaggtac cgagggccta tttcccatga ttccttcata    8280
tttgcatata cgatacaagg ctgttagaga gataattaga attaatttga ctgtaaacac    8340
aaagatatta gtacaaaata cgtgacgtag aaagtaataa tttcttgggt agtttgcagt    8400
tttaaaatta tgttttaaaa tggactatca tatgcttacc gtaacttgaa agtatttcga    8460
tttcttggct ttatatatct tgtggaaagg acgaaacacc gttcataggg atccaagttt    8520
tgtttaagag ctatgctgga aacagcatag caagtttaaa taaggctagt ccgttatcaa    8580
cttgaaaaag tggcaccgag tcggtgcttc attttttcctc cactgttgca agtttttttt    8640
cctgcagccc gggaattcgc tagctaggtc ttgaaaggag tgggaattgg ctccggtgcc    8700
cgtcagtggg cagagcgcac atcgcccaca gtccccgaga agtggggggg aggggtcggc    8760
aattgatccg gtgcctagag aaggtggcgc ggggtaaact gggaaagtga tgtcgtgtac    8820
tggctccgcc ttttttcccga gggtggggga gaaccgtata aagtgcagt agtcgccgtg    8880 aacgttcttt ttcgcaacgg gtttgccgcc agaacacagg accggttcta gagcgctgcc    8940
```

```
accatgttag ctgacgctgt ctcacgcctg gtcctgggta agtttggtga cctgaccgac   9000
aacttctcct cccctcacgc tcgcagaaaa gtgctggctg gagtcgtcat gacaacaggc   9060
acagatgtta aagatgccaa ggtgataagt gtttctacag gaacaaaatg tattaatggt   9120
gaatacatga gtgatcgtgg ccttgcatta aatgactgcc atgcagaaat aatatctcgg   9180
agatccttgc tcagatttct ttatacacaa cttgagcttt acttaaataa caaagatgat   9240
caaaaaagat ccatctttca gaaatcagag cgaggggggt ttaggctgaa ggagaatgtc   9300
cagtttcatc tgtacatcag cacctctccc tgtggagatg ccagaatctt ctcaccacat   9360
gagccaatcc tggaagaacc agcagataga cacccaaatc gtaaagcaag aggacagcta   9420
cggaccaaaa tagagtctgg tcaggggacg attccagtgc gctccaatgc gagcatccaa   9480
acgtgggacg gggtgctgca aggggagcgg ctgctcacca tgtcctgcag tgacaagatt   9540
gcacgctgga acgtggtggg catccaggga tccctgctca gcattttcgt ggagcccatt   9600
tacttctcga gcatcatcct gggcagcctt taccacgggg accacctttc cagggccatg   9660
taccagcgga tctccaacat agaggacctg ccacctctct cacccctcaa caagcctttg   9720
ctcagtggca tcagcaatgc agaagcacgg cagccaggga aggcccccaa cttcagtgtc   9780
aactggacgg taggcgactc cgctattgag gtcatcaacg ccacgactgg gaaggatgag   9840
ctgggccgcg cgtcccgcct gtgtaagcac gcgttgtact gtcgctggat gcgtgtgcac   9900
ggcaaggttc cctcccactt actacgctcc aagattacca agcccaacgt gtaccatgag   9960
tccaagctgg cggcaaagga gtaccaggcc gccaaggcgc gtctgttcac agccttcatc  10020
aaggcgggc tgggggcctg ggtggagaag cccaccgagc aggaccagtt ctcactcacg  10080
cccagtggaa gtgagacacc gggaacctca gagagcgcca cgccagaaag catggacaag  10140
aagtacagca tcggcctggc catcggcacc aactctgtgg gctgggccgt gatcaccgac  10200
gagtacaagg tgcccagcaa gaaattcaag gtgctgggca acaccgaccg gcacagcatc  10260
aagaagaacc tgatcggcgc cctgctgttc gacagcggag aaacagccga ggccacccgg  10320
ctgaagagaa ccgccagaag aagatacacc agacggaaga accggatctg ctatctgcaa  10380
gagatcttca gcaacgagat ggccaaggtg gacgacagct tcttccacag actgaagag  10440
tccttcctgg tggaagagga taagaagcac gagcggcacc ccatcttcgg caacatcgtg  10500
gacgaggtgg cctaccacga gaagtacccc accatctacc acctgagaaa gaaactggtg  10560
gacagcaccg acaaggccga cctgcggctg atctatctgg ccctggccca catgatcaag  10620
ttccggggc acttcctgat cgaggcgac ctgaaccccg acaacagcga cgtggacaag  10680
ctgttcatcc agctggtgca gacctacaac cagctgttcg aggaaaaccc catcaacgcc  10740
agcggcgtgg acgccaaggc catcctgtct gccagactga gcaagagcag acggctggaa  10800
aatctgatcg cccagctgcc cggcgagaag aagaatggcc tgttcggcaa cctgattgcc  10860
ctgagcctgg gcctgacccc caacttcaag agcaacttcg acctggccga ggatgccaaa  10920
ctgcagctga gcaaggacac ctacgacgac gacctggaca acctgctggc ccagatcggc  10980
gaccagtacg ccgacctgtt tctggccgcc aagaacctgt ccgacgccat cctgctgagc  11040
gacatcctga gagtgaacac cgagatcacc aaggcccccc tgagcgcctc tatgatcaag  11100
agatacgacg agcaccacca ggacctgacc ctgctgaaag ctctcgtgcg gcagcagctg  11160
cctgagaagt acaaagagat tttcttcgac cagagcaaga acggctacgc cggctacatc  11220
gatggcggag ccagccagga agagttctac aagttcatca gcccatcct ggaaaagatg  11280
```

```
gacggcaccg aggaactgct cgtgaagctg aacagagagg acctgctgcg gaagcagcgg    11340
accttcgaca acggcagcat ccccaccag atccacctgg agagctgca cgccattctg      11400 cggcggcagg aagattttta cccattcctg aaggacaacc gggaaaagat cgagaagatc    11460
ctgaccttcc gcatccccta ctacgtgggc cctctggcca ggggaaacag cagattcgcc    11520
tggatgacca gaaagagcga ggaaaccatc accccctgga acttcgagga agtggtggac    11580
aagggcgcca gcgcccagag cttcatcgag cggatgacca acttcgataa gaacctgccc    11640
aacgagaagg tgctgcccaa gcacagcctg ctgtacgagt acttcaccgt gtacaacgag    11700
ctgaccaaag tgaaatacgt gaccgaggga atgagaaagc ccgccttcct gagcggcgag    11760
cagaaaaaag ccatcgtgga cctgctgttc aagaccaacc ggaaagtgac cgtgaagcag    11820
ctgaaagagg actacttcaa gaaaatcgag tgcttcgact ccgtggaaat ctccggcgtg    11880
gaagatcggt tcaacgcctc cctgggcaca taccacgatc tgctgaaaat tatcaaggac    11940
aaggacttcc tggacaatga ggaaaacgag gacattctgg aagatatcgt gctgaccctg    12000
acactgtttg aggacagaga gatgatcgag gaacggctga aaacctatgc ccacctgttc    12060
gacgacaaag tgatgaagca gctgaagcgg cggagataca ccggctgggg caggctgagc    12120
cggaagctga tcaacggcat ccgggacaag cagtccggca agacaatcct ggatttcctg    12180
aagtccgacg gcttcgccaa cagaaacttc atgcagctga tccacgacga cagcctgacc    12240
tttaaagagg acatccagaa agcccaggtg tccggccagg gcgatagcct gcacgagcac    12300
attgccaatc tggccggcag ccccgccatt aagaagggca tcctgcagac agtgaaggtg    12360
gtggacgagc tcgtgaaagt gatgggccgg cacaagcccg agaacatcgt gatcgaaatg    12420
gccagagaga accagaccac ccagaaggga cagaagaaca ccgcgagag aatgaagcgg    12480 atcgaagagg gcatcaaaga gctgggcagc cagatcctga aagaacaccc cgtggaaaac    12540
acccagctgc agaacgagaa gctgtacctg tactacctgc agaatgggcg ggatatgtac    12600
gtggaccagg aactggacat caaccggctg tccgactacg atgtggacgc tatcgtgcct    12660
cagagctttc tgaaggacga ctccatcgat aacaaagtgc tgactcggag cgacaagaac    12720
cggggcaaga gcgacaacgt gcccctccga aggtcgtga agaagatgaa gaactactgg    12780
cgccagctgc tgaatgccaa gctgattacc cagaggaagt tcgacaatct gaccaaggcc    12840
gagagaggcg gcctgagcga actggataag gccggcttca tcaagagaca gctggtggaa    12900
acccggcaga tcacaaagca cgtggcacag atcctggact cccggatgaa cactaagtac    12960
gacgagaacg acaaactgat ccgggaagtg aaagtgatca ccctgaagtc caagctggtg    13020
tccgatttcc ggaaggattt ccagttttac aaagtgcgcg agatcaacaa ctaccaccac    13080
gcccacgacg cctacctgaa cgccgtcgtg ggaaccgccc tgatcaaaaa gtaccctaag    13140
ctggaaagcg agttcgtgta cggcgactac aaggtgtacg acgtgcggaa gatgatcgcc    13200
aagagcgagc aggaaatcgg caaggctacc gccaagtact tcttctacag caacatcatg    13260
aactttttca gaccgagat tacctggcc aacggcgaga tccggaagcg gcctctgatc    13320
gagacaaacg gcgaaacagg cgagatcgtg tgggataagg ccgggacttt gccaccgtg    13380 cggaaagtgc tgtctatgcc ccaagtgaat atcgtgaaaa agaccgaggt gcagacaggc    13440
ggcttcagca aagagtctat cctgcccaag aggaacagcg acaagctgat cgccagaaag    13500
aaggactggg accctaagaa gtacggcggc ttcgacagcc ccaccgtggc ctattctgtg    13560
ctggtggtgg ccaaagtgga aaagggcaag tccaagaaac tgaagagtgt gaaagagctg    13620
ctggggatca ccatcatgga aagaagcagc ttcgagaaga atccccatcga ctttctggaa    13680
```

```
gccaagggct acaaagaagt gaaaaaggac ctgatcatca agctgcctaa gtactccctg   13740
ttcgagctgg aaaacggccg gaagagaatg ctggcctctg ccggcgaact gcagaaggga   13800
aacgaactgg ccctgccctc caaatatgtg aacttcctgt acctggccag ccactatgag   13860
aagctgaagg gctcccccga ggataatgag cagaaacagc tgtttgtgga acagcacaaa   13920
cactacctgg acgagatcat cgagcagatc agcgagttct ccaagagagt gatcctggcc   13980
gacgctaatc tggacaaggt gctgagcgcc tacaacaagc acagagacaa gcctatcaga   14040
gagcaggccg agaatatcat ccacctgttt accctgacca atctgggagc cctgccgcc    14100 ttcaagtact tgacaccac catcgaccgg aagaggtaca ccagcaccaa agaggtgctg     14160
gacgccaccc tgatccacca gagcatcacc ggcctgtacg agacacggat cgacctgtct   14220
cagctgggag gcgacaagcg acctgccgcc                                    14250
```

<210> SEQ ID NO 36
<211> LENGTH: 380
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

```
Met Leu Ala Asp Ala Val Ser Arg Leu Val Leu Gly Lys Phe Gly Asp
1               5                   10                  15

Leu Thr Asp Asn Phe Ser Ser Pro His Ala Arg Arg Lys Val Leu Ala
            20                  25                  30

Gly Val Val Met Thr Thr Gly Thr Asp Val Lys Asp Ala Lys Val Ile
        35                  40                  45

Ser Val Ser Thr Gly Thr Lys Cys Ile Asn Gly Glu Tyr Met Ser Asp
    50                  55                  60

Arg Gly Leu Ala Leu Asn Asp Cys His Ala Glu Ile Ile Ser Arg Arg
65                  70                  75                  80

Ser Leu Leu Arg Phe Leu Tyr Thr Gln Leu Glu Leu Tyr Leu Asn Asn
                85                  90                  95

Lys Asp Asp Gln Lys Arg Ser Ile Phe Gln Lys Ser Glu Arg Gly Gly
            100                 105                 110

Phe Arg Leu Lys Glu Asn Val Gln Phe His Leu Tyr Ile Ser Thr Ser
        115                 120                 125

Pro Cys Gly Asp Ala Arg Ile Phe Ser Pro His Glu Pro Ile Leu Glu
    130                 135                 140

Glu Pro Ala Asp Arg His Pro Asn Arg Lys Ala Arg Gly Gln Leu Arg
145                 150                 155                 160

Thr Lys Ile Glu Ser Gly Gln Gly Thr Ile Pro Val Arg Ser Asn Ala
                165                 170                 175

Ser Ile Gln Thr Trp Asp Gly Val Leu Gln Gly Glu Arg Leu Leu Thr
            180                 185                 190

Met Ser Cys Ser Asp Lys Ile Ala Arg Trp Asn Val Val Gly Ile Gln
        195                 200                 205

Gly Ser Leu Leu Ser Ile Phe Val Glu Pro Ile Tyr Phe Ser Ser Ile
    210                 215                 220

Ile Leu Gly Ser Leu Tyr His Gly Asp His Leu Ser Arg Ala Met Tyr
225                 230                 235                 240

Gln Arg Ile Ser Asn Ile Glu Asp Leu Pro Pro Leu Tyr Thr Leu Asn
                245                 250                 255
```

```
Lys Pro Leu Leu Ser Gly Ile Ser Asn Ala Glu Ala Arg Gln Pro Gly
            260                 265                 270

Lys Ala Pro Asn Phe Ser Val Asn Trp Thr Val Gly Asp Ser Ala Ile
            275                 280                 285

Glu Val Ile Asn Ala Thr Thr Gly Lys Asp Leu Gly Arg Ala Ser
290                 295                 300

Arg Leu Cys Lys His Ala Leu Tyr Cys Arg Trp Met Arg Val His Gly
305                 310                 315                 320

Lys Val Pro Ser His Leu Leu Arg Ser Lys Ile Thr Lys Pro Asn Val
            325                 330                 335

Tyr His Glu Ser Lys Leu Ala Ala Lys Glu Tyr Gln Ala Ala Lys Ala
            340                 345                 350

Arg Leu Phe Thr Ala Phe Ile Lys Ala Gly Leu Gly Ala Trp Val Glu
            355                 360                 365

Lys Pro Thr Glu Gln Asp Gln Phe Ser Leu Thr Pro
            370                 375                 380

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Gly Ser Glu Thr Pro Gly Thr Ser Glu Ser Ala Thr Pro Glu Ser
1               5                   10                  15

<210> SEQ ID NO 38
<211> LENGTH: 1368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160
```

```
Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575
```

-continued

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe

|   |   |   |   |   |   |   |   |   |   |
|---|---|---|---|---|---|---|---|---|---|
| | | 995 | | | 1000 | | | 1005 | |
| Val | Tyr | Gly | Asp | Tyr | Lys | Val | Tyr | Asp | Val | Arg | Lys | Met | Ile | Ala |
| | | 1010 | | | | 1015 | | | | 1020 | | | | |
| Lys | Ser | Glu | Gln | Glu | Ile | Gly | Lys | Ala | Thr | Ala | Lys | Tyr | Phe | Phe |
| | | 1025 | | | | 1030 | | | | 1035 | | | | |
| Tyr | Ser | Asn | Ile | Met | Asn | Phe | Phe | Lys | Thr | Glu | Ile | Thr | Leu | Ala |
| | | 1040 | | | | 1045 | | | | 1050 | | | | |
| Asn | Gly | Glu | Ile | Arg | Lys | Arg | Pro | Leu | Ile | Glu | Thr | Asn | Gly | Glu |
| | | 1055 | | | | 1060 | | | | 1065 | | | | |
| Thr | Gly | Glu | Ile | Val | Trp | Asp | Lys | Gly | Arg | Asp | Phe | Ala | Thr | Val |
| | | 1070 | | | | 1075 | | | | 1080 | | | | |
| Arg | Lys | Val | Leu | Ser | Met | Pro | Gln | Val | Asn | Ile | Val | Lys | Lys | Thr |
| | | 1085 | | | | 1090 | | | | 1095 | | | | |
| Glu | Val | Gln | Thr | Gly | Gly | Phe | Ser | Lys | Glu | Ser | Ile | Leu | Pro | Lys |
| | | 1100 | | | | 1105 | | | | 1110 | | | | |
| Arg | Asn | Ser | Asp | Lys | Leu | Ile | Ala | Arg | Lys | Lys | Asp | Trp | Asp | Pro |
| | | 1115 | | | | 1120 | | | | 1125 | | | | |
| Lys | Lys | Tyr | Gly | Gly | Phe | Asp | Ser | Pro | Thr | Val | Ala | Tyr | Ser | Val |
| | | 1130 | | | | 1135 | | | | 1140 | | | | |
| Leu | Val | Val | Ala | Lys | Val | Glu | Lys | Gly | Lys | Ser | Lys | Lys | Leu | Lys |
| | | 1145 | | | | 1150 | | | | 1155 | | | | |
| Ser | Val | Lys | Glu | Leu | Leu | Gly | Ile | Thr | Ile | Met | Glu | Arg | Ser | Ser |
| | | 1160 | | | | 1165 | | | | 1170 | | | | |
| Phe | Glu | Lys | Asn | Pro | Ile | Asp | Phe | Leu | Glu | Ala | Lys | Gly | Tyr | Lys |
| | | 1175 | | | | 1180 | | | | 1185 | | | | |
| Glu | Val | Lys | Lys | Asp | Leu | Ile | Ile | Lys | Leu | Pro | Lys | Tyr | Ser | Leu |
| | | 1190 | | | | 1195 | | | | 1200 | | | | |
| Phe | Glu | Leu | Glu | Asn | Gly | Arg | Lys | Arg | Met | Leu | Ala | Ser | Ala | Gly |
| | | 1205 | | | | 1210 | | | | 1215 | | | | |
| Glu | Leu | Gln | Lys | Gly | Asn | Glu | Leu | Ala | Leu | Pro | Ser | Lys | Tyr | Val |
| | | 1220 | | | | 1225 | | | | 1230 | | | | |
| Asn | Phe | Leu | Tyr | Leu | Ala | Ser | His | Tyr | Glu | Lys | Leu | Lys | Gly | Ser |
| | | 1235 | | | | 1240 | | | | 1245 | | | | |
| Pro | Glu | Asp | Asn | Glu | Gln | Lys | Gln | Leu | Phe | Val | Glu | Gln | His | Lys |
| | | 1250 | | | | 1255 | | | | 1260 | | | | |
| His | Tyr | Leu | Asp | Glu | Ile | Ile | Glu | Gln | Ile | Ser | Glu | Phe | Ser | Lys |
| | | 1265 | | | | 1270 | | | | 1275 | | | | |
| Arg | Val | Ile | Leu | Ala | Asp | Ala | Asn | Leu | Asp | Lys | Val | Leu | Ser | Ala |
| | | 1280 | | | | 1285 | | | | 1290 | | | | |
| Tyr | Asn | Lys | His | Arg | Asp | Lys | Pro | Ile | Arg | Glu | Gln | Ala | Glu | Asn |
| | | 1295 | | | | 1300 | | | | 1305 | | | | |
| Ile | Ile | His | Leu | Phe | Thr | Leu | Thr | Asn | Leu | Gly | Ala | Pro | Ala | Ala |
| | | 1310 | | | | 1315 | | | | 1320 | | | | |
| Phe | Lys | Tyr | Phe | Asp | Thr | Thr | Ile | Asp | Arg | Lys | Arg | Tyr | Thr | Ser |
| | | 1325 | | | | 1330 | | | | 1335 | | | | |
| Thr | Lys | Glu | Val | Leu | Asp | Ala | Thr | Leu | Ile | His | Gln | Ser | Ile | Thr |
| | | 1340 | | | | 1345 | | | | 1350 | | | | |
| Gly | Leu | Tyr | Glu | Thr | Arg | Ile | Asp | Leu | Ser | Gln | Leu | Gly | Gly | Asp |
| | | 1355 | | | | 1360 | | | | 1365 | | | | |

<210> SEQ ID NO 39
<211> LENGTH: 14230
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39

```
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt gcgctgcttc gcgatgtacg ggccagatat acgcgttgac     240
attgattatt gactagttat taatagtaat caattacggg gtcattagtt catagcccat     300
atatggagtt ccgcgttaca taacttacgg taaatggccc gcctggctga ccgcccaacg     360
acccccgccc attgacgtca ataatgacgt atgttcccat agtaacgcca atagggactt     420
tccattgacg tcaatgggtg gagtatttac ggtaaactgc ccacttggca gtacatcaag     480
tgtatcatat gccaagtacg ccccctattg acgtcaatga cggtaaatgg cccgcctggc     540
attatgccca gtacatgacc ttatgggact ttcctacttg gcagtacatc tacgtattag     600
tcatcgctat taccatggtg atgcggtttt ggcagtacat caatgggcgt ggatagcggt     660
ttgactcacg gggatttcca agtctccacc ccattgacgt caatgggagt ttgttttggc     720
accaaaatca acgggacttt ccaaaatgtc gtaacaactc cgccccattg acgcaaatgg     780
gcggtaggcg tgtacggtgg gaggtctata taagcagcgc gttttgcctg tactgggtct     840
ctctggttag accagatctg agcctgggag ctctctggct aactagggaa cccactgctt     900
aagcctcaat aaagcttgcc ttgagtgctt caagtagtgt gtgcccgtct gttgtgtgac     960
tctggtaact agagatccct cagacccttt tagtcagtgt ggaaaatctc tagcagtggc    1020
gcccgaacag ggacttgaaa gcgaaaggga accagagga gctctctcga cgcaggactc     1080
ggcttgctga agcgcgcacg gcaagaggcg aggggcggcg actggtgagt acgccaaaaa    1140
ttttgactag cggaggctag aaggagagag atgggtgcga gagcgtcagt attaagcggg    1200
ggagaattag atcgcgatgg gaaaaaattc ggttaaggcc agggggaaag aaaaaatata    1260
aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
caggatcaga agaacttaga tcattatata atacagtagc aaccctctat tgtgtgcatc    1440
aaaggataga gataaaagac accaaggaag ctttagacaa gatagaggaa gagcaaaaca    1500
aaagtaagac caccgcacag caagcggccg ctgatcttca gacctggagg aggagatatg    1560
agggacaatt ggagaagtga attatataaa tataaagtag taaaaattga accattagga    1620
gtagcaccca ccaaggcaaa gagaagagtg gtgcagagaa aaaaagagc agtgggaata    1680
ggagctttgt tccttgggtt cttgggagca gcaggaagca ctatgggcgc agcgtcaatg    1740
acgctgacgg tacaggccag acaattattg tctggtatag tgcagcagca gaacaatttg    1800
ctgagggcta ttgaggcgca acagcatctg ttgcaactca cagtctgggg catcaagcag    1860
ctccaggcaa gaatcctggc tgtggaaaga tacctaaagg atcaacagct cctggggatt    1920
tggggttgct ctggaaaact catttgcacc actgctgtgc cttggaatgc tagttggagt    1980
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
```

```
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagagacag agacagatcc attcgattag tgaacggatc ggcactgcgt    2400
gcgccaattc tgcagacaaa tggcagtatt catccacaat tttaaagaaa aaggggggat    2460 tgggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta aggtaccgag ggcctatttc ccatgattcc ttcatatttg    2640
catatacgat acaaggctgt tagagagata attagaatta atttgactgt aaacacaaag    2700
atattagtac aaaatacgtg acgtagaaag taataatttc ttgggtagtt tgcagtttta    2760
aaattatgtt ttaaaatgga ctatcatatg cttaccgtaa cttgaaagta tttcgatttc    2820
ttggctttat atatcttgtg gaaaggacga acaccgtttt aagagctatg ctggaaacag    2880
catagcaagt ttaaataagg ctagtccgtt atcaacttga aaaagtggca ccagagtcggt    2940 gcttcattac ttcggcccag agctgctcct tttttttcctg cagcccggga attcgctagc    3000
taggtcttga aaggagtggg aattggctcc ggtgcccgtc agtgggcaga gcgcacatcg    3060
cccacagtcc ccgagaagtt ggggggaggg gtcggcaatt gatccggtgc ctagagaagg    3120
tggcgcgggg taaactggga aagtgatgtc gtgtactggc tccgcctttt tcccgagggt    3180 ggggagaac cgtatataag tgcagtagtc gccgtgaacg ttcttttttcg caacgggttt    3240 gccgccagaa cacaggaccg gttctagagc gctgccacca tgttagctga cgctgtctca    3300
cgcctggtcc tgggtaagtt tggtgacctg accgacaact tctcctcccc tcacgctcgc    3360
agaaaagtgc tggctggagt cgtcatgaca acaggcacag atgttaaaga tgccaaggtg    3420
ataagtgttt ctacaggaac aaaatgtatt aatggtgaat acatgagtga tcgtggcctt    3480
gcattaaatg actgccatgc agaaataata tctcggagat ccttgctcag atttctttat    3540
acacaacttg agctttactt aaataacaaa gatgatcaaa aaagatccat ctttcagaaa    3600
tcagagcgag gggggtttag gctgaaggag aatgtccagt ttcatctgta catcagcacc    3660
tctccctgtg gagatgccag aatcttctca ccacatgagc caatcctgga agaaccagca    3720
gatagacacc caaatcgtaa agcaagagga cagctacgga ccaaaataga gtctggtcag    3780
gggacgattc cagtgcgctc caatgcgagc atccaaacgt gggacggggt gctgcaaggg    3840
gagcggctgc tcaccatgtc ctgcagtgac aagattgcac gctggaacgt ggtgggcatc    3900
cagggatccc tgctcagcat tttcgtggag cccatttact tctcgagcat catcctgggc    3960
agcctttacc acgggaccaa cctttccagg gccatgtacc agcggatctc caacatagag    4020
gacctgccac ctctctacac cctcaacaag cctttgctca gtggcatcag caatgcagaa    4080
gcacggcagc cagggaaggc cccccaacttc agtgtcaact ggacggtagg cgactccgct    4140
attgaggtca tcaacgccac gactgggaag gatgagctgg gccgcgcgtc ccgcctgtgt    4200
aagcacgcgt tgtactgtcg ctggatgcgt gtgcacggca aggttccctc ccacttacta    4260
cgctccaaga ttaccaagcc caacgtgtac catgagtcca agctggcggc aaaggagtac    4320
caggccgcca aggcgcgtct gttcacagcc ttcatcaagg cggggctggg ggcctgggtg    4380
gagaagccca ccgagcagga ccagttctca ctcacgccca gtggaagtga cacccggga    4440 acctcagaga gcgccacgcc agaaagcatg gacaagaagt acagcatcgg cctggccatc    4500
ggcaccaact ctgtgggctg gccgtgatc accgacgagt acaaggtgcc cagcaagaaa    4560
```

-continued

```
ttcaaggtgc tgggcaacac cgaccggcac agcatcaaga agaacctgat cggcgccctg    4620
ctgttcgaca gcggagaaac agccgaggcc acccggctga agagaaccgc cagaagaaga    4680
tacaccagac ggaagaaccg gatctgctat ctgcaagaga tcttcagcaa cgagatggcc    4740
aaggtggacg acagcttctt ccacagactg gaagagtcct tcctggtgga agaggataag    4800
aagcacgagc ggcaccccat cttcggcaac atcgtggacg aggtggccta ccacgagaag    4860
taccccacca tctaccacct gagaaagaaa ctggtggaca gcaccgacaa ggccgacctg    4920
cggctgatct atctggccct ggcccacatg atcaagttcc ggggccactt cctgatcgag    4980
ggcgacctga accccgacaa cagcgacgtg gacaagctgt tcatccagct ggtgcagacc    5040
tacaaccagc tgttcgagga aaaccccatc aacgccagcg gcgtggacgc caaggccatc    5100
ctgtctgcca gactgagcaa gagcagacgc ctggaaaatc tgatcgccca gctgcccggc    5160
gagaagaaga atggcctgtt cggcaacctg attgccctga gcctgggcct gaccccaac    5220
ttcaagagca cttcgacct ggccgaggat gccaaactgc agctgagcaa ggacacctac    5280
gacgacgacc tggacaacct gctggcccag atcggcgacc agtacgccga cctgtttctg    5340
gccgccaaga acctgtccga cgccatcctg ctgagcgaca tcctgagagt gaacaccgag    5400
atcaccaagg cccccctgag cgcctctatg atcaagagat acgacgagca ccaccaggac    5460
ctgaccctgc tgaaagctct cgtgcggcag cagctgcctg agaagtacaa agagatttc    5520
ttcgaccaga gcaagaacgg ctacgccggc tacatcgatg gcggagccag ccaggaagag    5580
ttctacaagt tcatcaagcc catcctggaa aagatggacg gcaccgagga actgctcgtg    5640
aagctgaaca gagaggacct gctgcggaag cagcggacct tcgacaacgg cagcatcccc    5700
caccagatcc acctgggaga gctgcacgcc attctgcggc ggcaggaaga ttttttaccca    5760
ttcctgaagg acaaccggga aaagatcgag aagatcctga ccttccgcat ccctactac    5820
gtgggccctc tggccagggg aaacagcaga ttcgcctgga tgaccagaaa gagcgaggaa    5880
accatcaccc cctggaactt cgaggaagtg gtggacaagg gcgccagcgc ccagagcttc    5940
atcgagcgga tgaccaactt cgataagaac ctgcccaacg agaaggtgct gcccaagcac    6000
agcctgctgt acgagtactt caccgtgtac aacgagctga ccaaagtgaa atacgtgacc    6060
gagggaatga gaaagcccgc cttcctgagc ggcgagcaga aaaaagccat cgtggacctg    6120
ctgttcaaga ccaaccggaa agtgaccgtg aagcagctga agaggacta cttcaagaaa    6180
atcgagtgct tcgactccgt ggaaatctcc ggcgtggaag atcggttcaa cgcctccctg    6240
ggcacatacc acgatctgct gaaaattatc aaggacaagg acttcctgga caatgaggaa    6300
aacgaggaca ttctggaaga tatcgtgctg accctgacac tgtttgagga cagagagatg    6360
atcgaggaac ggctgaaaac ctatgcccac ctgttcgacg acaaagtgat gaagcagctg    6420
aagcggcgga gatacaccgg ctggggcagg ctgagccgga agctgatcaa cggcatccgg    6480
gacaagcagt ccggcaagac aatcctggat ttcctgaagt ccgacggctt cgccaacaga    6540
aacttcatgc agctgatcca cgacgacagc ctgaccttta aagaggacat ccagaaagcc    6600
caggtgtccg gccagggcga tagcctgcac gagcacattg ccaatctggc cggcagcccc    6660
gccattaaga agggcatcct gcagacagtg aaggtggtgg acgagctcgt gaaagtgatg    6720
ggccggcaca agcccgagaa catcgtgatc gaaatggcca gagagaacca gaccacccag    6780
aagggacaga agaacagccg cgagagaatg aagcggatcg aagagggcat caaagagctg    6840
ggcagccaga tcctgaaaga acaccccgtg gaaaacaccc agctgcagaa cgagaagctg    6900
tacctgtact acctgcagaa tgggcgggat atgtacgtgg accaggaact ggacatcaac    6960
```

-continued

```
cggctgtccg actacgatgt ggacgctatc gtgcctcaga gctttctgaa ggacgactcc    7020
atcgataaca aagtgctgac tcggagcgac aagaaccggg gcaagagcga caacgtgccc    7080
tccgaagagg tcgtgaagaa gatgaagaac tactggcgcc agctgctgaa tgccaagctg    7140
attacccaga ggaagttcga caatctgacc aaggccgaga gaggcggcct gagcgaactg    7200
gataaggccg gcttcatcaa gagacagctg gtggaaaccc ggcagatcac aaagcacgtg    7260
gcacagatcc tggactcccg gatgaacact aagtacgacg agaacgacaa actgatccgg    7320
gaagtgaaag tgatcaccct gaagtccaag ctggtgtccg atttccggaa ggatttccag    7380
ttttacaaag tgcgcgagat caacaactac caccacgccc acgacgccta cctgaacgcc    7440
gtcgtgggaa ccgccctgat caaaaagtac cctaagctgg aaagcgagtt cgtgtacggc    7500
gactacaagg tgtacgacgt gcggaagatg atcgccaaga gcgagcagga aatcggcaag    7560
gctaccgcca agtacttctt ctacagcaac atcatgaact ttttcaagac cgagattacc    7620
ctggccaacg gcgagatccg gaagcggcct ctgatcgaga caaacggcga aacaggcgag    7680
atcgtgtggg ataagggccg ggactttgcc accgtgcgga aagtgctgtc tatgccccaa    7740
gtgaatatcg tgaaaaagac cgaggtgcag acaggcggct tcagcaaaga gtctatcctg    7800
cccaagagga acagcgacaa gctgatcgcc agaaagaagg actgggaccc taagaagtac    7860
ggcggcttcg acagccccac cgtggcctat tctgtgctgg tggtggccaa agtggaaaag    7920
ggcaagtcca agaaactgaa gagtgtgaaa gagctgctgg ggatcaccat catggaaaga    7980
agcagcttcg agaagaatcc catcgacttt ctggaagcca agggctacaa agaagtgaaa    8040
aaggacctga tcatcaagct gcctaagtac tccctgttcg agctggaaaa cggccggaag    8100
agaatgctgg cctctgccgg cgaactgcag aagggaaacg aactggccct gccctccaaa    8160
tatgtgaact tcctgtacct ggccagccac tatgagaagc tgaagggctc ccccgaggat    8220
aatgagcaga acagctgtgtt tgtggaacag cacaaacact acctggacga gatcatcgag    8280
cagatcagcg agttctccaa gagagtgatc ctggccgacg ctaatctgga caaggtgctg    8340
agcgcctaca acaagcacag agacaagcct atcagagagc aggccgagaa tatcatccac    8400
ctgtttaccc tgaccaatct gggagcccct gccgccttca gtactttga caccaccatc    8460
gaccggaaga ggtacaccag caccaaagag gtgctggacg ccaccctgat ccaccagagc    8520
atcaccggcc tgtacgagac acggatcgac ctgtctcagc tgggaggcga caagcgacct    8580
gccgccacaa agaaggctgg acaggctaag aagaagaaag attacaaaga cgatgacgat    8640
aagggatccg gcgcaacaaa cttctctctg ctgaaacaag ccgagatgtg cgaagagaat    8700
cctggaccga ccgagtacaa gcccacggtg cgcctcgcca cccgcgacga cgtccccagg    8760
gccgtacgca ccctcgccgc cgcgttcgcc gactaccccg ccacgcgcca caccgtcgat    8820
ccggaccgcc acatcgagcg ggtcaccgag ctgcaagaac tcttcctcac gcgcgtcggg    8880
ctcgacatcg gcaaggtgtg gtcgcggac acggcgccg cggtggcggt ctggaccacg    8940
ccggagagcg tcgaagcggg ggcggtgttc gccgagatcg gcccgcgcat ggccgagttg    9000
agcggttccc ggctggccgc gcagcaacag atggaaggcc tcctggcgcc gcaccggccc    9060
aaggagcccc gtggttcct ggccaccgtc ggagtctcgc cgaccacca gggcaagggt    9120
ctggcagcg ccgtcgtgct ccccggagtg gaggcggccg agcgcgccgg ggtgcccgcc    9180
ttcctggaga cctccgcgcc ccgcaacctc cccttctacg agcggctcgg cttcaccgtc    9240
accgccgacg tcgaggtgcc cgaaggaccg cgcacctggt gcatgacccg caagcccggt    9300
```

-continued

```
gcctgaacgc gttaagtcga caatcaacct ctggattaca aaatttgtga aagattgact    9360
ggtattctta actatgttgc tccttttacg ctatgtggat acgctgcttt aatgcctttg    9420
tatcatgcta ttgcttcccg tatggctttc attttctcct ccttgtataa atcctggttg    9480
ctgtctcttt atgaggagtt gtggcccgtt gtcaggcaac gtggcgtggt gtgcactgtg    9540
tttgctgacg caaccccac tggttggggc attgccacca cctgtcagct cctttccggg     9600
actttcgctt tccccctccc tattgccacg gcggaactca tcgccgcctg ccttgcccgc    9660
tgctggacag gggctcggct gttgggcact gacaattccg tggtgttgtc ggggaaatca    9720
tcgtcctttc cttggctgct cgcctgtgtt gccacctgga ttctgcgcgg gacgtccttc    9780
tgctacgtcc cttcggccct caatccagcg gaccttcctt cccgcggcct gctgccggct    9840
ctgcggcctc ttccgcgtct tcgccttcgc cctcagacga gtcggatctc cctttgggcc    9900
gcctccccgc gtcgacttta agaccaatga cttacaaggc agctgtagat cttagccact    9960
ttttaaaaga aaggggggga ctggaagggc taattcactc ccaacgaaga caagatctgc   10020
tttttgcttg tactgggtct ctctggttag accagatctg agcctgggag ctctctggct   10080
aactagggaa cccactgctt aagcctcaat aaagcttgcc ttgagtgctt caagtagtgt   10140
gtgcccgtct gttgtgtgac tctggtaact agagatccct cagacccttt tagtcagtgt   10200
ggaaaatctc tagcagggcc cgtttaaacc cgctgatcag cctcgactgt gccttctagt   10260
tgccagccat ctgttgtttg cccctccccc gtgccttcct tgaccctgga aggtgccact   10320
cccactgtcc tttcctaata aaatgaggaa attgcatcgc attgtctgag taggtgtcat   10380
tctattctgg ggggtggggt ggggcaggac agcaaggggg aggattggga agacaatagc   10440
aggcatgctg gggatgcggt gggctctatg gcttctgagg cggaaagaac cagctggggc   10500 tctaggggt atccccacgc gccctgtagc ggcgcattaa gcgcggcggg tgtggtggtt   10560
acgcgcagcg tgaccgctac acttgccagc gccctagcgc ccgctccttt cgctttcttc   10620
ccttcctttc tcgccacgtt cgccggcttt ccccgtcaag ctctaaatcg ggggctccct   10680
ttagggttcc gatttagtgc tttacggcac ctcgacccca aaaaacttga ttagggtgat   10740
ggttcacgta gtgggccatc gccctgatag acggtttttc gccctttgac gttggagtcc   10800
acgttcttta atagtggact cttgttccaa actggaacaa cactcaaccc tatctcggtc   10860
tattcttttg atttataagg gattttgccg atttcggcct attggttaaa aaatgagctg   10920
atttaacaaa aatttaacgc gaattaattc tgtggaatgt gtgtcagtta gggtgtggaa   10980
agtccccagg ctccccagca ggcagaagta tgcaaagcat gcatctcaat tagtcagcaa   11040
ccaggtgtgg aaagtcccca ggctccccag caggcagaag tatgcaaagc atgcatctca   11100
attagtcagc aaccatagtc ccgcccctaa ctccgcccat cccgccccta actccgccca   11160
gttccgccca ttctccgccc catggctgac taattttttt tatttatgca gaggccgagg   11220
ccgcctctgc ctctgagcta ttccagaagt agtgaggagg cttttttgga ggcctaggct   11280
tttgcaaaaa gctcccggga gcttgtatat ccatttcgg atctgatcag cacgtgttga    11340
caattaatca tcggcatagt atatcggcat agtataatac gacaaggtga ggaactaaac   11400 catgccaag ttgaccagtg ccgttccggt gctcaccgcg cgcgacgtcg ccggagcggt    11460
cgagttctgg accgaccggc tcgggttctc ccggacttc gtggaggacg acttcgccgg    11520
tgtggtccgg gacgacgtga ccctgttcat cagcgcggtc caggaccagg tggtgccgga   11580
caacaccctg gctgggtgt gggtgcgcgg cctggacgag ctgtacgccg agtggtcgga   11640
ggtcgtgtcc acgaacttcc gggacgcctc cgggccggcc atgaccgaga tcggcgagca   11700
```

```
gccgtggggg cgggagttcg ccctgcgcga cccggccggc aactgcgtgc acttcgtggc   11760
cgaggagcag gactgacacg tgctacgaga tttcgattcc accgccgcct tctatgaaag   11820
gttgggcttc ggaatcgttt tccgggacgc cggctggatg atcctccagc gcggggatct   11880
catgctggag ttcttcgccc accccaactt gtttattgca gcttataatg gttacaaata   11940
aagcaatagc atcacaaatt tcacaaataa agcatttttt tcactgcatt ctagttgtgg   12000
tttgtccaaa ctcatcaatg tatcttatca tgtctgtata ccgtcgacct ctagctagag   12060
cttggcgtaa tcatggtcat agctgtttcc tgtgtgaaat tgttatccgc tcacaattcc   12120
acacaacata cgagccggaa gcataaagtg taaagcctgg ggtgcctaat gagtgagcta   12180
actcacatta attgcgttgc gctcactgcc cgctttccag tcgggaaacc tgtcgtgcca   12240
gctgcattaa tgaatcggcc aacgcgcggg gagaggcggt ttgcgtattg ggcgctcttc   12300
cgcttcctcg ctcactgact cgctgcgctc ggtcgttcgg ctgcggcgag cggtatcagc   12360
tcactcaaag gcggtaatac ggttatccac agaatcaggg gataacgcag gaaagaacat   12420
gtgagcaaaa ggccagcaaa aggccaggaa ccgtaaaaag gccgcgttgc tggcgttttt   12480
ccataggctc cgcccccctg acgagcatca caaaaatcga cgctcaagtc agaggtggcg   12540
aaacccgaca ggactataaa gataccaggc gtttccccct ggaagctccc tcgtgcgctc   12600
tcctgttccg accctgccgc ttaccggata cctgtccgcc tttctccctt cgggaagcgt   12660
ggcgctttct catagctcac gctgtaggta tctcagttcg gtgtaggtcg ttcgctccaa   12720
gctgggctgt gtgcacgaac cccccgttca gcccgaccgc tgcgccttat ccggtaacta   12780
tcgtcttgag tccaacccgg taagacacga cttatcgcca ctggcagcag ccactggtaa   12840
caggattagc agagcgaggt atgtaggcgg tgctacagag ttcttgaagt ggtggcctaa   12900
ctacggctac actagaagaa cagtatttgg tatctgcgct ctgctgaagc cagttacctt   12960
cggaaaaaga gttggtagct cttgatccgg caaacaaacc accgctggta gcggtggttt   13020
ttttgtttgc aagcagcaga ttacgcgcag aaaaaaagga tctcaagaag atcctttgat   13080
cttttctacg gggtctgacg ctcagtggaa cgaaaactca cgttaaggga ttttggtcat   13140
gagattatca aaaaggatct tcacctagat ccttttaaat taaaaatgaa gttttaaatc   13200
aatctaaagt atatatgagt aaacttggtc tgacagttac caatgcttaa tcagtgaggc   13260
acctatctca gcgatctgtc tatttcgttc atccatagtt gcctgactcc ccgtcgtgta   13320
gataactacg atacgggagg gcttaccatc tggccccagt gctgcaatga taccgcgaga   13380
cccacgctca ccggctccag atttatcagc aataaaccag ccagccggaa gggccgagcg   13440
cagaagtggt cctgcaactt tatccgcctc catccagtct attaattgtt gccgggaagc   13500
tagagtaagt agttcgccag ttaatagttt gcgcaacgtt gttgccattg ctacaggcat   13560
cgtggtgtca cgctcgtcgt ttggtatggc ttcattcagc tccggttccc aacgatcaag   13620
gcgagttaca tgatccccca tgttgtgcaa aaaagcggtt agctccttcg gtcctccgat   13680
cgttgtcaga agtaagttgg ccgcagtgtt atcactcatg gttatggcag cactgcataa   13740
ttctcttact gtcatgccat ccgtaagatg cttttctgtg actggtgagt actcaaccaa   13800
gtcattctga gaatagtgta tgcggcgacc gagttgctct tgcccggcgt caatacggga   13860
taataccgcg ccacatagca gaactttaaa agtgctcatc attggaaaac gttcttcggg   13920
gcgaaaactc tcaaggatct taccgctgtt gagatccagt tcgatgtaac ccactcgtgc   13980
acccaactga tcttcagcat cttttacttt caccagcgtt tctgggtgag caaaaacagg   14040
```

```
aaggcaaaat gccgcaaaaa agggaataag ggcgacacgg aaatgttgaa tactcatact   14100 cttcctttt caatattatt gaagcattta tcagggttat tgtctcatga gcggatacat   14160
atttgaatgt atttagaaaa ataaacaaat aggggttccg cgcacatttc cccgaaaagt   14220
gccacctgac                                                         14230
```

<210> SEQ ID NO 40
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Met Leu Ala Asp Ala Val Ser Arg Leu Val Leu Gly Lys Phe Gly Asp
1               5                   10                  15

Leu Thr Asp Asn Phe Ser Ser Pro His Ala Arg Arg Lys Val Leu Ala
            20                  25                  30

Gly Val Val Met Thr Thr Gly Thr Asp Val Lys Asp Ala Lys Val Ile
        35                  40                  45

Ser Val Ser Thr Gly Thr Lys Cys Ile Asn Gly Glu Tyr Met Ser Asp
50                  55                  60

Arg Gly Leu Ala Leu Asn Asp Cys His Ala Glu Ile Ile Ser Arg Arg
65                  70                  75                  80

Ser Leu Leu Arg Phe Leu Tyr Thr Gln Leu Glu Leu Tyr Leu Asn Asn
                85                  90                  95

Lys Asp Asp Gln Lys Arg Ser Ile Phe Gln Lys Ser Glu Arg Gly Gly
            100                 105                 110

Phe Arg Leu Lys Glu Asn Val Gln Phe His Leu Tyr Ile Ser Thr Ser
        115                 120                 125

Pro Cys Gly Asp Ala Arg Ile Phe Ser Pro His Glu Pro Ile Leu Glu
130                 135                 140

Glu Pro Ala Asp Arg His Pro Asn Arg Lys Ala Arg Gly Gln Leu Arg
145                 150                 155                 160

Thr Lys Ile Glu Ser Gly Gln Gly Thr Ile Pro Val Arg Ser Asn Ala
                165                 170                 175

Ser Ile Gln Thr Trp Asp Gly Val Leu Gln Gly Glu Arg Leu Leu Thr
            180                 185                 190

Met Ser Cys Ser Asp Lys Ile Ala Arg Trp Asn Val Val Gly Ile Gln
        195                 200                 205

Gly Ser Leu Leu Ser Ile Phe Val Glu Pro Ile Tyr Phe Ser Ser Ile
210                 215                 220

Ile Leu Gly Ser Leu Tyr His Gly Asp His Leu Ser Arg Ala Met Tyr
225                 230                 235                 240

Gln Arg Ile Ser Asn Ile Glu Asp Leu Pro Pro Leu Tyr Thr Leu Asn
                245                 250                 255

Lys Pro Leu Leu Ser Gly Ile Ser Asn Ala Glu Ala Arg Gln Pro Gly
            260                 265                 270

Lys Ala Pro Asn Phe Ser Val Asn Trp Thr Val Gly Asp Ser Ala Ile
        275                 280                 285

Glu Val Ile Asn Ala Thr Thr Gly Lys Asp Glu Leu Gly Arg Ala Ser
290                 295                 300

Arg Leu Cys Lys His Ala Leu Tyr Cys Arg Trp Met Arg Val His Gly
305                 310                 315                 320
```

Lys Val Pro Ser His Leu Leu Arg Ser Lys Ile Thr Lys Pro Asn Val
            325                 330                 335

Tyr His Glu Ser Lys Leu Ala Ala Lys Glu Tyr Gln Ala Ala Lys Ala
            340                 345                 350

Arg Leu Phe Thr Ala Phe Ile Lys Ala Gly Leu Gly Ala Trp Val Glu
            355                 360                 365

Lys Pro Thr Glu Gln Asp Gln Phe Ser Leu Thr Pro
            370                 375                 380

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ser Gly Ser Glu Thr Pro Gly Thr Ser Glu Ser Ala Thr Pro Glu Ser
1               5                   10                  15

<210> SEQ ID NO 42
<211> LENGTH: 1368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
        210                 215                 220

```
Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
```

-continued

```
                645                 650                 655
Thr Gly Trp Gly Arg Leu Ser Arg Lys Leu Ile Asn Gly Ile Arg Asp
                    660                 665                 670
Lys Gln Ser Gly Lys Thr Ile Leu Asp Phe Leu Lys Ser Asp Gly Phe
                    675                 680                 685
Ala Asn Arg Asn Phe Met Gln Leu Ile His Asp Asp Ser Leu Thr Phe
                690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                        725                 730                 735
Ile Leu Gln Thr Val Lys Val Val Asp Glu Leu Val Lys Val Met Gly
                    740                 745                 750
Arg His Lys Pro Glu Asn Ile Val Ile Glu Met Ala Arg Glu Asn Gln
                        755                 760                 765
Thr Thr Gln Lys Gly Gln Lys Asn Ser Arg Glu Arg Met Lys Arg Ile
        770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                    805                 810                 815
Gln Asn Gly Arg Asp Met Tyr Val Asp Gln Glu Leu Asp Ile Asn Arg
                820                 825                 830
Leu Ser Asp Tyr Asp Val Asp Ala Ile Val Pro Gln Ser Phe Leu Lys
            835                 840                 845
Asp Asp Ser Ile Asp Asn Lys Val Leu Thr Arg Ser Asp Lys Asn Arg
    850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                        885                 890                 895
Phe Asp Asn Leu Thr Lys Ala Glu Arg Gly Gly Leu Ser Glu Leu Asp
                    900                 905                 910
Lys Ala Gly Phe Ile Lys Arg Gln Leu Val Glu Thr Arg Gln Ile Thr
            915                 920                 925
Lys His Val Ala Gln Ile Leu Asp Ser Arg Met Asn Thr Lys Tyr Asp
        930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                    965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala
        1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
```

-continued

Thr Gly Glu Ile Val Trp Asp Lys Gly Arg Asp Phe Ala Thr Val
    1070            1075                1080

Arg Lys Val Leu Ser Met Pro Gln Val Asn Ile Val Lys Lys Thr
    1085            1090                1095

Glu Val Gln Thr Gly Gly Phe Ser Lys Glu Ser Ile Leu Pro Lys
    1100            1105                1110

Arg Asn Ser Asp Lys Leu Ile Ala Arg Lys Lys Asp Trp Asp Pro
    1115            1120                1125

Lys Lys Tyr Gly Gly Phe Asp Ser Pro Thr Val Ala Tyr Ser Val
    1130            1135                1140

Leu Val Val Ala Lys Val Glu Lys Gly Lys Ser Lys Lys Leu Lys
    1145            1150                1155

Ser Val Lys Glu Leu Leu Gly Ile Thr Ile Met Glu Arg Ser Ser
    1160            1165                1170

Phe Glu Lys Asn Pro Ile Asp Phe Leu Glu Ala Lys Gly Tyr Lys
    1175            1180                1185

Glu Val Lys Lys Asp Leu Ile Ile Lys Leu Pro Lys Tyr Ser Leu
    1190            1195                1200

Phe Glu Leu Glu Asn Gly Arg Lys Arg Met Leu Ala Ser Ala Gly
    1205            1210                1215

Glu Leu Gln Lys Gly Asn Glu Leu Ala Leu Pro Ser Lys Tyr Val
    1220            1225                1230

Asn Phe Leu Tyr Leu Ala Ser His Tyr Glu Lys Leu Lys Gly Ser
    1235            1240                1245

Pro Glu Asp Asn Glu Gln Lys Gln Leu Phe Val Glu Gln His Lys
    1250            1255                1260

His Tyr Leu Asp Glu Ile Ile Glu Gln Ile Ser Glu Phe Ser Lys
    1265            1270                1275

Arg Val Ile Leu Ala Asp Ala Asn Leu Asp Lys Val Leu Ser Ala
    1280            1285                1290

Tyr Asn Lys His Arg Asp Lys Pro Ile Arg Glu Gln Ala Glu Asn
    1295            1300                1305

Ile Ile His Leu Phe Thr Leu Thr Asn Leu Gly Ala Pro Ala Ala
    1310            1315                1320

Phe Lys Tyr Phe Asp Thr Thr Ile Asp Arg Lys Arg Tyr Thr Ser
    1325            1330                1335

Thr Lys Glu Val Leu Asp Ala Thr Leu Ile His Gln Ser Ile Thr
    1340            1345                1350

Gly Leu Tyr Glu Thr Arg Ile Asp Leu Ser Gln Leu Gly Gly Asp
    1355            1360                1365

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gttcataggg atccaagttt t                                        21

<210> SEQ ID NO 44
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 44
tttcctccac tgttgcaaag                                                    20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ccagcgccca ccgcccccag                                                    20

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
acttcggccc agagctgctc c                                                  21

<210> SEQ ID NO 47
<211> LENGTH: 4921
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47 ttttttcct gcagcccggg aaggatctgc gatcgctccg gtgcccgtca gtgggcagag          60
cgcacatcgc ccacagtccc cgagaagttg gggggagggg tcggcaattg aacgggtgcc       120
tagagaaggt ggcgcggggt aaactgggaa agtgatgtcg tgtactggct ccgccttttt       180
cccgagggtg ggggagaacc gtatataagt gcagtagtcg ccgtgaacgt tcttttttcgc      240 aacgggtttg ccgccagaac acagctgaag cttcgagggg ctcgcatctc tccttcacgc       300
gcccgccgcc ctacctgagg ccgccatcca cgccggttga gtcgcgttct gccgcctccc       360
gcctgtggtg cctcctgaac tgcgtccgcc gtctaggtaa gtttaaagct caggtcgaga       420
ccgggccttt gtccggcgct cccttggagc ctacctagac tcagccggct ctccacgctt       480
tgcctgaccc tgcttgctca actctacgtc tttgtttcgt tttctgttct gcgccgttac       540
agatccaagc tgtgaccggc gcctacgcta gatggtgagc aagggcgagg aggataacat       600
ggccatcatc aaggagttca tgcgcttcaa ggtgcacatg gagggctccg tgaacggcca       660
cgagttcgag atcgagggcg agggcgaggg ccgcccctac gagggcaccc agaccgccaa       720
gctgaaggtg accaagggtg gccccctgcc cttcgcctgg gacatcctgt ccctcagtt        780 catgtacggc tccaaggcct acgtgaagca ccccgccgac atccccgact acttgaagct       840
gtccttcccc gagggcttca gtgggagcg cgtgatgaac ttcgaggacg gcggcgtggt        900
gaccgtgacc caggactcct ccctgcagga cggcgagttc atctacaagg tgaagctgcg       960
cggcaccaac ttcccctccg acggccccgt aatgcagaag aagaccatgg gctgggaggc      1020
```

-continued

```
ctcctccgag cggatgtacc ccgaggacgg cgccctgaag ggcgagatca agcagaggct    1080
gaagctgaag gacggcggcc actacgacgc tgaggtcaag accacctaca aggccaagaa    1140
gcccgtgcag ctgcccggcg cctacaacgt caacatcaag ttggacatca cctcccacaa    1200
cgaggactac accatcgtgg aacagtacga acgcgccgag ggcgccacct ccaccggcgg    1260
catggacgag ctgtacaagt aatccgagct cggtaccaag cttaagttta aaccgctgat    1320
cagcctcgac tgtgccttct agttgccagc catctgttgt ttgcccctcc cccgtgcctt    1380
ccttgaccct ggaaggtgcc actcccactg tcctttccta ataaaatgag gaaattgcat    1440
cgcattgtct gagtaggtgt cattctattc tggggggtgg ggtggggcag gacagcaagg    1500
gggaggattg ggaagacaat agcaggcatg ctggggatgc ggtgggctct atgggggatc    1560
cactagttct agagcggccg ccaccgcggt ggagctccag cttttgttcc ctttagtgag    1620
ggttaattgc gcgcttggcg taatcatggt catagctgtt cctgtgtga aattgttatc     1680 cgctcacaat tccacacaac atacgagccg aagcataaa gtgtaaagcc tggggtgcct    1740
aatgagtgag ctaactcaca ttaattgcgt tgcgctcact gcccgctttc cagtcggaa     1800 acctgtcgtg ccagctgcat taatgaatcg gccaacgcgc ggggagaggc ggtttgcgta    1860
ttgggcgctc ttccgcttcc tcgctcactg actcgctgcg ctcggtcgtt cggctgcggc    1920
gagcggtatc agctcactca aaggcggtaa tacggttatc cacagaatca ggggataacg    1980
caggaaagaa catgtgagca aaaggccagc aaaaggccag gaaccgtaaa aaggccgcgt    2040
tgctggcgtt tttccatagg ctccgccccc ctgacgagca tcacaaaaat cgacgctcaa    2100
gtcagaggtg gcgaaacccg acaggactat aaagatacca ggcgtttccc cctggaagct    2160
ccctcgtgcg ctctcctgtt ccgaccctgc cgcttaccgg atacctgtcc gcctttctcc    2220
cttcgggaag cgtggcgctt tctcatagct cacgctgtag gtatctcagt tcggtgtagg    2280
tcgttcgctc caagctgggc tgtgtgcacg aaccccccgt tcagcccgac cgctgcgcct    2340
tatccggtaa ctatcgtctt gagtccaacc cggtaagaca cgacttatcg ccactggcag    2400
cagccactgg taacaggatt agcagagcga ggtatgtagg cggtgctaca gagttcttga    2460
agtggtggcc taactacggc tacactagaa ggacagtatt tggtatctgc gctctgctga    2520
agccagttac cttcggaaaa agagttggta gctcttgatc cggcaaacaa accaccgctg    2580
gtagcggtgg tttttttgtt tgcaagcagc agattacgcg cagaaaaaaa ggatctcaag    2640
aagatccttt gatcttttct acggggtctg acgctcagtg gaacgaaaac tcacgttaag    2700
ggattttggt catgagatta tcaaaaagga tcttcaccta gatccttta aattaaaaat    2760 gaagttttaa atcaatctaa agtatatatg agtaaacttg gtctgacagt taccaatgct    2820
taatcagtga ggcacctatc tcagcgatct gtctatttcg ttcatccata gttgcctgac    2880
tccccgtcgt gtagataact acgatacggg agggcttacc atctggcccc agtgctgcaa    2940
tgataccgcg agacccacgc tcaccggctc cagatttatc agcaataaac cagccagccg    3000
gaagggccga gcgcagaagt ggtcctgcaa ctttatccgc ctccatccag tctattaatt    3060
gttgccggga agctagagta agtagttcgc cagttaatag tttgcgcaac gttgttgcca    3120
ttgctacagg catcgtggtg tcacgctcgt cgtttggtat ggcttcattc agctccggtt    3180
cccaacgatc aaggcgagtt acatgatccc ccatgttgtg caaaaaagcg gttagctcct    3240
tcggtcctcc gatcgttgtc agaagtaagt tggccgcagt gttatcactc atggttatgg    3300
cagcactgca taattctctt actgtcatgc catccgtaag atgcttttct gtgactggtg    3360
agtactcaac caagtcattc tgagaatagt gtatgcggcg accgagttgc tcttgcccgg    3420
```

```
cgtcaatacg ggataatacc gcgccacata gcagaacttt aaaagtgctc atcattggaa    3480
aacgttcttc ggggcgaaaa ctctcaagga tcttaccgct gttgagatcc agttcgatgt    3540
aacccactcg tgcacccaac tgatcttcag catcttttac tttcaccagc gtttctgggt    3600
gagcaaaaac aggaaggcaa aatgccgcaa aaaggggaat aagggcgaca cggaaatgtt    3660
gaatactcat actcttcctt tttcaatatt attgaagcat ttatcagggt tattgtctca    3720
tgagcggata catatttgaa tgtatttaga aaaataaaca aataggggtt ccgcgcacat    3780
ttccccgaaa agtgccacct aaattgtaag cgttaatatt tgttaaaat tcgcgttaaa     3840 tttttgttaa atcagctcat tttttaacca ataggccgaa atcggcaaaa tcccttataa    3900
atcaaaagaa tagaccgaga tagggttgag tgttgttcca gtttggaaca agagtccact    3960
attaaagaac gtggactcca acgtcaaagg gcgaaaaacc gtctatcagg gcgatggccc    4020
actacgtgaa ccatcaccct aatcaagttt ttttggggtcg aggtgccgta agcactaaa    4080 tcggaaccct aaagggagcc cccgatttag agcttgacgg ggaaagccgg cgaacgtggc    4140
gagaaaggaa gggaagaaag cgaaaggagc gggcgctagg gcgctggcaa gtgtagcggt    4200
cacgctgcgc gtaaccacca cacccgccgc gcttaatgcg ccgctacagg gcgcgtccca    4260
ttcgccattc aggctgcgca actgttggga agggcgatcg gtgcgggcct cttcgctatt    4320
acgccagctg gcgaaagggg gatgtgctgc aaggcgatta agttgggtaa cgccagggtt    4380
ttcccagtca cgacgttgta aaacgacggc cagtgagcgc gcgtaatacg actcactata    4440
gggcgaattg ggtaccgggc cccccctcga ggtcgacggt atcgataagc ttgatatcgt    4500
gtacaaaaaa gcaggcttta aggaaccaa ttcagtcgac tggatccggt accaaggtcg     4560
ggcaggaaga gggcctattt cccatgattc cttcatattt gcatatacga tacaaggctg    4620
ttagagagat aattagaatt aatttgactg taaacacaaa gatattagta caaaatacgt    4680
gacgtagaaa gtaataattt cttgggtagt ttgcagtttt aaaattatgt tttaaaatgg    4740
actatcatat gcttaccgta acttgaaagt atttcgattt cttggcttta tatatcttgt    4800
ggaaaggacg aaacaccggt tatagtactc tggaaacaga atctactata acaaggcaaa    4860
atgccgtgtt tatctcgtca acttgttggc gagattcatt gtgtcggcca cggaacaggc    4920
a                                                                    4921
```

<210> SEQ ID NO 48
<211> LENGTH: 9842
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

```
gacggatcgg gagatctccc gatccctat ggtgcactct cagtacaatc tgctctgatg       60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
```

```
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaacgg gccctctaga ctcgagcggc cgccactgtg ctggatatct gcagagaacc    960
atgttagctg acgctgtctc acgcctggtc ctgggtaagt ttggtgacct gaccgacaac   1020
ttctcctccc ctcacgctcg cagaaaagtg ctggctggag tcgtcatgac aacaggcaca   1080
gatgttaaag atgccaaggt gataagtgtt tctacaggaa caaaatgtat taatggtgaa   1140
tacatgagtg atcgtggcct tgcattaaat gactgccatg cagaaataat atctcggaga   1200
tccttgctca gatttcttta tacacaactt gagctttact taaataacaa agatgatcaa   1260
aaaagatcca tctttcagaa atcagagcga ggggggttta ggctgaagga gaatgtccag   1320
tttcatctgt acatcagcac ctctccctgt ggagatgcca gaatcttctc accacatgag   1380
ccaatcctgg aagaaccagc agatagacac ccaaatcgta aagcaagagg acagctacgg   1440
accaaaatag agtctggtca ggggacgatt ccagtgcgct ccaatgcgag catccaaacg   1500
tgggacgggg tgctgcaagg ggagcggctg ctcaccatgt cctgcagtga caagattgca   1560
cgctggaacg tggtgggcat ccagggatcc ctgctcagca ttttcgtgga gcccatttac   1620
ttctcgagca tcatcctggg cagcctttac cacgggacc accttccag gccatgtac    1680
```

```
acctacttcc ccgaggaact gcggagcgtg aagtacgcct acaacgccga cctgtacaac    2880
gccctgaacg acctgaacaa tctcgtgatc accagggacg agaacgagaa gctggaatat    2940
tacgagaagt tccagatcat cgagaacgtg ttcaagcaga agaagaagcc caccctgaag    3000
cagatcgcca agaaatcct cgtgaacgaa gaggatatta agggctacag agtgaccagc     3060
accggcaagc ccgagttcac caacctgaag gtgtaccacg acatcaagga cattaccgcc    3120
cggaaagaga ttattgagaa cgccgagctg ctggatcaga ttgccaagat cctgaccatc    3180
taccagagca gcgaggacat ccaggaagaa ctgaccaatc tgaactccga gctgacccag    3240
gaagagatcg agcagatctc taatctgaag ggctataccg gcacccacaa cctgagcctg    3300
aaggccatca acctgatcct ggacgagctg tggcacacca cgacaaccca gatcgctatc    3360
ttcaaccggc tgaagctggt gcccaagaag gtggacctgt cccagcagaa agagatcccc    3420
accaccctgg tggacgactt catcctgagc cccgtcgtga agaagcttt catccagagc     3480 atcaaagtga tcaacgccat catcaagaag tacggcctgc ccaacgacat cattatcgag    3540
ctggcccgcg agaagaactc caaggacgcc cagaaaatga tcaacgagat gcagaagcgg    3600
aaccggcaga ccaacgagcg gatcgaggaa atcatccgga ccaccggcaa agagaacgcc    3660
aagtacctga tcgagaagat caagctgcac gacatgcagg aaggcaagtg cctgtacagc    3720
ctggaagcca tccctctgga agatctgctg aacaacccct tcaactatga ggtggaccac    3780
atcatcccca agcgtgtgtc cttcgacaac agcttcaaca acaaggtgct cgtgaagcag    3840
gaagaagcca gcaagaaggg caaccggacc ccattccagt acctgagcag cagcgacagc    3900
aagatcagct acgaaacctt caagaagcac atcctgaatc tggccaaggg caagggcaga    3960
atcagcaaga ccaagaaaga gtatctgctg gaagaacggg acatcaacag gttctccgtg    4020
cagaaagact tcatcaaccg gaacctggtg gataccagat acgccaccag aggcctgatg    4080
aacctgctgc ggagctactt cagagtgaac aacctggacg tgaaagtgaa gtccatcaat    4140
ggcggcttca ccagctttct gcggcggaag tggaagttta gaaagagcg gaacaagggg    4200 tacaagcacc acgccgagga cgccctgatc attgccaacg ccgatttcat cttcaaagag    4260
tggaagaaac tggacaaggc caaaaagtg atggaaaacc agatgttcga ggaaaagcag     4320
gccgagagca tgcccgagat cgaaaccgag caggagtaca agagatcttt catcacccc     4380 caccagatca agcacattaa ggacttcaag gactacaagt acagccaccg ggtgacaag    4440 aagcctaata gagagctgat taacgacacc ctgtactcca cccggaagga cgacaagggc    4500
aacacccctg acgtgaacaa tctgaacggc ctgtacgaca aggacaatga caagctgaaa    4560
aagctgatca acaagagccc cgaaaagctg ctgatgtacc accacgaccc ccagacctac    4620
cagaaactga gctgattat ggaacagtac ggcgacgaga agaatcccct gtacaagtac    4680
tacgaggaaa ccgggaacta cctgaccaag tactccaaaa aggacaacgg ccccgtgatc    4740
aagaagatta gtattacgg caacaaactg aacgcccatc tggacatcac cgacgactac    4800
cccaacagca gaaacaaggt cgtgaagctg tccctgaagc cctacagatt cgacgtgtac    4860
ctggacaatg gcgtgtacaa gttcgtgacc gtgaagaatc tggatgtgat caaaaagaa    4920 aactactacg aagtgaatag caagtgctat gaggaagcta gaagctgaa gaagatcagc    4980 aaccaggccg agtttatcgc ctccttctac aacaacgatc tgatcaagat caacggcgag    5040
ctgtatagag tgatcggcgt gaacaacgac ctgctgaacc ggatcgaagt gaacatgatc    5100
gacatcacct accgcgagta cctggaaaac atgaacgaca gaggcccccc aggatcatt     5160 aagacaatcg cctccaagac ccagagcatt aagaagtaca gcacagacat tctgggcaac    5220
```

-continued

```
ctgtatgaag tgaaatctaa gaagcaccct cagatcatca aaaagggcgc ctatccctat   5280
gacgtgcccg attatgccag cctgggcagc ggctcccca agaaaaaacg caaggtggaa    5340
gatcctaaga aaaagcggaa agtggacgtg taaccaccac actggactag tggatccgag   5400
ctcggtacca agcttaagtt taaaccgctg atcagcctcg actgtgcctt ctagttgcca   5460
gccatctgtt gtttgcccct cccccgtgcc ttccttgacc ctggaaggtg ccactcccac   5520
tgtccttttcc taataaaatg aggaaattgc atcgcattgt ctgagtaggt gtcattctat  5580
tctgggggt ggggtggggc aggacagcaa ggggggaggat tgggaagaca atagcaggca   5640
tgctggggat gcggtgggct ctatggcttc tgaggcggaa agaaccagct ggggctctag   5700
ggggtatccc cacgcgccct gtagcggcgc attaagcgcg gcgggtgtgg tggttacgcg   5760
cagcgtgacc gctacacttg ccagcgccct agcgcccgct cctttcgctt tcttcccttc   5820
ctttctcgcc acgttcgccg gctttccccg tcaagctcta aatcggggc tccctttagg    5880
gttccgattt agtgctttac ggcacctcga ccccaaaaaa cttgattagg gtgatggttc    5940
acgtagtggg ccatcgccct gatagacggt ttttcgccct tgacgttgg agtccacgtt    6000
ctttaatagt ggactcttgt tccaaactgg aacaacactc aaccctatct cggtctattc    6060
ttttgattta aagggatttt gccgatttc ggcctattgg ttaaaaaatg agctgattta     6120
acaaaaattt aacgcgaatt aattctgtgg aatgtgtgtc agttagggtg tggaaagtcc    6180
ccaggctccc cagcaggcag aagtatgcaa agcatgcatc tcaattagtc agcaaccagg    6240
tgtggaaagt ccccaggctc cccagcaggc agaagtatgc aaagcatgca tctcaattag    6300
tcagcaacca tagtcccgcc cctaactccg cccatcccgc ccctaactcc gcccagttcc    6360
gcccattctc cgccccatgg ctgactaatt tttttatt tatgcagagg cgaggccgcc      6420
tctgcctctg agctattcca gaagtagtga ggaggcttt tggaggcct aggcttttgc     6480
aaaaagctcc cgggagcttg tatatccatt ttcggatctg atcaagagac aggatgagga   6540
tcgtttcgca tgattgaaca agatggattg cacgcaggtt ctccggccgc ttgggtggag   6600
aggctattcg ctatgactg ggcacaacag acaatcggct gctctgatgc cgccgtgttc    6660
cggctgtcag cgcaggggcg cccggttctt tttgtcaaga ccgacctgtc cggtgccctg   6720
aatgaactgc aggacgaggc agcgcggcta tcgtggctgg ccacgacggg cgttccttgc   6780
gcagctgtgc tcgacgttgt cactgaagcg ggaagggact ggctgctatt gggcgaagtg   6840
ccggggcagg atctcctgtc atctcaccgt gctcctgccg agaaagtatc catcatggct   6900
gatgcaatgc ggcggctgca tacgcttgat ccggctacct gcccattcga ccaccaagcg   6960
aaacatcgca tcgagcgagc acgtactcgg atggaagccg gtcttgtcga tcaggatgat   7020
ctggacgaag agcatcaggg gctcgcgcca gccgaactgt tcgccaggct caaggcgcgc   7080
atgcccgacg gcgaggatct cgtcgtgacc catggcgatg cctgcttgcc gaatatcatg   7140
gtggaaaatg gccgcttttc tggattcatc gactgtggcc ggctgggtgt ggcggaccgc   7200
tatcaggaca tagcgttggc tacccgtgat attgctgaag agcttggcgg cgaatgggct   7260
gaccgcttcc tcgtgcttta cggtatcgcc gctcccgatt cgcagcgcat cgccttctat   7320
cgccttcttg acgagttctt ctgagcggga ctctggggtt cgaaatgacc gaccaagcga   7380
cgcccaacct gccatcacga gatttcgatt ccaccgccgc cttctatgaa aggttgggct   7440
tcggaatcgt tttccgggac gccggctgga tgatcctcca gcgcgggat ctcatgctgg    7500
agttcttcgc ccacccccaac ttgtttattg cagcttataa tggttacaaa taaagcaata   7560
```

-continued

| | |
|---|---|
| gcatcacaaa tttcacaaat aaagcatttt tttcactgca ttctagttgt ggtttgtcca | 7620 |
| aactcatcaa tgtatcttat catgtctgta taccgtcgac tctagctag agcttggcgt | 7680 |
| aatcatggtc atagctgttt cctgtgtgaa attgttatcc gctcacaatt ccacacaaca | 7740 |
| tacgagccgg aagcataaag tgtaaagcct ggggtgccta atgagtgagc taactcacat | 7800 |
| taattgcgtt gcgctcactg cccgctttcc agtcgggaaa cctgtcgtgc cagctgcatt | 7860 |
| aatgaatcgg ccaacgcgcg gggagaggcg gtttgcgtat tgggcgctct tccgcttcct | 7920 |
| cgctcactga ctcgctgcgc tcggtcgttc ggctgcggcg agcggtatca gctcactcaa | 7980 |
| aggcggtaat acggttatcc acagaatcag gggataacgc aggaaagaac atgtgagcaa | 8040 |
| aaggccagca aaaggccagg aaccgtaaaa aggccgcgtt gctggcgttt ttccataggc | 8100 |
| tccgcccccc tgacgagcat cacaaaaatc gacgctcaag tcagaggtgg cgaaacccga | 8160 |
| caggactata aagataccag gcgtttcccc ctggaagctc cctcgtgcgc tctcctgttc | 8220 |
| cgaccctgcc gcttaccgga tacctgtccg cctttctccc ttcgggaagc gtggcgcttt | 8280 |
| ctcatagctc acgctgtagg tatctcagtt cggtgtaggt cgttcgctcc aagctgggct | 8340 |
| gtgtgcacga accccccgtt cagcccgacc gctgcgcctt atccggtaac tatcgtcttg | 8400 |
| agtccaaccc ggtaagacac gacttatcgc cactggcagc agccactggt aacaggatta | 8460 |
| gcagagcgag gtatgtaggc ggtgctacag agttcttgaa gtggtggcct aactacggct | 8520 |
| acactagaag aacagtattt ggtatctgcg ctctgctgaa gccagttacc ttcggaaaaa | 8580 |
| gagttggtag ctcttgatcc ggcaaacaaa ccaccgctgg tagcggtttt tttgtttgca | 8640 |
| agcagcagat tacgcgcaga aaaaaaggat ctcaagaaga tcctttgatc ttttctacgg | 8700 |
| ggtctgacgc tcagtggaac gaaaactcac gttaagggat tttggtcatg agattatcaa | 8760 |
| aaaggatctt cacctagatc cttttaaatt aaaaatgaag ttttaaatca atctaaagta | 8820 |
| tatatgagta aacttggtct gacagttacc aatgcttaat cagtgaggca cctatctcag | 8880 |
| cgatctgtct atttcgttca tccatagttg cctgactccc cgtcgtgtag ataactacga | 8940 |
| tacgggaggg cttaccatct ggccccagtg ctgcaatgat accgcgagac ccacgctcac | 9000 |
| cggctccaga tttatcagca ataaaccagc cagccggaag ggccgagcgc agaagtggtc | 9060 |
| ctgcaacttt atccgcctcc atccagtcta ttaattgttg ccgggaagct agagtaagta | 9120 |
| gttcgccagt taatagtttg cgcaacgttg ttgccattgc tacaggcatc gtggtgtcac | 9180 |
| gctcgtcgtt tggtatggct tcattcagct ccggttccca acgatcaagg cgagttacat | 9240 |
| gatccccat gttgtgcaaa aaagcggtta gctccttcgg tcctccgatc gttgtcagaa | 9300 |
| gtaagttggc cgcagtgtta tcactcatgg ttatggcagc actgcataat tctcttactg | 9360 |
| tcatgccatc cgtaagatgc ttttctgtga ctggtgagta ctcaaccaag tcattctgag | 9420 |
| aatagtgtat gcggcgaccg agttgctctt gcccggcgtc aatacgggat aataccgcgc | 9480 |
| cacatagcag aactttaaaa gtgctcatca ttggaaaacg ttcttcgggg cgaaaactct | 9540 |
| caaggatctt accgctgttg agatccagtt cgatgtaacc cactcgtgca cccaactgat | 9600 |
| cttcagcatc ttttactttc accagcgttt ctgggtgagc aaaaacagga aggcaaaatg | 9660 |
| ccgcaaaaaa gggaataagg gcgacacgga aatgttgaat actcatactc ttcctttttc | 9720 |
| aatattattg aagcatttat cagggttatt gtctcatgag cggatacata tttgaatgta | 9780 |
| tttagaaaaa taaacaaata ggggttccgc gcacatttcc ccgaaaagtg ccacctgacg | 9840 |
| tc | 9842 |

```
<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Ser Gly Ser
1

<210> SEQ ID NO 50
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Leu Ala Asp Ala Val Ser Arg Leu Val Leu Gly Lys Phe Gly Asp
1               5                   10                  15

Leu Thr Asp Asn Phe Ser Ser Pro His Ala Arg Arg Lys Val Leu Ala
            20                  25                  30

Gly Val Val Met Thr Thr Gly Thr Asp Val Lys Asp Ala Lys Val Ile
        35                  40                  45

Ser Val Ser Thr Gly Thr Lys Cys Ile Asn Gly Glu Tyr Met Ser Asp
    50                  55                  60

Arg Gly Leu Ala Leu Asn Asp Cys His Ala Glu Ile Ile Ser Arg Arg
65                  70                  75                  80

Ser Leu Leu Arg Phe Leu Tyr Thr Gln Leu Glu Leu Tyr Leu Asn Asn
                85                  90                  95

Lys Asp Asp Gln Lys Arg Ser Ile Phe Gln Lys Ser Glu Arg Gly Gly
            100                 105                 110

Phe Arg Leu Lys Glu Asn Val Gln Phe His Leu Tyr Ile Ser Thr Ser
        115                 120                 125

Pro Cys Gly Asp Ala Arg Ile Phe Ser Pro His Glu Pro Ile Leu Glu
    130                 135                 140

Glu Pro Ala Asp Arg His Pro Asn Arg Lys Ala Arg Gly Gln Leu Arg
145                 150                 155                 160

Thr Lys Ile Glu Ser Gly Glu Gly Thr Ile Pro Val Arg Ser Asn Ala
                165                 170                 175

Ser Ile Gln Thr Trp Asp Gly Val Leu Gln Gly Glu Arg Leu Leu Thr
            180                 185                 190

Met Ser Cys Ser Asp Lys Ile Ala Arg Trp Asn Val Val Gly Ile Gln
        195                 200                 205

Gly Ser Leu Leu Ser Ile Phe Val Glu Pro Ile Tyr Phe Ser Ser Ile
    210                 215                 220

Ile Leu Gly Ser Leu Tyr His Gly Asp His Leu Ser Arg Ala Met Tyr
225                 230                 235                 240

Gln Arg Ile Ser Asn Ile Glu Asp Leu Pro Pro Leu Tyr Thr Leu Asn
                245                 250                 255

Lys Pro Leu Leu Ser Gly Ile Ser Asn Ala Glu Ala Arg Gln Pro Gly
            260                 265                 270

Lys Ala Pro Asn Phe Ser Val Asn Trp Thr Val Gly Asp Ser Ala Ile
        275                 280                 285

Glu Val Ile Asn Ala Thr Thr Gly Lys Asp Glu Leu Gly Arg Ala Ser
```

-continued

```
                290                 295                 300
Arg Leu Cys Lys His Ala Leu Tyr Cys Arg Trp Met Arg Val His Gly
305                 310                 315                 320

Lys Val Pro Ser His Leu Leu Arg Ser Lys Ile Thr Lys Pro Asn Val
                325                 330                 335

Tyr His Glu Ser Lys Leu Ala Ala Lys Glu Tyr Gln Ala Ala Lys Ala
                340                 345                 350

Arg Leu Phe Thr Ala Phe Ile Lys Ala Gly Leu Gly Ala Trp Val Glu
            355                 360                 365

Lys Pro Thr Glu Gln Asp Gln Phe Ser Leu Thr Pro
    370                 375                 380

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Tyr Pro Tyr Asp Val Pro Asp Tyr Ala
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Lys Lys Lys Arg Lys Val
1               5

<210> SEQ ID NO 53
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
                20                  25                  30

Asp Ala Ala Val Phe Arg Leu Ser Ala Gln Gly Arg Pro Val Leu Phe
            35                  40                  45

Val Lys Thr Asp Leu Ser Gly Ala Leu Asn Glu Leu Gln Asp Glu Ala
        50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125
```

```
Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260

<210> SEQ ID NO 54
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
                35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
```

```
            210                 215                 220
Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
                260                 265                 270

Arg Gln Ile Ala Glu Ile Gly Ala Ser Leu Ile Lys His Trp
            275                 280                 285

<210> SEQ ID NO 55
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
        50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235
```

DIRECTED EDITING OF CELLULAR RNA VIA NUCLEAR DELIVERY OF CRISPR/CAS9

CROSS-REFERENCE TO RELATED APPLICATION

This application claims priority under 35 U.S.C. § 119(e) to U.S. Provisional Application No. 62/504,497 filed May 10, 2017, the content of which is incorporated herein by reference in its entirety.

STATEMENT OF GOVERNMENT SUPPORT

This invention was made with government support under Grant Nos. HG004659 and NS075449 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 23, 2018, is named 114198-0221_SL.TXT and is 432,171 bytes in size.

BACKGROUND

Present strategies aimed to target and manipulate RNA in living cells mainly rely on the use of antisense oligonucleotides (ASO) or engineered RNA binding proteins (RBP). Although ASO therapies have shown great promise in eliminating pathogenic transcripts or modulating RBP binding, they are synthetic in construction and thus cannot be encoded within DNA. This complicates potential gene therapy strategies, which would rely on regular administration of ASOs throughout the lifetime of the patient. Furthermore, they are incapable of modulating the genetic sequence of RNA. Although RBPs such as the Pumilio and FBF homology family (PUF) of proteins can be designed to recognize target transcripts and fuse to RNA modifying effectors to allow for specific recognition and manipulation, platforms based on these types of constructs require extensive protein engineering for each target and may prove to be difficult and costly.

Current systems used to directly edit RNA rely either on non encodable components, such as chemical fusion of guide RNAs to an editase moiety (e.g., SNAP tag), or relatively low affinity tethering by fusion of encodable aptamer binding moieties (e.g., BoxB protein).

Current CRISPR/Cas RNA targeting systems typically use a single guide RNA and optionally an oligonucleotide of alternating 2' OMe RNA and DNA bases (PAMmer) to provide a simple and rapidly programmable system for targeting of specific RNA molecules in live cells. However, improvements and/or alternatives to these systems can help address issues relating to efficiency, specificity and/or off-target editing events. The present disclosure addresses these needs and provides related advantages.

SUMMARY OF THE DISCLOSURE

Accordingly, provided herein are fully encodable and highly specific CRISPR/Cas systems, compositions, and methods to achieve efficient and reversible manipulation and modulation of target RNA with simplicity, reliability and versatility.

In some aspects, provided herein are recombinant expression systems for CRISPR/Cas-directed RNA editing of a target RNA comprising, consisting of, or consisting essentially of: (A) a nucleic acid sequence encoding a CRISPR/Cas RNA editing fusion protein comprising a nuclease-dead CRISPR associated endonuclease (dCas) fused to a catalytically active deaminase domain of Adenosine Deaminase acting on RNA (ADAR); and (B) a nucleic acid sequence encoding an extended single guide RNA (esgRNA) comprising: (i) a short extension sequence of homology to the target RNA comprising a mismatch for a target adenosine, and (ii) a dCas scaffold binding sequence. In some embodiments, said expression system expresses a dCas-ADAR nucleoprotein complex capable of CRISPR/Cas RNA-RNA base-specific Adenosine to Inosine (A-I) editing of the target sequence.

In some embodiments of the recombinant expression systems, the esgRNA further comprises (iii) a spacer sequence comprising a region of homology to the target RNA.

In some embodiments of the recombinant expression systems, (A) and (B) are comprised within the same vector or comprised within different vectors. In some embodiments of the recombinant expression systems, the vector is a viral vector. In some embodiments of the recombinant expression systems, the viral vector is an adeno-associated viral vector (AAV), lentiviral vector, or an adenoviral vector.

In some embodiments of the recombinant expression systems, the ADAR is selected from the group consisting of ADAR1, ADAR2, and ADAR3. In some embodiments, the catalytically active deaminase domain of ADAR is the catalytically active deaminase domain of ADAR2. In some embodiments of the recombinant expression systems, the catalytically active deaminase domain of ADAR2 is (1) a wildtype catalytically active deaminase domain of human ADAR2 or (2) a mutant human catalytically active deaminase domain of ADAR2 with increased catalytic activity compared to the wildtype human ADAR2. In some embodiments of the recombinant expression systems, the mutant human catalytically active deaminase domain of ADAR2 comprises a E488Q mutation.

In some embodiments of the recombinant expression systems, the dCas is nuclease-dead Cas9 (dCas9). In some embodiments of the recombinant expression systems, the dCas9 N-terminal domain is fused to the C-terminus of the catalytically active deaminase domain of ADAR. In some embodiments of the recombinant expression systems, the dCas is fused to the catalytically active deaminase domain of ADAR via a linker. In some embodiments of the recombinant expression systems, the linker is a semi-flexible XTEN peptide linker. In some embodiments, the linker is a GSGS linker (SEQ ID NO: 49).

In some embodiments of the recombinant expression systems, the short extension sequence of the esgRNA is a 3' extension sequence. In some embodiments of the recombinant expression systems, the short extension sequence of the esgRNA comprises a region of homology capable of near-perfect RNA-RNA base pairing with the target sequence. In some embodiments of the recombinant expression systems, the short extension sequence of the esgRNA further comprises a second mismatch for an adenosine within the target RNA. In some embodiments of the recombinant expression systems, the short extension sequence of the esgRNA further comprises a third mismatch for an adenosine within the target RNA and optionally a fourth mismatch for an adenosine within the target RNA. In some embodiments of the recombinant expression systems, the short extension sequence of the esgRNA is about 15 nucleotides to about 60 nucleotides in length.

In some embodiments of the recombinant expression systems, the esgRNA further comprises a marker sequence.

In some embodiments of the recombinant expression systems, the esgRNA further comprises a RNA polymerase III promoter sequence. In some embodiments of the recombinant expression systems, the RNA polymerase III promoter sequence is a U6 promoter sequence.

In some embodiments of the recombinant expression systems, the esgRNA comprises a linker sequence between the spacer sequence and the scaffold sequence.

In some embodiments of the recombinant expression systems, the sequences of the esgRNA (i), (ii), and (iii) are situated 3' to 5' in the esgRNA.

In some embodiments of the recombinant expression systems, the expression system further comprises a nucleic acid encoding a PAM sequence.

In some aspects, provided herein are vectors comprising, consisting of, or consisting essentially of a nucleic acid encoding an extended single guide RNA (esgRNA) comprising (i) a short extension sequence of homology to a target RNA comprising a mismatch for a target adenosine, (ii) a dCas scaffold binding sequence, and (iii) a sequence complementary to the target sequence (spacer sequence), wherein (i), (ii) and (iii) are situated 3' to 5' in the esgRNA.

In some embodiments of the vectors, the vector is a viral vector. In some embodiments of the vectors, the viral vector is an adeno-associated viral vector (AAV), lentiviral vector, or an adenoviral vector. In some embodiments of the vectors, the vectors further comprise an expression control element.

In some aspects, provided herein are viral particles comprising a vector comprising, consisting of, or consisting essentially of a nucleic acid encoding an extended single guide RNA (esgRNA) comprising (i) a short extension sequence of homology to a target RNA comprising a mismatch for a target adenosine, (ii) a dCas scaffold binding sequence, and (iii) a sequence complementary to the target sequence (spacer sequence), wherein (i), (ii) and (iii) are situated 3' to 5' in the esgRNA. In some embodiments, provided herein are viral particles comprising one or more vectors comprising (A) a nucleic acid sequence encoding a CRISPR/Cas RNA editing fusion protein comprising a nuclease-dead CRISPR associated endonuclease (dCas) fused to a catalytically active deaminase domain of Adenosine Deaminase acting on RNA (ADAR); and (B) a nucleic acid sequence encoding an extended single guide RNA (esgRNA) comprising: (i) a short extension sequence of homology to the target RNA comprising a mismatch for a target adenosine, and (ii) a dCas scaffold binding sequence.

In some aspects, provided herein are cells comprising recombinant expression systems, viral particles, and/or vectors comprising, consisting of, or consisting essentially of a nucleic acid encoding an extended single guide RNA (esgRNA) comprising (i) a short extension sequence of homology to a target RNA comprising a mismatch for a target adenosine, (ii) a dCas scaffold binding sequence, and (iii) a sequence complementary to the target sequence (spacer sequence), wherein (i), (ii) and (iii) are situated 3' to 5' in the esgRNA. In some embodiments, provided herein are cells comprising one or more viral particles, recombinant expression systems, and/or vectors comprising (A) a nucleic acid sequence encoding a CRISPR/Cas RNA editing fusion protein comprising a nuclease-dead CRISPR associated endonuclease (dCas) fused to a catalytically active deaminase domain of Adenosine Deaminase acting on RNA (ADAR); and (B) a nucleic acid sequence encoding an extended single guide RNA (esgRNA) comprising: (i) a short extension sequence of homology to the target RNA comprising a mismatch for a target adenosine, and (ii) a dCas scaffold binding sequence.

Also provided herein are methods of selective RNA editing comprising, consisting of, or consisting essentially of administering any one of the recombinant expression systems, viral particles, and/or vectors comprising, consisting of, or consisting essentially of a nucleic acid encoding an extended single guide RNA (esgRNA) comprising (i) a short extension sequence of homology to a target RNA comprising a mismatch for a target adenosine, (ii) a dCas scaffold binding sequence, and (iii) a sequence complementary to the target sequence (spacer sequence), wherein (i), (ii) and (iii) are situated 3' to 5' in the esgRNA to a cell. In some embodiments, the methods further comprise administering an antisense synthetic oligonucleotide compound comprising alternating 2'OMe RNA and DNA bases (PAMmer). In some embodiments, the method is in vitro or in vivo. In some embodiments, provided herein are methods of selective RNA editing comprising, consisting of, or consisting essentially of administering any one of the recombinant expression systems, viral particles, and/or vectors comprising, consisting of, or consisting essentially of (A) a nucleic acid sequence encoding a CRISPR/Cas RNA editing fusion protein comprising a nuclease-dead CRISPR associated endonuclease (dCas) fused to a catalytically active deaminase domain of Adenosine Deaminase acting on RNA (ADAR); and (B) a nucleic acid sequence encoding an extended single guide RNA (esgRNA) comprising: (i) a short extension sequence of homology to the target RNA comprising a mismatch for a target adenosine, and (ii) a dCas scaffold binding sequence.

Also provided herein are methods of characterizing the effects of directed cellular RNA editing on processing and dynamics comprising administering any one of the recombinant expression systems, viral particles, and/or vectors comprising, consisting of, or consisting essentially of a nucleic acid encoding an extended single guide RNA (esgRNA) comprising (i) a short extension sequence of homology to a target RNA comprising a mismatch for a target adenosine, (ii) a dCas scaffold binding sequence, and (iii) a sequence complementary to the target sequence (spacer sequence), wherein (i), (ii) and (iii) are situated 3' to 5' in the esgRNA to a sample and determining its effects. In some embodiments, the sample is derived from a subject. In some embodiments, the method is in vitro or in vivo. In some embodiments, provided herein are methods of characterizing the effects of directed cellular RNA editing on processing and dynamics comprising administering any one of the recombinant expression systems, viral particles, and/or vectors comprising, consisting of, or consisting essentially of (A) a nucleic acid sequence encoding a CRISPR/Cas RNA editing fusion protein comprising a nuclease-dead CRISPR associated endonuclease (dCas) fused to a catalytically active deaminase domain of Adenosine Deaminase acting on RNA (ADAR); and (B) a nucleic acid sequence encoding an extended single guide RNA (esgRNA) comprising: (i) a short extension sequence of homology to the target RNA comprising a mismatch for a target adenosine, and (ii) a dCas scaffold binding sequence to a sample and determining its effects.

In other aspects, provided herein are methods of treating a disease or condition in a subject comprising administering any one of the recombinant expression systems, viral particles, and/or vectors comprising, consisting of, or consisting essentially of a nucleic acid encoding an extended single guide RNA (esgRNA) comprising (i) a short extension sequence of homology to a target RNA comprising a mismatch for a target adenosine, (ii) a dCas scaffold binding sequence, and (iii) a sequence complementary to the target sequence (spacer sequence), wherein (i), (ii) and (iii) are situated 3' to 5' in the esgRNA to a subject or a sample isolated from a subject. In some embodiments, provided herein are methods of treating a disease or condition in a subject comprising administering any one of the recombinant expression systems, viral particles, and/or vectors comprising, consisting of, or consisting essentially of (A) a nucleic acid sequence encoding a CRISPR/Cas RNA editing fusion protein comprising a nuclease-dead CRISPR associated endonuclease (dCas) fused to a catalytically active deaminase domain of Adenosine Deaminase acting on RNA (ADAR); and (B) a nucleic acid sequence encoding an extended single guide RNA (esgRNA) comprising: (i) a short extension sequence of homology to the target RNA comprising a mismatch for a target adenosine, and (ii) a dCas scaffold binding sequence to a subject or a sample isolated from a subject.

In some embodiments, the methods further correcting a G to A mutation in a target RNA. In some embodiments, the disease is selected from the group of Hurler's syndrome, Cystic fibrosis, Duchenne muscular dystrophy, spinal cord injury, stroke, traumatic brain injury, hearing loss (through noise overexposure or ototoxicity), multiple sclerosis, Alzheimer's disease, amyotrophic lateral sclerosis (ALS), Parkinson's disease, alcoholism, alcohol withdrawal, over-rapid benzodiazepine withdrawal, and Huntington's disease.

In other aspects, provided herein are kits comprising, consisting of, or consisting of one or more of: recombinant expression systems, viral particles, and/or vectors comprising, consisting of, or consisting essentially of (A) a nucleic acid sequence encoding a CRISPR/Cas RNA editing fusion protein comprising a nuclease-dead CRISPR associated endonuclease (dCas) fused to a catalytically active deaminase domain of Adenosine Deaminase acting on RNA (ADAR); and (B) a nucleic acid sequence encoding an extended single guide RNA (esgRNA) comprising: (i) a short extension sequence of homology to the target RNA comprising a mismatch for a target adenosine, and (ii) a dCas scaffold binding sequence and instructions for use. In some embodiments, the instructions are for use according to any one of the methods described herein.

BRIEF DESCRIPTION OF THE DRAWINGS

FIG. 1A shows (i) a conceptual concept of CREDIT in living cells for the editing of a variety of RNAs that can cause various diseases, such as cancer and neurodegeneration and (ii) that the binding of the dCas9-deaminase fusion to guide RNA directs the hybridization of guide-extension around target adenosines generating double-stranded RNA (dsRNA) A-I base-specific editing targets. In particular, FIG. 1B shows a CREDIT recombinant expression system comprised of the Streptococcus pyogenes Cas9 protein fused by an XTEN linker to the deaminase domain (DD) of human ADARB1 (ADAR2), and a single guide RNA (sgRNA) with a 3' short RNA extension (esgRNA). The fluorescent imaging data of FIG. 1C shows that the recombinant expression system of FIG. 1B requires targeted dual guide RNA with 3' extension directing deamination and allows reversal of premature termination codon (PTC) mediated silencing of expression from eGFP reporter transcripts. FIG. 1D shows FACS quantification of recombinant expression systems utilizing wild-type and hyper-active deaminase fusions to RCas9 directed by targeting and non-targeting guides.

FIG. 13A shows an illustration of an ADAR2(E488Q)-dSpCas9 fusion construct with an XTEN linker (Sp-CREDITv1) and an illustration of an ADAR2 (E488Q)-dSaCas9 fusion construct with an GSGS linker (SEQ ID NO: 49) (Sa-CREDITv1). FIG. 1B shows the results of an experiment wherein the efficiency of Sp-CREDITv1 is compared to the efficiency of Sa-CREDITv1. This data shows successful editing of the GFP reporter by both CREDIT systems, with Sa-CREDITv1 exhibiting the highest frequency of edited cells.

DETAILED DESCRIPTION

Figure 1A:
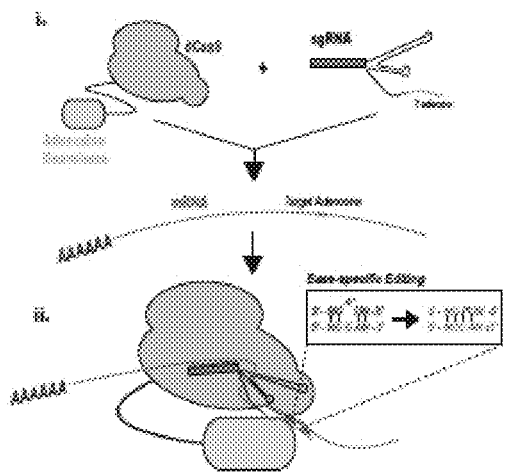
FIGS. 1A-1D illustrate, without limitation, embodiments of the recombinant expression system and data relating thereto.

Embodiments according to the present disclosure will be described more fully hereinafter. Aspects of the disclosure may, however, be embodied in different forms and should not be construed as limited to the embodiments set forth herein. Rather, these embodiments are provided so that this disclosure will be thorough and complete, and will fully convey the scope of the invention to those skilled in the art. The terminology used in the description herein is for the purpose of describing particular embodiments only and is not intended to be limiting.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. While not explicitly defined below, such terms should be interpreted according to their common meaning.

The terminology used in the description herein is for the purpose of describing particular embodiments only and is not intended to be limiting of the invention. All publications, patent applications, patents and other references mentioned herein are incorporated by reference in their entirety.

The practice of the present technology will employ, unless otherwise indicated, conventional techniques of tissue culture, immunology, molecular biology, microbiology, cell biology, and recombinant DNA, which are within the skill of the art.

Unless the context indicates otherwise, it is specifically intended that the various features of the invention described herein can be used in any combination. Moreover, the disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless explicitly indicated otherwise, all specified embodiments, features, and terms intend to include both the recited embodiment, feature, or term and biological equivalents thereof.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

Definitions

As used in the description of the invention and the appended claims, the singular forms "a," "an" and "the" are intended to include the plural forms as well, unless the context clearly indicates otherwise.

The term "about," as used herein when referring to a measurable value such as an amount or concentration and the like, is meant to encompass variations of 20%, 10%, 5%, 1%, 0.5%, or even 0.1% of the specified amount.

The terms or "acceptable," "effective," or "sufficient" when used to describe the selection of any components, ranges, dose forms, etc. disclosed herein intend that said component, range, dose form, etc. is suitable for the disclosed purpose.

"Polynucleotide" or "nucleotide," as used interchangeably herein, refer to polymers of nucleotides of any length, and include DNA and RNA. A polynucleotide or nucleotide sequence could be either double-stranded or single-stranded. When a polynucleotide or nucleotide sequence is single stranded, it could refer to either of the two complementary strands. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (such as methyl phosphonates, phosphotriesters, phosphoamidates, cabamates, etc.) and with charged linkages (such as phosphorothioates, phosphorodithioates, etc.), those containing pendant moieties, such as, for example, proteins (such as nucleases, toxins, antibodies, signal peptides, ply-L-lysine, etc.), those with intercalators (such as acridine, psoralen, etc.), those containing chelators (such as metals, radioactive metals, boron, oxidative metals, etc.), those containing alkylators, those with modified linkages (such as alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR 2 ("amidate"), P(O)R, P(O)OR', CO or CH 2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Nucleic acids", "nucleic acid molecules," or "nucleic acid sequences" are used interchangeably herein to refer to polynucleotides and/or oligonucleotides. In some embodiments, nucleic acid is used interchangeably with polynucleotide and/or oligonucleotide.

As used herein, "substantially complementary or substantially matched" means that two nucleic acid sequences have at least 90% sequence identity. Preferably, the two nucleic acid sequences have at least 95%, 96%, 97%, 98%, 99% or 100% of sequence identity. Alternatively, "substantially complementary or substantially matched" means that two nucleic acid sequences can hybridize under high stringency condition(s).

As used herein, "improve" means a change of at least about 1%, 2%, 5%, 10%, 15%, 20%, 25%, 30%, 35%, 40%, 35%, 50%, 55%, 60%, 65%, 70%, 75%, 80%, 85%, 90%, 95%, 100%, 125%, 150%, 175%, 200%, 225%, 250%, 275%, 300%, 350%, 400%, 450%, 500%, 600%, 700%, 800%, 900%, 1000% or more or any value between any of the listed values. Alternatively, "improve" could mean a change of at least about 1-fold, 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, 60-fold, 70-fold, 80-fold, 90-fold, 100-fold, 500-fold, 1000-fold, 2000-fold or more or any value between any of the listed values.

As used herein, "nuclease null" or "nuclease dead" may refer to a polypeptide with reduced nuclease activity, reduced endo- or exo-DNAse activity or RNAse activity, reduced nickase activity, or reduced ability to cleave DNA and/or RNA. Non-limiting examples of Cas-associated endonucleases that are nuclease dead include endonucleases with mutations that render the RuvC and/or HNH nuclease domains inactive. For example, S. pyogenes Cas9 can be rendered inactive by point mutations D10A and H840A, resulting in a nuclease dead Cas9 molecule that cannot cleave target DNA or RNA. The dCas9 molecule retains the ability to bind to target RNA based on the gRNA targeting sequence.

As used herein, "reduced nuclease activity" means a decline in nuclease, nickase, DNAse, or RNAse activity of at least about 1%, 2%, 5%, 10%, 15%, 20%, 25%, 30%, 35%, 40%, 35%, 50%, 55%, 60%, 65%, 70%, 75%, 80%, 85%, 90%, 95%, 100% or more or any value between any of the listed values. Alternatively, "reduced nuclease activity" may refer to a decline of at least about 1-fold, 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, 60-fold, 70-fold, 80-fold, 90-fold, 100-fold, 500-fold, 1000-fold, 2000-fold or more or any value between any of the listed values.

As used herein, "increased catalytic activity" means an increase in catalytic activity of e.g. deaminase activity of at least about 1%, 2%, 5%, 10%, 15%, 20%, 25%, 30%, 35%, 40%, 35%, 50%, 55%, 60%, 65%, 70%, 75%, 80%, 85%, 90%, 95%, 100% or more or any value between any of the listed values as compared to the corresponding wild type catalytic activity (e.g., wild type deaminase activity). Alternatively, "increased catalytic activity" may refer to an increase of at least about 1-fold, 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, 60-fold, 70-fold, 80-fold, 90-fold, 100-fold, 500-fold, 1000-fold, 2000-fold or more or any value between any of the listed values as compared to the corresponding wild type catalytic activity (e.g., wild type deaminase activity).

As used herein, the term "ADAR" refers to a double-stranded RNA specific adenosine deaminase which catalyzes the hydrolytic deamination of adenosine to inosine in double-stranded RNA (dsRNA), referred to as A to I editing and also known as Adenosine Deaminase Acting on RNA. Non-limiting exemplary sequences of this protein and annotation of its domains is found under UniProt reference number P55265 (human) and Q99MU3 (mouse).

The term "adeno-associated virus" or "AAV" as used herein refers to a member of the class of viruses associated with this name and belonging to the genus dependoparvovirus, family Parvoviridae. Multiple serotypes of this virus are known to be suitable for gene delivery; all known serotypes can infect cells from various tissue types. At least 11, sequentially numbered, are disclosed in the prior art. Non-limiting exemplary serotypes useful in the methods disclosed herein include any of the 11 serotypes, e.g., AAV2 and AAV8.

Also as used herein, "and/or" refers to and encompasses any and all possible combinations of one or more of the associated listed items, as well as the lack of combinations when interpreted in the alternative ("or").

The term "aptamer" as used herein refers to single stranded DNA or RNA molecules that can bind to one or more selected targets with high affinity and specificity. Non-limiting exemplary targets include but are not limited to proteins or peptides.

The term "Cas-associated" refers to a CRISPR (Clustered Regularly Interspaced Short Palindromic Repeats) associated endonuclease. "Cas9" is a Cas-associated endonuclease referred to by this name (UniProtKB G3ECR1 (CAS9_STRTR)). DeadCas-9 or "dCas9" is a Cas9 endonuclease which lacks or substantially lacks endonuclease and/or cleavage activity. A non-limiting example of dCas9 is the dCas9 encoded in AddGene plasmid. #74710, which is commercially available through the AddGene database.

The term "cell" as used herein may refer to either a prokaryotic or eukaryotic cell, optionally obtained from a subject or a commercially available source.

The term "gRNA" or "guide RNA" as used herein refers to the guide RNA sequences used to target specific genes for correction employing the CRISPR technique. Techniques of designing gRNAs and donor therapeutic polynucleotides for target specificity are well known in the art. For example, Doench, J., et al. Nature biotechnology 2014; 32(12):1262-7 and Graham, D., et al. Genome Biol. 2015; 16: 260, incorporated by reference herein.

As used herein, the term "CRISPR" refers to a technique of sequence specific genetic manipulation relying on the clustered regularly interspaced short palindromic repeats pathway, which unlike RNA interference regulates gene expression at a transcriptional level. The term "gRNA" or "guide RNA" as used herein refers to the guide RNA sequences used to target specific genes for correction employing the CRISPR technique. Techniques of designing gRNAs and donor therapeutic polynucleotides for target specificity are well known in the art. For example, Doench, J., et al. Nature biotechnology 2014; 32(12):1262-7 and Graham, D., et al. Genome Biol. 2015; 16: 260. "Single guide RNA" or "sgRNA" is a specific type of gRNA that combines tracrRNA (transactivating RNA), which binds to Cas9 to activate the complex to create the necessary strand breaks, and crRNA (CRISPR RNA), comprising complimentary nucleotides to the tracrRNA, into a single RNA construct. As described herein, an "extended single guide RNA" or "esgRNA" is a specific type of sgRNA that includes an extension sequence of homology to the target RNA comprising a mismatch for a target adenosine of the target RNA to be edited in a manner such that a A-C mismatch is formed with a target transcript generating a 'pseudo-dsRNA' substrate to be edited at the bulged adenosine residue.

As used herein, the term "comprising" is intended to mean that the compositions and methods include the recited elements, but do not exclude others. As used herein, the transitional phrase "consisting essentially of" (and grammatical variants) is to be interpreted as encompassing the recited materials or steps "and those that do not materially affect the basic and novel characteristic(s)" of the recited embodiment. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising." "Consisting of" shall mean excluding more than trace elements of other ingredients and substantial method steps for administering the compositions disclosed herein. Aspects defined by each of these transition terms are within the scope of the present disclosure.

The term "encode" as it is applied to nucleic acid sequences refers to a polynucleotide which is said to "encode" a polypeptide if, in its native state or when manipulated by methods well known to those skilled in the art, can be transcribed and/or translated to produce the mRNA for the polypeptide and/or a fragment thereof. The antisense strand is the complement of such a nucleic acid, and the encoding sequence can be deduced therefrom.

The terms "equivalent" or "biological equivalent" are used interchangeably when referring to a particular molecule, biological, or cellular material and intend those having minimal homology while still maintaining desired structure or functionality.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell. The expression level of a gene may be determined by measuring the amount of mRNA or protein in a cell or tissue sample; further, the expression level of multiple genes can be determined to establish an expression profile for a particular sample.

As used herein, the term "sample" can refer to a composition comprising targets. Suitable samples for analysis by the disclosed methods, devices, and systems include cells, tissues, organs, or organisms or compositions obtained from cells, tissues or organisms. In some embodiments, samples are isolated from a subject.

As used herein, the term "functional" may be used to modify any molecule, biological, or cellular material to intend that it accomplishes a particular, specified effect.

A "gene delivery vehicle" is defined as any molecule that can carry inserted polynucleotides into a host cell. Examples of gene delivery vehicles are liposomes, micelles biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide disclosed herein can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extra-chromosomal replicon (e.g., a plasmid) or a nuclear or mitochondrial chromosome. A number of "vectors" are known to be capable of mediating transfer of genes to mammalian cells, as is known in the art and described herein.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmid vectors". Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacterium produces proteins to confer its antibiotic resistance, it can also be induced to produce large amounts of proteins from the inserted gene.

A "yeast artificial chromosome" or "YAC" refers to a vector used to clone large DNA fragments (larger than 100 kb and up to 3000 kb). It is an artificially constructed chromosome and contains the telomeric, centromeric, and replication origin sequences needed for replication and preservation in yeast cells. Built using an initial circular plasmid, they are linearized by using restriction enzymes, and then DNA ligase can add a sequence or gene of interest within the linear molecule by the use of cohesive ends. Yeast expression vectors, such as YACs, YIps (yeast integrating plasmid), and YEps (yeast episomal plasmid), are extremely useful as one can get eukaryotic protein products with posttranslational modifications as yeasts are themselves eukaryotic cells, however YACs have been found to be more unstable than BACs, producing chimeric effects.

A "viral vector" is defined as a recombinantly produced virus or viral particle that comprises a polynucleotide to be delivered into a host cell, either in vivo, ex vivo or in vitro.

Examples of viral vectors include retroviral vectors, adenovirus vectors, adeno-associated virus vectors, alphavirus vectors and the like. Infectious tobacco mosaic virus (TMV)-based vectors can be used to manufacturer proteins and have been reported to express Griffithsin in tobacco leaves (O'Keefe et al. (2009) Proc. Nat. Acad. Sci. USA 106(15):6099-6104). Alphavirus vectors, such as Semliki Forest virus-based vectors and Sindbis virus-based vectors, have also been developed for use in gene therapy and immunotherapy. See, Schlesinger & Dubensky (1999) Curr. Opin. Biotechnol. 5:434-439 and Ying et al. (1999) Nat. Med. 5(7):823-827. In aspects where gene transfer is mediated by a retroviral vector, a vector construct refers to the polynucleotide comprising the retroviral genome or part thereof, and a therapeutic gene. Further details as to modern methods of vectors for use in gene transfer may be found in, for example, Kotterman et al. (2015) Viral Vectors for Gene Therapy: Translational and Clinical Outlook Annual Review of Biomedical Engineering 17.

As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. Ads do not require integration into the host cell genome. Recombinant Ad derived vectors, particularly those that reduce the potential for recombination and generation of wild-type virus, have also been constructed. Such vectors are commercially available from sources such as Takara Bio USA (Mountain View, Calif.), Vector Biolabs (Philadelphia, Pa.), and Creative Biogene (Shirley, N.Y.). Wild-type AAV has high infectivity and specificity integrating into the host cell's genome. See, Wold and Toth (2013) Curr. Gene. Ther. 13(6):421-433, Hermonat & Muzyczka (1984) Proc. Natl. Acad. Sci. USA 81:6466-6470, and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Agilent Technologies (Santa Clara, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include DNA/liposome complexes, micelles and targeted viral protein-DNA complexes. Liposomes that also comprise a targeting antibody or fragment thereof can be used in the methods disclosed herein. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins disclosed herein are other non-limiting techniques.

"Homology" or "identity" or "similarity" refers to sequence similarity between two peptides or between two nucleic acid molecules. Homology can be determined by comparing a position in each sequence that may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure.

"Homology" or "identity" or "similarity" can also refer to two nucleic acid molecules that hybridize under stringent conditions.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

As used herein, the term "specifically binds" refers to the binding specificity of a specific binding pair. Hybridization by a target-specific nucleic acid sequence of a particular target polynucleotide sequence in the presence of other potential targets is one characteristic of such binding. Specific binding involves two different nucleic acid molecules wherein one of the nucleic acid molecules specifically hybridizes with the second nucleic acid molecule through chemical or physical means. The two nucleic acid molecules are related in the sense that their binding with each other is such that they are capable of distinguishing their binding partner from other assay constituents having similar characteristics. The members of the binding component pair are referred to as ligand and receptor (anti-ligand), specific binding pair (SBP) member and SBP partner, and the like.

The term "isolated" as used herein refers to molecules or biologicals or cellular materials being substantially free from other materials.

As used herein, the term "linker" refers to a short peptide sequence that may occur between two protein domains. Linkers may often comprise flexible amino acid residues, e.g. glycine or serine, to allow for free movement of adjacent but fused protein domains. "XTEN" refers to any one of the exemplary linkers provided in Schellenberger et al. (2009) Nat Biotechnol. 27:1186-1190. doi: 10.1038/nbt. 1588 or equivalent variants thereof.

As used herein, the term "organ" is a structure which is a specific portion of an individual organism, where a certain function or functions of the individual organism is locally performed and which is morphologically separate. Non-limiting examples of organs include the skin, blood vessels, cornea, thymus, kidney, heart, liver, umbilical cord, intestine, nerve, lung, placenta, pancreas, thyroid and brain.

The term "photospacer adjacent motif" or "PAM" refers to a sequence that activates the nuclease domain of Cas9. A "PAMmer" refers to a PAM-presenting oligonucleotide. As used herein, the term PAMmer generally refers to an anti-sense synthetic oligonucleotide composed alternating 2'OMe RNA and DNA bases and/or other variations of a PAM presenting oligonucleotide that can optimize the CRISPR/Cas9 system and generate specific cleavage of RNA targets without cross reactivity between non-target RNA or against genomic DNA. See, e.g., O'Connell et al. (2014) Nature. 516(7530):263-266.

The term "promoter" as used herein refers to any sequence that regulates the expression of a coding sequence, such as a gene. Promoters may be constitutive, inducible, repressible, or tissue-specific, for example. A "promoter" is a control sequence that is a region of a polynucleotide sequence at which initiation and rate of transcription are controlled. It may contain genetic elements at which regulatory proteins and molecules may bind such as RNA polymerase and other transcription factors. Non-limiting exemplary promoters include CMV promoter and U6 promoter.

The term "protein", "peptide" and "polypeptide" are used interchangeably and in their broadest sense to refer to a compound of two or more subunits of amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise a protein's or peptide's sequence. Proteins and peptides are known to have a C-terminus, referring to the end with an unbound carboxy group on the terminal amino acid, and an N-terminus, referring to the end with an unbound amine group on the terminal amino acid. As used herein the term "amino acid" refers to either natural and/or unnatural or synthetic amino acids, including glycine and both the D and L optical isomers, amino acid analogs and peptidomimetics. The term "fused" in context of a protein or polypeptide refers to the linkage between termini of two or more proteins or polypeptides (or domains thereof) to form a fusion protein.

As used herein, the term "recombinant expression system" refers to a genetic construct for the expression of certain genetic material or proteins formed by recombination.

As used herein, the term "subject" is used interchangeably with "patient" and is intended to mean any animal. In some embodiments, the subject may be a mammal. In some embodiments, the mammal is a non-human mammal. In some embodiments, the mammal is a bovine, equine, porcine, murine, feline, canine, simian, rat, or human.

The term "tissue" is used herein to refer to tissue of a living or deceased organism or any tissue derived from or designed to mimic a living or deceased organism. The tissue may be healthy, diseased, and/or have genetic mutations. The biological tissue may include any single tissue (e.g., a collection of cells that may be interconnected) or a group of tissues making up an organ or part or region of the body of an organism. The tissue may comprise a homogeneous cellular material or it may be a composite structure such as that found in regions of the body including the thorax which for instance can include lung tissue, skeletal tissue, and/or muscle tissue. Exemplary tissues include, but are not limited to those derived from liver, lung, thyroid, skin, pancreas, blood vessels, bladder, kidneys, brain, biliary tree, duodenum, abdominal aorta, iliac vein, heart and intestines, including any combination thereof.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

As used herein, the term "vector" intends a recombinant vector that retains the ability to infect and transduce non-dividing and/or slowly-dividing cells and integrate into the target cell's genome. The vector may be derived from or based on a wild-type virus. Aspects of this disclosure relate to an adeno-associated virus vector.

A number of other vector elements are disclosed herein; e.g., plasmids, promoters, linkers, signals, etc. The nature and function of these vector elements are commonly understood in the art and a number of these vector elements are commercially available. Non-limiting exemplary sequences thereof, e.g., SEQ ID NOS: 1-8 are disclosed herein and further description thereof is provided herein below and/or illustrated in FIGS. 3-10.

CRISPR/Cas Directed RNA-Editing (CREDIT)

Figure 1B:
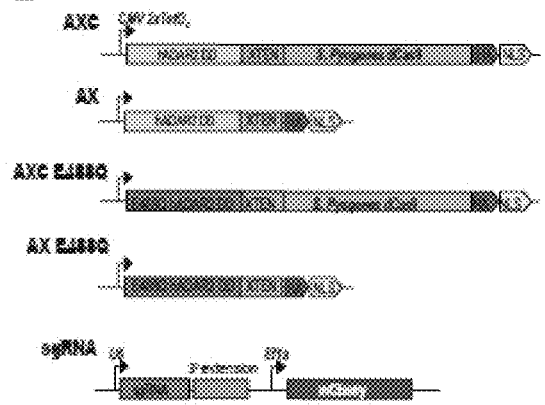

Disclosed herein is an efficient, versatile and simplified platform technology for performing programmable RNA editing at single-nucleotide resolution using RNA-targeting CRISPR/Cas (RCas). This approach, which Applicants have termed "Cas-directed RNA editing" or "CREDIT," provides a means to reversibly alter genetic information in a temporal manner, unlike traditional CRISPR/Cas9 driven genomic engineering which relies on permanently altering DNA sequence. Recombinant expression systems are engineered to induce edits to specific RNA bases as determined by the guide RNA design. As such, in some embodiments, Applicants provide a fully encodeable recombinant expression system comprising a nuclease-dead version of *Streptococcus pyogenes* Cas9 (dCas9) fused to an ADAR deaminase domain and a corresponding extended single guide RNA (esgRNA). In some embodiments, the system generates recombinant proteins with effector deaminase enzyme complexes capable of performing ribonucleotide base modification to alter how the sequence of the RNA molecule is recognized by cellular machinery. In some embodiments, the CREDIT expression system comprises A) a nucleic acid sequence encoding a nuclease-dead CRISPR associated endonuclease (dCas) fused to a catalytically active deaminase domain of ADAR (Adenosine Deaminase acting on RNA) and B) an extended single guide RNA (esgRNA) sequence comprising i) a short extension sequence of homology to the target RNA comprising a mismatch for a target adenosine, ii) a dCas scaffold binding sequence, and optionally iii) a sequence complementary to the target RNA sequence (also known as a spacer sequence in a sgRNA context). Exemplary constructs that express CREDIT expression system components include, without limitation, dCas9 fused to catalytically active deaminase domains of human ADAR2 (hADAR2DD, E488QhADAR2DD) using an 'XTEN' linker peptide for spatial separation (FIG. 1B). With dCas9 as a surrogate RBD (RNA-Binding Domain), Applicants engineered and customized single guide RNAs (sgRNAs) with unique short extension sequences (esgRNA) to direct hADAR2DD to RNA sites for target specific A-I editing. For the purposes of the present disclosure, CRISPR/ Cas associated endonucleases other than Cas9 or Cas9 orthologs (e.g., Cas13 (also known as C2c2), Cpf1, Cas6f/ Csy4, CasX, CasY, and CasRx) are also provided herein for use in the CREDIT expression system. See also Wright et al., Biology and Applications of CRISPR Systems: Harnessing Nature's Toolbox for Genome Engineering, Cell, Vol. 164 (1-2): 29-44, 2016.

In some embodiments disclosed herein, dCas polypeptide has been engineered to recognize a target RNA, wherein the inactive Cas polypeptide is associated with an effector. In some embodiments, the dCas polypeptide is a *Streptococcus pyogenes* dCas9 polypeptide. In some embodiments, the dCas9 polypeptide comprises a mutation, such as D10A, H840A, or both, in the *Streptococcus pyogenes* Cas9 polypeptide. This repurposed or engineered dCas9 polypeptide-comprising nucleoprotein complex that binds to RNA is referred to herein as RdCas9. CRISPR has revolutionized genome engineering by allowing simply-programmed recognition of DNA in human cells and supported related technologies in imaging and gene expression modulation. In WO 2017/091630, incorporated by reference in its entirety herein, an analogous means to target RNA using an RCas9 was developed. In this earlier work, engineered nucleoprotein complexes comprise a Cas9 protein and a single guide RNA (sgRNA). Together, the Cas9 protein and sgRNA components were engineered to hypothetically recognize any target RNA sequence. Optionally, in such systems, an (chemically-modified or synthetic) antisense PAMmer oligonucleotide could be included in the RCas9 system to simulate a DNA substrate for recognition by Cas9 via hybridization to the target RNA. However, surprisingly highly effective RNA targeting without PAMmer was also shown. Now, herein is disclosed RdCas-ADAR RNA editing systems which do not require a PAMmer and as such are fully encodeable Cas9-mediated RNA targeting systems which provide a reversible platform for modification of target RNA.

For the purposes of the present disclosure, Cas9 endonucleases used herein include, without limitation, orthologs derived from archaeal or bacterial Cas9 polypeptides. Such polypeptides can be derived from, without limitations *Haloferax mediteranii, Mycobacterium tuberculosis, Francisella tularensis* subsp. *novicida, Pasteurella multocida, Neisseria meningitidis, (Campylobacter jejune, Streptococcus thermophilus* LMD-9 CRISPR 3, iCampqlobacter ari CF89-12, *Avcoplasma galisepticum* str. F, *Nitratifractor salsuginis* str DSM 1651 1, *Parvibaculum lavamentivorans, Roseburia intestialis, Neisseria cinerea, Gluconacetobaccter diazotrophicus, Azospirillum* B510, *Sphaerochaeta globus* str. Buddy, *Flavobacterium columnare, Fhlviicola tajjensis, Bacteroides coprophilus, Mycoplasma mobile, Lactobacillus farciminis, Streptococcus pasteurianus, Lactobacillus johnsonii, Staphylococcus pseudintermedius, Filifactor alocis, Treponema denticola, Legionella pneumophila* str. Paris, *Sutterella wadsworthensis, Corynebacter diphtheriae*, or *Streptococcus aureus; Frainciscella novicida* (e.g., *Francisella novicida* CPf1), or *Natronobacterium gregoryi* Argonaute. Each of these respective candidate Cas polypeptides are modified and/or repurposed to target RNA and fused to an ADAR deaminase domain for use in the systems disclosed herein, which system additionally comprises an extended sgRNA (esgRNA) which comprises a guide "scaffold sequence" which comprises all or part of, or is derived from, the wild type (WT) cognate guide nucleic acid of each of these respective bacteria or archaeal organisms. In some embodiments, Cas endonucleases for use herein include, without limitation, Cas13 (c2C2), Cpf1, CasX, CasY, and CasRx.

Further nonlimiting examples of orthologs and biological equivalents Cas9 are provided in the table below:

| Name | Protein Sequence |
|---|---|
| S. pyogenes Cas9 SEQ ID NO: 1 | MDKKYSIGLDIGTNSVGWAVITDEYKVPSKKFKVLGNTDRHSIKKNLIGALLFD SGETAEATRLKRTARRRYTRRKNRICYLQEIFSNEMAKVDDSFFHRLEESFLVE EDKKHERHPIFGNIVDEVAYHEKYPTIYHLRKKLVDSTDKADLRLIYLALAHMI KFRGHFLIEGDLNPDNSDVDKLFIQLVQTYNQLFEENPINASGVDAKAILSARLS KSRRLENLIAQLPGEKKNGLFGNLIALSLGLTPNFKSNFDLAEDAKLQLSKDTY DDDLDNLLAQIGDQYADLFLAAKNLSDAILLSDILRVNTEITKAPLSASMIKRYD EHHQDLTLLKALVRQQLPEKYKEIFFDQSKNGYAGYIDGGASQEEFYKFIKPILE KMDGTEELLVKLNREDLLRKQRTFDNGSIPHQIHLGELHAILRRQEDFYPFLKD NREKIEKILTFRIPYYVGPLARGNSRFAWMTRKSEETITPWNFEEVVDKGASAQ SFIERMTNFDKNLPNEKVLPKHSLLYEYFTVYNELTKVKYVTEGMRKPAFLSGE QKKAIVDLLFKTNRKVTVKQLKEDYFKKIECFDSVEISGVEDRFNASLGTYHDL LKIIKDKDFLDNEENEDILEDIVLTLTLFEDREMIEERLKTYAHLFDDKVMKQLK RRRYTGWGRLSRKLINGIRDKQSGKTILDFLKSDGFANRNFMQLIHDDSLTFKE DIQKAQVSGQGDSLHEHIANLAGSPAIKKGILQTVKVVDELVKVMGRHKPENIV IEMARENQTTQKGQKNSRERMKRIEEGIKELGSQILKEHPVENTQLQNEKLYLY YLQNGRDMYVDQELDINRLSDYDVDHIVPQSFLKDDSIDNKVLTRSDKNRGKS DNVPSEEVVKKMKNYWRQLLNAKLITQRKFDNLTKAERGGLSELDKAGFIKR QLVETRQITKHVAQILDSRMNTKYDENDKLIREVKVITLKSKLVSDFRKDFQFY KVREINNYHHAHDAYLNAVVGTALIKKYPKLESEFVYGDYKVYDVRKMIAKS EQEIGKATAKYFFYSNIMNFFKTEITLANGEIRKRPLIETNGETGEIVWDKGRDF ATVRKVLSMPQVNIVKKTEVQTGGFSKESILPKRNSDKLIARKKDWDPKKYGG FDSPTVAYSVLVVAKVEKGKSKKLKSVKELLGITIMERSSFEKNPIDFLEAKGY KEVKKDLIIKLPKYSLFELENGRKRMLASAGELQKGNELALPSKYVNFLYLASH YEKLKGSPEDNEQKQLFVEQHKHYLDEIIEQISEFSKRVILADANLDKVLSAYN KHRDKPIREQAENIIHLFTLTNLGAPAAFKYFDTTIDRKRYTSTKEVLDATLIHQS ITGLYETRIDLSQLGGD* |
| Staphylococcus aureus Cas9 SEQ ID NO: 2 | MKRNYILGLDIGITSVGYGIIDYETRDVIDAGVRLFKEANVENNEGRRSKRGAR RLKRRRRHRIQRVKKLLFDYNLLTDHSELSGINPYEARVKGLSQKLSEEEFSAA LLHLAKRRGVHNVNEVEEDTGNELSTKEQISRNSKALEEKYVAELQLERLKKD GEVRGSINRFKTSDYVKEAKQLLKVQKAYHQLDQSFIDTYIDLLETRRTYYEGP GEGSPFGWKDIKEWYEMLMGHCTYFPEELRSVKYAYNADLYNALNDLNNLVI TRDENEKLEYYEKFQIIENVFKQKKKPTLKQIAKEILVNEEDIKGYRVTSTGKPE FTNLKVYHDIKDITARKEIIENAELLDQIAKILTIYQSSEDIQEELTNLNSELTQEEI EQISNLKGYTGTHNLSLKAINLILDELWHTNDNQIAIFNRLKLVPKKVDLSQQKE IPTTLVDDFILSPVVKRSFIQSIKVINAIIKKYGLPNDIIIELAREKNSKDAQKMINE MQKRNRQTNERIEEIIRTTGKENAKYLIEKIKLHDMQEGKCLYSLEAIPLEDLLN NPFNYEVDHIIPRSVSFDNSFNNKVLVKQEENSKKGNRTPFQYLSSSDSKISYET FKKHILNLAKGKGRISKTKKEYLLEERDINRFSVQKDFINRNLVDTRYATRGLM NLLRSYFRVNNLDVKVKSINGGFTSFLRRKWKFKKERNKGYKHHAEDALIIAN ADFIFKEWKKLDKAKKVMENQMFEEKQAESMPEIETEQEYKEIFITPHQIKHIK DFKDYKYSHRVDKKPNRELINDTLYSTRKDDKGNTLIVNNLNGLYDKDNDKL KKLINKSPEKLLMYHHDPQTYQKLKLIMEQYGDEKNPLYKYYEETGNYLTKYS KKDNGPVIKKIKYYGNKLNAHLDITDDYPNSRNKVVKLSLKPYRFDVYLDNGV YKFVTVKNLDVIKKENYYEVNSKCYEEAKKLKKISNQAEFIASFYNNDLIKING ELYRVIGVNNDLLNRIEVNMIDITYREYLENMNDKRPPRIIKTIASKTQSIKKYST DILGNLYEVKSKKHPQIIKKG* |
| S. thermophilus CRISPR 1 Cas9 SEQ ID NO: 3 | MSDLVLGLDIGIGSVGVGILNKVTGEIIHKNSRIFPAAQAENNLVRRTNRQGRRL ARRKKHRRVRLNRLFEESGLITDPTKISINLNPYQLRVKGLTDELSNEELFIALKN MVKHRGISYLDDASDDGNSSVGDYAQIVKENSKQLETKTPGQIQLERYQTYGQ LRGDFTVEKDGKKHRLINVFPTSAYRSEALRILQTQQEFNPQITDEFINRYLEILT GKRKYYHGPGNEKSRTDYGRYRTSGETLDNIFGILIGKCTFYPDEFRAAKASYT AQEFNLLNDLNNLTVPTETKKLSKEQKNQIINYVKNEKAMGPAKLFKYIAKLLS CDVADIKGYRIDKSGKAEIHTFEAYRKMKTLETLDIEQMDRETLDKLAYVLTLN TEREGIQEALEHEFADGSFSQKQVDELVQFRKANSSIFGKGWHNFSVKLMMELI PELYETSEEQMTILTRLGKQKTTSSSNKTKYIDEKLLTEEIYNPVVAKSVRQAIKI VNAAIKEYGDFDNIVIEMARETNEDDEKKAIQKIQKANKDEKDAAMLK AANQYNGKAELPHSVFHGHKQLATKIRLWHQQGERCLYTGKTISIHDLINNSN QFEVDHILPLSITFDDSLANKVLVYATANQEKGQRTPYQALDSMDDAWSFREL KAFVRESKTLSNKKKEYLLTEEDISKFDVRKKFIERNLVDTRYASRVVLNALQE HFRAHKIDTKVSVVRGQFTSQLRRHWGIEKTRDTYHHHAVDALIIAASSQLNL WKKQKNTLVSYSEDQLLDIETGELISDDEYKESVFKAPYQHFVDTLKSKEFEDSI LFSYQVDSKFNRKISDATIYATRQAKVGKDKADETYVLGKIKDIYTQDGYDAF MKIYKKDKSKFLMYRHDPQTFEKVIEPILENYPNKQINDKGKEVPCNPFLKYKE EHGYIRKYSKKGNGPEIKSLKYYDSKLGNHIDITPKDSNNKVVLQSVSPWRADV YFNKTTGKYEILGLKYADLQFDKGTGTYKISQEKYNDIKKKEGVDSDSEFKFTL YKNDLLLVKDTETKEQQLFRFLSRTMPKQKHYVELKPYDKQKFEGGEALIKVL GNVANSGQCKKGLGKSNISIYKVRTDVLGNQHIIKNEGDKPKLDF* |
| N. meningitidis Cas9 SEQ ID NO: 4 | MAAFKPNPINYILGLDIGIASVGWAMVEIDEDENPICLIDLGVRVFERAEVPKTG DSLAMARRLARSVRRLTRRRAHRLLRARRLLKREGVLQAADFDENGLIKSLPN TPWQLRAAALDRKLTPLEWSAVLLHLIKHRGYLSQRKNEGETADKELGALLKG VADNAHALQTGDFRTPAELALNKFEKESGHIRNQRGDYSHTFSRKDLQAELILL FEKQKEFGNPHVSGGLKEGIETLLMTQRPALSGDAVQKMLGHCTFEPAEPKAA KNTYTAERFIWLTKLNNLRILEQGSERPLTDTERATLMDEPYRKSKLTYAQARK |

-continued

| Name | Protein Sequence |
|---|---|
| | LLGLEDTAFFKGLRYGKDNAEASTLMEMKAYHAISRALEKEGLKDKKSPLNLS<br>PELQDEIGTAFSLFKTDEDITGRLKDRIQPEILEALLKHISFDKFVQISLKALRRIV<br>PLMEQGKRYDEACAEIYGDHYGKKNTEEKIYLPPIPADEIRNPVVLRALSQARK<br>VINGVVRRYGSPARIHIETAREVGKSFKDRKEIEKRQEENRKDREKAAAKFREY<br>FPNFVGEPKSKDILKLRLYEQQHGKCLYSGKEINLGRLNEKGYVEIDHALPFSRT<br>WDDSFNNKVLVLGSENQNKGNQTPYEYFNGKDNSREWQEFKARVETSRFPRS<br>KKQRILLQKFDEDGFKERNLNDTRYVNRFLCQFVADRMRLTGKGKKRVFASN<br>GQITNLLRGFWGLRKVRAENDRHHALDAVVVACSTVAMQQKITRFVRYKEMN<br>AFDGKTIDKETGEVLHQKTHFPQPWEFFAQEVMIRVFGKPDGKPEFEEADTPEK<br>LRTLLAEKLSSRPEAVHEYVTPLFVSRAPNRKMSGQGHMETVKSAKRLDEGVS<br>VLRVPLTQLKLKDLEKMVNREREPKLYEALKARLEAHKDDPAKAFAEPFYKY<br>DKAGNRTQQVKAVRVEQVQKTGVWVRNHNGIADNATMVRVDVFEKGDKYY<br>LVPIYSWQVAKGILPDRAVVQGKDEEDWQLIDDSFNFKFSLHPNDLVEVITKKA<br>RMFGYFASCHRGTGNINIRIHDLDHKIGKNGILEGIGVKTALSFQKYQIDELGKEI<br>RPCRLKKRPPVR* |
| *Parvibaculum lavamentivorans* Cas9<br>SEQ ID NO: 5 | MERIFGFDIGTTSIGFSVIDYSSTQSAGNIQRLGVRIFPEARDPDGTPLNQQRRQK<br>RMMRRQLRRRIRRKALNETLHEAGFLPAYGSADWPVVMADEPYELRRRGLE<br>EGLSAYEFGRAIYHLAQHRHFKGRELEESDTPDPDVDDEKEAANERAATLKAL<br>KNEQTTLGAWLARRPPSDRKRGIHAHRNVVAEEFERLWEVQSKFHPALKSEEM<br>RARISDTIFAQRPVFWRKNTLGECRFMPGEPLCPKGSWLSQQRRMLEKLNNLAI<br>AGGNARPLDAEERDAILSKLQQQASMSWPGVRSALKALYKQRGEPGAEKSLK<br>FNLELGGESKLLGNALEAKLADMFGPDWPAHPRKQEIRHAVHERLWAADYGE<br>TPDKKRVIILSEKDRKAHREAAANSFVADFGITGEQAAQLQALKLPTGWEPYSI<br>PALNLFLAELEKGERFGALVNGPDWEGWRRTNFPHRNQPTGEILDKLPSPASKE<br>ERERISQLRNPTVVRTQNELRKVVNNLIGLYGKPDRIRIEVGRDVGKSKEREEI<br>QSGIRRNEKQRKKATEDLIKNGIANPSRDDVEKWILWKEGQERCPYTGDQIGFN<br>ALFREGRYEVEHIWPRSRSFDNSPRNKTLCRKDVNIEKGNRMPFEAFGHDEDR<br>WSAIQIRLQGMVSAKGGTGMSPGKVKRFLAKTMPEDFAARQLNDTRYAAKQI<br>LAQLKRLWPDMGPEAPVKVEAVTGQVTAQLRKLWTLNNILADDGEKTRADH<br>RHHAIDALTVACTHPGMTNKLSRYWQLRDDPRAEKPALTPPWDTIRADAEKA<br>VSEIVVSHRVRKKVSGPLHKETTYGDTGTDIKTKSGTYRQFVTRKKIESLSKGEL<br>DEIRDPRIKEIVAAHVAGRGGDPKKAFPPYPCVSPGGPEIRKVRLTSKQQLNLM<br>AQTGNGYADLGSNHHIAIYRLPDGKADFEIVSLFDASRRLAQRNPIVQRTRADG<br>ASFVMSLAAGEAIMIPEGSKKGIWIVQGVWASGQVVLERDTDADHSTTTRPMP<br>NPILKDDAKKVSIDPIGRVRPSND* |
| *Corynebacter diphtheria* Cas9<br>SEQ ID NO: 6 | MKYHVGIDVGTFSVGLAAIEVDDAGMPIKTLSLVSHIHDSGLDPDEIKSAVTRL<br>ASSGIARRTRRLYRRKRRRLQQLDKFIQRQGWPVIELEDYSDPLYPWKVRAELA<br>ASYIADEKERGEKLSVALRHIARHRGWRNPYAKVSSLYLPDGPSDAFKAIREEI<br>KRASGQPVPETATVGQMVTLCELGTLKLRGEGGVLSARLQQSDYAREIQEICR<br>MQEIGQELYRKIIDVVFAAESPKGSASSRVGKDPLQPGKNRALKASDAFQRYRI<br>AALIGNLRVRVDGEKRILSVEEKNLVFDHLVNLTPKKEPEWVTIAEILGIDRGQL<br>IGTATMTDDGERAGARPPTHDTNRSIVNSRIAPLVDWWKTASALEQHAMVKAL<br>SNAEVDDFDSPEGAKVQAFFADLDDDVHAKLDSLHLPVGRAAYSEDTLVRLTR<br>RMLSDGVDLYTARLQEFGIEPSWTPPTPRIGEPVGNPAVDRVLKTVSRWLESAT<br>KTWGAPERVIIEHVREGFVTEKRAREMDGDMRRRAARNAKLFQEMQEKLNVQ<br>GKPSRADLWRYQSVQRQNCQCAYCGSPITFSNSEMDHIVPRAGQGSTNTRENL<br>VAVCHRCNQSKGNTPFAIWAKNTSIEGVSVKEAVERTRHWVTDTGMRSTDFK<br>KFTKAVVERFQRATMDEEIDARSMESVAWMANELRSRVAQHFASHGTTVRVY<br>RGSLTAEARRASGISGKLKFFDGVGKSRLDRRHHAIDAAVIAFTSDYVAETLAV<br>RSNLKQSQAHRQEAPQWREFTGKDAEHRAAWRVWCQKMEKLSALLTEDLRD<br>DRVVVMSNVRLRLGNGSAHKETIGKLSKVKLSSQLSVSDIDKASSEALWCALT<br>REPGFDPKEGLPANPERHIRVNGTHVYAGDNIGLFPVSAGSIALRGGYAELGSSF<br>HHARVYKITSGKKPAFAMLRVYTIDLLPYRNQDLFSVELKPQTMSMRQAEKKL<br>RDALATGNAEYLGWLVVDDELVVDTSKIATDQVKAVEAELGTIRRWRVDGFF<br>SPSKLRLRPLQMSKEGIKKESAPELSKIIDRPGWLPAVNKLFSDGNVTVVRRDSL<br>GRVRLESTAHLPVTWKVQ* |
| *Streptococcus pasteurianus* Cas9<br>SEQ ID NO: 7 | MTNGKILGLDIGIASVGVGIIEAKTGKVVHANSRLFSAANAENNAERRGFRGSR<br>RLNRRKKHRVKRVRDLFEKYGIVTDFRNLNLNPYELRVKGLTEQLKNEELFAA<br>LRTISKRRGISYLDDAEDDSTGSTDYAKSIDENRRLLKNKTPGQIQLERLEKYGQ<br>LRGNFTVYDENGEAHRLINVFSTSDYEKEARKILETQADYNKKITAEFIDDYVEI<br>LTQKRKYYHGPGNEKSRTDYGRFRTDGTTLENIFGILIGKCNFYPDEYRASKAS<br>YTAQEYNFLNDLNNLKVSTETGKLSTEQKESLVEFAKNTATLGPAKLLKEIAKI<br>LDCKVDEIKGYREDDKGKPDLHTFEPYRKLKFNLESINIDDLSREVIDKLADILT<br>LNTEREGIEDAIKRNLPNQFTEEQISEIIKVRKSQSTAFNKGWHSFSAKLMNELIP<br>ELYATSDEQMTILTRLEKFKVNKKSSKNTKTIDEKEVTDEIYNPVVAKSVRQTIK<br>IINNAAVKKYGDFDKIVIEMPRDKNADDEKKFIDKRNKENKKEKDDALKRAAYL<br>YNSSDKLPDEVFHGNKQLETKIRLWYQQGERCLYSGKPISIQELVHNSNNFEID<br>HILPLSLSFDDSLANKVLVYAWTNQEKGQKTPYQVIDSMDAAWSFREMKDYV<br>LKQKGLGKKKRDYLLTTENIDKIEVKKKFIERNLVDTRYASRVVLNSLQSALRE<br>LGKDTKVSVVRGQFTSQLRRKWKIDKSRETYHHHAVDALIIAASSQLKLWEKQ<br>DNPMFVDYGKNQVVDKQTGEILSVSDDEYKELVFQPPYQGFVNTISSKGFEDEI<br>LFSYQVDSKYNRKVSDATIYSTRKAKIGKDKKEETYVLGKIKDIYSQNGFDTFIK<br>KYNKDKTQFLMYQKDSLTWENVIEVILRDYPTTKKSEDGKNDVKCNPFEEYRR<br>ENGLICKYSKKGKGTPIKSLKYYDKKLGNCIDITPEESRNKVILQSINPWRADVY |

| Name | Protein Sequence |
| --- | --- |
| | FNPETLKYELMGLKYSDLSFEKGTGNYHISQEKYDAIKEKEGIGKKSEFKFTLY<br>RNDLILIKDIASGEQEIYRFLSRTMPNVNHYVELKPYDKEKFDNVQELVEALGE<br>ADKVGRCIKGLNKPNISIYKVRTDVLGNKYFVKKKGDKPKLDFKNNKK* |
| Neisseria cinerea Cas9<br>SEQ ID NO: 8 | MAAFKPNPMNYILGLDIGIASVGWAIVEIDEEENPIRLIDLGVRVFERAEVPKTG<br>DSLAAARRLARSVRRLTRRRAHRLLRARRLLKREGVLQAADFDENGLIKSLPN<br>TPWQLRAAALDRKLTPLEWSAVLLHLIKHRGYLSQRKNEGETADKELGALLKG<br>VADNTHALQTGDFRTPAELALNKFEKESGHIRNQRGDYSHTFNRKDLQAELNL<br>LFEKQKEFGNPHVSDGLKEGIETLLMTQRPALSGDAVQKMLGHCTFEPTEPKA<br>AKNTYTAERFVWLTKLNNLRILEQGSERPLTDTERATLMDEPYRKSKLTYAQA<br>RKLLDLDDTAFFKGLRYGKDNAEASTLMEMKAYHAISRALEKEGLKDKKSPL<br>NLSPELQDEIGTAFSLFKTDEDITGRLKDRVQPEILEALLKHISFDKFVQISLKAL<br>RRIVPLMEQGNRYDEACTEIYGDHYGKKNTEEKIYLPPIPADEIRNPVVLRALSQ<br>ARKVINGVVRRYGSPARIHIETAREVGKSFDRKEIEKRQEENRKDREKSAAKF<br>REYFPNFVGEPKSKDILKLRLYEQQHGKCLYSGKEINLGRLNEKGYVEIDHALP<br>FSRTWDDSFNNKVLALGSENQNKGNQTPYEYFNGKDNSREWQEFKARVETSR<br>FPPRSKKQRILLQKFDEDGFKERNLNDTRYINRFLCQFVADHMLLTGKGKRRVF<br>ASNGQITNLLRGFWGLRKVRAENDRHHALDAVVVACSTIAMQQKITRFVRYKE<br>MNAFDGKTIDKETGEVLHQKAHFPQPWEFFAQEVMIRVFGKPDGKPEFEEADT<br>PEKLRTLLAEKLSSRPEAVHKYVTPLFISRAPNRKMSGQGHMETVKSAKRLDE<br>GISVLRVPLTQLKLKDLEKMVNREREPKLYEALKARLEAHKDDPAKAFAEPFY<br>KYDKAGNRTQQVKAVRVEQVQKTGVWVHNHNGIADNATIVRVDVFEKGGKY<br>YLVPIYSWQVAKGILPDRAVVQGKDEEDWTVMDDSFEFKFVLYANDLIKLTAK<br>KNEFLGYFVSLNRATGAIDIRTHDTDSTKGKNGIFQSVGVKTALSFQKYQIDEL<br>GKEIRPCRLKKRPPVR* |
| Campylobacter lari Cas9<br>SEQ ID NO: 9 | MRILGFDIGINSIGWAFVENDELKDCGVRIFTKAENPKNKESLALPRRNARSSRR<br>RLKRRKARLIAIKRILAKELKLNYKDYVAADGELPKAYEGSLASVYELRYKALT<br>QNLETKDLARVILHIAKHRGYMNKNEKKSNDAKKGKILSALKNNALKLENYQS<br>VGEYFYKEFFQKYKKNTKNFIKIRNTKDNYNNCVLSSDLEKELKLILEKQKEFG<br>YNYSEDFINEILKVAFFQRPLKDFSHLVGACTFFEEEKRACKNSYSAWEFVALT<br>KIINEIKSLEKISGEIVPTQTINEVLNLILDKGSITYKKFRSCINLHESISFKSLKYD<br>ENAENAKLIDFRKLVEFKKALGVHSLSRQELDQISTHITLIKDNVKLKTVLEKYN<br>LSNEQINNLLEIEFNDYINLSFKALGMILPLMREGKRYDEACEIANLKPKTVDEK<br>KDFLPAFCDSIFAHELSNPVVNRAISEYRKVLNALLKKYGKVHKIHLELARDVG<br>LSKKAREKIEKEQKENQAVNAWALKECENIGLKASAKNILKLKLWKEQKEICIY<br>SGNKISIEHLKDEKALEVDHIYPYSRSFDDSFINKVLVFTKENQEKLNKTPFEAF<br>GKNIEKWSKIQTLAQNLPYKKKNKILDENFKDKQQEDFISRNLNDTRYIATLIAK<br>YTKEYLNFLLLSENENANLKSGEKGSKIHVQTISGMLTSVLRHTWGFDKKDRN<br>NHLHHALDAIIVAYSTNSIIKAFSDFRKNQELLKARFYAKELTSDNYKHQVKFFE<br>PFKSFREKILSKIDEIFVSKPPRKRARRALHKDTFHSENKIIDKCSYNSKEGLQIAL<br>SCGRVRKIGTKYVENDTIVRVDIFKKQNKFYAIPIYAMDFALGILPNKIVITGKD<br>KNNNPKQWQTIDESYEFCFSLYKNDLILLQKKNMQEPEFAYYNDFSISTSSICVE<br>KHDNKFENLTSNQKLLFSNAKEGSVKVESLGIQNLKVFEKYIITPLGDKIKADFQ<br>PRENISLKTSKKYGLR* |
| T. denticola Cas9<br>SEQ ID NO: 10 | MKKEIKDYFLGLDVGTGSVGWAVTDTDYKLLKANRKDLWGMRCFETAETAE<br>VRRLHRGARRRIERRKKRIKLLQELFSQEIAKTDEGFFQRMKESPFYAEDKTILQ<br>ENTLFNDKDFADKTYHKAYPTINHLIKAWIENKVKPDPRLLYLACHNIIKRGH<br>FLFEGDFDSENQFDTSIQALFEYLREDMEVDIDADSQKVKEILKDSSLKNSEKQS<br>RLNKILGLKPSDKQKKAITNLISGNKINFADLYDNPDLKDAEKNSISFSKDDFDA<br>LSDDLASILGDSFELLLKAKAVYNCSVLSKVIGDEQYLSFAKVKIYEKHKTDLT<br>KLKNVIKKHFPKDYKKVFGYNKNEKNNNNYSGYVGVCKTKSKKLIINNSVNQ<br>EDFYKFLKTILSAKSEIKEVNDILTEIETGTFLPKQISKSNAEIPYQLRKMELEKIL<br>SNAEKHFSPLKQKDEKGLSHSEKIIMLLTFKIPYYIGPINDNHKKFFPDRCWVVK<br>KEKSPSGKTTPWNFFDHIDKEKTAEAFITSRTNFCTYLVGESVLPKSSLLYSEYT<br>VLNEINNLQIIIDGKNICDIKLKQKIYEDLFKKYKKITQKQISTFIKHEGICNKTDE<br>VIILGIDKECTSSLKSYIELKNIFGKQVDEISTKNMLEEIIRWATIYDEGEGKTILK<br>TKIKAEYGKYCSDEQIKKILNLKFSGWGRLSRKFLETVTSEMPGFSEPVNIITAM<br>RETQNNLMELLSSEFTFTENIKKINSGFEDAEKQFSYDGLVKPLFLSPSVKKML<br>WQTLKLVKEISHITQAPPKKIFIEMAKGAELEPARTKTRLKILQDLYNNCKNDA<br>DAFSSEIKDLSGKIENEDNLRLRSDKLYLYYTQLGKCMYCGKPIEIGHVFDTSNY<br>DIDHIYPQSKIKDDSISNRVLVCSSCNKNEKEDYPLKSEIQSKQRGFWNFLQRNN<br>FISLEKLNRLTRATPISDDETAKFIARQLVETRQATKVAAKVLEKMFPETKIVYS<br>KAETVSMFRNKFDIVKCREINDFHHAHDAYLNIVVGNVYNTKFTNNPWNFIKE<br>KRDNPKIADTYNYYKVFDYDVKRNNITAWEKGKTIITVKDMLKRNTPIYTRQA<br>ACKKGELFNQTIMKKGLGQHPLKKEGPFSNISKYGGYNKVSAAYYTLIEYEEK<br>GNKIRSLETIPLYLVKDIQKDQDVLKSYLTDLLGKKEFKILVPKIKINSLLKINGF<br>PCHITGKTNDSFLLRPAVQFCCSNNEVLYFKKIIRFSEIRSQREKIGKTISPYEDLS<br>FRSYIKENLWKKTKNDEIGEKEFYDLLQKKNLEIYDMLLTKHKDTIYKKRPNSA<br>TIDILVKGKEKFKSLIIENQFEVILEILKLFSATRNVSDLQHIGGSKYSGVAKIGNK<br>ISSLDNCILIYQSITGIFEKRIDLLKV* |
| S. mutans Cas9<br>SEQ ID NO: 11 | MKKPYSIGLDIGTNSVGWAVVTDDYKVPAKKMKVLGNTDKSHIEKNLLGALL<br>FDSGNTAEDRRLKRTARRRYTRRRNRILYLQEIFSEEMGKVDDSFFHRLEDSFL<br>VTEDKRGERHPIFGNLEEEVKYHENFPTIYHLRQYLADNPEKVDLRLVYLALAH<br>IIKFRGHFLIEGKFDTRNNDVQRLFQEFLAVYDNTFENSSLQEQNVQVEEILTDKI |

| Name | Protein Sequence |
|---|---|
| | SKSAKKDRVLKLFPNEKSNGRFAEFLKLIVGNQADFKKHFELEEKAPLQFSKDT<br>YEEELEVLLAQIGDNYAELFLSAKKLYDSILLSGILTVTDVGTKAPLSASMIQRY<br>NEHQMDLAQLKQFIRQKLSDKYNEVFSDVSKDGYAGYIDGKTNQEAFYKYLK<br>GLLNKIEGSGYFLDKIEREDFLRKQRTFDNGSIPHQIHLQEMRAIIRRQAEFYPFL<br>ADNQDRIEKLLTFRIPYYVGPLARGKSDFAWLSRKSADKITPWNFDEIVDKESS<br>AEAFINRMTNYDLYLPNQKVLPKHSLLYEKFTVYNELTKVKYKTEQGKTAFFD<br>ANMKQEIFDGVFKVYRKVTKDKLMDFLEKEFDEFRIVDLTGLDKENKVFNASY<br>GTYHDLCKILDKDFLDNSKNEKILEDIVLTLTLFEDREMIRKRLENYSDLLTKEQ<br>VKKLERRHYTGWGRLSAELIHGIRNKESRKTILDYLIDDGNSNRNFMQLINDDA<br>LSFKEEIAKAQVIGETDNLNQVVSDIAGSPAIKKGILQSLKIVDELVKIMGHQPE<br>NIVVEMARENQFTNQGRRNSQQRLKGLTDSIKEFGSQILKEHPVENSQLQNDRL<br>FLYYLQNGRDMYTGEELDIDYLSQYDIDHIIPQAFIKDNSIDNRVLTSSKENRGK<br>SDDVPSKDVVRKMKSYWSKLLSAKLITQRKFDNLTKAERGGLTDDDKAGFIKR<br>QLVETRQITKHVARILDERFNTETDENNKKIRQVKIVTLKSNLVSNFRKEFELYK<br>VREINDYHHAHDAYLNAVIGKALLGVYPQLEPEFVYGDYPHFHGHKENKATA<br>KKFFYSNIMNFFKKDDVRTDKNGEIIWKKDEHISNIKKVLSYPQVNIVKKVEEQ<br>TGGFSKESILPKGNSDKLIPRKTKKFYWDTKKYGGFDSPIVAYSILVIADIEKGKS<br>KKLKTVKALVGVTIMEKMTFERDPVAFLERKGYRNVQEENIIKLPKYSLFKLEN<br>GRKRLLASARELQKGNEIVLPNHLGTLLYHAKNIHKVDEPKHLDYVDKHKDEF<br>KELLDVVSNFSKKYTLAEGNLEKIKELYAQNNGEDLKELASSFINLLTFTAIGAP<br>ATFKFFDKNIDRKRYTSTTEILNATLIHQSITGLYETRIDLNKLGGD |
| S. thermophilus CRISPR 3 Cas9<br>SEQ ID NO: 12 | MTKPYSIGLDIGTNSVGWAVTTDNYKVPSKKMKVLGNTSKKYIKKNLLGVLLF<br>DSGITAEGRRLKRTARRRYTRRRNRILYLQEIFSTEMATLDDAFFQRLDDSFLVP<br>DDKRDSKYPIFGNLVEEKAYHDEFPTIYHLRKYLADSTKKADLRLVYLALAHM<br>IKYRGHFLIEGEFNSKNNDIQKNFQDFLDTYNAIFESDLSLENSKQLEEIVKDKIS<br>KLEKKDRILKLFPGEKNSGIFSEFLKLIVGNQADFRKCFNLDEKASLHFSKESYD<br>EDLETLLGYIGDDYSDVFLKAKKLYDAILLSGFLTVTDNETEAPLSSAMIKRYN<br>EHKEDLALLKEYIRNISLKTYNEVFKDDTKNGYAGYIDGKTNQEDFYVYLKKL<br>LAEFEGADYFLEKIDREDFLRKQRTFDNGSIPYQIHLQEMRAILDKQAKFYPPLA<br>KNKERIEKILTFRIPYYVGPLARGNSDFAWSIRKRNEKITPWNFEDVIDKESSAE<br>AFINRMTSFDLYLPEEKVLPKHSLLYETFNVYNELTKVRFIAESMRDYQFLDSK<br>QKKDIVRLYFKDKRKCVTDKDIIEYLHAIYGYDGIELKGIEKQFNSSLSTYHDLLN<br>IINDKEFLDDSSNEAIIEEIIHTLTIFEDREMIKQRLSKFENIFDKSVLKKLSRRHYT<br>GWGKLSAKLINGIRDEKSGNTILDYLIDDGISNRNFMQLIHDDALSFKKKIQKAQ<br>IIGDEDKGNIKEVVKSLPGSPAIKKGILQSIKIVDELVKVMGGRKPESIVVEMARE<br>NQYTNQGKSNSQQRLKRLEKSLKELGSKILKENIPAKLSKIDNNALQNDRLYLY<br>YLQNGKDMYTGDDLDIDRLSNYDIDHIIPQAFLKDNSIDNKVLVSSASNRGKSD<br>DVPSLEVVKKRKTFWYQLLKSKLISQRKFDNLTKAERGGLSPEDKAGFIQRQLV<br>ETRQITKHVARLLDEKFNNKKDENNRAVRTVKIITLKSTLVSQFRKDFELYKVR<br>EINDFHHAHDAYLNAVVASALLKKYPKLEPEFVYGDYPKYNSFRERKSATEKV<br>YFYSNIMNIFKKSISLADGRVIERPLIEVNEETGESVWNKESDLATVRRVLSYPQ<br>VNNVVKKVEEQNHGLDRGKPKGLFNANLSSKPKPNSNENLVGAKEYLDPKKYG<br>GYAGISNSFTVLVKGTIEKGAKKKITNVLEFQGISILDRINYRKDKLNFLLEKGY<br>KDIELIIELPKYSLFELSDGSRRMLASILSTNNKRGEIHKGNQIFLSQKFVKLLYH<br>AKRISNTINENHRKYVENHKKEFEELFYYILEFNENYVGAKKNGKLLNSAFQSW<br>QNHSIDELCSSFIGPTGSERKGLFELTSRGSAADFEFLGVKIPRYRDYTPSSLLKD<br>ATLIHQSVTGLYETRIDLAKLGEG |
| C. jejuni Cas9<br>SEQ ID NO: 13 | MARILAFDIGISSIGWAFSENDELKDCGVRIFTKVENPKTGESLALPRRLARSAR<br>KRLARRKARLNHLKHLIANEFKLNYEDYQSFDESLAKAYKGSLISPYELRFRAL<br>NELLSKQDFARVILHIAKRRGYDDIKNSDDKEKGAILKAIKQNEEKLANYQSVG<br>EYLYKEYFQKFKENSKEFTNVRNKKESYERCIAQSFLKDELKLIFKKQREFGFSF<br>SKKFEEEVLSVAFYKRALKDFSHLVGNCSFFTDEKRAPKNSPLAFMFVALTRIIN<br>LLNNLKNTEGILYTKDDLNALLNEVLKNGTLTYKQTKKLLGLSDDYEFKGEKG<br>TYFIEFKKYKEFIKALGEHNLSQDDLNEIAKDITLIKDEIKLKKALAKYDLNQNQ<br>IDSLSKLEFKDHLNISFKALKLVTPLMLEGKKYDEACNELNLKVAINEDKKDFL<br>PAFNETYYKDEVTNPVVLRAIKEYRKVLNALLKKYGKVHKINIELAREVGKNH<br>SQRAKIEKEQNENYKAKKDAELECEKLGLKINSKNILKLRLFKEQKEFCAYSGE<br>KIKISDLQDEKMLEIDHIYPYSRSFDDSYMNKVLVFTKQNQEKLNQTPFEAFGN<br>DSAKWQKIEVLAKNLPTKKQKRILDKNYKDKEQKNFKDRNLNDTRYIARLVL<br>NYTKDYLDFLPLSDDENTKLNDTQKGSKVHVEAKSGMLTSALRHTWGFSAKD<br>RNNHLHHAIDAVIIAYANNSIVKAFSDFKKEQESNSAELYAKKISELDYKNKRK<br>FFEPFSGFRQKVLDKIDEIFVSKPERKKPSGALHEETFRKEEEFYQSYGGKEGVL<br>KALELGKIRKVNGKIVKNGDMFRVDIFKHKKTNKFYAVPIYTMDFALKVLPNK<br>AVARSKKGEIKDWILMDENYEFCFSLYKDSLILIQTKDMQEPEFVYYNAFTSST<br>VSLIVSKHDNKFETLSKNQKILFKNANEKEVIAKSIGIQNLKVFEKYIVSALGEVT<br>KAEFRQREDFKK |
| P. multocida Cas9<br>SEQ ID NO: 14 | MQTTNLSYILGLDLGIASVGWAVVEINENEDPIGLIDVGVRIFERAEVPKTGESL<br>ALSRRLARSTRRLIRRRAHRLLLAKRFLKREGILSTIDLEKGLPNQAWELRVAGL<br>ERRLSAIEWGAVLLHLIKHRGYLSKRKNESQTNNKELGALLSGVAQNHQLLQS<br>DDYRTPAELALKKFAKEEGHIRNQRGAYTHTFNRLDLLAELNLLFAQQHQFGN<br>PHCKEHIQQYMTELLMWQKPALSGEAILKMLGKCTHEKNEFKAAKHTYSAER<br>FVWLTKLNNLRILEDGAERALNEEERQLLINHPYEKSKLTYAQVRKLLGLSEQA<br>IFKHLRYSKENAESATFMELKAWHAIRKALENQGLKDTWQDLAKKPDLLDEIG<br>TAFSLYKTDEDIQQYLTNKVPNSVINALLVSLNFDKFIELSLKSLRKILPLMEQG |

| Name | Protein Sequence |
|---|---|
| | KRYDQACREIYGHHYGEANQKTSQLLPAIPAQEIRNPVVLRTLSQARKVINAIIR<br>QYGSPARVHIETGRELGKSFKERREIQKQQEDNRTKRESAVQKFKELFSDFSSEP<br>KSKDILKFRLYEQQHGKCLYSGKEINIHRLNEKGYVEIDHALPFSRTWDDSFNN<br>KVLVLASENQNKGNQTPYEWLQGKINSERWKNFVALVLGSQCSAAKKQRLLT<br>QVIDDNKFIDRNLNDTRYIARFLSNYIQENLLLVGKNKKNVFTPNGQITALLRSR<br>WGLIKARENNNRHHALDAIVVACATPSMQQKITRFIRFKEVHPYKIENRYEMV<br>DQESGEIISPHFPEPWAYFRQEVNIRVFDNHPDTVLKEMLPDRPQANHQFVQPL<br>FVSRAPTRKMSGQGHMETIKSAKRLAEGISVLRIPLTQLKPNLLENMVNKEREP<br>ALYAGLKARLAEFNQDPAKAFATPFYKQGGQQVKAIRVEQVQKSGVLVRENN<br>GVADNASIVRTDVFIKNNKFFLVPIYTWQVAKGILPNKAIVAHKNEDEWEEMD<br>EGAKFKFSLFPNDLVELKTKKEYFFGYYIGLDRATGNISLKEHDGEISKGKDGV<br>YRVGVKLALSFEKYQVDELGKNRQICRPQQRQPVR |
| *F. novicida* Cas9<br>SEQ ID NO: 15 | MNFKILPIAIDLGVKNTGVFSAFYQKGTSLERLDNKNGKVYELSKDSYTLLMNN<br>RTARRHQRRGIDRKQLVKRLFKLIWTEQLNLEWDKDTQQAISFLFNRRGFSFIT<br>DGYSPEYLNIVPEQVKAILMDIFDDYNGEDDLDSYLKLATEQESKISEIYNKLM<br>QKILEFKLMKLCTDIKDDKVSTKTLKEITSYEFELLADYLANYSESLKTQKFSYT<br>DKQGNLKELSYYHHDKYNIQEFLKRHATINDRILDTLLTDDLDIWNFNFEKFDF<br>DKNEEKLQNQEDKDHIQAHLHHFVFAVNKIKSEMASGGRHRSQYFQEITNVLD<br>ENNHQEGYLKNFCENLHNKKYSNLSVKNLVNLIGNLSNLELKPLRKYFNDKIH<br>AKADHWDEQKFTETYCHWILGEWRVGVKDQDKKDGAKYSYKDLCNELKQK<br>VTKAGLVDFLLELDPCRTIPPYLDNNNRKPPKCQSLILNPKFLDNQYPNWQQYL<br>QELKKLQSIQNYLDSFETDLKVLKSSKDQPYFVEYKSSNQQIASGQRDYKDLDA<br>RILQFIFDRVKASDELLLNEIYFQAKKLKQKASSELEKLESSKKLDEVIANSQLSQ<br>ILKSQHTNGIFEQGTFLHLVCKYYKQRQRARDSRLYIMPEYRYDKKLHKYNNT<br>GRFDDDNQLLTYCNHKPRQKRYQLLNDLAGVLQVSPNFLKDKIGSDDDLFISK<br>WLVEHIRGFKKACEDSLKIQKDNRGLLNHKINIARNTKGKCEKEIFNLICKIEGS<br>EDKKGNYKHGLAYELGVLLFGEPNEASKPEFDRKIKKFNSIYSFAQIQQIAFAER<br>KGNANTCAVCSADNAHRMQQIKITEPVEDNKDKIILSAKAQRLPAIPTRIVDGA<br>VKKMATILAKNIVDDNWQNIKQVLSAKHQLHIPIITESNAFEFEPALADVKGKS<br>LKDRRKKALERISPENIFKDKNNRIKEFAKGISAYSGANLTDGDFDGAKEELDHI<br>IPRSHKKYGTLNDEANLICVTRGDNKNKGNRIFCLRDLADNYKLKQFETTDDLE<br>IEKKIADTIWDANKKDFKFGNYRSFINLTPQEQKAFRHALFLADENPIKQAVIRA<br>INNRNRTFVNGTQRYFAEVLANNIYLRAKKENLNTDKISFDYFGIPTIGNGRGIA<br>EIRQLYEKVDSDIQAYAKGDKPQASYSHLIDAMLAFCIAADEHRNDGSIGLEID<br>KNYSLYPLDKNTGEVFTKDIFSQIKITDNEFSDKKLVRKKAIEGFNTHRQMTRD<br>GIYAENYLPILIHKELNEVRKGYTWKNSEEIKIFKGKKYDIQQLNNLVYCLKFV<br>DKPISIDIQISTLEELRNILTTNNIAATAEYYYINLKTQKLHEYYIENYNTALGYK<br>KYSKEMEFLRSLAYRSERVKIKSIDDVKQVLDKDSNFIIGKITLPFKKEWQRLYR<br>EWQNTTIKDDYEFLKSFFNVKSITKLHKKVRKDFSLPISTNEGKFLVKRKTWDN<br>NFIYQILNDSDSRADGTKPFIPAFDISKNEIVEAIIDSFTSKNIFWLPKNIELQKVD<br>NKNIFAIDTSKWFEVETPSDLRDIGIATIQYKIDNNSRPKVRVKLDYVIDDDSKIN<br>YFMNHSLLKSRYPDKVLEILKQSTIIEFESSGFNKTIKEMLGMKLAGIYNETSNN |
| *Lactobacillus buchneri* Cas9<br>SEQ ID NO: 16 | MKVNNYHIGLDIGTSSIGWVAIGKDGKPLRVKGKTAIGARLFQEGNPAADRRM<br>FRTTRRRLSRRKWRLKLLEEIFDPYITPVDSTFFARLKQSNLSPKDSRKEFKGSM<br>LFPDLTDMQYHKNYPTIYHLRHALMTQDKKFDIRMVYLAIHHIVKYRGNFLNS<br>TPVDSFKASKVDFVDQFKKLNELYAAINPEESFKINLANSEDIGHQFLDPSIRKF<br>DKKQIPKIVPVMMNDKVTDRLNGKIASEIIHAILGYKAKLDVVLQCTPVDSKP<br>WALKFDDEDIDAKLEKILPEMDENQQSIVAILQNLYSQVTLNQIVPNGMSLSES<br>MIEKYNDHHDHLKLYKKLIDQLADPKKKAVLKKAYSQYVGDDGKVIEQAEFW<br>SSVKKNLDDSELSKQIMDLIDAEKFMPKQRTSQNGVIPHQLHQRELDEIIEHQSK<br>YYPWLVEINPNKHDLHLAKYKIEQLVAFRVPYYVGPMITPKDQAESAETVFSW<br>MERKGTETGQITPWNFDEKVDRKASANRFIKRMTTKDTYLIGEDVLPDESLLYE<br>KPFKVLNELNMVRVNGKLLKVADKQAIFQDLFENYKHVSVKKLQNYIKAKTGL<br>PSDPEISGLSDPEHFNNSLGTYNDFKKLFGSKVDEPDLQDDFEKIVEWSTVFEDK<br>KILREKLNEITWLSDQQKDVLESSRYQGWGRLSKKLLTGIVNDQGERIIDKLWN<br>TNKNFMQIQSDDDFAKRIHEANADQMQAVDVEDVLADAYTSPQNKKAIRQVV<br>KVVDDIQKAMGGVAPKYISIEFTRSEDRNPRRTISRQRQLENTLKDTAKSLAKSI<br>NPELLSELDNAAKSKKGLTDRLYLYFTQLGKDIYTGEPINIDELNKYDIDHILPQ<br>AFIKDNSLDNRVLVLTAVNNGKSDNVPLRMFGAKMGHFWKQLAEAGLISKRK<br>LKNLQTDPDTISKYAMHGFIRRQLVETSQVIKLVANILGDKYRNDDTKIIEITAR<br>MNHQMRDEFGFIKNREINDYHHAFDAYLTAFLGRYLHRYIKLRPYFVYGDFK<br>KFREDKVTMRNFNFLHDLTDDTQEKIADAETGEVIWDRENSIQQLKDVYHYKF<br>MLISHEVYTLRGAMFNQTVYPASDAGKRKLIPVKADRPVNVYGGYSGSADAY<br>MAIVRIHNKKGDKYRVVGVPMRALDRLDAAKNVSDADFDRALKDVLAPQLT<br>KTKKKSRKTGEITQVIEDFEIVLGKVMYRQLMIDGDKKFMLGSSTYQYNAKQLV<br>LSDQSVKTLASKGRLDPLQESMDYNNVYTEILDKVNQYFSLYDMNKFRHKLN<br>LGFSKFISFPNHNVLDGNTKVSSGKREILQEILNGLHANPTFGNLKDVGITTPFG<br>QLQQPNGILLSDETKIRYQSPTGLFERTVSLKDL |
| *Listeria innocua* Cas9<br>SEQ ID NO: 17 | MKKPYTIGLDIGTNSVGWAVLTDQYDLVKRKMKIAGDSEKKQIKKNFWGVRL<br>FDEGQTAADRRMARTARRRIERRRNRISYLQGIFAEEMSKTDANFFCRLSDSFY<br>VDNEKRNSRHPFFATIEEEVEYHKNYPTIYHLREELVNSSEKADLRLVYLALAHI<br>IKYRGNFLIEGALDTQNTSVDGIYKQFIQTYNQVFASGIEDGSLKKLEDNKDVA<br>KILVEKVTRKEKLERILKLYPGEKSAGMFAQFISLIVGSKGNFQKPFDLIEKSDIE<br>CAKDSYEEDLESLLALIGDEYAELFVAAKNAYSAVVLSSIITVAETETNAKLSAS |

-continued

| Name | Protein Sequence |
|---|---|
| | MIERFDTHEEDLGELKAFIKLHLPKHYEEIFSNTEKHGYAGYIDGKTKQADFYK<br>YMKMTLENIEGADYFIAKIEKENFLRKQRTFDNGAIPHQLHLEELEAILHQQAK<br>YYPPLKENYDKIKSLVTFRIPYFVGPLANGQSEFAWLTRKADGEIRPWNIEEKV<br>DFGKSAVDFIEKMTNKDTYLPKENVLPKHSLCYQKYLVYNELTKVRYINDQGK<br>TSYFSGQEKEQIFNDLFKQKRKVKKKDLELFLRNMSHVESPTIEGLEDSFNSSYS<br>TYHDLLKVGIKQEILDNPVNTEMLENIVKILTVFEDKRMIKEQLQQFSDVLDGV<br>VLKKLERRHYTGWGRLSAKLLMGIRDKQSHLTILDYLMNDDGLNRNLMQLIN<br>DSNLSFKSIIEKEQVTTADKDIQSIVADLAGSPAIKKGILQSLKIVDELVSVMGYP<br>PQTIVVEMARENQTTGKGKNNSRPRYKSLEKAIKEFGSQILKEHPTDNQELRNN<br>RLYLYYLQNGKDMYTGQDLDIHNLSNYDIDHIVPQSFITDNSIDNLVLTSSAGN<br>REKGDDVPPLEIVRKRKVFWEKLYQGNLMSKRKFDYLTKAERGGLTEADKAR<br>FIHRQLVETRQITKNVANILHQRFNYEKDDHGNTMKQVRIVTLKSALVSQFRKQ<br>FQLYKVRDVNDYHHAHDAYLNGVVANTLLKVYPQLEPEFVYGDYHQFDWFK<br>ANKATAKKQFYTNIMLFFAQKDRIIDENGEILWDKKYLDTVKKVMSYRQMNIV<br>KKTEIQKGEFSKATIKPKGNSSKLIPRKTNWDPMKYGGLDSPNMAYAVVIEYA<br>KGKNKLVFEKKIIRVTIMERKAFEKDEKAFLEEQGYRQPKVLAKLPKYTLYECE<br>EGRRRMLASANEAQKGNQQVLPNHLVTLLHHAANCEVSDGKSLDYIESNREM<br>FAELLAHVSEFAKRYTLAEANLNKINQLFEQNKEGDIKAIAQSFVDLMAFNAM<br>GAPASFKFFETTIERKRYNNLKELLNSTIIYQSITGLYESRKRLDD |
| *L. pneumophilia*<br>Cas9<br>SEQ ID NO: 18 | MESSQILSPIGIDLGGKFTGVCLSHLEAFAELPNHANTKYSVILIDHNNFQLSQA<br>QRRATRHRVRNKKRNQFVKRVALQLFQHILSRDLNAKEETALCHYLNNRGYT<br>YVDTDLDEYIKDETTINLLKELLPSESEHNFIDWFLQKMQSSEFRKILVSKVEEK<br>KDDKELKNAVKNIKNFITGFEKNSVEGHRHRKVYFENIKSDITKDNQLDSIKKKI<br>PSVCLSNLLGHLSNLQWKNLHRYLAKNPKQFDEQTFGNEFLRMLKNFRHLKGS<br>QESLAVRNLIQQLEQSQDYISILEKTPPEITIPPYEARTNTGMEKDQSLLLNPEKL<br>NNLYPNWRNLIPGIIDAHPFLEKDLEHTKLRDRKRIISPSKQDEKRDSYILQRYLD<br>LNKKIDKFKIKKQLSFLGQGKQLPANLIETQKEMETHFNSSLVSVLIQIASAYNK<br>EREDAAQGIWFDNAFSLCELSNINPPRKQKILPLLVGAILSEDFINNKDKWAKFK<br>IFWNTHKIGRTSLKSKCKEIEEARKNSGNAFKIDYEEALNHPEHSNNKALIKIIQT<br>IPDIIQAIQSHLGHNDSQALIYHNPFSLSQLYTILETKRDGFHKNCVAVTCENYW<br>RSQKTEIDPEISYASRLPADSVRPFDGVLARMMQRLAYEIAMAKWEQIKHIPDN<br>SSLLIPIYLEQNRFEFEESFKKIKGSSSDKTLEQAIEKQNIQWEEKFQRIINASMNI<br>CPYKGASIGGQGEIDHIYPRSLSKKHFGVIFNSEVNLIYCSSQGNREKKEEHYLL<br>EHLSPLYLKHQFGTDNVSDIKNFISQNVANIKKYISFHLLTPEQQKAARHALFLD<br>YDDEAFKTITKFLMSQQKARVNGTQKFLGKQIMEFLSTLADSKQLQLEFSIKQIT<br>AEEVHDHRELLSKQEPKLVKSRQQSFPSHAIDATLTMSIGLKEFPQFSQELDNS<br>WFINHLMPDEVHLNPVRSKEKYNKPNISSTPLFKDSLYAERFIPVWVKGETFAIG<br>FSEKDLFEIKPSNKEKLFTLLKTYSTKNPGESLQELQAKSKAKWLYFPINKTLAL<br>EFLHHYFHKEIVTPDDTTVCHFINSLRYYTKKESITVKILKEPMPVLSVKFESSKK<br>NVLGSFKHTIALPATKDWERLFNHPNFLALKANPAPNPKEFNEFIRKYFLSDNN<br>PNSDIPNNGHNIKPQKHKAVRKVFSLPVIPGNAGTMMRIRRKDNKGQPLYQLQ<br>TIDDTPSMGIQINEDRLVKQEVLMDAYKTRNLSTIDGINNSEGQAYATFDNWLT<br>LPVSTFKPEIIKLEMKPHSKTRRYIRITQSLADFIKTIDEALMIKPSDSIDDPLNMP<br>NEIVCKNLFGNELKPRDGKMKIVSTGKIVTYEFESDSTPQWIQTLYVTQLKKQP |
| *N. lactamica* Cas9<br>SEQ ID NO: 19 | MAAFKPNPMNYILGLDIGIASVGWAMVEVDEEENPIRLIDLGVRVFERAEVPKT<br>GDSLAMARRLARSVRRLTRRRAHRLLRARRLLKREGVLQDADFDENGLVKSL<br>PNTPWQLRAAALDRKLTCLEWSAVLLHLVKHRGYLSQRKNEGETADKELGAL<br>LKGVADNAHALQTGDFRTPAELALNKFEKESGHIRNQRGDYSHTFSRKDLQAE<br>LNLLFEKQKEFGNPHVSDGLKEDIETLLMAQRPALSGDAVQKMLGHCTFEPAE<br>PKAAKNTYTAERFIWLTKLNNLRILEQGSERPLTDTERATLMDEPYRKSKLTYA<br>QARKLLGLEDTAFFKGLRYGKDNAEASTLMEMKAYHAISRALEKEGLKDKKS<br>PLNLSTELQDEIGTAFSLFKTDKDITGRLKDRVQPEILEALLKHISFDKFVQISLK<br>ALRRIVPLMEQGKRYDEACAEIYGDHYCKKNAEEKIYLPPIPADEIRNPVVLRA<br>LSQARKVINCVVRRYGSPARIHIETAREVGKSFKDRKEIEKRQEENRKDREKAA<br>AKFREYFPNFVGEPKSKDILKLRLYEQQHGKCLYSGKEINLVRLNEKGYVEIDH<br>ALPFSRTWDDSFNNKVLVLGSENQNKGNQTPYEYFNGKDNSREWQEFKARVE<br>TSRFPPRSKKQRILLQKFDEEGFKERNLNDTRYVNRFLCQFVADHILLTGKGKRR<br>VFASNGQITNLLRGFWGLRKVRTENDRHHALDAVVVACSTVAMQQKITRFVR<br>YKEMNAFDGKTIDKETGEVLHQKAHFPQPWEFFAQEVMIRVFGKPDGKPEFEE<br>ADTPEKLRTLLAEKLSSRPEAVHEYVTPLFVSRAPNRKMSGQGHMETVKSAKR<br>LDEGISVLRVPLTQKLKGLEKMVNREREPKLYDALKAQLETHKDDPAKAFAE<br>PFYKYDKAGSRTQQVKAVRIEQVQKTGVWVRNHNGIADNATMRVDVFEKG<br>GKYYLVPIYSWQVAKGILPDRAVVAFKDEEDWTVMDDSFEFRFVLYANDLIKL<br>TAKKNEFLGYFVSLNRATGAIDRTHDTDSTKGKNGIFQSVGVKTALSFQKNQI<br>DELGKEIRPCRLKKRPPVR |
| *N. meningitides*<br>Cas9<br>SEQ ID NO: 20 | MAAFKPNPINYILGLDIGIASVGWAMVEIDEDENPICLIDLGVRVFERAEVPKTG<br>DSLAMARRLARSVRRLTRRRAHRLLRARRLLKREGVLQAADFDENGLIKSLPN<br>TPWQLRAAALDRKLTPLEWSAVLLHLIKHRGYLSQRKNEGETADKELGALLKG<br>VADNAHALQTGDFRTPAELALNKFEKESGHIRNQRGDYSHTFSRKDLQAELILL<br>FEKQKEFGNPHVSGGLKEGIETLLMTQRPALSGDAVQKMLGHCTFEPAEPKAA<br>KNTYTAERFIWLTKLNNLRILEQGSERPLTDTERATLMDEPYRKSKLTYAQARK<br>LLGLEDTAFFKGLRYGKDNAEASTLMEMKAYHAISRALEKEGLKDKKSPLNLS<br>PELQDEIGTAFSLFKTDEDITGRLKDRIQPEILEALLKHISFDKFVQISLKALRRIV<br>PLMEQGKRYDEACAEIYGDHYGKKNTEEKIYLPPIPADEIRNPVVLRALSQARK |

| Name | Protein Sequence |
|---|---|
| | VINGVVRRYGSPARIHIETAREVGKSFKDRKEIEKRQEENRKDREKAAAKFREY<br>FPNFVGEPKSKDILKLRLYEQQHGKCLYSGKEINLGRLNEKGYVEIDHALPFSRT<br>WDDSFNNKVLVLGSENQNKGNQTPYEYFNGKDNSREWQEFKARVETSRFPRS<br>KKQRILLQKFDEDGFKERNLNDTRYVNRFLCQFVADRMRLTGKGKKRVFASN<br>GQITNLLRGFWGLRKVRAENDRHHALDAVVVACSTVAMQQKITRFVRYKEMN<br>AFDGKTIDKETGEVLHQKTHFPQPWEFFAQEVMIRVFGKPDGKPEFEEADTPEK<br>LRTLLAEKLSSRPEAVHEYVTPLFVSRAPNRKMSGQGHMETVKSAKRLDEGVS<br>VLRVPLTQLKLKDLEKMVNREREPKLYEALKARLEAHKDDPAKAFAEPFYKY<br>DKAGNRTQQVKAVRVEQVQKTGVWVRNHNGIADNATMVRVDVFEKGDKYY<br>LVPIYSWQVAKGILPDRAVVQGKDEEDWQLIDDSFNFKFSLHPNDLVEVITKKA<br>RMFGYFASCHRGTGNINIRIHDLDHKIGKNGILEGIGVKTALSFQKYQIDELGKEI<br>RPCRLKKRPPVR |
| *B. longum* Cas9<br>SEQ ID NO: 21 | MLSRQLLGASHLARPVSYSYNVQDNDVHCSYGERCFMRGKRYRIGIDVGLNSV<br>GLAAVEVSDENSPVRLLNAQSVIHDGGVDPQKNKEAITRKNMSGVARRTRRM<br>RRRKRERLHKLDMLLGKFGYPVIEPESLDKPFEEWHVRAELATRYIEDDELRRE<br>SISIALRHMARHRGWRNPYRQVDSLISDNPYSKQYGELKEKAKAYNDDATAAE<br>EESTPAQLVVAMLDAGYAEAPRLRWRTGSKKPDAEGYLPVRLMQEDNANELK<br>QIFRVQRVPADEWKPLFRSVFYAVSPKGSAEQRVGQDPLAPEQARALKASLAF<br>QEYRIANVITNLRIKDASAELRKLTVDEKQSIYDQLVSPSSEDITWSDLCDFLGF<br>KRSQLKGVGSLTEDGEERISSRPPRLTSVQRIYESDNKIRKPLVAWWKSASDNE<br>HEAMIRLLSNTVDIDKVREDVAYASAIEFIDGLDDDALTKLDSVDLPSGRAAYS<br>VETLQKLTRQMLTTDDDLHEARKTLFNVTDSWRPPADPIGEPLGNPSVDRVLK<br>NVNRYLMNCQQRWGNPVSVNIEHVRSSFSSVAFARKDKREYEKNNEKRSIFRS<br>SLSEQLRADEQMEKVRESDLRRLEAIQRQNGQCLYCGRTITFRTCEMDHIVPRK<br>GVGSTNTRTNFAAVCAECNRMKSNTPFAIWARSEDAQTRGVSLAEAKKRVTM<br>FTFNPKSYAPREVKAFKQAVIARLQQTEDDAAIDNRSIESVAWMADELHRRID<br>WYFNAKQYVNSASIDDAEAETMKTTVSVFQGRVTASARRAAGIEGKIHPIGQQ<br>SKTRLDRRHHAVDASVIAMMNTAAAQTLMERESLRESQRLIGLMPGERSWKE<br>YPYEGTSRYESFHLWLDNMDVLLELLNDALDNDRIAVMQSQRYVLGNSIAHD<br>ATIHPLEKVPLGSAMSADLIRRASTPALWCALTRLPDYDEKEGLPEDSHREIRV<br>HDTRYSADDEMGFFASQAAQIAVQEGSADIGSAIHHARVYRCWKTNAKGVRK<br>YFYGMIRVFQTDLLRACHDDLFTVPLPPQSISMRYGEPRVVQALQSGNAQYLG<br>SLVVGDEIEMDFSSLDVDGQIGEYLQFFSQFSGGNLAWKHWVVDGFFNQTQLR<br>IRPRYLAAEGLAKAFSDDVVPDGVQKIVTKQGWLPPVNTASKTAVRIVRRNAF<br>GEPRLSSAHHMPCSWQWRHE |
| *A. muciniphila* Cas9<br>SEQ ID NO: 22 | MSRSLTFSFDIGYASIGWAVIASASHDDADPSVCGCGTVLFPKDDCQAFKRREY<br>RRLRRNIRSRRVRIERIGRLLVQAQIITPEMKETSGHPAPFYLASEALKGHRTLAP<br>IELWHVLRWYAHNRGYDNNASWSNSLSEDGGNGEDTERVKHAQDLMDKHGT<br>ATMAETICRELKLEEGKADAPMEVSTPAYKNLNTAFPRLIVEKEVRRILELSAPL<br>IPGLTAEIIELIAQHHPLTTEQRGVLLQHGIKLARRYRGSLLFGQLIPRFDNRIISR<br>CPVTWAQVYEAELKKGNSEQSARERAEKLSKVPTANCPEFYEYRMARILCNIR<br>ADGEPLSAEIRRELMNQARQEGKLTKASLEKAISSRLGKETETNVSNYFTLHPD<br>SEEALYLNPAVEVLQRSGIGQILSPSVYRIAANRLRRGKSVTPNYLLNLLKSRGE<br>SGEALEKKIEKESKKKEADYADTPLKPKYATGRAPYARTVLKKVVEEILDGEDP<br>TRPARGEAHPDGELKAHDGCLYCLLDTDSSVNQHQKERRLDTMTNNHLVRHR<br>MLILDRLLKDLIQDFADGQKDRISRVCVEVGKELTTFSAMDSKKIQRELTLRQK<br>SHTDAVNRLKRKLPGKALSANLIRKCRIAMDMNWTCPFTGATYGDHELENLEL<br>EHIVPHSFRQSNALSSLVLTWPGVNRMKGQRTGYDFVEQEQENPVPDKPNLHI<br>CSLNNYRELVEKLDDKKGHEDDRRRKKKRKALLMVRGLSHKHQSQNHEAMK<br>EIGMTEGMMTQSSHLMKLACKSIKTSLPDAHIDMIPGAVTAEVRKAWDVFGVF<br>KELCPEAADPDSGKILKENLRSLTHLHHALDACVLGLIPYIIPAHHNGLLRRVLA<br>MRRIPEKLIPQVRPVANQRHYVLNDDGRMMLRDLSASLKENIREQLMEQRVIQ<br>HVPADMGGALLKETMQRVLSVDGSGEDAMVSLSKKKDGKKEKNQVKASKLV<br>GVFPEGPSKLKALKAAIEIDGNYGVALDPKPVVIRHIKVFKRIMALKEQNGGKP<br>VRILKKGMLIHLTSSKDPKHAGVWRIESIQDSKGGVKLDLQRAHCAVPKNKTH<br>ECNWREVDLISLLKKYQMKRYPTSYTGTPR |
| *O. laneus* Cas9<br>SEQ ID NO: 23 | METTLGIDLGTNSIGLALVDQEEHQILYSGVRIFPEGINKDTIGLGEKEESRNATR<br>RAKRQMRRQYFRKKLRKAKLLELLIAYDMCPLKPEDVRRWKNWBKQQKSTV<br>RQFPDTPAFREWLKQNPYELRKQAVTEDVTRPELGRILYQMIQRRGFLSSRKGK<br>EEGKIFTGKDRMVGIDETRKNLQKQTLGAYLYDIAPKNGEKYRFRTERVRARY<br>TLRDMYIREFEIIWQRQAGHLGLAHEQATRKKNIFLEGSATNVRNSKLITHLQA<br>KYGRGHVLIEDTRITVTFQLPLKEVLGGKIEIEEEQLKFKSNESVLFWQRPLRSQ<br>KSLLSKCVFEGRNFYDPVHQKWIIAGPTPAPLSHPEFEEFRAYQFINNHYGKNEH<br>LTAIQREAVFELMCTESKDFNFEKIPKHLKLFEKFNFDDTTKVPACTTISQLRKL<br>FPHPVWEEKREEIWHCFYFYDDNTLLFEKLQKDYALQTNDLEKIKKIRLSESYG<br>NVSLKAIRRINPYLKKGYAYSTAVLLGGIRNSFGKRFEYFKEYEPEIEKAVCRIL<br>KEKNAEGEVIRKIKDYLVHNRFGFAKNDRAFQKLYHHSQAITTQAQKERLPET<br>GNLRNPIVQQGLNELRRTVNKLLATCREKYGPSFKFDHIHVEMGRELRSSKTER<br>EKQSRQIRENEKKNEAAKVKLAEYGLKAYRDNIQKYLLYKEIEEKGGTVCCPY<br>TGKTLNISHTLGSDNSVQIEHIIPYSISLDDSLANKTLCDATFNREKGELTPYDFY<br>QKDPSPEKWGASSWEEIEDRAFRLLPYAKAQRFIRRKPQESNEFISRQLNDTRYI<br>SKKAVEYLSAICSDVKAFPGQLTAELRHLWGLNNILQSAPDITFPLPVSATENHR<br>EYYVITNEQNEVIRLFPKQGETPRTEKGELLLTGEVERKVFRCKGMQEFQTDVS<br>DGKYWRRIKLSSSVTWSPLFAPKPISADGQIVLKGRIEKGVFVCNQLKQKLKTG |

| Name | Protein Sequence |
|---|---|
| | LPDGSYWISLPVISQTFKEGESVNNSKLTSQQVQLFGRVREGIFRCHNYQCPASG<br>ADGNFWCTLDTDTAQPAFTPIKNAPPGVGGGQIILTGDVDDKGIFHADDDLHYE<br>LPASLPKGKYYGIFTVESCDPTLIPIELSAPKTSKGENLIEGNIWVDEHTGEVRFD<br>PKKNREDQRHHAIDAIVIALSSQSLFQRLSTYNARRENKKRGLDSTEHFPSPWP<br>GFAQDVRQSVVPLLVSYKQNPKTLCKISKTLYKDGKKIHSCGNAVRGQLHKET<br>VYGQRTAPGATEKSYHIRKDIRELKTSKHIGKVVDITIRQMLLKHLQENYHIDIT<br>QEFNIPSNAFFKEGVYRIFLPNKHGEPVPIKKIRMKEELGNAERLKDNINQYVNP<br>RNNHHVMIYQDADGNLKEEIVSFWSVIERQNQGQPIYQLPREGRNIVSILQINDT<br>FLIGLKEEEPEVYRNDLSTLSKHLYRVQKLSGMYYTFRHHLASTLNNEREEFRI<br>QSLEAWKRANPVKVQIDEIGRITFLNGPLC |

In some embodiments, a nucleic acid sequence encoding a dCas endonuclease is a codon optimized dCas. An example of a codon optimized sequence, is in this instance, a sequence optimized for expression in, without limitation, a eukaryote, animal, and/or mammal e.g., a human (i.e. being optimized for expression in humans); see, e.g., SaCas9 human codon optimized sequence in WO 2014/093622, incorporated by reference herein in its entirety.

In some embodiments, a dCas endonuclease for use in the system provided herein is a variant Cas endonuclease comprising mutations which cause the endonuclease to lack cleavage activity or substantially lack cleavage activity as compared to its corresponding wild type Cas endonuclease. For example, with reference to WO 2017/091630, incorporated herein by reference in its entirety, in one embodiment disclosed herein, the Cas9 active sites (10 and 840) can be mutated to Alanine (D10A and H840A) to eliminate the cleavage activity of Streptococcus pyogenes Cas9, producing nuclease-deficient or dead Cas9 (i.e., dCas9). The RuvC domain is distributed among 3 non-contiguous portions of the dCas9 primary structure (residues 1-60, 719-775, and 910-1099). The Rec lobe is composed of residues 61-718. The HNH domain is composed of residues 776-909. The PAM-ID domain is composed of residues 1100-1368. The REC lobe can be considered the structural scaffold for recognition of the sgRNA and target DNA/RNA. The NUC lobe contains the two nuclease domains (HNH and RuvC), plus the PAM-interaction domain (PAM-ID), which recognizes an optional PAM sequence. In this prior work, for example and without limitation, an about 98-nucleotide sgRNA, is typically divided into two major structural components: the first contains the target-specific guide or "spacer" segment (nucleotides 1-20) plus the repeat-tetraloop-anti-repeat and stem-loop 1 (SL1) regions; the second contains stem-loops 2 and 3 (SL2, SL3). Accordingly, the guide-through-SL1 RNA segment is bound mainly by the Cas9 REC lobe and the SL2-SL3 segment is bound mainly by the NUC lobe.

In some embodiments of the dCas9 used in the system disclosed herein, a minimal (i.e., with as few nucleotide base pairs as possible) construct of Cas9 is engineered that will recognize a target RNA sequence with high affinity. In some embodiments, the smallest construct encoding dCas9 will be a REC-only construct. In some embodiments, the constructs will comprise less minimized constructs lacking the HNH, PAM-ID, parts of each domain, lacking both of each domain, or combinations thereof. In some embodiments, the HNH domain will be excised by inserting a five-residue flexible linker between residues 775 and 909 (ΔHNH). In some embodiments, all or part of the PAM-ID are removed. In some embodiments, truncating Cas9 at residue 1098 (ΔPAM-ID #1), fusing residues 1138 and 1345 with an 8-residue linker (ΔPAM-ID #2), or fusing residues 1138 with 1200 and 1218 with 1339 (with 5-residue and 2-residue linkers, respectively: ΔPAM-ID #3) are used to remove all or part of the PAM-ID. The ΔPAM-ID #2 and 3 constructs will retain elements of the PAM-ID that contribute to binding of the sgRNA repeat-anti-repeat (residues 1099-1138) and SL2-SL3 (residues 1200-1218 and 1339-1368) segments. In some embodiments, the HNH deletion will be combined with the three PAM-ID deletions. In some embodiments, Cas9 variants which lack or substantially lack nuclease and/or cleavage activity according to WO 2016/19655, incorporated herein by reference in its entirety, are examples of dCas9 used in the recombinant expression systems disclosed herein.

Accordingly for use in the recombinant expression systems disclosed herein are nucleic acid sequences encoding dCas-ADAR deaminase domain fusion proteins. In one embodiment, dCas9 is fused to a catalytically active ADAR deaminase domain. In the context of such systems a corresponding extended single guide RNA (esgRNA) is used to target and edit adenosines of the target RNA. The system generates recombinant proteins with effector deaminase enzymes capable of performing ribonucleotide base modification to alter how sequence of the RNA molecule is recognized by cellular machinery. In one embodiment the dCas and the ADAR deaminase domain are separated by a linker. In another embodiment, the linker is, without limitation, an XTEN linker which is a flexible linker used to isolate adjacent proteins domains. XTEN linkers are known in the art and can be found for example in WO 2013/130684, incorporated herein by reference in its entirety herein.

RNA editing is a natural process whereby the diversity of gene products of a given sequence is increased by minor modification in the RNA. Typically, the modification involves the conversion of adenosine (A) to inosine (I), resulting in an RNA sequence which is different from that encoded by the genome. RNA modification is generally ensured by the ADAR enzyme, whereby the pre-RNA target forms an imperfect duplex RNA by base-pairing between the exon that contains the adenosine to be edited and an intronic non-coding element. A classic example of A-I editing is the glutamate receptor GluR-B mRNA, whereby the change results in modified conductance properties of the channel (Higuchi M, et al. Cell. 1993; 75: 1361-70).

For the purposes of the present disclosure, ADAR (Adenosine deaminase acting on RNA) deaminase domains can be ADAR 1, ADAR 2, or ADAR 3 deaminase domains. See Nishikura, K. A-to-I editing of coding and non-coding RNAs by ADARs. Nat Rev Mol Cell Biol 17, 83-96, doi:10.1038/nrm.2015.4 (2016).

In some embodiments, the ADAR deaminase domain is derived from all or part of ADAR1 (Uniprot P55265). A non-limiting exemplary sequence of ADAR1 is provided below (SEQ ID NO: 24):

```
MAEIKEKICDYLFNVSDSSALNLAKNIGLTKARDINAVLIDMERQGDVYR

QGTTPPIWHLTDKKRERMQIKRNTNSVPETAPAAIPETKRNAEFLTCNIP

TSNASNNMVTTEKVENGQEPVIKLENRQEARPEPARLKPPVHYNGPSKAG

YVDFENGQWATDDIPDDLNSIRAAPGEFRAIMEMPSFYSHGLPRCSPYKK

LTECQLKNPISGLLEYAQFASQTCEFNMIEQSGPPHEPRFKFQVVINGRE

FPPAEAGSKKVAKQDAAMKAMTILLEEAKAKDSGKSEESSHYSTEKESEK

TAESQTPTPSATSFFSGKSPVTTLLECMHKLGNSCEFRLLSKEGPAHEPK

FQYCVAVGAQTFPSVSAPSKKVAKQMAAEEAMKALHGEATNSMASDNQPE

GMISESLDNLESMMPNKVRKIGELVRYLNTNPVGGLLEYARSHGFAAEFK

LVDQSGPPHEPKFVYQAKVGGRWFPAVCAHSKKQGKQEAADAALRVLIGE

NEKAERMGFTEVTPVTGASLRRTMLLLSRSPEAQPKTLPLTGSTFHDQIA

MLSHRCFNTLTNSFQPSLLGRKILAAIIMKKDSEDMGVVVSLGTGNRCVK

GDSLSLKGETVNDCHAEIISRRGFIRFLYSELMKYNSQTAKDSIFEPAKG

GEKLQIKKTVSFHLYISTAPCGDGALFDKSCSDRAMESTESRHYPVFENP

KQGKLRTKVENGEGTIPVESSDIVPTWDGIRLGERLRTMSCSDKILRWNV

LGLQGALLTHFLQPIYLKSVTLGYLFSQGHLTRAICCRVTRDGSAFEDGL

RHPFIVNHPKVGRVSIYDSKRQSGKTKETSVNWCLADGYDLEILDGTRGT

VDGPRNELSRVSKKNIFLLFKKLCSFRYRRDLLRLSYGEAKKAARDYETA

KNYFKKGLKDMGYGNWISKPQEEKNFYLCPV
```

In some embodiments, the ADAR deaminase domain is derived from all or part of ADAR2 (Uniprot P78563). A non-limiting exemplary sequence of ADAR2 is provided below (SEQ ID NO: 25):

```
MDIEDEENMSSSSTDVKENRNLDNVSPKDGSTPGPGEGSQLSNGGGGGPG

RKRPLEEGSNGHSKYRLKKRRKTPGPVLPKNALMQLNEIKPGLQYTLLSQ

TGPVHAPLFVMSVEVNGQVFEGSGPTKKKAKLHAAEKALRSFVQFPNASE

AHLAMGRTLSVNTDFTSDQADFPDTLFNGFETPDKAEPPFYVGSNGDDSF

SSSGDLSLSASPVPASLAQPPLPVLPPFPPPSGKNPVMILNELRPGLKYD

FLSESGESHAKSFVMSVVVDGQFFEGSGRNKKLAKARAAQSALAAIFNLH

LDQTPSRQPIPSEGLQLHLPQVLADAVSRLVLGKFGDLTDNFSSPHARRK

VLAGVVMTTGTDVKDAKVISVSTGTKCINGEYMSDRGLALNDCHAEIISR

RSLLRFLYTQLELYLNNKDDQKRSIFQKSERGGFRLKENVQFHLYISTSP

CGDARIFSPHEPILEEPADRHPNRKARGQLRTKIESGEGTIPVRSNASIQ

TWDGVLQGERLLTMSCSDKIARWNVVGIQGSLLSIFVEPIYFSSIILGSL

YHGDHLSRAMYQRISNIEDLPPLYTLNKPLLSGISNAEARQPGKAPNFSV

NWTVGDSAIEVINATTGKDELGRASRLCKHALYCRWMRVHGKVPSHLLRS

KITKPNVYHESKLAAKEYQAAKARLFTAFIKAGLGAWVEKPTEQDQFSLT

P
```

In some embodiments, the ADAR deaminase domain is derived from all or part of ADAR3 (Uniprot Q9NS39): A non-limiting exemplary sequence of ADAR2 is provided below (SEQ ID NO: 26):

```
MASVLGSGRGSGGLSSQLKCKSKRRRRRSKRKDKVSILSTFLAPFKHLS

PGITNTEDDDTLSTSSAEVKENRNVGNLAARPPPSGDRARGGAPGAKRKR

PLEEGNGGHLCKLQLVWKKLSWSVAPKNALVQLHELRPGLQYRTVSQTGP

VHAPVFAVAVEVNGLTFEGTGPTKKKAKMRAAELALRSFVQFPNACQAHL

AMGGGPGPGTDFTSDQADFPDTLFQEFEPPAPRPGLAGGRPGDAALLSAA

YGRRRLLCRALDLVGPTPATPAAPGERNPVVLLNRLRAGLRYVCLAEPAE

RRARSFVMAVSVDGRTFEGSGRSKKLARGQAAQAALQELFDIQMPGHAPG

RARRTPMPQEFADSISQLVTQKFREVTTDLTPMHARHKALAGIVMTKGLD

ARQAQVVALSSGTKCISGEHLSDQGLVVNDCHAEVVARRAFLHFLYTQLE

LHLSKRREDSERSIFVRLKEGGYRLRENILFHLYVSTSPCGDARLHSPYE

ITTDLHSSKHLVRKFRGHLRTKIESGEGTVPVRGPSAVQTWDGVLLGEQL

ITMSCTDKIARWNVLGLQGALLSHFVEPVYLQSIVVGSLHHTGHLARVMS

HRMEGVGQLPASYRHNRPLLSGVSDAEARQPGKSPPFSMNWVVGSADLEI

INATTGRRSCGGPSRLCKHVLSARWARLYGRLSTRTPSPGDTPSMYCEAK

LGAHTYQSVKQQLFKAFQKAGLGTWVRKPPEQQQFLLTL
```

In some embodiments, ADAR domains can include mutations which result in increased catalytic activity compared to wild type ADAR domains. In some embodiments, the catalytically active deaminase domain (DD) is derived from a wildtype human ADAR2 or a human ADAR2 DD bearing a mutation (E488Q) that increases enzymatic activity and affinity for RNA substrate (Phelps et al., January 2015, Nuc. Acid Res., 43(2): 1123-1132; Kuttan & Bass, November 2012, PNAS 109(48): E3295-E3304).

Because the catalytic domain of ADAR2, independent of its RNA recognition motif, preferably deaminates unpaired adenosine residues in dsRNA regions, Applicants modified the structure of the single guide RNA (sgRNA) component of the system disclosed herein to improve substrate specificity to single-nucleotide resolution. It has been reported that gRNAs engineered with supplementary 3' terminal cassettes maintain their targeting capacity in live cells (Konermann et al. January 2015, Nature, 517: 583-588).

Applicants developed a CRISPR/Cas-mediated RNA editing (CREDIT) platform based on the strategic modification of the system's sgRNA structure comprising an additional region of homology capable of base pairing with target RNA over the desired site of editing. Such a modification to the sgRNA structure generates the disclosed system's extended sgRNA (i.e., esgRNA), and results in an A-to-C mismatch with a target transcript generating a 'pseudo-dsRNA' substrate to be edited at the bulged adenosine (see FIG. 1A). The CREDIT platform and the systems disclosed herein thus provides the ability to target virtually any adenosine in the transcriptome to direct conversion to inosine (i.e., A-I RNA editing), which is ultimately read by translational and splicing machinery as guanosine.

Due to its overall design simplicity as well as its fully encodable nature, the recombinant expression systems disclosed herein provide high utility and engineering versatility when compared to other similar RNA modifying systems and methods. Because dCas9 binds with picomolar affinity to the sgRNA scaffold sequence, and because this improved system uses dual guide architecture as per the extended single guide RNA i.e., esgRNA, structure, to increase both target affinity and specificity, direct RNA editing with minimal potential off-target editing events is efficiently achieved.

In some embodiments, the esgRNA can be designed with a i) scaffold sequence and ii) a short extension sequence but without a spacer sequence.

In one embodiment, the esgRNA is composed of at least two regions, i) a region of homology capable of near-perfect RNA-RNA base pairing (i.e., a short extension sequence of homology to the target RNA) and ii) a dCas9-binding region (i.e., scaffold sequence). In one embodiment, the short extension sequence comprises a mismatch which forms an A-C mismatch with a target transcriptome and generates a 'pseudo-RNA' substrate to be edited at the bulged adenosine residue. As such, the homology region of the short extension sequence determines the specificity of the recombinant expression system disclosed herein, and in particular it determines specifically which RNA base in the cellular transcriptome is edited. The RNA base that is edited is distinguished by a mismatched adenosine residue among the homology region and the target RNA duplex. See FIG. 1A. The orientation of the homology region of the short extension sequence and the scaffold is flexible. In one embodiment, the scaffold sequence is located at the 5' end of the esgRNA. In another embodiment, the short extension sequence carrying the homology region capable of near-perfect RNA-RNA base pairing is located at the 3' end of the esgRNA. In another embodiment, the short extension sequence is located at the 5' end of the esgRNA. For the purposes of the present disclosure, the "3' end" or "5' end" refers in either scenario of the esgRNA to an end terminus of the esgRNA. In another embodiment, the esgRNA additionally comprises a third region, iii) a spacer sequence which comprises a second homology region to the target RNA. In one embodiment, the spacer sequence is located at the 5' end of the scaffold sequence. The spacer sequence is complementary to the target RNA but does not require a mismatch to effect the A-I editing of the target RNA. In one embodiment, the spacer sequence is located on the 5' end of the scaffold sequence. In another embodiment, the short extension sequence is located on the 3' end of the scaffold sequence or on the 5' end of the spacer sequence. In another embodiment, the short extension sequence is located on an end terminus of the esgRNA. In another embodiment, the short extension sequence is continuous to the spacer sequence. In another embodiment, the short extension sequence is discontinuous to the spacer sequence. In another embodiment, the esgRNA comprising i-iii) in a 3' to 5' orientation.

In some embodiments, nucleoprotein complexes are complexed with a single guide RNA (sgRNA) or as disclosed herein an extended single guide RNA (esgRNA). In some embodiments, the single guide RNA or esgRNA carries extensions (other than and in addition to the short extension sequence of homology in the esgRNA capable of editing target adenosines) of secondary structures in the single guide RNA or esgRNA scaffold sequence. In some embodiments, the single guide RNA or esgRNA comprises one or more point mutations that improve expression levels of the single guide RNAs (or esgRNAs) via removal of partial or full transcription termination sequences or sequences that destabilize single guide RNAs (or esgRNAs) after transcription via action of trans-acting nucleases. In some embodiments, the single guide RNA (or esgRNA) comprises an alteration at the 5' end which stabilizes said single guide RNA or esgRNA against degradation. In some embodiments, the single guide RNA or esgRNA comprises an alteration at the 5' end which improves RNA targeting. In some embodiments, the alteration at the 5' end of said single guide RNA or esgRNA is selected from the group consisting of 2'O-methyl, phosphorothioates, and thiophosphonoacetate linkages and bases. In some embodiments, the single guide RNA or esgRNA comprises 2'-fluorine, 2'O-methyl, and/or 2'-methoxyethyl base modifications in the spacer or scaffold region of the sgRNA or esgRNA to improve target recognition or reduce nuclease activity on the single guide RNA or esgRNA. In some embodiments, the single guide RNA comprises one or more methylphosphonate, thiophosponoacetate, or phosphorothioate linkages that reduce nuclease activity on the target RNA.

In some embodiments, the single guide RNA or esgRNA can recognize the target RNA, for example, by hybridizing to the target RNA. In some embodiments, the single guide RNA or esgRNA comprises a sequence that is complementary to the target RNA. In some embodiments, the single guide RNA or esgRNA has a length that is, is about, is less than, or is more than, 10 nt, 20 nt, 30 nt, 40 nt, 50 nt, 60 nt, 70 nt, 80 nt, 90 nt, 100 nt, 110 nt, 120 nt, 130 nt, 140 nt, 150 nt, 160 nt, 170 nt, 180 nt, 190 nt, 200 nt, 300 nt, 400 nt, 500 nt, 1,000 nt, 2,000 nt, or a range between any two of the above values. In some embodiments, the single guide RNA or esgRNA can comprise one or more modified nucleotides.

In additional embodiments, a variety of RNA targets can be recognized by the single guide RNA or esgRNA. For example, a target RNA can be messenger RNA (mRNA), ribosomal RNA (rRNA), signal recognition particle RNA (SRP RNA), transfer RNA (tRNA), small nuclear RNA (snRNA), small nucleolar RNA (snoRNA), antisense RNA (aRNA), long noncoding RNA (lncRNA), microRNA (miRNA), piwi-interacting RNA (piRNA), small interfering RNA (siRNA), short hairpin RNA (shRNA), retrotransposon RNA, viral genome RNA, viral noncoding RNA, or the like. In some embodiments, a target RNA can be an RNA involved in pathogenesis or a therapeutic target for conditions such as cancers, neurodegeneration, cutaneous conditions, endocrine conditions, intestinal diseases, infectious conditions, neurological disorders, liver diseases, heart disorders, autoimmune diseases, or the like.

In further embodiments, exemplary G to A mutation target RNA and corresponding diseases, conditions and/or syndromes to be treated are, without limitation:

SDHB (Succinate Dehydrogenase Complex Iron Sulfure Subunit B) for treating Paraganglioma, gastric stromal sarcoma, Paragangliomas 4, Pheochromocytoma, Paragangliomas 1, and/or Hereditary cancer-predisposing syndrome;

DPYD (Dihydropyrimidine Dehydrogenase) for treating Dihydropyrimidine dehydrogenase deficiency, Hirschsprung disease 1, Fluorouracil response, Pyrimidine analogues response—Toxicity/ADR, capecitabine response—Toxicity/ADR, fluorouracil response—Toxicity/ADR, and/or tegafur response—Toxicity/ADR;

MSH2 (mutS Homolog 2) for treating Lynch syndrome, tumor predisposition syndrome, and/or Turcot syndrome;

MSH6 (mutS Homolog 6) for treating Lynch syndrome;

DYSF (Dysferlin) for treating Miyoshi muscular dystrophy 1, and/or Limb-girdle muscular dystrophy—type 2B;

SCN1A (Sodium Voltage-Gated Channel Alpha Subunit 1) for treating Severe myoclonic epilepsy in infancy;

TTN (Titin)/TTN-AS1 for treating Primary dilated cardiomyopathy;

VHL (von Hippel-Lindau Tumor Suppressor) for treating Von Hippel-Lindau syndrome; and/or Hereditary cancer-predisposing syndrome;

MLH1 (mutL homolog 1) for treating Lynch syndrome, Hereditary cancer-predisposing syndrome, and/or tumor predisposition syndrome;

PDE6B (Phosphodiesterase 6B) for treating Retinitis pigmentosa and/or Retinitis pigmentosa 40;

CC2D2A (Coiled-coil and C2 Domain Containing 2A) for treating Familial aplasia of the vermis and/or Joubert syndrome 9;

FRAS1 (Fraser extracellular matrix complex subunit 1) for treating Cryptophthalmos syndrome;

DSP (Desmoplakin) for treating Arrhythmogenic right ventricular cardiomyopathy—type 8 and/or Cardiomyopathy;

PMS2 (PMS 1 homolog 2, mismatch repair system component) for treating Lynch syndrome and/or tumor predisposition syndrome;

ASL (Argininosuccinate lyase) for treating Argininosuccinic aciduria;

ELN (Elastin) for treating Supravalvar aortic stenosis;

SLC26A4 (Solute Carrier Family 26 Member 4) for treating Enlarged vestibular aqueduct syndrome and/or Pendred's syndrome;

CFTR (Cystic Fibrosis Transmembrane Conductance Regulator) for treating Cystic Fibrosis;

CNGB3 (Cyclic Nucleotide Gated Channel Beta 3) for treating Achromatopsia 3;

FANCC (Fanconi Anemia Complementation Group C)—C9orf3 for treating Fanconi anemia and/or Hereditary cancer-predisposing syndrome;

PTEN (Phosphatase and Tensin homolog) for treating Hereditary cancer-predisposing syndrome, Bannayan-Riley-Ruvalcaba syndrome, Cowden syndrome, Breast cancer, Autism spectrum disorder, Head and neck squamous cell carcinoma, lung cancer, and/or prostate cancer;

ANO5 (Anoctamin 5) for treating Limb-girdle muscular dystrophy—type 2L, Gnathodiaphyseal dysplasmia, Miyoshi myopathy, and/or Miyoshi muscular dystrophy 3;

MYBPC3 (Myosin Binding Protein C, Cardiac) for treating Primary familial hypertrophic cardiomyopathy;

MEN1 (Menin 1) for treating Familial isolated hyperparathyroidism, multiple endocrine neoplasia, primary macronodular adrenal hyperplasia, and/or tumors;

ATM (ATM serine/threonine kinase) and/or ATM-C11orf65 for treating Ataxia-telangiectasia syndrome, and/or Hereditary cancer-predisposing syndrome;

PKP2 (Plakophilin 2) for treating Arrhythmogenic right ventricular cardiomyopathy—type 9 and/or Arrhythmogenic right ventricular cardiomyopathy;

PAH (Phenylalanine Hydroxylase) for treating Phenylketonuria;

GJB2 (Gap Junction Protein Beta 2) for treating Deafness, autosomal recessive 1A, Non-syndromic genetic deafness and/or Hearing impairment;

B3GLCT (beta 3-glucosyltransferase) for treating Peters plus syndrome;

BRCA2 (BRCA2, DNA repair associated) for treating Familial cancer of breast, Breast-ovarian cancer—familial 2, Hereditary cancer-predisposing syndrome, Fanconi anemia, complementation group D1, Hereditary breast and ovarian cancer syndrome, Hereditary cancer-predisposing syndrome, Breast-ovarian cancer—familial 1, and/or Hereditary breast and ovarian cancer syndrome;

MYH7 (Myosin Heavy Chain 7) for treating Primary dilated cardiomyopathy, Cardiomyopathy, and/or Cardiomyopathy—left ventricular noncompaction;

FBN1 (Fibrillin 1) for treating Marfan syndrome;

HEXA (Hexosaminidase Subunit Alpha) for treating Tay-Sachs disease;

TSC2 (TSC Complex Subunit 2) for treating Tuberous sclerosis 2, and/or Tuberous sclerosis syndrome;

CREBBP (CREB binding protein) for treating Rubinstein-Taybi syndrome;

CDH1 (Cadherin 1) for treating Hereditary diffuse gastric cancer, Tumor predisposition syndrome, and/or Hereditary cancer-predisposing syndrome;

SPG7 (SPG7, paraplegin matrix AAA peptidase subunit) for treating Spastic paraplegia 7;

BRCA1 (BRCA1, DNA repair associated) for treating Breast-ovarian cancer—familial 1, Hereditary breast and ovarian cancer syndrome, and/or Hereditary cancer-predisposing syndrome;

BRIP1 (BRCA1 Interacting Protein C-Terminal Helicase 1) for treating Familial cancer of breast and/or Tumor predisposition syndrome;

LDLR (Low Density Lipoprotein Receptor) and/or LDLR-MIR6886 for treating Familial hypercholesterolemia and/or Hypercholesterolaemia;

BCKDHA (Branced Chain Keto acid dehydrogenase E1, alpha polypeptide) for treating Maple syrup urine disease;

CHEK2 (Checkpoint Kinase 2) for treating Familial cancer of breast, Breast and colorectal cancer—susceptibility to, and/or Hereditary cancer-predisposing syndrome;

DMD (Dystrophin) for treating Becker muscular dystrophy, Duchenne muscular dystrophy, and/or Dilated cardiomyopathy 3B; and/or IDUA (Iduronidase, alpha-L) for treating Hurler syndrome, Dysostosis multiplex, Mucopolysaccharidosis, MPS-I-H/S, and/or Mucopolysaccharidosis type I.

In some embodiments, the esgRNA comprises a short extension sequence of homology to the target RNA which is about 10-100 nucleotides in length, or about 10, 15-60, 20-50, or 25-40, or any range therebetween nucleotides in length. In some embodiments, the short extension sequence of the esgRNA, without limitation, comprising about 1 mismatch or 2, 3, 4, or 5 mismatches.

In some embodiments, the single guide RNA or esgRNA includes, but is not limited to including, sequences which bind or hybridize to target RNA, such as spacer sequences comprising additional regions of homology (in addition to the short extension sequence of homology disclosed herein) to the target RNA such that RNA recognition is supported with specificity and provides uniquely flexible and accessible manipulation of the genome. See WO 2017/091630 incorporated by reference in its entirety herein.

Non-limiting exemplary spacer sequences and extension sequences designed for esgRNA targeting the CFTR mRNA (cystic fibrosis transmembrane conductance regulator, Ref Seq: NM_000492) and the IDUA mRNA (iduronidase, Ref Seq: NM_000203) are provided in the table below:

| Target | spacer sequence | ADAR extension sequence |
|---|---|---|
| CFTR | gttcatagggatccaagttttt (SEQ ID NO: 43) | tttcctccactgttgcaaag (SEQ ID NO: 44) |
| IDUA | ccagcgcccaccgccccag (SEQ ID NO: 45) | actttcggcccagagctgctcc (SEQ ID NO: 46) |

In one embodiment, the system disclosed herein comprises nucleic acid sequences which are minimalized to a nucleotide length which fits in a single vector. In some embodiments, the vector is an AAV vector. AAV vectors are capable of packaging transgenes which are about 4.5 kbs in size. In some instances, AAV vectors are capable of packaging larger transgenes such as about 4.6 kb, 4.7 kb, 4.8 kb, 4.9 kb, 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, 7.0 kb, 7.5 kb, 8.0 kb, 9.0 kb, 10.0 kb, 11.0 kb, 12.0 kb, 13.0 kb, 14.0 kb, 15.0 kb, or larger are used.

In another embodiment, the system disclosed herein comprises, without limitation, one or more promoter sequences for driving expression of the system components. Exemplary promoters for expressing small RNAs, without limitation, are polymerase III promoters such as U6 and H1. Other promoters for driving expression of system components are, without limitation, EF1alpha (or its short, intronless form, EFS), CAG (CMV enhancer, chicken beta-Actin promoter and rabbit beta-Globin splice acceptor site fusion), mini CMV (cytomegalovirus), CMV, MCK (muscle creatin kinase), MCK/SV40, desmin, and/or c512 (Glutamate carboxypeptidase II).

In one embodiment, the recombinant expression system is encoded in DNA carried by a vector, e.g., adeno-associated virus (AAV), and can be delivered to appropriate tissues via one of the following methods: use of specific AAV serotypes that display specific tissue tropism (such as AAV-9 targeting neurons or muscle); injection of naked DNA encoding the RdCas9 system into tissue such as muscle or liver; use of nanoparticles composed of lipids, polymers, or other synthetic or natural materials that carry DNA or RNA encoding the therapeutic recombinant expression system; or any of the above where the system is split between two separate viruses or DNA molecules so that: one virus encodes the dCas9 protein-ADAR fusion and the other virus encodes the sgRNA; or one virus encodes the dCas9 protein and/or the sgRNA while the other virus encodes the ADAR protein and/or the sgRNA. In embodiments in which the portions of CREDIT are encoded on separate vectors, the encoded portions of dCas9 and ADAR can interact with one another so as to form a functional dCas9—ADAR nucleoprotein complex. Exemplary split systems can be seen in Wright et al., Rational design of a split-Cas9 enzyme complex. PNAS 112:2984-2989 (2015), the content of which is hereby incorporated by reference in its entirety).

To use exemplary recombinant expression systems as provided herein in treatment of a human subject or animal, the vector, e.g., the AAV, system can, for example, be injected by the following methods: (1) Skeletal muscle tissue (intramuscular) at multiple sites simultaneously (relevant indication: myotonic dystrophy)—injection of $10^{11}$-$10^{14}$ GC (genome copies) per injection into major muscle group such as the abdominal muscles, biceps, deltoids, erector spinae, gastrocnemius, soleus, gluteus, hamstrings, latissimus dorsi, rhomboids, obliques, pectoralis, quadriceps, trapezius and/or triceps; (2) Intravenous delivery of a targeted AAV serotype such as AAV-9 or AAV-6 for muscle targeting—injection of $10^{11}$-$10^{14}$ GC per injection for a total of $10^{12}$-$10^{17}$ GC delivered; 3. Subpial spinal injection of AAV-6, AAV-9 or another serotype displaying neuronal tropism—injection of $10^{11}$-$10^{17}$ GC in a single or multiple doses; 4. Intracranial injection of AAV-6, AAV-9 or another serotype displaying neuronal tropism-injection of $10^{11}$-$10^{17}$ GC in a single or multiple doses.

In other embodiments, recombinant expression systems disclosed herein may be formulated by methods known in the art. In addition, any route of administration may be envisioned such as, e.g., by any conventional route of administration including, but not limited to oral, pulmonary, intraperitoneal (ip), intravenous (iv), intramuscular (im), subcutaneous (sc), transdermal, buccal, nasal, sublingual, ocular, rectal and vaginal. In addition, administration directly to the nervous system may include, and are not limited to, intracerebral, intraventricular, intracerebroventricular, intrathecal, intracisternal, intraspinal or peri-spinal routes of administration by delivery via intracranial or intravertebral needles or catheters with or without pump devices. Any dose or frequency of administration that provides the therapeutic effect described herein is suitable for use in the present treatment. In a particular embodiment, the subject is administered a viral vector encoding the recombinant expression system according to the disclosure by the intramuscular route. In one embodiment, the vector is an AAV vector as defined above, is an AAV9 vector. In some embodiments, the human subject may receive a single injection of the vector. Additionally, standard pharmaceutical methods can be employed to control the duration of action. These are well known in the art and include control release preparations and can include appropriate macromolecules, for example polymers, polyesters, polyamino acids, polyvinyl, pyrrolidone, ethylenevinylacetate, methyl cellulose, carboxymethyl cellulose or protamine sulfate. In addition, the pharmaceutical composition may comprise nanoparticles that contain the recombinant expression system of the present disclosure.

Also provided by this invention is a composition comprising, consisting of, or consisting essentially of one or more of a recombinant expression system, vector, cell, or viral particle as described herein and a carrier. In some embodiments, the carrier is a pharmaceutically acceptable carrier.

In some embodiments, the recombinant expression systems as disclosed herein can optionally include the additional administration of a PAMmer oligonucleotide, i.e., co-administration with the disclosed systems simultaneously or sequentially of a corresponding PAMmer. Selection techniques for PAMmer oligonucleotide sequences are well known in the art and can be found for example, in WO 2015/089277, incorporated herein by reference in its entirety. Although a PAMmer may in some instances increase binding affinity of dCas9 to RNA in vivo as well as in vitro, Applicants' prior work WO 2017/091630, incorporated herein by reference in its entirety, surprisingly found that a PAMmer is not required to achieve RNA recognition and editing. To simplify Applicants' delivery strategy herein and to maintain the disclosed systems herein as fully encodeable systems, the experiments below were performed in the absence of a PAMmer. A schematic of this mechanism is outlined in FIG. 1A.

Disclosed herein are methods of using recombinant expression systems as disclosed herein as a research tool, e.g. to characterize the effects of directed cellular RNA editing on processing and dynamics.

Additionally disclosed herein are methods of using recombinant expression systems as disclosed herein as a therapeutic for diseases, e.g. by using viral (AAV) or other vector-based delivery approaches to deliver the recombinant expression systems for in vivo or ex vivo RNA editing to treat a disease in need of such editing.

Non-limiting examples of targets and related diseases include, but are not limited to, premature termination codon RNA diseases such as Hurler's syndrome, Cystic fibrosis, Duchenne muscular dystrophy, others, as well as diseases associated with deficiencies in RNA editing such as excitotoxic neuronal disorders affiliated with under-editing of the Q/R residue of AMPA subunit GluA2. Excitotoxicity may be involved in spinal cord injury, stroke, traumatic brain injury, hearing loss (through noise overexposure or ototoxicity), and in neurodegenerative diseases of the central nervous system (CNS) such as multiple sclerosis, Alzheimer's disease, amyotrophic lateral sclerosis (ALS), Parkinson's disease, alcoholism or alcohol withdrawal and especially over-rapid benzodiazepine withdrawal, and also Huntington's disease.

EXAMPLES

The following examples are non-limiting and illustrative of procedures which can be used in various instances in carrying the disclosure into effect. Additionally, all reference disclosed herein below are incorporated by reference in their entirety.

Figure 1C:
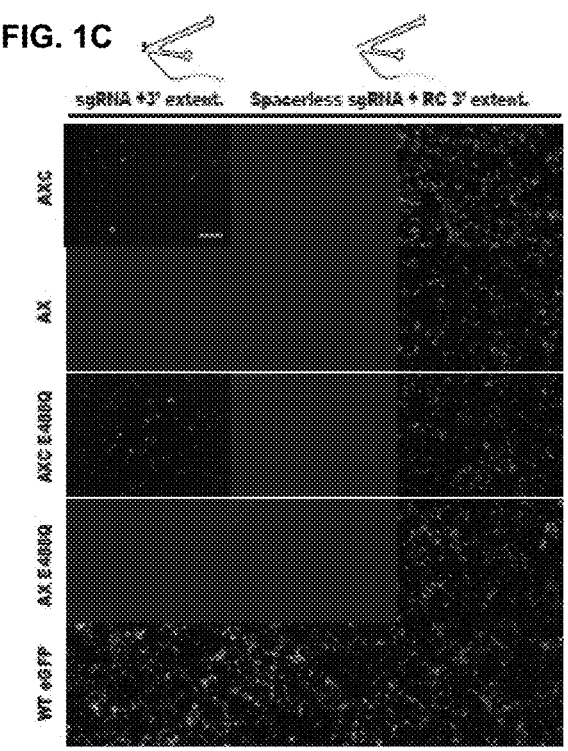
Figure 1D:
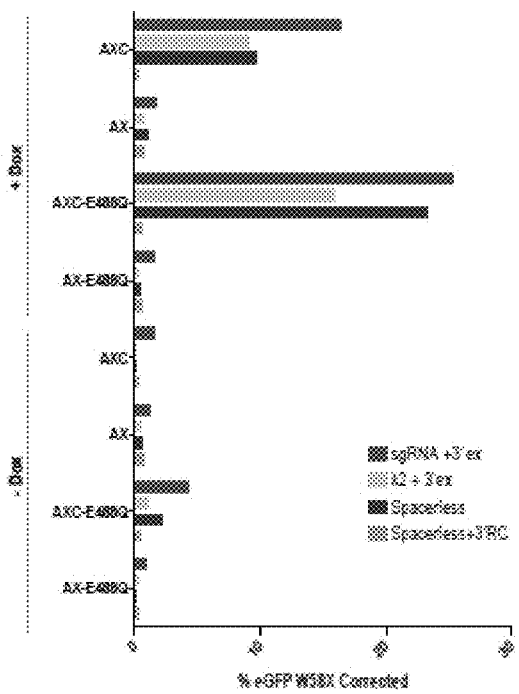
Figure 2:
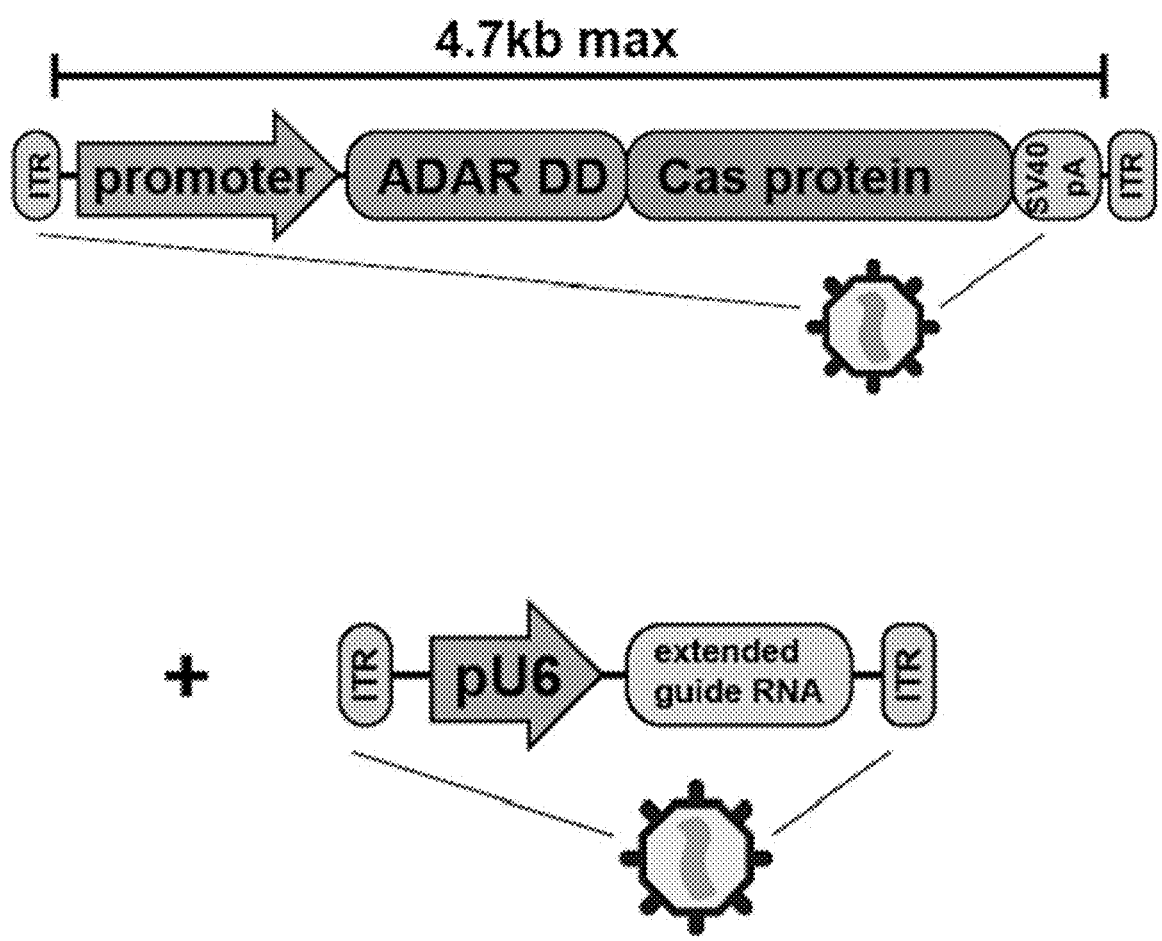
FIG. 2 illustrates, without limitation, an exemplary recombinant expression system as an AAV-based vector system. The AAV system comprises vectors carrying the nucleic acid sequence encoding the ADAR Deaminase domain/Cas endonuclease fusion protein and the extended single guide RNA (esgRNA) to be packaged as AAV virions.
Figure 3:
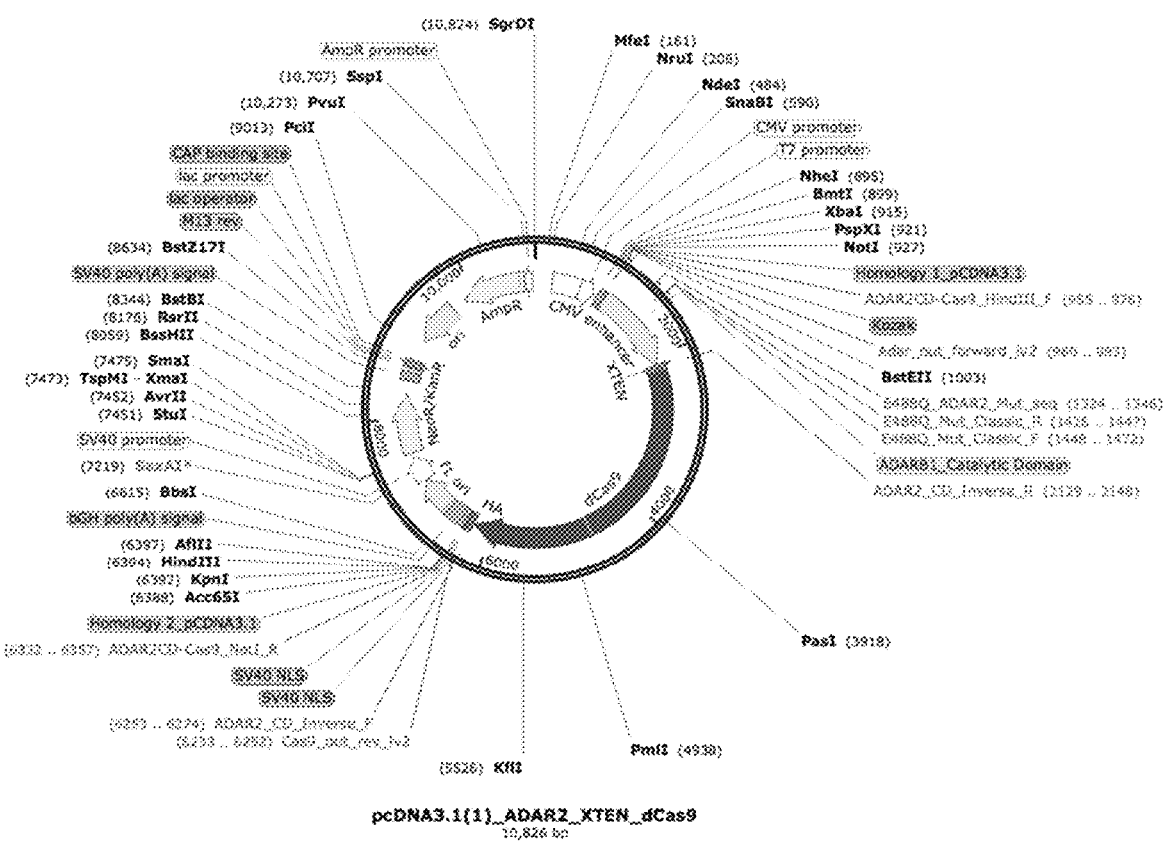
FIG. 3 illustrates a map of pcDNA3.1(1)_ADAR2_XTEN_dCas9 (SEQ ID NO: 27). The CMV enhancer is located at position 235 to 614 (380 bp in length) and drives constitutive expression of recombinant protein in mammalian cells. The CMV promoter is located at position 615 to 818 (204 bp in length) and drives constitutive expression of recombinant protein in mammalian cells. The ADARB1 Catalytic Domain is located at position 961 to 2100 (1140 bp in length) and encodes a catalytically-active deaminating domain of human ADAR2 (ADARB1). XTEN is located at position 2101 to 2148 (48 bp in length) and encodes a peptide linker connecting recombinant protein domains. dCas9 is located at position 2149 to 6252 (4104 bp in length) and encodes a catalytically-inactive (D10A and H841A) CRISPR-Cas9 protein from Streptococcus pyogenes. HA is located at position 6256 to 6282 (27 bp in length) and encodes human influenza hemagglutinin (HA) epitope tag. 2×SV40 NLS is located at position 6301 to 6348 (48 bp in length) and encodes a Nuclear localization signal (NLS) derived from Simian Virus 40 (SV40) large T-antigen. bGH poly(A) signal is located at position 6426 to 6650 (225 bp in length) and encodes a bovine growth hormone (bGH) polyadenylation signal.
Figure 4:
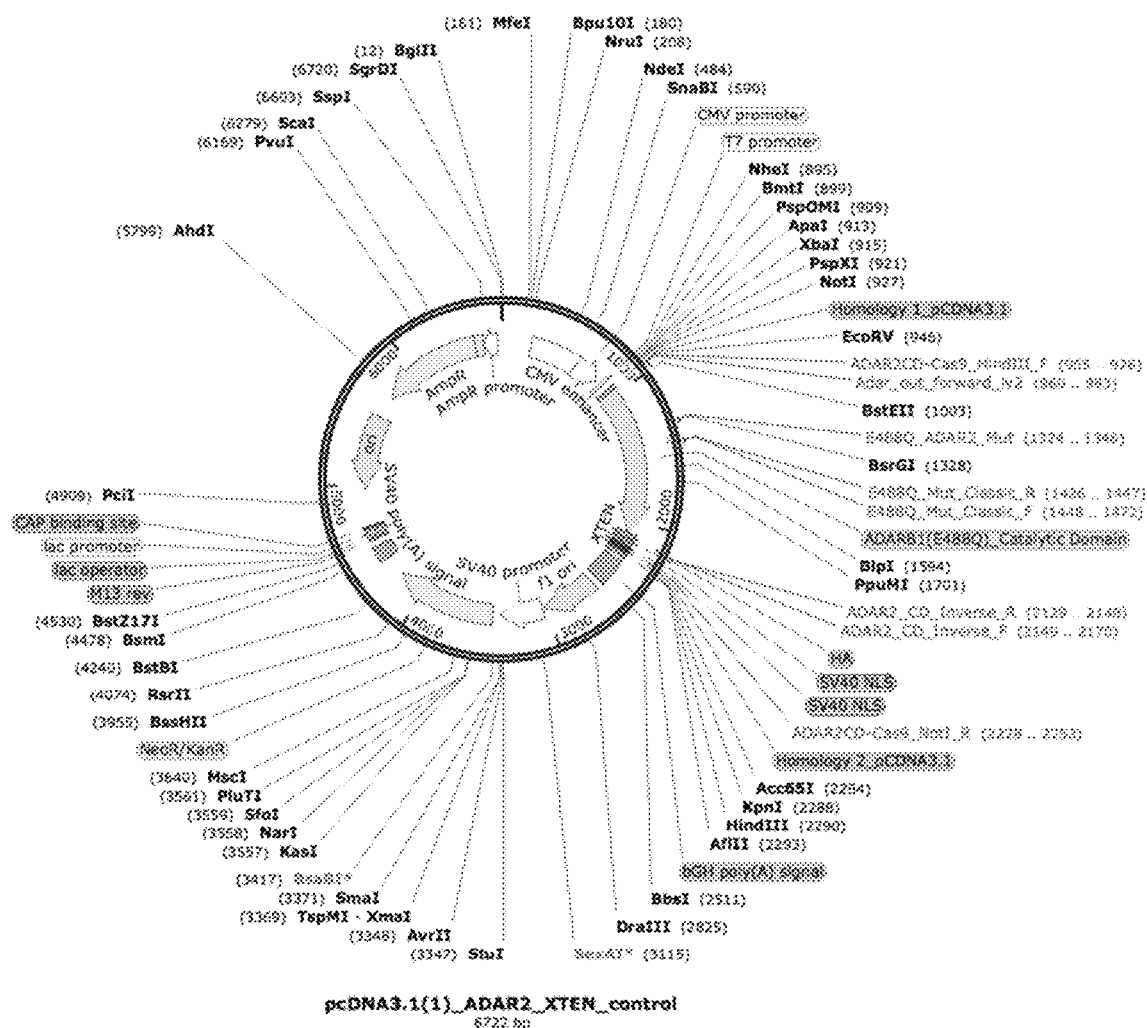
FIG. 4 illustrates a map of pcDNA3.1(1)_ADAR2_XTEN_control (SEQ ID NO: 28). A CMV enhancer is located at position 235 to 614 (380 bp in length) and drives constitutive expression of recombinant protein in mammalian cells. A CMV promoter is located at position 615 to 818 (204 bp in length) and drives constitutive expression of recombinant protein in mammalian cells. An ADARB1 Catalytic Domain is located at position 961 to 2100 (1140 bp in length) and encodes a catalytically-active deaminating domain of human ADAR2 (ADARB1). XTEN is located at position 2101 to 2148 (48 bp) and encodes a peptide linker connecting recombinant protein domains. HA is located at position 2152 to 2178 (27 bp) and encodes human influenza hemagglutinin (HA) epitope tag 2×SV40 NLS is located at position 2197 to 2244 (48 bp) nuclear localization signal (NLS) derived from Simian Virus 40 (SV40) large T-antigen. bGH poly(A) signal is located at position 2322 to 2546 (225 bp) and encodes bovine growth hormone (bGH) polyadenylation signal.
Figure 5:
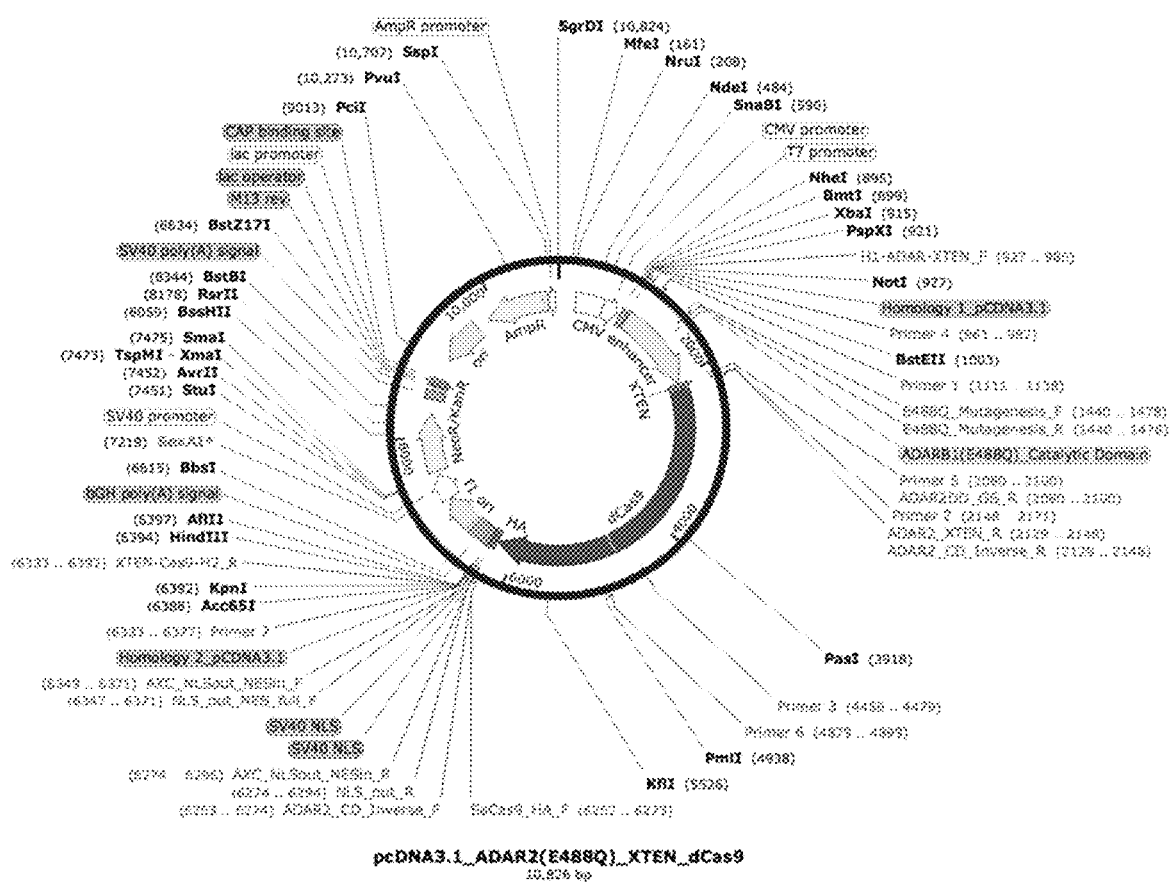
FIG. 5 illustrates a map of pcDNA3.1_ADAR2 (E488Q)_XTEN_dCas9 (SEQ ID NO: 29). A CMV enhancer is located at position 235 to 614 (380 bp) and drives constitutive expression of recombinant protein in mammalian cells. A CMV promoter is located at position 615 to 818 (204 bp) and drives constitutive expression of recombinant protein in mammalian cells. ADARB1(E488Q) Catalytic Domain is located at position 961 to 2100 (1140 bp) and encodes a catalytically-active deaminating domain of human ADAR2 (ADARB1) with hyperactive point mutation (E488Q). XTEN is located at position 2101 to 2148 (48 bp) and encodes a peptide linker connecting recombinant protein domains. dCas9 is located at position 2149 to 6252 (4104 bp) and encodes a catalytically-inactive (D10A and H841A) CRISPR-Cas9 protein from *Streptococcus pyogenes*. HA is located at position 6256 to 6282 (27 bp) and encodes human influenza hemagglutinin (HA) epitope tag. 2×SV40 NLS is located at position 6301 to 6348 (48 bp) and encodes a nuclear localization signal (NLS) derived from Simian Virus 40 (SV40) large T-antigen bGH. poly(A) signal is located at position 6426 to 6650 (225 bp) and encodes bovine growth hormone (bGH) polyadenylation signal.
Figure 6:
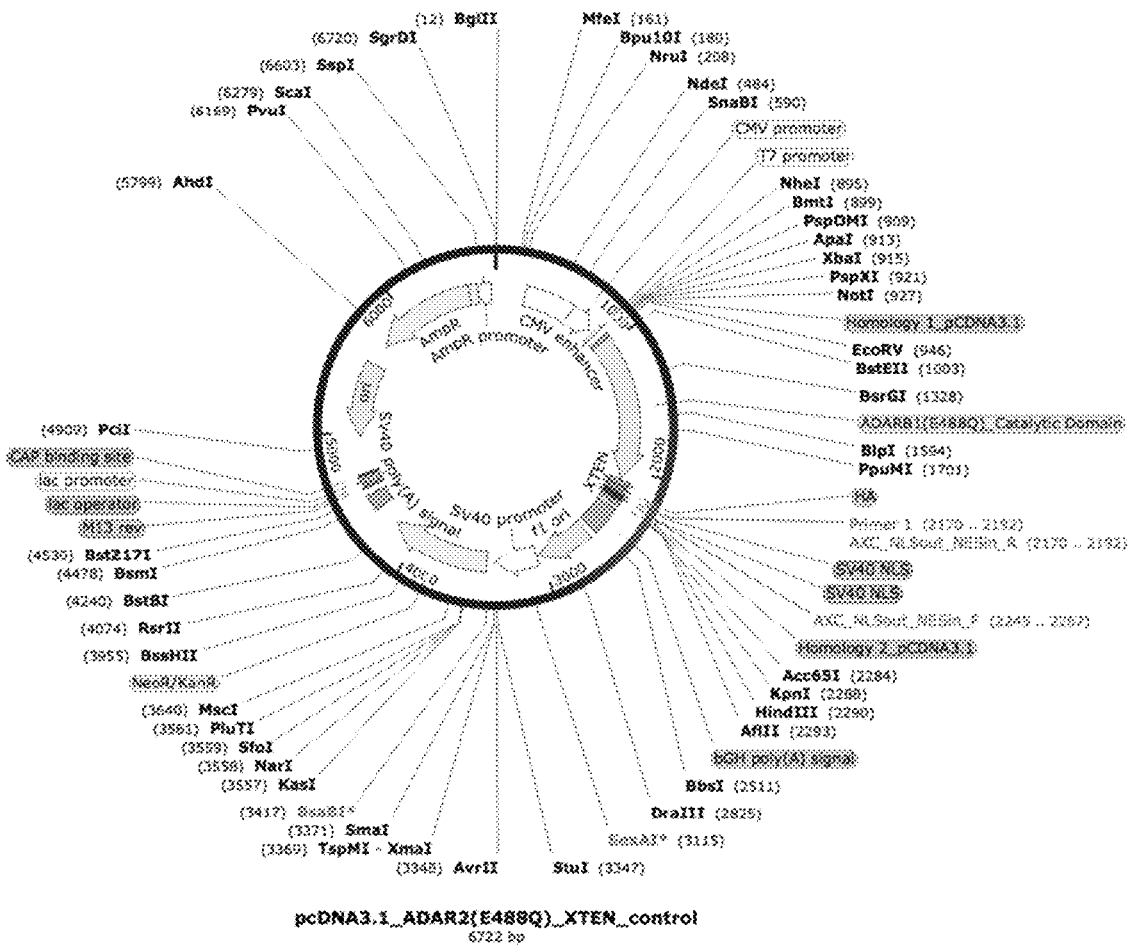
FIG. 6 illustrates a map of pcDNA3.1_ADAR2(E488Q)_XTEN_control (SEQ ID NO: 30). A CMV enhancer is located at position 235 to 614 (380 bp) and drives constitutive expression of recombinant protein in mammalian cells. A CMV promoter is located at position 615 to 818 (204 bp) and drives constitutive expression of recombinant protein in mammalian cells. ADARB1(E488Q) Catalytic Domain is located at position 961 to 2100 (1140 bp) and encodes a catalytically-active deaminating domain of human ADAR2 (ADARB1) with hyperactive point mutation (E488Q). XTEN is located at position 2101 to 2148 (48 bp) and encodes a peptide linker connecting recombinant protein domains. HA is located at position 2152 to 2178 (27 bp) and encodes a human influenza hemagglutinin (HA) epitope tag. 2×SV40 NLS is located at position 2197 to 2244 (48 bp) and encodes a nuclear localization signal (NLS) derived from Simian Virus 40 (SV40) large T-antigen. bGH poly(A) signal is located at position 2322 to 2546 (225 bp) and encodes bovine growth hormone (bGH) polyadenylation signal.
Figure 7:
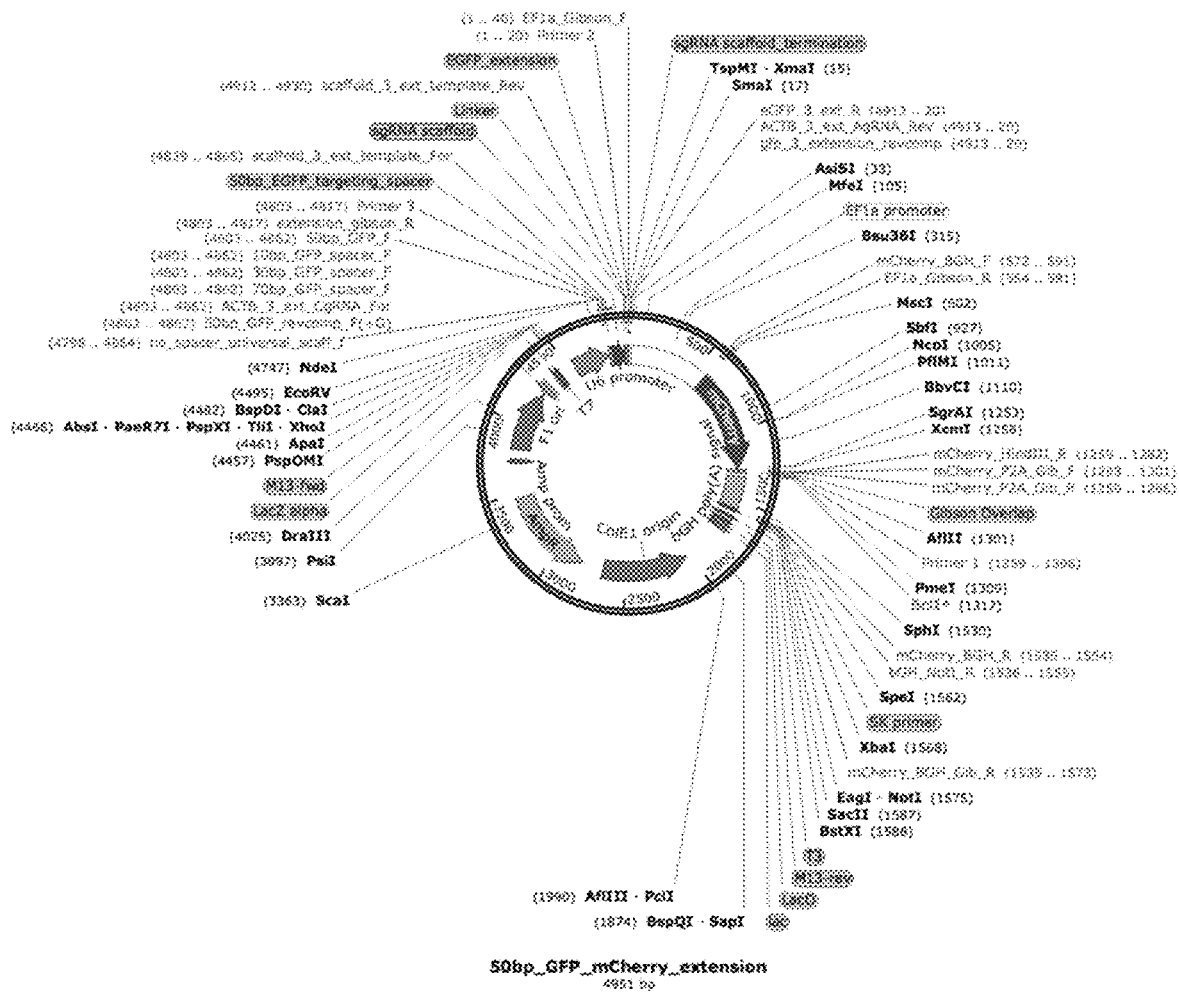
FIG. 7 illustrates a map of 50 bp_GFP_mCherry_extension (SEQ ID NO: 31). A U6 promoter is located at position 4555 to 4817 (263 bp) and is a Pol III promoter driving expression of sgRNA in mammalian cells. An EGFP targeting spacer is located at position 4818 to 4838 (21 bp) and encodes a spacer sequence of sgRNA that targets complementary EGFP reporter mRNA. An sgRNA scaffold is located at position 4839 to 4924 (86 bp) and encodes an sgRNA scaffold for *Streptococcus pyogenes* CRISPR-Cas9 system with (F+E) modification (Chen et al. 2014). Linker is located at position 4925 to 4930 (6 bp) encoding a linker sequence bridging the sgRNA scaffold with the extension sequence. And EGFP extension is located at position 4931 to 4951 (21 bp) encoding an RNA extension sequence that base pairs with target site and forces A-to-I editing using A-C mismatch. A sgRNA scaffold termination site is located at position 1 to 7 (7 bp) comprising a Poly(T) sequence that terminates Pol III RNA synthesis. An Ef1a promoter is located at position 21 to 566 (546 bp) which is a constitutive promoter driving protein expression in mammalian cells. mCherry is located at position 572 to 1282 (711 bp) encoding a monomeric derivative of DsRed fluorescent protein. A bGH poly(A) signal is located at position 1330 to 1554 (225 bp) encoding a bovine growth hormone (bGH) polyadenylation signal.
Figure 8:
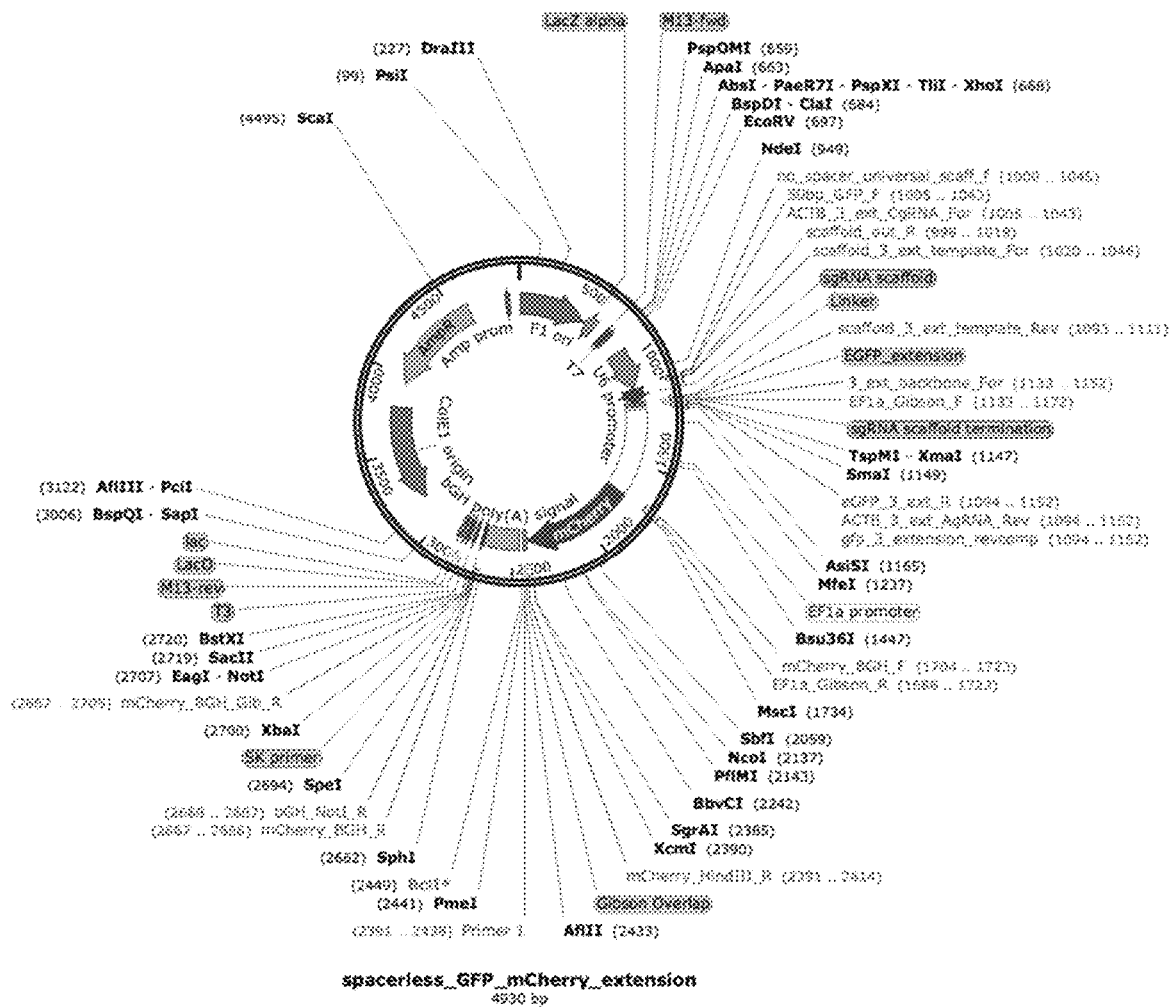
FIG. 8 illustrates a map of spacerless_GFP_mCherry_extension (SEQ ID NO: 32). A U6 promoter is located at position 757 to 1019 (263 bp) and is a Pol III promoter driving expression of sgRNA in mammalian cells. An sgRNA scaffold is located at position 1020 to 1105 (86 bp) encoding an sgRNA scaffold for *Streptococcus pyogenes* CRISPR-Cas9 system with (F+E) modification (Chen et al. 2014). A Linker is located at position 1106 to 1111 (6 bp) comprising a linker sequence bridging the sgRNA scaffold with the extension sequence. An EGFP extension is located at position 1112 to 1132 (21 bp) encoding an RNA extension sequence that base pairs with target site and forces A-to-I editing using A-C mismatch. An sgRNA scaffold termination is located at position 1133 to 1139 (7 bp) comprising a poly(T) sequence that terminates Pol III RNA synthesis. An Ef1a promoter is located at position 1153 to 1698 (546 bp) and is a constitutive promoter driving protein expression in mammalian cells. mCherry is located at position 1704 to 2414 (711 bp) encoding a monomeric derivative of DsRed fluorescent protein. A bGH poly(A) signal is located at position 2462 to 2686 (225 bp) encoding bovine growth hormone (bGH) polyadenylation signal.
Figure 9:
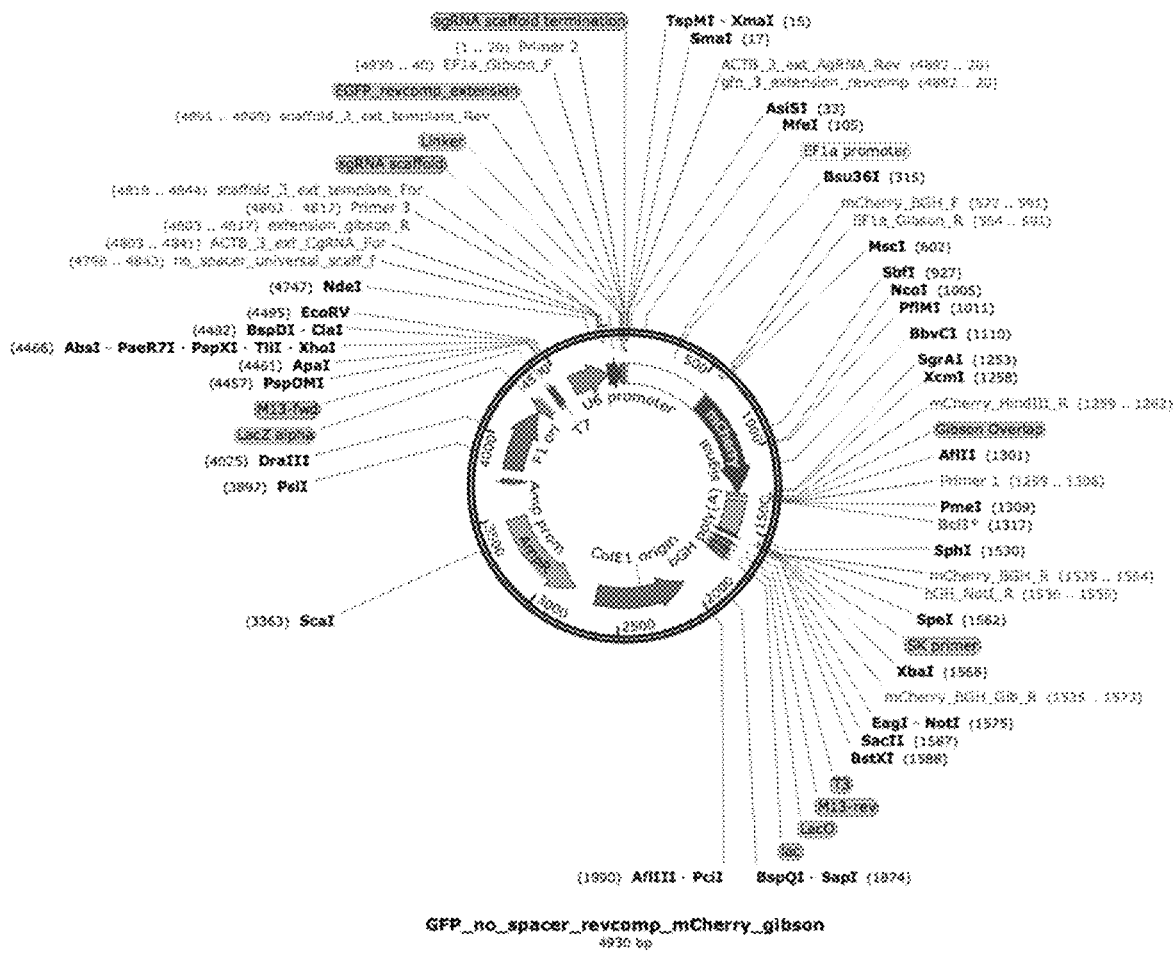
FIG. 9 illustrates a map of GFP_no_spacer_revcompmCherry_gibson (SEQ ID NO: 33). A U6 promoter is located at position 4555 to 4817 (263 bp) and is a Pol III promoter driving expression of sgRNA in mammalian cells. An sgRNA scaffold is located at position 4818 to 4903 (86 bp) and encodes a sgRNA scaffold for *Streptococcus pyogenes* CRISPR-Cas9 system with (F+E) modification (Chen et al. 2014). A linker is located at position 4904 to 4909 (6 bp) encoding a linker sequence bridging the sgRNA scaffold with the extension sequence. An EGFP revcomp extension is located at position 4910 to 4930 (21 bp) encoding an RNA reverse complement extension sequence that matches the sequence of the EGFP mRNA target site. An sgRNA scaffold termination is located at position 1 to 7 (7 bp) comprising a poly(T) sequence that terminates Pol III RNA synthesis. An Ef1a promoter is located at position 21 to 566 (546 bp) and is a constitutive promoter driving protein expression in mammalian cells. mCherry is located at position 572 to 1282 (711 bp) encoding a monomeric derivative of DsRed fluorescent protein. A bGH poly(A) signal is located at position 1330 to 1554 (225 bp) encoding a bovine growth hormone (bGH) polyadenylation signal.
Figure 10:
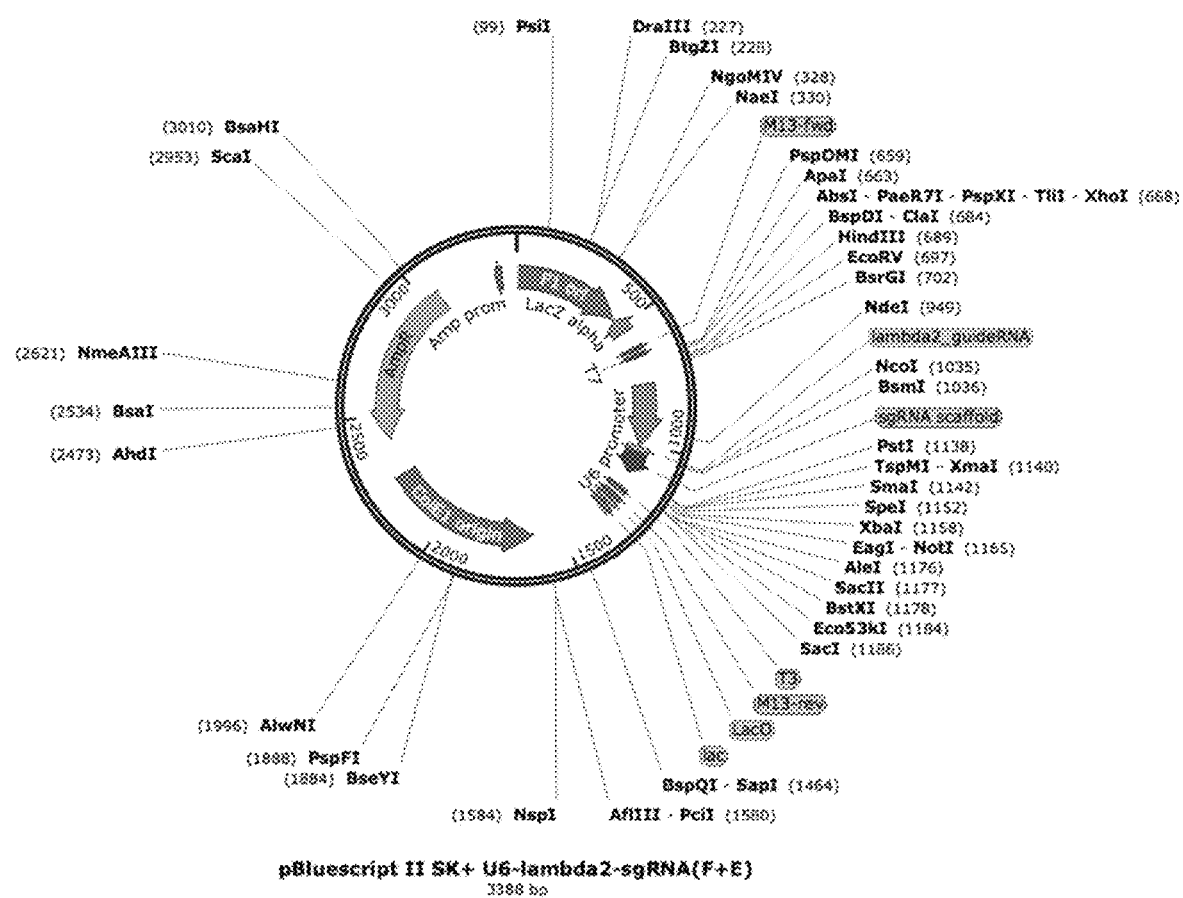
FIG. 10 illustrates a map of pBluescript II SK+ U6-lambda2-sgRNA(F+E) (SEQ ID NO: 34). A U6 promoter is located at position 757 to 1019 (263 bp) and is a Pol III promoter driving expression of sgRNA in mammalian cells. A lambda2 guideRNA is located at position 1020 to 1039 (20 bp) encoding a non-targeting sgRNA sequence targeting lambda phage 2. An sgRNA scaffold is located at position 1041 to 1132 (92 bp) encoding a sgRNA scaffold for *Streptococcus pyogenes* CRISPR-Cas9 system with (F+E) modification (Chen et al. 2014).
Figure 11:
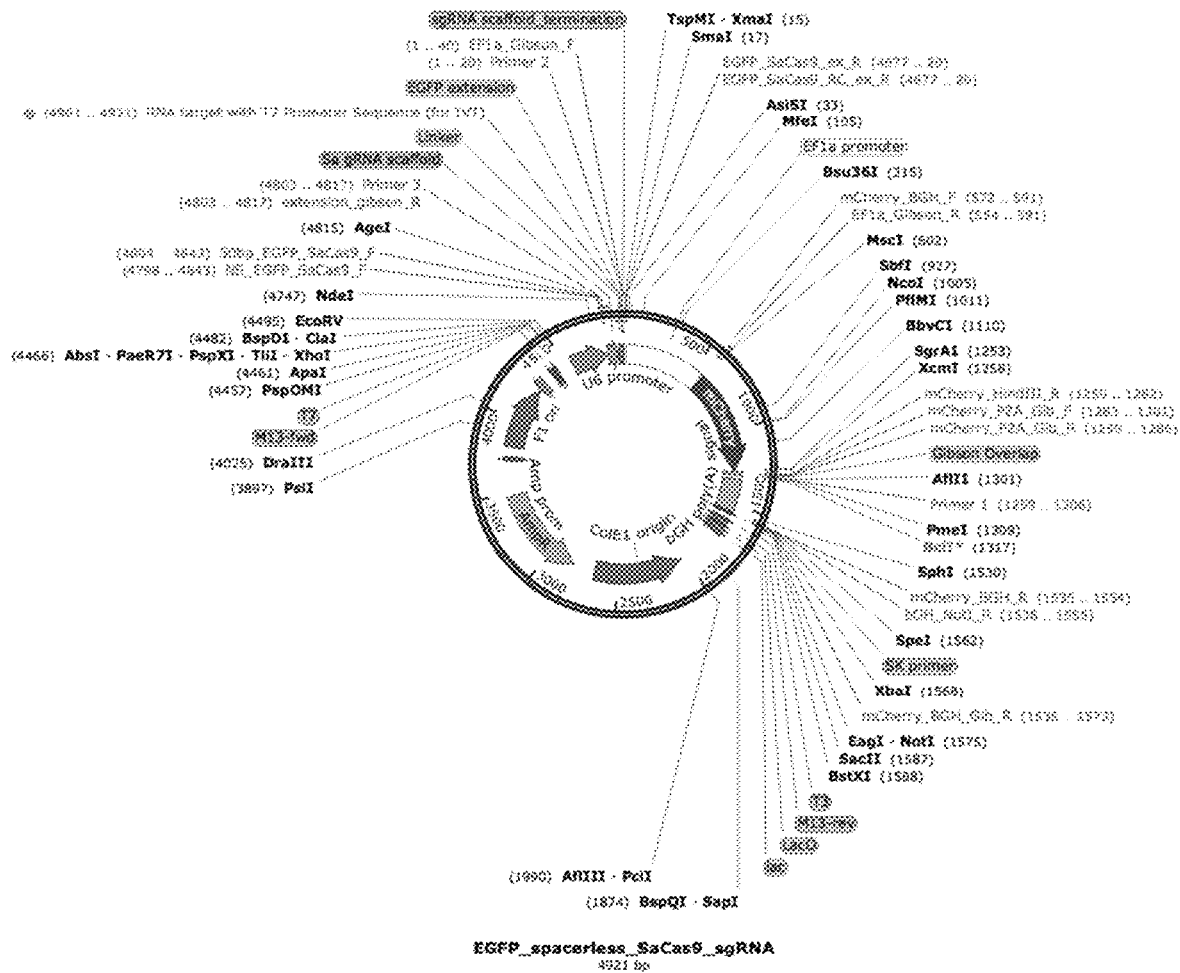
FIG. 11 illustrates a map of EGFP_spacerless_SaCas9_sgRNA (SEQ ID NO: 47). A U6 promoter is located at position 4555 to 4817 (263 bp) and is a Pol III promoter driving expression of sgRNA in mammalian cells. An Sa sgRNA scaffold is located at position 4819 to 4894 (76 bp) encoding an sgRNA scaffold for *Staphylococcus aureus* CRISPR-Cas9 system with A-U base flip (Chen et al. 2016). A linker is located at position 4895 to 4900 (6 bp) encoding a linker sequence bridging the sgRNA scaffold with the extension sequence. An EGFP extension is located at position 4901 to 4921 (21 bp) encoding an RNA extension sequence that base pairs with target site and forces A-to-I editing using A-C mismatch. An sgRNA scaffold termination site is located at position 1 to 7 (7 bp) comprising a poly(T) sequence that terminates pol III RNA synthesis. An Ef1a promoter is located at position 21 to 566 (546 bp) which is a constitutive promoter driving protein expression in mammalian cells. mCherry is located at position 572 to 1282 (711 bp) encoding a monomeric derivative of DsRed fluorescent protein. A bGH poly(A) signal is located at position 1330 to 1554 (225 bp) encoding bovine growth hormone (bGH) polyadenylation signal.
Figure 12:
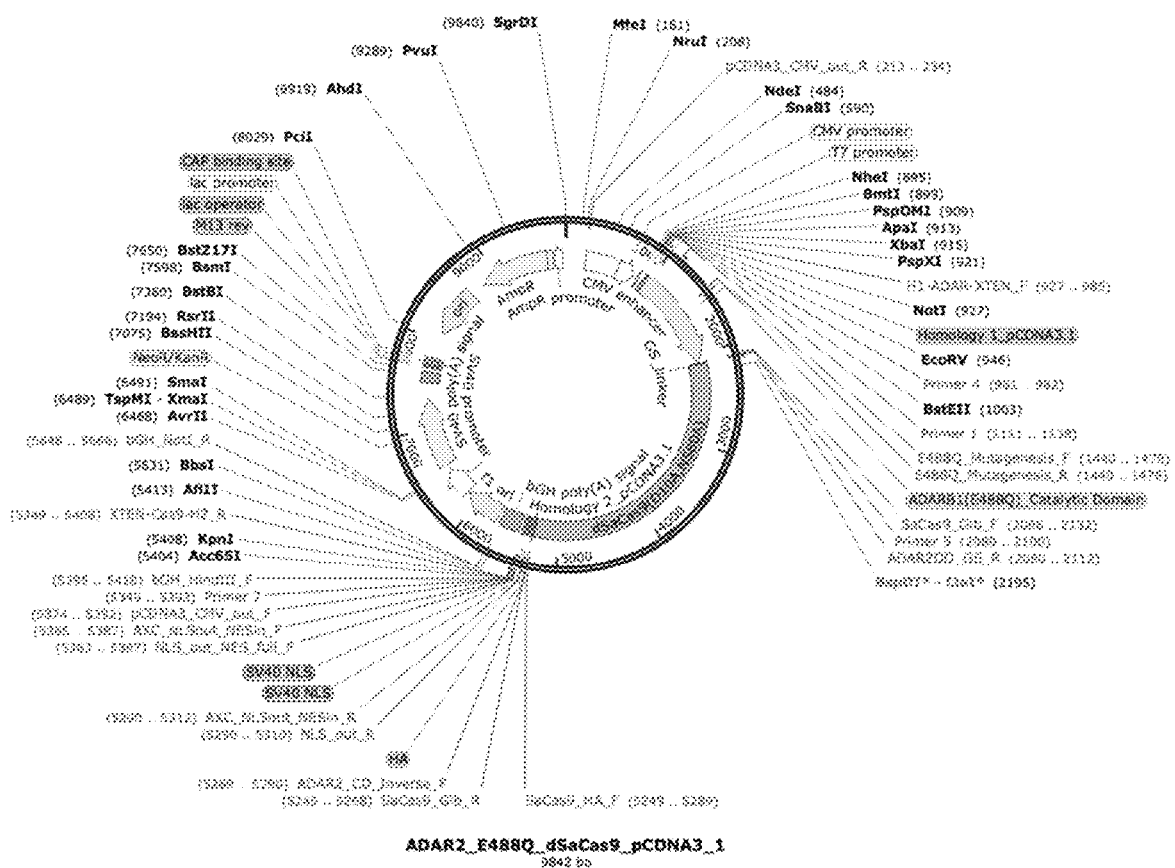
FIG. 12 illustrates a map of ADAR2_E488Q_dSaCas9_pCDNA3_1 (SEQ ID NO: 48). A CMV enhancer is located at position 235 to 614 (380 bp) and drives constitutive expression of recombinant protein in mammalian cells. A CMV promoter is located at position 615 to 818 (204 bp) and drives constitutive expression of recombinant protein in mammalian cells. ADARB1 Catalytic Domain is located at position 961 to 2100 (1140 bp) and encodes a catalytically-active deaminating domain of human ADAR2 (ADARB1). A GS linker is located at position 2101 to 2112 (12 bp) and encodes a Glycine-Serine peptide linker to bridge protein domains. A dSaCas9 is located at position 2113 to 5268 (3156 bp) encoding a catalytically-inactive (with point mutations D10A and N580A) CRISPR-Cas9 protein from Staphylococcus aureus. HA is located at position 5272 to 5298 (27 bp) encoding human influenza hemagglutinin (HA) epitope tag. A 2×SV40 NLS is located at position 5317 to 5364 (48 bp) nuclear localization signal (NLS) derived from Simian Virus 40 (SV40) large T-antigen. A bGH poly(A) signal is located at position 5442 to 5666 (225 bp) encoding a bovine growth hormone (bGH) polyadenylation signal.

Described below are prototypes of the recombinant expression system generated by Applicant that 1) recognize and edit a reporter mRNA construct in living cells at a base specific level and 2) reverse premature termination codon (PTC) mediated silencing of expression from eGFP reporter transcripts in living cells (see FIGS. 1C and 1D).

Example 1—Directed Editing of Cellular RNA Via Nuclear Delivery of CRISPR/Cas9 Plasmid Construction The sequence encoding dCas9-2×NLS was cloned from pCDNA3.1-dCas9-2×NLS-EGFP (Addgene plasmid #74710). For the ADAR2-XTEN-dCas9 fusion product, the dCas9 sequence fused to an XTEN peptide linker and an ADAR2 catalytic domain (PCR amplified from human ADAR2 ORF) into a pCDNA3.1 (Invitrogen) backbone using Gibson assembly. The dCas9 moiety was removed by inverse PCR using primers flanking the dCas9-NLS sequence to generate the ADAR2-XTEN fusion. PCR-mediated site-directed mutagenesis was performed to generate the ADAR2-XTEN-dCas9 E488Q and ADAR2-XTEN E488Q mutant variants, using the ADAR2-XTEN-dCas9 and ADAR2-XTEN respectively as templates. All fusion sequences were cloned into pCDNA5/FRT/TO (Invitrogen) through PCR amplification and restriction digestion using FastDigest HindIII and NotI (Thermo Fisher).

To construct the esgRNA backbone, sequences for mammalian Ef1a promoter, mCherry ORF, and BGH poly(A) signal were Gibson assembled into pBlueScript II SK (+) (Agilent) backbone bearing a modified sgRNA scaffold (Chen et al. 2013) driven by a U6 polymerase III promoter. Individual sgRNAs bearing a 3' extension sequences were generated by PCR amplifying the modified sgRNA scaffold using tailed primers bearing the spacer and extension sequences and Gibson assembling into the pBlueScript II SK(+)-mCherry vector downstream of the U6 promoter.
Cell Lines and Transfections Flp-In T-REX 293 were cultured in Dulbecco's modified eagle medium (DMEM) supplemented with 10% fetal bovine serum (Gibco). Cells were passaged every 3-4 days using TrypLE Express (Gibco) and maintained in a tissue culture incubator at 37° C. with 5% $CO_2$.

Stable, doxycycline-inducible lines were generated by seeding cells on 10 cm tissue culture dished and co-transfecting at 60-70% confluency with 1 ug pCDNA5/FRT/TO bearing the ADAR2 fusion constructs along with 9 ug pOG44 (Invitrogen), which encodes the Flp recombinase using polyethylenimine (PEI). Cells were subsequently passaged to 25% confluency and selected with 5 ug/ml blasticidin and 100 ug/ml hygromycin B (Gibco) after 48 hours. Cells remained under selection until individual hygromycin-resistant colonies identified, and 8-10 colonies were picked for expansion and validation.

Prior to transfection, $0.1 \times 10^6$ cells were seeded onto a 24-well plate 24 hours prior to the day of transfection and pre-incubated with doxycycline at a final concentration of 1 ug/ml for 24 hours. Cells were then co-transfected with 150 ug of respective sgRNA-mCherry constructs with 350 ug of W58X mutant or WT eGFP reporter construct (generous gifts from Stafforst lab) using Lipofectamine 3000 (Invitrogen). Cells were kept under doxycycline induction for 48 hours following transfection before imaging and FACS analysis. Images were captured using a Zeiss fluorescence microscope at 20× magnification.
Flow Cytometry Analysis Cells were dissociated with TrypLE Express using standard protocol. Cells were then resuspended in 1×DPBS (Corning) supplemented with 5% FBS, passed through a 35 m nylon cell strainer, and subjected to flow cytometry analysis using an LSRFortessa or Accuri instrument (BD). Cells were appropriately gated and analyzed for GFP (FITC) fluorescence. To normalize for transfection efficiency, individual values of percent eGFP corrected for each fusion-esgRNA pair was calculated by taking the fraction of GFP-positive cells from the W58X eGFP transfection population and dividing by the fraction of GFP-positive cells when instead transfected with the WT eGFP reporter. FACS analysis was analyzed using FlowJo software and compiled results were plotted using Graphpad Prism 6.

Discussion

In these experiments, and without limitation, the recombinant expression system described above comprises A) nucleic acid sequences encoding a nuclease-dead Cas9 (dCas9) protein fused to the catalytic deaminase domain of the human ADAR2 protein, and B) an extended single guide RNA (esgRNA) sequence driven by a U6 polymerase III promoter. The systems were delivered to the nuclei of mammalian cells with the appropriate transfection reagents and the sequences bind and edit target mRNA after forming an RCas9-RNA recognition complex. This allows for selective RNA editing in which targeted adenosine residues are deaminated to inosine to be recognized as guanosine by the cellular machinery.

The catalytically active deaminase domains (DD) described in the above systems were either wildtype human ADAR2 or human ADAR2 DD bearing a mutation (E488Q) that increases enzymatic activity and affinity for RNA substrate as compared to wildtype human ADAR2. The DD was fused to a semi-flexible XTEN peptide linker at its C-terminus, which was then fused to dCas9 at its N-terminus (FIG. 1B). To control for RNA-recognition independent background editing, fusion constructs lacking the dCas9 moiety were also generated (AX, AX-488Q).

The esgRNA construct was modified with a region of homology capable of near-perfect RNA-RNA base pairing with over the desired site of editing. The homology region comprises a mismatch of the targeted adenosine, forcing an A-C mispairing and the generation of a 'pseudo-dsRNA' substrate on the target transcript (FIG. 1A). This generates a means of programmable RNA substrate recognition as well as simultaneous base-specific deamination. Furthermore, these modified esgRNA constructs were cloned into a vector additionally comprising a marker gene, e.g., mCherry construct driven by a separate Ef1a pol II promoter, as shown in the examples. This provided for the sorting of cells transfected with the esgRNA using flow-cytometry, and furthermore enrichment of cells with targeted RNA editing.

Figure 13A:
FIGS. 13A-13B illustrate a comparison between a recombinant expression system comprising a nuclease dead Cas9 derived from S. pyogenes (dSpCas9) and a nuclease dead Cas9 derived from S. aureus (dSaCas9). dSaCas9 is significantly smaller than dSpCas9, which provides efficiency in viral packaging.
Figure 13A:
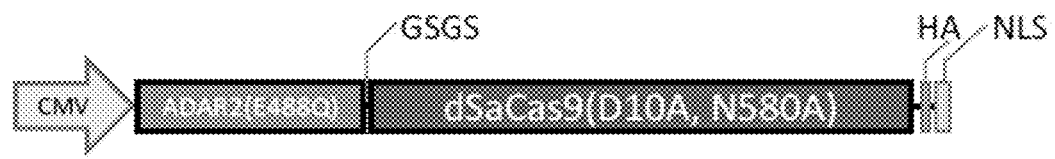
Figure 13B:
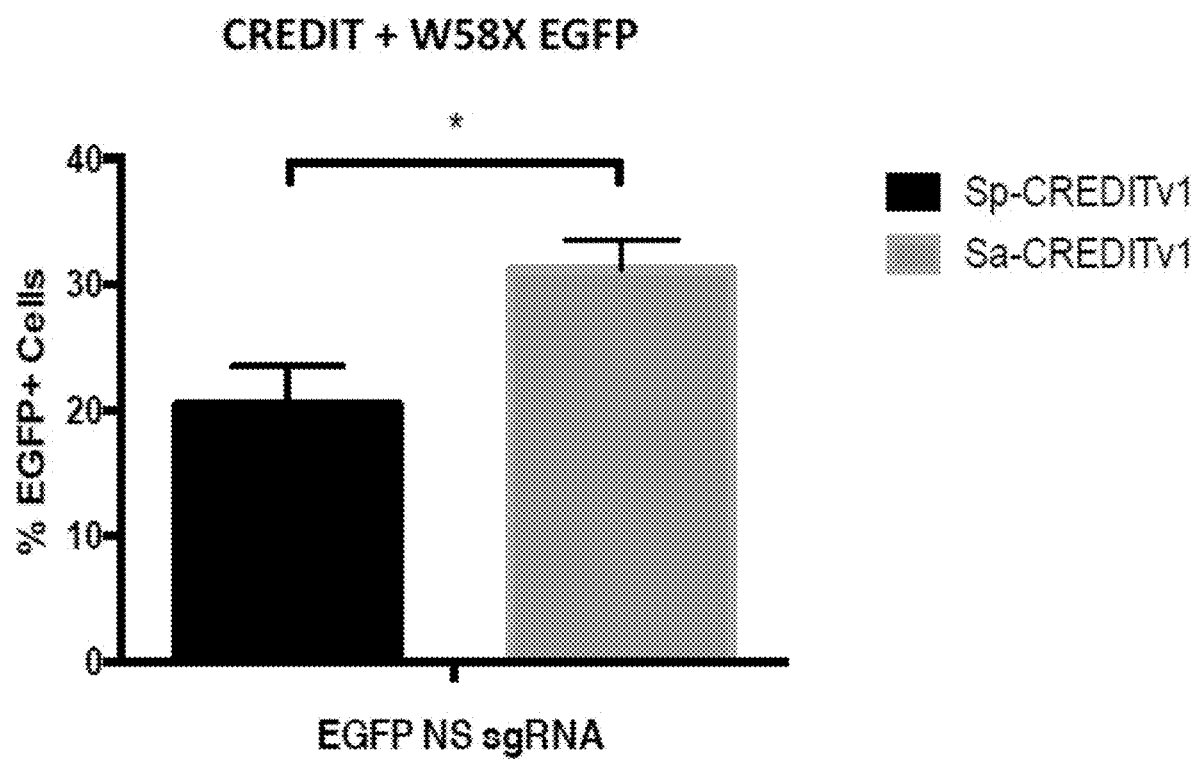

Example 2—Comparison of dSpCas9 and dSaCas9 CREDIT Systems dSaCas9 is significantly smaller than dSpCas9, which provides efficiency in viral packaging. A CREDIT system was prepared comprising (1) an ADAR2(E488Q)-dSaCas9 fusion with a GSGS linker (SEQ ID NO: 12) ("GSGS" disclosed as SEQ ID NO: 49) and (2) an esgRNA with a scaffold sequence specific to SaCas9 that targets an EGFP reporter (SEQ ID NO: 11). The efficiency of mRNA editing by this system was compared to a system comprising ADAR2(E488Q)-dSpCas9, as shown in FIG. 13B. ADAR2-dSaCas9 resulted in about 30% of target cells expressing successfully edited EGFP RNA, as compared to about 20% by ADAR2-dSpCas9. Overall, this data shows successful editing by both ADAR2-dSaCas9 and ADAR2-dSpCas9.

Example 3—Treatment of Limb-Girdle Muscular Dystrophy—Type 2B

Limb-girdle muscular dystrophy—type 2B is caused by a defect in the Dysferlin gene. By developing methods to accurately correct Dysferlin mRNA in a subject, a fully functional dysferlin protein can be expressed in patients with this disorder.

The recombinant expression systems of the present disclosure allow for simple correction of the mutant dysferlin mRNA. When combined with the disclosed AAV delivery system, these systems can be used to efficiently target every major muscle with a single intravenous administration, and provide a robust therapeutic strategy to treat muscular dystrophy. Because the AAV will ultimately be used to target skeletal muscle, an AAV with skeletal muscle tropism should be used such as AAV1, AAV6, AAV7, AAV8, or AAV9.

Viral particles are prepared as described herein. Briefly, Flp-In T-REX 293 cells are transfected vectors as described in Example 1. An esgRNA is designed to target the mutant locus within the subject's dysferlin mRNA. The esgRNA can be designed to target a mutation in one or more of the following dysferlin mRNAs: NM_001130455, NM_001130976, NM_001130977, NM_001130978, NM_001130979, NM_001130980, NM_001130981, NM_001130982, NM_001130983, NM_001130984, NM_001130985, NM_001130986, NM_001130987, or NM_003494). In some embodiments, the subject's dysferlin mRNA is sequenced prior to design of the esgRNA to confirm the presence of a correctable A point mutation. A nucleic acid encoding the esgRNA is cloned into a suitable vector. Following transfection of the packaging cells, assembled viral particles are harvested and tested for Cas9 protein expression, as well as expression of esgRNA. The packaged virus is also assayed for viral titer which should range from about 10^8 GC/mL to 10^17 GC/mL, with titer optimally of about 10^13 GC/mL. Viral titer can be assayed by western blot or by viral genome copy number by qPCR and compared to copy number standard samples.

Modified viral particles can be administered ex vivo or in vitro to muscle stem or progenitor cells from subjects with Limb-girdle muscular dystrophy—type 2B. Upon integration of the viral vectors, the modified cells are transplanted back into subject via intramuscular injection. Effectiveness of cell therapy with the cells treated with modified AAV is measured by improved muscle morphology, decreases in sarcolemmal localization of the multimeric dystrophin-glycoprotein complex and neuronal nitric-oxide synthase, as well as detection of dysferlin expression.

Alternatively, the viral particles can be administered in vivo to muscle tissue through, for example, localized or systemic delivery such as intramuscular injection, intraperitoneal injection, or intravenous injection. Effectiveness of viral gene therapy is measured by improved muscle morphology as well as detection of dysferlin expression.

Efficiency of CRISPR-mediated RNA editing is assayed by designing PCR primers that detect a reverse transcribed copy of the repaired dysferlin mRNA fragment. Expression of repaired gene product can also be detected by PCR, histological staining, or western blot of treated muscle tissue.

Example 4—Editing of CFTR mRNA

Cystic fibrosis is a genetic disorder that affects the lungs, pancreas, liver, kidneys, and intestine. Long-term symptoms include difficulty breathing and coughing up mucus as a result of frequent lung infections. Other signs and symptoms may include sinus infections, poor growth, fatty stool, clubbing of the fingers and toes, and infertility. Cystic fibrosis is caused by mutations in the cystic fibrosis transmembrane conductance regulator (CFTR) gene. By developing methods to accurately correct CFTR mRNA in a subject, a fully functional CFTR protein can be expressed in these patients.

The recombinant expression systems of the present disclosure allow for simple correction of CFTR mRNA. When combined with the a viral delivery system such as AAV or lentivirus, these systems can be used to efficiently target affected tissues and provide a robust therapeutic strategy to treat Cystic Fibrosis. AAV with lung tropism include but are not limited to AAV4, AAV5, AAV6, and AAV9.

An esgRNA is designed to target the mutant locus within the subject's CTFR mRNA. In some embodiments, the subject's CFTR mRNA is sequenced prior to design of the esgRNA to confirm the presence of a correctable A point mutation. A nucleic acid encoding the esgRNA is cloned into a suitable vector. A non-limiting example of a suitable CFTR targeting spacer sequence is SEQ ID NO: 43. A non-limiting example of a suitable CFTR extension sequence is SEQ ID NO: 44. A non-limiting example of a lentiviral plasmid comprising an esgRNA targeted to CFTR is LCV2_purpo_ CFTR_51_1217_gibson (SEQ ID NO: 35).

Following transfection of the packaging cells, assembled viral particles are harvested and tested for Cas9 protein expression, as well as expression of esgRNA. The packaged virus is also assayed for viral titer which should range from about 10^8 GC/mL to 10^17 GC/mL, with titer optimally of about 10^13 GC/mL. Viral titer can be assayed by western blot or by viral genome copy number by qPCR and compared to copy number standard samples.

Viral particles can be administered in vivo to the subject through, for example, localized or systemic delivery such as intraperitoneal injection, organ-targeted injection, or intravenous injection. Effectiveness of viral gene therapy is measured by improved lung function, a reduction or amelioration of one or more symptoms of Cystic Fibrosis, and/or detection of corrected CFTR protein expression.

Efficiency of CRISPR-mediated RNA editing is assayed by designing PCR primers that detect a reverse transcribed copy of the repaired CFTR mRNA fragment. Expression of repaired gene product can also be detected by PCR, histological staining, or western blot of treated lung tissue.

Example 5—Editing of IDUA mRNA

Hurler syndrome is a genetic disorder that results in the buildup of glycosaminoglycans due to a deficiency of alpha-L iduronidase (IDUA), an enzyme responsible for the degradation of mucopolysaccharides in lysosomes. Without this enzyme, a buildup of dermatan sulfate and heparan sulphate occurs in the body. Symptoms include but are not limited to hepatosplenomegaly, dwarfism, unique facial features, progressive mental retardation, and early death due to organ damage.

The recombinant expression systems of the present disclosure allow for simple correction of IDUA mRNA. When combined with the a viral delivery system such as AAV or lentivirus, these systems can be used to provide a robust therapeutic strategy to treat Hurler syndrome.

An esgRNA is designed to target the mutant locus within the subject's IDUA mRNA. In some embodiments, the subject's IDUA mRNA is sequenced prior to design of the esgRNA to confirm the presence of a correctable A point mutation. A nucleic acid encoding the esgRNA is cloned into a suitable vector. A non-limiting example of a suitable IDUA targeting spacer sequence is SEQ ID NO: 45. A non-limiting example of a suitable IDUA extension sequence is SEQ ID NO: 46. A non-limiting example of a lentiviral plasmid comprising an esgRNA targeted to IDUA is AXCM_LCV2_puro_IDUA_No-spacer_gibson (SEQ ID NO: 39).

Following transfection of the packaging cells, assembled viral particles are harvested and tested for Cas9 protein expression, as well as expression of esgRNA. The packaged virus is also assayed for viral titer which should range from about $10^8$ GC/mL to $10^{17}$ GC/mL, with titer optimally of about $10^{13}$ GC/mL. Viral titer can be assayed by western blot or by viral genome copy number by qPCR and compared to copy number standard samples.

Viral particles can be administered in vivo to the subject through, for example, systemic delivery such as intravenous injection. Effectiveness of viral gene therapy is measured by decrease in the amount of heparin sulphate in the subject, a reduction or amelioration of one or more symptoms of Hurler syndrome, and/or detection of corrected IDUA protein expression.

Efficiency of CRISPR-mediated RNA editing is assayed by designing PCR primers that detect a reverse transcribed copy of the repaired IDUA mRNA fragment. Expression of repaired gene product can also be detected by PCR, histological staining, or western blot of treated tissues.

EQUIVALENTS

It should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be with the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

REFERENCES

1. Fukuda, M., et al., Construction of a guide-RNA for site-directed RNA mutagenesis utilising intracellular A-to-I RNA editing. Sci Rep, 2017. 7: p. 41478.
2. Halo et al "NanoFlares for the detection, isolation, and culture of live tumor cells from human blood" PNAS doi: 10.1073/pnas.1418637111.
3. Hanswillemenke et al., Site-Directed RNA Editing in Vivo Can Be Triggered by the Light-Driven Assembly of an Artificial Riboprotein. J Am Chem Soc, 2015. 137(50): p. 15875-81.
4. Hua et al "Peripheral SMN restoration is essential for long-term rescue of a severe spinal muscular atrophy mouse model." Nature. 2011 Oct. 5; 478(7367):123-6. doi: 10.1038/nature10485.
5. McMahon et al., TRIBE: Hijacking an RNA-Editing Enzyme to Identify Cell-Specific Targets of RNA-Binding Proteins. Cell, 2016. 165(3): p. 742-53.
6. Montiel-Gonzalez et al "An efficient system for selectively altering genetic information within mRNAs." Nucleic Acids Res. 2016 44: e157. doi: 10.1093/nar/gkw738.
7. Montiel-Gonzalez et al "Correction of mutations within the cystic fibrosis transmembrane conductance regulator by site-directed RNA editing." PNAS. 2013 110: 18285-90.
8. Schneider et al "Optimal guideRNAs for re-directing deaminase activity of hADAR1 and hADAR2 in trans." Nucleic Acids Res. 2014 42: e87. doi: 10.1093/nar/gku272.
9. Wang et al "Engineering splicing factors with designed specificities" Nat Methods. 2009 November; 6(11): 825-830. 10.1038/nmeth.1379
10. WO 2015089277
11. WO 2016183402

Sequences

Provided below are exemplary sequences of the constructs described herein.

```
pcDNA3.1(1) ADAR2 XTEN dCas9 (SEQ ID NO: 27)
LOCUS Exported 10826 bp ds-DNA circular
DEFINITION synthetic circular DNA
SOURCE synthetic DNA construct
ORGANISM recombinant plasmid
REFERENCE 1 (bases 1 to 10826)
FEATURES Location/Qualifiers
source 1 . . . 10826
/organism="recombinant plasmid"
/mol_type="other DNA"
enhancer 235 . . . 614
/label=CMV enhancer
/note="human cytomegalovirus immediate early enhancer"
promoter 615 . . . 818
/label=CMV promoter
/note="human cytomegalovirus (CMV) immediate early
promoter"
promoter 863 . . . 881
/label=T7 promoter
/note="promoter for bacteriophage T7 RNA polymerase"
misc_feature 927 . . . 954
/label=Homology 1_pCDNA3.1
primer_bind 955 . . . 976
/label=ADAR2CD-Cas9_HindIII_F
misc_feature 955 . . . 960
/label=Kozak
primer_bind 960 . . . 983
/label=Adar_out_forward_lv2
CDS 961 . . . 2100
/codon_start=1
/label=ADARB1_Catalytic Domain
                                              (SEQ ID NO: 50)
/translation="MLADAVSRLVLGKFGDLTDNFSSPHARRKVLAGVVMTTGTDVKDA
KVISVSTGTKCINGEYMSDRGLALNDCHAEIISRRSLLRFLYTQLELYLNNKDDQKRSI
FQKSERGGFRLKENVQFHLYISTSPCGDARIFSPHEPILEEPADRHPNRKARGQLRTKI
ESGEGTIPVRSNASIQTWDGVLQGERLLTMSCSDKIARWNVVGIQGSLLSIFVEPIYFS
SIILGSLYHGDHLSRAMYQRISNIEDLPPLYTLNKPLLSGISNAEARQPGKAPNFSVNW
TVGDSAIEVINATTGKDELGRASRLCKHALYCRWMRVHGKVPSHLLRSKITKPNVYHES
KLAAKEYQAAKARLFTAFIKAGLGAWVEKPTEQDQFSLTP"
primer_bind 1324 . . . 1346
/label=E488Q_ADAR2_Mut_seq
primer_bind complement(1426 . . . 1447)
/label=E488Q_Mut_Classic_R
primer_bind 1448 . . . 1472
/label=E488Q_Mut_Classic_F
CDS 2101 . . . 2148
/codon_start=1
/label=XTEN
/translation="SGSETPGTSESATPES" (SEQ ID NO: 37)
primer_bind complement(2129 . . . 2148)
/label=ADAR2_CD_Inverse_R
CDS 2149 . . . 6252
/codon_start=1
/product="catalytically dead mutant of the Cas9
endonuclease from the Streptococcus pyogenes Type II
CRISPR/Cas system"
/label=dCas9
/note="RNA-guided DNA-binding protein that lacks
endonuclease activity due to the D10A mutation in the RuvC
catalytic domain and the H840A mutation in the HNH
catalytic domain"
                                              (SEQ ID NO: 42)
/translation="MDKKYSIGLAIGTNSVGWAVITDEYKVPSKKFKVLGNTDRHSIKK
NLIGALLFDSGETAEATRLKRTARRRYTRRKNRICYLQEIFSNEMAKVDDSFFHRLEES
FLVEEDKKHERHPIFGNIVDEVAYHEKYPTIYHLRKKLVDSTDKADLRLIYLALAHMIK
FRGHFLIEGDLNPDNSDVDKLFIQLVQTYNQLFEENPINASGVDAKAILSARLSKSRRL
ENLIAQLPGEKKNGLFGNLIALSLGLTPNFKSNFDLAEDAKLQLSKDTYDDDLDNLLAQ
IGDQYADLFLAAKNLSDAILLSDILRVNTEITKAPLSASMIKRYDEHHQDLTLLKALVR
QQLPEKYKEIFFDQSKNGYAGYIDGGASQEEFYKFIKPILEKMDGTEELLVKLNREDLL
RKQRTFDNGSIPHQIHLGELHAILRRQEDFYPFLKDNREKIEKILTFRIPYYVGPLARG
NSRFAWMTRKSEETITPWNFEEVVDKGASAQSFIERMTNFDKNLPNEKVLPKHSLLYEY
FTVYNELTKVKYVTEGMRKPAFLSGEQKKAIVDLLFKTNRKVTVKQLKEDYFKKIECFD
SVEISGVEDRFNASLGTYHDLLKIIKDKDFLDNEENEDILEDIVLTLTLFEDREMIEER
LKTYAHLFDDKVMKQLKRRRYTGWGRLSRKLINGIRDKQSGKTILDFLKSDGFANRNFM
QLIHDDSLTFKEDIQKAQVSGQGDSLHEHIANLAGSPAIKKGILQTVKVVDELVKVMGR
HKPENIVIEMARENQTTQKGQKNSRERMKRIEEGIKELGSQILKEHPVENTQLQNEKLY
```

-continued

LYYLQNGRDMYVDQELDINRLSDYDVDAIVPQSFLKDDSIDNKVLTRSDKNRGKSDNVP
SEEVVKKMKNYWRQLLNAKLITQRKFDNLTKAERGGLSELDKAGFIKRQLVETRQITKH
VAQILDSRMNTKYDENDKLIREVKVITLKSKLVSDFRKDFQFYKVREINNYHHAHDAYL
NAVVGTALIKKYPKLESEFVYGDYKVYDVRKMIAKSEQEIGKATAKYFFYSNIMNFFKT
EITLANGEIRKRPLIETNGETGEIVWDKGRDFATVRKVLSMPQVNIVKKTEVQTGGFSK
ESILPKRNSDKLIARKKDWDPKKYGGFDSPTVAYSVLVVAKVEKGKSKKLKSVKELLGI
TIMERSSFEKNPIDFLEAKGYKEVKKDLIIKLPKYSLFELENGRKRMLASAGELQKGNE
LALPSKYVNFLYLASHYEKLKGSPEDNEQKQLFVEQHKHYLDEIIEQISEFSKRVILAD
ANLDKVLSAYNKHRDKPIREQAENIIHLFTLTNLGAPAAFKYFDTTIDRKRYTSTKEVL
DATLIHQSITGLYETRIDLSQLGGD"
primer_bind complement(6233 . . . 6252)
/label=Cas9_out_rev_lv2
primer_bind 6253 . . . 6274
/label=ADAR2_CD_Inverse_F
CDS 6256 . . . 6282
/codon_start=1
/product="HA (human influenza hemagglutinin) epitope tag"
/label=HA
/translation="YPYDVPDYA" (SEQ ID NO: 51)
CDS 6301 . . . 6321
/codon_start=1
/product="nuclear localization signal of SV40 large T
antigen"
/label=SV40 NLS
/translation="PKKKRKV" (SEQ ID NO: 52)
CDS 6328 . . . 6348
/codon_start=1
/product="nuclear localization signal of SV40 large T
antigen"
/label=SV40 NLS
/translation="PKKKRKV" (SEQ ID NO: 52)
primer_bind complement(6332 . . . 6357)
/label=ADAR2CD-Cas9_NotI_R
misc_feature 6358 . . . 6392
/label=Homology 2_pCDNA3.1
polyA_signal 6426 . . . 6650
/label=bGH poly(A) signal
/note="bovine growth hormone polyadenylation signal"
rep_origin 6696 . . . 7124
/direction=RIGHT
/label=f1 ori
/note="f1 bacteriophage origin of replication; arrow
indicates direction of (+) strand synthesis"
promoter 7138 . . . 7467
/label=SV40 promoter
/note="SV40 enhancer and early promoter"
rep_origin 7318 . . . 7453
/label=SV40 ori
/note="SV40 origin of replication"
CDS 7534 . . . 8328
/codon_start=1
/gene="aph(3')-II (or nptII)"
/product="aminoglycoside phosphotransferase from Tn5"
/label=NeoR/KanR
/note="confers resistance to neomycin, kanamycin, and G418
(Geneticin(R))"
(SEQ ID NO: 53)
/translation="MIEQDGLHAGSPAAWVERLFGYDWAQQTIGCSDAAVFRLSAQGRP
VLFVKTDLSGALNELQDEAARLSWLATTGVPCAAVLDVVTEAGRDWLLLGEVPGQDLLS
SHLAPAEKVSIMADAMRRLHTLDPATCPFDHQAKHRIERARTRMEAGLVDQDDLDEEHQ
GLAPAELFARLKARMPDGEDLVVTHGDACLPNIMVENGRFSGFIDCGRLGVADRYQDIA
LATRDIAEELGGEWADRFLVLYGIAAPDSQRIAFYRLLDEFF"
polyA_signal 8502 . . . 8623
/label=SV40 poly(A) signal
/note="SV40 polyadenylation signal"
primer_bind complement(8672 . . . 8688)
/label=M13 rev
/note="common sequencing primer, one of multiple similar
variants"
protein_bind 8696 . . . 8712
/label=lac operator
/bound_moiety="lac repressor encoded by lacI"
/note="The lac repressor binds to the lac operator to
inhibit transcription in E. coli. This inhibition can be
relieved by adding lactose or
isopropyl-beta-D-thiogalactopyranoside (IPTG)."
promoter complement(8720 . . . 8750)
/label=lac promoter
/note="promoter for the E. coli lac operon"
protein_bind 8765 . . . 8786
/label=CAP binding site

```
-continued
/bound_moiety="E. coli catabolite activator protein"
/note="CAP binding activates transcription in the presence
of cAMP."
rep_origin  complement(9074 . . . 9659)
/direction=LEFT
/label=ori
/note="high-copy-number ColE1/pMB1/pBR322/pUC origin of
replication"
CDS         complement(9830 . . . 10690)
/codon_start=1
/gene="bla"
/product="beta-lactamase"
/label=AmpR
/note="confers resistance to ampicillin, carbenicillin, and
related antibiotics"
                                                   (SEQ ID NO: 54)
/translation="MSIQHFRVALIPFFAAFCLPVFAHPETLVKVKDAEDQLGARVGYI
ELDLNSGKILESFRPEERFPMMSTFKVLLCGAVLSRIDAGQEQLGRRIHYSQNDLVEYS
PVTEKHLTDGMTVRELCSAAITMSDNTAANLLLTTIGGPKELTAFLHNMGDHVTRLDRW
EPELNEAIPNDERDTTMPVAMATTLRKLLTGELLTLASRQQLIDWMEADKVAGPLLRSA
LPAGWFIADKSGAGERGSRGIIAALGPDGKPSRIVVIYTTGSQATMDERNRQIAEIGAS
LIKHW"
promoter    complement(10691 . . . 10795)
/gene="bla"
/label=AmpR promoter
ORIGIN
    1 gacggatcgg gagatctccc gatcccctat ggtgcactct cagtacaatc tgctctgatg
   61 ccgcatagtt aagccagtat ctgctccctg cttgtgtgtt ggaggtcgct gagtagtgcg
  121 cgagcaaaat ttaagctaca acaaggcaag gcttgaccga caattgcatg aagaatctgc
  181 ttagggttag gcgttttgcg ctgcttcgcg atgtacgggc cagatatacg cgttgacatt
  241 gattattgac tagttattaa tagtaatcaa ttacggggtc attagttcat agcccatata
  301 tggagttccg cgttacataa cttacggtaa atggcccgcc tggctgaccg cccaacgacc
  361 cccgcccatt gacgtcaata atgacgtatg ttcccatagt aacgccaata gggactttcc
  421 attgacgtca atgggtggag tatttacggt aaactgccca cttggcagta catcaagtgt
  481 atcatatgcc aagtacgccc cctattgacg tcaatgacgg taaatggccc gcctggcatt
  541 atgcccagta catgacctta tgggactttc ctacttggca gtacatctac gtattagtca
  601 tcgctattac catggtgatg cggttttggc agtacatcaa tgggcgtgga tagcggtttg
  661 actcacgggg atttccaagt ctccacccca ttgacgtcaa tgggagtttg ttttggcacc
  721 aaaatcaacg ggactttcca aatgtcgta acaactccgc cccattgacg caaatgggcg
  781 gtaggcgtgt acggtgggag gtctatataa gcagagctct ctggctaact agagaaccca
  841 ctgcttactg gcttatcgaa attaatacga ctcactatag ggagacccaa gctggctagc
  901 gtttaaacgg gccctctaga ctcgagcggc cgccactgtg ctggatatct gcagagaacc
  961 atgttagctg acgctgtctc acgcctggtc ctgggtaagt ttggtgacct gaccgacaac
 1021 ttctcctccc ctcacgctcg cagaaaagtg ctggctggag tcgtcatgac aacaggcaca
 1081 gatgttaaag atgccaaggt gataagtgtt tctacaggaa caaaatgtat taatggtgaa
 1141 tacatgagtg atcgtggcct tgcattaaat gactgccatg cagaaataat atctcggaga
 1201 tccttgctca gatttcttta tacacaactt gagcttact taaataacaa agatgatcaa
 1261 aaaagatcca tctttcagaa atcagagcga ggggggttta ggctgaagga gaatgtccag
 1321 tttcatctgt acatcagcac ctctccctgt ggagatgcca gaatcttctc accacatgag
 1381 ccaatcctgg aagaaccagc agatagacac ccaaatcgta aagcaagagg acagctacgg
 1441 accaaaatag agtctggtga ggggacgatt ccagtgcgct ccaatgcgag catccaaacg
 1501 tgggacgggg tgctgcaagg ggagcggctg ctcaccatgt cctgcagtga caagattgca
 1561 cgctggaacg tggtgggcat ccagggatcc ctgctcagca ttttcgtgga gcccatttac
 1621 ttctcgagca tcatcctggg cagcctttac cacggggacc cctttccag ggccatgtac
```

-continued

```
1681 cagcggatct ccaacataga ggacctgcca cctctctaca ccctcaacaa gcctttgctc
1741 agtggcatca gcaatgcaga agcacggcag ccagggaagg cccccaactt cagtgtcaac
1801 tggacggtag gcgactccgc tattgaggtc atcaacgcca cgactgggaa ggatgagctg
1861 ggccgcgcgt cccgcctgtg taagcacgcg ttgtactgtc gctggatgcg tgtgcacggc
1921 aaggttccct cccacttact acgctccaag attaccaagc caacgtgta ccatgagtcc
1981 aagctggcgc aaaggagta ccaggccgcc aaggcgcgtc tgttcacagc cttcatcaag
2041 gcggggctgg gggcctgggt ggagaagccc accgagcagg accagttctc actcacgccc
2101 agtggaagtg agacaccggg aacctcagag agcgccacgc cagaaagcat ggacaagaag
2161 tacagcatcg gcctggccat cggcaccaac tctgtgggct gggccgtgat caccgacgag
2221 tacaaggtgc ccagcaagaa attcaaggtg ctgggcaaca ccgaccggca cagcatcaag
2281 aagaacctga tcggcgccct gctgttcgac agcggagaaa cagccgaggc cacccggctg
2341 aagagaaccg ccagaagaag ataccacaga cggaagaacc ggatctgcta tctgcaagag
2401 atcttcagca acgagatggc caaggtggac gacagcttct tccacagact ggaagagtcc
2461 ttcctggtgg aagaggataa gaagcacgag cggcacccca tcttcggcaa catcgtggac
2521 gaggtggcct accacgagaa gtaccccacc atctaccacc tgagaaagaa actggtggac
2581 agcaccgaca aggccgacct gcggctgatc tatctggccc tggcccacat gatcaagttc
2641 cggggccact tcctgatcga gggcgacctg aaccccgaca cagcgacgt ggacaagctg
2701 ttcatccagc tggtgcagac ctacaaccag ctgttcgagg aaaacccat caacgccagc
2761 ggcgtggacg ccaaggccat cctgtctgcc agactgagca gagcagacg gctggaaaat
2821 ctgatcgccc agctgccgg cgagaagaag aatggcctgt tcggcaacct gattgccctg
2881 agcctgggcc tgacccccaa cttcaagagc aacttcgacc tggccgagga tgccaaactg
2941 cagctgagca aggacaccta cgacgacgac ctggacaacc tgctggccca gatcggcgac
3001 cagtacgccg acctgtttct ggccgccaag aacctgtccg acgccatcct gctgagcgac
3061 atcctgagag tgaacaccga gatcaccaag gcccccctga gcgcctctat gatcaagaga
3121 tacgacgagc accaccagga cctgaccctg ctgaaagctc tcgtgcggca gcagctgcct
3181 gagaagtaca agagatttt cttcgaccag agcaagaacg gctacgccgg ctacatcgat
3241 ggcggagcca gccaggaaga gttctacaag ttcatcaagc ccatcctgga aaagatggac
3301 ggcaccgagg aactgctcgt gaagctgaac agagaggacc tgctgcggaa gcagcggacc
3361 ttcgacaacg gcagcatccc ccaccagatc cacctgggag agctgcacgc cattctgcgg
3421 cggcaggaag attttacccc attcctgaag gacaaccggg aaaagatcga aagatcctg
3481 accttccgca tcccctacta cgtgggccct ctggccaggg gaaacagcag attcgcctgg
3541 atgaccagaa agagcgagga aaccatcacc ccctggaact tcgaggaagt ggtggacaag
3601 ggcgccagcg cccagagctt catcgagcgg atgaccaact tcgataagaa cctgcccaac
3661 gagaaggtgc tgcccaagca cagcctgctg tacgagtact tcaccgtgta caacgagctg
3721 accaaagtga aatacgtgac cgagggaatg agaaagcccg ccttcctgag cggcgagcag
3781 aaaaaagcca tcgtggacct gctgttcaag accaaccgga agtgaccgt gaagcagctg
3841 aaagaggact acttcaagaa aatcgagtgc ttcgactccg tggaaatctc cggcgtggaa
3901 gatcggttca acgcctccct gggcacatac cacgatctgc tgaaaattat caaggacaag
3961 gacttcctgg acaatgagga aaacgaggac attctggaag atatcgtgct gacctgaca
4021 ctgtttgagg acagagagat gatcgaggaa cggctgaaaa cctatgccca cctgttcgac
```

-continued

```
4081 gacaaagtga tgaagcagct gaagcggcgg agatacaccg gctggggcag gctgagccgg 4141 aagctgatca acggcatccg ggacaagcag tccggcaaga caatcctgga tttcctgaag 4201 tccgacggct tcgccaacag aaacttcatg cagctgatcc acgacgacag cctgaccttt 4261 aaagaggaca tccagaaagc ccaggtgtcc ggccagggcg atagcctgca cgagcacatt 4321 gccaatctgg ccggcagccc cgccattaag aagggcatcc tgcagacagt gaaggtggtg 4381 gacgagctcg tgaaagtgat gggccggcac aagcccgaga acatcgtgat cgaaatggcc 4441 agagagaacc agaccaccca gaagggacag aagaacagcc gcgagagaat gaagcggatc 4501 gaagagggca tcaaagagct gggcagccag atcctgaaag aacacccgt ggaaaacacc 4561 cagctgcaga acgagaagct gtacctgtac tacctgcaga atgggcggga tatgtacgtg 4621 gaccaggaac tggacatcaa ccggctgtcc gactacgatg tggacgctat cgtgcctcag 4681 agctttctga aggacgactc catcgataac aaagtgctga ctcggagcga caagaaccgg 4741 ggcaagagcg acaacgtgcc ctccgaagag gtcgtgaaga agatgaagaa ctactggcgc 4801 cagctgctga atgccaagct gattacccag aggaagttcg acaatctgac caaggccgag 4861 agaggcggcc tgagcgaact ggataaggcc ggcttcatca agagacagct ggtggaaacc 4921 cggcagatca caaagcacgt ggcacagatc ctggactccc ggatgaacac taagtacgac 4981 gagaacgaca aactgatccg ggaagtgaaa gtgatcaccc tgaagtccaa gctggtgtcc 5041 gatttccgga aggatttcca gttttacaaa gtgcgcgaga tcaacaacta ccaccacgcc 5101 cacgacgcct acctgaacgc cgtcgtggga accgccctga tcaaaaagta ccctaagctg 5161 gaaagcgagt tcgtgtacgg cgactacaag gtgtacgacg tgcggaagat gatcgccaag 5221 agcgagcagg aaatcggcaa ggctaccgcc aagtacttct tctacagcaa catcatgaac 5281 tttttcaaga ccgagattac cctggccaac ggcgagatcc ggaagcggcc tctgatcgag 5341 acaaacggcg aaacaggcga gatcgtgtgg gataagggcc gggactttgc caccgtgcgg 5401 aaagtgctgt ctatgcccca agtgaatatc gtgaaaaaga ccgaggtgca gacaggcggc 5461 ttcagcaaag agtctatcct gcccaagagg aacagcgaca agctgatcgc cagaaagaag 5521 gactgggacc ctaagaagta cggcggcttc gacagcccca ccgtggccta ttctgtgctg 5581 gtggtggcca agtggaaaa gggcaagtcc aagaaactga gagtgtgaa agagctgctg 5641 gggatcacca tcatggaaag aagcagcttc gagaagaatc ccatcgactt tctggaagcc 5701 aagggctaca aagaagtgaa aaaggacctg atcatcaagc tgcctaagta ctccctgttc 5761 gagctggaaa acggccggaa gagaatgctg gcctctgccg cgaactgca aagggaaac 5821 gaactggccc tgcctccaa atatgtgaac ttcctgtacc tggccagcca ctatgagaag 5881 ctgaagggct cccccgagga taatgagcag aaacagctgt ttgtggaaca gcacaaacac 5941 tacctggacg agatcatcga gcagatcagc gagttctcca agagagtgat cctggccgac 6001 gctaatctgg acaaggtgct gagcgcctac aacaagcaca gagacaagcc tatcagagag 6061 caggccgaga atatcatcca cctgtttacc ctgaccaatc tgggagcccc tgccgccttc 6121 aagtactttg acaccaccat cgaccggaag aggtacacca gcaccaaaga ggtgctggac 6181 gccaccctga tccaccagag catcaccggc ctgtacgaga cacggatcga cctgtctcag 6241 ctgggaggcg acgcctatcc ctatgacgtg cccgattatg ccagcctggg cagcggctcc 6301 cccaagaaaa acgcaaggt ggaagatcct aagaaaagc ggaaagtgga cgtgtaacca 6361 ccacactgga ctagtggatc cgagctcggt accaagctta gtttaaaccc gctgatcagc 6421 ctcgactgtg ccttctagtt gccagccatc tgttgtttgc cctcccccg tgccttcctt 6481 gaccctggaa ggtgccactc ccactgtcct ttcctaataa aatgaggaaa ttgcatcgca
```

-continued

```
6541 ttgtctgagt aggtgtcatt ctattctggg gggtggggtg gggcaggaca gcaagggga 6601 ggattgggaa dacaatagca ggcatgctgg ggatgcggtg ggctctatgg cttctgaggc 6661 ggaaagaacc agctggggct ctaggggta tccccacgcg ccctgtagcg gcgcattaag 6721 cgcggcgggt gtggtggtta cgcgcagcgt gaccgctaca cttgccagcg ccctagcgcc 6781 cgctcctttc gctttcttcc cttcctttct cgccacgttc gccggctttc cccgtcaagc 6841 tctaaatcgg gggctcccctt tagggttccg atttagtgct ttacggcacc tcgaccccaa 6901 aaaacttgat tagggtgatg gttcacgtag tgggccatcg ccctgataga cggttttcg 6961 ccctttgacg ttggagtcca cgttctttaa tagtggactc ttgttccaaa ctggaacaac 7021 actcaaccct atctcggtct attctttga tttataaggg attttgccga tttcggccta 7081 ttggttaaaa aatgagctga tttaacaaaa atttaacgcg aattaattct gtggaatgtg 7141 tgtcagttag ggtgtggaaa gtccccaggc tccccagcag gcagaagtat gcaaagcatg 7201 catctcaatt agtcagcaac caggtgtgga aagtccccag gctccccagc aggcagaagt 7261 atgcaaagca tgcatctcaa ttagtcagca accatagtcc cgccctaac tccgcccatc 7321 ccgcccctaa ctccgcccag ttccgcccat tctccgcccc atggctgact aatttttttt 7381 atttatgcag aggccgaggc cgcctctgcc tctgagctat ccagaagta gtgaggaggc 7441 ttttttggag gcctaggctt ttgcaaaaag ctcccgggag cttgtatatc cattttcgga 7501 tctgatcaag agacaggatg aggatcgttt cgcatgattg aacaagatgg attgcacgca 7561 ggttctccgg ccgcttggt ggagaggcta ttcggctatg actgggcaca acagacaatc 7621 ggctgctctg atgccgccgt gttccggctg tcagcgcagg ggcgcccggt tctttttgtc 7681 aagaccgacc tgtccggtgc cctgaatgaa ctgcaggacg aggcagcgcg gctatcgtgg 7741 ctggccacga cgggcgttcc ttgcgcagct gtgctcgacg ttgtcactga agcgggaagg 7801 gactggctgc tattgggcga agtgccgggg caggatctcc tgtcatctca ccttgctcct 7861 gccgagaaag tatccatcat ggctgatgca atgcggcggc tgcatacgct tgatccggct 7921 acctgcccat tcgaccacca agcgaaacat cgcatcgagc gagcacgtac tcggatggaa 7981 gccggtcttg tcgatcagga tgatctggac gaagagcatc aggggctcgc gccagccgaa 8041 ctgttcgcca ggctcaaggc gcgcatgccc gacggcgagg atctcgtcgt gacccatggc 8101 gatgcctgct tgccgaatat catggtggaa aatggccgct tttctggatt catcgactgt 8161 ggccggctgg gtgtggcgga ccgctatcag gacatagcgt tggctacccg tgatattgct 8221 gaagagcttg gcggcgaatg ggctgaccgc ttcctcgtgc tttacggtat cgccgctccc 8281 gattcgcagc gcatcgcctt ctatcgcctt cttgacgagt tcttctgagc gggactctgg 8341 ggttcgaaat gaccgaccaa gcgacgccca acctgccatc acgagatttc gattccaccg 8401 ccgccttcta tgaaaggttg ggcttcggaa tcgttttccg gacgccggc tggatgatcc 8461 tccagcgcgg ggatctcatg ctggagttct tcgcccaccc caacttgttt attgcagctt 8521 ataatggtta caaataaagc aatagcatca caaatttcac aaataaagca ttttttcac 8581 tgcattctag ttgtggtttg tccaaactca tcaatgtatc ttatcatgtc tgtataccgt 8641 cgacctctag ctagagcttg gcgtaatcat ggtcatagct gtttcctgtg tgaaattgtt 8701 atccgctcac aattccacac aacatacgag ccggaagcat aaagtgtaaa gcctggggtg 8761 cctaatgagt gagctaactc acattaattg cgttgcgctc actgcccgct ttccagtcgg 8821 gaaacctgtc gtgccagctg cattaatgaa tcggccaacg cgcggggaga ggcggtttgc 8881 gtattgggcg ctcttccgct tcctcgctca ctgactcgct gcgctcggtc gttcggctgc
```

-continued

```
8941 ggcgagcggt atcagctcac tcaaaggcgg taatacggtt atccacagaa tcaggggata 9001 acgcaggaaa gaacatgtga gcaaaaggcc agcaaaaggc caggaaccgt aaaaaggccg 9061 cgttgctggc gtttttccat aggctccgcc cccctgacga gcatcacaaa aatcgacgct 9121 caagtcagag gtggcgaaac ccgacaggac tataaagata ccaggcgttt ccccctggaa 9181 gctccctcgt gcgctctcct gttccgaccc tgccgcttac cggatacctg tccgcctttc 9241 tcccttcggg aagcgtggcg ctttctcata gctcacgctg taggtatctc agttcggtgt 9301 aggtcgttcg ctccaagctg ggctgtgtgc acgaaccccc cgttcagccc gaccgctgcg 9361 ccttatccgg taactatcgt cttgagtcca acccggtaag acacgactta tcgccactgg 9421 cagcagccac tggtaacagg attagcagag cgaggtatgt aggcggtgct acagagttct 9481 tgaagtggtg gcctaactac ggctacacta gaagaacagt atttggtatc tgcgctctgc 9541 tgaagccagt taccttcgga aaaagagttg gtagctcttg atccggcaaa caaaccaccg 9601 ctggtagcgg tggtttttttgtt tgcaagcagc agattacgcg cagaaaaaaa ggatctcaag 9661 aagatccttt gatcttttct acggggtctg acgctcagtg gaacgaaaac tcacgttaag 9721 ggatttggt catgagatta tcaaaaagga tcttcaccta gatccttta aattaaaaat 9781 gaagttttaa atcaatctaa agtatatatg agtaaacttg gtctgacagt taccaatgct 9841 taatcagtga ggcacctatc tcagcgatct gtctatttcg ttcatccata gttgcctgac 9901 tccccgtcgt gtagataact acgatacggg agggcttacc atctggcccc agtgctgcaa 9961 tgataccgcg agacccacgc tcaccggctc cagatttatc agcaataaac cagccagccg 10021 gaagggccga gcgcagaagt ggtcctgcaa ctttatccgc ctccatccag tctattaatt 10081 gttgccggga agctagagta agtagttcgc cagttaatag tttgcgcaac gttgttgcca 10141 ttgctacagg catcgtggtg tcacgctcgt cgtttggtat ggcttcattc agctccggtt 10201 cccaacgatc aaggcgagtt acatgatccc ccatgttgtg caaaaaagcg gttagctcct 10261 tcggtcctcc gatcgttgtc agaagtaagt tggccgcagt gttatcactc atggttatgg 10321 cagcactgca taattctctt actgtcatgc catccgtaag atgcttttct gtgactggtg 10381 agtactcaac caagtcattc tgagaatagt gtatgcggcg accgagttgc tcttgcccgg 10441 cgtcaatacg ggataatacc gcgccacata gcagaacttt aaaagtgctc atcattggaa 10501 aacgttcttc ggggcgaaaa ctctcaagga tcttaccgct gttgagatcc agttcgatgt 10561 aacccactcg tgcacccaac tgatcttcag catcttttac tttcaccagc gtttctgggt 10621 gagcaaaaac aggaaggcaa aatgccgcaa aaagggaat aagggcgaca cggaaatgtt 10681 gaatactcat actcttcctt tttcaatatt attgaagcat ttatcagggt tattgtctca 10741 tgagcggata catatttgaa tgtatttaga aaaataaaca ataggggtt ccgcgcacat 10801 ttccccgaaa agtgccacct gacgtc
``` pcDNA3.1(1)_ADAR2_XTEN_control (SEQ ID NO: 28).
LOCUS Exported 6722 bp ds-DNA circular
DEFINITION synthetic circular DNA
FEATURES Location/Qualifiers
source 1 . . . 6722
/organism="synthetic DNA construct"
/mol_type="other DNA"
enhancer 235 . . . 614
/label=CMV enhancer
/note="human cytomegalovirus immediate early enhancer"
promoter 615 . . . 818
/label=CMV promoter
/note="human cytomegalovirus (CMV) immediate early promoter"
promoter 863 . . . 881
/label=T7 promoter
/note="promoter for bacteriophage T7 RNA polymerase"

```
misc_feature    927 . . . 954
/label=Homology 1_pCDNA3.1
primer_bind     955 . . . 976
/label=ADAR2CD-Cas9_HindIII_F
primer_bind     960 . . . 983
/label=Adar_out_forward_lv2
CDS             961 . . . 2100
/codon_start=1
/label=ADARB1(E488Q)_Catalytic Domain
                                                (SEQ ID NO: 50)
/translation="MLADAVSRLVLGKFGDLTDNFSSPHARRKVLAGVVMTTGTDVKDA
KVISVSTGTKCINGEYMSDRGLALNDCHAEIISRRSLLRFLYTQLELYLNNKDDQKRSI
FQKSERGGFRLKENVQFHLYISTSPCGDARIFSPHEPILEEPADRHPNRKARGQLRTKI
ESGEGTIPVRSNASIQTWDGVLQGERLLTMSCSDKIARWNVVGIQGSLLSIFVEPIYFS
SIILGSLYHGDHLSRAMYQRISNIEDLPPLYTLNKPLLSGISNAEARQPGKAPNFSVNW
TVGDSAIEVINATTGKDELGRASRLCKHALYCRWMRVHGKVPSHLLRSKITKPNVYHES
KLAAKEYQAAKARLFTAFIKAGLGAWVEKPTEQDQFSLTP"
primer_bind     1324 . . . 1346
/label=E488Q_ADAR2_Mut
primer_bind     complement(1426 . . . 1447)
/label=E488Q_Mut_Classic_R
primer_bind     1448 . . . 1472
/label=E488Q_Mut_Classic_F
CDS             2101 . . . 2148
/codon_start=1
/label=XTEN
/translation="SGSETPGTSESATPES" (SEQ ID NO: 37)
primer_bind     complement(2129 . . . 2148)
/label=ADAR2_CD_Inverse_R
primer_bind     2149 . . . 2170
/label=ADAR2_CD_Inverse_F
CDS             2152 . . . 2178
/codon_start=1
/product="HA (human influenza hemagglutinin) epitope tag"
/label=HA
/translation="YPYDVPDYA" (SEQ ID NO: 51)
CDS             2197 . . . 2217
/codon_start=1
/product="nuclear localization signal of SV40 large T
antigen"
/label=SV40 NLS
/translation="PKKKRKV" (SEQ ID NO: 52)
CDS             2224 . . . 2244
/codon_start=1
/product="nuclear localization signal of SV40 large T
antigen"
/label=SV40 NLS
/translation="PKKKRKV" (SEQ ID NO: 52)
primer_bind     complement(2228 . . . 2253)
/label=ADAR2CD-Cas9_NotI_R
misc_feature    2254 . . . 2288
/label=Homology 2_pCDNA3.1
polyA_signal    2322 . . . 2546
/label=bGH poly(A) signal
/note="bovine growth hormone polyadenylation signal"
rep_origin      2592 . . . 3020
/direction=RIGHT
/label=f1 ori
/note="f1 bacteriophage origin of replication; arrow
indicates direction of (+) strand synthesis"
promoter        3034 . . . 3363
/label=SV40 promoter
/note="SV40 enhancer and early promoter"
rep_origin      3214 . . . 3349
/label=SV40 ori
/note="SV40 origin of replication"
CDS             3430 . . . 4224
/codon_start=1
/gene="aph(3')-II (or nptII)"
/product="aminoglycoside phosphotransferase from Tn5"
/label=NeoR/KanR
/note="confers resistance to neomycin, kanamycin, and G418
(Geneticin(R))"
                                                (SEQ ID NO: 53)
/translation="MIEQDGLHAGSPAAWVERLFGYDWAQQTIGCSDAAVFRLSAQGRP
VLFVKTDLSGALNELQDEAARLSWLATTGVPCAAVLDVVTEAGRDWLLLGEVPGQDLLS
SHLAPAEKVSIMADAMRRLHTLDPATCPFDHQAKHRIERARTRMEAGLVDQDDLDEEHQ
GLAPAELFARLKARMPDGEDLVVTHGDACLPNIMVENGRFSGFIDCGRLGVADRYQDIA
LATRDIAEELGGEWADRFLVLYGIAAPDSQRIAFYRLLDEFF"
polyA_signal    4398 . . . 4519
/label=SV40 poly(A) signal
```

-continued

```
/note="SV40 polyadenylation signal"
primer_bind    complement(4568 . . . 4584)
/label=M13 rev
/note="common sequencing primer, one of multiple similar
variants"
protein_bind   4592 . . . 4608
/label=lac operator
/bound_moiety="lac repressor encoded by lacI"
/note="The lac repressor binds to the lac operator to
inhibit transcription in E. coli. This inhibition can be
relieved by adding lactose or
isopropyl-beta-D-thiogalactopyranoside (IPTG)."
promoter       complement(4616 . . . 4646)
/label=lac promoter
/note="promoter for the E. coli lac operon"
protein_bind   4661 . . . 4682
/label=CAP binding site
/bound_moiety="E. coli catabolite activator protein"
/note="CAP binding activates transcription in the presence
of cAMP."
rep_origin     complement(4970 . . . 5555)
/direction=LEFT
/label=ori
/note="high-copy-number ColE1/pMB1/pBR322/pUC origin of
replication"
CDS            complement(5726 . . . 6586)
/codon_start=1
/gene="bla"
/product="beta-lactamase"
/label=AmpR
/note="confers resistance to ampicillin, carbenicillin, and
related antibiotics"
                                                    (SEQ ID NO: 54)
/translation="MSIQHFRVALIPFFAAFCLPVFAHPETLVKVKDAEDQLGARVGYI
ELDLNSGKILESFRPEERFPMMSTFKVLLCGAVLSRIDAGQEQLGRRIHYSQNDLVEYS
PVTEKHLTDGMTVRELCSAAITMSDNTAANLLLTTIGGPKELTAFLHNMGDHVTRLDRW
EPELNEAIPNDERDTTMPVAMATTLRKLLTGELLTLASRQQLIDWMEADKVAGPLLRSA
LPAGWFIADKSGAGERGSRGIIAALGPDGKPSRIVVIYTTGSQATMDERNRQIAEIGAS
LIKHW" promoter    complement(6587 . . . 6691)
/gene="bla"
/label=AmpR promoter
ORIGIN
    1 gacggatcgg gagatctccc gatcccctat ggtgcactct cagtacaatc tgctctgatg
   61 ccgcatagtt aagccagtat ctgctccctg cttgtgtgtt ggaggtcgct gagtagtgcg
  121 cgagcaaaat ttaagctaca caaggcaag gcttgaccga caattgcatg aagaatctgc
  181 ttagggttag gcgttttgcg ctgcttcgcg atgtacgggc cagatatacg cgttgacatt
  241 gattattgac tagttattaa tagtaatcaa ttacggggtc attagttcat agcccatata
  301 tggagttccg cgttacataa cttacggtaa atggcccgcc tggctgaccg cccaacgacc
  361 cccgcccatt gacgtcaata atgacgtatg ttcccatagt aacgccaata gggactttcc
  421 attgacgtca atgggtggag tatttacggt aaactgccca cttggcagta catcaagtgt
  481 atcatatgcc aagtacgccc cctattgacg tcaatgacgg taaatggccc gcctggcatt
  541 atgcccagta catgacctta tgggactttc ctacttggca gtacatctac gtattagtca
  601 tcgctattac catggtgatg cggttttggc agtacatcaa tgggcgtgga tagcggtttg
  661 actcacgggg atttccaagt ctccacccca ttgacgtcaa tgggagtttg ttttggcacc
  721 aaaatcaacg ggactttcca aaatgtcgta acaactccgc cccattgacg caaatgggcg
  781 gtaggcgtgt acggtgggag gtctatataa gcagagctct ctggctaact agagaaccca
  841 ctgcttactg gcttatcgaa attaatacga ctcactatag ggagacccaa gctggctagc
  901 gtttaaacgg gccctctaga ctcgagcggc cgccactgtg ctggatatct gcagagaacc
  961 atgttagctg acgctgtctc acgcctggtc ctgggtaagt tggtgacct gaccgacaac
 1021 ttctcctccc ctcacgctcg cagaaaagtg ctggctggag tcgtcatgac aacaggcaca
 1081 gatgttaaag atgccaaggt gataagtgtt tctacaggaa caaatgtat taatggtgaa
 1141 tacatgagtg atcgtggcct tgcattaaat gactgccatg cagaaataat atctcggaga
```

-continued

```
1201 tccttgctca gatttcttta tacacaactt gagctttact taaataacaa agatgatcaa
1261 aaaagatcca tctttcagaa atcagagcga ggggggttta ggctgaagga gaatgtccag
1321 tttcatctgt acatcagcac ctctccctgt ggagatgcca gaatcttctc accacatgag
1381 ccaatcctgg aagaaccagc agatagacac ccaaatcgta aagcaagagg acagctacgg
1441 accaaaatag agtctggtga ggggacgatt ccagtgcgct ccaatgcgag catccaaacg
1501 tgggacgggg tgctgcaagg ggagcggctg ctcaccatgt cctgcagtga caagattgca
1561 cgctggaacg tggtgggcat ccagggatcc ctgctcagca ttttcgtgga gcccatttac
1621 ttctcgagca tcatcctggg cagcctttac acggggacc acctttccag gccatgtac
1681 cagcggatct ccaacataga ggacctgcca cctctctaca ccctcaacaa gcctttgctc
1741 agtggcatca gcaatgcaga agcacggcag ccagggaagg ccccaactt cagtgtcaac
1801 tggacggtag gcgactccgc tattgaggtc atcaacgcca cgactgggaa ggatgagctg
1861 ggccgcgcgt cccgcctgtg taagcacgcg ttgtactgtc gctggatgcg tgtgcacggc
1921 aaggttccct cccacttact acgctccaag attaccaagc caacgtgta ccatgagtcc
1981 aagctggcgg caaaggagta ccaggccgcc aaggcgcgtc tgttcacagc cttcatcaag
2041 gcggggctgg gggcctgggt ggagaagccc accgagcagg accagttctc actcacgccc
2101 agtggaagtg agacaccggg aacctcagag agcgccacgc cagaaagcgc ctatccctat
2161 gacgtgcccg attatgccag cctgggcagc ggctccccca agaaaaaacg caaggtggaa
2221 gatcctaaga aaaagcggaa agtggacgtg taaccaccac actggactag tggatccgag
2281 ctcggtacca agcttaagtt taaaccgctg atcagcctcg actgtgcctt ctagttgcca
2341 gccatctgtt gtttgcccct ccccgtgcc ttccttgacc ctggaaggtg ccactcccac
2401 tgtcctttcc taataaaatg aggaaattgc atcgcattgt ctgagtaggt gtcattctat
2461 tctgggggt ggggtggggc aggacagcaa gggggaggat tgggaagaca atagcaggca
2521 tgctggggat gcggtgggct ctatggcttc tgaggcggaa agaaccagct ggggctctag
2581 ggggtatccc cacgcgccct gtagcggcgc attaagcgcg gcgggtgtgg tggttacgcg
2641 cagcgtgacc gctacacttg ccagcgccct agcgcccgct cctttcgctt tcttcccttc
2701 ctttctcgcc acgttcgccg gctttccccg tcaagctcta aatcgggggc tccctttagg
2761 gttccgattt agtgctttac ggcacctcga ccccaaaaaa cttgattagg gtgatggttc
2821 acgtagtggg ccatcgccct gatagacggt ttttcgccct ttgacgttgg agtccacgtt
2881 ctttaatagt ggactcttgt tccaaactgg aacaacactc aaccctatct cggtctattc
2941 ttttgattta agggatt tgccgatttc ggcctattgg ttaaaaaatg agctgattta
3001 acaaaaattt aacgcgaatt aattctgtgg aatgtgtgtc agttagggtg tggaaagtcc
3061 ccaggctccc cagcaggcag aagtatgcaa agcatgcatc tcaattagtc agcaaccagg
3121 tgtggaaagt ccccaggctc cccagcaggc agaagtatgc aaagcatgca tctcaattag
3181 tcagcaacca tagtcccgcc cctaactccg cccatcccgc cctaactcc gcccagttcc
3241 gcccattctc cgccccatgg ctgactaatt ttttttattt atgcagaggc cgaggccgcc
3301 tctgcctctg agctattcca gaagtagtga ggaggctttt ttggaggcct aggcttttgc
3361 aaaaagctcc cggagcttg tatatccatt ttcggatctg atcaagagac aggatgagga
3421 tcgtttcgca tgattgaaca agatggattg cacgcaggtt ctccggccgc ttgggtggag
3481 aggctattcg gctatgactg ggcacaacag acaatcggct gctctgatgc cgccgtgttc
3541 cggctgtcag cgcaggggcg cccggttctt tttgtcaaga ccgacctgtc cggtgccctg
```

-continued

```
3601 aatgaactgc aggacgaggc agcgcggcta tcgtggctgg ccacgacggg cgttccttgc 3661 gcagctgtgc tcgacgttgt cactgaagcg ggaagggact ggctgctatt gggcgaagtg 3721 ccggggcagg atctcctgtc atctcacctt gctcctgccg agaaagtatc catcatggct 3781 gatgcaatgc ggcggctgca tacgcttgat ccggctacct gcccattcga ccaccaagcg 3841 aaacatcgca tcgagcgagc acgtactcgg atggaagccg gtcttgtcga tcaggatgat 3901 ctggacgaag agcatcaggg gctcgcgcca gccgaactgt tcgccaggct caaggcgcgc 3961 atgcccgacg gcgaggatct cgtcgtgacc catggcgatg cctgcttgcc gaatatcatg 4021 gtggaaaatg gccgcttttc tggattcatc gactgtggcc ggctgggtgt ggcggaccgc 4081 tatcaggaca tagcgttggc tacccgtgat attgctgaag agcttggcgg cgaatgggct 4141 gaccgcttcc tcgtgcttta cggtatcgcc gctcccgatt cgcagcgcat cgccttctat 4201 cgccttcttg acgagttctt ctgagcggga ctctggggtt cgaaatgacc gaccaagcga 4261 cgcccaacct gccatcacga gatttcgatt ccaccgccgc cttctatgaa aggttgggct 4321 tcggaatcgt tttccgggac gccggctgga tgatcctcca gcgcgggat ctcatgctgg 4381 agttcttcgc ccaccccaac ttgtttattg cagcttataa tggttacaaa taaagcaata 4441 gcatcacaaa tttcacaaat aaagcatttt tttcactgca ttctagttgt ggtttgtcca 4501 aactcatcaa tgtatcttat catgtctgta taccgtcgac ctctagctag agcttggcgt 4561 aatcatggtc atagctgttt cctgtgtgaa attgttatcc gctcacaatt ccacacaaca 4621 tacgagccgg aagcataaag tgtaaagcct ggggtgccta atgagtgagc taactcacat 4681 taattgcgtt gcgctcactg cccgctttcc agtcgggaaa cctgtcgtgc cagctgcatt 4741 aatgaatcgg ccaacgcgcg gggagaggcg gtttgcgtat tgggcgctct ccgcttcct 4801 cgctcactga ctcgctgcgc tcggtcgttc ggctgcggcg agcggtatca gctcactcaa 4861 aggcggtaat acggttatcc acagaatcag gggataacgc aggaaagaac atgtgagcaa 4921 aaggccagca aaaggccagg aaccgtaaaa aggccgcgtt gctggcgttt ttccataggc 4981 tccgccccc tgacgagcat cacaaaaatc gacgctcaag tcagaggtgg cgaaacccga 5041 caggactata aagataccag gcgtttcccc ctggaagctc cctcgtgcgc tctcctgttc 5101 cgaccctgcc gcttaccgga tacctgtccg cctttctccc ttcgggaagc gtggcgcttt 5161 ctcatagctc acgctgtagg tatctcagtt cggtgtaggt cgttcgctcc aagctgggct 5221 gtgtgcacga accccccgtt cagcccgacc gctgcgcctt atccggtaac tatcgtcttg 5281 agtccaaccc ggtaagacac gacttatcgc cactggcagc agccactggt aacaggatta 5341 gcagagcgag gtatgtaggc ggtgctacag agttcttgaa gtggtggcct aactacggct 5401 acactagaag aacagtattt ggtatctgcg ctctgctgaa gccagttacc ttcggaaaaa 5461 gagttggtag ctcttgatcc ggcaaacaaa ccaccgctgg tagcggtttt tttgtttgca 5521 agcagcagat tacgcgcaga aaaaaaggat ctcaagaaga tcctttgatc ttttctacgg 5581 ggtctgacgc tcagtggaac gaaaactcac gttaagggat tttggtcatg agattatcaa 5641 aaaggatctt cacctagatc cttttaaatt aaaaatgaag ttttaaatca atctaaagta 5701 tatatgagta aacttggtct gacagttacc aatgcttaat cagtgaggca cctatctcag 5761 cgatctgtct atttcgttca tccatagttg cctgactccc cgtcgtgtag ataactacga 5821 tacgggaggg cttaccatct ggccccagtg ctgcaatgat accgcgagac ccacgctcac 5881 cggctccaga tttatcagca ataaaccagc cagccggaag ggccgagcgc agaagtggtc 5941 ctgcaacttt atccgcctcc atccagtcta ttaattgttg ccgggaagct agagtaagta 6001 gttcgccagt taatagtttg cgcaacgttg ttgccattgc tacaggcatc gtggtgtcac
```

```
6061 gctcgtcgtt tggtatggct tcattcagct ccggttccca acgatcaagg cgagttacat 6121 gatccccat gttgtgcaaa aaagcggtta gctccttcgg tcctccgatc gttgtcagaa 6181 gtaagttggc cgcagtgtta tcactcatgg ttatggcagc actgcataat tctcttactg 6241 tcatgccatc cgtaagatgc ttttctgtga ctggtgagta ctcaaccaag tcattctgag 6301 aatagtgtat gcggcgaccg agttgctctt gcccggcgtc aatacgggat aataccgcgc 6361 cacatagcag aactttaaaa gtgctcatca ttggaaaacg ttcttcgggg cgaaaactct 6421 caaggatctt accgctgttg agatccagtt cgatgtaacc cactcgtgca cccaactgat 6481 cttcagcatc ttttactttc accagcgttt ctgggtgagc aaaaacagga aggcaaaatg 6541 ccgcaaaaaa gggaataagg gcgacacgga aatgttgaat actcatactc ttcctttttc 6601 aatattattg aagcatttat cagggttatt gtctcatgag cggatacata tttgaatgta 6661 tttagaaaaa taaacaaata ggggttccgc gcacatttcc ccgaaaagtg ccacctgacg 6721 tc
``` pcDNA3.1_ADAR2(E488Q)_XTEN_dCas9 (SEQ ID NO: 29).
LOCUS Exported 10826 bp ds-DNA circular
DEFINITION synthetic circular DNA
SOURCE synthetic DNA construct
ORGANISM synthetic DNA construct
REFERENCE 1 (bases 1 to 10826)
FEATURES Location/Qualifiers
source 1 . . . 10826
/organism="synthetic DNA construct"
/mol_type="other DNA"
enhancer 235 . . . 614
/label=CMV enhancer
/note="human cytomegalovirus immediate early enhancer"
promoter 615 . . . 818
/label=CMV promoter
/note="human cytomegalovirus (CMV) immediate early
promoter"
promoter 863 . . . 881
/label=T7 promoter
/note="promoter for bacteriophage T7 RNA polymerase"
primer_bind 927 . . . 985
/label=H1-ADAR-XTEN_F
misc_feature 927 . . . 954
/label=Homology 1_pCDNA3.1
CDS 961 . . . 2100
/codon_start=1
/label=ADARB1(E488Q)_Catalytic Domain
(SEQ ID NO: 40)
/translation="MLADAVSRLVLGKFGDLTDNFSSPHARRKVLAGVVMTTGTDVKDA
KVISVSTGTKCINGEYMSDRGLALNDCHAEIISRRSLLRFLYTQLELYLNNKDDQKRSI
FQKSERGGFRLKENVQFHLYISTSPCGDARIFSPHEPILEEPADRHPNRKARGQLRTKI
ESGQGTIPVRSNASIQTWDGVLQGERLLTMSCSDKIARWNVVGIQGSLLSIFVEPIYFS
SIILGSLYHGDHLSRAMYQRISNIEDLPPLYTLNKPLLSGISNAEARQPGKAPNFSVNW
TVGDSAIEVINATTGKDELGRASRLCKHALYCRWMRVHGKVPSHLLRSKITKPNVYHES
KLAAKEYQAAKARLFTAFIKAGLGAWVEKPTEQDQFSLTP"
primer_bind 961 . . . 982
/label=Primer 4
primer_bind 1111 . . . 1138
/label=Primer 1
primer_bind 1440 . . . 1478
/label=E488Q_Mutagenesis_F
primer_bind complement(1440 . . . 1478)
/label=E488Q_Mutagenesis_R
primer_bind complement(2080 . . . 2100)
/label=ADAR2DD_GS_R
primer_bind complement(2080 . . . 2100)
/label=Primer 5
CDS 2101 . . . 2148
/codon_start=1
/label=XTEN
/translation="SGSETPGTSESATPES" (SEQ ID NO: 41)
primer_bind complement(2129 . . . 2148)
/label=ADAR_XTEN_R
primer_bind complement(2129 . . . 2148)
/label=ADAR2_CD_Inverse_R
primer_bind 2148 . . . 2171

```
-continued
/label=Primer 2
CDS 2149 . . . 6252
/codon_start=1
/product="catalytically dead mutant of the Cas9
endonuclease from the Streptococcus pyogenes Type II
CRISPR/Cas system"
/label=dCas9
/note="RNA-guided DNA-binding protein that lacks
endonuclease activity due to the D10A mutation in the RuvC
catalytic domain and the H840A mutation in the HNH
catalytic domain"
                                             (SEQ ID NO: 42)
/translation="MDKKYSIGLAIGTNSVGWAVITDEYKVPSKKFKVLGNTDRHSIKK
NLIGALLFDSGETAEATRLKRTARRRYTRRKNRICYLQEIFSNEMAKVDDSFFHRLEES
FLVEEDKKHERHPIFGNIVDEVAYHEKYPTIYHLRKKLVDSTDKADLRLIYLALAHMIK
FRGHFLIEGDLNPDNSDVDKLFIQLVQTYNQLFEENPINASGVDAKAILSARLSKSRRL
ENLIAQLPGEKKNGLFGNLIALSLGLTPNFKSNFDLAEDAKLQLSKDTYDDDLDNLLAQ
IGDQYADLFLAAKNLSDAILLSDILRVNTEITKAPLSASMIKRYDEHHQDLTLLKALVR
QQLPEKYKEIFFDQSKNGYAGYIDGGASQEEFYKFIKPILEKMDGTEELLVKLNREDLL
RKQRTFDNGSIPHQIHLGELHAILRRQEDFYPFLKDNREKIEKILTFRIPYYVGPLARG
NSRFAWMTRKSEETITPWNFEEVVDKGASAQSFIERMTNFDKNLPNEKVLPKHSLLYEY
FTVYNELTKVKYVTEGMRKPAFLSGEQKKAIVDLLFKTNRKVTVKQLKEDYFKKIECFD
SVEISGVEDRFNASLGTYHDLLKIIKDKDFLDNEENEDILEDIVLTLTLFEDREMIEER
LKTYAHLFDDKVMKQLKRRRYTGWGRLSRKLINGIRDKQSGKTILDFLKSDGFANRNFM
QLIHDDSLTFKEDIQKAQVSGQGDSLHEHIANLAGSPAIKKGILQTVKVVDELVKVMGR
HKPENIVIEMARENQTTQKGQKNSRERMKRIEEGIKELGSQILKEHPVENTQLQNEKLY
LYYLQNGRDMYVDQELDINRLSDYDVDAIVPQSFLKDDSIDNKVLTRSDKNRGKSDNVP
SEEVVKKMKNYWRQLLNAKLITQRKFDNLTKAERGGLSELDKAGFIKRQLVETRQITKH
VAQILDSRMNTKYDENDKLIREVKVITLKSKLVSDFRKDFQFYKVREINNYHHAHDAYL
NAVVGTALIKKYPKLESEFVYGDYKVYDVRKMIAKSEQEIGKATAKYFFYSNIMNFFKT
EITLANGEIRKRPLIETNGETGEIVWDKGRDFATVRKVLSMPQVNIVKKTEVQTGGFSK
ESILPKRNSDKLIARKKDWDPKKYGGFDSPTVAYSVLVVAKVEKGKSKKLKSVKELLGI
TIMERSSFEKNPIDFLEAKGYKEVKKDLIIKLPKYSLFELENGRKRMLASAGELQKGNE
LALPSKYVNFLYLASHYEKLKGSPEDNEQKQLFVEQHKHYLDEIIEQISEFSKRVILAD
ANLDKVLSAYNKHRDKPIREQAENIIHLFTLTNLGAPAAFKYFDTTIDRKRYTSTKEVL
DATLIHQSITGLYETRIDLSQLGGD"
primer_bind complement(4458 . . . 4479)
/label=Primer 3
primer_bind 4879 . . . 4899
/label=Primer 6
primer_bind 6252 . . . 6273
/label=SaCas9_HA_F
primer_bind 6253 . . . 6274
/label=ADAR2_CD_Inverse_F
CDS 6256 . . . 6282
/codon_start=1
/product="HA (human influenza hemagglutinin) epitope tag"
/label=HA
/translation="YPYDVPDYA" (SEQ ID NO: 51)
primer_bind complement(6274 . . . 6296)
/label=AXC_NLSout_NESin_R
primer_bind complement(6274 . . . 6294)
/label=NLS_out_R
CDS 6301 . . . 6321
/codon_start=1
/product="nuclear localization signal of SV40 large T
antigen"
/label=SV40 NLS
/translation="PKKKRKV" (SEQ ID NO: 52)
CDS 6328 . . . 6348
/codon_start=1
/product="nuclear localization signal of SV40 large T
antigen"
/label=SV40 NLS
/translation="PKKKRKV" (SEQ ID NO: 52)
primer_bind complement(6333 . . . 6392)
/label=XTEN-Cas9-H2_R
primer_bind complement(6333 . . . 6377)
/label=Primer 7
primer_bind 6347 . . . 6371
/label=NLS_out_NES_full_F
primer_bind 6349 . . . 6371
/label=AXC_NLSout_NESin_F
misc_feature 6358 . . . 6392
/label=Homology 2_pCDNA3.1
polyA_signal 6426 . . . 6650
/label=bGH poly(A) signal
/note="bovine growth hormone polyadenylation signal"
rep_origin 6696 . . . 7124
/direction=RIGHT
/label=f1 ori
```

-continued

```
/note="f1 bacteriophage origin of replication; arrow
indicates direction of (+) strand synthesis"
promoter 7138 . . . 7467
/label=SV40 promoter
/note="SV40 enhancer and early promoter"
rep_origin 7318 . . . 7453
/label=SV40 ori
/note="SV40 origin of replication"
CDS 7534 . . . 8328
/codon_start=1
/gene="aph(3')-II (or nptII)"
/product="aminoglycoside phosphotransferase from Tn5"
/label=NeoR/KanR
/note="confers resistance to neomycin, kanamycin, and G418
(Geneticin(R))"
                                                (SEQ ID NO: 53)
/translation="MIEQDGLHAGSPAAWVERLFGYDWAQQTIGCSDAAVFRLSAQGRP
VLFVKTDLSGALNELQDEAARLSWLATTGVPCAAVLDVVTEAGRDWLLLGEVPGQDLLS
SHLAPAEKVSIMADAMRRLHTLDPATCPFDHQAKHRIERARTRMEAGLVDQDDLDEEHQ
GLAPAELFARLKARMPDGEDLVVTHGDACLPNIMVENGRFSGFIDCGRLGVADRYQDIA
LATRDIAEELGGEWADRFLVLYGIAAPDSQRIAFYRLLDEFF"
polyA_signal 8502 . . . 8623
/label=SV40 poly(A) signal
/note="SV40 polyadenylation signal"
primer_bind complement(8672 . . . 8688)
/label=M13 rev
/note="common sequencing primer, one of multiple similar
variants"
protein_bind 8696 . . . 8712
/label=lac operator
/bound_moiety="lac repressor encoded by lacI"
/note="The lac repressor binds to the lac operator to
inhibit transcription in E. coli. This inhibition can be
relieved by adding lactose or
isopropyl-beta-D-thiogalactopyranoside (IPTG)."
promoter complement(8720 . . . 8750)
/label=lac promoter
/note="promoter for the E. coli lac operon"
protein_bind 8765 . . . 8786
/label=CAP binding site
/bound_moiety="E. coli catabolite activator protein"
/note="CAP binding activates transcription in the presence
of cAMP."
rep_origin complement(9074 . . . 9659)
/direction=LEFT
/label=ori
/note="high-copy-number ColE1/pMB1/pBR322/pUC origin of
replication"
CDS complement(9830 . . . 10690)
/codon_start=1
/gene="bla"
/product="beta-lactamase"
/label=AmpR
/note="confers resistance to ampicillin, carbenicillin, and
related antibiotics"
                                                (SEQ ID NO: 54)
/translation="MSIQHFRVALIPFFAAFCLPVFAHPETLVKVKDAEDQLGARVGYI
ELDLNSGKILESFRPEERFPMMSTFKVLLCGAVLSRIDAGQEQLGRRIHYSQNDLVEYS
PVTEKHLTDGMTVRELCSAAITMSDNTAANLLLTTIGGPKELTAFLHNMGDHVTRLDRW
EPELNEAIPNDERDTTMPVAMATTLRKLLTGELLTLASRQQLIDWMEADKVAGPLLRSA
LPAGWFIADKSGAGERGSRGIIAALGPDGKPSRIVVIYTTGSQATMDERNRQIAEIGAS
LIKHW"
promoter complement(10691 . . . 10795)
/gene="bla"
/label=AmpR promoter
ORIGIN
    1 gacggatcgg gagatctccc gatcccctat ggtgcactct cagtacaatc tgctctgatg
   61 ccgcatagtt aagccagtat ctgctccctg cttgtgtgtt ggaggtcgct gagtagtgcg
  121 cgagcaaaat ttaagctaca acaaggcaag gcttgaccga caattgcatg aagaatctgc
  181 ttagggttag gcgttttgcg ctgcttcgcg atgtacgggc cagatatacg cgttgacatt
  241 gattattgac tagttattaa tagtaatcaa ttacggggtc attagttcat agcccatata
  301 tggagttccg cgttacataa cttacggtaa atggcccgcc tggctgaccg cccaacgacc
  361 cccgcccatt gacgtcaata atgacgtatg ttcccatagt aacgccaata gggactttcc
  421 attgacgtca atgggtggag tatttacggt aaactgccca cttggcagta catcaagtgt
```

-continued

```
 481 atcatatgcc aagtacgccc cctattgacg tcaatgacgg taaatggccc gcctggcatt 541 atgcccagta catgacctta tgggactttc ctacttggca gtacatctac gtattagtca 601 tcgctattac catggtgatg cggttttggc agtacatcaa tgggcgtgga tagcggtttg 661 actcacgggg atttccaagt ctccacccca ttgacgtcaa tgggagtttg ttttggcacc 721 aaaatcaacg ggactttcca aaatgtcgta acaactccgc cccattgacg caaatgggcg 781 gtaggcgtgt acggtgggag gtctatataa gcagagctct ctggctaact agagaaccca 841 ctgcttactg gcttatcgaa attaatacga ctcactatag ggagacccaa gctggctagc 901 gtttaaacgg gccctctaga ctcgagcggc cgccactgtg ctggatatct gcagagaacc 961 atgttagctg acgctgtctc acgcctggtc ctgggtaagt ttggtgacct gaccgacaac 1021 ttctcctccc ctcacgctcg cagaaaagtg ctggctggag tcgtcatgac aacaggcaca 1081 gatgttaaag atgccaaggt gataagtgtt tctacaggaa caaaatgtat taatggtgaa 1141 tacatgagtg atcgtggcct tgcattaaat gactgccatg cagaaataat atctcggaga 1201 tccttgctca gatttcttta tacacaactt gagctttact taaataacaa agatgatcaa 1261 aaaagatcca tctttcagaa atcagagcga gggggttta ggctgaagga gaatgtccag 1321 tttcatctgt acatcagcac ctctccctgt ggagatgcca gaatcttctc accacatgag 1381 ccaatcctgg aagaaccagc agatagacac ccaaatcgta aagcaagagg acagctacgg 1441 accaaaatag agtctggtca ggggacgatt ccagtgcgct ccaatgcgag catccaaacg 1501 tgggacgggg tgctgcaagg ggagcggctg ctcaccatgt cctgcagtga caagattgca 1561 cgctggaacg tggtgggcat ccagggatcc ctgctcagca ttttcgtgga gcccatttac 1621 ttctcgagca tcatcctggg cagcctttac cacgggacc acctttccag gccatgtac 1681 cagcggatct ccaacataga ggacctgcca cctctctaca ccctcaacaa gcctttgctc 1741 agtggcatca gcaatgcaga agcacggcag ccagggaagg cccccaactt cagtgtcaac 1801 tggacggtag gcgactccgc tattgaggtc atcaacgcca cgactgggaa ggatgagctg 1861 ggccgcgcgt cccgcctgtg taagcacgcg ttgtactgtc gctggatgcg tgtgcacggc 1921 aaggttccct cccacttact acgctccaag attaccaagc caacgtgta ccatgagtcc 1981 aagctggcgg caaaggagta ccaggccgcc aaggcgcgtc tgttcacagc cttcatcaag 2041 gcggggctgg gggcctgggt ggagaagccc accgagcagg accagttctc actcacgccc 2101 agtggaagtg agacaccggg aacctcagag agcgccacgc cagaaagcat ggacaagaag 2161 tacagcatcg gcctggccat cggcaccaac tctgtgggct gggccgtgat caccgacgag 2221 tacaaggtgc ccagcaagaa attcaaggtg ctgggcaaca ccgaccggca cagcatcaag 2281 aagaacctga tcggcgccct gctgttcgac agcggagaaa cagccgaggc cacccggctg 2341 aagagaaccg ccagaagaag atacaccaga cggaagaacc ggatctgcta tctgcaagag 2401 atcttcagca acgagatggc caaggtggac acagcttct ccacagact ggaagagtcc 2461 ttcctggtgg aagaggataa gaagcacgag cggcacccca tcttcggcaa catcgtggac 2521 gaggtggcct accacgagaa gtaccccacc atctaccacc tgagaaagaa actggtggac 2581 agcaccgaca aggccgacct gcggctgatc tatctggccc tggcccacat gatcaagttc 2641 cggggccact tcctgatcga gggcgacctg aaccccgaca acagcgacgt ggacaagctg 2701 ttcatccagc tggtgcagac ctacaaccag ctgttcgagg aaaaccccat caacgccagc 2761 ggcgtggacg ccaaggccat cctgtctgcc agactgagca gagcagacg gctggaaaat 2821 ctgatcgccc agctgcccgg cgagaagaag aatggcctgt tcggcaacct gattgccctg
```

-continued

```
2881 agcctgggcc tgaccccccaa cttcaagagc aacttcgacc tggccgagga tgccaaactg
2941 cagctgagca aggacaccta cgacgacgac ctggacaacc tgctggccca gatcggcgac
3001 cagtacgccg acctgtttct ggccgccaag aacctgtccg acgccatcct gctgagcgac
3061 atcctgagag tgaacaccga gatcaccaag gccccctga cgcctctat gatcaagaga
3121 tacgacgagc accaccagga cctgaccctg ctgaaagctc tcgtgcggca gcagctgcct
3181 gagaagtaca aagagatttt cttcgaccag agcaagaacg gctacgccgg ctacatcgat
3241 ggcggagcca gccaggaaga gttctacaag ttcatcaagc ccatcctgga aaagatggac
3301 ggcaccgagg aactgctcgt gaagctgaac agagaggacc tgctgcggaa gcagcggacc
3361 ttcgacaacg gcagcatccc ccaccagatc cacctgggag agctgcacgc cattctgcgg
3421 cggcaggaag atttttaccc attcctgaag gacaaccggg aaaagatcga agatcctg
3481 accttccgca tcccctacta cgtgggccct ctggccaggg aaacagcag attcgcctgg
3541 atgaccagaa agagcgagga aaccatcacc ccctggaact tcgaggaagt ggtggacaag
3601 ggcgccagcg cccagagctt catcgagcgg atgaccaact tcgataagaa cctgcccaac
3661 gagaaggtgc tgcccaagca cagcctgctg tacgagtact tcaccgtgta caacgagctg
3721 accaaagtga aatacgtgac cgagggaatg agaaagcccg ccttcctgag cggcgagcag
3781 aaaaaagcca tcgtggacct gctgttcaag accaaccgga aagtgaccgt gaagcagctg
3841 aaagaggact acttcaagaa aatcgagtgc ttcgactccg tggaaatctc cggcgtggaa
3901 gatcggttca acgcctccct gggcacatac cacgatctgc tgaaaattat caaggacaag
3961 gacttcctgg acaatgagga aaacgaggac attctggaag atatcgtgct gaccctgaca
4021 ctgtttgagg acagagagat gatcgaggaa cggctgaaaa cctatgccca cctgttcgac
4081 gacaaagtga tgaagcagct gaagcggcgg agatacaccg ctggggcag gctgagccgg
4141 aagctgatca acggcatccg ggacaagcag tccggcaaga caatcctgga tttcctgaag
4201 tccgacggct tcgccaacag aaacttcatg cagctgatcc acgacgacag cctgaccttt
4261 aaagaggaca tccagaaagc ccaggtgtcc ggccagggcg atagcctgca cgagcacatt
4321 gccaatctgg ccggcagccc cgccattaag aagggcatcc tgcagacagt gaaggtggtg
4381 gacgagctcg tgaaagtgat gggccggcac aagcccgaga acatcgtgat cgaaatggcc
4441 agagagaacc agaccaccca gaagggacag aagaacagcc gcgagagaat gaagcggatc
4501 gaagagggca tcaaagagct gggcagccag atcctgaaag aacacccgt ggaaaacacc
4561 cagctgcaga acgagaagct gtacctgtac tacctgcaga atgggcggga tatgtacgtg
4621 gaccaggaac tggacatcaa ccggctgtcc gactacgatg tggacgctat cgtgcctcag
4681 agctttctga aggacgactc catcgataac aaagtgctga ctcggagcga caagaaccgg
4741 ggcaagagcg acaacgtgcc ctccgaagag gtcgtgaaga agatgaagaa ctactggcgc
4801 cagctgctga atgccaagct gattacccag aggaagttcg acaatctgac caaggccgag
4861 agaggcggcc tgagcgaact ggataaggcc ggcttcatca agagacagct ggtggaaacc
4921 cggcagatca caaagcacgt ggcacagatc ctggactccc ggatgaacac taagtacgac
4981 gagaacgaca aactgatccg ggaagtgaaa gtgatcaccc tgaagtccaa gctggtgtcc
5041 gatttccgga aggatttcca gttttacaaa gtgcgcgaga tcaacaacta ccaccacgcc
5101 cacgacgcct acctgaacgc cgtcgtggga accgccctga tcaaaaagta ccctaagctg
5161 gaaagcgagt tcgtgtacgg cgactacaag gtgtacgacg tgcggaagat gatcgccaag
5221 agcgagcagg aaatcggcaa ggctaccgcc aagtacttct ctacagcaa catcatgaac
5281 tttttcaaga ccgagattac cctggccaac ggcgagatcc ggaagcggcc tctgatcgag
```

-continued

```
5341 acaaacggcg aaacaggcga gatcgtgtgg gataagggcc gggactttgc caccgtgcgg 5401 aaagtgctgt ctatgcccca agtgaatatc gtgaaaaaga ccgaggtgca gacaggcggc 5461 ttcagcaaag agtctatcct gcccaagagg aacagcgaca agctgatcgc cagaaagaag 5521 gactgggacc ctaagaagta cggcggcttc gacagcccca ccgtggccta ttctgtgctg 5581 gtggtggcca agtggaaaa gggcaagtcc aagaaactga gagtgtgaa agagctgctg 5641 gggatcacca tcatggaaag aagcagcttc gagaagaatc ccatcgactt tctggaagcc 5701 aagggctaca agaagtgaa aaaggacctg atcatcaagc tgcctaagta ctccctgttc 5761 gagctggaaa acggccggaa gagaatgctg gcctctgccg gcgaactgca aagggaaac 5821 gaactggccc tgccctccaa atatgtgaac ttcctgtacc tggccagcca ctatgagaag 5881 ctgaagggct cccccgagga taatgagcag aaacagctgt tgtggaaca gcacaaacac 5941 tacctggacg agatcatcga gcagatcagc gagttctcca agagagtgat cctggccgac 6001 gctaatctgg acaaggtgct gagcgcctac aacaagcaca gagacaagcc tatcagagag 6061 caggccgaga atatcatcca cctgtttacc ctgaccaatc tgggagcccc tgccgccttc 6121 aagtactttg acaccaccat cgaccggaag aggtacacca gcaccaaaga ggtgctggac 6181 gccaccctga tccaccagag catcaccggc ctgtacgaga cacggatcga cctgtctcag 6241 ctggaggcg acgcctatcc ctatgacgtg cccgattatg ccagcctggg cagcggctcc 6301 cccaagaaaa aacgcaaggt ggaagatcct aagaaaaagc ggaaagtgga cgtgtaacca 6361 ccacactgga ctagtggatc cgagctcggt accaagctta agtttaaacc gctgatcagc 6421 ctcgactgtg ccttctagtt gccagccatc tgttgtttgc ccctcccccg tgccttcctt 6481 gaccctggaa ggtgccactc ccactgtcct ttcctaataa aatgaggaaa ttgcatcgca 6541 ttgtctgagt aggtgtcatt ctattctggg gggtggggtg gggcaggaca gcaaggggga 6601 ggattgggaa gacaatagca ggcatgctgg ggatgcggtg gctctatgg cttctgaggc 6661 ggaaagaacc agctggggct ctaggggta tccccacgcg ccctgtagcg cgcattaag 6721 cgcggcgggt gtggtggtta cgcgcagcgt gaccgctaca cttgccagcg ccctagcgcc 6781 cgctcctttc gctttcttcc cttcctttct cgccacgttc gccggctttc cccgtcaagc 6841 tctaaatcgg gggctccctt tagggttccg atttagtgct ttacggcacc tcgaccccaa 6901 aaaacttgat tagggtgatg gttcacgtag tgggccatcg ccctgataga cggtttttcg 6961 ccctttgacg ttggagtcca cgttctttaa tagtggactc ttgttccaaa ctggaacaac 7021 actcaaccct atctcggtct attcttttga tttataaggg attttgccga tttcggccta 7081 ttggttaaaa aatgagctga tttaacaaaa atttaacgcg aattaattct gtggaatgtg 7141 tgtcagttag ggtgtggaaa gtccccaggc tccccagcag gcagaagtat gcaaagcatg 7201 catctcaatt agtcagcaac caggtgtgga aagtcccag gctccccagc aggcagaagt 7261 atgcaaagca tgcatctcaa ttagtcagca accatagtcc cgcccctaac tccgcccatc 7321 ccgcccctaa ctccgcccag ttccgcccat tctccgcccc atggctgact aatttttttt 7381 atttatgcag aggccgaggc cgcctctgcc tctgagctat tccagaagta gtgaggaggc 7441 tttttttggag gcctaggctt ttgcaaaaag ctcccgggag cttgtatatc cattttcgga 7501 tctgatcaag agacaggatg aggatcgttt cgcatgattg aacaagatgg attgcacgca 7561 ggttctccgg ccgcttgggt ggagaggcta ttcggctatg actgggcaca acagacaatc 7621 ggctgctctg atgccgccgt gttccggctg tcagcgcagg ggcgcccggt tctttttgtc 7681 aagaccgacc tgtccggtgc cctgaatgaa ctgcaggacg aggcagcgcg gctatcgtgg
```

```
7741 ctggccacga cgggcgttcc ttgcgcagct gtgctcgacg ttgtcactga agcgggaagg
7801 gactggctgc tattgggcga agtgccgggg caggatctcc tgtcatctca ccttgctcct
7861 gccgagaaag tatccatcat ggctgatgca atgcggcggc tgcatacgct tgatccggct
7921 acctgcccat tcgaccacca agcgaaacat cgcatcgagc gagcacgtac tcggatggaa
7981 gccggtcttg tcgatcagga tgatctggac gaagagcatc aggggctcgc gccagccgaa
8041 ctgttcgcca ggctcaaggc gcgcatgccc gacggcgagg atctcgtcgt gacccatggc
8101 gatgcctgct tgccgaatat catggtggaa atggccgct tttctggatt catcgactgt
8161 ggccggctgg gtgtggcgga ccgctatcag gacatagcgt tggctacccg tgatattgct
8221 gaagagcttg gcggcgaatg ggctgaccgc ttcctcgtgc tttacggtat cgccgctccc
8281 gattcgcagc gcatcgcctt ctatcgcctt cttgacgagt tcttctgagc gggactctgg
8341 ggttcgaaat gaccgaccaa gcgacgccca acctgccatc acgagatttc gattccaccg
8401 ccgccttcta tgaaaggttg gcttcggaa tcgttttccg ggacgccggc tggatgatcc
8461 tccagcgcgg ggatctcatg ctggagttct tcgcccaccc caacttgttt attgcagctt
8521 ataatggtta caaataaagc aatagcatca caaatttcac aaataaagca ttttttttcac
8581 tgcattctag ttgtggtttg tccaaactca tcaatgtatc ttatcatgtc tgtataccgt
8641 cgacctctag ctagagcttg gcgtaatcat ggtcatagct gtttcctgtg tgaaattgtt
8701 atccgctcac aattccacac aacatacgag ccggaagcat aaagtgtaaa gcctggggtg
8761 cctaatgagt gagctaactc acattaattg cgttgcgctc actgcccgct ttccagtcgg
8821 gaaacctgtc gtgccagctg cattaatgaa tcggccaacg cgcggggaga ggcggtttgc
8881 gtattgggcg ctcttccgct tcctcgctca ctgactcgct gcgctcggtc gttcggctgc
8941 ggcgagcggt atcagctcac tcaaaggcgg taatacggtt atccacagaa tcaggggata
9001 acgcaggaaa gaacatgtga gcaaaaggcc agcaaaaggc caggaaccgt aaaaaggccg
9061 cgttgctggc gttttccat aggctccgcc cccctgacga gcatcacaaa aatcgacgct
9121 caagtcagag gtggcgaaac ccgacaggac tataaagata ccaggcgttt ccccctggaa
9181 gctccctcgt gcgctctcct gttccgaccc tgccgcttac cggatacctg tccgcctttc
9241 tcccttcggg aagcgtggcg ctttctcata gctcacgctg taggtatctc agttcggtgt
9301 aggtcgttcg ctccaagctg ggctgtgtgc acgaaccccc cgttcagccc gaccgctgcg
9361 ccttatccgg taactatcgt cttgagtcca acccggtaag acacgactta tcgccactgg
9421 cagcagccac tggtaacagg attagcagag cgaggtatgt aggcggtgct acagagttct
9481 tgaagtggtg gcctaactac ggctacacta agaacagt atttggtatc tgcgctctgc
9541 tgaagccagt taccttcgga aaagagttg gtagctcttg atccggcaaa caaaccaccg
9601 ctggtagcgg ttttttttgtt tgcaagcagc agattacgcg cagaaaaaaa ggatctcaag
9661 aagatccttt gatcttttct acggggtctg acgctcagtg gaacgaaaac tcacgttaag
9721 ggattttggt catgagatta tcaaaaagga tcttcaccta gatccttta aattaaaaat
9781 gaagttttaa atcaatctaa agtatatatg agtaaacttg gtctgacagt taccaatgct
9841 taatcagtga ggcacctatc tcagcgatct gtctatttcg ttcatccata gttgcctgac
9901 tccccgtcgt gtagataact acgatacggg agggcttacc atctggcccc agtgctgcaa
9961 tgataccgcg agacccacgc tcaccggctc cagatttatc agcaataaac cagccagccg
10021 gaagggccga gcgcagaagt ggtcctgcaa ctttatccgc ctccatccag tctattaatt
10081 gttgccggga agctagagta agtagttcgc cagttaatag tttgcgcaac gttgttgcca
10141 ttgctacagg catcgtggtg tcacgctcgt cgtttggtat ggcttcattc agctccggtt
```

-continued

```
10201 cccaacgatc aaggcgagtt acatgatccc ccatgttgtg caaaaaagcg gttagctcct 10261 tcggtcctcc gatcgttgtc agaagtaagt tggccgcagt gttatcactc atggttatgg 10321 cagcactgca taattctctt actgtcatgc catccgtaag atgcttttct gtgactggtg 10381 agtactcaac caagtcattc tgagaatagt gtatgcggcg accgagttgc tcttgcccgg 10441 cgtcaatacg ggataatacc gcgccacata gcagaacttt aaaagtgctc atcattggaa 10501 aacgttcttc ggggcgaaaa ctctcaagga tcttaccgct gttgagatcc agttcgatgt 10561 aacccactcg tgcacccaac tgatcttcag catcttttac tttcaccagc gtttctgggt 10621 gagcaaaaac aggaaggcaa aatgccgcaa aaaagggaat aagggcgaca cggaaatgtt 10681 gaatactcat actcttcctt tttcaatatt attgaagcat ttatcagggt tattgtctca 10741 tgagcggata catatttgaa tgtatttaga aaaataaaca aataggggtt ccgcgcacat 10801 ttccccgaaa agtgccacct gacgtc
``` pcDNA3.1_ADAR2(E488Q)_XTEN_control (SEQ ID NO: 30).
LOCUS Exported 6722 bp ds-DNA circular
DEFINITION synthetic circular DNA
SOURCE synthetic DNA construct
ORGANISM synthetic DNA construct
REFERENCE 1 (bases 1 to 6722)
FEATURES Location/Qualifiers
source 1 . . . 6722
/organism="synthetic DNA construct"
/mol_type="other DNA"
enhancer 235 . . . 614
/label=CMV enhancer
/note="human cytomegalovirus immediate early enhancer"
promoter 615 . . . 818
/label=CMV promoter
/note="human cytomegalovirus (CMV) immediate early promoter"
promoter 863 . . . 881
/label=T7 promoter
/note="promoter for bacteriophage T7 RNA polymerase"
misc_feature 927 . . . 954
/label=Homology_1_pCDNA3.1
primer_bind 954 . . . 976
/label=ADARB1_lcv2_fw
primer_bind 955 . . . 976
/label=ADAR2CD-Cas9_HindIII_F
primer_bind 958 . . . 983
/label=AXC_lcv2_EFS-NS_fw
primer_bind 960 . . . 983
/label=Adar_out_forward_lv2
CDS 961 . . . 2100
/codon_start=1
/label=ADARB1(E488Q) Catalytic Domain
(SEQ ID NO: 41)
/translation="MLADAVSRLVLGKFGDLTDNFSSPHARRKVLAGVVMTTGTDVKDA
KVISVSTGTKCINGEYMSDRGLALNDCHAEIISRRSLLRFLYTQLELYLNNKDDQKRSI
FQKSERGGFRLKENVQFHLYISTSPCGDARIFSPHEPILEEPADRHPNRKARGQLRTKI
ESGQGTIPVRSNASIQTWDGVLQGERLLTMSCSDKIARWNVVGIQGSLLSIFVEPIYFS
SIILGSLYHGDHLSRAMYQRISNIEDLPPLYTLNKPLLSGISNAEARQPGKAPNFSVNW
TVGDSAIEVINATTGKDELGRASRLCKHALYCRWMRVHGKVPSHLLRSKITKPNVYHES
KLAAKEYQAAKARLFTAFIKAGLGAWVEKPTEQDQFSLTP"
primer_bind 1324 . . . 1346
/label=E488Q_ADAR2_Mut_seq
primer_bind complement(1426 . . . 1447)
/label=E488Q_Mut_Classic_R
primer_bind 1440 . . . 1478
/label=E488Q_Mutagenesis_F
primer_bind complement(1440 . . . 1478)
/label=E488Q_Mutagenesis_R
primer_bind 1448 . . . 1472
/label=E488Q_Mut_Classic_F
CDS 2101 . . . 2148
/codon_start=1
/label=XTEN
/translation="SGSETPGTSESATPES" (SEQ ID NO: 41)
primer_bind complement(2129 . . . 2148)
/label=ADAR2_CD_Inverse_R
primer_bind 2149 . . . 2170

```
                            -continued
/label=ADAR2_CD_Inverse_F
CDS 2152 . . . 2178
/codon_start=1
/product="HA (human influenza hemagglutinin) epitope tag"
/label=HA
/translation="YPYDVPDYA" (SEQ ID NO: 51)
primer_bind complement(2170 . . . 2192)
/label=AXC_NLSout_NESin_R
primer_bind complement(2170 . . . 2192)
/label=Primer 1
CDS 2197 . . . 2217
/codon_start=1
/product="nuclear localization signal of SV40 large T
antigen"
/label=SV40 NLS
/translation="PKKKRKV" (SEQ ID NO: 52)
CDS 2224 . . . 2244
/codon_start=1
/product="nuclear localization signal of SV40 large T
antigen"
/label=SV40 NLS
/translation="PKKKRKV" (SEQ ID NO: 52)
primer_bind 2245 . . . 2267
/label=AXC_NLSout_NESin_F
misc_feature 2254 . . . 2288
/label=Homology 2_pCDNA3.1
polyA_signal 2322 . . . 2546
/label=bGH poly(A) signal
/note="bovine growth hormone polyadenylation signal"
rep_origin 2592 . . . 3020
/direction=RIGHT
/label=f1 ori
/note="f1 bacteriophage origin of replication; arrow
indicates direction of (+) strand synthesis"
promoter 3034 . . . 3363
/label=SV40 promoter
/note="SV40 enhancer and early promoter"
rep_origin 3214 . . . 3349
/label=SV40 ori
/note="SV40 origin of replication"
CDS 3430 . . . 4224
/codon_start=1
/gene="aph(3')-II (or nptII)"
/product="aminoglycoside phosphotransferase from Tn5"
/label=NeoR/KanR
/note="confers resistance to neomycin, kanamycin, and G418
(Geneticin(R))"
                                                            (SEQ ID NO: 53)
/translation="MIEQDGLHAGSPAAWVERLFGYDWAQQTIGCSDAAVFRLSAQGRP
VLFVKTDLSGALNELQDEAARLSWLATTGVPCAAVLDVVTEAGRDWLLLGEVPGQDLLS
SHLAPAEKVSIMADAMRRLHTLDPATCPFDHQAKHRIERARTRMEAGLVDQDDLDEEHQ
GLAPAELFARLKARMPDGEDLVVTHGDACLPNIMVENGRFSGFIDCGRLGVADRYQDIA
LATRDIAEELGGEWADRFLVLYGIAAPDSQRIAFYRLLDEFF"
polyA_signal 4398 . . . 4519
/label=SV40 poly(A) signal
/note="SV40 polyadenylation signal"
primer_bind complement(4568 . . . 4584)
/label=M13 rev
/note="common sequencing primer, one of multiple similar
variants"
protein_bind 4592 . . . 4608
/label=lac operator
/bound_moiety="lac repressor encoded by lacI"
/note="The lac repressor binds to the lac operator to
inhibit transcription in E. coli. This inhibition can be
relieved by adding lactose or
isopropyl-beta-D-thiogalactopyranoside (IPTG)."
promoter complement(4616 . . . 4646)
/label=lac promoter
/note="promoter for the E. coli lac operon"
protein_bind 4661 . . . 4682
/label=CAP binding site
/bound_moiety="E. coli catabolite activator protein"
/note="CAP binding activates transcription in the presence
of cAMP."
rep_origin complement(4970 . . . 5555)
/direction=LEFT
/label=ori
/note="high-copy-number ColE1/pMB1/pBR322/pUC origin of
replication"
CDS complement(5726 . . . 6586)
```

```
/codon_start=1
/gene="bla"
/product="beta-lactamase"
/label=AmpR
/note="confers resistance to ampicillin, carbenicillin, and
related antibiotics"
                                                   (SEQ ID NO: 54)
/translation="MSIQHFRVALIPFFAAFCLPVFAHPETLVKVKDAEDQLGARVGYI
ELDLNSGKILESFRPEERFPMMSTFKVLLCGAVLSRIDAGQEQLGRRIHYSQNDLVEYS
PVTEKHLTDGMTVRELCSAAITMSDNTAANLLLTTIGGPKELTAFLHNMGDHVTRLDRW
EPELNEAIPNDERDTTMPVAMATTLRKLLTGELLTLASRQQLIDWMEADKVAGPLLRSA
LPAGWFIADKSGAGERGSRGIIAALGPDGKPSRIVVIYTTGSQATMDERNRQIAEIGAS
LIKHW"
promoter complement(6587 . . . 6691)
/gene="bla"
/label=AmpR promoter
ORIGIN
    1 gacggatcgg gagatctccc gatcccctat ggtgcactct cagtacaatc tgctctgatg
   61 ccgcatagtt aagccagtat ctgctccctg cttgtgtgtt ggaggtcgct gagtagtgcg
  121 cgagcaaaat ttaagctaca acaaggcaag gcttgaccga caattgcatg aagaatctgc
  181 ttagggttag gcgttttgcg ctgcttcgcg atgtacgggc cagatatacg cgttgacatt
  241 gattattgac tagttattaa tagtaatcaa ttacggggtc attagttcat agcccatata
  301 tggagttccg cgttacataa cttacggtaa atggcccgcc tggctgaccg cccaacgacc
  361 cccgcccatt gacgtcaata atgacgtatg ttcccatagt aacgccaata gggactttcc
  421 attgacgtca atgggtggag tatttacggt aaactgccca cttggcagta catcaagtgt
  481 atcatatgcc aagtacgccc cctattgacg tcaatgacgg taaatggccc gcctggcatt
  541 atgcccagta catgacctta tgggactttc ctacttggca gtacatctac gtattagtca
  601 tcgctattac catggtgatg cggttttggc agtacatcaa tgggcgtgga tagcggtttg
  661 actcacgggg atttccaagt ctccacccca ttgacgtcaa tgggagtttg ttttggcacc
  721 aaaatcaacg ggactttcca aatgtcgta acaactccgc cccattgacg caaatgggcg
  781 gtaggcgtgt acggtgggag gtctatataa gcagagctct ctggctaact agagaaccca
  841 ctgcttactg gcttatcgaa attaatacga ctcactatag ggagacccaa gctggctagc
  901 gtttaaacgg gccctctaga ctcgagcggc cgccactgtg ctggatatct gcagagaacc
  961 atgttagctg acgctgtctc acgcctggtc ctgggtaagt ttggtgacct gaccgacaac
 1021 ttctcctccc ctcacgctcg cagaaaagtg ctggctggag tcgtcatgac aacaggcaca
 1081 gatgttaaag atgccaaggt gataagtgtt tctacaggaa caaatgtat taatggtgaa
 1141 tacatgagtg atcgtggcct tgcattaaat gactgccatg cagaaataat atctcggaga
 1201 tccttgctca gatttcttta tacacaactt gagcttact taaataacaa agatgatcaa
 1261 aaaagatcca tcttcagaa atcagagcga gggggttta ggctgaagga gaatgtccag
 1321 tttcatctgt acatcagcac ctctccctgt ggagatgcca gaatcttctc accacatgag
 1381 ccaatcctgg aagaaccagc agatagacac ccaaatcgta aagcaagagg acagctacgg
 1441 accaaaatag agtctggtca ggggacgatt ccagtgcgct ccaatgcgag catccaaacg
 1501 tgggacgggg tgctgcaagg ggagcggctg ctcaccatgt cctgcagtga caagattgca
 1561 cgctggaacg tggtgggcat ccagggatcc ctgctcagca ttttcgtgga gcccatttac
 1621 ttctcgagca tcatcctggg cagcctttac cacggggacc acctttccag ggccatgtac
 1681 cagcggatct ccaacataga ggacctgcca cctctctaca cctcaacaa gcctttgctc
 1741 agtggcatca gcaatgcaga agcacggcag ccagggaagg cccccaactt cagtgtcaac
 1801 tggacggtag gcgactccgc tattgaggtc atcaacgcca cgactgggaa ggatgagctg
 1861 ggccgcgcgt cccgcctgtg taagcacgcg ttgtactgtc gctggatgcg tgtgcacggc
```

-continued

```
1921 aaggttccct cccacttact acgctccaag attaccaagc ccaacgtgta ccatgagtcc
1981 aagctggcgg caaaggagta ccaggccgcc aaggcgcgtc tgttcacagc cttcatcaag
2041 gcggggctgg gggcctgggt ggagaagccc accgagcagg accagttctc actcacgccc
2101 agtggaagtg agacaccggg aacctcagag agcgccacgc cagaaagcgc ctatccctat
2161 gacgtgcccg attatgccag cctgggcagc ggctccccca agaaaaaacg caaggtggaa
2221 gatcctaaga aaaagcggaa agtggacgtg taaccaccac actggactag tggatccgag
2281 ctcggtacca agcttaagtt taaaccgctg atcagcctcg actgtgcctt ctagttgcca
2341 gccatctgtt gtttgcccct cccccgtgcc ttccttgacc ctggaaggtg ccactcccac
2401 tgtccttttcc taataaaatg aggaaattgc atcgcattgt ctgagtaggt gtcattctat
2461 tctgggggt ggggtggggc aggacagcaa ggggaggat tgggaagaca atagcaggca
2521 tgctggggat gcggtgggct ctatggcttc tgaggcggaa agaaccagct ggggctctag
2581 ggggtatccc cacgcgccct gtagcggcgc attaagcgcg gcgggtgtgg tggttacgcg
2641 cagcgtgacc gctacacttg ccagcgccct agcgcccgct cctttcgctt tcttcccttc
2701 ctttctcgcc acgttcgccg gctttccccg tcaagctcta aatcggggc tccctttagg
2761 gttccgattt agtgctttac ggcacctcga ccccaaaaaa cttgattagg gtgatggttc
2821 acgtagtggg ccatcgccct gatagacggt ttttcgccct tgacgttgg agtccacgtt
2881 ctttaatagt ggactcttgt tccaaactgg aacaacactc aaccctatct cggtctattc
2941 ttttgattta taagggattt tgccgatttc ggcctattgg ttaaaaaatg agctgattta
3001 acaaaaattt aacgcgaatt aattctgtgg aatgtgtgtc agttagggtg tggaaagtcc
3061 ccaggctccc cagcaggcag aagtatgcaa agcatgcatc tcaattagtc agcaaccagg
3121 tgtggaaagt ccccaggctc cccagcaggc agaagtatgc aaagcatgca tctcaattag
3181 tcagcaacca tagtcccgcc cctaactccg cccatcccgc cctaactcc gcccagttcc
3241 gcccattctc cgccccatgg ctgactaatt ttttttattt atgcagaggc cgaggccgcc
3301 tctgcctctg agctattcca gaagtagtga ggaggctttt ttggaggcct aggcttttgc
3361 aaaaagctcc cgggagcttg tatatccatt ttcggatctg atcaagagac aggatgagga
3421 tcgtttcgca tgattgaaca agatggattg cacgcaggtt ctccggccgc ttgggtggag
3481 aggctattcg gctatgactg ggcacaacag acaatcggct gctctgatgc cgccgtgttc
3541 cggctgtcag cgcaggggcg cccggttctt tttgtcaaga ccgacctgtc cggtgccctg
3601 aatgaactgc aggacgaggc agcgcggcta tcgtggctgg ccacgacggg cgttccttgc
3661 gcagctgtgc tcgacgttgt cactgaagcg ggaagggact ggctgctatt gggcgaagtg
3721 ccggggcagg atctcctgtc atctcacctt gctcctgccg agaaagtatc catcatggct
3781 gatgcaatgc ggcggctgca tacgcttgat ccggctacct gcccattcga ccaccaagcg
3841 aaacatcgca tcgagcgagc acgtactcgg atggaagccg gtcttgtcga tcaggatgat
3901 ctggacgaag agcatcaggg gctcgcgcca gccgaactgt tcgccaggct caaggcgcgc
3961 atgcccgacg gcgaggatct cgtcgtgacc catggcgatg cctgcttgcc gaatatcatg
4021 gtggaaaatg gccgcttttc tggattcatc gactgtggcc ggctgggtgt ggcggaccgc
4081 tatcaggaca tagcgttggc tacccgtgat attgctgaag agcttggcgg cgaatgggct
4141 gaccgcttcc tcgtgcttta cggtatcgcc gctcccgatt cgcagcgcat cgccttctat
4201 cgccttcttg acgagttctt ctgagcggga ctctggggtt cgaaatgacc gaccaagcga
4261 cgcccaacct gccatcacga gatttcgatt ccaccgccgc cttctatgaa aggttgggct
4321 tcggaatcgt tttccgggac gccggctgga tgatcctcca gcgcgggat ctcatgctgg
```

-continued

```
4381 agttcttcgc ccaccccaac ttgtttattg cagcttataa tggttacaaa taaagcaata
4441 gcatcacaaa tttcacaaat aaagcatttt tttcactgca ttctagttgt ggtttgtcca
4501 aactcatcaa tgtatcttat catgtctgta taccgtcgac ctctagctag agcttggcgt
4561 aatcatggtc atagctgttt cctgtgtgaa attgttatcc gctcacaatt ccacacaaca
4621 tacgagccgg aagcataaag tgtaaagcct ggggtgccta atgagtgagc taactcacat
4681 taattgcgtt gcgctcactg cccgctttcc agtcgggaaa cctgtcgtgc cagctgcatt
4741 aatgaatcgg ccaacgcgcg gggagaggcg gtttgcgtat tgggcgctct tccgcttcct
4801 cgctcactga ctcgctgcgc tcggtcgttc ggctgcggcg agcggtatca gctcactcaa
4861 aggcggtaat acggttatcc acagaatcag gggataacgc aggaaagaac atgtgagcaa
4921 aaggccagca aaaggccagg aaccgtaaaa aggccgcgtt gctggcgttt ttccataggc
4981 tccgcccccc tgacgagcat cacaaaaatc gacgctcaag tcagaggtgg cgaaacccga
5041 caggactata aagataccag gcgtttcccc ctggaagctc cctcgtgcgc tctcctgttc
5101 cgaccctgcc gcttaccgga tacctgtccg cctttctccc ttcgggaagc gtggcgcttt
5161 ctcatagctc acgctgtagg tatctcagtt cggtgtaggt cgttcgctcc aagctgggct
5221 gtgtgcacga accccccgtt cagcccgacc gctgcgcctt atccggtaac tatcgtcttg
5281 agtccaaccc ggtaagacac gacttatcgc cactggcagc agccactggt aacaggatta
5341 gcagagcgag gtatgtaggc ggtgctacag agttcttgaa gtggtggcct aactacggct
5401 acactagaag aacagtattt ggtatctgcg ctctgctgaa gccagttacc ttcggaaaaa
5461 gagttggtag ctcttgatcc ggcaaacaaa ccaccgctgg tagcggtttt tttgtttgca
5521 agcagcagat tacgcgcaga aaaaaaggat ctcaagaaga tcctttgatc ttttctacgg
5581 ggtctgacgc tcagtggaac gaaaactcac gttaagggat tttggtcatg agattatcaa
5641 aaaggatctt cacctagatc cttttaaatt aaaaatgaag ttttaaatca atctaaagta
5701 tatatgagta aacttggtct gacagttacc aatgcttaat cagtgaggca cctatctcag
5761 cgatctgtct atttcgttca tccatagttg cctgactccc cgtcgtgtag ataactacga
5821 tacgggaggg cttaccatct ggccccagtg ctgcaatgat accgcgagac ccacgctcac
5881 cggctccaga tttatcagca ataaaccagc cagccggaag ggccgagcgc agaagtggtc
5941 ctgcaacttt atccgcctcc atccagtcta ttaattgttg ccgggaagct agagtaagta
6001 gttcgccagt taatagtttg cgcaacgttg ttgccattgc tacaggcatc gtggtgtcac
6061 gctcgtcgtt tggtatggct tcattcagct ccggttccca acgatcaagg cgagttacat
6121 gatcccccat gttgtgcaaa aaagcggtta gctccttcgg tcctccgatc gttgtcagaa
6181 gtaagttggc cgcagtgtta tcactcatgg ttatggcagc actgcataat tctcttactg
6241 tcatgccatc cgtaagatgc ttttctgtga ctggtgagta ctcaaccaag tcattctgag
6301 aatagtgtat gcggcgaccg agttgctctt gcccggcgtc aatacgggat aataccgcgc
6361 cacatagcag aactttaaaa gtgctcatca ttggaaaacg ttcttcgggg cgaaaactct
6421 caaggatctt accgctgttg agatccagtt cgatgtaacc cactcgtgca cccaactgat
6481 cttcagcatc ttttactttc accagcgttt ctgggtgagc aaaaacagga aggcaaaatg
6541 ccgcaaaaaa gggaataagg gcgacacgga aatgttgaat actcatactc ttcctttttc
6601 aatattattg aagcatttat cagggttatt gtctcatgag cggatacata tttgaatgta
6661 tttagaaaaa taaacaaata ggggttccgc gcacatttcc ccgaaaagtg ccacctgacg
6721 tc
```

-continued

50bp_GFP_mCherry_extension (SEQ ID NO: 31).
LOCUS Exported 4951 bp ds-DNA circular
DEFINITION synthetic circular DNA
SOURCE synthetic DNA construct
ORGANISM recombinant plasmid
REFERENCE 1 (bases 1 to 4951)
FEATURES Location/Qualifiers
source 1 . . . 4951
/organism="recombinant plasmid"
/mol_type="other DNA"
primer_bind 1 . . . 40
/label=EF1a_Gibson_F
primer_bind 1 . . . 20
/label=Primer 2
misc_feature 1 . . . 7
/label=sgRNA scaffold_termination
promoter 21 . . . 566
/label=EF1a promoter
primer_bind complement(554 . . . 591)
/label=EF1a_Gibson_R
CDS 572 . . . 1282
/codon_start=1
/product="monomeric derivative of DsRed fluorescent protein
(Shaner et al., 2004)"
/label=mCherry
/note="mammalian codon-optimized"
(SEQ ID NO: 54)
/translation="MVSKGEEDNMAIIKEFMRFKVHMEGSVNGHEFEIEGEGEGRPYEG
TQTAKLKVTKGGPLPFAWDILSPQFMYGSKAYVKHPADIPDYLKLSFPEGFKWERVMNF
EDGGVVTVTQDSSLQDGEFIYKVKLRGTNFPSDGPVMQKKTMGWEASSERMYPEDGALK
GEIKQRLKLKDGGHYDAEVKTTYKAKKPVQLPGAYNVNIKLDITSHNEDYTIVEQYERA
EGRHSTGGMDELYK"
primer_bind 572 . . . 591
/label=mCherry_BGH_F
primer_bind complement(1259 . . . 1306)
/label=Primer 1
primer_bind complement(1259 . . . 1286)
/label=mCherry_P2A_Gib_R
primer_bind complement(1259 . . . 1282)
/label=mCherry_HindIII_R
misc_feature 1283 . . . 1306
/label=Gibson Overlap
primer_bind 1283 . . . 1301
/label=mCherry_P2A_Gib_F
polyA_signal 1330 . . . 1554
/label=bGH poly(A) signal
/note="bovine growth hormone polyadenylation signal"
primer_bind complement(1535 . . . 1573)
/label=mCherry_BGH_Gib_R
primer_bind complement(1535 . . . 1554)
/label=mCherry_BGH_R
primer_bind complement(1536 . . . 1555)
/label=bGH_NotI_R
primer_bind complement(1558 . . . 1573)
/label=SK primer
/note="common sequencing primer, one of multiple similar
variants"
primer_bind complement(1608 . . . 1627)
/label=T3
primer_bind complement(1645 . . . 1665)
/label=M13-rev
misc_binding complement(1671 . . . 1693)
/label=LacO
promoter complement(1698 . . . 1727)
/label=lac
rep_origin complement(2033 . . . 2661)
/direction=LEFT
/label=ColE1 origin
CDS complement(2813 . . . 3472)
/label=AmpR
promoter complement(3712 . . . 3740)
/label=Amp prom
rep_origin 3811 . . . 4251
/direction=RIGHT
/label=F1 ori
CDS complement(4258 . . . 4326)
/label=LacZ alpha
primer_bind 4397 . . . 4414
/label=M13-fwd
primer_bind 4424 . . . 4443
/label=T7

```
promoter 4555 . . . 4817
/label=U6 promoter
primer_bind 4798 . . . 4864
/label=no_spacer_universal_scaff_f
primer_bind 4803 . . . 4862
/label=50bp_GFP_F
primer_bind 4803 . . . 4862
/label=50bp_GFP_revcomp_F(+G)
primer_bind 4803 . . . 4862
/label=10bp_GFP_spacer_F
primer_bind 4803 . . . 4862
/label=30bp_GFP_spacer_F
primer_bind 4803 . . . 4862
/label=70bp_GFP_spacer_F
primer_bind 4803 . . . 4862
/label=ACTB_3_ext_CgRNA_For
primer_bind complement(4803 . . . 4817)
/label=Primer 3
primer_bind complement(4803 . . . 4817)
/label=extension_gibson_R
misc_feature 4818 . . . 4838
/label=50bp_EGFP_targeting_spacer
misc_feature 4839 . . . 4924
/label=sgRNA scaffold
primer_bind 4839 . . . 4865
/label=scaffold_3_ext_template_For
primer_bind complement(4912 . . . 4930)
/label=scaffold_3_ext_template_Rev
primer_bind complement(join(4913 . . . 4951,1 . . . 20))
/label=eGFP_3_ext_R
primer_bind complement(join(4913 . . . 4951,1 . . . 20))
/label=gfp_3_extension_revcomp
primer_bind complement(join(4913 . . . 4951,1 . . . 20))
/label=ACTB_3_ext_AgRNA_Rev
misc_feature 4925 . . . 4930
/label=Linker
misc_feature 4931 . . . 4951
/label=EGFP_extension
ORIGIN
    1 ttttttttcct gcagcccggg aaggatctgc gatcgctccg gtgccgtca gtgggcagag
   61 cgcacatcgc ccacagtccc cgagaagttg ggggagggg tcggcaattg aacgggtgcc
  121 tagagaaggt ggcgcggggt aaactggaa agtgatgtcg tgtactggct ccgccttttt
  181 cccgagggtg ggggagaacc gtatataagt gcagtagtcg ccgtgaacgt tcttttcgc
  241 aacgggtttg ccgccagaac acagctgaag cttcgagggg ctcgcatctc tccttcacgc
  301 gcccgccgcc ctacctgagg ccgccatcca cgccggttga gtcgcgttct gccgcctccc
  361 gcctgtggtg cctcctgaac tgcgtccgcc gtctaggtaa gtttaaagct caggtcgaga
  421 ccgggccttt gtccggcgct cccttggagc ctacctagac tcagccggct ctccacgctt
  481 tgcctgaccc tgcttgctca actctacgtc tttgtttcgt tttctgttct gcgccgttac
  541 agatccaagc tgtgaccggc gcctacgcta gatggtgagc aagggcgagg aggataacat
  601 ggccatcatc aaggagttca tgcgcttcaa ggtgcacatg gagggctccg tgaacggcca
  661 cgagttcgag atcgagggcg agggcgaggg ccgcccctac gagggcaccc agaccgccaa
  721 gctgaaggtg accaagggtg gccccctgcc cttcgcctgg gacatcctgt cccctcagtt
  781 catgtacggc tccaaggcct acgtgaagca ccccgccgac atccccgact acttgaagct
  841 gtccttcccc gagggcttca gtgggagcg cgtgatgaac ttcgaggacg gcggcgtggt
  901 gaccgtgacc caggactcct ccctgcagga cggcgagttc atctacaagg tgaagctgcg
  961 cggcaccaac ttcccctccg acggccccgt aatgcagaag aagaccatgg gctgggaggc
 1021 ctcctccgag cggatgtacc ccgaggacgg cgccctgaag ggcagatca agcagaggct
 1081 gaagctgaag gacggcggcc actacgacgc tgaggtcaag accacctaca aggccaagaa
 1141 gcccgtgcag ctgccggcg cctacaacgt caacatcaag ttggacatca cctcccacaa
 1201 cgaggactac accatcgtgg aacagtacga acgcgccgag ggccgccact ccaccggcgg
```

-continued

```
1261 catggacgag ctgtacaagt aatccgagct cggtaccaag cttaagttta aaccgctgat 1321 cagcctcgac tgtgccttct agttgccagc catctgttgt ttgcccctcc cccgtgcctt 1381 ccttgaccct ggaaggtgcc actcccactg tccttcccta ataaaatgag gaaattgcat 1441 cgcattgtct gagtaggtgt cattctattc tggggggtgg ggtggggcag gacagcaagg 1501 gggaggattg ggaagacaat agcaggcatg ctggggatgc ggtgggctct atggggatc 1561 cactagttct agagcggccg ccaccgcggt ggagctccag cttttgttcc ctttagtgag 1621 ggttaattgc gcgcttggcg taatcatggt catagctgtt tcctgtgtga aattgttatc 1681 cgctcacaat tccacacaac atacgagccg aagcataaa gtgtaaagcc tggggtgcct 1741 aatgagtgag ctaactcaca ttaattgcgt tgcgctcact gcccgctttc cagtcgggaa 1801 acctgtcgtg ccagctgcat taatgaatcg gccaacgcgc ggggagaggc ggtttgcgta 1861 ttgggcgctc ttccgcttcc tcgctcactg actcgctgcg ctcggtcgtt cggctgcggc 1921 gagcggtatc agctcactca aaggcggtaa tacggttatc cacagaatca ggggataacg 1981 caggaaagaa catgtgagca aaaggccagc aaaaggccag gaaccgtaaa aaggccgcgt 2041 tgctggcgtt tttccatagg ctccgccccc ctgacgagca tcacaaaaat cgacgctcaa 2101 gtcagaggtg gcgaaacccg acaggactat aaagatacca ggcgtttccc cctggaagct 2161 ccctcgtgcg ctctcctgtt ccgaccctgc cgcttaccgg atacctgtcc gcctttctcc 2221 cttcgggaag cgtggcgctt tctcatagct cacgctgtag gtatctcagt tcggtgtagg 2281 tcgttcgctc caagctgggc tgtgtgcacg aaccccccgt tcagcccgac cgctgcgcct 2341 tatccggtaa ctatcgtctt gagtccaacc cggtaagaca cgacttatcg ccactggcag 2401 cagccactgg taacaggatt agcagagcga ggtatgtagg cggtgctaca gagttcttga 2461 agtggtggcc taactacggc tacactagaa ggacagtatt tggtatctgc gctctgctga 2521 agccagttac cttcggaaaa agagttggta gctcttgatc cggcaaacaa accaccgctg 2581 gtagcggtgg tttttttgtt tgcaagcagc agattacgcg cagaaaaaaa ggatctcaag 2641 aagatccttt gatcttttct acggggtctg acgctcagtg gaacgaaaac tcacgttaag 2701 ggattttggt catgagatta tcaaaaagga tcttcaccta gatcctttta aattaaaaat 2761 gaagttttaa atcaatctaa agtatatatg agtaaacttg gtctgacagt taccaatgct 2821 taatcagtga ggcacctatc tcagcgatct gtctatttcg ttcatccata gttgcctgac 2881 tccccgtcgt gtagataact acgatacggg agggcttacc atctggcccc agtgctgcaa 2941 tgataccgcg agacccacgc tcaccggctc cagatttatc agcaataaac cagccagccg 3001 gaagggccga gcgcagaagt ggtcctgcaa ctttatccgc ctccatccag tctattaatt 3061 gttgccggga agctagagta agtagttcgc cagttaatag tttgcgcaac gttgttgcca 3121 ttgctacagg catcgtggtg tcacgctcgt cgtttggtat ggcttcattc agctccggtt 3181 cccaacgatc aaggcgagtt acatgatccc ccatgttgtg caaaaaagcg gttagctcct 3241 tcggtcctcc gatcgttgtc agaagtaagt tggccgcagt gttatcactc atggttatgg 3301 cagcactgca taattctctt actgtcatgc catccgtaag atgcttttct gtgactggtg 3361 agtactcaac caagtcattc tgagaatagt gtatgcggcg accgagttgc tcttgcccgg 3421 cgtcaatacg ggataatacc gcgccacata gcagaacttt aaaagtgctc atcattggaa 3481 aacgttcttc ggggcgaaaa ctctcaagga tcttaccgct gttgagatcc agttcgatgt 3541 aacccactcg tgcacccaac tgatcttcag catcttttac tttcaccagc gtttctgggt 3601 gagcaaaaac aggaaggcaa aatgccgcaa aaagggaat aagggcgaca cggaaatgtt 3661 gaatactcat actcttcctt tttcaatatt attgaagcat ttatcagggt tattgtctca
```

-continued

```
3721 tgagcggata catatttgaa tgtatttaga aaaataaaca aatagggtt ccgcgcacat 3781 ttccccgaaa agtgccacct aaattgtaag cgttaatatt ttgttaaaat tcgcgttaaa 3841 tttttgttaa atcagctcat tttttaacca ataggccgaa atcggcaaaa tcccttataa 3901 atcaaaagaa tagaccgaga tagggttgag tgttgttcca gtttggaaca agagtccact 3961 attaaagaac gtggactcca acgtcaaagg gcgaaaaacc gtctatcagg gcgatggccc 4021 actacgtgaa ccatcaccct aatcaagttt tttggggtcg aggtgccgta aagcactaaa 4081 tcggaaccct aaagggagcc ccgatttag agcttgacgg ggaaagccgg cgaacgtggc 4141 gagaaaggaa gggaagaaag cgaaaggagc gggcgctagg gcgctggcaa gtgtagcggt 4201 cacgctgcgc gtaaccacca cacccgccgc gcttaatgcg ccgctacagg gcgcgtccca 4261 ttcgccattc aggctgcgca actgttggga agggcgatcg gtgcgggcct cttcgctatt 4321 acgccagctg gcgaaagggg gatgtgctgc aaggcgatta agttgggtaa cgccagggtt 4381 ttcccagtca cgacgttgta aaacgacggc cagtgagcgc gcgtaatacg actcactata 4441 gggcgaattg ggtaccgggc cccccctcga ggtcgacggt atcgataagc ttgatatcgt 4501 gtacaaaaaa gcaggcttta aaggaaccaa ttcagtcgac tggatccggt accaaggtcg 4561 ggcaggaaga gggcctattt cccatgattc cttcatattt gcatatacga tacaaggctg 4621 ttagagagat aattagaatt aatttgactg taaacacaaa gatattagta caaaatacgt 4681 gacgtagaaa gtaataattt cttgggtagt ttgcagtttt aaaattatgt tttaaaatgg 4741 actatcatat gcttaccgta acttgaaagt atttcgattt cttggcttta tatatcttgt 4801 ggaaaggacg aaacaccgaa gtcatgccgt ttcatgtggt ttaagagcta tgctggaaac 4861 agcatagcaa gtttaaataa ggctagtccg ttatcaactt gaaaaagtgg caccgagtcg 4921 gtgcttcatt gtgtcggcca cggaacaggc a
``` spacerless_GFP_mCherry_extension (SEQ ID NO: 32).
LOCUS Exported 4930 bp ds-DNA circular
DEFINITION synthetic circular DNA
SOURCE synthetic DNA construct
ORGANISM recombinant plasmid
REFERENCE 1 (bases 1 to 4930)
FEATURES Location/Qualifiers
source 1 . . . 4930
/organism="recombinant plasmid"
/mol_type="other DNA"
rep_origin 13 . . . 453
/direction=RIGHT
/label=F1 ori
CDS complement(460 . . . 528)
/label=LacZ alpha
primer_bind 599 . . . 616
/label=M13-fwd
primer_bind 626 . . . 645
/label=T7
promoter 757 . . . 1019
/label=U6 promoter
primer_bind complement(998 . . . 1019)
/label=scaffold_out_R
primer_bind 1000 . . . 1045
/label=no_spacer_universal_scaff_f
primer_bind 1005 . . . 1043
/label=50bp_GFP_F
primer_bind 1005 . . . 1043
/label=ACTB_3_ext_CgRNA_For
misc_feature 1020 . . . 1105
/label=sgRNA scaffold
primer_bind 1020 . . . 1046
/label=scaffold_3_ext_template_For
primer_bind complement(1093 . . . 1111)
/label=scaffold_3_ext_template_Rev
primer_bind complement(1094 . . . 1152)
/label=eGFP_3_ext_R
primer_bind complement(1094 . . . 1152)

-continued

```
/label=gfp_3_extension_revcomp
primer_bind   complement(1094 . . . 1152)
/label=ACTB_3_ext_AgRNA_Rev
misc_feature  1106 . . . 1111
/label=Linker
misc_feature  1112 . . . 1132
/label=EGFP_extension
primer_bind   1133 . . . 1172
/label=EF1a_Gibson_F
primer_bind   1133 . . . 1152
/label=3_ext_backbone_For
misc_feature  1133 . . . 1139
/label=sgRNA scaffold termination
promoter      1153 . . . 1698
/label=EF1a promoter
primer_bind   complement(1686 . . . 1723)
/label=EF1a_Gibson_R
CDS           1704 . . . 2414
/codon_start=1
/product="monomeric derivative of DsRed fluorescent protein
(Shaner et al., 2004)"
/label=mCherry
/note="mammalian codon-optimized"
                                                 (SEQ ID NO: 55)
/translation="MVSKGEEDNMAIIKEFMRFKVHMEGSVNGHEFEIEGEGEGRPYEG
TQTAKLKVTKGGPLPFAWDILSPQFMYGSKAYVKHPADIPDYLKLSFPEGFKWERVMNF
EDGGVVTVTQDSSLQDGEFIYKVKLRGTNFPSDGPVMQKKTMGWEASSERMYPEDGALK
GEIKQRLKLKDGGHYDAEVKTTYKAKKPVQLPGAYNVNIKLDITSHNEDYTIVEQYERA
EGRHSTGGMDELYK"
primer_bind   1704 . . . 1723
/label=mCherry_BGH_F
primer_bind   complement(2391 . . . 2438)
/label=Primer 1
primer_bind   complement(2391 . . . 2414)
/label=mCherry_HindIII_R
misc_feature  2415 . . . 2438
/label=Gibson Overlap
polyA_signal  2462 . . . 2686
/label=bGH poly(A) signal
/note="bovine growth hormone polyadenylation signal"
primer_bind   complement(2667 . . . 2705)
/label=mCherry_BGH_Gib_R
primer_bind   complement(2667 . . . 2686)
/label=mCherry_BGH_R
primer_bind   complement(2668 . . . 2687)
/label=bGH_NotI_R
primer_bind   complement(2690 . . . 2705)
/label=SK primer
/note="common sequencing primer, one of multiple similar
variants"
primer_bind   complement(2740 . . . 2759)
/label=T3
primer_bind   complement(2777 . . . 2797)
/label=M13-rev
misc_binding  complement(2803 . . . 2825)
/label=LacO
promoter      complement(2830 . . . 2859)
/label=lac
rep_origin    complement(3165 . . . 3793)
/direction=LEFT
/label=ColE1 origin
CDS           complement(3945 . . . 4604)
/label=AmpR
promoter      complement(4844 . . . 4872)
/label=Amp prom
ORIGIN
    1 ctaaattgta agcgttaata ttttgttaaa attcgcgtta aattttttgtt aaatcagctc
   61 attttttaac caataggccg aaatcggcaa atcccttat aaatcaaaag aatagaccga
  121 gatagggttg agtgttgttc cagtttggaa caagagtcca ctattaaaga acgtggactc
  181 caacgtcaaa gggcgaaaaa ccgtctatca gggcgatggc ccactacgtg aaccatcacc
  241 ctaatcaagt ttttggggt cgaggtgccg taaagcacta atcgaacc ctaaagggag
  301 cccccgattt agagcttgac ggggaaagcc ggcgaacgtg gcgagaaagg aagggaagaa
  361 agcgaaagga gcgggcgcta gggcgctggc aagtgtagcg gtcacgctgc gcgtaaccac
  421 cacacccgcc gcgcttaatg cgccgctaca gggcgcgtcc cattcgccat tcaggctgcg
```

-continued

```
 481 caactgttgg gaagggcgat cggtgcgggc ctcttcgcta ttacgccagc tggcgaaagg
 541 gggatgtgct gcaaggcgat taagttgggt aacgccaggg ttttcccagt cacgacgttg
 601 taaaacgacg ccagtgagc gcgcgtaata cgactcacta tagggcgaat tgggtaccgg
 661 gcccccctc gaggtcgacg gtatcgataa gcttgatatc gtgtacaaaa aagcaggctt
 721 taaaggaacc aattcagtcg actggatccg gtaccaaggt cgggcaggaa gagggcctat
 781 ttcccatgat tccttcatat ttgcatatac gatacaaggc tgttagagag ataattagaa
 841 ttaatttgac tgtaaacaca aagatattag tacaaaatac gtgacgtaga aagtaataat
 901 ttcttgggta gtttgcagtt ttaaaattat gttttaaaat ggactatcat atgcttaccg
 961 taacttgaaa gtatttcgat ttcttggctt tatatatctt gtggaaagga cgaaacaccg
1021 tttaagagct atgctggaaa cagcatagca agtttaaata aggctagtcc gttatcaact
1081 tgaaaaagtg gcaccgagtc ggtgcttcat tgtgtcggcc acggaacagg catttttttc
1141 ctgcagcccg ggaaggatct gcgatcgctc cggtgcccgt cagtgggcag agcgcacatc
1201 gcccacagtc cccgagaagt tggggggagg ggtcggcaat tgaacgggtg cctagagaag
1261 gtggcgcggg gtaaactggg aaagtgatgt cgtgtactgg ctccgccttt ttcccgaggg
1321 tgggggagaa ccgtatataa gtgcagtagt cgccgtgaac gttcttttc gcaacgggtt
1381 tgccgccaga acacagctga agcttcgagg ggctcgcatc tctccttcac gcgcccgccg
1441 ccctacctga ggccgccatc cacgccggtt gagtcgcgtt ctgccgcctc ccgcctgtgg
1501 tgcctcctga actgcgtccg ccgtctaggt aagtttaaag ctcaggtcga gaccgggcct
1561 ttgtccggcg ctcccttgga gcctacctag actcagccgg ctctccacgc tttgcctgac
1621 cctgcttgct caactctacg tctttgtttc gttttctgtt ctgcgccgtt acagatccaa
1681 gctgtgaccg gcgcctacgc tagatggtga gcaagggcga ggaggataac atggccatca
1741 tcaaggagtt catgcgcttc aaggtgcaca tggagggctc cgtgaacggc cacgagttcg
1801 agatcgaggg cgagggcgag ggccgcccct acgagggcac ccagaccgcc aagctgaagg
1861 tgaccaaggg tggccccctg cccttcgcct gggacatcct gtcccctcag ttcatgtacg
1921 gctccaaggc ctacgtgaag caccccgccg acatccccga ctacttgaag ctgtccttcc
1981 ccgagggctt caagtgggag cgcgtgatga acttcgagga cggcggcgtg gtgaccgtga
2041 cccaggactc ctccctgcag gacggcgagt tcatctacaa ggtgaagctg cgcggcacca
2101 acttcccctc cgacggcccc gtaatgcaga agaagaccat gggctgggag gcctcctccg
2161 agcggatgta ccccgaggac ggcgccctga agggcgagat caagcagagg ctgaagctga
2221 aggacggcgg ccactacgac gctgaggtca agaccaccta caaggccaag aagcccgtgc
2281 agctgcccgg cgcctacaac gtcaacatca gttggacat cacctcccac aacgaggact
2341 acaccatcgt ggaacagtac gaacgcgccg agggccgcca ctccaccggc ggcatggacg
2401 agctgtacaa gtaatccgag ctcggtacca agcttaagtt taaaccgctg atcagcctcg
2461 actgtgcctt ctagttgcca gccatctgtt gtttgcccct ccccgtgcc ttccttgacc
2521 ctggaaggtg ccactcccac tgtccttttcc taataaaatg aggaaattgc atcgcattgt
2581 ctgagtaggt gtcattctat tctgggggg ggggtggggc aggacagcaa ggggaggat
2641 tgggaagaca atagcaggca tgctgggat gcggtgggct ctatgggga tccactagtt
2701 ctagagcggc cgccaccgcg gtggagctcc agcttttgtt cccttagtg agggttaatt
2761 gcgcgcttgg cgtaatcatg gtcatagctg tttcctgtgt gaaattgtta tccgctcaca
2821 attccacaca acatacgagc cggaagcata aagtgtaaag cctggggtgc ctaatgagtg
```

```
2881 agctaactca cattaattgc gttgcgctca ctgcccgctt tccagtcggg aaacctgtcg 2941 tgccagctgc attaatgaat cggccaacgc gcggggagag gcggtttgcg tattgggcgc 3001 tcttccgctt cctcgctcac tgactcgctg cgctcggtcg ttcggctgcg gcgagcggta 3061 tcagctcact caaaggcggt aatacggtta tccacagaat cagggggataa cgcaggaaag 3121 aacatgtgag caaaaggcca gcaaaaggcc aggaaccgta aaaaggccgc gttgctggcg 3181 ttttccata ggctccgccc ccctgacgag catcacaaaa atcgacgctc aagtcagagg 3241 tggcgaaacc cgacaggact ataaagatac caggcgtttc ccctggaag ctccctcgtg 3301 cgctctcctg ttccgaccct gccgcttacc ggatacctgt ccgcctttct cccttcggga 3361 agcgtggcgc tttctcatag ctcacgctgt aggtatctca gttcggtgta ggtcgttcgc 3421 tccaagctgg gctgtgtgca cgaaccccc gttcagcccg accgctgcgc cttatccggt 3481 aactatcgtc ttgagtccaa cccggtaaga cacgacttat cgccactggc agcagccact 3541 ggtaacagga ttagcagagc gaggtatgta ggcggtgcta cagagttctt gaagtggtgg 3601 cctaactacg gctacactag aaggacagta tttggtatct gcgctctgct gaagccagtt 3661 accttcggaa aaagagttgg tagctcttga tccggcaaac aaaccaccgc tggtagcggt 3721 ggtttttttg tttgcaagca gcagattacg cgcagaaaaa aaggatctca agaagatcct 3781 ttgatctttt ctacggggtc tgacgctcag tggaacgaaa actcacgtta agggattttg 3841 gtcatgagat tatcaaaaag gatcttcacc tagatccttt taaattaaaa atgaagtttt 3901 aaatcaatct aaagtatata tgagtaaact tggtctgaca gttaccaatg cttaatcagt 3961 gaggcaccta tctcagcgat ctgtctattt cgttcatcca tagttgcctg actccccgtc 4021 gtgtagataa ctacgatacg ggagggctta ccatctggcc ccagtgctgc aatgataccg 4081 cgagacccac gctcaccggc tccagattta tcagcaataa accagccagc cggaagggcc 4141 gagcgcagaa gtggtcctgc aactttatcc gcctccatcc agtctattaa ttgttgccgg 4201 gaagctagag taagtagttc gccagttaat agtttgcgca acgttgttgc cattgctaca 4261 ggcatcgtgg tgtcacgctc gtcgtttggt atggcttcat tcagctccgg ttcccaacga 4321 tcaaggcgag ttacatgatc ccccatgttg tgcaaaaaag cggttagctc cttcggtcct 4381 ccgatcgttg tcagaagtaa gttggccgca gtgttatcac tcatggttat ggcagcactg 4441 cataattctc ttactgtcat gccatccgta agatgctttt ctgtgactgg tgagtactca 4501 accaagtcat tctgagaata gtgtatgcgg cgaccgagtt gctcttgccc ggcgtcaata 4561 cgggataata ccgcgccaca tagcagaact ttaaaagtgc tcatcattgg aaaacgttct 4621 tcggggcgaa aactctcaag gatcttaccg ctgttgagat ccagttcgat gtaacccact 4681 cgtgcaccca actgatcttc agcatctttt actttcacca cgtttctggg gtgagcaaaa 4741 acaggaaggc aaaatgccgc aaaaaaggga ataagggcga cacggaaatg ttgaatactc 4801 atactcttcc tttttcaata ttattgaagc atttatcagg gttattgtct catgagcgga 4861 tacatatttg aatgtatta gaaaaataaa caaataggg ttccgcgcac atttccccga 4921 aaagtgccac
```

GFP_no_spacer_revcomp_mCherry_gibson (SEQ ID NO: 33).
LOCUS Exported 4930 bp ds-DNA circular
DEFINITION synthetic circular DNA
SOURCE synthetic DNA construct
ORGANISM recombinant plasmid
REFERENCE 1 (bases 1 to 4930)
FEATURES Location/Qualifiers
source 1 . . . 4930
/organism="recombinant plasmid"
/mol_type="other DNA"
primer_bind 1 . . . 20

-continued

```
/label=Primer 2
misc_feature 1 . . . 7
/label=sgRNA scaffold termination
promoter 21 . . . 566
/label=EF1a promoter
primer_bind complement(554 . . . 591)
/label=EF1a_Gibson_R
CDS 572 . . . 1282
/codon_start=1
/product="monomeric derivative of DsRed fluorescent protein
(Shaner et al., 2004)"
/label=mCherry
/note="mammalian codon-optimized"
                                                  (SEQ ID NO: 55)
/translation="MVSKGEEDNMAIIKEFMRFKVHMEGSVNGHEFEIEGEGEGRPYEG
TQTAKLKVTKGGPLPFAWDILSPQFMYGSKAYVKHPADIPDYLKLSFPEGFKWERVMNF
EDGGVVTVTQDSSLQDGEFIYKVKLRGTNFPSDGPVMQKKTMGWEASSERMYPEDGALK
GEIKQRLKLKDGGHYDAEVKTTYKAKKPVQLPGAYNVNIKLDITSHNEDYTIVEQYERA
EGRHSTGGMDELYK"
primer_bind 572 . . . 591
/label=mCherry_BGH_F
primer_bind complement(1259 . . . 1306)
/label=Primer 1
primer_bind complement(1259 . . . 1282)
/label=mCherry_HindIII_R
misc_feature 1283 . . . 1306
/label=Gibson Overlap
polyA_signal 1330 . . . 1554
/label=bGH poly(A) signal
/note="bovine growth hormone polyadenylation signal"
primer_bind complement(1535 . . . 1573)
/label=mCherry_BGH_Gib_R
primer_bind complement(1535 . . . 1554)
/label=mCherry_BGH_R
primer_bind complement(1536 . . . 1555)
/label=bGH_NotI_R
primer_bind complement(1558 . . . 1573)
/label=SK primer
/note="common sequencing primer, one of multiple similar
variants"
primer_bind complement(1608 . . . 1627)
/label=T3
primer_bind complement(1645 . . . 1665)
/label=M13-rev
misc_binding complement(1671 . . . 1693)
/label=LacO
promoter complement(1698 . . . 1727)
/label=lac
rep_origin complement(2033 . . . 2661)
/direction=LEFT
/label=ColE1 origin
CDS complement(2813 . . . 3472)
/label=AmpR
promoter complement(3712 . . . 3740)
/label=Amp prom
rep_origin 3811 . . . 4251
/direction=RIGHT
/label=F1 ori
CDS complement(4258 . . . 4326)
/label=LacZ alpha
primer_bind 4397 . . . 4414
/label=M13-fwd
primer_bind 4424 . . . 4443
/label=T7
promoter 4555 . . . 4817
/label=U6 promoter
primer_bind 4798 . . . 4843
/label=no_spacer_universal_scaff_f
primer_bind 4803 . . . 4841
/label=ACTB_3_ext_CgRNA_For
primer_bind complement(4803 . . . 4817)
/label=Primer 3
primer_bind complement(4803 . . . 4817)
/label=extension_gibson_R
misc_feature 4818 . . . 4903
/label=sgRNA scaffold
primer_bind 4818 . . . 4844
/label=scaffold_3_ext_template_For
primer_bind complement(4891 . . . 4909)
/label=scaffold_3_ext_template_Rev
primer_bind complement(join(4892 . . . 4930,1 . . . 20))
```

```
                            -continued
/label=gfp_3_extension_revcomp
primer_bind   complement(join(4892 . . . 4930,1 . . . 20))
/label=ACTB_3_ext_AgRNA_Rev
misc_feature  4904 . . . 4909
/label=Linker
misc_feature  4910 . . . 4930
/label=EGFP_revcomp_extension
primer_bind   join(4930,1 . . . 40)
/label=EF1a_Gibson_F
ORIGIN
     1 tttttttcct gcagcccggg aaggatctgc gatcgctccg gtgcccgtca gtgggcagag
    61 cgcacatcgc ccacagtccc cgagaagttg gggggagggg tcggcaattg aacgggtgcc
   121 tagagaaggt ggcgcggggt aaactgggaa agtgatgtcg tgtactggct ccgcctttt
   181 cccgagggtg ggggagaacc gtatataagt gcagtagtcg ccgtgaacgt tctttttcgc
   241 aacgggtttg ccgccagaac acagctgaag cttcgagggg ctcgcatctc tccttcacgc
   301 gcccgccgcc ctacctgagg ccgccatcca cgccggttga gtcgcgttct gccgcctccc
   361 gcctgtggtg cctcctgaac tgcgtccgcc gtctaggtaa gtttaaagct caggtcgaga
   421 ccgggccttt gtccggcgct cccttggagc ctacctagac tcagccggct ctccacgctt
   481 tgcctgaccc tgcttgctca actctacgtc tttgtttcgt tttctgttct gcgccgttac
   541 agatccaagc tgtgaccggc gcctacgcta atggtgagc aagggcgagg aggataacat
   601 ggccatcatc aaggagttca tgcgcttcaa ggtgcacatg gagggctccg tgaacggcca
   661 cgagttcgag atcgagggcg agggcgaggg ccgcccctac gagggcaccc agaccgccaa
   721 gctgaaggtg accaagggtg gccccctgcc cttcgcctgg gacatcctgt cccctcagtt
   781 catgtacggc tccaaggcct acgtgaagca ccccgccgac atccccgact acttgaagct
   841 gtccttcccc gagggcttca gtgggagcg cgtgatgaac ttcgaggacg gcggcgtggt
   901 gaccgtgacc caggactcct ccctgcagga cggcgagttc atctacaagg tgaagctgcg
   961 cggcaccaac ttcccctccg acggccccgt aatgcagaag aagaccatgg gctgggaggc
  1021 ctcctccgag cggatgtacc ccgaggacgg cgccctgaag ggcagatca agcagaggct
  1081 gaagctgaag gacggcggcc actacgacgc tgaggtcaag accacctaca aggccaagaa
  1141 gcccgtgcag ctgcccggcg cctacaacgt caacatcaag ttggacatca cctcccacaa
  1201 cgaggactac accatcgtgg aacagtacga acgcgccgag ggccgccact ccaccggcgg
  1261 catggacgag ctgtacaagt aatccgagct cggtaccaag cttaagttta aaccgctgat
  1321 cagcctcgac tgtgccttct agttgccagc catctgttgt ttgcccctcc cccgtgcctt
  1381 ccttgaccct ggaaggtgcc actcccactg tcctttccta ataaaatgag gaaattgcat
  1441 cgcattgtct gagtaggtgt cattctattc tggggggtgg ggtggggcag gacagcaagg
  1501 gggaggattg ggaagacaat agcaggcatg ctggggatgc ggtgggctct atggggatc
  1561 cactagttct agagcggccg ccaccgcggt ggagctccag cttttgttcc ctttagtgag
  1621 ggttaattgc gcgcttggcg taatcatggt catagctgtt tcctgtgtga aattgttatc
  1681 cgctcacaat tccacacaac atacgagccg aagcataaa gtgtaaagcc tggggtgcct
  1741 aatgagtgag ctaactcaca ttaattgcgt tgcgctcact gcccgctttc cagtcgggaa
  1801 acctgtcgtg ccagctgcat taatgaatcg gccaacgcgc ggggagaggc ggtttgcgta
  1861 ttgggcgctc ttccgcttcc tcgctcactg actcgctgcg ctcggtcgtt cggctgcggc
  1921 gagcggtatc agctcactca aaggcggtaa tacggttatc cacagaatca ggggataacg
  1981 caggaaagaa catgtgagca aaaggccagc aaaaggccag gaaccgtaaa aaggccgcgt
  2041 tgctggcgtt tttccatagg ctccgccccc ctgacgagca tcacaaaaat cgacgctcaa
  2101 gtcagaggtg gcgaaacccg acaggactat aaagatacca ggcgtttccc cctggaagct
```

-continued

```
2161 ccctcgtgcg ctctcctgtt ccgaccctgc cgcttaccgg ataccgtcc gcctttctcc
2221 cttcgggaag cgtggcgctt tctcatagct cacgctgtag gtatctcagt tcggtgtagg
2281 tcgttcgctc caagctgggc tgtgtgcacg aaccccccgt tcagcccgac cgctgcgcct
2341 tatccggtaa ctatcgtctt gagtccaacc cggtaagaca cgacttatcg ccactggcag
2401 cagccactgg taacaggatt agcagagcga ggtatgtagg cggtgctaca gagttcttga
2461 agtggtggcc taactacggc tacactagaa ggacagtatt tggtatctgc gctctgctga
2521 agccagttac cttcggaaaa agagttggta gctcttgatc cggcaaacaa accaccgctg
2581 gtagcggtgg ttttttttgtt tgcaagcagc agattacgcg cagaaaaaaa ggatctcaag
2641 aagatccttt gatcttttct acggggtctg acgctcagtg gaacgaaaac tcacgttaag
2701 ggattttggt catgagatta tcaaaaagga tcttcaccta gatccttta aattaaaaat
2761 gaagttttaa atcaatctaa agtatatatg agtaaacttg gtctgacagt taccaatgct
2821 taatcagtga ggcacctatc tcagcgatct gtctatttcg ttcatccata gttgcctgac
2881 tccccgtcgt gtagataact acgatacggg agggcttacc atctggcccc agtgctgcaa
2941 tgataccgcg agacccacgc tcaccggctc cagatttatc agcaataaac cagccagccg
3001 gaagggccga gcgcagaagt ggtcctgcaa ctttatccgc ctccatccag tctattaatt
3061 gttgccggga agctagagta agtagttcgc cagttaatag tttgcgcaac gttgttgcca
3121 ttgctacagg catcgtggtg tcacgctcgt cgtttggtat ggcttcattc agctccggtt
3181 cccaacgatc aaggcgagtt acatgatccc ccatgttgtg caaaaaagcg gttagctcct
3241 tcggtcctcc gatcgttgtc agaagtaagt tggccgcagt gttatcactc atggttatgg
3301 cagcactgca taattctctt actgtcatgc catccgtaag atgcttttct gtgactggtg
3361 agtactcaac caagtcattc tgagaatagt gtatgcggcg accgagttgc tcttgcccgg
3421 cgtcaatacg ggataatacc gcgccacata gcagaacttt aaaagtgctc atcattggaa
3481 aacgttcttc ggggcgaaaa ctctcaagga tcttaccgct gttgagatcc agttcgatgt
3541 aacccactcg tgcacccaac tgatcttcag catcttttac tttcaccagc gtttctgggt
3601 gagcaaaaac aggaaggcaa aatgccgcaa aaaagggaat aagggcgaca cggaaatgtt
3661 gaatactcat actcttcctt tttcaatatt attgaagcat ttatcagggt tattgtctca
3721 tgagcggata catatttgaa tgtatttaga aaaataaaca ataggggtt ccgcgcacat
3781 ttccccgaaa agtgccacct aaattgtaag cgttaatatt tgttaaaat tcgcgttaaa
3841 tttttgttaa atcagctcat ttttaacca ataggccgaa atcggcaaaa tcccttataa
3901 atcaaaagaa tagaccgaga tagggttgag tgttgttcca gtttggaaca agagtccact
3961 attaaagaac gtggactcca acgtcaaagg gcgaaaaacc gtctatcagg gcgatggccc
4021 actacgtgaa ccatcaccct aatcaagttt tttggggtcg aggtgccgta agcactaaa
4081 tcggaaccct aaagggagcc cccgatttag agcttgacgg ggaaagccgg cgaacgtggc
4141 gagaaaggaa gggaagaaag cgaaaggagc gggcgctagg gcgctggcaa gtgtagcggt
4201 cacgctgcgc gtaaccacca cacccgccgc gcttaatgcg ccgctacagg gcgcgtccca
4261 ttcgccattc aggctgcgca actgttggga agggcgatcg gtgcgggcct cttcgctatt
4321 acgccagctg gcgaaagggg gatgtgctgc aaggcgatta agttgggtaa cgccagggtt
4381 ttcccagtca cgacgttgta aaacgacggc cagtgagcgc gcgtaatacg actcactata
4441 gggcgaattg ggtaccgggc cccccctcga ggtcgacggt atcgataagc ttgatatcgt
4501 gtacaaaaaa gcaggcttta aaggaaccaa ttcagtcgac tggatccggt accaaggtcg
```

```
4561 ggcaggaaga gggcctattt cccatgattc cttcatattt gcatatacga tacaaggctg 4621 ttagagagat aattagaatt aatttgactg taaacacaaa gatattagta caaaatacgt 4681 gacgtagaaa gtaataattt cttgggtagt ttgcagtttt aaaattatgt tttaaaatgg 4741 actatcatat gcttaccgta acttgaaagt atttcgattt cttggcttta tatatcttgt 4801 ggaaaggacg aaacaccgtt taagagctat gctggaaaca gcatagcaag tttaaataag 4861 gctagtccgt tatcaacttg aaaaagtggc accgagtcgg tgcttcattt gcctgttccg 4921 tggccgacac
``` pBluescript II SK+ U6-lambda2-sgRNA(F + E) (SEQ ID NO: 34).
LOCUS Exported 3388 bp ds-DNA circular
DEFINITION synthetic circular DNA
SOURCE synthetic DNA construct
ORGANISM synthetic DNA construct
REFERENCE 1 (bases 1 to 3388)
FEATURES Location/Qualifiers
source 1 . . . 3388
/organism="synthetic DNA construct"
/mol_type="other DNA"
rep_origin 13 . . . 453
/direction=RIGHT
/label=F1 ori
CDS complement(460 . . . 528)
/label=LacZ alpha
primer_bind 599 . . . 616
/label=M13-fwd
primer_bind 626 . . . 645
/label=T7
promoter 757 . . . 1019
/label=U6 promoter
misc_feature 1020 . . . 1039
/label=lambda2_guideRNA
misc_feature 1041 . . . 1132
/label=sgRNA scaffold
primer_bind complement(1198 . . . 1217)
/label=T3
primer_bind complement(1235 . . . 1255)
/label=M13-rev
misc_binding complement(1261 . . . 1283)
/label=LacO
promoter complement(1288 . . . 1317)
/label=lac
rep_origin complement(1623 . . . 2251)
/direction=LEFT
/label=ColE1 origin
CDS complement(2403 . . . 3062)
/label=AmpR
promoter complement(3302 . . . 3330)
/label=Amp prom
ORIGIN

```
   1 ctaaattgta agcgttaata ttttgttaaa attcgcgtta aattttttgtt aaatcagctc 61 attttttaac caataggccg aaatcggcaa aatcccttat aaatcaaaag aatagaccga 121 gatagggttg agtgttgttc cagtttggaa caagagtcca ctattaaaga acgtggactc 181 caacgtcaaa gggcgaaaaa ccgtctatca gggcgatggc ccactacgtg aaccatcacc 241 ctaatcaagt tttttggggt cgaggtgccg taaagcacta aatcggaacc ctaaagggag 301 cccccgattt agagcttgac ggggaaagcc ggcgaacgtg gcgagaaagg aagggaagaa 361 agcgaaagga gcgggcgcta gggcgctggc aagtgtagcg gtcacgctgc gcgtaaccac 421 cacacccgcc gcgcttaatg cgccgctaca gggcgcgtcc cattcgccat tcaggctgcg 481 caactgttgg gaagggcgat cggtgcgggc ctcttcgcta ttacgccagc tggcgaaagg 541 gggatgtgct gcaaggcgat taagttgggt aacgccaggg ttttcccagt cacgacgttg 601 taaaacgacg gccagtgagc gcgcgtaata cgactcacta tagggcgaat gggtaccgg 661 gccccccctc gaggtcgacg gtatcgataa gcttgatatc gtgtacaaaa aagcaggctt 721 taaaggaacc aattcagtcg actggatccg gtaccaaggt cgggcaggaa gagggcctat
```

-continued

```
 781 ttcccatgat tccttcatat ttgcatatac gatacaaggc tgttagagag ataattagaa
 841 ttaatttgac tgtaaacaca aagatattag tacaaaatac gtgacgtaga aagtaataat
 901 ttcttgggta gtttgcagtt ttaaaattat gttttaaaat ggactatcat atgcttaccg
 961 taacttgaaa gtatttcgat ttcttggctt tatatatctt gtggaaagga cgaaacaccg
1021 tgataagtgg aatgccatgg tttaagagct atgctggaaa cagcatagca agtttaaata
1081 aggctagtcc gttatcaact tgaaaaagtg gcaccgagtc ggtgcttttt ttcctgcagc
1141 ccgggggatc cactagttct agagcggccg ccaccgcggt ggagctccag cttttgttcc
1201 ctttagtgag ggttaattgc gcgcttggcg taatcatggt catagctgtt tcctgtgtga
1261 aattgttatc cgctcacaat tccacacaac atacgagccg gaagcataaa gtgtaaagcc
1321 tggggtgcct aatgagtgag ctaactcaca ttaattgcgt tgcgctcact gcccgctttc
1381 cagtcgggaa acctgtcgtg ccagctgcat taatgaatcg gccaacgcgc ggggagaggc
1441 ggtttgcgta ttgggcgctc ttccgcttcc tcgctcactg actcgctgcg ctcggtcgtt
1501 cggctgcggc gagcggtatc agctcactca aaggcggtaa tacggttatc cacagaatca
1561 ggggataacg caggaaagaa catgtgagca aaaggccagc aaaaggccag gaaccgtaaa
1621 aaggccgcgt tgctggcgtt tttccatagg ctccgccccc ctgacgagca tcacaaaaat
1681 cgacgctcaa gtcagaggtg gcgaaacccg acaggactat aaagatacca ggcgtttccc
1741 cctggaagct ccctcgtgcg ctctcctgtt ccgaccctgc cgcttaccgg atacctgtcc
1801 gcctttctcc cttcgggaag cgtggcgctt tctcatagct cacgctgtag gtatctcagt
1861 tcggtgtagg tcgttcgctc caagctgggc tgtgtgcacg aaccccccgt tcagcccgac
1921 cgctgcgcct tatccggtaa ctatcgtctt gagtccaacc cggtaagaca cgacttatcg
1981 ccactggcag cagccactgg taacaggatt agcagagcga ggtatgtagg cggtgctaca
2041 gagttcttga agtggtggcc taactacggc tacactagaa ggacagtatt tggtatctgc
2101 gctctgctga agccagttac cttcggaaaa agagttggta gctcttgatc cggcaaacaa
2161 accaccgctg gtagcggtgg tttttttgtt tgcaagcagc agattacgcg cagaaaaaaa
2221 ggatctcaag aagatccttt gatcttttct acggggtctg acgctcagtg gaacgaaaac
2281 tcacgttaag ggattttggt catgagatta tcaaaaagga tcttcaccta gatcctttta
2341 aattaaaaat gaagttttaa atcaatctaa agtatatatg agtaaacttg gtctgacagt
2401 taccaatgct taatcagtga ggcacctatc tcagcgatct gtctatttcg ttcatccata
2461 gttgcctgac tccccgtcgt gtagataact acgatacggg agggcttacc atctggcccc
2521 agtgctgcaa tgataccgcg agacccacgc tcaccggctc cagatttatc agcaataaac
2581 cagccagccg gaagggccga gcgcagaagt ggtcctgcaa ctttatccgc ctccatccag
2641 tctattaatt gttgccggga agctagagta agtagttcgc cagttaatag tttgcgcaac
2701 gttgttgcca ttgctacagg catcgtggtg tcacgctcgt cgtttggtat ggcttcattc
2761 agctccggtt cccaacgatc aaggcgagtt acatgatccc ccatgttgtg caaaaaagcg
2821 gttagctcct tcggtcctcc gatcgttgtc agaagtaagt tggccgcagt gttatcactc
2881 atggttatgg cagcactgca taattctctt actgtcatgc catccgtaag atgcttttct
2941 gtgactggtg agtactcaac caagtcattc tgagaatagt gtatgcggcg accgagttgc
3001 tcttgcccgg cgtcaatacg ggataatacc gcgccacata gcagaacttt aaaagtgctc
3061 atcattggaa aacgttcttc ggggcgaaaa ctctcaagga tcttaccgct gttgagatcc
3121 agttcgatgt aacccactcg tgcacccaac tgatcttcag catctttac tttcaccagc
3181 gtttctgggt gagcaaaaac aggaaggcaa aatgccgcaa aaaagggaat aagggcgaca
```

```
3241 cggaaatgtt gaatactcat actcttcctt tttcaatatt attgaagcat ttatcagggt 3301 tattgtctca tgagcggata catatttgaa tgtatttaga aaaataaaca aatagggttt 3361 ccgcgcacat ttccccgaaa agtgccac
```

```
EGFP_spacerless_SaCas9_sgRNA (SEQ ID NO: 47)
LOCUS Exported 4921 bp ds-DNA circular
DEFINITION synthetic circular DNA
SOURCE synthetic DNA construct
ORGANISM recombinant plasmid
REFERENCE 1 (bases 1 to 4921)
FEATURES Location/Qualifiers
source 1 . . . 4921
/organism="recombinant plasmid"
/mol_type="other DNA"
primer_bind 1 . . . 40
/label=EF1a_Gibson_F
primer_bind 1 . . . 20
/label=Primer 2
misc_feature 1 . . . 7
/label=sgRNA scaffold_termination
promoter 21 . . . 566
/label=EF1a promoter
primer_bind complement(554 . . . 591)
/label=EF1a_Gibson_R
CDS 572 . . . 1282
/codon_start=1
/product="monomeric derivative of DsRed fluorescent protein
(Shaner et al., 2004)"
/label=mCherry
/note="mammalian codon-optimized"
                                          (SEQ ID NO: 55)
/translation="MVSKGEEDNMAIIKEFMRFKVHMEGSVNGHEFEIEGEGEGRPYEG
TQTAKLKVTKGGPLPFAWDILSPQFMYGSKAYVKHPADIPDYLKLSFPEGFKWERVMNF
EDGGVVTVTQDSSLQDGEFIYKVKLRGTNFPSDGPVMQKKTMGWEASSERMYPEDGALK
GEIKQRLKLKDGGHYDAEVKTTYKAKKPVQLPGAYNVNIKLDITSHNEDYTIVEQYERA
EGRHSTGGMDELYK"
primer_bind 572 . . . 591
/label=mCherry_BGH_F
primer_bind complement(1259 . . . 1306)
/label=Primer 1
primer_bind complement(1259 . . . 1286)
/label=mCherry_P2A_Gib_R
primer_bind complement(1259 . . . 1282)
/label=mCherry_HindIII_R
misc_feature 1283 . . . 1306
/label=Gibson Overlap
primer_bind 1283 . . . 1301
/label=mCherry_P2A_Gib_F
polyA_signal 1330 . . . 1554
/label=bGH poly(A) signal
/note="bovine growth hormone polyadenylation signal"
primer_bind complement(1535 . . . 1573)
/label=mCherry_BGH_Gib_R
primer_bind complement(1535 . . . 1554)
/label=mCherry_BGH_R
primer_bind complement(1536 . . . 1555)
/label=bGH_NotI_R
primer_bind complement(1558 . . . 1573)
/label=SK primer
/note="common sequencing primer, one of multiple similar
variants"
primer_bind complement(1608 . . . 1627)
/label=T3
primer_bind complement(1645 . . . 1665)
/label=M13-rev
misc_binding complement(1671 . . . 1693)
/label=LacO
promoter complement(1698 . . . 1727)
/label=lac
rep_origin complement(2033 . . . 2661)
/direction=LEFT
/label=ColE1 origin
CDS complement(2813 . . . 3472)
/label=AmpR
promoter complement(3712 . . . 3740)
/label=Amp prom
rep_origin 3811 . . . 4251
/direction=RIGHT
```

```
          /label=F1 ori
CDS       complement(4258 . . . 4326)
          /label=LacZ alpha
primer_bind 4397 . . . 4414
          /label=M13-fwd
primer_bind 4424 . . . 4443
          /label=T7
promoter  4555 . . . 4817
          /label=U6 promoter
primer_bind 4798 . . . 4843
          /label=NS_EGFP_SaCas9_F
primer_bind complement(4803 . . . 4817)
          /label=Primer 3
primer_bind complement(4803 . . . 4817)
          /label=extension_gibson_R
primer_bind 4804 . . . 4843
          /label=50bp_EGFP_SaCas9_F
misc_RNA  4819 . . . 4894
          /label=Sa gRNA scaffold
          /note="guide RNA scaffold for the Staphylococcus aureus
          CRISPR/Cas9 system"
primer_bind complement(join(4877 . . . 4921,1 . . . 20))
          /label=EGFP_SaCas9_RC_ex_R
primer_bind complement(join(4877 . . . 4921,1 . . . 20))
          /label=EGFP_SaCas9_ex_R
misc_feature 4895 . . . 4900
          /label=Linker
misc_feature 4901 . . . 4921
          /label=EGFP extension
primer_bind 4901 . . . 4921
          /label=RNA target with T7 Promoter Sequence (for IVT)
ORIGIN
     1 tttttttcct gcagcccggg aaggatctgc gatcgctccg gtgcccgtca gtgggcagag 61 cgcacatcgc ccacagtccc cgagaagttg gggggagggg tcggcaattg aacgggtgcc 121 tagagaaggt ggcgcggggt aaactgggaa agtgatgtcg tgtactggct ccgcctttt 181 cccgagggtg ggggagaacc gtatataagt gcagtagtcg ccgtgaacgt tctttttcgc 241 aacgggtttg ccgccagaac acagctgaag cttcgagggg ctcgcatctc tccttcacgc 301 gcccgccgcc ctacctgagg ccgccatcca cgccggttga gtcgcgttct gccgcctccc 361 gcctgtggtg cctcctgaac tgcgtccgcc gtctaggtaa gtttaaagct caggtcgaga 421 ccgggccttt gtccggcgct cccttggagc ctacctagac tcagccggct ctccacgctt 481 tgcctgaccc tgcttgctca actctacgtc tttgtttcgt tttctgttct gcgccgttac 541 agatccaagc tgtgaccggc gcctacgcta gatggtgagc aagggcgagg aggataacat 601 ggccatcatc aaggagttca tgcgcttcaa ggtgcacatg gagggctccg tgaacggcca 661 cgagttcgag atcgagggcg agggcgaggg ccgcccctac gagggcaccc agaccgccaa 721 gctgaaggtg accaagggtg gccccctgcc cttcgcctgg gacatcctgt cccctcagtt 781 catgtacggc tccaaggcct acgtgaagca ccccgccgac atccccgact acttgaagct 841 gtccttcccc gagggcttca gtgggagcg cgtgatgaac ttcgaggacg gcggcgtggt 901 gaccgtgacc caggactcct ccctgcagga cggcgagttc atctacaagg tgaagctgcg 961 cggcaccaac ttcccctccg acggccccgt aatgcagaag aagaccatgg gctgggaggc 1021 ctcctccgag cggatgtacc ccgaggacgg cgccctgaag ggcgagatca gcagaggct 1081 gaagctgaag gacggcggcc actacgacgc tgaggtcaag accacctaca aggccaagaa 1141 gcccgtgcag ctgcccggcg cctacaacgt caacatcaag ttggacatca cctcccacaa 1201 cgaggactac accatcgtgg aacagtacga acgcgccgag ggccgccact ccaccggcgg 1261 catggacgag ctgtacaagt aatccgagct cggtaccaag cttaagttta aaccgctgat 1321 cagcctcgac tgtgccttct agttgccagc catctgttgt ttgcccctcc ccgtgccttt 1381 ccttgaccct ggaaggtgcc actcccactg tcctttccta ataaaatgag gaaattgcat 1441 cgcattgtct gagtaggtgt cattctattc tggggggtgg ggtggggcag gacagcaagg
```

-continued

```
1501 gggaggattg ggaagacaat agcaggcatg ctggggatgc ggtgggctct atgggggatc
1561 cactagttct agagcggccg ccaccgcggt ggagctccag cttttgttcc ctttagtgag
1621 ggttaattgc gcgcttggcg taatcatggt catagctgtt tcctgtgtga aattgttatc
1681 cgctcacaat tccacacaac atacgagccg aagcataaa gtgtaaagcc tggggtgcct
1741 aatgagtgag ctaactcaca ttaattgcgt tgcgctcact gcccgctttc cagtcgggaa
1801 acctgtcgtg ccagctgcat taatgaatcg gccaacgcgc ggggagaggc ggtttgcgta
1861 ttgggcgctc ttccgcttcc tcgctcactg actcgctgcg ctcggtcgtt cggctgcggc
1921 gagcggtatc agctcactca aaggcggtaa tacggttatc cacagaatca ggggataacg
1981 caggaaagaa catgtgagca aaaggccagc aaaaggccag gaaccgtaaa aaggccgcgt
2041 tgctggcgtt tttccatagg ctccgccccc ctgacgagca tcacaaaaat cgacgctcaa
2101 gtcagaggtg gcgaaacccg acaggactat aaagatacca ggcgtttccc cctggaagct
2161 ccctcgtgcg ctctcctgtt ccgaccctgc cgcttaccgg atacctgtcc gcctttctcc
2221 cttcgggaag cgtggcgctt tctcatagct cacgctgtag gtatctcagt tcggtgtagg
2281 tcgttcgctc caagctgggc tgtgtgcacg aaccccccgt tcagcccgac cgctgcgcct
2341 tatccggtaa ctatcgtctt gagtccaacc cggtaagaca cgacttatcg ccactggcag
2401 cagccactgg taacaggatt agcagagcga ggtatgtagg cggtgctaca gagttcttga
2461 agtggtggcc taactacggc tacactagaa ggacagtatt tggtatctgc gctctgctga
2521 agccagttac cttcggaaaa agagttggta gctcttgatc cggcaaacaa accaccgctg
2581 gtagcggtgg tttttttgtt tgcaagcagc agattacgcg cagaaaaaaa ggatctcaag
2641 aagatccttt gatcttttct acggggtctg acgctcagtg gaacgaaaac tcacgttaag
2701 ggattttggt catgagatta tcaaaaagga tcttcaccta gatccttta aattaaaaat
2761 gaagttttaa atcaatctaa agtatatatg agtaaacttg gtctgacagt taccaatgct
2821 taatcagtga ggcacctatc tcagcgatct gtctatttcg ttcatccata gttgcctgac
2881 tccccgtcgt gtagataact acgatacggg agggcttacc atctggcccc agtgctgcaa
2941 tgataccgcg agacccacgc tcaccggctc cagatttatc agcaataaac cagccagccg
3001 gaagggccga gcgcagaagt ggtcctgcaa ctttatccgc ctccatccag tctattaatt
3061 gttgccggga agctagagta agtagttcgc cagttaatag tttgcgcaac gttgttgcca
3121 ttgctacagg catcgtggtg tcacgctcgt cgtttggtat ggcttcattc agctccggtt
3181 cccaacgatc aaggcgagtt acatgatccc ccatgttgtg caaaaaagcg gttagctcct
3241 tcggtcctcc gatcgttgtc agaagtaagt tggccgcagt gttatcactc atggttatgg
3301 cagcactgca taattctctt actgtcatgc catccgtaag atgcttttct gtgactggtg
3361 agtactcaac caagtcattc tgagaatagt gtatgcggcg accgagttgc tcttgcccgg
3421 cgtcaatacg gataatacc gcgccacata gcagaacttt aaaagtgctc atcattggaa
3481 aacgttcttc ggggcgaaaa ctctcaagga tcttaccgct gttgagatcc agttcgatgt
3541 aacccactcg tgcacccaac tgatcttcag catcttttac tttcaccagc gtttctgggt
3601 gagcaaaaac aggaaggcaa aatgccgcaa aaaagggaat aagggcgaca cggaaatgtt
3661 gaatactcat actcttcctt tttcaatatt attgaagcat ttatcagggt tattgtctca
3721 tgagcggata catatttgaa tgtatttaga aaaataaaca aataggggtt ccgcgcacat
3781 ttccccgaaa agtgccacct aaattgtaag cgttaatatt tgttaaaat tcgcgttaaa
3841 ttttttgttaa atcagctcat tttttaacca ataggccgaa atcggcaaaa tcccttataa
```

```
3901 atcaaaagaa tagaccgaga tagggttgag tgttgttcca gtttggaaca agagtccact 3961 attaaagaac gtggactcca acgtcaaagg gcgaaaaacc gtctatcagg gcgatggccc 4021 actacgtgaa ccatcaccct aatcaagttt tttggggtcg aggtgccgta aagcactaaa 4081 tcggaacccT aaagggagcc cccgatttag agcttgacgg ggaaagccgg cgaacgtggc 4141 gagaaaggaa gggaagaaag cgaaaggagc gggcgctagg gcgctggcaa gtgtagcggt 4201 cacgctgcgc gtaaccacca cacccgccgc gcttaatgcg ccgctacagg gcgcgtccca 4261 ttcgccattc aggctgcgca actgttggga agggcgatcg gtgcgggcct cttcgctatt 4321 acgccagctg gcgaaagggg gatgtgctgc aaggcgatta agttgggtaa cgccagggtt 4381 ttcccagtca cgacgttgta aaacgacggc cagtgagcgc gcgtaatacg actcactata 4441 gggcgaattg ggtaccgggc cccccctcga ggtcgacggt atcgataagc ttgatatcgt 4501 gtacaaaaaa gcaggcttta aaggaaccaa ttcagtcgac tggatccggt accaaggtcg 4561 ggcaggaaga gggcctattt cccatgattc cttcatattt gcatatacga tacaaggctg 4621 ttagagagat aattagaatt aatttgactg taaacacaaa gatattagta caaaatacgt 4681 gacgtagaaa gtaataattt cttgggtagt ttgcagtttt aaaattatgt tttaaatgg 4741 actatcatat gcttaccgta acttgaaagt atttcgattt cttggcttta tatatcttgt 4801 ggaaaggacg aaacaccggt tatagtactc tggaaacaga atctactata acaaggcaaa 4861 atgccgtgtt tatctcgtca acttgttggc gagattcatt gtgtcggcca cggaacaggc 4921 a
```

ADAR2_E488Q_dSaCas9_pCDNA3_1 (SEQ ID NO: 48)
LOCUS Exported 9842 bp ds-DNA circular
DEFINITION synthetic circular DNA
SOURCE synthetic DNA construct
ORGANISM recombinant plasmid
REFERENCE 1 (bases 1 to 9842)
FEATURES Location/Qualifiers
source 1 . . . 9842
/organism="recombinant plasmid"
/mol_type="other DNA"
primer_bind complement(213 . . . 234)
/label=pCDNA3_CMV_out_R
enhancer 235 . . . 614
/label=CMV enhancer
/note="human cytomegalovirus immediate early enhancer"
promoter 615 . . . 818
/label=CMV promoter
/note="human cytomegalovirus (CMV) immediate early promoter"
promoter 863 . . . 881
/label=T7 promoter
/note="promoter for bacteriophage T7 RNA polymerase"
primer_bind 927 . . . 985
/label=H1-ADAR-XTEN_F
misc_feature 927 . . . 954
/label=Homology 1_pCDNA3.1
CDS 961 . . . 2100
/codon_start=1
/label=ADARB1(E488Q)_Catalytic Domain
(SEQ ID NO: 40)
/translation="MLADAVSRLVLGKFGDLTDNFSSPHARRKVLAGVVMTTGTDVKDA
KVISVSTGTKCINGEYMSDRGLALNDCHAEIISRRSLLRFLYTQLELYLNNKDDQKRSI
FQKSERGGFRLKENVQFHLYISTSPCGDARIFSPHEPILEEPADRHPNRKARGQLRTKI
ESGQGTIPVRSNASIQTWDGVLQGERLLTMSCSDKIARWNVVGIQGSLLSIFVEPIYFS
SIILGSLYHGDHLSRAMYQRISNIEDLPPLYTLNKPLLSGISNAEARQPGKAPNFSVNW
TVGDSAIEVINATTGKDELGRASRLCKHALYCRWMRVHGKVPSHLLRSKITKPNVYHES
KLAAKEYQAAKARLFTAFIKAGLGAWVEKPTEQDQFSLTP"
primer_bind 961 . . . 982
/label=Primer 4
primer_bind 1111 . . . 1138
/label=Primer 1
primer_bind 1440 . . . 1478
/label=E488Q_Mutagenesis_F
primer_bind complement(1440 . . . 1478)
/label=E488Q_Mutagenesis_R

```
-continued
primer_bind    complement(2080 . . . 2112)
/label=ADAR2DD_GS_R
primer_bind    complement(2080 . . . 2100)
/label=Primer 5
primer_bind    2086 . . . 2132
/label=SaCas9_Gib_F
misc_feature   2101 . . . 2112
/label=GS_linker
misc_feature   2113 . . . 5268
/label=dSaCas9(D10A,N580A)
primer_bind    complement(5245 . . . 5268)
/label=SaCas9_Gib_R
primer_bind    5249 . . . 5289
/label=SaCas9_HA_F
primer_bind    5269 . . . 5290
/label=ADAR2_CD_Inverse_F
CDS            5272 . . . 5298
/codon_start=1
/product="HA (human influenza hemagglutinin) epitope tag"
/label=HA
/translation="YPYDVPDYA" (SEQ ID NO: 51)
primer_bind    complement(5290 . . . 5312)
/label=AXC_NLSout_NESin_R
primer_bind    complement(5290 . . . 5310)
/label=NLS_out_R
CDS            5317 . . . 5337
/codon_start=1
/product="nuclear localization signal of SV40 large T
antigen"
/label=SV40 NLS
/translation="PKKKRKV" (SEQ ID NO: 52)
CDS            5344 . . . 5364
/codon_start=1
/product="nuclear localization signal of SV40 large T
antigen"
/label=SV40 NLS
/translation="PKKKRKV" (SEQ ID NO: 52)
primer_bind    complement(5349 . . . 5408)
/label=XTEN-Cas9-H2_R
primer_bind    complement(5349 . . . 5393)
/label=Primer 7
primer_bind    5363 . . . 5387
/label=NLS_out_NES_full_F
primer_bind    5365 . . . 5387
/label=AXC_NLSout_NESin_F
misc_feature   5374 . . . 5408
/label=Homology 2_pCDNA3.1
primer_bind    5374 . . . 5392
/label=pCDNA3_CMV_out_F
primer_bind    5395 . . . 5418
/label=bGH_HindIII_F
polyA_signal   5442 . . . 5666
/label=bGH poly(A) signal
/note="bovine growth hormone polyadenylation signal"
primer_bind    complement(5648 . . . 5666)
/label=bGH_NotI_R
rep_origin     5712 . . . 6140
/direction=RIGHT
/label=f1 ori
/note="f1 bacteriophage origin of replication; arrow
indicates direction of (+) strand synthesis"
promoter       6154 . . . 6483
/label=SV40 promoter
/note="SV40 enhancer and early promoter"
rep_origin     6334 . . . 6469
/label=SV40 ori
/note="SV40 origin of replication"
CDS            6550 . . . 7344
/codon_start=1
/gene="aph(3')-II (or nptII)"
/product="aminoglycoside phosphotransferase from Tn5"
/label=NeoR/KanR
/note="confers resistance to neomycin, kanamycin, and G418
(Geneticin(R))"
                                                    (SEQ ID NO: 53)
/translation="MIEQDGLHAGSPAAWVERLFGYDWAQQTIGCSDAAVFRLSAQGRP
VLFVKTDLSGALNELQDEAARLSWLATTGVPCAAVLDVVTEAGRDWLLLGEVPGQDLLS
SHLAPAEKVSIMADAMRRLHTLDPATCPFDHQAKHRIERARTRMEAGLVDQDDLDEEHQ
GLAPAELFARLKARMPDGEDLVVTHGDACLPNIMVENGRFSGFIDCGRLGVADRYQDIA
LATRDIAEELGGEWADRFLVLYGIAAPDSQRIAFYRLLDEFF"
polyA_signal   7518 . . . 7639
```

```
/label=SV40 poly(A) signal
/note="SV40 polyadenylation signal"
primer bind complement(7688 . . . 7704)
/label=M13 rev
/note="common sequencing primer, one of multiple similar
variants"
protein_bind 7712 . . . 7728
/label=lac operator
/bound_moiety="lac repressor encoded by lacI"
/note="The lac repressor binds to the lac operator to
inhibit transcription in E. coli. This inhibition can be
relieved by adding lactose or
isopropyl-beta-D-thiogalactopyranoside (IPTG)."
promoter complement(7736 . . . 7766)
/label=lac promoter
/note="promoter for the E. coli lac operon"
protein_bind 7781 . . . 7802
/label=CAP binding site
/bound_moiety="E. coli catabolite activator protein"
/note="CAP binding activates transcription in the presence
of cAMP."
rep_origin complement(8090 . . . 8675)
/direction=LEFT
/label=ori
/note="high-copy-number ColE1/pMB1/pBR322/pUC origin of
replication"
CDS complement(8846 . . . 9706)
/codon_start=1
/gene="bla"
/product="beta-lactamase"
/label=AmpR
/note="confers resistance to ampicillin, carbenicillin, and
related antibiotics"
                                                    (SEQ ID NO: 54)
/translation="MSIQHFRVALIPFFAAFCLPVFAHPETLVKVKDAEDQLGARVGYI
ELDLNSGKILESFRPEERFPMMSTFKVLLCGAVLSRIDAGQEQLGRRIHYSQNDLVEYS
PVTEKHLTDGMTVRELCSAAITMSDNTAANLLLTTIGGPKELTAFLHNMGDHVTRLDRW
EPELNEAIPNDERDTTMPVAMATTLRKLLTGELLTLASRQQLIDWMEADKVAGPLLRSA
LPAGWFIADKSGAGERGSRGIIAALGPDGKPSRIVVIYTTGSQATMDERNRQIAEIGAS
LIKHW"
promoter complement(9707 . . . 9811)
/gene="bla"
/label=AmpR promoter
ORIGIN
    1 gacggatcgg gagatctccc gatcccctat ggtgcactct cagtacaatc tgctctgatg
   61 ccgcatagtt aagccagtat ctgctccctg cttgtgtgtt ggaggtcgct gagtagtgcg
  121 cgagcaaaat ttaagctaca acaaggcaag gcttgaccga caattgcatg aagaatctgc
  181 ttagggttag gcgttttgcg ctgcttcgcg atgtacgggc cagatatacg cgttgacatt
  241 gattattgac tagttattaa tagtaatcaa ttacggggtc attagttcat agcccatata
  301 tggagttccg cgttacataa cttacggtaa atggcccgcc tggctgaccg cccaacgacc
  361 cccgcccatt gacgtcaata atgacgtatg ttcccatagt aacgccaata gggactttcc
  421 attgacgtca atgggtggag tatttacggt aaactgccca cttggcagta catcaagtgt
  481 atcatatgcc aagtacgccc cctattgacg tcaatgacgg taaatggccc gcctggcatt
  541 atgcccagta catgacctta tgggactttc ctacttggca gtacatctac gtattagtca
  601 tcgctattac catggtgatg cggttttggc agtacatcaa tgggcgtgga tagcggtttg
  661 actcacgggg atttccaagt ctccacccca ttgacgtcaa tgggagtttg ttttggcacc
  721 aaaatcaacg ggactttcca aaatgtcgta acaactccgc cccattgacg caaatgggcg
  781 gtaggcgtgt acggtgggag gtctatataa gcagagctct ctggctaact agagaaccca
  841 ctgcttactg gcttatcgaa attaatacga ctcactatag ggagacccaa gctggctagc
  901 gtttaaacgg gccctctaga ctcgagcggc cgccactgtg ctggatatct gcagagaacc
  961 atgttagctg acgctgtctc acgcctggtc ctgggtaagt ttggtgacct gaccgacaac
 1021 ttctcctccc ctcacgctcg cagaaaagtg ctggctggag tcgtcatgac aacaggcaca
 1081 gatgttaaag atgccaaggt gataagtgtt tctacaggaa caaaatgtat taatggtgaa
```

-continued

```
1141 tacatgagtg atcgtggcct tgcattaaat gactgccatg cagaaataat atctcggaga
1201 tccttgctca gatttcttta tacacaactt gagctttact taaataacaa agatgatcaa
1261 aaaagatcca tctttcagaa atcagagcga ggggggttta ggctgaagga gaatgtccag
1321 tttcatctgt acatcagcac ctctccctgt ggagatgcca gaatcttctc accacatgag
1381 ccaatcctgg aagaaccagc agatagacac ccaaatcgta aagcaagagg acagctacgg
1441 accaaaatag agtctggtca ggggacgatt ccagtgcgct ccaatgcgag catccaaacg
1501 tgggacgggg tgctgcaagg ggagcggctg ctcaccatgt cctgcagtga caagattgca
1561 cgctggaacg tggtgggcat ccagggatcc ctgctcagca ttttcgtgga gcccatttac
1621 ttctcgagca tcatcctggg cagcctttac cacggggacc acctttccag ggccatgtac
1681 cagcggatct ccaacataga ggacctgcca cctctctaca ccctcaacaa gcctttgctc
1741 agtggcatca gcaatgcaga agcacggcag ccagggaagg cccccaactt cagtgtcaac
1801 tggacggtag gcgactccgc tattgaggtc atcaacgcca cgactgggaa ggatgagctg
1861 ggccgcgcgt cccgcctgtg taagcacgcg ttgtactgtc gctggatgcg tgtgcacggc
1921 aaggttccct cccacttact acgctccaag attaccaagc caacgtgta ccatgagtcc
1981 aagctggcgg caaaggagta ccaggccgcc aaggcgcgtc tgttcacagc cttcatcaag
2041 gcggggctgg gggcctgggt ggagaagccc accgagcagg accagttctc actcacgccc
2101 ggatccggat ccaagcggaa ctacatcctg gcctggcca tcggcatcac cagcgtgggc
2161 tacggcatca tcgactacga gacacgggac gtgatcgatg ccggcgtgcg gctgttcaaa
2221 gaggccaacg tggaaaacaa cgagggcagg cggagcaaga gaggcgccag aaggctgaag
2281 cggcggaggc ggcatagaat ccagagagtg aagaagctgc tgttcgacta caacctgctg
2341 accgaccaca gcgagctgag cggcatcaac ccctacgagg ccagagtgaa gggcctgagc
2401 cagaagctga gcgaggaaga gttctctgcc gccctgctgc acctggccaa gagaagaggc
2461 gtgcacaacg tgaacgaggt ggaagaggac accggcaacg agctgtccac caaagagcag
2521 atcagccgga acagcaaggc cctggaagag aaatacgtgg ccgaactgca gctggaacgg
2581 ctgaagaaag acggcgaagt gcggggcagc atcaacagat tcaagaccag cgactacgtg
2641 aaagaagcca acagctgct gaaggtgcag aaggcctacc accagctgga ccagagcttc
2701 atcgacacct catcgacct gctggaaacc cggcggacct actatgaggg acctggcgag
2761 ggcagcccct tcggctggaa ggacatcaaa gaatggtacg agatgctgat gggccactgc
2821 acctacttcc ccgaggaact gcggagcgtg aagtacgcct acaacgccga cctgtacaac
2881 gccctgaacg acctgaacaa tctcgtgatc accagggacg agaacgagaa gctggaatat
2941 tacgagaagt tccagatcat cgagaacgtg ttcaagcaga agaagaagcc caccctgaag
3001 cagatcgcca agaaatcct cgtgaacgaa gaggatatta agggctacag agtgaccagc
3061 accggcaagc cgagttcac caacctgaag gtgtaccacg acatcaagga cattaccgcc
3121 cggaaagaga ttattgagaa cgccgagctg ctggatcaga ttgccaagat cctgaccatc
3181 taccagagca gcgaggacat ccaggaagaa ctgaccaatc tgaactccga gctgacccag
3241 gaagagatcg agcagatctc taatctgaag ggctataccg gcacccacaa cctgagcctg
3301 aaggccatca acctgatcct ggacgagctg tggcacacca cgacaaccca gatcgctatc
3361 ttcaaccggc tgaagctggt gcccaagaag gtggacctgt cccagcagaa agagatcccc
3421 accaccctgg tggacgactt catcctgagc cccgtcgtga agagaagctt catccagagc
3481 atcaaagtga tcaacgccat catcaagaag tacggcctgc ccaacgacat cattatcgag
```

-continued

```
3541 ctggcccgcg agaagaactc caaggacgcc cagaaaatga tcaacgagat gcagaagcgg
3601 aaccggcaga ccaacgagcg gatcgaggaa atcatccgga ccaccggcaa agagaacgcc
3661 aagtacctga tcgagaagat caagctgcac gacatgcagg aaggcaagtg cctgtacagc
3721 ctggaagcca tccctctgga agatctgctg aacaacccct tcaactatga ggtggaccac
3781 atcatcccca gaagcgtgtc cttcgacaac agcttcaaca caaggtgct cgtgaagcag
3841 gaagaagcca gcaagaaggg caaccggacc ccattccagt acctgagcag cagcgacagc
3901 aagatcagct acgaaacctt caagaagcac atcctgaatc tggccaaggg caagggcaga
3961 atcagcaaga ccaagaaaga gtatctgctg gaagaacggg acatcaacag gttctccgtg
4021 cagaaagact tcatcaaccg gaacctggtg gataccagat acgccaccag aggcctgatg
4081 aacctgctgc ggagctactt cagagtgaac aacctggacg tgaaagtgaa gtccatcaat
4141 ggcggcttca ccagctttct gcggcggaag tggaagttta agaaagagcg gaacaagggg
4201 tacaagcacc acgccgagga cgccctgatc attgccaacg ccgatttcat cttcaaagag
4261 tggaagaaac tggacaaggc caaaaaagtg atggaaaacc agatgttcga ggaaagcag
4321 gccgagagca tgcccgagat cgaaaccgag caggagtaca agagatcttt catcaccccc
4381 caccagatca agcacattaa ggacttcaag gactacaagt acagccaccg ggtggacaag
4441 aagcctaata gagagctgat taacgacacc ctgtactcca cccggaagga cgacaagggc
4501 aacaccctga tcgtgaacaa tctgaacggc ctgtacgaca aggacaatga caagctgaaa
4561 aagctgatca acaagagccc cgaaaagctg ctgatgtacc accacgaccc ccagacctac
4621 cagaaactga agctgattat ggaacagtac ggcgacgaga gaatcccct gtacaagtac
4681 tacgaggaaa ccgggaacta cctgaccaag tactccaaaa aggacaacgg ccccgtgatc
4741 aagaagatta agtattacgg caacaaactg aacgcccatc tggacatcac cgacgactac
4801 cccaacagca gaaacaaggt cgtgaagctg tccctgaagc cctacagatt cgacgtgtac
4861 ctggacaatg gcgtgtacaa gttcgtgacc gtgaagaatc tggatgtgat caaaaaagaa
4921 aactactacg aagtgaatag caagtgctat gaggaagcta agaagctgaa gaagatcagc
4981 aaccaggccg agtttatcgc ctccttctac aacaacgatc tgatcaagat caacggcgag
5041 ctgtatagag tgatcggcgt gaacaacgac ctgctgaacc ggatcgaagt gaacatgatc
5101 gacatcacct accgcgagta cctggaaaac atgaacgaca gaggccccc caggatcatt
5161 aagacaatcg cctccaagac ccagagcatt aagaagtaca gcacagacat tctgggcaac
5221 ctgtatgaag tgaaatctaa gaagcaccct cagatcatca aaaagggcgc ctatcctat
5281 gacgtgcccg attatgccag cctgggcagc ggctcccca agaaaaaacg caaggtggaa
5341 gatcctaaga aaaagcggaa agtggacgtg taaccaccac actggactag tggatccgag
5401 ctcggtacca agcttaagtt taaaccgctg atcagcctcg actgtgcctt ctagttgcca
5461 gccatctgtt gtttgcccct cccccgtgcc ttccttgacc ctggaaggtg ccactcccac
5521 tgtcctttcc taataaaatg aggaaattgc atcgcattgt ctgagtaggt gtcattctat
5581 tctgggggt ggggtggggc aggacagcaa ggggaggat tgggaagaca atagcaggca
5641 tgctggggat gcggtgggct ctatggcttc tgaggcggaa agaaccagct ggggctctag
5701 ggggtatccc cacgcgccct gtagcggcgc attaagcgcg gcgggtgtgg tggttacgcg
5761 cagcgtgacc gctacacttg ccagcgccct agcgcccgct cctttcgctt tcttcccttc
5821 ctttctcgcc acgttcgccg gctttccccg tcaagctcta aatcggggc tccctttagg
5881 gttccgattt agtgctttac ggcacctcga ccccaaaaaa cttgattagg gtgatggttc
5941 acgtagtggg ccatcgccct gatagacggt ttttcgccct ttgacgttgg agtccacgtt
```

-continued

```
6001 ctttaatagt ggactcttgt tccaaactgg aacaacactc aaccctatct cggtctattc
6061 ttttgattta taagggattt tgccgatttc ggcctattgg ttaaaaaatg agctgattta
6121 acaaaaattt aacgcgaatt aattctgtgg aatgtgtgtc agttagggtg tggaaagtcc
6181 ccaggctccc cagcaggcag aagtatgcaa agcatgcatc tcaattagtc agcaaccagg
6241 tgtggaaagt ccccaggctc cccagcaggc agaagtatgc aaagcatgca tctcaattag
6301 tcagcaacca tagtcccgcc cctaactccg cccatcccgc ccctaactcc gcccagttcc
6361 gcccattctc cgccccatgg ctgactaatt ttttttattt atgcagaggc cgaggccgcc
6421 tctgcctctg agctattcca gaagtagtga ggaggctttt ttggaggcct aggcttttgc
6481 aaaaagctcc cgggagcttg tatatccatt ttcggatctg atcaagagac aggatgagga
6541 tcgtttcgca tgattgaaca agatggattg cacgcaggtt ctccggccgc ttgggtggag
6601 aggctattcg gctatgactg ggcacaacag acaatcggct gctctgatgc cgccgtgttc
6661 cggctgtcag cgcaggggcg cccggttctt tttgtcaaga ccgacctgtc cggtgccctg
6721 aatgaactgc aggacgaggc agcgcggcta tcgtggctgg ccacgacggg cgttccttgc
6781 gcagctgtgc tcgacgttgt cactgaagcg ggaagggact ggctgctatt gggcgaagtg
6841 ccggggcagg atctcctgtc atctcacctt gctcctgccg agaaagtatc catcatggct
6901 gatgcaatgc ggcggctgca tacgcttgat ccggctacct gcccattcga ccaccaagcg
6961 aaacatcgca tcgagcgagc acgtactcgg atggaagccg gtcttgtcga tcaggatgat
7021 ctggacgaag agcatcaggg gctcgcgcca gccgaactgt tcgccaggct caaggcgcgc
7081 atgcccgacg gcgaggatct cgtcgtgacc catggcgatg cctgcttgcc gaatatcatg
7141 gtggaaaatg gccgcttttc tggattcatc gactgtggcc ggctgggtgt ggcggaccgc
7201 tatcaggaca tagcgttggc tacccgtgat attgctgaag agcttggcgg cgaatgggct
7261 gaccgcttcc tcgtgcttta cggtatcgcc gctcccgatt cgcagcgcat cgccttctat
7321 cgccttcttg acgagttctt ctgagcggga ctctggggtt cgaaatgacc gaccaagcga
7381 cgcccaacct gccatcacga gatttcgatt ccaccgccgc cttctatgaa aggttgggct
7441 tcggaatcgt tttccgggac gccggctgga tgatcctcca gcgcgggat ctcatgctgg
7501 agttcttcgc ccaccccaac ttgtttattg cagcttataa tggttacaaa taaagcaata
7561 gcatcacaaa tttcacaaat aaagcatttt tttcactgca ttctagttgt ggtttgtcca
7621 aactcatcaa tgtatcttat catgtctgta taccgtcgac ctctagctag agcttggcgt
7681 aatcatggtc atagctgttt cctgtgtgaa attgttatcc gctcacaatt ccacacaaca
7741 tacgagccgg aagcataaag tgtaaagcct ggggtgccta atgagtgagc taactcacat
7801 taattgcgtt gcgctcactg cccgctttcc agtcgggaaa cctgtcgtgc cagctgcatt
7861 aatgaatcgg ccaacgcgcg gggagaggcg gtttgcgtat tgggcgctct tccgcttcct
7921 cgctcactga ctcgctgcgc tcggtcgttc ggctgcggcg agcggtatca gctcactcaa
7981 aggcggtaat acggttatcc acagaatcag gggataacgc aggaaagaac atgtgagcaa
8041 aaggccagca aaaggccagg aaccgtaaaa aggccgcgtt gctggcgttt ttccataggc
8101 tccgccccc tgacgagcat cacaaaaatc gacgctcaag tcagaggtgg cgaaacccga
8161 caggactata aagataccag gcgtttcccc ctggaagctc cctcgtgcgc tctcctgttc
8221 cgaccctgcc gcttaccgga tacctgtccg cctttctccc ttcgggaagc gtggcgcttt
8281 ctcatagctc acgctgtagg tatctcagtt cggtgtaggt cgttcgctcc aagctgggct
8341 gtgtgcacga accccccgtt cagcccgacc gctgcgcctt atccggtaac tatcgtcttg
```

```
8401 agtccaaccc ggtaagacac gacttatcgc cactggcagc agccactggt aacaggatta 8461 gcagagcgag gtatgtaggc ggtgctacag agttcttgaa gtggtggcct aactacggct 8521 acactagaag aacagtattt ggtatctgcg ctctgctgaa gccagttacc ttcggaaaaa 8581 gagttggtag ctcttgatcc ggcaaacaaa ccaccgctgg tagcggtttt tttgtttgca 8641 agcagcagat tacgcgcaga aaaaaggat ctcaagaaga tcctttgatc ttttctacgg 8701 ggtctgacgc tcagtggaac gaaaactcac gttaaggat tttggtcatg agattatcaa 8761 aaaggatctt cacctagatc cttttaaatt aaaaatgaag ttttaaatca atctaaagta 8821 tatatgagta aacttggtct gacagttacc aatgcttaat cagtgaggca cctatctcag 8881 cgatctgtct atttcgttca tccatagttg cctgactccc cgtcgtgtag ataactacga 8941 tacgggaggg cttaccatct ggccccagtg ctgcaatgat accgcgagac ccacgctcac 9001 cggctccaga tttatcagca ataaaccagc cagccggaag ggccgagcgc agaagtggtc 9061 ctgcaacttt atccgcctcc atccagtcta ttaattgttg ccgggaagct agagtaagta 9121 gttcgccagt taatagtttg cgcaacgttg ttgccattgc tacaggcatc gtggtgtcac 9181 gctcgtcgtt tggtatggct tcattcagct ccggttccca acgatcaagg cgagttacat 9241 gatcccccat gttgtgcaaa aaagcggtta gctccttcgg tcctccgatc gttgtcagaa 9301 gtaagttggc cgcagtgtta tcactcatgg ttatggcagc actgcataat tctcttactg 9361 tcatgccatc cgtaagatgc ttttctgtga ctggtgagta ctcaaccaag tcattctgag 9421 aatagtgtat gcggcgaccg agttgctctt gcccggcgtc aatacgggat aataccgcgc 9481 cacatagcag aactttaaaa gtgctcatca ttggaaaacg ttcttcgggg cgaaaactct 9541 caaggatctt accgctgttg agatccagtt cgatgtaacc cactcgtgca cccaactgat 9601 cttcagcatc ttttactttc accagcgttt ctgggtgagc aaaaacagga aggcaaaatg 9661 ccgcaaaaaa gggaataagg gcgacacgga aatgttgaat actcatactc ttccttttc 9721 aatattattg aagcatttat cagggttatt gtctcatgag cggatacata tttgaatgta 9781 tttagaaaaa taaacaaata ggggttccgc gcacatttcc ccgaaaagtg ccacctgacg 9841 tc
```

LCV2_puro_CFTR_51_1217_gibson (SEQ ID NO: 35)
LOCUS Exported 14250 bp ds-DNA circular
DEFINITION synthetic circular DNA
KEYWORDS LCV2_puro_CFTR_51_1217_gibson
SOURCE synthetic DNA construct
ORGANISM recombinant plasmid
REFERENCE 1 (bases 1 to 14250)
FEATURES Location/Qualifiers
source 1 . . . 14250
/organism="recombinant plasmid"
/mol_type="other DNA"
misc_feature 1 . . . 33
/note="NLS"
misc_feature 34 . . . 57
/note="FLAG"
misc_feature 58 . . . 123
/note="P2A"
CDS 124 . . . 720
/note="Puro"
misc_binding 736 . . . 1324
/note="WPRE"
misc_feature 736 . . . 755
/note="mCherry_PCR_tail"
LTR 1395 . . . 1630
/note="3'LTR"
rep_origin 4079 . . . 4304
/note="ColE1"
misc_feature 4516 . . . 5322
/note="AmpR"
LTR 6472 . . . 6660
/note="5' LTR (R and U5 portions; U3 was replaced by the

```
                                CMV promoter)"
misc_feature    6711 . . . 6848
                /note="Psi"
misc_feature    6768 . . . 6771
                /note="SD; splice donor"
misc_feature    6815 . . . 7179
                /note="gag"
misc_feature    7325 . . . 7566
                /note="RRE"
misc_feature    8084 . . . 8201
                /note="CPPT; central polypurine tract"
promoter        8252 . . . 8500
                /note="Human U6"
misc_feature    8522 . . . 8607
                /note="sgRNA scaffold"
misc_feature    8608 . . . 8613
                /note="Linker"
promoter        8665 . . . 8920
                /note="EFS-NS"
CDS             8944 . . . 10083
                /codon_start=1
                /note="ADARB1_Catalytic Domain" (SEQ ID NO: 36)
                /translation="MLADAVSRLVLGKFGDLTDNFSSPHARRKVLAGVVMTTGTDVKDAKVIS
                VSTGTKCINGEYMSDRGLALNDCHAEIISRRSLLRFLYTQLELYLNNKDDQKRSIFQKSE
                RGGFRLKENVQFHLYISTSPCGDARIFSPHEPILEEPADRHPNRKARGQLRTKIESGQGTIP
                VRSNASIQTWDGVLQGERLLTMSCSDKIARWNVVGIQGSLLSIFVEPIYFSSIILGSLYHG
                DHLSRAMYQRISNIEDLPPLYTLNKPLLSGISNAEARQPGKAPNFSVNWTVGDSAIEVIN
                ATTGKDELGRASRLCKHALYCRWMRVHGKVPSHLLRSKITKPNVYHESKLAAKEYQA
                AKARLFTAFIKAGLGAWVEKPTEQDQFSLTP"
misc_feature    8944 . . . 8946
                /note="hSpCas9"
CDS             10084 . . . 10131
                /codon_start=1
                /note="XTEN"
                /translation="SGSETPGTSESATPES" (SEQ ID NO: 37)
CDS             10132 . . . 14235
                /codon_start=1
                /product="catalytically dead mutant of the Cas9
                endonuclease from the Streptococcus pyogenes Type II
                CRISPR/Cas system"
                /note="dCas9"
                /note="RNA-guided DNA-binding protein that lacks
                endonuclease activity due to the D10A mutation in the RuvC
                catalytic domain and the H840A mutation in the HNH
                catalytic domain" (SEQ ID NO: 38)
                /translation="MDKKYSIGLAIGTNSVGWAVITDEYKVPSKKFKVLGNTDRHSIKKNLIGAL
                LFDSGETAEATRLKRTARRRYTRRKNRICYLQEIFSNEMAKVDDSFFHRLEESFLVEEDK
                KHERHPIFGNIVDEVAYHEKYPTIYHLRKKLVDSTDKADLRLIYLALAHMIKFRGHFLIE
                GDLNPDNSDVDKLFIQLVQTYNQLFEENPINASGVDAKAILSARLSKSRRLENLIAQLPG
                EKKNGLFGNLIALSLGLTPNFKSNFDLAEDAKLQLSKDTYDDDLDNLLAQIGDQYADLF
                LAAKNLSDAILLSDILRVNTEITKAPLSASMIKRYDEHHQDLTLLKALVRQQLPEKYKEIF
                FDQSKNGYAGYIDGGASQEEFYKFIKPILEKMDGTEELLVKLNREDLLRKQRTFDNGSIP
                HQIHLGELHAILRRQEDFYPFLKDNREKIEKILTFRIPYYVGPLARGNSRFAWMTRKSEET
                ITPWNFEEVVDKGASAQSFIERMTNFDKNLPNEKVLPKHSLLYEYFTVYNELTKVKYVT
                EGMRKPAFLSGEQKKAIVDLLFKTNRKVTVKQLKEDYFKKIECFDSVEISGVEDRFNAS
                LGTYHDLLKIIKDKDFLDNEENEDILEDIVLTLTLFEDREMIEERLKTYAHLFDDKVMKQ
                LKRRRYTGWGRLSRKLINGIRDKQSGKTILDFLKSDGFANRNFMQLIHDDSLTFKEDIQK
                AQVSGQGDSLHEHIANLAGSPAIKKGILQTVKVVDELVKVMGRHKPENIVIEMARENQT
                TQKGQKNSRERMKRIEEGIKELGSQILKEHPVENTQLQNEKLYLYYLQNGRDMYVDQE
                LDINRLSDYDVDAIVPQSFLKDDSIDNKVLTRSDKNRGKSDNVPSEEVVKKMKNYWRQ
                LLNAKLITQRKFDNLTKAERGGLSELDKAGFIKRQLVETRQITKHVAQILDSRMNTKYD
                ENDKLIREVKVITLKSKLVSDFRKDFQFYKVREINNYHHAHDAYLNAVVGTALIKKYPK
                LESEFVYGDYKVYDVRKMIAKSEQEIGKATAKYFFYSNIMNFFKTEITLANGEIRKRPLIE
                TNGETGEIVWDKGRDFATVRKVLSMPQVNIVKKTEVQTGGFSKESILPKRNSDKLIARK
                KDWDPKKYGGFDSPTVAYSVLVVAKVEKGKSKKLKSVKELLGITIMERSSFEKNPIDFL
                EAKGYKEVKKDLIIKLPKYSLFELENGRKRMLASAGELQKGNELALPSKYVNFLYLASH
                YEKLKGSPEDNEQKQLFVEQHKHYLDEIIEQISEFSKRVILADANLDKVLSAYNKHRDKP
                IREQAENIIHLFTLTNLGAPAAFKYFDTTIDRKRYTSTKEVLDATLIHQSITGLYETRIDLS
                QLGGD"
ORIGIN (SEQ ID NO: 35)
    1 acaaagaagg ctggacaggc taagaagaag aaagattaca aagacgatga cgataaggga 61 tccggcgcaa caaacttctc tctgctgaaa caagccggag atgtcgaaga gaatcctgga 121 ccgaccgagt acaagcccac ggtgcgcctc gccaccgcg acgacgtccc cagggccgta 181 cgcacccteg ccgccgcgtt cgccgactac cccgccacgc gccacaccgt cgatccggac 241 cgccacatcg agcgggtcac cgagctgcaa gaactcttcc tcacgcgcgt cgggctcgac 301 atcggcaagg tgtgggtcgc ggacgacggc gccgcggtgg cggtctggac cacgccgag
```

-continued

```
 361 agcgtcgaag cggggggcggt gttcgccgag atcggcccgc gcatggccga gttgagcggt
 421 tcccggctgg ccgcgcagca acagatggaa ggcctcctgg cgccgcaccg gcccaaggag
 481 cccgcgtggt tcctggccac cgtcggagtc tcgcccgacc accagggcaa gggtctgggc
 541 agcgccgtcg tgctccccgg agtggaggcg gccgagcgcg ccggggtgcc cgccttcctg
 601 gagacctccg cgccccgcaa cctccccttc tacgagcggc tcggcttcac cgtcaccgcc
 661 gacgtcgagg tgcccgaagg accgcgcacc tggtgcatga cccgcaagcc cggtgcctga
 721 acgcgttaag tcgacaatca acctctggat tacaaaattt gtgaaagatt gactggtatt
 781 cttaactatg ttgctccttt tacgctatgt ggatacgctg ctttaatgcc tttgtatcat
 841 gctattgctt cccgtatggc tttcattttc tcctccttgt ataaatcctg gttgctgtct
 901 ctttatgagg agttgtggcc cgttgtcagg caacgtggcg tggtgtgcac tgtgtttgct
 961 gacgcaaccc ccactggttg gggcattgcc accacctgtc agctcctttc cgggactttc
1021 gctttcccccc tccctattgc cacggcggaa ctcatcgccg cctgccttgc ccgctgctgg
1081 acaggggctc ggctgttggg cactgacaat tccgtggtgt tgtcggggaa atcatcgtcc
1141 tttccttggc tgctcgcctg tgttgccacc tggattctgc gcgggacgtc cttctgctac
1201 gtcccttcgg ccctcaatcc agcggaccta ccttcccgcg gcctgctgcc ggctctgcgg
1261 cctcttccgc gtcttcgcct tcgccctcag acgagtcgga tctcccttgg gccgcctcc
1321 ccgcgtcgac tttaagacca atgacttaca aggcagctgt agatcttagc cactttttaa
1381 aagaaaaggg gggactggaa gggctaattc actcccaacg aagacaagat ctgcttttg
1441 cttgtactgg gtctctctgg ttagaccaga tctgagcctg ggagctctct ggctaactag
1501 ggaacccact gcttaagcct caataaagct tgccttgagt gcttcaagta gtgtgtgccc
1561 gtctgttgtg tgactctggt aactagagat ccctcagacc cttttagtca gtgtggaaaa
1621 tctctagcag ggcccgttta aacccgctga tcagcctcga ctgtgccttc tagttgccag
1681 ccatctgttg tttgccctc ccccgtgcct tccttgaccc tggaaggtgc cactcccact
1741 gtcctttcct aataaaatga ggaaattgca tcgcattgtc tgagtaggtg tcattctatt
1801 ctggggggtg gggtggggca ggacagcaag ggggaggatt gggaagacaa tagcaggcat
1861 gctggggatg cggtgggctc tatggcttct gaggcggaaa gaaccagctg ggctctagg
1921 gggtatcccc acgcgccctg tagcggcgca ttaagcgcgg cgggtgtggt ggttacgcgc
1981 agcgtgaccg ctacacttgc cagcgcccta gcgcccgctc cttttcgcttt cttcccttcc
2041 tttctcgcca cgttcgccgg ctttccccgt caagctctaa atcgggggct cccttaggg
2101 ttccgattta gtgctttacg gcacctcgac cccaaaaaac ttgattaggg tgatggttca
2161 cgtagtgggc catcgccctg atagacggtt tttcgccctt tgacgttgga gtccacgttc
2221 tttaatagtg gactcttgtt ccaaactgga acaacactca accctatctc ggtctattct
2281 tttgatttat aagggatttt gccgatttcg gcctattggt taaaaaatga gctgatttaa
2341 caaaaattta acgcgaatta attctgtgga atgtgtgtca gttagggtgt ggaaagtccc
2401 caggctcccc agcaggcaga agtatgcaaa gcatgcatct caattagtca gcaaccaggt
2461 gtggaaagtc cccaggctcc ccagcaggca gaagtatgca aagcatgcat ctcaattagt
2521 cagcaaccat agtcccgccc ctaactccgc ccatcccgcc cctaactccg cccagttccg
2581 cccattctcc gccccatggc tgactaattt tttttattta tgcagaggcc gaggccgcct
2641 ctgcctctga gctattccag aagtagtgag gaggcttttt tggaggccta ggcttttgca
2701 aaaagctccc gggagcttgt atatccattt tcggatctga tcagcacgtg ttgacaatta
```

-continued

```
2761 atcatcggca tagtatatcg gcatagtata atacgacaag gtgaggaact aaaccatggc 2821 caagttgacc agtgccgttc cggtgctcac cgcgcgcgac gtcgccggag cggtcgagtt 2881 ctggaccgac cggctcgggt tctcccggga cttcgtggag gacgacttcg ccggtgtggt 2941 ccgggacgac gtgaccctgt tcatcagcgc ggtccaggac caggtggtgc cggacaacac 3001 cctggcctgg gtgtgggtgc gcggcctgga cgagctgtac gccgagtggt cggaggtcgt 3061 gtccacgaac ttccgggacg cctccggggcc ggccatgacc gagatcggcg agcagccgtg 3121 ggggcgggag ttcgccctgc gcgacccggc cggcaactgc gtgcacttcg tggccgagga 3181 gcaggactga cacgtgctac gagatttcga ttccaccgcc gccttctatg aaaggttggg 3241 cttcggaatc gttttccggg acgccggctg gatgatcctc cagcgcgggg atctcatgct 3301 ggagttcttc gcccacccca acttgtttat tgcagcttat aatggttaca aataaagcaa 3361 tagcatcaca aatttcacaa ataaagcatt tttttcactg cattctagtt gtggtttgtc 3421 caaactcatc aatgtatctt atcatgtctg tataccgtcg acctctagct agagcttggc 3481 gtaatcatgg tcatagctgt ttcctgtgtg aaattgttat ccgctcacaa ttccacacaa 3541 catacgagcc ggaagcataa agtgtaaagc ctggggtgcc taatgagtga gctaactcac 3601 attaattgcg ttgcgctcac tgcccgcttt ccagtcggga aacctgtcgt gccagctgca 3661 ttaatgaatc ggccaacgcg cggggagagg cggtttgcgt attgggcgct cttccgcttc 3721 ctcgctcact gactcgctgc gctcggtcgt tcggctgcgg cgagcggtat cagctcactc 3781 aaaggcggta atacggttat ccacagaatc aggggataac gcaggaaaga acatgtgagc 3841 aaaaggccag caaaaggcca ggaaccgtaa aaaggccgcg ttgctggcgt ttttccatag 3901 gctccgcccc cctgacgagc atcacaaaaa tcgacgctca agtcagaggt ggcgaaaccc 3961 gacaggacta taaagatacc aggcgtttcc ccctggaagc tccctcgtgc gctctcctgt 4021 tccgaccctg ccgcttaccg gatacctgtc cgcctttctc ccttcgggaa gcgtggcgct 4081 ttctcatagc tcacgctgta ggtatctcag ttcggtgtag gtcgttcgct ccaagctggg 4141 ctgtgtgcac gaaccccccg ttcagcccga ccgctgcgcc ttatccggta actatcgtct 4201 tgagtccaac ccggtaagac acgacttatc gccactggca gcagccactg gtaacaggat 4261 tagcagagcg aggtatgtag gcggtgctac agagttcttg aagtggtggc ctaactacgg 4321 ctacactaga agaacagtat ttggtatctg cgctctgctg aagccagtta ccttcggaaa 4381 aagagttggt agctcttgat ccggcaaaca aaccaccgct ggtagcggtg gtttttttgt 4441 ttgcaagcag cagattacgc gcagaaaaaa aggatctcaa gaagatcctt tgatcttttc 4501 tacggggtct gacgctcagt ggaacgaaaa ctcacgttaa gggattttgg tcatgagatt 4561 atcaaaaagg atcttcacct agatcctttt aaattaaaaa tgaagtttta atcaatcta 4621 aagtatatat gagtaaactt ggtctgacag ttaccaatgc ttaatcagtg aggcacctat 4681 ctcagcgatc tgtctatttc gttcatccat agttgcctga ctccccgtcg tgtagataac 4741 tacgatacgg gagggcttac catctggccc cagtgctgca atgataccgc gagacccacg 4801 ctcaccggct ccagatttat cagcaataaa ccagccagcc ggaagggccg agcgcagaag 4861 tggtcctgca actttatccg cctccatcca gtctattaat tgttgccggg aagctagagt 4921 aagtagttcg ccagttaata gtttgcgcaa cgttgttgcc attgctacag gcatcgtggt 4981 gtcacgctcg tcgtttggta tggcttcatt cagctccggt tcccaacgat caaggcgagt 5041 tacatgatcc cccatgttgt gcaaaaaagc ggttagctcc ttcggtcctc cgatcgttgt 5101 cagaagtaag ttggccgcag tgttatcact catggttatg gcagcactgc ataattctct 5161 tactgtcatg ccatccgtaa gatgcttttc tgtgactggt gagtactcaa ccaagtcatt
```

```
5221 ctgagaatag tgtatgcggc gaccgagttg ctcttgcccg gcgtcaatac gggataatac
5281 cgcgccacat agcagaactt taaaagtgct catcattgga aaacgttctt cggggcgaaa
5341 actctcaagg atcttaccgc tgttgagatc cagttcgatg taacccactc gtgcacccaa
5401 ctgatcttca gcatctttta ctttcaccag cgtttctggg tgagcaaaaa caggaaggca
5461 aaatgccgca aaaagggaa taagggcgac acggaaatgt tgaatactca tactcttcct
5521 ttttcaatat tattgaagca tttatcaggg ttattgtctc atgagcggat acatatttga
5581 atgtatttag aaaaataaac aaatagggggt tccgcgcaca tttccccgaa aagtgccacc
5641 tgacgtcgac ggatcgggag atctcccgat cccctatggt gcactctcag tacaatctgc
5701 tctgatgccg catagttaag ccagtatctg ctccctgctt gtgtgttgga ggtcgctgag
5761 tagtgcgcga gcaaaattta agctacaaca aggcaaggct tgaccgacaa ttgcatgaag
5821 aatctgctta gggttaggcg ttttgcgctg cttcgcgatg tacgggccag atatacgcgt
5881 tgacattgat tattgactag ttattaatag taatcaatta cggggtcatt agttcatagc
5941 ccatatatgg agttccgcgt tacataactt acggtaaatg gcccgcctgg ctgaccgccc
6001 aacgacccc gcccattgac gtcaataatg acgtatgttc ccatagtaac gccaataggg
6061 actttccatt gacgtcaatg ggtggagtat ttacggtaaa ctgcccactt ggcagtacat
6121 caagtgtatc atatgccaag tacgccccct attgacgtca atgacggtaa atggcccgcc
6181 tggcattatg cccagtacat gaccttatgg gactttccta cttggcagta catctacgta
6241 ttagtcatcg ctattaccat ggtgatgcgg ttttggcagt acatcaatgg gcgtggatag
6301 cggtttgact cacggggatt tccaagtctc cacccccattg acgtcaatgg gagtttgttt
6361 tggcaccaaa atcaacggga ctttccaaaa tgtcgtaaca actccgcccc attgacgcaa
6421 atgggcggta ggcgtgtacg gtgggaggtc tatataagca gcgcgttttg cctgtactgg
6481 gtctctctgg ttagaccaga tctgagcctg ggagctctct ggctaactag ggaacccact
6541 gcttaagcct caataaagct tgccttgagt gcttcaagta gtgtgtgccc gtctgttgtg
6601 tgactctggt aactagagat ccctcagacc cttttagtca gtgtggaaaa tctctagcag
6661 tggcgcccga acagggactt gaaagcgaaa gggaaaccag aggagctctc tcgacgcagg
6721 actcggcttg ctgaagcgcg cacggcaaga ggcgaggggc ggcgactggt gagtacgcca
6781 aaaattttga ctagcggagg ctagaaggag agagatgggt gcgagagcgt cagtattaag
6841 cggggggagaa ttagatcgcg atgggaaaaa attcggttaa ggccaggggg aaagaaaaaa
6901 tataaattaa aacatatagt atgggcaagc agggagctag aacgattcgc agttaatcct
6961 ggcctgttag aaacatcaga aggctgtaga caaatactgg gacagctaca accatccctt
7021 cagacaggat cagaagaact tagatcatta tataatacag tagcaaccct ctattgtgtg
7081 catcaaagga tagagataaa agacaccaag gaagctttag acaagataga ggaagagcaa
7141 aacaaaagta agaccaccgc acagcaagcg gccgctgatc ttcagacctg gaggaggaga
7201 tatgagggac aattggagaa gtgaattata taaatataaa gtagtaaaaa ttgaaccatt
7261 aggagtagca cccaccaagg caaagagaag agtggtgcag agagaaaaaa gagcagtggg
7321 aataggagct ttgttccttg ggttcttggg agcagcagga agcactatgg gcgcagcgtc
7381 aatgacgctg acggtacagg ccagacaatt attgtctggt atagtgcagc agcagaacaa
7441 tttgctgagg gctattgagg cgcaacagca tctgttgcaa ctcacagtct ggggcatcaa
7501 gcagctccag gcaagaatcc tggctgtgga aagataccta aaggatcaac agctcctggg
7561 gatttggggt tgctctggaa aactcatttg caccactgct gtgccttgga atgctagttg
```

-continued

```
7621 gagtaataaa tctctggaac agatttggaa tcacacgacc tggatggagt gggacagaga
7681 aattaacaat tacacaagct taatacactc cttaattgaa gaatcgcaaa accagcaaga
7741 aaagaatgaa caagaattat tggaattaga taaatgggca agtttgtgga attggtttaa
7801 cataacaaat tggctgtggt atataaaatt attcataatg atagtaggag gcttggtagg
7861 tttaagaata gttttgctg tactttctat agtgaataga gttaggcagg gatattcacc
7921 attatcgttt cagacccacc tcccaacccc gaggggaccc gacaggcccg aaggaataga
7981 agaagaaggt ggagagagag acagagacag atccattcga ttagtgaacg gatcggcact
8041 gcgtgcgcca attctgcaga caaatggcag tattcatcca caattttaaa agaaaagggg
8101 ggattggggg gtacagtgca ggggaaagaa tagtagacat aatagcaaca gacatacaaa
8161 ctaaagaatt acaaaaacaa attacaaaaa ttcaaaattt tcgggtttat tacagggaca
8221 gcagagatcc agtttggtta attaaggtac cgagggccta tttcccatga ttccttcata
8281 tttgcatata cgatacaagg ctgttagaga gataattaga attaatttga ctgtaaacac
8341 aaagatatta gtacaaaata cgtgacgtag aaagtaataa tttcttgggt agtttgcagt
8401 ttttaaaatta tgttttaaaa tggactatca tatgcttacc gtaacttgaa agtatttcga
8461 ttttcttggct ttatatatct tgtggaaagg acgaaacacc gttcataggg atccaagttt
8521 tgtttaagag ctatgctgga aacagcatag caagtttaaa taaggctagt ccgttatcaa
8581 cttgaaaaag tggcaccgag tcggtgcttc attttcctc cactgttgca aagtttttt
8641 cctgcagccc gggaattcgc tagctaggtc ttgaaaggag tgggaattgg ctccggtgcc
8701 cgtcagtggg cagagcgcac atcgcccaca gtccccgaga agttgggggg aggggtcggc
8761 aattgatccg gtgcctagag aaggtggcgc ggggtaaact gggaaagtga tgtcgtgtac
8821 tggctccgcc ttttcccga gggtggggga gaaccgtata taagtgcagt agtcgccgtg
8881 aacgttcttt ttcgcaacgg gtttgccgcc agaacacagg accggttcta gagcgctgcc
8941 accatgttag ctgacgctgt ctcacgcctg gtcctgggta agtttggtga cctgaccgac
9001 aacttctcct cccctcacgc tcgcagaaaa gtgctggctg gagtcgtcat gacaacaggc
9061 acagatgtta aagatgccaa ggtgataagt gtttctacag gaacaaaatg tattaatggt
9121 gaatacatga gtgatcgtgg ccttgcatta aatgactgcc atgcagaaat aatatctcgg
9181 agatccttgc tcagatttct ttatacacaa cttgagcttt acttaaataa caaagatgat
9241 caaaaaagat ccatctttca gaaatcagag cgaggggggt ttaggctgaa ggagaatgtc
9301 cagtttcatc tgtacatcag cacctctccc tgtggagatg ccagaatctt ctcaccacat
9361 gagccaatcc tggaagaacc agcagataga cacccaaatc gtaaagcaag aggacagcta
9421 cggaccaaaa tagagtctgg tcaggggacg attccagtgc gctccaatgc gagcatccaa
9481 acgtgggacg gggtgctgca aggggagcgg ctgctcacca tgtcctgcag tgacaagatt
9541 gcacgctgga acgtggtggg catccaggga tccctgctca gcatttcgt ggagcccatt
9601 tacttctcga gcatcatcct gggcagcctt taccacgggg accacctttc cagggccatg
9661 taccagcgga tctccaacat agaggacctg ccacctctct acaccctcaa caagcctttg
9721 ctcagtggca tcagcaatgc agaagcacgg cagccaggga aggcccccaa cttcagtgtc
9781 aactggacgg taggcgactc cgctattgag gtcatcaacg ccacgactgg aaggatgag
9841 ctgggccgcg cgtcccgcct gtgtaagcac gcgttgtact gtcgctggat gcgtgtgcac
9901 ggcaaggttc cctcccactt actacgctcc aagattacca gcccaacgt gtaccatgag
9961 tccaagctgg cggcaaagga gtaccaggcc gccaaggcgc gtctgttcac agccttcatc
10021 aaggcggggc tgggggcctg ggtggagaag cccaccgagc aggaccagtt ctcactcacg
```

```
10081 cccagtggaa gtgagacacc gggaacctca gagagcgcca cgccagaaag catggacaag 10141 aagtacagca tcggcctggc catcggcacc aactctgtgg gctgggccgt gatcaccgac 10201 gagtacaagg tgcccagcaa gaaattcaag gtgctgggca acaccgaccg gcacagcatc 10261 aagaagaacc tgatcggcgc cctgctgttc gacagcggaa aaacagccga ggccacccgg 10321 ctgaagagaa ccgccagaag aagatacacc agacggaaga accggatctg ctatctgcaa 10381 gagatcttca gcaacgagat ggccaaggtg gacgacagct tcttccacag actggaagag 10441 tccttcctgg tggaagagga taagaagcac gagcggcacc ccatcttcgg caacatcgtg 10501 gacgaggtgg cctaccacga gaagtacccc accatctacc acctgagaaa gaaactggtg 10561 gacagcaccg acaaggccga cctgcggctg atctatctgg ccctggccca catgatcaag 10621 ttccggggcc acttcctgat cgagggcgac ctgaaccccg acaacagcga cgtggacaag 10681 ctgttcatcc agctggtgca gacctacaac cagctgttcg aggaaaaccc catcaacgcc 10741 agcggcgtgg acgccaaggc catcctgtct gccagactga gcaagagcag acggctggaa 10801 aatctgatcg cccagctgcc cggcgagaag aagaatggcc tgttcggcaa cctgattgcc 10861 ctgagcctgg gcctgacccc caacttcaag agcaacttcg acctggccga ggatgccaaa 10921 ctgcagctga gcaaggacac ctacgacgac gacctggaca acctgctggc ccagatcggc 10981 gaccagtacg ccgacctgtt tctggccgcc aagaacctgt ccgacgccat cctgctgagc 11041 gacatcctga gagtgaacac cgagatcacc aaggcccccc tgagcgcctc tatgatcaag 11101 agatacgacg agcaccacca ggacctgacc ctgctgaaag ctctcgtgcg gcagcagctg 11161 cctgagaagt acaaagagat tttcttcgac cagagcaaga acggctacgc cggctacatc 11221 gatggcggag ccagccagga agagttctac aagttcatca agcccatcct ggaaaagatg 11281 gacggcaccg aggaactgct cgtgaagctg aacagagagg acctgctgcg gaagcagcgg 11341 accttcgaca acggcagcat cccccaccag atccacctgg gagagctgca cgccattctg 11401 cggcggcagg aagattttta cccattcctg aaggacaacc gggaaaagat cgagaagatc 11461 ctgaccttcc gcatccccta ctacgtgggc cctctggcca ggggaaacag cagattcgcc 11521 tggatgacca gaaagagcga ggaaaccatc acccccctgga acttcgagga agtggtggac 11581 aagggcgcca gcgcccagag cttcatcgag cggatgacca acttcgataa gaacctgccc 11641 aacgagaagg tgctgcccaa gcacagcctg ctgtacgagt acttcaccgt gtacaacgag 11701 ctgaccaaag tgaaatacgt gaccgaggga atgagaaagc ccgccttcct gagcggcgag 11761 cagaaaaaag ccatcgtgga cctgctgttc aagaccaacc ggaaagtgac cgtgaagcag 11821 ctgaaagagg actacttcaa gaaaatcgag tgcttcgact ccgtggaaat ctccggcgtg 11881 gaagatcggt tcaacgcctc cctgggcaca taccacgatc tgctgaaaat tatcaaggac 11941 aaggacttcc tggacaatga ggaaaacgag gacattctgg aagatatcgt gctgaccctg 12001 acactgtttg aggacagaga gatgatcgag gaacggctga aaacctatgc ccacctgttc 12061 gacgacaaag tgatgaagca gctgaagcgg cggagataca ccggctgggg caggctgagc 12121 cggaagctga tcaacggcat ccgggacaag cagtccggca agacaatcct ggatttcctg 12181 aagtccgacg gcttcgccaa cagaaacttc atgcagctga tccacgacga cagcctgacc 12241 tttaaagagg acatccagaa agcccaggtg tccggccagg gcgatagcct gcacgagcac 12301 attgccaatc tggccggcag ccccgccatt aagaagggca tcctgcagac agtgaaggtg 12361 gtggacgagc tcgtgaaagt gatgggccgg cacaagcccg agaacatcgt gatcgaaatg 12421 gccagagaga accagaccac ccagaaggga cagaagaaca gccgcgagag aatgaagcgg
```

```
12481 atcgaagagg gcatcaaaga gctgggcagc cagatcctga agaacaccc cgtggaaaac 12541 acccagctgc agaacgagaa gctgtacctg tactacctgc agaatgggcg ggatatgtac 12601 gtggaccagg aactggacat caaccggctg tccgactacg atgtggacgc tatcgtgcct 12661 cagagctttc tgaaggacga ctccatcgat aacaaagtgc tgactcggag cgacaagaac 12721 cggggcaaga gcgacaacgt gccctccgaa gaggtcgtga agaagatgaa gaactactgg 12781 cgccagctgc tgaatgccaa gctgattacc cagaggaagt tcgacaatct gaccaaggcc 12841 gagagaggcg gcctgagcga actggataag gccggcttca tcaagagaca gctggtggaa 12901 acccggcaga tcacaaagca cgtggcacag atcctggact cccggatgaa cactaagtac 12961 gacgagaacg acaaactgat ccgggaagtg aaagtgatca ccctgaagtc caagctggtg 13021 tccgatttcc ggaaggattt ccagttttac aaagtgcgcg agatcaacaa ctaccaccac 13081 gcccacgacg cctacctgaa cgccgtcgtg ggaaccgccc tgatcaaaaa gtaccctaag 13141 ctggaaagcg agttcgtgta cggcgactac aaggtgtacg acgtgcggaa gatgatcgcc 13201 aagagcgagc aggaaatcgg caaggctacc gccaagtact tcttctacag caacatcatg 13261 aactttttca gaccgagat accctggcc aacggcgaga tccggaagcg gcctctgatc 13321 gagacaaacg gcgaaacagg cgagatcgtg tgggataagg gccgggactt tgccaccgtg 13381 cggaaagtgc tgtctatgcc ccaagtgaat atcgtgaaaa agaccgaggt gcagacaggc 13441 ggcttcagca aagagtctat cctgcccaag aggaacagcg acaagctgat cgccagaaag 13501 aaggactggg accctaagaa gtacggcggc ttcgacagcc ccaccgtggc ctattctgtg 13561 ctggtggtgg ccaaagtgga aaagggcaag tccaagaaac tgaagagtgt gaaagagctg 13621 ctggggatca ccatcatgga aagaagcagc ttcgagaaga tcccatcga ctttctggaa 13681 gccaagggct acaaagaagt gaaaaaggac ctgatcatca agctgcctaa gtactccctg 13741 ttcgagctgg aaaacggccg gaagagaatg ctggcctctg ccggcgaact gcagaaggga 13801 aacgaactgg ccctgccctc caaatatgtg aacttcctgt acctgccag ccactatgag 13861 aagctgaagg gctcccccga ggataatgag cagaaacagc tgtttgtgga acagcacaaa 13921 cactacctgg acgagatcat cgagcagatc agcgagttct ccaagagagt gatcctggcc 13981 gacgctaatc tggacaaggt gctgagcgcc tacaacaagc acagagacaa gcctatcaga 14041 gagcaggccg agaatatcat ccacctgttt accctgacca atctgggagc ccctgccgcc 14101 ttcaagtact tgacaccac catcgaccgg aagaggtaca ccagcaccaa agaggtgctg 14161 gacgccaccc tgatccacca gagcatcacc ggcctgtacg agacacggat cgacctgtct 14221 cagctgggag gcgacaagcg acctgccgcc
```

AXCM_LCV2_puro_IDUA_No-spacer_gibson (SEQ ID NO: 39)
LOCUS Exported 14230 bp ds-DNA circular
DEFINITION synthetic circular DNA
KEYWORDS AXCM_LCV2_puro_IDUA_No-spacer_gibson
SOURCE synthetic DNA construct
ORGANISM synthetic DNA construct
REFERENCE 1 (bases 1 to 14230)
FEATURES Location/Qualifiers
source 1 . . . 14230
/organism="synthetic DNA construct"
/mol_type="other DNA"
LTR 828 . . . 1016
/note="5' LTR (R and U5 portions; U3 was replaced by the CMV promoter)"
misc_feature 1067 . . . 1204
/note="Psi"
misc_feature 1124 . . . 1127
/note="SD; splice donor"
misc_feature 1171 . . . 1535
/note="gag"
misc_feature 1681 . . . 1922

```
/note="RRE"
misc_feature   2440 . . . 2557
/note="CPPT; central polypurine tract"
promoter       2608 . . . 2856
/note="Human U6"
misc_feature   2857 . . . 2942
/note="sgRNA scaffold"
misc_feature   2943 . . . 2948
/note="Linker"
promoter       3001 . . . 3256
/note="EFS-NS"
CDS            3280 . . . 4419
/codon_start=1
/note="ADARB1_Catalytic Domain" (SEQ ID NO: 40)
/translation="MLADAVSRLVLGKFGDLTDNFSSPHARRKVLAGVVMTTGTDVKDAKVIS
VSTGTKCINGEYMSDRGLALNDCHAEIISRRSLLRFLYTQLELYLNNKDDQKRSIFQKSE
RGGFRLKENVQFHLYISTSPCGDARIFSPHEPILEEPADRHPNRKARGQLRTKIESGQGTIP
VRSNASIQTWDGVLQGERLLTMSCSDKIARWNVVGIQGSLLSIFVEPIYFSSIILGSLYHG
DHLSRAMYQRISNIEDLPPLYTLNKPLLSGISNAEARQPGKAPNFSVNWTVGDSAIEVIN
ATTGKDELGRASRLCKHALYCRWMRVHGKVPSHLLRSKITKPNVYHESKLAAKEYQA
AKARLFTAFIKAGLGAWVEKPTEQDQFSLTP"
misc_feature   3280 . . . 3282
/note="hSpCas9"
CDS            4420 . . . 4467
/codon_start=1
/note="XTEN"
/translation="SGSETPGTSESATPES" (SEQ ID NO: 41)
CDS            4468 . . . 8571
/codon_start=1
/product="catalytically dead mutant of the Cas9
endonuclease from the Streptococcus pyogenes Type II
CRISPR/Cas system"
/note="dCas9"
/note="RNA-guided DNA-binding protein that lacks
endonuclease activity due to the D10A mutation in the RuvC
catalytic domain and the H840A mutation in the HNH
catalytic domain" (SEQ ID NO: 42)
/translation="MDKKYSIGLAIGTNSVGWAVITDEYKVPSKKFKVLGNTDRHSIKKNLIGAL
LFDSGETAEATRLKRTARRRYTRRKNRICYLQEIFSNEMAKVDDSFFHRLEESFLVEEDK
KHERHPIFGNIVDEVAYHEKYPTIYHLRKKLVDSTDKADLRLIYLALAHMIKFRGHFLIE
GDLNPDNSDVDKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQIGDQYADLF
LAAKNLSDAILLSDILRVNTEITKAPLSASMIKRYDEHHQDLTLLKALVRQQLPEKYKEIF
FDQSKNGYAGYIDGGASQEEFYKFIKPILEKMDGTEELLVKLNREDLLRKQRTFDNGSIP
HQIHLGELHAILRRQEDFYPFLKDNREKIEKILTFRIPYYVGPLARGNSRFAWMTRKSEET
ITPWNFEEVVDKGASAQSFIERMTNFDKNLPNEKVLPKHSLLYEYFTVYNELTKVKYVT
EGMRKPAFLSGEQKKAIVDLLFKTNRKVTVKQLKEDYFKKIECFDSVEISGVEDRFNAS
LGTYHDLLKIIKDKDFLDNEENEDILEDIVLTLTLFEDREMIEERLKTYAHLFDDKVMKQ
LKRRRYTGWGRLSRKLINGIRDKQSGKTILDFLKSDGFANRNFMQLIHDDSLTFKEDIQK
AQVSGQGDSLHEHIANLAGSPAIKKGILQTVKVVDELVKVMGRHKPENIVIEMARENQT
TQKGQKNSRERMKRIEEGIKELGSQILKEHPVENTQLQNEKLYLYYLQNGRDMYVDQE
LDINRLSDYDVDAIVPQSFLKDDSIDNKVLTRSDKNRGKSDNVPSEEVVKKMKNYWRQ
LLNAKLITQRKFDNLTKAERGGLSELDKAGFIKRQLVETRQITKHVAQILDSRMNTKYD
ENDKLIREVKVITLKSKLVSDFRKDFQFYKVREINNYHHAHDAYLNAVVGTALIKKYPK
LESEFVYGDYKVYDVRKMIAKSEQEIGKATAKYFFYSNIMNFFKTEITLANGEIRKRPLIE
TNGETGEIVWDKGRDFATVRKVLSMPQVNIVKKTEVQTGGFSKESILPKRNSDKLIARK
KDWDPKKYGGFDSPTVAYSVLVVAKVEKGKSKKLKSVKELLGITIMERSSFEKNPIDFL
EAKGYKEVKKDLIIKLPKYSLFELENGRKRMLASAGELQKGNELALPSKYVNFLYLASH
YEKLKGSPEDNEQKQLFVEQHKHYLDEIIEQISEFSKRVILADANLDKVLSAYNKHRDKP
IREQAENIIHLFTLTNLGAPAAFKYFDTTIDRKRYTSTKEVLDATLIHQSITGLYETRIDLS
QLGGD"
misc_feature   8572 . . . 8619
/note="NLS"
CDS            8572
/codon_start=1
/product="catalytically dead mutant of the Cas9
endonuclease from the Streptococcus pyogenes Type II
CRISPR/Cas system"
/note="dCas9"
/note="RNA-guided DNA-binding protein that lacks
endonuclease activity due to the D10A mutation in the RuvC
catalytic domain and the H840A mutation in the HNH
catalytic domain"
/translation=""
misc_feature   8620 . . . 8643
/note="FLAG"
misc_feature   8644 . . . 8709
/note="P2A"
CDS            8710 . . . 9306
/note="Puro"
misc_binding   9322 . . . 9910
```

/note="WPRE"
LTR 9981 . . . 10216
/note="3' LTR"
rep_origin 12665 . . . 12890
/note="ColE1"
misc_feature 13102 . . . 13908
/note="AmpR"
ORIGIN (SEQ ID NO: 39)

```
   1 gtcgacggat cgggagatct cccgatcccc tatggtgcac tctcagtaca atctgctctg
  61 atgccgcata gttaagccag tatctgctcc ctgcttgtgt gttggaggtc gctgagtagt
 121 gcgcgagcaa aatttaagct acaacaaggc aaggcttgac cgacaattgc atgaagaatc
 181 tgcttagggt taggcgtttt gcgctgcttc gcgatgtacg ggccagatat acgcgttgac
 241 attgattatt gactagttat taatagtaat caattacggg gtcattagtt catagcccat
 301 atatggagtt ccgcgttaca taacttacgg taaatggccc gcctggctga ccgcccaacg
 361 accccccgcc cattgacgtc aataatgacgt atgttcccat agtaacgcca atagggactt
 421 tccattgacg tcaatgggtg gagtatttac ggtaaactgc ccacttggca gtacatcaag
 481 tgtatcatat gccaagtacg ccccctattg acgtcaatga cggtaaatgg cccgcctggc
 541 attatgccca gtacatgacc ttatgggact ttcctacttg gcagtacatc tacgtattag
 601 tcatcgctat taccatggtg atgcggtttt ggcagtacat caatgggcgt ggatagcggt
 661 ttgactcacg gggatttcca agtctccacc ccattgacgt caatgggagt ttgttttggc
 721 accaaaatca acgggacttt ccaaaatgtc gtaacaactc cgccccattg acgcaaatgg
 781 gcggtaggcg tgtacggtgg gaggtctata taagcagcgc gttttgcctg tactgggtct
 841 ctctggttag accagatctg agcctgggag ctctctggct aactagggaa cccactgctt
 901 aagcctcaat aaagcttgcc ttgagtgctt caagtagtgt gtgcccgtct gttgtgtgac
 961 tctggtaact agagatccct cagacccttt tagtcagtgt ggaaaatctc tagcagtggc
1021 gcccgaacag ggacttgaaa gcgaaaggga accagagga gctctctcga cgcaggactc
1081 ggcttgctga gcgcgcacg gcaagaggcg aggggcggcg actggtgagt acgccaaaaa
1141 ttttgactag cggaggctag aaggagagag atgggtgcga gagcgtcagt attaagcggg
1201 ggagaattag atcgcgatgg gaaaaaattc ggttaaggcc agggggaaag aaaaaatata
1261 aattaaaaca tatagtatgg gcaagcaggg agctagaacg attcgcagtt aatcctggcc
1321 tgttagaaac atcagaaggc tgtagacaaa tactgggaca gctacaacca tcccttcaga
1381 caggatcaga agaacttaga tcattatata atacagtagc aaccctctat tgtgtgcatc
1441 aaaggataga gataaaagac accaaggaag ctttagacaa gatagaggaa gagcaaaaca
1501 aaagtaagac caccgcacag caagcggccg ctgatcttca gacctggagg aggagatatg
1561 agggacaatt ggagaagtga attatataaa tataaagtag taaaaattga accattagga
1621 gtagcaccca ccaaggcaaa gagaagagtg gtgcagagag aaaaaagagc agtgggaata
1681 ggagctttgt tccttgggtt cttgggagca gcaggaagca ctatgggcgc agcgtcaatg
1741 acgctgacgg tacaggccag acaattattg tctggtatag tgcagcagca gaacaatttg
1801 ctgagggcta ttgaggcgca acagcatctg ttgcaactca cagtctgggg catcaagcag
1861 ctccaggcaa gaatcctggc tgtggaaaga tacctaaagg atcaacagct cctgggggatt
1921 tggggttgct ctggaaaact catttgcacc actgctgtgc cttggaatgc tagttggagt
1981 aataaatctc tggaacagat ttggaatcac acgacctgga tggagtggga cagagaaatt
2041 aacaattaca caagcttaat acactcctta attgaagaat cgcaaaacca gcaagaaaag
2101 aatgaacaag aattattgga attagataaa tgggcaagtt tgtggaattg gtttaacata
2161 acaaattggc tgtggtatat aaaattattc ataatgatag taggaggctt ggtaggttta
```

```
-continued 2221  agaatagttt  ttgctgtact  ttctatagtg  aatagagtta  ggcagggata  ttcaccatta 2281  tcgtttcaga  cccacctccc  aaccccgagg  ggacccgaca  ggcccgaagg  aatagaagaa 2341  gaaggtggag  agagagacag  agacagatcc  attcgattag  tgaacggatc  ggcactgcgt 2401  gcgccaattc  tgcagacaaa  tggcagtatt  catccacaat  tttaaaagaa  aaggggggat 2461  tggggggtac  agtgcagggg  aaagaatagt  agacataata  gcaacagaca  tacaaactaa 2521  agaattacaa  aaacaaatta  caaaaattca  aaattttcgg  gtttattaca  gggacagcag 2581  agatccagtt  tggttaatta  aggtaccgag  ggcctatttc  ccatgattcc  ttcatatttg 2641  catatacgat  acaaggctgt  tagagagata  attagaatta  atttgactgt  aaacacaaag 2701  atattagtac  aaaatacgtg  acgtagaaag  taataatttc  ttgggtagtt  tgcagtttta 2761  aaattatgtt  ttaaaatgga  ctatcatatg  cttaccgtaa  cttgaaagta  tttcgatttc 2821  ttggctttat  atatcttgtg  gaaaggacga  acaccgtttt  aagagctatg  ctggaaacag 2881  catagcaagt  ttaaataagg  ctagtccgtt  atcaacttga  aaaagtggca  ccgagtcggt 2941  gcttcattac  ttcggcccag  agctgctcct  tttttcctg   cagcccggga  attcgctagc 3001  taggtcttga  aaggagtggg  aattggctcc  ggtgcccgtc  agtgggcaga  gcgcacatcg 3061  cccacagtcc  ccgagaagtt  ggggggaggg  gtcggcaatt  gatccggtgc  ctagagaagg 3121  tggcgcgggg  taaactggga  aagtgatgtc  gtgtactggc  tccgcctttt  tcccgagggt 3181  gggggagaac  cgtatataag  tgcagtagtc  gccgtgaacg  ttcttttcg   caacgggttt 3241  gccgccagaa  cacaggaccg  gttctagagc  gctgccacca  tgttagctga  cgctgtctca 3301  cgcctggtcc  tgggtaagtt  tggtgacctg  accgacaact  tctcctcccc  tcacgctcgc 3361  agaaaagtgc  tggctggagt  cgtcatgaca  acaggcacag  atgttaaaga  tgccaaggtg 3421  ataagtgttt  ctacaggaac  aaaatgtatt  aatggtgaat  acatgagtga  tcgtggcctt 3481  gcattaaatg  actgccatgc  agaaataata  tctcggagat  ccttgctcag  atttctttat 3541  acacaacttg  agctttactt  aaataacaaa  gatgatcaaa  aaagatccat  ctttcagaaa 3601  tcagagcgag  gggggtttag  gctgaaggag  aatgtccagt  ttcatctgta  catcagcacc 3661  tctccctgtg  gagatgccag  aatcttctca  ccacatgagc  caatcctgga  agaaccagca 3721  gatagacacc  caaatcgtaa  agcaagagga  cagctacgga  ccaaaataga  gtctggtcag 3781  gggacgattc  cagtgcgctc  caatgcgagc  atccaaacgt  gggacggggt  gctgcaaggg 3841  gagcggctgc  tcaccatgtc  ctgcagtgac  aagattgcac  gctggaacgt  ggtgggcatc 3901  cagggatccc  tgctcagcat  tttcgtggag  cccatttact  tctcgagcat  catcctgggc 3961  agcctttacc  acggggacca  cctttccagg  gccatgtacc  agcggatctc  caacatagag 4021  gacctgccac  ctctctacac  cctcaacaag  cctttgctca  gtggcatcag  caatgcagaa 4081  gcacggcagc  cagggaaggc  ccccaacttc  agtgtcaact  ggacggtagg  cgactccgct 4141  attgaggtca  tcaacgccac  gactgggaag  gatgagctgg  gccgcgcgtc  ccgcctgtgt 4201  aagcacgcgt  tgtactgtcg  ctggatgcgt  gtgcacggca  aggttccctc  ccacttacta 4261  cgctccaaga  ttaccaagcc  caacgtgtac  catgagtcca  agctggcggc  aaaggagtac 4321  caggccgcca  aggcgcgtct  gttcacagcc  ttcatcaagg  cggggctggg  ggcctgggtg 4381  gagaagccca  ccgagcagga  ccagttctca  ctcacgccca  gtggaagtga  gacaccggga 4441  acctcagaga  gcgccacgcc  agaaagcatg  gacaagaagt  acagcatcgg  cctggccatc 4501  ggcaccaact  ctgtgggctg  ggccgtgatc  accgacgagt  acaaggtgcc  cagcaagaaa 4561  ttcaaggtgc  tgggcaacac  cgaccggcac  agcatcaaga  agaacctgat  cggcgccctg
```

-continued

```
4621 ctgttcgaca gcggagaaac agccgaggcc acccggctga agagaaccgc cagaagaaga 4681 tacaccagac ggaagaaccg gatctgctat ctgcaagaga tcttcagcaa cgagatggcc 4741 aaggtggacg acagcttctt ccacagactg gaagagtcct tcctggtgga agaggataag 4801 aagcacgagc ggcaccccat cttcggcaac atcgtggacg aggtggccta ccacgagaag 4861 taccccacca tctaccacct gagaaagaaa ctggtggaca gcaccgacaa ggccgacctg 4921 cggctgatct atctggccct ggcccacatg atcaagttcc ggggccactt cctgatcgag 4981 ggcgacctga accccgacaa cagcgacgtg gacaagctgt tcatccagct ggtgcagacc 5041 tacaaccagc tgttcgagga aaaccccatc aacgccagcg gcgtggacgc caaggccatc 5101 ctgtctgcca gactgagcaa gagcagacgg ctggaaaatc tgatcgccca gctgccggc 5161 gagaagaaga atggcctgtt cggcaacctg attgccctga gcctgggcct gacccccaac 5221 ttcaagagca acttcgacct ggccgaggat gccaaactgc agctgagcaa ggacacctac 5281 gacgacgacc tggacaacct gctggcccag atcggcgacc agtacgccga cctgtttctg 5341 gccgccaaga acctgtccga cgccatcctg ctgagcgaca tcctgagagt gaacaccgag 5401 atcaccaagg cccccctgag cgcctctatg atcaagagat acgacgagca ccaccaggac 5461 ctgaccctgc tgaaagctct cgtgcggcag cagctgcctg agaagtacaa agagattttc 5521 ttcgaccaga gcaagaacgg ctacgccggc tacatcgatg gcggagccag ccaggaagag 5581 ttctacaagt tcatcaagcc catcctggaa aagatggacg gcaccgagga actgctcgtg 5641 aagctgaaca gagaggacct gctgcggaag cagcggacct tcgacaacgg cagcatcccc 5701 caccagatcc acctgggaga gctgcacgcc attctgcggc ggcaggaaga ttttacccca 5761 ttcctgaagg acaaccggga aaagatcgag aagatcctga ccttccgcat cccctactac 5821 gtgggccctc tggccagggg aaacagcaga ttcgcctgga tgaccagaaa gagcgaggaa 5881 accatcaccc cctggaactt cgaggaagtg gtggacaagg gcgccagcgc ccagagcttc 5941 atcgagcgga tgaccaactt cgataagaac ctgcccaacg agaaggtgct gcccaagcac 6001 agcctgctgt acgagtactt caccgtgtac aacgagctga ccaaagtgaa atacgtgacc 6061 gagggaatga gaaagcccgc cttcctgagc ggcgagcaga aaaaagccat cgtggacctg 6121 ctgttcaaga ccaaccggaa agtgaccgtg aagcagctga aagaggacta cttcaagaaa 6181 atcgagtgct tcgactccgt ggaaatctcc ggcgtggaag atcggttcaa cgcctccctg 6241 ggcacatacc acgatctgct gaaaattatc aaggacaagg acttcctgga caatgaggaa 6301 aacgaggaca ttctggaaga tatcgtgctg accctgacac tgtttgagga cagagagatg 6361 atcgaggaac ggctgaaaac ctatgcccac ctgttcgacg acaaagtgat gaagcagctg 6421 aagcggcgga gatacaccgg ctggggcagg ctgagccgga agctgatcaa cggcatccgg 6481 gacaagcagt ccggcaagac aatcctggat ttcctgaagt ccgacggctt cgccaacaga 6541 aacttcatgc agctgatcca cgacgacagc ctgaccttta agagggacat ccagaaagcc 6601 caggtgtccg gccagggcga tagcctgcac gagcacattg ccaatctggc cggcagcccc 6661 gccattaaga agggcatcct gcagacagtg aaggtggtgg acgagctcgt gaaagtgatg 6721 ggccggcaca agcccgagaa catcgtgatc gaaatggcca gagagaacca gaccacccag 6781 aagggacaga gaacagccg cgagagaatg aagcggatcg aagagggcat caaagagctg 6841 ggcagccaga tcctgaaaga acaccccgtg gaaaacaccc agctgcagaa cgagaagctg 6901 tacctgtact acctgcagaa tgggcgggat atgtacgtgg accaggaact ggacatcaac 6961 cggctgtccg actacgatgt ggacgctatc gtgcctcaga gctttctgaa ggacgactcc 7021 atcgataaca aagtgctgac tcggagcgac aagaaccggg gcaagagcga caacgtgccc
```

-continued

```
7081 tccgaagagg tcgtgaagaa gatgaagaac tactggcgcc agctgctgaa tgccaagctg
7141 attacccaga ggaagttcga caatctgacc aaggccgaga gaggcggcct gagcgaactg
7201 gataaggccg gcttcatcaa gagacagctg gtggaaaccc ggcagatcac aaagcacgtg
7261 gcacagatcc tggactcccg gatgaacact aagtacgacg agaacgacaa actgatccgg
7321 gaagtgaaag tgatcaccct gaagtccaag ctggtgtccg atttccggaa ggatttccag
7381 ttttacaaag tgcgcgagat caacaactac caccacgccc acgacgccta cctgaacgcc
7441 gtcgtgggaa ccgccctgat caaaaagtac cctaagctgg aaagcgagtt cgtgtacggc
7501 gactacaagg tgtacgacgt gcggaagatg atcgccaaga gcgagcagga aatcggcaag
7561 gctaccgcca agtacttctt ctacagcaac atcatgaact ttttcaagac cgagattacc
7621 ctggccaacg gcgagatccg gaagcggcct ctgatcgaga caaacggcga acaggcgag
7681 atcgtgtggg ataagggccg ggactttgcc accgtgcgga aagtgctgtc tatgccccaa
7741 gtgaatatcg tgaaaaagac cgaggtgcag acaggcggct tcagcaaaga gtctatcctg
7801 cccaagagga acagcgacaa gctgatcgcc agaaagaagg actgggaccc taagaagtac
7861 ggcggcttcg acagcccac cgtggcctat tctgtgctgg tggtggccaa agtggaaaag
7921 ggcaagtcca agaaactgaa gagtgtgaaa gagctgctgg ggatcaccat catggaaaga
7981 agcagcttcg agaagaatcc catcgacttt ctggaagcca agggctacaa agaagtgaaa
8041 aaggacctga tcatcaagct gcctaagtac tccctgttcg agctggaaaa cggccggaag
8101 agaatgctgg cctctgccgg cgaactgcag aagggaaacg aactggccct gcctccaaa
8161 tatgtgaact tcctgtacct ggccagccac tatgagaagc tgaagggctc ccccgaggat
8221 aatgagcaga acagctgtt tgtggaacag cacaaacact acctggacga gatcatcgag
8281 cagatcagcg agttctccaa gagagtgatc ctggccgacg ctaatctgga caaggtgctg
8341 agcgcctaca acaagcacag agacaagcct atcagagagc aggccgagaa tatcatccac
8401 ctgtttaccc tgaccaatct gggagcccct gccgccttca gtactttga caccaccatc
8461 gaccggaaga ggtacaccag caccaaagag gtgctggacg ccaccctgat ccaccagagc
8521 atcaccggcc tgtacgagac acggatcgac ctgtctcagc tgggaggcga caagcgacct
8581 gccgccacaa agaaggctgg acaggctaag aagaagaaag attacaaaga cgatgacgat
8641 aagggatccg gcgcaacaaa cttctctctg ctgaaacaag ccggagatgt cgaagagaat
8701 cctggaccga ccgagtacaa gcccacggtg cgcctcgcca cccgcgacga cgtccccagg
8761 gccgtacgca ccctcgccgc cgcgttcgcc gactacccccg ccacgcgcca caccgtcgat
8821 ccggaccgcc acatcgagcg ggtcaccgag ctgcaagaac tcttcctcac gcgcgtcggg
8881 ctcgacatcg gcaaggtgtg ggtcgcggac acggcgccg cggtggcggt ctggaccacg
8941 ccggagagcg tcgaagcggg ggcggtgttc gccgagatcg gcccgcgcat ggccgagttg
9001 agcggttccc ggctggccgc gcagcaacag atggaaggcc tcctggcgcc gcaccggccc
9061 aaggagcccg cgtggttcct ggccaccgtc ggagtctcgc ccgaccacca gggcaagggt
9121 ctgggcagcg ccgtcgtgct ccccggagtg gaggcggccg agcgcgccgg ggtgcccgcc
9181 ttcctggaga cctccgcgcc ccgcaacctc cccttctacg agcggctcgg cttcaccgtc
9241 accgccgacg tcgaggtgcc cgaaggaccg cgcacctggt gcatgacccg caagcccggt
9301 gcctgaacgc gttaagtcga caatcaacct ctggattaca aaatttgtga agattgact
9361 ggtattctta actatgttgc tccttttacg ctatgtggat acgctgcttt aatgcctttg
9421 tatcatgcta ttgcttcccg tatggctttc attttctcct ccttgtataa atcctggttg
```

```
9481 ctgtctctttt atgaggagtt gtggcccgtt gtcaggcaac gtggcgtggt gtgcactgtg 9541 tttgctgacg caaccccac tggttggggc attgccacca cctgtcagct cctttccggg 9601 actttcgctt tcccctccc tattgccacg gcggaactca tcgccgcctg ccttgcccgc 9661 tgctggacag gggctcggct gttgggcact gacaattccg tggtgttgtc ggggaaatca 9721 tcgtcctttc cttggctgct cgcctgtgtt gccacctgga ttctgcgcgg gacgtccttc 9781 tgctacgtcc cttcggccct caatccagcg gaccttcctt cccgcggcct gctgccggct 9841 ctgcggcctc ttccgcgtct tcgccttcgc cctcagacga gtcggatctc cctttgggcc 9901 gcctccccgc gtcgacttta agaccaatga cttacaaggc agctgtagat cttagccact 9961 ttttaaaaga aaagggggga ctggaagggc taattcactc ccaacgaaga caagatctgc 10021 tttttgcttg tactgggtct ctctggttag accagatctg agcctgggag ctctctggct 10081 aactagggaa cccactgctt aagcctcaat aaagcttgcc ttgagtgctt caagtagtgt 10141 gtgcccgtct gttgtgtgac tctggtaact agagatccct cagacccttt tagtcagtgt 10201 ggaaaatctc tagcagggcc cgtttaaacc cgctgatcag cctcgactgt gccttctagt 10261 tgccagccat ctgttgtttg cccctccccc gtgccttcct tgaccctgga aggtgccact 10321 cccactgtcc tttcctaata aaatgaggaa attgcatcgc attgtctgag taggtgtcat 10381 tctattctgg ggggtggggt ggggcaggac agcaaggggg aggattggga agacaatagc 10441 aggcatgctg gggatgcggt gggctctatg gcttctgagg cggaaagaac cagctggggc 10501 tctaggggt atccccacgc gccctgtagc ggcgcattaa gcgcggcggg tgtggtggtt 10561 acgcgcagcg tgaccgctac acttgccagc gccctagcgc ccgctccttt cgctttcttc 10621 ccttcctttc tcgccacgtt cgccggcttt ccccgtcaag ctctaaatcg gggctccct 10681 ttagggttcc gatttagtgc tttacggcac ctcgacccca aaaaacttga ttagggtgat 10741 ggttcacgta gtgggccatc gccctgatag acggtttttc gccctttgac gttggagtcc 10801 acgttcttta atagtggact cttgttccaa actggaacaa cactcaaccc tatctcggtc 10861 tattctttg attataagg gattttgccg atttcggcct attggttaaa aaatgagctg 10921 atttaacaaa aatttaacgc gaattaattc tgtggaatgt gtgtcagtta gggtgtggaa 10981 agtccccagg ctccccagca ggcagaagta tgcaaagcat gcatctcaat tagtcagcaa 11041 ccaggtgtgg aaagtcccca ggctccccag caggcagaag tatgcaaagc atgcatctca 11101 attagtcagc aaccatagtc ccgcccctaa ctccgcccat cccgcccta actccgccca 11161 gttccgccca ttctccgccc catggctgac taattttttt tatttatgca gaggccgagg 11221 ccgcctctgc ctctgagcta ttccagaagt agtgaggagg ctttttgga ggcctaggct 11281 tttgcaaaaa gctcccggga gcttgtatat ccattttcgg atctgatcag cacgtgttga 11341 caattaatca tcggcatagt atatcggcat agtataatac gacaaggtga ggaactaaac 11401 catggccaag ttgaccagtg ccgttccggt gctcaccgcg cgcgacgtcg ccggagcggt 11461 cgagttctgg accgaccggc tcgggttctc ccggacttcc gtggaggacg acttcgccgg 11521 tgtggtccgg gacgacgtga ccctgttcat cagcgcggtc caggaccagg tggtgccgga 11581 caacaccctg gcctgggtgt gggtgcgcgg cctggacgag ctgtacgccg agtggtcgga 11641 ggtcgtgtcc acgaacttcc gggacgcctc cgggccggcc atgaccgaga tcggcgagca 11701 gccgtggggg cggagttcg ccctgcgcga cccggccggc aactgcgtgc acttcgtggc 11761 cgaggagcag gactgacacg tgctacgaga tttcgattcc accgccgcct tctatgaaag 11821 gttgggcttc ggaatcgttt tccggacgc cggctggatg atcctccagc gcggggatct 11881 catgctggag ttcttcgccc accccaactt gtttattgca gcttataatg gttacaaata
```

-continued

```
11941 aagcaatagc atcacaaatt tcacaaataa agcatttttt tcactgcatt ctagttgtgg
12001 tttgtccaaa ctcatcaatg tatcttatca tgtctgtata ccgtcgacct ctagctagag
12061 cttggcgtaa tcatggtcat agctgtttcc tgtgtgaaat tgttatccgc tcacaattcc
12121 acacaacata cgagccggaa gcataaagtg taaagcctgg ggtgcctaat gagtgagcta
12181 actcacatta attgcgttgc gctcactgcc cgctttccag tcgggaaacc tgtcgtgcca
12241 gctgcattaa tgaatcggcc aacgcgcggg gagaggcggt ttgcgtattg ggcgctcttc
12301 cgcttcctcg ctcactgact cgctgcgctc ggtcgttcgg ctgcggcgag cggtatcagc
12361 tcactcaaag gcggtaatac ggttatccac agaatcaggg gataacgcag aaagaacat
12421 gtgagcaaaa ggccagcaaa aggccaggaa ccgtaaaaag gccgcgttgc tggcgttttt
12481 ccataggctc cgcccccctg acgagcatca caaaaatcga cgctcaagtc agaggtggcg
12541 aaacccgaca ggactataaa gataccaggc gtttccccct ggaagctccc tcgtgcgctc
12601 tcctgttccg accctgccgc ttaccggata cctgtccgcc tttctccctt cgggaagcgt
12661 ggcgctttct catagctcac gctgtaggta tctcagttcg gtgtaggtcg ttcgctccaa
12721 gctgggctgt gtgcacgaac cccccgttca gcccgaccgc tgcgccttat ccggtaacta
12781 tcgtcttgag tccaacccgg taagacacga cttatcgcca ctggcagcag ccactggtaa
12841 caggattagc agagcgaggt atgtaggcgg tgctacagag ttcttgaagt ggtggcctaa
12901 ctacggctac actagaagaa cagtatttgg tatctgcgct ctgctgaagc cagttacctt
12961 cggaaaaaga gttggtagct cttgatccgg caaacaaacc accgctggta gcggtggttt
13021 ttttgtttgc aagcagcaga ttacgcgcag aaaaaaagga tctcaagaag atcctttgat
13081 cttttctacg gggtctgacg ctcagtggaa cgaaaactca cgttaaggga ttttggtcat
13141 gagattatca aaaaggatct tcacctagat ccttttaaat taaaaatgaa gttttaaatc
13201 aatctaaagt atatatgagt aaacttggtc tgacagttac caatgcttaa tcagtgaggc
13261 acctatctca gcgatctgtc tatttcgttc atccatagtt gcctgactcc ccgtcgtgta
13321 gataactacg atacgggagg gcttaccatc tggccccagt gctgcaatga taccgcgaga
13381 cccacgctca ccggctccag atttatcagc aataaaccag ccagccggaa gggccgagcg
13441 cagaagtggt cctgcaactt tatccgcctc catccagtct attaattgtt gccgggaagc
13501 tagagtaagt agttcgccag ttaatagttt gcgcaacgtt gttgccattg ctacaggcat
13561 cgtggtgtca cgctcgtcgt ttggtatggc ttcattcagc tccggttccc aacgatcaag
13621 gcgagttaca tgatccccca tgttgtgcaa aaaagcggtt agctccttcg gtcctccgat
13681 cgttgtcaga agtaagttgg ccgcagtgtt atcactcatg gttatggcag cactgcataa
13741 ttctcttact gtcatgccat ccgtaagatg cttttctgtg actggtgagt actcaaccaa
13801 gtcattctga atagtgta tgcggcgacc gagttgctct tgcccggcgt caatacggga
13861 taataccgcg ccacatagca gaactttaaa agtgctcatc attggaaaac gttcttcggg
13921 gcgaaaactc tcaaggatct taccgctgtt gagatccagt tcgatgtaac ccactcgtgc
13981 acccaactga tcttcagcat cttttacttt caccagcgtt tctgggtgag caaaaacagg
14041 aaggcaaaat gccgcaaaaa agggaataag ggcgacacgg aaatgttgaa tactcatact
14101 cttcctttt caatattatt gaagcattta tcagggttat tgtctcatga gcggatacat
14161 atttgaatgt atttagaaaa ataaacaaat agggggttccg cgcacatttc cccgaaaagt
14221 gccacctgac
```

What is claimed is:

1. A recombinant expression system for CRISPR/Cas-directed RNA editing of a target RNA comprising:

(A) a nucleic acid sequence encoding a CRISPR/Cas RNA editing fusion protein comprising a nuclease-dead CRISPR associated endonuclease (dCas) fused to a catalytically active deaminase domain of Adenosine Deaminase acting on RNA 2 (ADAR2); and (B) a nucleic acid sequence encoding an extended single guide RNA (esgRNA) comprising: (i) a short extension sequence of homology to the target RNA comprising a mismatch for a target adenosine, (ii) a dCas scaffold binding sequence, and (iii) a spacer sequence comprising a region of homology to the target RNA, wherein the sequences of the esgRNA (i), (ii), and (iii) are situated 3' to 5' in the esgRNA.

2. The recombinant expression system of claim 1, wherein (A) and (B) are comprised within the same vector or comprised within different vectors.

3. The recombinant expression system of claim 1, wherein the catalytically active deaminase domain of ADAR2 comprises an E488Q mutation.

4. The recombinant expression system of claim 1, wherein the dCas N-terminal domain is fused to the C-terminus of the catalytically active deaminase domain of ADAR2.

5. The recombinant expression system of claim 1, wherein the dCas is fused to the catalytically active deaminase domain of ADAR2 via a linker.

6. The recombinant expression system of claim 5, wherein the linker is a semi-flexible XTEN peptide linker.

7. The recombinant expression system of claim 1, wherein the short extension sequence of the esgRNA comprises a region of homology capable of near-perfect RNA-RNA base pairing with the target sequence.

8. The recombinant expression system of claim 1, wherein the esgRNA further comprises a marker sequence.

9. The recombinant expression system of claim 1, wherein the esgRNA further comprises a RNA polymerase III promoter sequence.

10. The recombinant expression system of claim 9, wherein the RNA polymerase III promoter sequence is a U6 promoter sequence.

11. The recombinant expression system of claim 1, wherein the esgRNA comprises a linker sequence between the spacer sequence and the scaffold sequence.

12. The recombinant expression system of claim 2, wherein at least one vector is a viral vector.

13. The recombinant expression system of claim 12, wherein the viral vector is an adeno-associated viral vector (AAV), lentiviral vector, or an adenoviral vector.

14. A vector comprising a nucleic acid encoding an extended single guide RNA (esgRNA) comprising (i) a short extension sequence of homology to a target RNA comprising a mismatch for a target adenosine, (ii) a dCas scaffold binding sequence, and (iii) a sequence complementary to the target sequence (spacer sequence), wherein (i), (ii) and (iii) are situated 3' to 5' in the esgRNA.

15. The vector of claim 14, wherein the vector is a viral vector.

16. The vector of claim 15, wherein the viral vector is an adeno-associated viral vector (AAV), lentiviral vector, or an adenoviral vector.

17. The vector of claim 14, further comprising an expression control element.

18. A viral particle comprising the vector of claim 14.

19. An isolated cell comprising the recombinant expression system of claim 1.

20. A kit comprising:
(A) one or more selected from the group consisting of:
  (i) a recombinant expression system comprising:
    (a) a nucleic acid sequence encoding a CRISPR/Cas RNA editing fusion protein comprising a nuclease-dead CRISPR associated endonuclease (dCas) fused to a catalytically active deaminase domain of Adenosine Deaminase acting on RNA 2 (ADAR2); and
    (b) a nucleic acid sequence encoding an extended single guide RNA (esgRNA) comprising:
      (i) a short extension sequence of homology to the target RNA comprising a mismatch for a target adenosine,
      (ii) a dCas scaffold binding sequence, and
      (iii) a spacer sequence comprising a region of homology to the target RNA,
    wherein the sequences of the esgRNA (i), (ii), and (iii) are situated 3' to 5' in the esgRNA;
  (ii) a vector comprising a nucleic acid encoding (A)(i)(a) and (b);
  (iii) a vector comprising a nucleic acid encoding (A)(i)(b);
  (iv) a viral particle comprising the recombinant expression system of (A)(i)(a) and (b);
  (v) an isolated cell comprising the recombinant expression system of (A)(i)(a) and (b); and
  (vi) an esgRNA comprising (i) a short extension sequence of homology to a target RNA comprising a mismatch for a target adenosine, and (ii) a dCas scaffold binding sequence, and (iii) a spacer sequence comprising a region of homology to the target RNA, wherein the sequences of the esgRNA (i), (ii), and (iii) are situated 3' to 5' in the esgRNA and
(B) instructions for use.

* * * * *